US010195156B2

(12) United States Patent
Benenato et al.

(10) Patent No.: US 10,195,156 B2
(45) Date of Patent: Feb. 5, 2019

(54) COMPOUNDS AND COMPOSITIONS FOR INTRACELLULAR DELIVERY OF AGENTS

(71) Applicant: ModernaTX, Inc., Cambridge, MA (US)

(72) Inventors: Kerry E. Benenato, Sudbury, MA (US); William Butcher, Winthrop, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/004,850

(22) Filed: Jun. 11, 2018

(65) Prior Publication Data
US 2018/0333366 A1 Nov. 22, 2018

Related U.S. Application Data

(63) Continuation of application No. PCT/US2016/068300, filed on Dec. 22, 2016.

(60) Provisional application No. 62/413,345, filed on Oct. 26, 2016, provisional application No. 62/338,474, filed on May 18, 2016, provisional application No. 62/271,160, filed on Dec. 22, 2015, provisional application No. 62/271,146, filed on Dec. 22, 2015, provisional application No. 62/271,179, filed on Dec. 22, 2015, provisional application No. 62/271,137, filed on Dec. 22, 2015, provisional application No. 62/271,200, filed on Dec. 22, 2015.

(51) Int. Cl.
A61K 9/51 (2006.01)
C07D 295/185 (2006.01)
A61K 38/18 (2006.01)

(52) U.S. Cl.
CPC ........ A61K 9/5123 (2013.01); A61K 38/1808 (2013.01); A61K 38/1816 (2013.01); C07D 295/185 (2013.01)

(58) Field of Classification Search
None
See application file for complete search history.

(56) References Cited

U.S. PATENT DOCUMENTS

| 3,872,171 | A  | 3/1975  | Cronin et al.     |
|-----------|----|---------|-------------------|
| 4,957,735 | A  | 9/1990  | Huang             |
| 5,807,861 | A  | 9/1998  | Klein et al.      |
| 6,303,378 | B1 | 10/2001 | Bridenbaugh et al.|
| 6,395,253 | B2 | 5/2002  | Levy et al.       |
| 6,652,886 | B2 | 11/2003 | Ahn et al.        |
| 6,696,038 | B1 | 2/2004  | Mahato et al.     |
| 7,268,120 | B1 | 9/2007  | Horton et al.     |
| 7,371,404 | B2 | 5/2008  | Panzner et al.    |
| 7,943,168 | B2 | 5/2011  | Schlesinger et al.|
| 8,058,069 | B2 | 11/2011 | Yaworski et al.   |
| 8,158,601 | B2 | 4/2012  | Chen et al.       |
| 8,420,123 | B2 | 4/2013  | Troiano et al.    |
| 8,440,614 | B2 | 5/2013  | Castor            |
| 8,449,916 | B1 | 5/2013  | Bellaire et al.   |
| 8,450,298 | B2 | 5/2013  | Mahon et al.      |
| 8,460,696 | B2 | 6/2013  | Slobodkin et al.  |
| 8,460,709 | B2 | 6/2013  | Ausborn et al.    |
| 8,563,041 | B2 | 10/2013 | Grayson et al.    |
| 8,568,784 | B2 | 10/2013 | Lillard et al.    |
| 8,569,256 | B2 | 10/2013 | Heyes et al.      |
| 8,580,297 | B2 | 11/2013 | Essler et al.     |
| 8,603,499 | B2 | 12/2013 | Zale et al.       |
| 8,603,500 | B2 | 12/2013 | Zale et al.       |
| 8,603,501 | B2 | 12/2013 | Zale et al.       |
| 8,603,534 | B2 | 12/2013 | Zale et al.       |
| 8,603,535 | B2 | 12/2013 | Troiano et al.    |
| 8,609,142 | B2 | 12/2013 | Troiano et al.    |
| 8,613,951 | B2 | 12/2013 | Zale et al.       |
| 8,613,954 | B2 | 12/2013 | Zale et al.       |
| 8,617,608 | B2 | 12/2013 | Zale et al.       |
| 8,618,240 | B2 | 12/2013 | Podobinski et al. |
| 8,637,083 | B2 | 1/2014  | Troiano et al.    |
| 8,642,076 | B2 | 2/2014  | Manoharan et al.  |
| 8,652,487 | B2 | 2/2014  | Maldonado         |
| 8,652,528 | B2 | 2/2014  | Troiano et al.    |
| 8,663,599 | B1 | 3/2014  | Sung et al.       |
| 8,663,700 | B2 | 3/2014  | Troiano et al.    |
| 8,668,926 | B1 | 3/2014  | Mousa et al.      |

(Continued)

FOREIGN PATENT DOCUMENTS

| AU | 652831 B2    | 9/1994 |
|----|--------------|--------|
| CN | 102068701 A  | 5/2011 |

(Continued)

OTHER PUBLICATIONS

Akinc et al., Targeted Delivery of RNAi Therapeutics With Endogenous and Exogenous Ligand-Based Mechanisms, Mol Ther. 2010 17:1357-1364.

(Continued)

Primary Examiner — Mark L Shibuya
Assistant Examiner — Laura M Daniel
(74) Attorney, Agent, or Firm — Cooley LLP; Heidi A. Erlacher; Christine C. Pemberton

(57) ABSTRACT

The disclosure features amino lipids and compositions involving the same. Nanoparticle compositions include an amino lipid as well as additional lipids such as phospholipids, structural lipids, PEG lipids, or a combination thereof. Nanoparticle compositions further including therapeutic and/or prophylactic agents such as RNA are useful in the delivery of therapeutic and/or prophylactic agents to mammalian cells or organs to, for example, regulate polypeptide, protein, or gene expression.

30 Claims, 7 Drawing Sheets
Specification includes a Sequence Listing.

(56) References Cited

U.S. PATENT DOCUMENTS

| | | |
|---|---|---|
| 8,685,368 B2 | 4/2014 | Reineke |
| 8,691,750 B2 | 4/2014 | Constein et al. |
| 8,697,098 B2 | 4/2014 | Perumal et al. |
| 8,703,204 B2 | 4/2014 | Bloom et al. |
| 8,709,483 B2 | 4/2014 | Farokhzad et al. |
| 8,715,736 B2 | 5/2014 | Sachdeva et al. |
| 8,715,741 B2 | 5/2014 | Maitra et al. |
| 8,728,527 B2 | 5/2014 | Singh |
| 8,734,832 B2 | 5/2014 | O'Hagan et al. |
| 8,734,846 B2 | 5/2014 | Ali et al. |
| 8,734,853 B2 | 5/2014 | Sood et al. |
| 8,802,644 B2 | 8/2014 | Chen et al. |
| 9,006,487 B2 | 4/2015 | Anderson et al. |
| 9,029,590 B2 | 5/2015 | Colletti et al. |
| 9,394,234 B2 | 7/2016 | Chen et al. |
| 9,867,888 B2 | 1/2018 | Benenato |
| 9,868,691 B2 | 1/2018 | Benenato |
| 9,868,692 B2 | 1/2018 | Benenato |
| 9,868,693 B2 | 1/2018 | Benenato |
| 2003/0073619 A1 | 4/2003 | Mahato et al. |
| 2003/0092653 A1 | 5/2003 | Kisich et al. |
| 2004/0142474 A1 | 7/2004 | Mahato et al. |
| 2006/0008910 A1 | 1/2006 | Maclachlan et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2007/0252295 A1 | 11/2007 | Panzner et al. |
| 2009/0042825 A1 | 2/2009 | Matar et al. |
| 2009/0042829 A1 | 2/2009 | Matar et al. |
| 2011/0009641 A1 | 1/2011 | Anderson et al. |
| 2011/0200582 A1 | 8/2011 | Baryza et al. |
| 2011/0244026 A1 | 10/2011 | Guild et al. |
| 2012/0136073 A1 | 5/2012 | Yang et al. |
| 2012/0177724 A1 | 7/2012 | Irvine et al. |
| 2012/0178702 A1 | 7/2012 | Huang |
| 2012/0295832 A1 | 11/2012 | Constien et al. |
| 2013/0017223 A1 | 1/2013 | Hope et al. |
| 2013/0064894 A1 | 3/2013 | Martin et al. |
| 2013/0065942 A1 | 3/2013 | Matar et al. |
| 2013/0090372 A1 | 4/2013 | Budzik et al. |
| 2013/0108685 A1 | 5/2013 | Kuboyama et al. |
| 2013/0115273 A1 | 5/2013 | Yang et al. |
| 2013/0115274 A1 | 5/2013 | Knopov et al. |
| 2013/0116307 A1 | 5/2013 | Heyes et al. |
| 2013/0122104 A1 | 5/2013 | Yaworski et al. |
| 2013/0123338 A1 | 5/2013 | Heyes et al. |
| 2013/0129785 A1 | 5/2013 | Manoharan et al. |
| 2013/0130348 A1 | 5/2013 | Gu et al. |
| 2013/0142868 A1 | 6/2013 | Hoekman et al. |
| 2013/0142876 A1 | 6/2013 | Howard et al. |
| 2013/0150625 A1 | 6/2013 | Budzik et al. |
| 2013/0156845 A1 | 6/2013 | Manoharan et al. |
| 2013/0156849 A1 | 6/2013 | de Fougerolles et al. |
| 2013/0164400 A1 | 6/2013 | Knopov et al. |
| 2013/0171241 A1 | 7/2013 | Geall |
| 2013/0172406 A1 | 7/2013 | Zale et al. |
| 2013/0178541 A1 | 7/2013 | Stanton et al. |
| 2013/0183244 A1 | 7/2013 | Hanes et al. |
| 2013/0183355 A1 | 7/2013 | Jain et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0189351 A1 | 7/2013 | Geall |
| 2013/0195759 A1 | 8/2013 | Mirkin et al. |
| 2013/0195765 A1 | 8/2013 | Gho et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236500 A1 | 9/2013 | Zale et al. |
| 2013/0236533 A1 | 9/2013 | Von Andrian et al. |
| 2013/0236550 A1 | 9/2013 | Ausborn et al. |
| 2013/0243827 A1 | 9/2013 | Troiano et al. |
| 2013/0243848 A1 | 9/2013 | Lobovkina et al. |
| 2013/0243867 A1 | 9/2013 | Mohapatra et al. |
| 2013/0251766 A1 | 9/2013 | Zale et al. |
| 2013/0251816 A1 | 9/2013 | Zale et al. |
| 2013/0251817 A1 | 9/2013 | Zale et al. |
| 2013/0266617 A1 | 10/2013 | Mirosevich et al. |
| 2013/0273117 A1 | 10/2013 | Podobinski et al. |
| 2013/0274504 A1 | 10/2013 | Colletti et al. |
| 2013/0274523 A1 | 10/2013 | Bawiec, III et al. |
| 2013/0280334 A1 | 10/2013 | Karp et al. |
| 2013/0280339 A1 | 10/2013 | Zale et al. |
| 2013/0295183 A1 | 11/2013 | Troiano et al. |
| 2013/0295191 A1 | 11/2013 | Troiano et al. |
| 2013/0302432 A1 | 11/2013 | Zale et al. |
| 2013/0302433 A1 | 11/2013 | Troiano et al. |
| 2013/0315831 A1 | 11/2013 | Shi et al. |
| 2013/0330401 A1 | 12/2013 | Payne et al. |
| 2013/0338210 A1 | 12/2013 | Manoharan et al. |
| 2013/0344158 A1 | 12/2013 | Zale et al. |
| 2014/0017327 A1 | 1/2014 | Cheng et al. |
| 2014/0017329 A1 | 1/2014 | Mousa |
| 2014/0037573 A1 | 2/2014 | Eliasof et al. |
| 2014/0037660 A1 | 2/2014 | Folin-Mleczek et al. |
| 2014/0037714 A1 | 2/2014 | Quay et al. |
| 2014/0039032 A1 | 2/2014 | Kumboyama et al. |
| 2014/0044772 A1 | 2/2014 | Maclachlan et al. |
| 2014/0044791 A1 | 2/2014 | Basilion et al. |
| 2014/0045913 A1 | 2/2014 | Kumboyama et al. |
| 2014/0050775 A1 | 2/2014 | Slobodkin et al. |
| 2014/0057109 A1 | 2/2014 | Mechen et al. |
| 2014/0065172 A1 | 3/2014 | Echeverri et al. |
| 2014/0065204 A1 | 3/2014 | Hayes et al. |
| 2014/0065228 A1 | 3/2014 | Yarowoski et al. |
| 2014/0079774 A1 | 3/2014 | Brinker et al. |
| 2014/0093575 A1 | 4/2014 | Hammond et al. |
| 2014/0093579 A1 | 4/2014 | Zale et al. |
| 2014/0113137 A1 | 4/2014 | Podobinski et al. |
| 2014/0121263 A1 | 5/2014 | Fitzgerald et al. |
| 2014/0121393 A1 | 5/2014 | Manoharan et al. |
| 2014/0134260 A1 | 5/2014 | Heyes et al. |
| 2014/0141070 A1 | 5/2014 | Geall et al. |
| 2014/0141089 A1 | 5/2014 | Liang |
| 2014/0141483 A1 | 5/2014 | Bossard et al. |
| 2014/0142165 A1 | 5/2014 | Grayson et al. |
| 2014/0142254 A1 | 5/2014 | Fonnum et al. |
| 2014/0308304 A1 | 10/2014 | Manoharan et al. |
| 2015/0174260 A1 | 6/2015 | Yang et al. |
| 2015/0174261 A1 | 6/2015 | Kuboyama et al. |
| 2015/0284317 A1 | 10/2015 | Colletti et al. |
| 2015/0343062 A1 | 12/2015 | Kuboyama et al. |
| 2015/0376115 A1 | 12/2015 | Ansell et al. |
| 2016/0002178 A1 | 1/2016 | Fenton et al. |
| 2016/0009657 A1 | 1/2016 | Anderson et al. |
| 2016/0151284 A1 | 6/2016 | Heyes et al. |
| 2018/0201572 A1 | 7/2018 | Benenato |

FOREIGN PATENT DOCUMENTS

| | | |
|---|---|---|
| CN | 102204920 A | 10/2011 |
| CN | 102813929 A | 12/2012 |
| CN | 104644555 A | 5/2015 |
| EP | 0737750 | 10/1996 |
| EP | 2073848 B1 | 8/2013 |
| EP | 1404860 B1 | 11/2013 |
| WO | WO 1993/014778 | 8/1993 |
| WO | WO 1999/014346 A2 | 3/1999 |
| WO | WO 1999/052503 | 10/1999 |
| WO | WO 2003/086280 | 10/2003 |
| WO | WO 2005/034979 A2 | 4/2005 |
| WO | WO 2006/063249 A2 | 6/2006 |
| WO | WO 2008/042973 A2 | 4/2008 |
| WO | WO 2009/024599 | 2/2009 |
| WO | WO 2009/086558 A1 | 7/2009 |
| WO | WO 2009/127060 A1 | 10/2009 |
| WO | WO 2009/129385 A1 | 10/2009 |
| WO | WO 2009/129395 A1 | 10/2009 |
| WO | WO 2010/030739 A1 | 3/2010 |
| WO | WO 2010/042877 A1 | 4/2010 |
| WO | WO 2010/053572 A2 | 5/2010 |
| WO | WO 2010/054406 A1 | 5/2010 |
| WO | WO 2010/088537 A2 | 8/2010 |

(56) References Cited

FOREIGN PATENT DOCUMENTS

| | | |
|---|---|---|
| WO | WO 2010/129709 A1 | 11/2010 |
| WO | WO 2011/068810 A1 | 6/2011 |
| WO | WO 2011/127255 A1 | 10/2011 |
| WO | WO 2011/136368 A1 | 11/2011 |
| WO | WO 2012/000104 A1 | 1/2012 |
| WO | WO 2012/006376 A2 | 1/2012 |
| WO | WO 2012/006378 A1 | 1/2012 |
| WO | WO 2012/030901 A1 | 3/2012 |
| WO | WO 2012/031043 A1 | 3/2012 |
| WO | WO 2012/031046 A2 | 3/2012 |
| WO | WO 2012/054365 A2 | 4/2012 |
| WO | WO 2012/129483 A1 | 9/2012 |
| WO | WO 2012/149252 A2 | 11/2012 |
| WO | WO 2012/149255 A2 | 11/2012 |
| WO | WO 2012/149265 A2 | 11/2012 |
| WO | WO 2012/149282 A2 | 11/2012 |
| WO | WO 2012/149301 A2 | 11/2012 |
| WO | WO 2012/149376 A2 | 11/2012 |
| WO | WO 2012/149393 A2 | 11/2012 |
| WO | WO 2012/153338 A2 | 11/2012 |
| WO | WO 2012/170889 A1 | 12/2012 |
| WO | WO 2012/170930 A1 | 12/2012 |
| WO | WO 2013/006825 A1 | 1/2013 |
| WO | WO 2013/006834 A1 | 1/2013 |
| WO | WO 2013/006837 A1 | 1/2013 |
| WO | WO 2013/006838 A1 | 1/2013 |
| WO | WO 2013/006842 A2 | 1/2013 |
| WO | WO 2013/016058 A1 | 1/2013 |
| WO | WO 2013/033438 A2 | 3/2013 |
| WO | WO 2013/033563 A1 | 3/2013 |
| WO | WO 2013/049328 A1 | 4/2013 |
| WO | WO 2013/052167 A2 | 4/2013 |
| WO | WO 2013/056132 A2 | 4/2013 |
| WO | WO 2013/057715 A1 | 4/2013 |
| WO | WO 2013/059496 A1 | 4/2013 |
| WO | WO 2013/059922 A1 | 5/2013 |
| WO | WO 2013/064911 A2 | 5/2013 |
| WO | WO 2013/066903 A1 | 5/2013 |
| WO | WO 2013/067537 A1 | 5/2013 |
| WO | WO 2013/070872 A2 | 5/2013 |
| WO | WO 2013/072929 A2 | 5/2013 |
| WO | WO 2013/086322 A1 | 6/2013 |
| WO | WO 2013/086354 A1 | 6/2013 |
| WO | WO 2013/086373 A1 | 6/2013 |
| WO | WO 2013/086526 A1 | 6/2013 |
| WO | WO 2013/087083 A1 | 6/2013 |
| WO | WO 2013/087791 A1 | 6/2013 |
| WO | WO 2013/093648 A2 | 6/2013 |
| WO | WO 2013/135359 A1 | 9/2013 |
| WO | WO 2013/143555 A1 | 10/2013 |
| WO | WO 2013/143683 A1 | 10/2013 |
| WO | WO 2013/148186 A1 | 10/2013 |
| WO | WO 2013/148541 A1 | 10/2013 |
| WO | WO 2013/149141 A1 | 10/2013 |
| WO | WO 2013/151650 A1 | 10/2013 |
| WO | WO 2013/155487 A1 | 10/2013 |
| WO | WO 2013/155493 A9 | 10/2013 |
| WO | WO 2013/158127 A1 | 10/2013 |
| WO | WO 2013/158579 A1 | 10/2013 |
| WO | WO 2013/166498 A1 | 11/2013 |
| WO | WO 2013/173693 A1 | 11/2013 |
| WO | WO 2013/177421 A2 | 11/2013 |
| WO | WO 2013/185069 A1 | 12/2013 |
| WO | WO 2014/007398 A1 | 1/2014 |
| WO | WO 2014/008334 A1 | 1/2014 |
| WO | WO 2014/026284 A1 | 2/2014 |
| WO | WO 2014/028487 A1 | 2/2014 |
| WO | WO 2014/028763 A1 | 2/2014 |
| WO | WO 2014/047649 A1 | 3/2014 |
| WO | WO 2014/052634 A1 | 4/2014 |
| WO | WO 2014/054026 A1 | 4/2014 |
| WO | WO 2014/071072 A2 | 5/2014 |
| WO | WO 2014/072997 A1 | 5/2014 |
| WO | WO 2014/089486 A1 | 6/2014 |
| WO | WO 2014/144196 A1 | 9/2014 |
| WO | WO 2014/160243 A1 | 10/2014 |
| WO | WO 2014/172045 A1 | 10/2014 |
| WO | WO 2014/182661 A2 | 11/2014 |
| WO | WO 2014/210356 A1 | 12/2014 |
| WO | WO 2015/011633 A1 | 1/2015 |
| WO | WO 2015/130584 A2 | 9/2015 |
| WO | WO 2015/154002 A1 | 10/2015 |
| WO | WO 2015/199952 A1 | 12/2015 |
| WO | WO 2016/004202 A1 | 1/2016 |
| WO | WO 2016/004318 A1 | 1/2016 |
| WO | WO 2016/118697 A1 | 7/2016 |
| WO | WO 2016/118724 A1 | 7/2016 |
| WO | WO 2016/176330 A1 | 11/2016 |
| WO | WO 2017/015630 A2 | 1/2017 |
| WO | WO 2017/031232 A1 | 2/2017 |
| WO | WO 2017/049245 A2 | 3/2017 |
| WO | WO 2017/099823 A1 | 6/2017 |
| WO | WO 2017/127750 A1 | 7/2017 |
| WO | WO 2017/180917 A2 | 10/2017 |
| WO | WO 2017/192470 A1 | 11/2017 |
| WO | WO 2017/201317 A1 | 11/2017 |
| WO | WO 2017/201325 A1 | 11/2017 |
| WO | WO 2017/201333 A1 | 11/2017 |
| WO | WO 2017/201340 A2 | 11/2017 |
| WO | WO 2017/201347 A1 | 11/2017 |
| WO | WO 2017/201350 A1 | 11/2017 |
| WO | WO 2017/218704 A1 | 12/2017 |
| WO | WO 2018/089540 A1 | 5/2018 |

OTHER PUBLICATIONS

Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.

Andries, O., et al., Comparison of the gene transfer efficiency of mRNA/GL67 and pDNA/GL67 complexes in respiratory cells. Mol Pharmaceutics. 2012; 9: 2136-2145.

Bag, J., Recovery of normal protein synthesis in heat-shocked chicken myotubes by liposome-mediated transfer of mRNAs. Can. J. Biochem. Cell Biol. 1985; 63(3): 231-235.

Belliveau, N.M., et al., Microfluidic synthesis of highly potent limit-size lipid nanoparticles for in vivo delivery of siRNA. Mol Ther Nucleic Acids. Aug. 2012; 1(8): e37.

Bettinger, T. et al., Peptide-mediated RNA delivery: a novel approach for enhanced transfection of primary and post-mitotic cells. Nucleic Acids Res. Sep. 15, 2001;29(18):3882-91.

Bolhassani A., et al., Improvement of Different Vaccine Delivery Systems for Cancer Therapy, Molecular Cancer, Biomed Central, London, GB, 2011, vol. 10, No. 3, pp. 1-20.

Bonehill, A., et al., Single-step antigen loading and activation of dendritic cells by mRNA electroporation for the purpose of therapeutic vaccination in melanoma patients. Clin Cancer Res. May 2009; 15(10): 3366-3375.

Bouxsein, N.F., et al., Structure and gene silencing activities of monovalent and pentavalent cationic lipid vectors complexed with siRNA. Biochem. 2007; 46(16): 4785-4792.

Chen, D., et al., Rapid discovery of potent siRNA-containing lipid nanoparticles enabled by controlled microfluidic formulation. J Am Chem Soc. 2012; 134: 6948-6951.

Cun, D., et al., Preparation and characterization of poly(DL-lactide-co-glycolide) nanoparticles for siRNA delivery. International Journal of Pharmaceutics 390 (2010) 70-75.

Dahlman, J. E. et al., In vivo endothelial siRNA delivery using polymeric nanoparticles with low molecular weight, Nature Nanotechnology, 2014, pp. 1-8.

Delehanty, J. B., Peptides for Specific Intracellular Delivery and Targeting of Nanoparticles: Implications for Developing Nanoparticle-Mediated Drug Delivery, Future Science, Therapeutic Delivery, 2010, vol. 1, No. 3, pp. 411-433.

El Ouahabi, A., et al., Double long-chain amidine liposome-mediated self replicating RNA transfection. FEBS Letters. Feb. 1996; 380(1-2): 108-112.

(56) References Cited

OTHER PUBLICATIONS

Felgner, PL Cationic lipid/polynucleotide condensates for in vitro and in vivo polynucleotide delivery—the cytofectins. J. of Liposome Research. 1993; 3(1): 3-16.
Felgner, PL Particulate systems and polymers for in vitro and in vivo delivery of polynucleotides. Adv. Drug Delivery Rev. 1990; 5(3): 163-187.
Felgner, PL, et al., Lipofection: a highly efficient, lipid-mediated DNA-transfection procedure. Proc Natl Acad Sci U SA. Nov. 1987;84(21):7413-7.
Gao, X. et al., Nonviral gene delivery: what we know and what is next. AAPS J. Mar. 23, 2007;9(1):E92-104.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
He, K. et al., Synthesis and Separation of Diastereomers of Ribonucleoside 5'-(alpha-P-Borano)triphosphates. J Org Chem. Aug. 21, 1998;63(17):5769-5773.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Hoerr, I. et al., In vivo application of RNA leads to induction of specific cytotoxic T lymphocytes and antibodies. EurJ Immunol. Jan. 2000;30(1):1-7.
Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kang, H., Inhibition of MDR1 Gene Expression by Chimeric HNA Antisense Oligonucleotides, Nucleic Acids Research, 2004, vol. 32, No. 14, pp. 4411-4419.
Kariko, K. et al., Phosphate-enhanced transfection of cationic lipid-complexed mRNA and plasmid DNA. Biochim Biophys Acta. Mar. 2, 1998; 1369(2):320-34.
Kariko, K., et al., In vivo protein expression from mRNA delivered into adult rat brain. J. of Neuroscience Methods. Jan. 2001; 105(1): 77-86.
Kariko, K., et al., Incorporation of pseudouridine into mRNA yields superior nonimmunogenic vector with increased translational capacity and biological stability, Molecular Therapy, Nature Publishing Group, GB, vol. 16, No. 11, Nov. 1, 2008 (Nov. 1, 2008), pp. 1833-1840.
Keown, WA, et al., [41] Methods for Introducing DNA into Mammalian Cells. Methods in Enzymology, 1990, 185:527-37.
Kirpotin, D.B., et al., Antibody targeting of long-circulating lipidic nanoparticles does not increase tumor localization but does increase internalization in animal models. Cancer Res. 2006; 66: 6732-6740.
Kozielski, K. L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8,'No. 4',pp. 3232-3241.
Lai, S.K., et al., Mucus-penetrating nanoparticles for drug and gene delivery to mucosal tissues. Adv Drug Deliv Rev. Feb. 27, 2009; 61(2): 158-171.
Lai, S.K., et al., Rapid transport of large polymeric nanoparticles in fresh undiluted human mucus. PNAS. Jan. 30, 2007; 104(5): 1482-1487.
Lee, J. B. et al., Lipid Nanoparticle siRNA Systems for Silencing the Androgen Receptor in Human Prostate Cancer in Vivo, International Journal of Cancer, 2012, vol. 131, pp. 781-790.
Lehto, T., et al., Cell-penetrating peptides for the delivery of nucleic acids. Expert Opin. Drug Deliv. Jul. 2012; 9(7): 823-836.
Lewis, David, Dynamic Polyconjugates (DPC) Technology: An elegant solution to the siRNA delivery problem. Arrowhead Research Corp (NASDAQ: ARWR). Nov. 2011.
Li, L. et al., Overcoming obstacles to develop effective and safe siRNA therapeutics. Expert Opin Biol Ther. May 2009; 9(5): 609-19.

Li, L. et al., Preparation and gene delivery of alkaline amino acids-based cationic liposomes. Arch Pharm Res. Jul. 2008;31(7):924-31. Epub Aug. 14, 2008.
Lian T. et al., Trends and developments in liposome drug delivery systems. J Pharm Sci. Jun. 2001; 90(6):667-80.
Lopez-Berestein, G. et al., Treatment of systemic fungal infections with liposomal amphotericin B. Arch Intern Med. Nov. 1989; 149(11):2533-6.
Love et al., Lipid-like materials for low-dose, in vivo gene silencing, PNAS vol. 107 No. 5, pp. 1864-1869, Feb. 2, 2010.
Kanapathipillai, M. et al., Nanoparticle targeting of anti-cancer drugs that alter intracellular signaling or influence the tumor microenvironment, Adv. Drug Deliv. Rev. (2014), pp. 1-12.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Magee, W .E. et al., Marked stimulation of lymphocyte-mediated attack on tumor cells by target-directed liposomes containing immune RNA, Cancer Res., 1978, 38(4):1173-6.
Malone, R.W. et al., Cationic liposome-mediated RNA transfection. Proc Natl Acad Sci U S A. Aug. 1989; 86 (16):6077-81.
Martinon, F. et al., Induction of virus-specific cytotoxic T lymphocytes in vivo by liposome-entrapped mRNA. Eur J Immunol. Jul. 1993; 23(7):1719-22.
Maurer, N., et al., Spontaneous entrapment of polynucleotides upon electrostatic interaction with ethanol-destabilized cationic liposomes. Biophys J. May 2001; 80(5): 2310-2326.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review .
Mishra, R.K. et al., Improved leishmanicidal effect of phosphorothioate antisense oligonucleotides by LDL-mediated delivery. Biochim Biophys Acta. Nov. 7, 1995;1264(2):229-37.
Nair, S. et al., Soluble proteins delivered to dendritic cells via pH-sensitive liposomes induce primary cytotoxic T lymphocyte responses in vitro. J Exp Med. Feb. 1, 1992; 175(2):609-12.
Okumura, K., et al., Bax mRNA therapy using cationic liposomes for human malignant melanoma. J Gene Med. 2008; 10: 910-917.
Oster, C.G., et al. Comparative study of DNA encapsulation into PLGA microparticles using modified double emulsion methods and spray drying techniques. Journal of Microencapsulation, May 2005; 22(3): 235-244.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.
Pollard, C., et al., Type I IFN counteracts the induction of antigen-specific immune responses by lipid-based delivery of mRNA vaccines. Mol Ther. Jan. 2013; 21(1): 251-259.
Pulford, B., et al., Liposome-siRNA-peptide complexes cross the blood-brain barrier and significantly decrease PrPC on neuronal cells and PrPRES in infected cell cultures. PLoS ONE. 2010; 5(6): e11085.
Saito, R., et al., Distribution of liposomes into brain and rat brain tumor models by convection-enhanced delivery monitored with magnetic resonance imaging. Cancer Res. Apr. 2004; 64: 2572-2579.
Sakuma, S. et al., Mucoadhesion of polystyrene nanoparticles having surface hydrophilic polymeric chains in the gastrointestinal tract. Int J Pharm. Jan. 25, 1999; 177(2):161-72.
Schott, J.W., et al., Viral and non-viral approaches for transient delivery of mRNA and proteins. Current Gene Ther. 2011; 11 (5): 382-398.
Semple, S.C., et al., Efficient encapsulation of antisense oligonucleotides in lipid vesicles using ionizable aminolipids: formation of novel small multilamellar vesicle structures. Biochim Biophys Acta. Feb. 9, 2001; 1510(1-2): 152-166.
Shea, R.G. et al., Synthesis, hybridization properties and antiviral activity of lipid-oligodeoxynucleotide conjugates. Nucleic Acids Res.Jul. 11, 1990; 18(13):3777-83.

(56) References Cited

OTHER PUBLICATIONS

Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.

Svinarchuk, F.P. et al., Inhibition of HIV proliferation in MT-4 cells by antisense oligonucleotide conjugated to lipophilic groups. Biochimie. 1993; 75(1-2):49-54.

Tavernier, G., et al., mRNA as gene therapeutic: How to control protein expression. J. of Controlled Release. Mar. 2011; 150(3): 238-247.

Thess et al., Sequence-engineered mRNA Without Chemical Nucleoside Modifications Enables an Effective Protein Therapy in Large Animals. Mol Ther. Sep. 2015; 23(9):1456-64. doi: 10.1038/mt.2015.103. Epub Jun. 8, 2015.

Torchilin, V., Multifunctional and Stimuli-Sensitive Pharmaceutical Nanocarriers, Eur J. Pharm Biopharm, 2009, vol. 71, No. 3, pp. 431-444.

Tracy, M., "Progress in the Development of LNP Delivery for siRNA Advancing LNPs to the Clinic," International Liposome Research Days Meeting, Vancouver, Canada. Aug. 2010, pp. 1-52.

Treat, J. et al., in Liposomes in the Therapy of Infectious Disease and Cancer, Lopez-Berestein and Fidler (eds.), Liss, New York, 1989. 353-65.

Uzgun, S., et al., PEGylation improves nanoparticle formation and transfection efficiency of messenger RNA. Pharm Res. Sep. 2011; 28(9); 2223-2232.

Van Tendeloo, V.F. et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001; 98(1):49-56.

Wan et al., Lipid nanoparticle delivery systems for siRNA-based therapeutics. Drug Deliv Transl Res. Feb. 2014;4(1):74-83. doi:10.1007/s13346-013-0161-z.

Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Yamamoto et al., Current prospects for mRNA gene delivery, European Journal of Pharmaceutics and Biopharmaceutics 71 (2009) 484-489.

Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.

Zimmermann, E. et al., Electrolyte- and pH-stabilities of aqueous solid lipid nanoparticle (SLN™) dispersions in artificial gastrointestinal media. Eur J Pharm Biopharm. Sep. 2001;52(2):203-10.

Zohra, F.T., et al., Drastic effect of nanoapatite particles on liposome-mediated mRNA delivery to mammalian cells. Analytical Biochem. Oct. 2005; 345(1): 164-166.

Zohra, F.T., et al., Effective delivery with enhanced translational activity synergistically accelerates mRNA-based transfection. Biochem Biophys Res Comm. Jun. 2007; 358(1): 373-378.

Müller et al, "Solid lipid nanoparticles (SLN) for controlled drug delivery—a review of the state of the art," European Journal of Pharmaceutics and Biopharmaceutics, 50 (2000) 161-177.

Leung et al., "Lipid Nanoparticles for Short Interfering RNA Delivery", Advances in Genetics, 2014, vol. 88, Chapter 4, pp. 71-110.

Tam et al., "Advances in Lipid Nanoparticles for siRNA Delivery," Pharmaceutics 2013, 5, 498-507; doi:10.3390/pharmaceutics5030498.

Shah et al., "Lipid Nanoparticles: Production, Characterization and Stability," Springer International Publishing, 2014, 23 pages.

Abdelwahed et al., "Freeze-drying of nanoparticles: Formulation, process and storage considerations," Advanced Drug Delivery Reviews 58 (2006) 1688-1713.

Ashizawa et al., "Liposomal delivery of nucleic acid-based anticancer therapeutics: BP-100-1.01," Expert Opin. Drug Deliv., (2014) 12(7):1107-1120.

Jayaraman et al., "Maximizing the Potency of siRNA Lipid Nanoparticles for Hepatic Gene Silencing In Vivo," Angew. Chem. Int. Ed. 2012, 51, 8529-8533.

Morissette et al., "High-throughput crystallization: polymorphs, salts, co-crystals and solvates of pharmaceutical solids," Advanced Drug Delivery Reviews 56 (2004) 275-300.

FIGURE 1
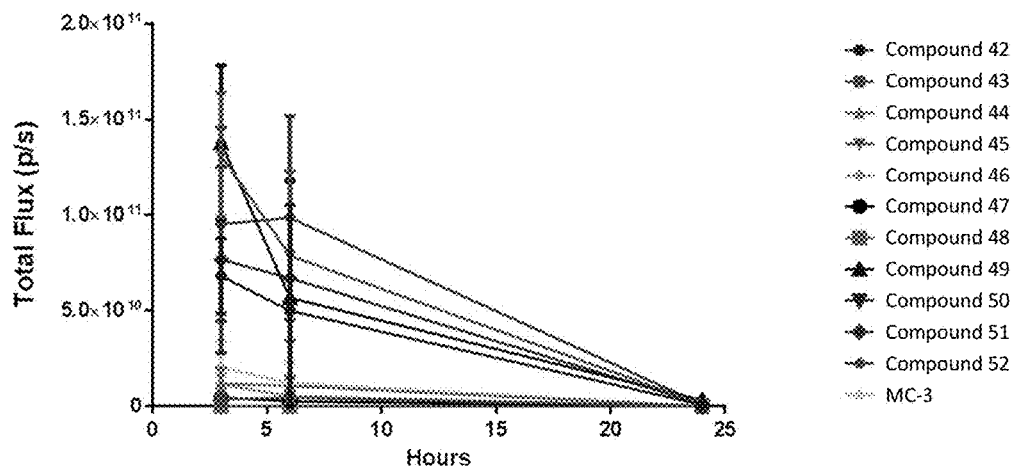
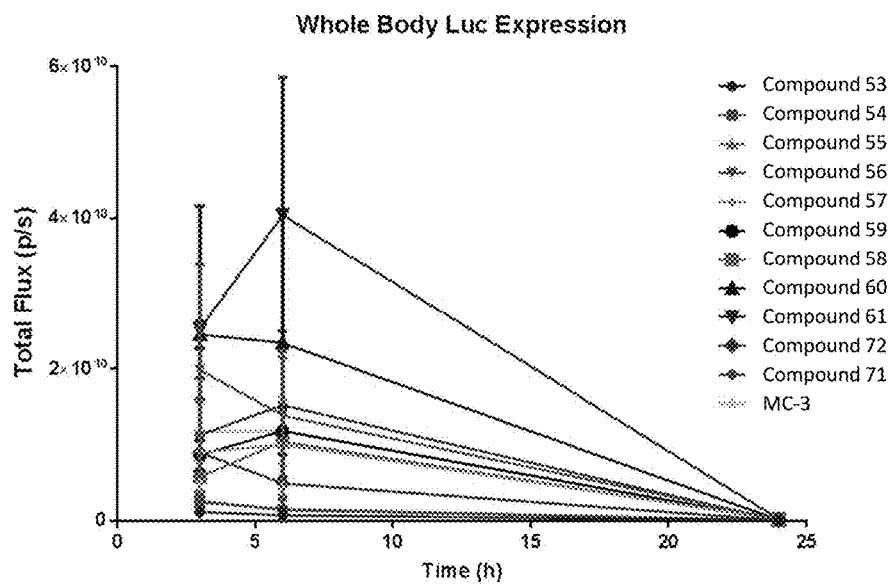
FIGURE 2
FIGURE 3
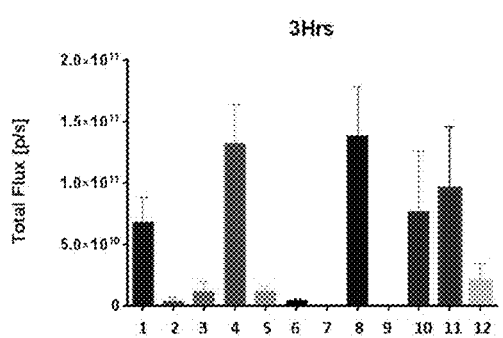
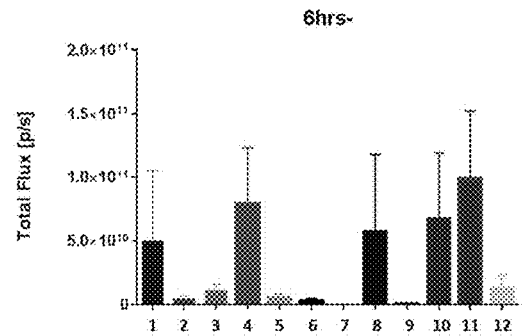

FIGURE 14
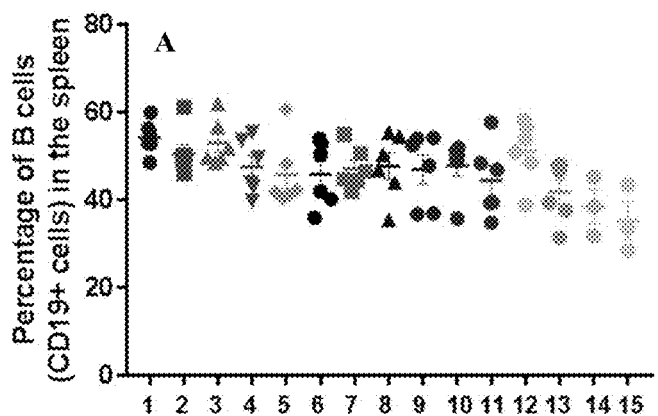
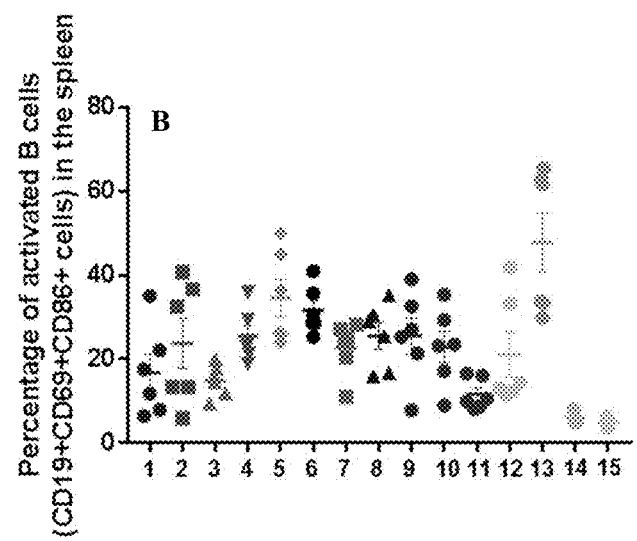
FIGRURE 15
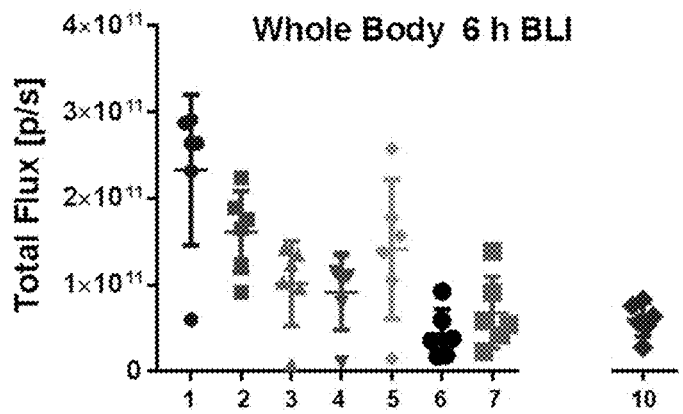

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 1
caaaggctct tttcagagcc acca                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 2
caaaggcucu uuucagagcc acca                                          24
```

COMPOUNDS AND COMPOSITIONS FOR INTRACELLULAR DELIVERY OF AGENTS

RELATED APPLICATIONS

This application is a continuation application of International Application PCT/US2016/068300, having an international filing date of Dec. 22, 2016, which claims priority to, and the benefit of, U.S. Provisional Application Nos. 62/271,160, filed Dec. 22, 2015, 62/271,179, filed Dec. 22, 2015, 62/271,137, filed Dec. 22, 2015, 62/271,200, filed Dec. 22, 2015, 62/271,146, filed Dec. 22, 2015; 62/338,474, filed May 18, 2016; 62/413,345, filed Oct. 26, 2016; the entire contents of each of which are incorporated herein by reference in their entireties.

INCORPORATION-BY-REFERENCE OF SEQUENCE LISTING

The contents of the text file named "MRNA018C01SL.txt", which was created on Jul. 27, 2018, and is 1011 bytes in size, are incorporated herein by reference in its entirety.

TECHNICAL FIELD

The present disclosure provides compounds, compositions comprising such compounds, and methods involving lipid nanoparticle compositions to deliver one or more therapeutic and/or prophylactic agents to and/or produce polypeptides in mammalian cells or organs. In addition to an amino lipid, lipid nanoparticle compositions of the disclosure may include one or more cationic and/or ionizable amino lipids, phospholipids including polyunsaturated lipids, PEG lipids, structural lipids, and/or therapeutic and/or prophylactic agents in specific fractions.

BACKGROUND

The effective targeted delivery of biologically active substances such as small molecule drugs, proteins, and nucleic acids represents a continuing medical challenge. In particular, the delivery of nucleic acids to cells is made difficult by the relative instability and low cell permeability of such species. Thus, there exists a need to develop methods and compositions to facilitate the delivery of therapeutic and/or prophylactic agents such as nucleic acids to cells.

Lipid-containing nanoparticle compositions, liposomes, and lipoplexes have proven effective as transport vehicles into cells and/or intracellular compartments for biologically active substances such as small molecule drugs, proteins, and nucleic acids. Such compositions generally include one or more "cationic" and/or amino (ionizable) lipids, phospholipids including polyunsaturated lipids, structural lipids (e.g., sterols), and/or lipids containing polyethylene glycol (PEG lipids). Cationic and/or ionizable lipids include, for example, amine-containing lipids that can be readily protonated. Though a variety of such lipid-containing nanoparticle compositions have been demonstrated, improvements in safety, efficacy, and specificity are still lacking.

SUMMARY

The present disclosure provides compounds and compositions and methods involving the same.

In one aspect, the disclosure provides a compound having the formula (I)

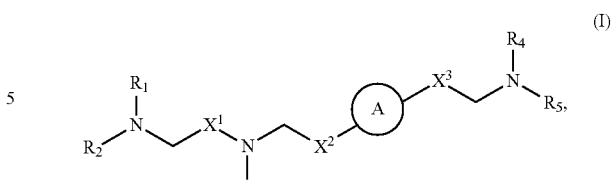

or a salt or isomer thereof, wherein
ring A is

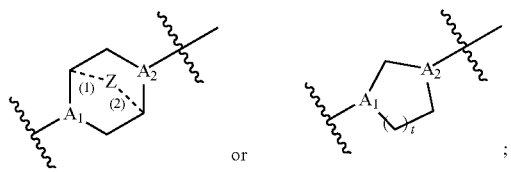

t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;
each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H; and
each R" is independently selected from the group consisting of $C_{3-12}$ alkyl and $C_{3-12}$ alkenyl,
wherein when ring A is

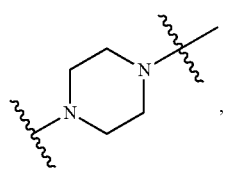 [SMILES: *N1CCN(*)CC1]

then
i) at least one of $X^1$, $X^2$, and $X^3$ is not —$CH_2$—; and/or
ii) at least one of $R_1$, $R_2$, $R_3$, $R_4$, and $R_5$ is —R"MR'.

The compounds of formula (I) may include one or more of the following features when applicable.

In some embodiments, the compound is of any of formulae (Ia1)-(Ia6):

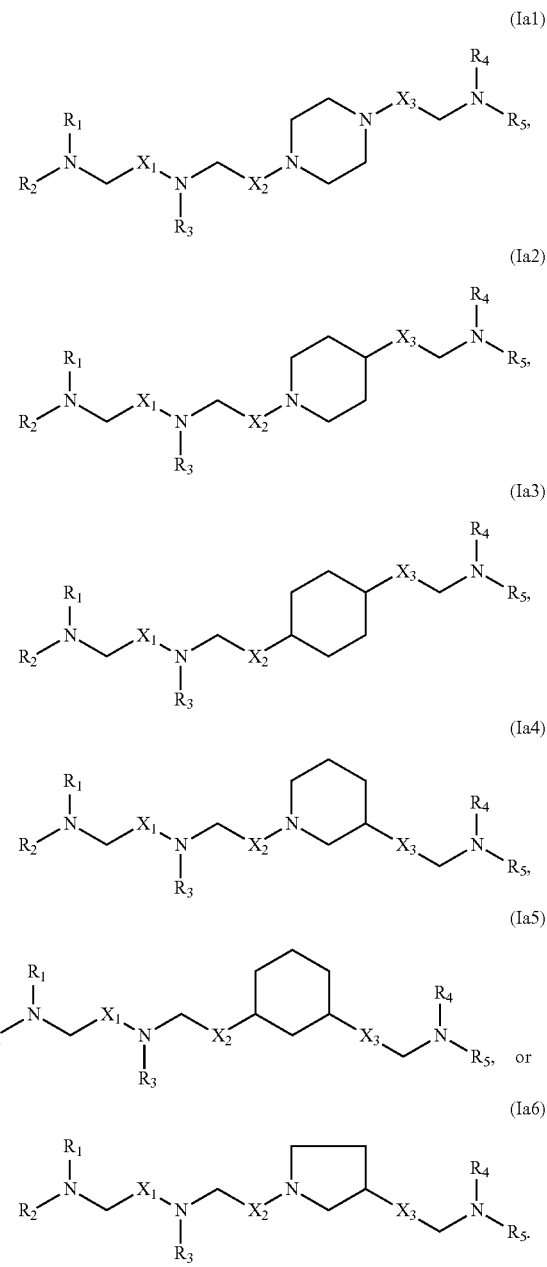

In some embodiments, at least one of $X^1$, $X^2$, and $X^3$ is not —CH$_2$—. For example, in certain embodiments, $X^1$ is not —CH$_2$—. In some embodiments, at least one of $X^1$, $X^2$, and $X^3$ is —C(O)—. In some embodiments, $X^3$ is a bond while each of $X^1$ and $X^2$ is not a bond. In some embodiments, none of $X^1$, $X^2$, and $X^3$ is a bond.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)— In some embodiments, at least one R" is C$_3$ alkyl. In certain embodiments, each R" is C$_3$ alkyl. In some embodiments, at least one R" is C$_5$ alkyl. In certain embodiments, each R" is C$_5$ alkyl. In some embodiments, at least one R" is C$_6$ alkyl. In certain embodiments, each R" is C$_6$ alkyl. In some embodiments, at least one R" is C$_7$ alkyl. In certain embodiments, each R" is C$_7$ alkyl. In some embodiments, at least one R' is C$_5$ alkyl. In certain embodiments, each R' is C$_5$ alkyl. In other embodiments, at least one R' is C$_1$ alkyl. In certain embodiments, each R' is C$_1$ alkyl. In some embodiments, at least one R' is C$_2$ alkyl. In certain embodiments, each R' is C$_2$ alkyl.

In some embodiments, at least one of $R_1$, $R_2$, $R_3$, $R_4$, and $R_5$ is C$_{12}$ alkyl. In certain embodiments, each of $R_1$, $R_2$, $R_3$, $R_4$, and $R_5$ are C$_{12}$ alkyl.

In another aspect, the disclosure provides a compound having formula (II):

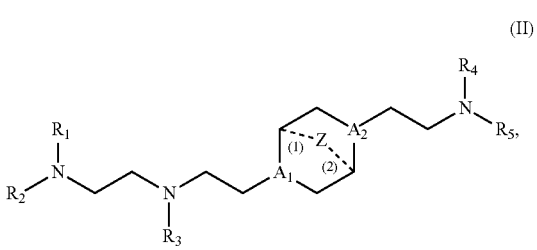

or a salt or isomer thereof, wherein $A_1$ and $A_2$ are each independently selected from CH or N and at least one of $A_1$ and $A_2$ is N;

Z is CH$_2$ or absent wherein when Z is CH$_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of C$_{6-20}$ alkyl and C$_{6-20}$ alkenyl;

wherein when ring A is

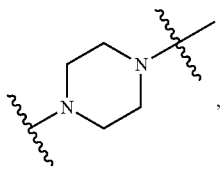 [SMILES: *N1CCN(*)CC1]

then i) $R_1$, $R_2$, $R_3$, $R_4$, and $R_5$ are the same, wherein $R_1$ is not C$_{12}$ alkyl, C$_{18}$ alkyl, or C$_{18}$ alkenyl;

ii) only one of $R_1$, $R_2$, $R_3$, $R_4$, and $R_5$ is selected from C$_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from C$_{6-20}$ alkenyl, and $R_4$ and $R_5$ are selected from C$_{6-20}$ alkyl; or v) $R_1$, $R_2$, and $R_3$ are selected from C$_{6-20}$ alkyl, and $R_4$ and $R_5$ are selected from C$_{6-20}$ alkenyl.

The compounds of formula (II) may include one or more of the following features when applicable.

In some embodiments, the compound is of formula (IIa):

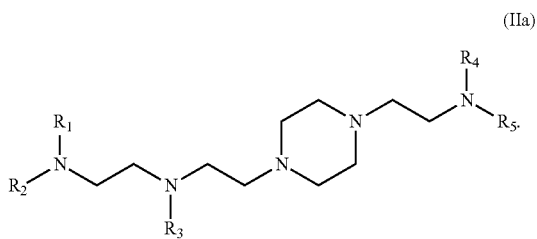

(IIa)

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In another aspect, the disclosure provides a compound according to formula (III):

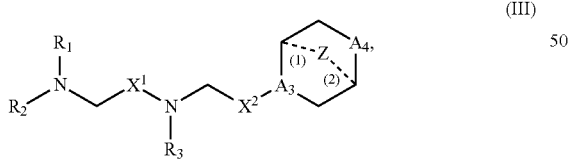

(III)

or a salt or isomer thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$ and $X^2$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

The compounds of formula (III) may include one or more of the following features when applicable.

In some embodiments, the compound is of formula (IIIa):

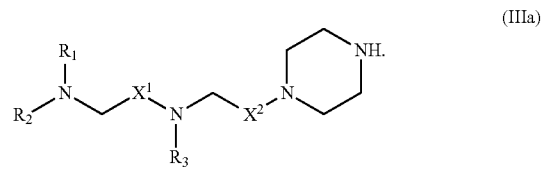

(IIIa)

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, at least one of $X^1$ and $X^2$ is not —CH$_2$—. For example, in certain embodiments, $X^1$ is not —CH$_2$—. In some embodiments, at least one of $X^1$ and $X^2$ is —C(O)—.

In another aspect, the disclosure provides a compound according to formula (Ib):

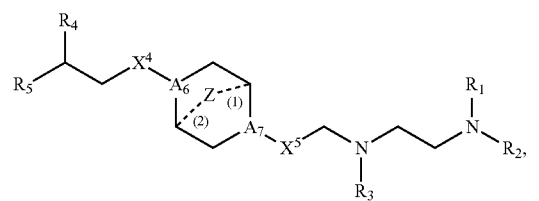

(Ib)

or a salt or isomer thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

$R_1$, $R_2$, $R_3$, $R_4$, and $R_5$ each are independently selected from the group consisting of $C_{5-20}$ alkyl and $C_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

The compounds of formula (Ib) may include one or more of the following features when applicable.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —CH$_2$— and $X^5$ is —C(O)—. In some embodiments, $X^4$ and $X^5$ are —C(O)—.

In an embodiment, the compound has the formula (IV)

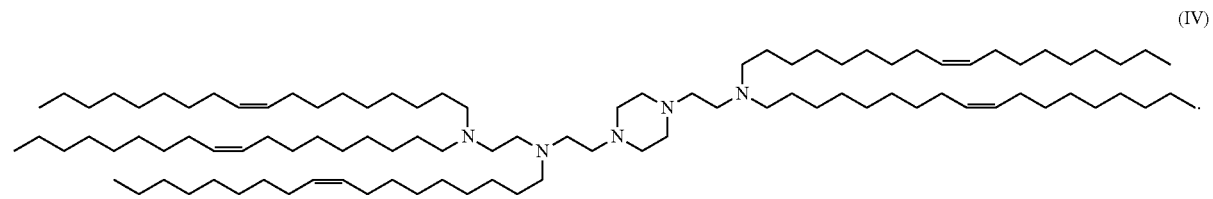 [SMILES: CCCCCCCC/C=C\CCCCCCCCN(CCCCCCCC/C=C\CCCCCCCC)CCN(CCCCCCCC/C=C\CCCCCCCC)CCN1CCN(CCN(CCCCCCCC/C=C\CCCCCCCC)CCCCCCCC/C=C\CCCCCCCC)CC1]

(IV)

In another aspect, the disclosure provides a compound having the formula (17-I):

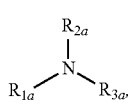

(17-I)

or a salt or isomer thereof, wherein $R_{1a}$ is —(CH$_2$)$_n{}^a$Q$^a$, where Q$^a$ is selected from a heterocycle, —OR$^a$, —O(CH$_2$)$_n{}^a$N(R$^a$)$_2$, —C(O)OR$^a$, —OC(O)R$^a$, —CX$^a{}_3$, —CX$^a{}_2$H, —CX$^a$H$_2$, —CN, —N(R$^a$)$_2$, —C(O)N(R$^a$)$_2$, —N(R$^a$)C(O)R$^a$, and —N(R$^a$)S(O)$_2$R$^a$ and each n$^a$ is independently selected from 1, 2, 3, 4, and 5;

$R_{2a}$ and $R_{3a}$ are each independently selected from the group consisting of $C_{3-24}$ alkyl, $C_{3-24}$ alkenyl, —R$^{a*}$Y$^a$R$^{a'''}$, —Y$^a$R$^{a'''}$, and —R$^{a*}$OR$^{a'''}$;

each Y$^a$ is independently a $C_{3-6}$ carbocycle;

each R$^{a*}$ is independently selected from the group consisting of $C_{1-12}$ alkyl and $C_{1-12}$ alkenyl;

each X$^a$ is independently selected from the group consisting of F, Cl, Br, and I;

each R$^a$ is independently selected from the group consisting of $C_{1-3}$ alkyl, $C_{2-3}$ alkenyl, and H; and each R$^{a'''}$ is selected from the group consisting of $C_{3-12}$ alkyl and $C_{3-12}$ alkenyl;

wherein $R_{2a}$ includes 7 or fewer carbon atoms.

In some embodiments, Q$^a$ is —OR$^a$. In certain embodiments, R$^a$ is H. In other embodiments, R$^a$ is —CH$_3$.

In some embodiments, n$^a$ is 1. In other embodiments, n$^a$ is 2. In other embodiments, n$^a$ is 3. In other embodiments, n$^a$ is 4. In some embodiments, n$^a$ is 5.

In some embodiments, $R_{3a}$ includes 7 or fewer carbon atoms.

In another aspect, the disclosure provides a compound having the formula (17-I)

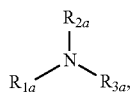

(17-I)

or a salt or isomer thereof, wherein $R_{1a}$ is —(CH$_2$)$_n{}^a$Q$^a$, where Q$^a$ is selected from a heterocycle, —OR$^a$, —O(CH$_2$)$_n{}^a$N(R$^a$)$_2$, —C(O)OR$^a$, —OC(O)R$^a$, —CX$^a{}_3$, —CX$^a{}_2$H, —CX$^a$H$_2$, —CN, —N(R$^a$)$_2$, —C(O)N(R$^a$)$_2$, —N(R$^a$)C(O)R$^a$, and —N(R$^a$)S(O)$_2$R$^a$ and each n$^a$ is independently selected from 1, 2, 3, 4, and 5;

each X$^a$ is independently selected from the group consisting of F, Cl, Br, and I;

$R_{2a}$ is selected from the group consisting of $C_{8-24}$ alkenyl;

$R_{3a}$ is selected from the group consisting of $C_{8-24}$ alkyl; and each R$^a$ is independently selected from the group consisting of $C_{1-3}$ alkyl, $C_{2-3}$ alkenyl, and H.

In some embodiments, Q$^a$ is —OR$^a$. In certain embodiments, R$^a$ is H. In other embodiments, R$^a$ is —CH$_3$.

In some embodiments, n$^a$ is 1. In other embodiments, n$^a$ is 2. In other embodiments, n$^a$ is 3. In other embodiments, n$^a$ is 4. In some embodiments, n$^a$ is 5.

In some embodiments, $R_{3a}$ is an alkyl including 9, 12, 14, or 18 carbon atoms.

In some embodiments, $R_{2a}$ is $C_{18}$ alkenyl (e.g., linoleyl).

In a further aspect, the disclosure provides a compound having the formula (17-I)

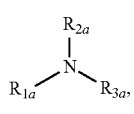

(17-I)

or a salt or isomer thereof, wherein $R_{1a}$ is —(CH$_2$)$_n{}^a$Q$^a$, where Q$^a$ is selected from a heterocycle, —OR$^a$, —O(CH$_2$)$_n{}^a$N(R$^a$)$_2$, —C(O)OR$^a$, —OC(O)R$^a$, —CX$^a{}_3$, —CX$^a{}_2$H, —CX$^a$H$_2$, —CN, —N(R$^a$)$_2$, —C(O)

$N(R^a)_2$, —$N(R)C(O)R^a$, and —$N(R^a)S(O)_2R^a$ and each $n^a$ is independently selected from 1, 2, 3, 4, and 5;

each $X^a$ is independently selected from the group consisting of F, Cl, Br, and I;

$R_{2a}$ is selected from the group consisting of $C_{13-20}$ alkyl;

$R_{3a}$ is selected from the group consisting of $C_{8-20}$ alkyl; and each $R^a$ is independently selected from the group consisting of $C_{1-3}$ alkyl, $C_{2-3}$ alkenyl, and H.

In some embodiments, $Q^a$ is —$OR^a$. In certain embodiments, $R^a$ is H. In other embodiments, $R^a$ is —$CH_3$.

In some embodiments, $n^a$ is 1. In other embodiments, $n^a$ is 2. In other embodiments, $n^a$ is 3. In other embodiments, $n^a$ is 4. In some embodiments, $n^a$ is 5.

In some embodiments, $R_{2a}$ and $R_{3a}$ are the same.

In some embodiments, $R_{2a}$ and/or $R_{3a}$ is $C_{14}$ alkyl.

In a further aspect, the disclosure provides a compound having the formula (17-I)

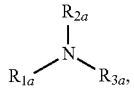

(17-I)

or a salt or isomer thereof, wherein $R_{1a}$ is —$(CH_2)_n{}^aQ^a$, where $Q^a$ is —$OR^a$, $R^a$ is selected from the group consisting of $C_{1-3}$ alkyl, $C_{2-3}$ alkenyl, and H, and $n^a$ is selected from 1, 2, 3, 4, and 5; and $R_{2a}$ and $R_{3a}$ are each independently selected from the group consisting of $C_{8-20}$ alkenyl, wherein i) $R^a$ is selected from the group consisting of $C_{1-3}$ alkyl and $C_{2-3}$ alkenyl; or ii) $R_{1a}$ is —$(CH_2)_2OH$, and $R_{2a}$ and $R_{3a}$ each include one or fewer double bonds.

In some embodiments, $R^a$ is H. In other embodiments, $R^a$ is —$CH_3$.

In some embodiments, $n^a$ is 1. In other embodiments, $n^a$ is 2. In other embodiments, $n^a$ is 3. In other embodiments, $n^a$ is 4. In some embodiments, $n^a$ is 5.

In certain embodiments, $R_{1a}$ is —$(CH_2)_2OCH_3$. In other embodiments, $R_{1a}$ is —$(CH_2)_2OH$.

In some embodiments, $R_{2a}$ is $C_{18}$ alkenyl (e.g., linoleyl). In certain embodiments, $R_{3a}$ is $C_{18}$ alkenyl (e.g., linoleyl).

In some embodiments, $R_{2a}$ and $R_{3a}$ are the same.

In another aspect, the disclosure provides a compound of formula (17-I)

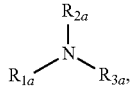

(17-I)

or a salt or isomer thereof, wherein $R_{1a}$ is —$(CH_2)_n{}^aQ^a$, where $Q^a$ is selected from a heterocycle, —$OR^a$, —$O(CH_2)_nN(R^a)_2$, —$C(O)OR^a$, —$OC(O)R^a$, —$CX^a{}_3$, —$CX^a{}_2H$, —$CX^aH_2$, —$CN$, —$N(R^a)_2$, —$C(O)N(R^a)_2$, —$N(R^a)C(O)R^a$, and —$N(R^a)S(O)_2R^a$ and each $n^a$ is independently selected from 1, 2, 3, 4, and 5;

each $X^a$ is independently selected from the group consisting of F, Cl, Br, and I;

$R_{2a}$ is selected from the group consisting of $C_{8-12}$ alkyl;

$R_{3a}$ is selected from the group consisting of $C_{8-20}$ alkyl; and each $R^a$ is independently selected from the group consisting of $C_{1-3}$ alkyl, $C_{2-3}$ alkenyl, and H.

In some embodiments, $Q^a$ is —$OR^a$. In certain embodiments, $R^a$ is H. In other embodiments, $R^a$ is —$CH_3$.

In some embodiments, $n^a$ is 1. In other embodiments, $n^a$ is 2. In other embodiments, $n^a$ is 3. In other embodiments, $n^a$ is 4. In some embodiments, $n^a$ is 5.

In certain embodiments, $Q^a$ is —$OR^a$ and $n^a$ is selected from 2, 3, and 4.

In some embodiments, $R_{2a}$ is $C_9$ alkyl. In other embodiments, $R_{2a}$ is $C_{12}$ alkyl.

In some embodiments, $R_{2a}$ and $R_{3a}$ are the same.

In another aspect, the disclosure provides a compound having the formula (19-I),

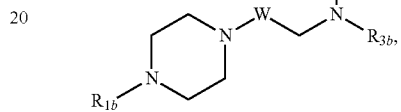

(19-I)

or a salt or isomer thereof, wherein $R_{1b}$ is selected from the group consisting of H, $C_{1-5}$ alkyl, $C_{2-5}$ alkenyl, —$R^{b''}M^bR^{b'}$, a $C_{3-6}$ carbocycle, —$(CH_2)_nQ^b$, and —$(CH_2)_nCHQ^bR^b$, where $Q^b$ is selected from a heterocycle, —$OR^b$, —$O(CH_2)_nN(R^b)_2$, —$C(O)OR^b$, —$OC(O)R^b$, —$CX^b{}_3$, —$CX^b{}_2H$, —$CX^bH_2$, —$CN$, —$N(R^b)_2$, —$C(O)N(R^b)_2$, —$N(R^b)C(O)R^b$, and —$N(R^b)S(O)_2R^b$ and each n is independently selected from 1, 2, 3, 4, and 5;

$R_{2b}$ and $R_{3b}$ are independently selected from the group consisting of $C_{1-20}$ alkyl, $C_{2-20}$ alkenyl, —$R^{b''}MR^{b'}$, —$R^{b*}YR^{b''}$, —$YR^{b''}$, and —$R^{b*}OR^{b''}$;

each $M^b$ is independently selected from the group consisting of —$C(O)O$—, —$OC(O)$—, —$C(O)N(R^{b'})$—, —$N(R^{b'})C(O)$—, —$C(O)$—, —$C(S)$—, —$C(S)S$—, —$SC(S)$—, —$CH(OH)$—, —$P(O)(OR^{b'})O$—, —$S(O)_2$—, an aryl group, and a heteroaryl group;

W is selected from the group consisting of —$CH_2$—, —$CHR^b$—, —$C(O)$—, —$CH(OH)$—, —$C(S)$—, and —$CH(SH)$—;

each $X^b$ is independently selected from the group consisting of F, Cl, Br, and I;

each $Y^b$ is independently a $C_{3-6}$ carbocycle;

each $R^{b*}$ is independently selected from the group consisting of $C_{1-12}$ alkyl and $C_{1-12}$ alkenyl;

each $R^b$ is independently selected from the group consisting of $C_{1-3}$ alkyl, a $C_{3-6}$ carbocycle, $C_{2-3}$ alkenyl, and H;

each $R^{b'}$ is independently selected from the group consisting of $C_{1-12}$ alkyl, $C_{2-12}$ alkenyl, and H; and each $R^{b''}$ is independently selected from the group consisting of $C_{3-12}$ alkyl and $C_{3-12}$ alkenyl.

In some embodiments, W is not —$CH_2$—. In particular such embodiments, W is —$C(O)$—.

In some embodiments, at least one of $R_{2b}$ and $R_{3b}$ is —$R^{b''}M^bR^{b'}$. In certain embodiments, at least one $M^b$ is —$C(O)O$—. In certain embodiments, at least one $R^{b''}$ is $C_5$ alkyl. In certain embodiments, at least one $R^{b'}$ is $C_5$ alkyl.

In some embodiments, $R_{2b}$ and/or $R_{3b}$ are selected from the group consisting of $C_{1-20}$ alkyl. For example, $R_{2b}$ and/or $R_{3b}$ may be alkyl groups including 9 or 12 carbon atoms. In other embodiments, $R_{2b}$ and/or $R_{3b}$ are selected from the group consisting of $C_{2-20}$ alkenyl. For example, $R_{2b}$ and/or $R_{3b}$ may be alkenyl groups including 18 carbon atoms (e.g., linoleyl groups). In certain embodiments, $R_{2b}$ and $R_{3b}$ are the same.

In some embodiments, $R_{1b}$ is H, while in other embodiments, $R_{1b}$ is selected from $C_{1-5}$ alkyl. For example, $R_{1b}$ may be $C_1$ alkyl.

In certain embodiments, Rib is $-(CH_2)_nQ^b$. In such embodiments, $Q^b$ is a heterocycle such as a phenyl group. For example, $Q^b$ may be a phenyl group with one or more substituents, as described herein.

Also disclosed herein are compounds of formula (19-II):

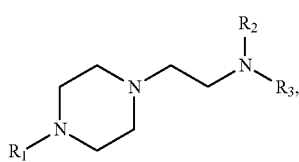

(19-II)

or salts or isomers thereof, wherein $R_{1b}$ is selected from the group consisting of $C_{6-20}$ alkyl; and $R_{2b}$ and $R_{3b}$ are independently selected from the group consisting of $C_{6-20}$ alkenyl.

In particular embodiments, $R_{1b}$ is $C_{12}$ alkyl.

In some embodiments, $R_{2b}$ and/or $R_{3b}$ are $C_{18}$ alkenyl (e.g., linoleyl).

In certain embodiments, $R_{2b}$ and $R_{3b}$ are both linoleyl.

In another aspect, the disclosure provides a compounds of formula (20-I):

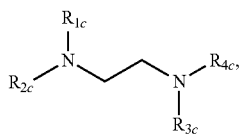

(20-I)

or a salt or isomer thereof, wherein $R_{1c}$ is selected from the group consisting of a $C_{3-6}$ carbocycle, $-(CH_2)_{n^c}Q^c$, $-(CH_2)_{n^c}CHQ^cR^c$, $-CHQ^cR^c$, and $-CQ^c(R^c)_2$, where $Q^c$ is selected from a heterocycle, $-OR^c$, $-O(CH_2)_{n^c}N(R^c)_2$, $-C(O)OR^c$, $-OC(O)R^c$, $-CX^c{}_3$, $-CX^c{}_2H$, $-CX^cH_2$, $-CN$, $-N(R^c)_2$, $-C(O)N(R^c)_2$, $-N(R^c)C(O)R^c$, and $-N(R^c)S(O)_2R^c$ and each $n^c$ is independently selected from 1, 2, 3, 4, and 5;

$R_{2c}$, $R_{3c}$, and $R_{4c}$ are independently selected from the group consisting of $C_{1-20}$ alkyl, $C_{2-20}$ alkenyl, $-R^{c"}M^cR^{c'}$, $-R^{c*}Y^cR^{c"}$, $-Y^cR^{c"}$, and $-R^{c*}OR^{c"}$;

each $M^c$ is independently selected from the group consisting of $-C(O)O-$, $-OC(O)-$, $-C(O)N(R^{c'})-$, $-N(R^{c'})C(O)-$, $-C(O)-$, $-C(S)-$, $-C(S)S-$, $-SC(S)-$, $-CH(OH)-$, $-P(O)(OR')O-$, $-S(O)_2-$, an aryl group, and a heteroaryl group;

each $X^c$ is independently selected from the group consisting of F, Cl, Br, and I;

each $Y^c$ is independently a $C_{3-6}$ carbocycle;

each $R^{c*}$ is independently selected from the group consisting of $C_{1-12}$ alkyl and $C_{1-12}$ alkenyl;

each $R^c$ is independently selected from the group consisting of $C_{1-3}$ alkyl, $C_{2-3}$ alkenyl, and H;

each $R^{c'}$ is independently selected from the group consisting of $C_{1-12}$ alkyl, $C_{2-12}$ alkenyl, and H; and each $R^{c"}$ is independently selected from the group consisting of $C_{3-12}$ alkyl and $C_{3-12}$ alkenyl, wherein i) $R_{1c}$ is selected from the group consisting of a $C_{3-6}$ carbocycle, $-(CH_2)_{n^c}Q^c$, $-(CH_2)_{n^c}CHQ^cR^c$, $-CHQ^cR^c$, and $-CQ^c(R^c)_2$, where $Q^c$ is selected from a heterocycle, $-O(CH_2)_{n^c}N(R^c)_2$, $-C(O)OR^c$, $-OC(O)R^c$, $-CX^c{}_3$, $-CX^c{}_2H$, $-CX^cH_2$, $-C(O)N(R^c)_2$, $-N(R^c)C(O)R^c$, and $-N(R^c)S(O)_2R^c$ and each $n^c$ is independently selected from 1, 2, 3, 4, and 5; and/or ii) at least one of $R_{2c}$, $R_{3c}$, and $R_{4c}$ is $-R^{c"}M^cR^{c'}$.

In some embodiments, $R_1$ is selected from the group consisting of $-(CH_2)_{n^c}Q^c$, $-(CH_2)_{n^c}CHQ^cR^c$, $-CHQ^cR^c$, and $-CQ^c(R^c)_2$, where $Q^c$ is selected from a heterocycle, $-O(CH_2)_{n^c}N(R^c)_2$, $-C(O)OR^c$, $-OC(O)R^c$, $-CX^c{}_3$, $-CX^c{}_2H$, $-CX^cH_2$, $-CN$, $-C(O)N(R^c)_2$, $-N(R^c)C(O)R^c$, and $-N(R^c)S(O)_2R^c$ and each n is independently selected from 1, 2, 3, 4, and 5. In certain embodiments, $R_{1c}$ is $-(CH_2)_nQ^c$. In some embodiments, $n^c$ is 2. In some embodiments, $Q^c$ is $-C(O)OR^c$, where $R^c$ is, for example, H.

In some embodiments, at least one of $R_{2c}$, $R_{3c}$, and $R_{4c}$ is $-R^{c"}M^cR^{c'}$. For example, $R_{2c}$, $R_{3c}$, and/or $R_{4c}$ may be $-R^{c"}M^cR^{c'}$. In some embodiments, at least one $M^c$ is $-C(O)O-$. In certain embodiments, each $M^c$ is $-C(O)O-$. In some embodiments, at least one $R^{c"}$ is $C_5$ or $C_7$ alkyl. In certain embodiments, each $R^{c"}$ is $C_5$ alkyl. In other embodiments, each $R^{c"}$ is $C_7$ alkyl. In some embodiments, at least one $R^{c'}$ is $C_5$, $C_7$, or $C_9$ alkyl. In certain embodiments, each $R^{c'}$ is $C_5$ alkyl. In other embodiments, each $R^{c'}$ is $C_7$ alkyl. In other embodiments, each $R^{c'}$ is $C_9$ alkyl. In some embodiments, $R^{c'}$ is branched.

In some embodiments, $R_{2c}$, $R_{3c}$, and $R_{4c}$ are selected from the group consisting of $C_{5-20}$ alkyl. In certain embodiments, $R_{2c}$, $R_{3c}$, and $R_{4c}$ are $C_{12}$ alkyl.

In some embodiments, $R_{2c}$ is selected from the group consisting of $C_{5-20}$ alkyl and $C_{5-20}$ alkenyl. For example, $R_{2c}$ may be $C_{12}$ alkyl.

In some embodiments, $R_{3c}$ is selected from the group consisting of $C_{5-20}$ alkyl and $C_{5-20}$ alkenyl. For example, $R_{3c}$ may be $C_6$, $C_9$, or $C_{12}$ alkyl.

In some embodiments, $R_{4c}$ is selected from the group consisting of $C_{5-20}$ alkyl and $C_{5-20}$ alkenyl. For example, $R_{4c}$ may be $C_6$, $C_9$, or $C_{12}$ alkyl.

In some embodiments, $R_{3c}$ and $R_{4c}$ are the same.

In yet another aspect, the disclosure provides a compound according to formula (20-I):

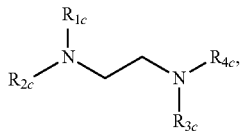

(20-I)

or a salt or isomer thereof, wherein $R_1$ is selected from the group consisting of $-(CH_2)_{n^c}Q^c$, $-(CH_2)_{n^c}CHQ^cR^c$, $-CHQ^cR^c$, and $-CQ^c(R^c)_2$, where $Q^c$ is selected from $-OR^c$, $-CN$, and $-N(R^c)_2$, and $n^c$ is selected from 1, 2, 3, 4, and 5;

$R_{2c}$ and $R_{3c}$ are independently selected from the group consisting of $C_{6-20}$ alkyl and $C_{6-20}$ alkenyl;

$R_{4c}$ is selected from the group consisting of $C_{13-20}$ alkyl and $C_{5-20}$ alkenyl; and each $R^c$ is independently selected from the group consisting of $C_{1-3}$ alkyl, $C_{2-3}$ alkenyl, and H.

In some embodiments, $R_{3c}$ is $C_{14}$ alkyl.

In some embodiments, $R_{4c}$ is $C_{14}$ alkyl.

In some embodiments, $R_{3c}$ is $C_{18}$ alkenyl. For example, $R_{3c}$ may be linoleyl.

In some embodiments, $R_{4c}$ is $C_{18}$ alkenyl. For example, $R_{4c}$ may be linoleyl.

In some embodiments, $R_{2c}$ is $C_{12}$ alkyl. In other embodiments, $R_{2c}$ is $C_{14}$ alkyl. In some embodiments, $R_{2c}$ is $C_{18}$ alkenyl. For example, $R_{2c}$ may be linoleyl.

In some embodiments, $R_{3c}$ and $R_{4c}$ are the same.

In some embodiments, $R_{1c}$ is —$(CH_2)_n{}^c Q^c$. In some embodiments, $Q^c$ is —$OR^c$. For example, $Q^c$ may be —OH. In some embodiments, $n^c$ is 2 or 3.

The disclosure also provides a compound having formula (20-I):

$$\text{(20-I)} \quad R_{2c}\!-\!\underset{\underset{R_{3c}}{|}}{\overset{\overset{R_{1c}}{|}}{N}}\!-\!CH_2CH_2\!-\!\underset{\underset{R_{3c}}{|}}{N}\!-\!R_{4c},$$

or a salt or isomer thereof, wherein $R_1$ is selected from the group consisting of —$(CH_2)_n{}^c Q^c$, —$(CH_2)_n{}^c CHQ^c R^c$, —$CHQ^c R^c$, and —$CQ^c(R^c)_2$, where $Q^c$ is selected from —$OR^c$, —CN, and —$N(R^c)_2$, and $n^c$ is selected from 1, 2, 3, 4, and 5;

$R_{2c}$, $R_{3c}$, and $R_{4c}$ are independently selected from the group consisting of $C_{6-20}$ alkyl and $C_{6-20}$ alkenyl; and each $R^c$ is independently selected from the group consisting of $C_{1-3}$ alkyl, $C_{2-3}$ alkenyl, and H;

wherein i) $R_{2c}$ is selected from the group consisting of $C_{1-11}$ alkyl and $C_{2-5}$ alkenyl, and/or ii) $R_{3c}$ is selected from the group consisting of $C_{1-11}$ alkyl and $C_{2-5}$ alkenyl.

In some embodiments, $R_{2c}$ is selected from the group consisting of $C_{1-11}$ alkyl and $C_{2-5}$ alkenyl. For example, $R_{2c}$ may be $C_6$ or $C_9$ alkyl.

In some embodiments, $R_{3c}$ is selected from the group consisting of $C_{1-11}$ alkyl and $C_{2-5}$ alkenyl. For example, $R_{3c}$ may be $C_6$ or $C_9$ alkyl.

In some embodiments, $R_{3c}$ is $C_{12}$ alkyl.

In some embodiments, $R_{2c}$ is $C_{12}$ alkyl.

In some embodiments, $R_{4c}$ is $C_6$, $C_9$, or $C_{12}$ alkyl.

In some embodiments, $R_{1c}$ is —$(CH_2)_n{}^c Q^c$. In certain embodiments, $Q^c$ is —$OR^c$. In some embodiments, $R^c$ is H. In some embodiments, $n^c$ is 2 or 3.

In still another aspect, the disclosure provides a compound according to formula (20-I):

$$\text{(20-I)} \quad R_{2c}\!-\!\underset{\underset{R_{3c}}{|}}{\overset{\overset{R_{1c}}{|}}{N}}\!-\!CH_2CH_2\!-\!\underset{\underset{R_{3c}}{|}}{N}\!-\!R_{4c},$$

or a salt or isomer thereof, wherein $R_{1c}$ is selected from the group consisting of —$(CH_2)_n{}^c Q^c$, —$(CH_2)_n{}^c CHQ^c R^c$, —$CHQ^c R^c$, and —$CQ^c(R^c)_2$, where $Q^c$ is selected from —$OR^c$, —CN, and —$N(R^c)_2$, and $n^c$ is selected from 1, 2, 3, 4, and 5;

$R_{2c}$ is selected from the group consisting of H, $C_{12-20}$ alkyl, and $C_{6-20}$ alkenyl;

$R_{3c}$ and $R_{4c}$ are $C_{12}$ alkyl; and each $R^c$ is independently selected from the group consisting of $C_{1-3}$ alkyl, $C_{2-3}$ alkenyl, and H.

In some embodiments, $R_{2c}$ is H. In other embodiments, $R_{2c}$ is $C_{12}$ alkyl or alkenyl. In some embodiments, $R_{2c}$ is $C_{14}$ alkyl. In other embodiments, $R_{2c}$ is $C_{18}$ alkenyl. For example, $R_{2c}$ may be linoleyl.

In some embodiments, $R_{1c}$ is —$(CH_2)_n{}^c Q^c$. In certain embodiments, $Q^c$ is —$OR^c$. For example, $Q^c$ may be OH. In some embodiments, $n^c$ is 2, 3, or 4.

In another aspect, the disclosure provides compounds of formula (21-I):

$$\text{(21-I)} \quad R_{1d}\!-\!\underset{\underset{R_{2d}}{|}}{N}\!-\!(\ )_{n^d}\!-\!M^d\!-\!*\!\overset{R_{3d}}{\underset{R_{4d},}{\diamondsuit}}\!(\ )_k$$

or salts or isomers thereof, wherein $R_{1d}$ and $R_{2d}$ are independently selected from the group consisting of H, $C_{1-5}$ alkyl, and $C_{2-5}$ alkenyl;

$n^d$ is selected from 1, 2, 3, 4, and 5;

k is selected from 0, 1, 2, and 3;

$R_{3d}$ and $R_{4d}$ are independently selected from the group consisting of $C_{1-20}$ alkyl, $C_{2-20}$ alkenyl, —$R^{d''}M^d R^{d'}$, —$R^{d*}Y^d R^{d''}$, —$Y^d R^{d''}$, and —$R^{d*}OR^{d''}$;

each $M^d$ is independently selected from the group consisting of —C(O)O—, —OC(O)—, —C(O)N($R_d{'}$)—, —N($R_d{'}$)C(O)—, —C(O)—, —C(S)—, —C(S)S—, —SC(S)—, —CH(OH)—, —P(O)(O$R_d{'}$)O—, and —S(O)$_2$—, or is absent;

each $R^{d'}$ is independently selected from the group consisting of $C_{1-12}$ alkyl, $C_{2-12}$ alkenyl, and H; each $Y^d$ is independently a $C_{3-6}$ carbocycle;

each $R_d^{*}$ is independently selected from the group consisting of $C_{1-12}$ alkyl and $C_{1-12}$ alkenyl;

each $R^{d'}$ is independently selected from the group consisting of $C_{1-12}$ alkyl, $C_{2-12}$ alkenyl, and H; and each $R_d{''}$ is independently selected from the group consisting of $C_{3-12}$ alkyl and $C_{3-12}$ alkenyl, wherein $R_{3d}$ and $R_{4d}$ are bound to either i) the same carbon atom or ii) adjacent carbon atoms.

In some embodiments, $R_{3d}$ and $R_{4d}$ are bound to the same carbon atom. For example, $R_{3d}$ and $R_{4d}$ may be bound to a carbon atom adjacent to C*. In certain embodiments, $R_{3d}$ and $R_{4d}$ are not bound to a carbon atom adjacent to C*.

In other embodiments, $R_{3d}$ and $R_{4d}$ are bound to adjacent carbon atoms. In certain embodiments, one or both of $R_{3d}$ and $R_{4d}$ are bound to carbon atoms adjacent to C*.

In some embodiments, k is 0. In other embodiments, k is 1, 2, or 3.

In certain embodiments, $M^d$ is absent. In other embodiments, $M^d$ is selected from the group consisting of —C(O)O—, —OC(O)—, —C(O)N($R^{d'}$)—, —N($R^{d'}$)C(O)—, —C(O)—, —C(S)—, —C(S)S—, —SC(S)—, —CH(OH)—, —P(O)(O$R^{d'}$)O—, and —S(O)$_2$—. In particular such embodiments, $M^d$ is —C(O)O—.

In some embodiments, $n^d$ is 1, 2, or 3.

In some embodiments, $R_{1d}$ and/or $R_{2d}$ are selected from $C_{1-5}$ alkyl. In certain embodiments, $R_{1d}$ and/or $R_{2d}$ are $C_1$ alkyl.

In certain embodiments, $R_{3d}$ and/or $R_{4d}$ are selected from $C_{2-20}$ alkenyl. In certain embodiments, $R_{3d}$ and/or $R_{4d}$ are alkenyl groups including 17, 18, or 19 carbon atoms. For example, $R_{3d}$ and/or $R_{4d}$ may be $C_{18}$ alkenyl groups (e.g., linoleyl).

In a further aspect, the disclosure features a nanoparticle composition including a lipid component comprising a compound as described above (e.g., a compound according to one of formulae (I), (Ia1)-(Ia6), (Ib), (II), (IIa), (III), (IIIa), (IV), (17-I), (19-I), (19-II), and (20-I)). In some embodiments, the lipid component of the nanoparticle composition includes a phospholipid. In certain embodiments, a phospholipid of a nanoparticle composition includes a phospholipid moiety and one or more fatty acid moieties, one or more of which may be unsaturated. For example, a nanoparticle composition may include a lipid according to formula (V)

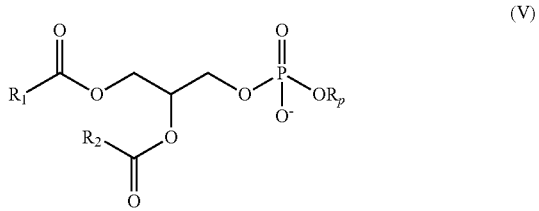

(V)

in which $R_p$ represents a phospholipid moiety and $R_1$ and $R_2$ represent unsaturated fatty acid moieties that may be the same or different.

A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, arachidic acid, arachidonic acid, phytanic acid, eicosapentaenoic acid, behenic acid, docosapentaenoic acid, and docosahexaenoic acid. For example, in certain embodiments, a phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanol amine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In certain embodiments, the phospholipid is DOPE. In other embodiments, the phospholipid is DSPC. Non-natural species including natural species with modifications and substitutions including branching, oxidation, cyclization, and alkynes are also contemplated.

In some embodiments, the lipid component of the nanoparticle composition includes a structural lipid. In certain embodiments, a structural lipid is selected from the group consisting of cholesterol, fecosterol, sitosterol, ergosterol, campesterol, stigmasterol, brassicasterol, tomatidine, ursolic acid, and alpha-tocopherol. In certain embodiments, the structural lipid is cholesterol.

In some embodiments, the lipid component of the nanoparticle composition includes a PEG lipid. In certain embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, and a PEG-modified dialkylglycerol.

In some embodiments, the nanoparticle composition includes a lipid component comprising a compound according to one of formulae (I), (Ia1)-(Ia6), (Ib), (II), (IIa), (III), (IIIa), (IV), (17-I), (19-I), (19-II), (20-I) and (21-I), a phospholipid (which may or may not be unsaturated), a PEG lipid, and a structural lipid. In certain embodiments, the lipid component of the nanoparticle composition includes about 30 mol % to about 60 mol % compound of one of formulae (I), (Ia1)-(Ia6), (Ib), (II), (IIa), (III), (IIIa), (IV), (17-I), (19-I), (19-II), (20-I) and (21-I), about 0 mol % to about 30 mol % phospholipid, about 18.5 mol % to about 48.5 mol % structural lipid, and about 0 mol % to about 10 mol % of PEG lipid. In some embodiments, the lipid component of the nanoparticle composition includes about 30 mol % to about 45 mol % compound of one of formulae (I), (Ia1)-(Ia6), (Ib), (II), (IIa), (III), (IIIa), (IV), (17-I), (19-I), (19-II), (20-I) and (21-I), about 5 mol % to about 25 mol % phospholipid, about 30 mol % to about 40 mol % structural lipid, and about 0 mol % to about 10 mol % of PEG lipid. In some embodiments, the lipid component of the nanoparticle composition includes about 35 mol % to about 55 mol % compound of one of formulae (I), (Ia1)-(Ia6), (Ib), (II), (IIa), (III), (IIIa), (IV), (17-I), (19-I), (19-II), (20-I) and (21-I), about 5 mol % to about 25 mol % phospholipid, about 30 mol % to about 40 mol % structural lipid, and about 0 mol % to about 10 mol % of PEG lipid. In certain embodiments, the lipid component includes about 50 mol % said compound, about 10 mol % phospholipid, about 38.5 mol % structural lipid, and about 1.5 mol % of PEG lipid. In other embodiments, the lipid component includes about 40 mol % said compound, about 20 mol % phospholipid, about 38.5 mol % structural lipid, and about 1.5 mol % of PEG lipid. In some of these embodiments, the phospholipid is DOPE, while in other embodiments the phospholipid is DSPC. In certain embodiments, the structural lipid is cholesterol. In certain embodiments, the PEG lipid is PEG-DMG. In any of the above, the total content of the lipid component may not exceed 100%.

In some embodiments, the nanoparticle composition includes more than one phospholipid, PEG lipid, structural lipid, or other lipid. In certain embodiments, the nanoparticle composition further includes a cationic and/or ionizable lipid such as an amino-lipid. In certain embodiments, a cationic and/or ionizable lipid is selected from the group consisting of 3-(didodecylamino)-N1,N1,4-tridodecyl-1-piperazineethanamine (KL10), N1-[2-(didodecylamino) ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA or MC3), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), (12Z, 15Z)—N,N-dimethyl-2-nonylhenicosa-12,15-dien-1-amine, and N,N-dimethyl-1-{(1S,2R)-2-octylcyclopropyl}heptadecan-8-amine.

In some embodiments, the nanoparticle composition includes a therapeutic and/or prophylactic agent. In certain embodiments, the therapeutic and/or prophylactic agent may be selected from the group consisting of a protein, a small molecule drug, a cytotoxic agent, a radioactive ion, a chemotherapeutic agent, a vaccine, a compound that elicits an immune response, and/or a nucleic acid (such as a deoxyribonucleic acid or a ribonucleic acid). In certain embodiments, the therapeutic and/or prophylactic agent is a ribonucleic acid (RNA). An RNA may be selected from the group consisting of a small interfering RNA (siRNA), an asymmetrical interfering RNA (aiRNA), a microRNA (miRNA), a Dicer-substrate RNA (dsRNA), a small hairpin RNA (shRNA), a messenger RNA (mRNA), and mixtures thereof. In certain embodiments, the therapeutic and/or prophylactic agent is a messenger RNA (mRNA). An RNA of a nanoparticle composition may be naturally or non-naturally occurring and may include one or more of a stem loop, a chain terminating nucleoside, a polyA sequence, a polyadenylation signal, and/or a 5' cap structure.

In some embodiments, the nanoparticle composition includes more than one therapeutic and/or prophylactic agent, such as one or more RNAs. The therapeutic and/or prophylactic agents may be of the same or different types (e.g., two mRNAs, two siRNAs, one mRNA and one siRNA, one mRNA and one small molecule drug, etc.).

In some embodiments, the encapsulation efficiency of a therapeutic and/or prophylactic agent of a nanoparticle composition is at least 50%. In certain embodiments, the encapsulation efficiency is at least 80%. In certain embodiments, the encapsulation efficiency is greater than 90%.

In some embodiments, the wt/wt ratio of the lipid component to a therapeutic and/or prophylactic agent in the nanoparticle composition is from about 10:1 to about 60:1. In certain embodiments, the wt/wt ratio is about 20:1.

In some embodiments, the N:P ratio of the nanoparticle composition is from about 2:1 to about 30:1. In certain embodiments, the N:P ratio is from about 2:1 to about 8:1. In certain embodiments, the N:P ratio is from about 5:1 to about 8:1. For example, the N:P ratio may be about 5.0:1, about 5.5:1, about 5.67:1, about 6.0:1, about 6.5:1, or about 7.0:1. In some embodiments, the mean size of a nanoparticle composition is from about 40 nm to about 150 nm. In certain embodiments, the mean size is from about 70 nm to about 100 nm. In one embodiment, the mean size may be about 80 to about 100 nm. In certain embodiments, the mean size may be about 80 nm. In other embodiments, the mean size may be about 100 nm.

The polydispersity index of the nanoparticle composition is from about 0 to about 0.25 in certain embodiments. In certain embodiments, the polydispersity index is from about 0.10 to about 0.20.

In some embodiments, the nanoparticle composition has a zeta potential of about −10 mV to about +20 mV.

In some embodiments, upon contacting the compound according to one of formulae (I), (Ia1)-(Ia6), (Ib), (II), (IIa), (III), (IIIa), and (IV) (e.g., any of Compounds 1-109) or a nanoparticle composition thereof with a mammalian cell, the cell uptake of the compound or nanoparticle composition is LDLR-independent. In some embodiments, the cell uptake of the compound or nanoparticle composition is LDLR-dependent. In some embodiments, the cell uptake of the compound or nanoparticle composition is apoE-independent. In some embodiments, the cell uptake of the compound or nanoparticle composition is apoE-dependent. In some embodiments, the cell uptake of the compound or nanoparticle composition is LDLR-apoE-interaction independent. In some embodiments, the cell uptake of the compound or nanoparticle composition is LDLR-apoE-interaction dependent.

In some embodiments, upon contacting the compound according to one of formulae (I), (Ia1)-(Ia6), (Ib), (II), (IIa), (III), (IIIa), and (IV) (e.g., any of Compounds 1-109) or the nanoparticle composition thereof with a mammalian cell to produce a polypeptide, the production of the polypeptide is higher in mammalian hepatocytes than cells from a different tissue (e.g., spleen or kidney).

In some embodiments, upon contacting the compound according to one of formulae (I), (Ia1)-(Ia6), (Ib), (II), (IIa), (III), (IIIa), and (IV) (e.g., any of Compounds 1-109) or the nanoparticle composition thereof with a mammalian cell to produce a polypeptide, the production of the polypeptide occurs substantively in mammalian hepatocytes (e.g., little or no production of the polypeptide in other cells, e.g., spleen cells or renal cells).

In some embodiments, the nanoparticle composition includes one or more other components including, but not limited to, one or more pharmaceutically acceptable excipients, small hydrophobic molecules, therapeutic and/or prophylactic agents, carbohydrates, polymers, permeability enhancing molecules, buffers, and surface altering agents.

In yet another aspect, the disclosure features a pharmaceutical composition comprising a nanoparticle composition according to the preceding aspects and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In a further aspect, the disclosure provides a method of delivering a therapeutic and/or prophylactic agent (e.g., an mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound according to one of formulae (I), (Ia1)-(Ia6), (Ib), (II), (IIa), (III), (IIIa), (IV), (17-I), (19-I), (19-II), (20-I) and (21-I) and (ii) a therapeutic and/or prophylactic agent, in which administering involves contacting the cell with the nanoparticle composition, whereby the therapeutic and/or prophylactic agent is delivered to the cell.

In another aspect, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound according to one of formulae (I), (Ia1)-(Ia6), (Ib), (II), (IIa), (III), (IIIa), (IV), (17-I), (19-I), (19-II), (20-I) and (21-I) and (ii) an mRNA encoding the polypeptide of interest, whereby the mRNA is capable of being translated in the cell to produce the polypeptide.

In yet another aspect, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound according to one of formulae (I), (Ia1)-(Ia6), (Ib), (II), (IIa), (III), (IIIa), (IV), (17-I), (19-I), (19-II), (20-I) and (21-I) and (ii) a therapeutic and/or prophylactic agent (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In a further aspect, the disclosure provides a method of delivering (e.g., specifically delivering) a therapeutic and/or prophylactic agent to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound according to one of formulae (I), (Ia1)-(Ia6), (Ib), (II), (IIa), (III), (IIIa), (IV), (17-I), (19-I), (19-II), (20-I) and (21-I) and (ii) a therapeutic and/or prophylactic agent (e.g., an mRNA), in which administering involves contacting the cell with the nanoparticle composition, whereby the therapeutic and/or prophylactic agent is delivered to the organ such as liver.

In a further aspect, the disclosure features a method for the enhanced delivery of a therapeutic and/or prophylactic agent (e.g., an mRNA) to a target tissue (e.g., a liver, spleen, lung, or femur). This method includes administering to a subject (e.g., a mammal) a nanoparticle composition, the composition including (i) a lipid component including a compound according to one of formulae (I), (Ia1)-(Ia6), (Ib), (II), (IIa), (III), (IIIa), (IV), (17-I), (19-I), (19-II), (20-I) and (21-I), a phospholipid, a structural lipid, and a PEG lipid; and (ii) a therapeutic and/or prophylactic agent, the administering including contacting the target tissue with the nanoparticle composition, whereby the therapeutic and/or prophylactic agent is delivered to the target tissue. In some embodiments, the delivery is enhanced as compared to a reference composition which comprises a reference lipid instead of a compound of one of formulae (I), (Ia1)-(Ia6), (Ib), (II), (IIa), (III), (IIIa), (IV), (17-I), (19-I), (19-II), (20-I) and (21-I).

In yet another aspect, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of one of formulae (I), (Ia1)-(Ia6), (Ib), (II), (IIa), (III), (IIIa), (IV), (17-1), (19-1), (19-II), (20-1) and (21-1). For example, the cellular immune response is an innate immune response, an adaptive immune response, or both.

In certain embodiments of the above aspects, a cell contacted in a method is in a mammal.

In any of the preceding aspects, a mammal may be, for example, a rodent, non-human primate, or a human. In certain embodiments, the mammal is a human. In certain embodiments, the mammal is LDLR-deficient, or apoE-deficient, or both. In certain embodiments, the mammal is not LDLR-deficient. In certain embodiments, the mammal is not apoE-deficient. In certain embodiments, the mammal is neither LDLR-deficient nor apoE-deficient. In certain embodiments, the mammal has an abnormal LDLR-apoE interaction. In certain embodiments, the mammal has a normal LDLR-apoE interaction.

In any of the preceding aspects, a therapeutic and/or prophylactic agent may be an mRNA.

In some embodiments of the above methods, the therapeutic and/or prophylactic agent may be specifically delivered to a target tissue of interest (e.g., a mammalian liver, spleen, lung, or femur).

In some embodiments of the above methods, a polypeptide of interest may be specifically produced in a target cell or tissue of interest (e.g., a hepatocyte, a mammalian liver, spleen, lung, or femur), e.g., the production of polypeptide is substantively higher in the target cell or tissue than in a non-target cell/tissue.

In some embodiments, the nanoparticle composition is administered intravenously, intramuscularly, intradermally, subcutaneously, intra-arterially, intra-tumor, or by inhalation. A dose of about 0.001 mg/kg to about 10 mg/kg of therapeutic and/or prophylactic agent (e.g., mRNA) is administered to a mammal in certain embodiments.

In any of the preceding aspects, in some embodiments, the delivery (e.g., delivery efficiency) of the therapeutic and/or prophylactic agent to the mammalian cell is LDLR-independent. In some embodiments, the delivery of the therapeutic and/or prophylactic agent to the mammalian cell is LDLR-dependent. In some embodiments, the delivery of the therapeutic and/or prophylactic agent to the mammalian cell is apoE-independent. In some embodiments, the delivery of the therapeutic and/or prophylactic agent to the mammalian cell is apoE-dependent. In some embodiments, the delivery of the therapeutic and/or prophylactic agent to the mammalian cell is LDLR-apoE-interaction independent. In some embodiments, the delivery of the therapeutic and/or prophylactic agent to the mammalian cell is LDLR-apoE-interaction dependent.

In any of the preceding aspects, in some embodiments, the production (e.g., yield) of the polypeptide of interest in the mammalian cell is LDLR-independent. In some embodiments, the production of the polypeptide of interest in the mammalian cell is LDLR-dependent. In some embodiments, the production of the polypeptide of interest in the mammalian cell is apoE-independent. In some embodiments, the production of the polypeptide of interest in the mammalian cell is apoE-dependent. In some embodiments, the production of the polypeptide of interest in the mammalian cell is LDLR-apoE-interaction independent. In some embodiments, the production of the polypeptide of interest in the mammalian cell is LDLR-apoE-interaction dependent.

In the preceding aspects, one or more nanoparticle compositions each including one or more therapeutic and/or prophylactic agents may be used in combination. In some embodiments, one or more nanoparticle compositions each including one or more therapeutic and/or prophylactic agents may be simultaneously contacted with a cell or delivered to a mammalian cell or organ. In other embodiments, the one or more nanoparticle compositions are contacted with a cell or delivered to a mammalian cell or organ at different times.

In the preceding aspects, one or more additional therapeutic and/or prophylactic agents or compounds may be used in combination with a nanoparticle composition including a therapeutic and/or prophylactic agent. In some embodiments, an additional therapeutic and/or prophylactic agent or compound may be administered at or near the same time as a nanoparticle composition (e.g., within one hour). In other embodiments, an additional therapeutic and/or prophylactic agent or compound may be administered before or after (e.g., one or more hours before or after) a nanoparticle composition as a pretreatment or post-treatment therapy. In some embodiments, an additional therapeutic and/or prophylactic agent or compound is selected from the group consisting of an anti-inflammatory compound, a steroid (e.g., a corticosteroid), a statin, an estradiol, a BTK inhibitor, an S1P1 agonist, a glucocorticoid receptor modulator (GRM), or an anti-histamine. In certain embodiments, an additional therapeutic and/or prophylactic agent or compound is selected from the group consisting of dexamethasone, methotrexate, acetaminophen, an H1 receptor blocker, or an H2 receptor blocker.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The above and further features will be more clearly appreciated from the following detailed description when taken in conjunction with the accompanying drawings.

FIG. 1 is a pair of graphs comparing luciferase expression levels in mice (whole body) after administration of nanoparticle compositions containing compounds of the disclosure over time.

FIG. 2 is a graph summarizing luciferase expression levels at 3 h after administration of nanoparticle compositions containing compounds of the disclosure. Total light flux values were acquired via body luminescent imaging (BLI) 3 h after administration. In this Figure, the numbers 1-12 refer to the compositions containing Compounds 42-52 and MC3 respectively.

FIG. 3 is a graph summarizing luciferase expression levels at 6 hr after administration of nanoparticle compositions containing compounds of the disclosure. Total light flux values were acquired via BLI 6 h after administration. In this Figure, the numbers 1-12 refer to the compositions containing Compounds 42-52 and MC3 respectively.

FIG. 14 is a pair of graphs showing percentages of activated B-cells in the spleens of CD-1 mice dosed with compounds of the disclosure, compared to MC3, and compared to mice not having received any treatment (naïve test subject). PBS is used as control. Graph A shows the percentage of CD19+ cells. Graph B shows the percentage of CD19+ CD69+ CD86+ cells. Numbers 1-13 refer to compositions containing the following: 1: Compound 73, 2: Compound 80, 3: Compound 70; 4: Compound 81; 5: Compound 69; 6: Compound 82; 7: Compound 83; 8: Compound 62; 9: Compound 84; 10: Compound 85; 11: Compound 86; 12: Compound 87; 13: MC3; 14: PBS; 15: treatment naïve subject.

FIG. 15 is a graph summarizing luciferase expression levels at 6 h after administration of nanoparticle compositions containing compounds of the disclosure to CD-1 mice at a dose of 0.5 mpk. Total light flux values were acquired via body luminescent imaging (BLI) 6 h after administration. In this Figure, the numbers 1-7 and 10 refer to the compositions containing Compounds 4-10 and MC3 respectively.

DETAILED DESCRIPTION

Figure 4:
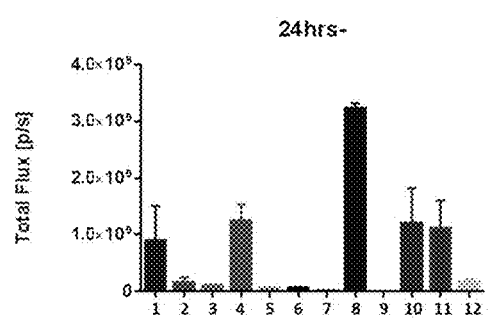
FIG. 4 is graph summarizing luciferase expression levels at 24 h after administration of nanoparticle compositions containing compounds of the disclosure. Total light flux values were acquired via BLI 24 h after administration. In this Figure, the numbers 1-12 refer to the compositions containing Compounds 42-52 and MC3 respectively.
Figure 5:
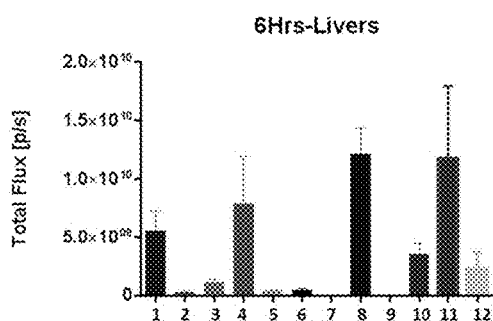
FIG. 5 is graph summarizing expression levels of luciferase in mouse liver 6 hours after administration of nanoparticle compositions including compounds of the disclosure. In this Figure, the numbers 1-12 refer to the compositions containing Compounds 42-52 and MC3 respectively.
Figure 6:
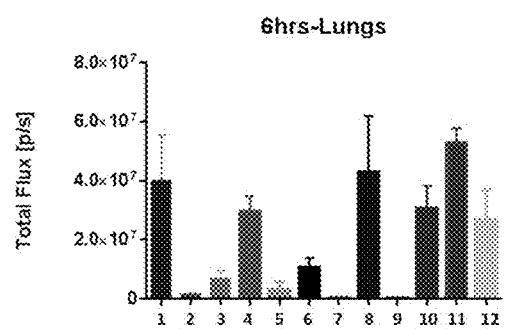
FIG. 6 is a graph summarizing expression levels of luciferase in mouse lungs 6 hours after administration of nanoparticle compositions including compounds of the disclosure. In this Figure, the numbers 1-12 refer to the compositions containing Compounds 42-52 and MC3 respectively.
Figure 7:
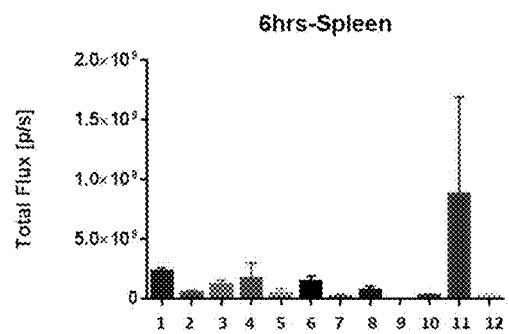
FIG. 7 is a graph summarizing expression levels of luciferase in mouse spleen 6 hours after administration of nanoparticle compositions including compounds of the disclosure. In this Figure, the numbers 1-12 refer to the compositions containing Compounds 42-52 and MC3 respectively.
Figure 8:
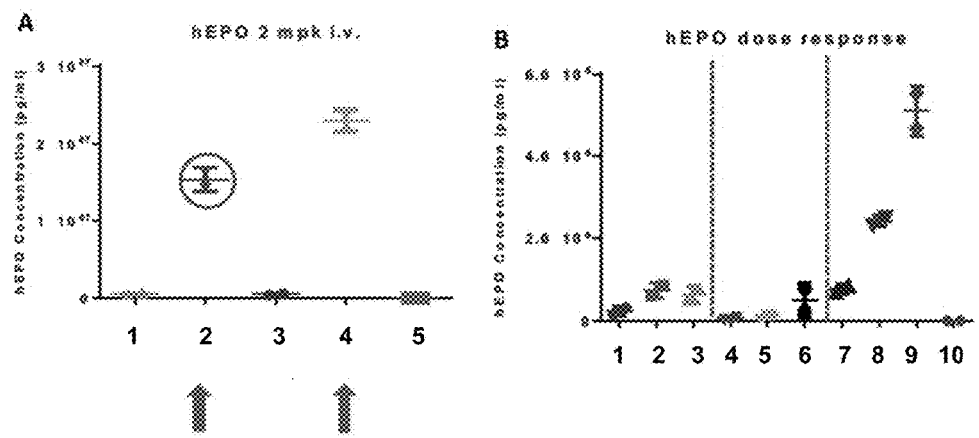
FIG. 8 is a pair of graphs illustrating hEPO expression levels in rats dosed with compounds of the disclosure as compared to with KL22, showing that KL22 and its chain length derivatives (previously showing improved protein expression in mice), do not express hEPO in rats. PBS (phosphate buffered saline) is used as control. Graph A compares the hEPO concentration after administration of nanoparticle compositions containing Compound 23, Compound 11, KL22, and MC3 at 2 mpk, i.v. administration. Compound 11 LNP showed hEPO expression comparable to MC3 and improved tolerability as compared to KL22. Graph B illustrates the results of a dose response study using Compound 20, KL22, and MC3 at dose of 0.2, 0.5 and 1 mpk. KL22 and Compound 23 were shown to be toxic at the 2 mg/kg dose. In Graph A, the numbers 1-5 refer to compositions containing the following: 1: Compound 23, 2: Compound 11, 3: KL22; 4: MC3; 5: PBS. In Graph B, the numbers 1-9 refer to compositions containing the following: 1: Compound 20, 0.2 mpk; 2: Compound 20, 0.5 mpk; 3: Compound 20, 1 mpk; 4: KL22, 0.2 mpk; 5: KL22, 0.5 mpk; 6: KL22, 1 mpk; 7: MC3, 0.2 mpk; 8: MC3, 0.5 mpk; 9: MC3, 1 mpk; 10: PBS.
Figure 9:
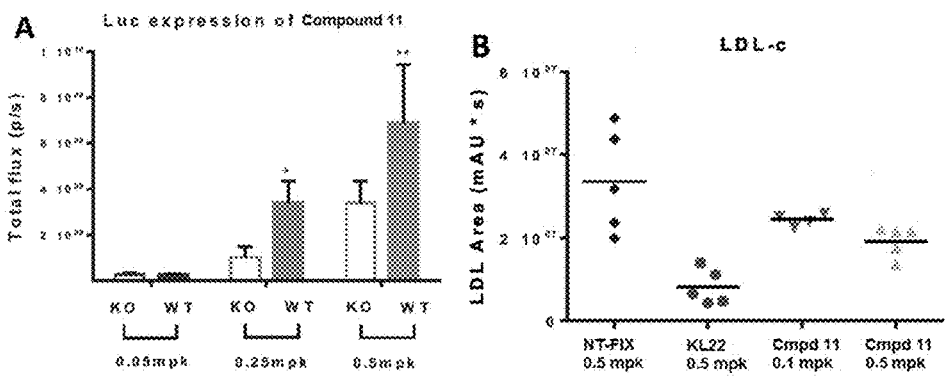
FIG. 9 is a pair of graphs illustrating performance of Compound 11 as an LDLr independent lipid. Graph A is a bar graph showing expression of luciferase induced by administration of nanoparticle compositions including Compound 11 at dosages of 0.05 mpk, 0.25 mpk, and 0.5 mpk to LDLR −/− knockout and wild-type mice. Graph B shows LDL-c levels in LDLR knockout mice after administration of a control mRNA, i.e., non-translating Factor IX ("NT-FIX") and various compositions comprising mRNAs encoding the LDL receptor in mice, with KL22 at 0.5 mpk, or with Compound 11 at 0.5 and 1 mpk. LDL-c levels in mice were found to drop with nanoparticle composition containing Compound 11.
Figure 10:
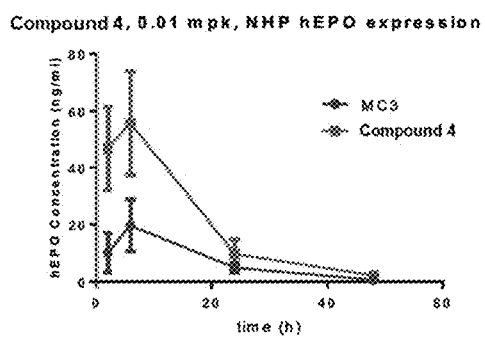
FIG. 10 is a graph showing hEPO levels in non-human primates up to ~50 h after administration of a nanoparticle composition containing Compound 4, compared to a composition containing MC3. The Compound 4 LNP demonstrated 3-fold expression of hEPO compared to MC3, establishing Compound 4 as an LDLr independent lipid that translates to higher species.
Figure 11:
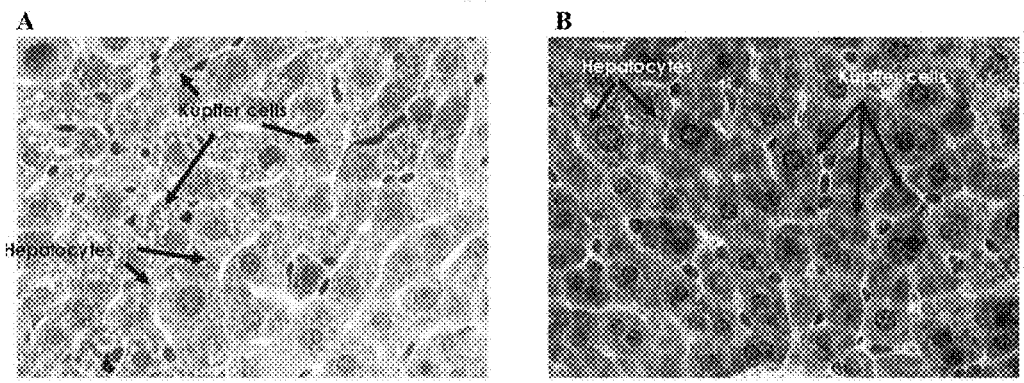
FIG. 11 is a pair of images comparing the results of a mouse liver immunohistochemistry (IHC) using mRNA expressing green fluorescent protein (GFP) after administration of nanoparticle compositions containing Compound 4 and MC3. Graph A shows CD-1 mouse liver cells after administration of GFP mRNA in a MC3 LNP, 6 h after intravenous administration at a dose of 0.5 mpk. GFP mRNA Protein expression from the MC3 LNP composition was observed in both hepatocytes and Kupffer cells. Graph B shows LDLR knockout mouse liver cells after administration of GFP mRNA in a Compound 4 LNP, 8 h after intravenous administration at a dose of 0.5 mpk. In contrast to MC3, the LNP containing Compound 4 appears to show less protein expression in Kupffer cells.
Figure 12:
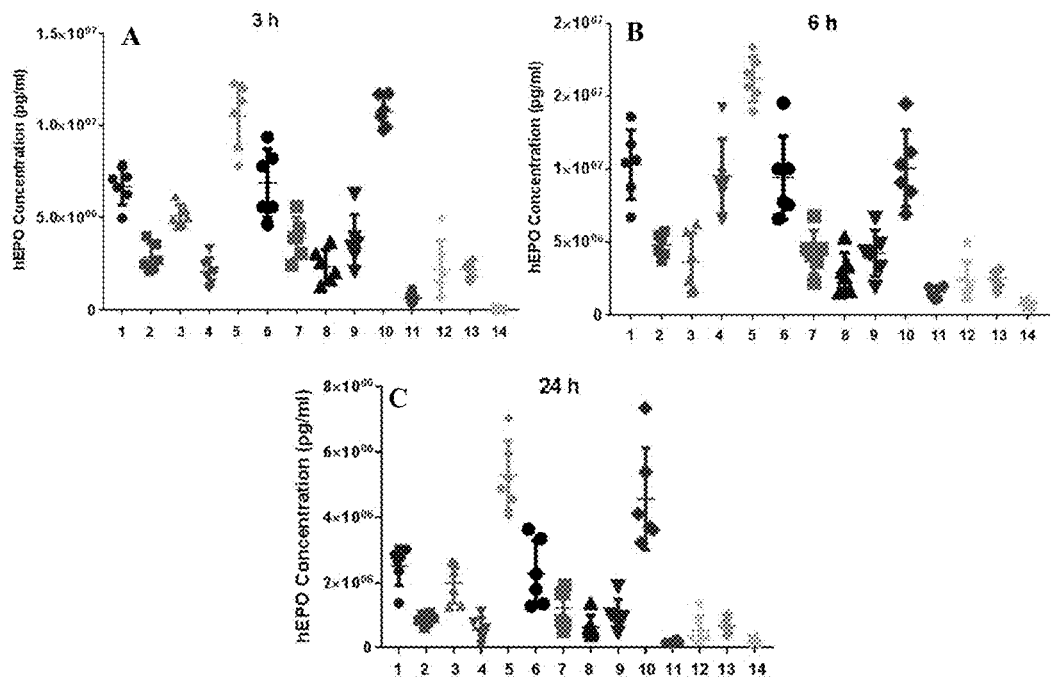
FIG. 12 is a set of graphs illustrating hEPO expression levels in CD-1 mice dosed with compounds of the disclosure, compared to MC3. PBS is used as control. Graph A shows the hEPO concentration 3 h after administration of the nanoparticle compositions. Graph B shows the hEPO concentration 6 h after administration of the nanoparticle compositions. Graph C shows the hEPO concentration 24 h after administration of the nanoparticle compositions. In graphs A-C numbers 1-14 refer to compositions containing the following: 1: Compound 73, 2: Compound 80, 3: Compound 70; 4: Compound 81; 5: Compound 69; 6: Compound 82; 7: Compound 83; 8: Compound 62; 9: Compound 84; 10: Compound 85; 11: Compound 86; 12: Compound 87; 13: MC3; 14: PBS.
Figure 13:
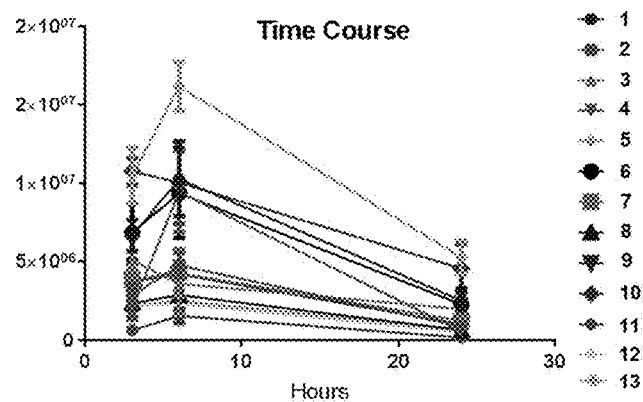
FIG. 13 is a graph showing hEPO levels (pg/mL) in CD-1 mice up to ~25 h after administration of a nanoparticle composition containing compounds of the disclosure, compared to a composition containing MC3. Numbers 1-13 refer to compositions containing the following: 1: Compound 73, 2: Compound 80, 3: Compound 70; 4: Compound 81; 5: Compound 69; 6: Compound 82; 7: Compound 83; 8: Compound 62; 9: Compound 84; 10: Compound 85; 11: Compound 86; 12: Compound 87; 13: MC3.
Figure 16:
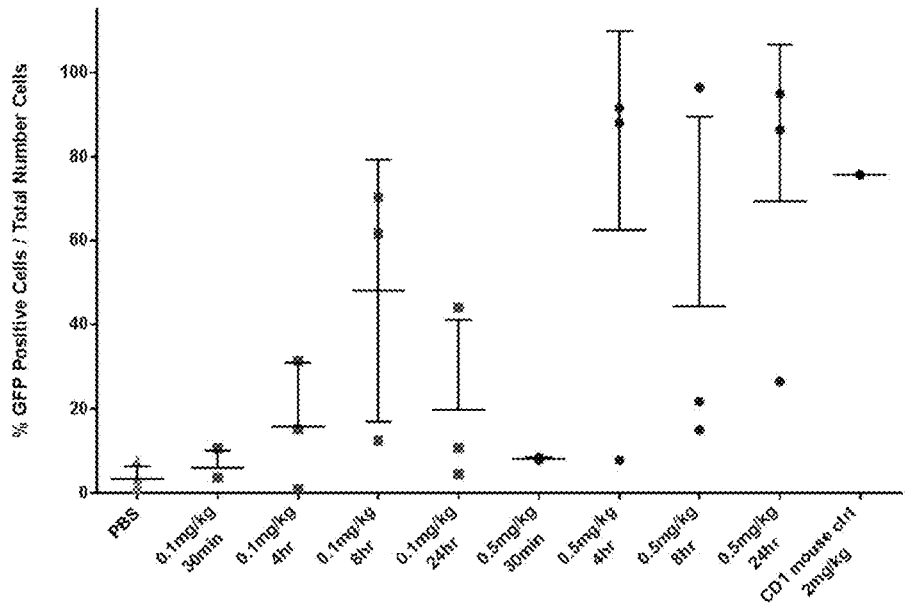
FIG. 16 is a graph showing GFP levels in the livers of LDLR knockout mice at 30 min to 24 h after intravenous administration of an eGFP RNA in a lipid composition containing Compound 4. The liver GFP levels were determined via IHC. The square markers represent the number of GFP positive cells following administration of a dose of 0.1 mpk of the composition. The circular markers represent the number of GFP positive cells following administration of a dose of 0.5 mpk of the composition.
Figure 17:
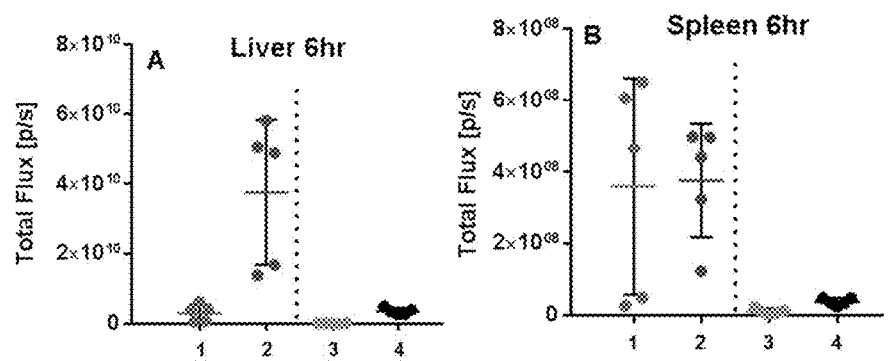
FIG. 17 is a pair of graphs showing the ApoE dependence of luciferase ("Luc") expression following administration of a composition containing Luc mRNA and Compound 4 to mice at a dose 0.5 mpk. The expression following administration of a composition containing Luc mRNA and MC3 is presented for comparison. Graph A shows the total flux in the liver 6 h after administration. The % change in Luc expression in livers of ApoE knockout vs. wild-type mice (i.e., (WT mean expression-KO mean expression)/WT mean expression]*100%) was 91.9% for Compound 4 and 97.5% for MC3. Graph B shows the total flux in the spleen 6 h after administration. The % change in expression in spleens of ApoE knockout vs. wild-type mice was 4.34% for Compound 4 and 72.2% for MC3. Numbers 1-4 refer to the following: 1: Composition containing Compound 4, administered to ApoE knockout mice; 2: Composition containing Compound 4, administered to wild-type mice; 3: Composition containing MC3, administered to ApoE knockout mice; 4: Composition containing MC3, administered to wild-type mice.
Figure 18:
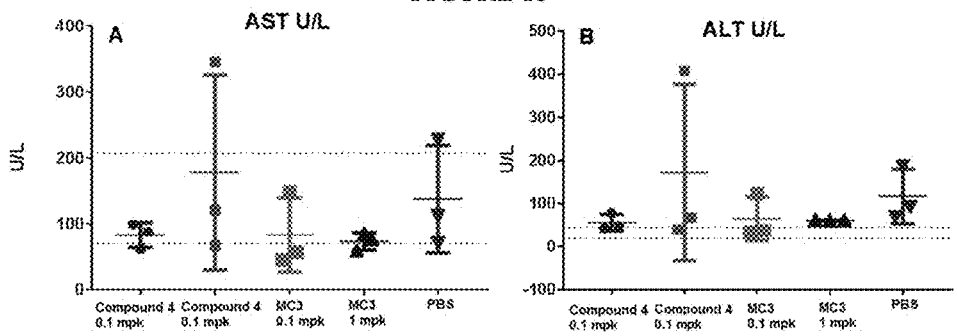
FIG. 18 is a pair of graphs showing the effect of a composition containing Compound 4 on liver enzymes. The composition was administered to rats at 0.1 mpk and 1 mpk. The effects of MC3 are shown for comparison. PBS is used as a control. Graph A shows the effect on aspartate aminotransferase (AST). Graph B shows the effect on alanine aminotransferase (ALT).
Figure 19:
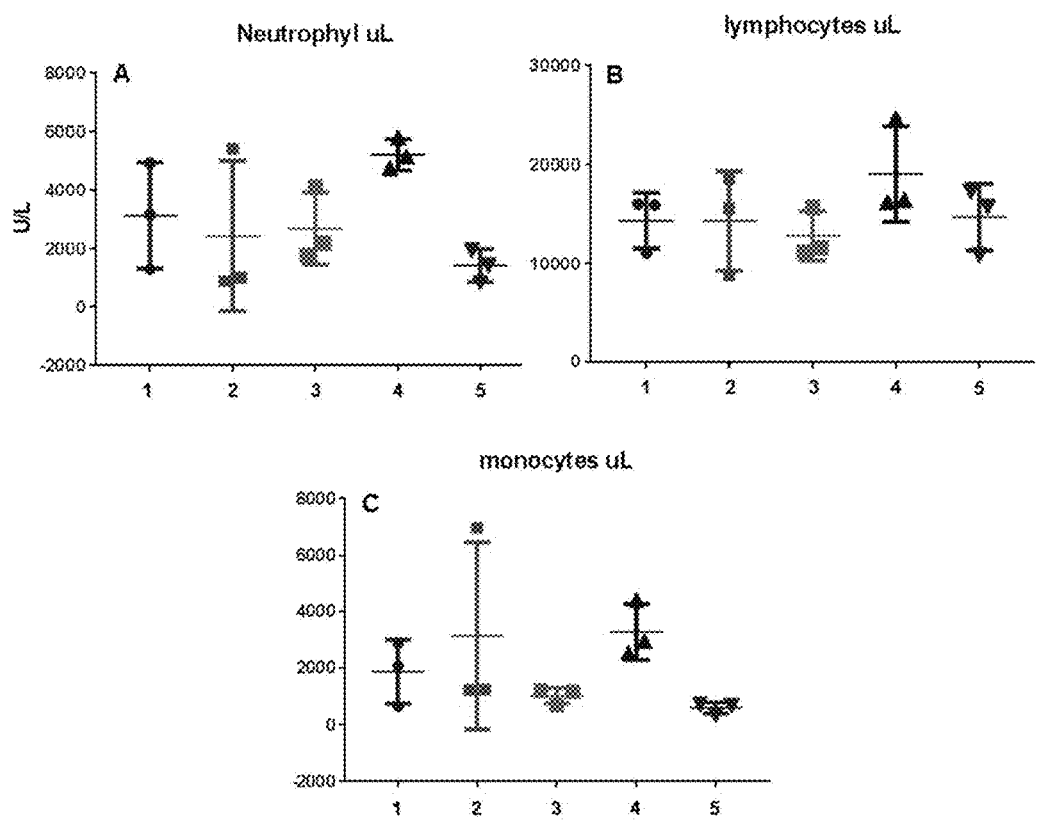
FIG. 19 is a set of graphs showing immune cell activation by a composition containing Compound 4. The effects of MC3 are shown for comparison. PBS (phosphate buffered saline) is used as control. Compositions were administered to rats at 0.1 mpk or 1 mpk. Graph A shows the effect on activation of neutrophil. Graph B shows the effect on activation of lymphocytes. Graph C shows the effect on activation of monocytes. Numbers 1-5 in Graphs A-C refer to the following: 1: Compound 4, 0.1 mpk; 2: Compound 4; 1 mpk; 3: MC3, 0.1 mpk 4: MC3, 1 mpk; 5: PBS.
Figure 20:
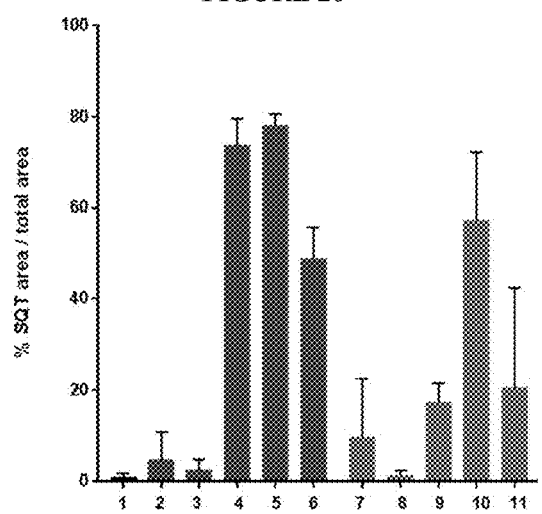
FIG. 20 is a graph showing the expression of Stefin A Quadruple Mutant-Tracy (SQT) protein in mouse liver determined via FLAG IHC at different time points following intravenous administration of various nanoparticle compositions comprising SQT mRNA and lipids disclosed herein. Numbers 1-11 in the figure refer to the following: 1: 0 h, PBS; 2: 0 h, Compound 4; 3: 0.5 h, Compound 4; 4: 4 h, Compound 4; 5: 8 h, Compound 4; 6: 24 h, Compound 4; 7: 0 h, MC3; 8: 0.5 h, MC3; 9: 4 h, MC3; 10: 8 h, MC3; 11: 24 h, MC3.

The disclosure relates to novel lipids and lipid nanoparticle compositions including a novel lipid. The disclosure also provides methods of delivering a therapeutic and/or prophylactic agent to a mammalian cell, specifically delivering a therapeutic and/or prophylactic agent to a mammalian organ, producing a polypeptide of interest in a mammalian cell, and treating a disease or disorder in a mammal in need thereof. For example, a method of producing a polypeptide of interest in a cell involves contacting a nanoparticle composition comprising an mRNA with a mammalian cell, whereby the mRNA may be translated to produce the polypeptide of interest. A method of delivering a therapeutic and/or prophylactic agent to a mammalian cell or organ may involve administration of a nanoparticle composition including the therapeutic and/or prophylactic agent to a subject, in which the administration involves contacting the cell or organ with the composition, whereby the therapeutic and/or prophylactic agent is delivered to the cell or organ.

Lipids

The present disclosure provides lipids including a central piperazine moiety. The lipids described herein may be advantageously used in lipid nanoparticle compositions for the delivery of therapeutic and/or prophylactic agents to mammalian cells or organs. For example, the lipids described herein have little or no immunogenicity. For example, the lipid compound of any of formulae (I), (Ia1)-(Ia6), (Ib), (II), (IIa), (III), (IIIa), (IV), (17-I), (19-I), (19-II), (20-I) and (21-I) has a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent.

Lipids may be compounds of formula (I),

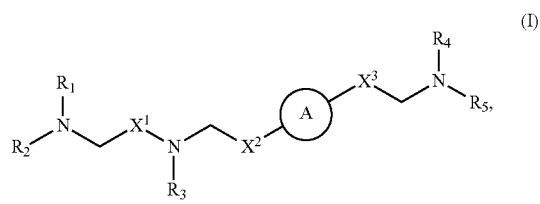
(I)

or salts or isomers thereof, wherein
ring A is

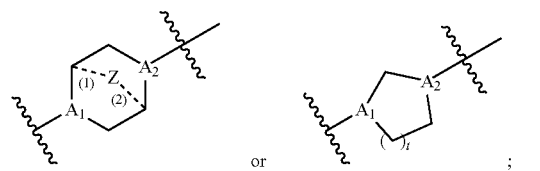

t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$X^1$, $X^2$, and $X^3$ are independently selected from the group consisting of a bond, —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;
each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and
each R" is independently selected from the group consisting of $C_{3-12}$ alkyl and $C_{3-12}$ alkenyl,
wherein when ring A is

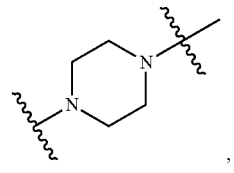 [SMILES: *N1CCN(*)CC1]

then
i) at least one of $X^1$, $X^2$, and $X^3$ is not —CH$_2$—; and/or
ii) at least one of $R_1$, $R_2$, $R_3$, $R_4$, and $R_5$ is —R"MR'.

In some embodiments, the compound is of any of formulae (Ia1)-(Ia6):

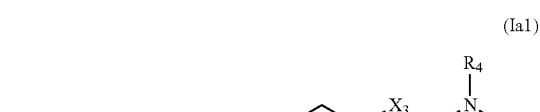
(Ia1)

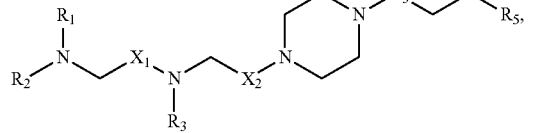
(Ia2)

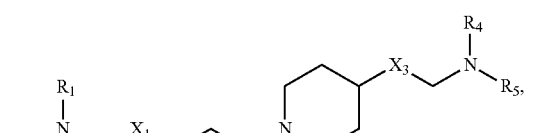
(Ia3)

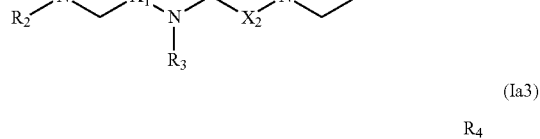
(Ia4)

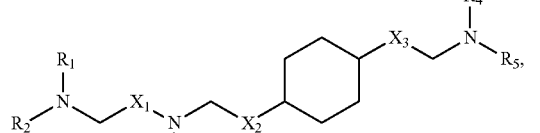
(Ia5)

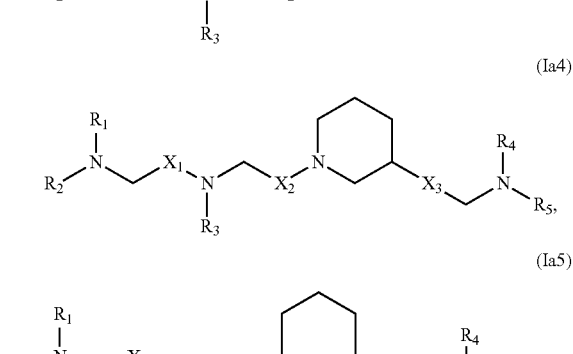

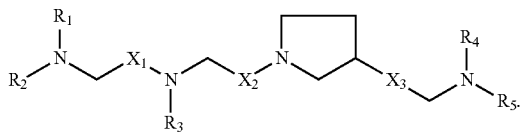

(Ia6)

The compounds of Formula (I) or any of (Ia1)-(Ia6) include one or more of the following features when applicable.

In some embodiments, ring A is

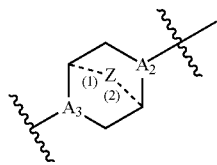

In some embodiments, ring A is

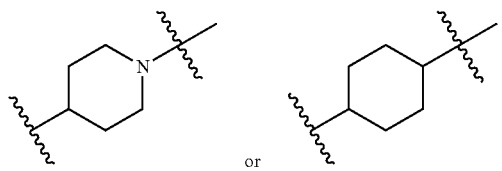

In some embodiments, ring A is

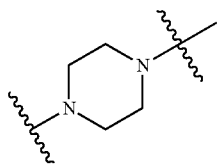

In some embodiments, ring A is

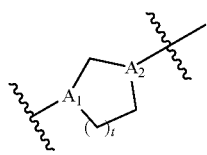

In some embodiments, ring A is

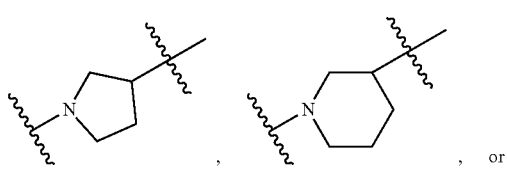

In some embodiments, ring A is

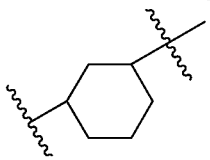

In some embodiments, ring A is

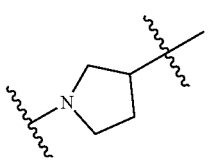 or 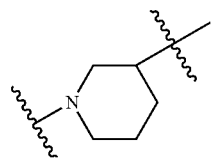

wherein ring, in which the N atom is connected with $X^2$.

In some embodiments, Z is $CH_2$.
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.
In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.
In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.
In some embodiments, $X^3$ is a bond or —$(CH_2)_2$—.
In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.
In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.
In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In certain embodiments, the compound is selected from the group consisting of:
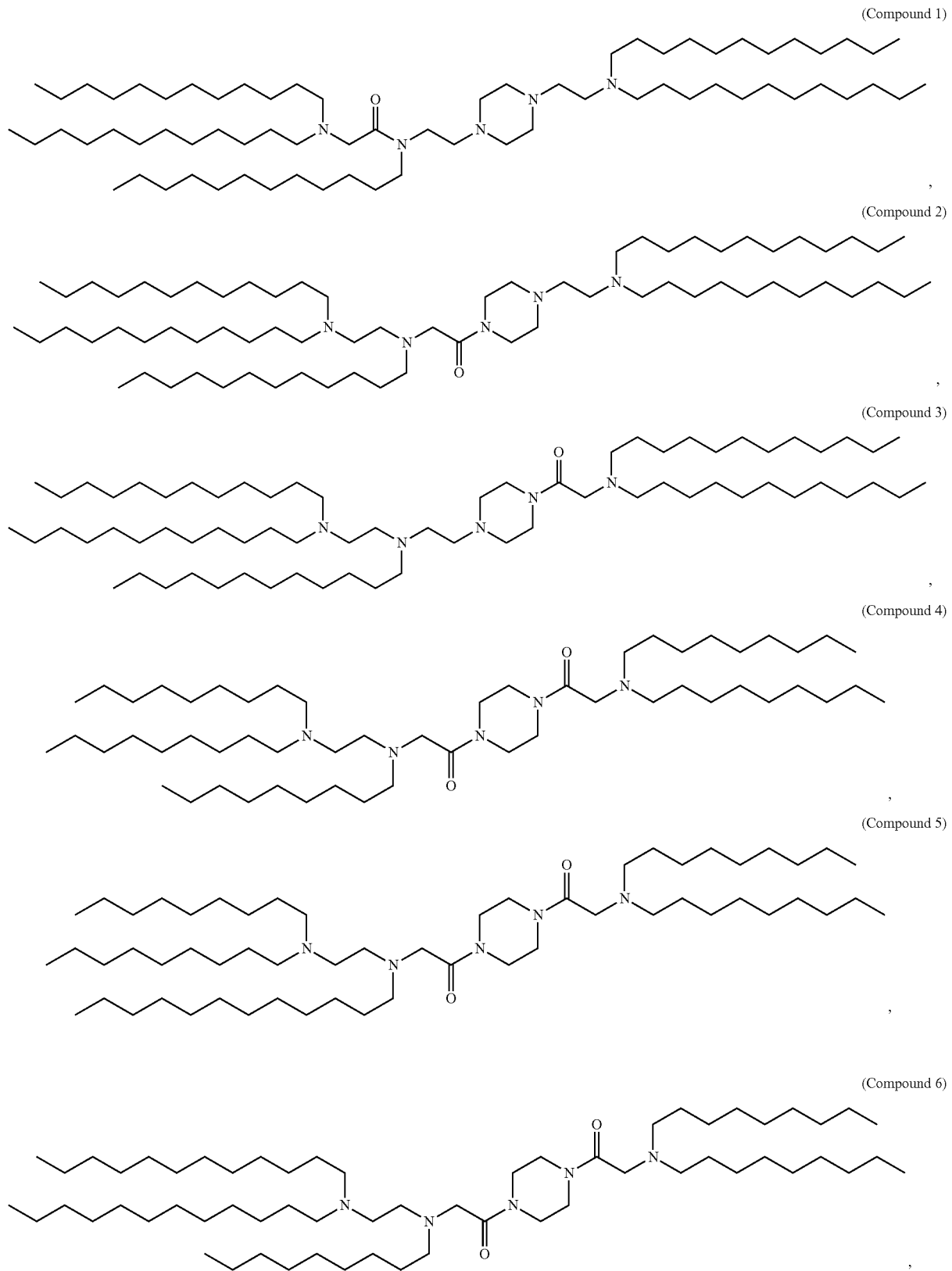

(Compound 7)
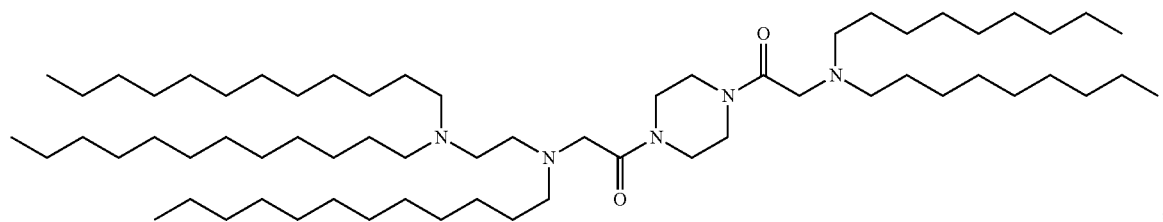
(Compound 8)
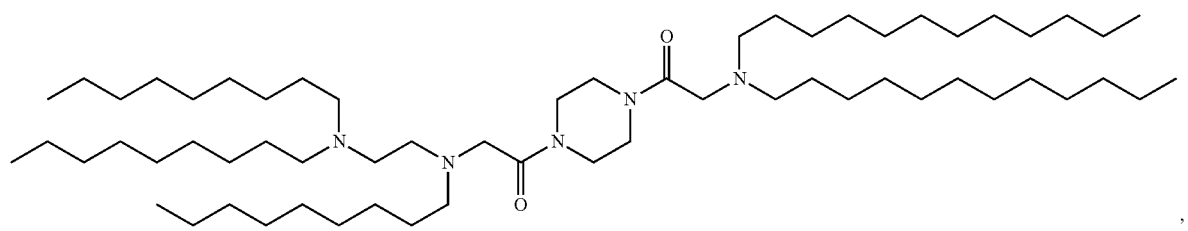
(Compound 9)
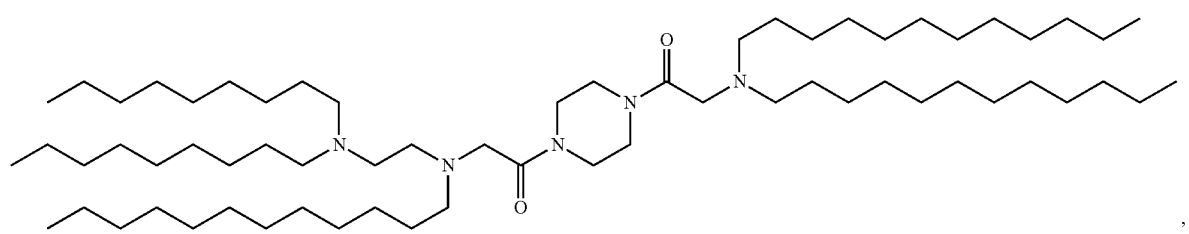
(Compound 10)
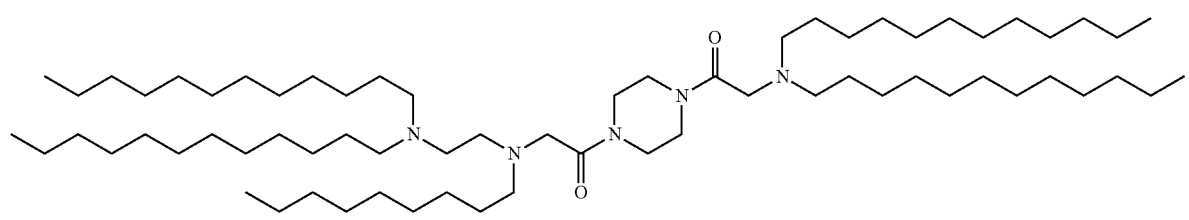
(Compound 11)
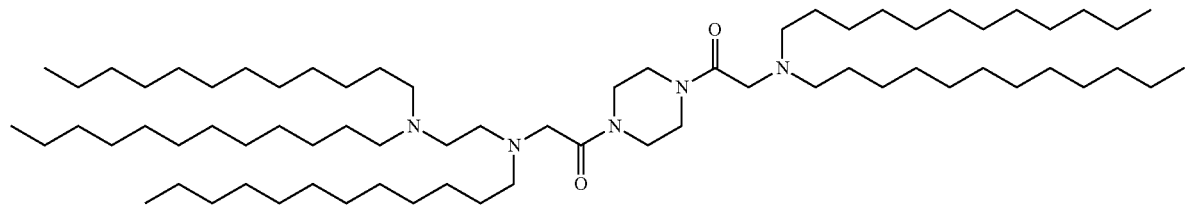
(Compound 12)
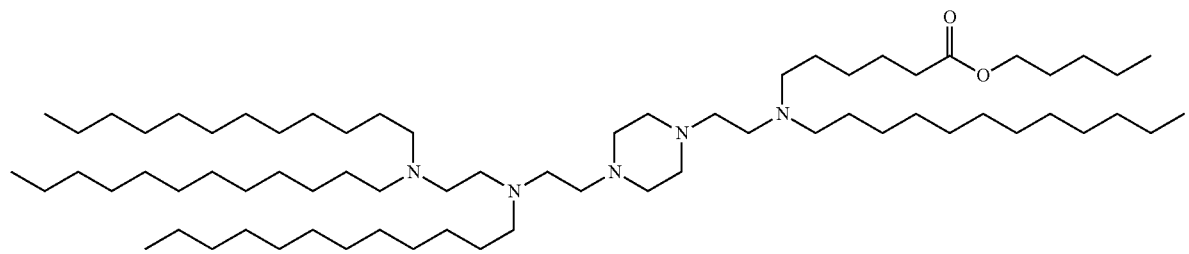

(Compound 13)
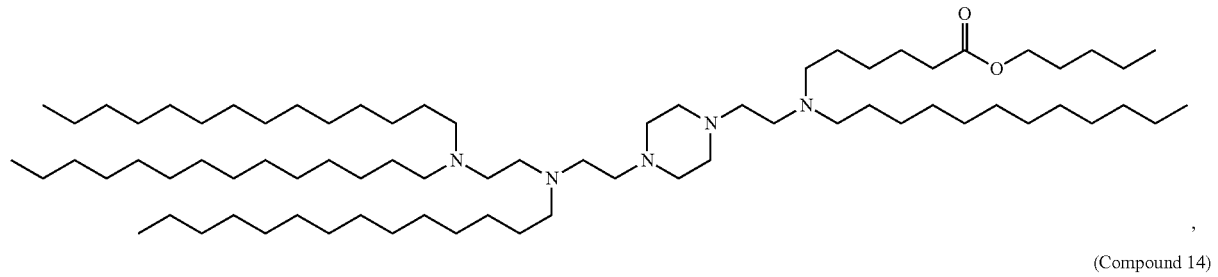
(Compound 14)
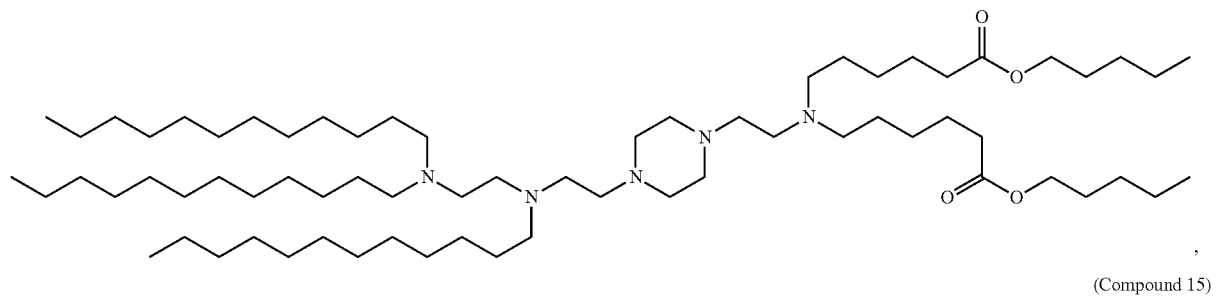
(Compound 15)
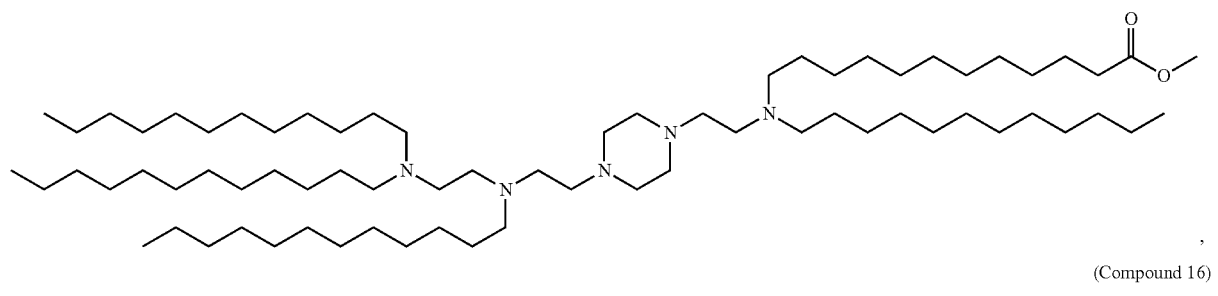
(Compound 16)
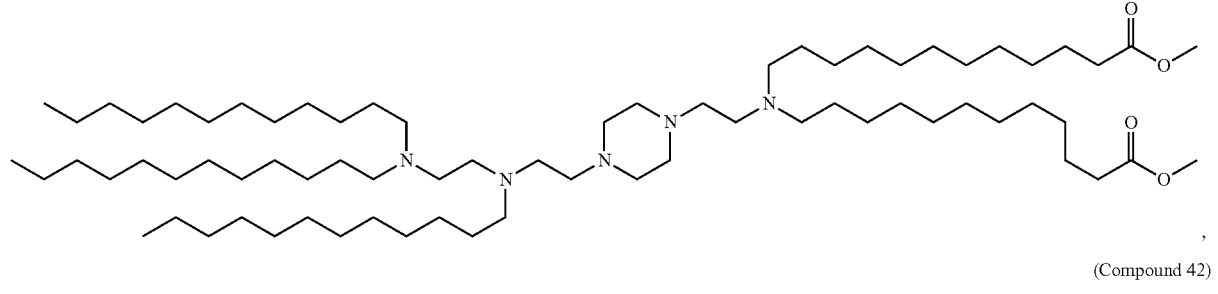
(Compound 42)
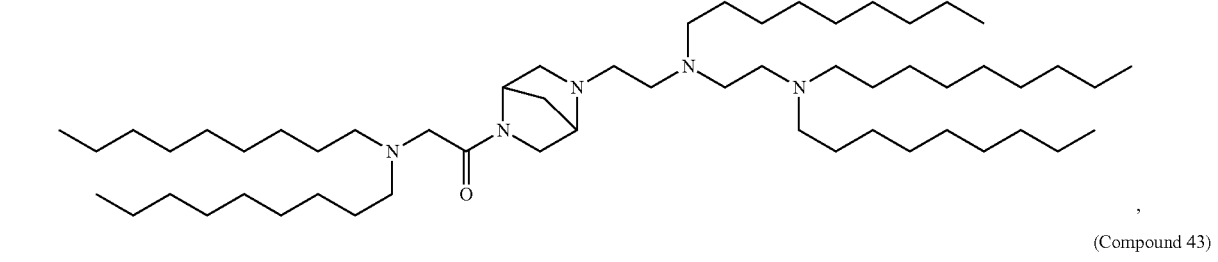
(Compound 43)
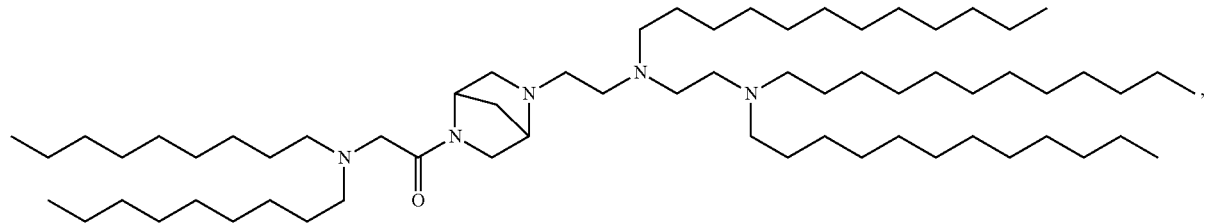

-continued
(Compound 44)
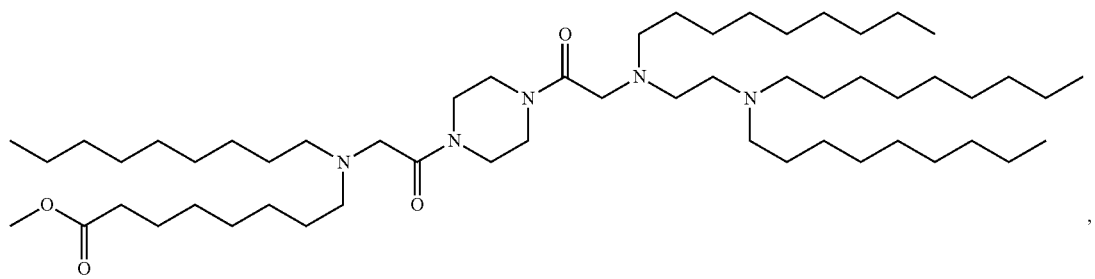
(Compound 45)
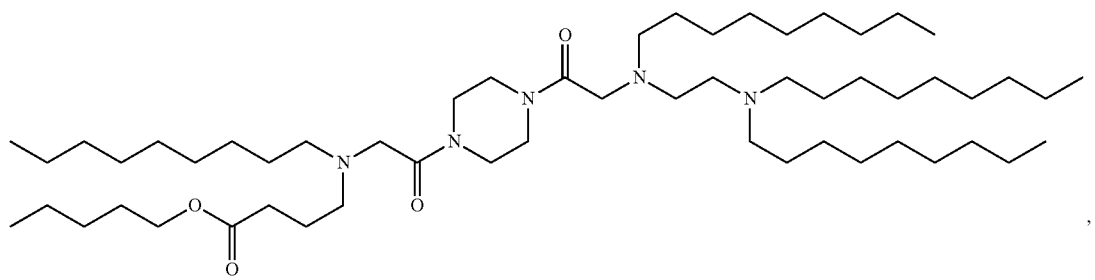
(Compound 46)
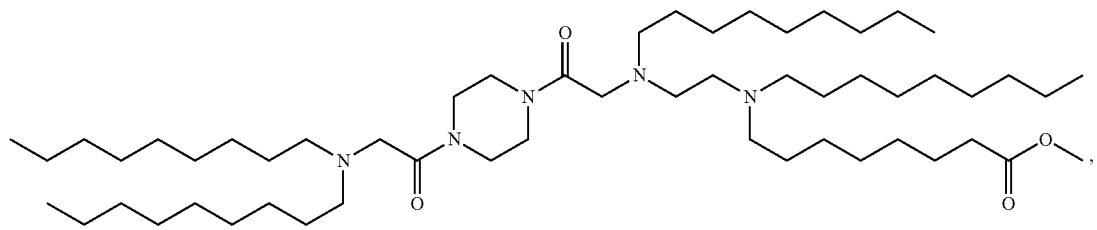
(Compound 47)
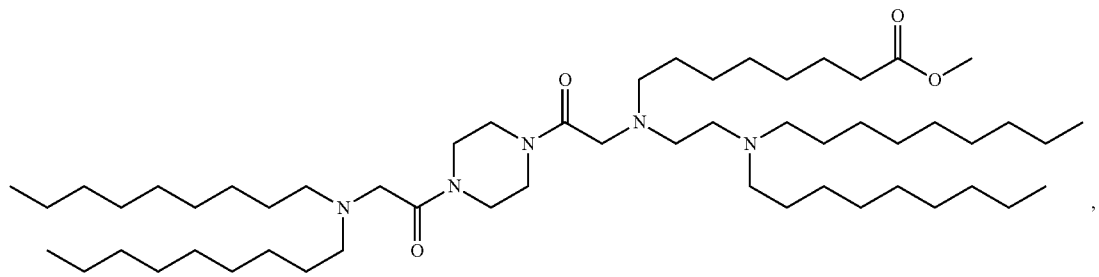
(Compound 48)
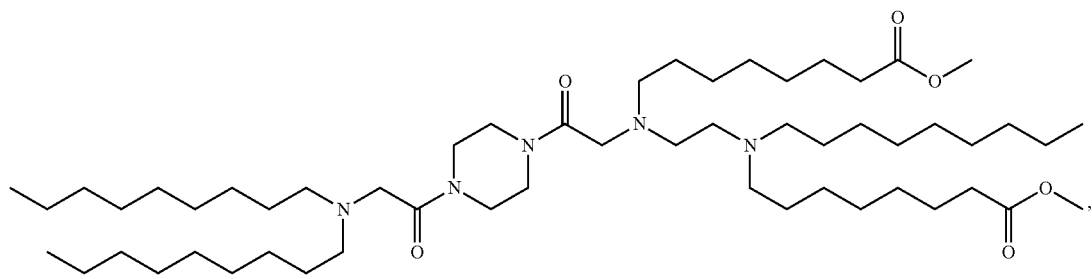

-continued
(Compound 49)
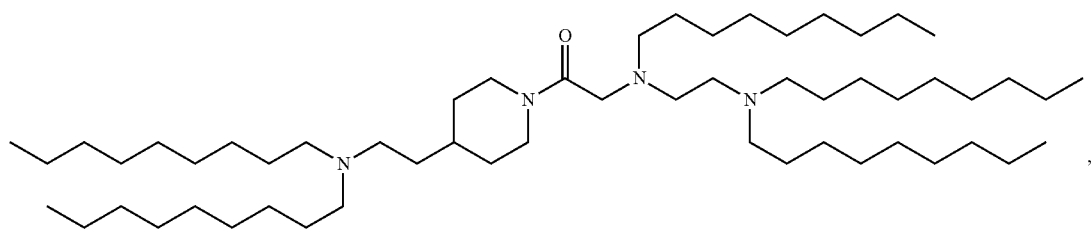
(Compound 50)
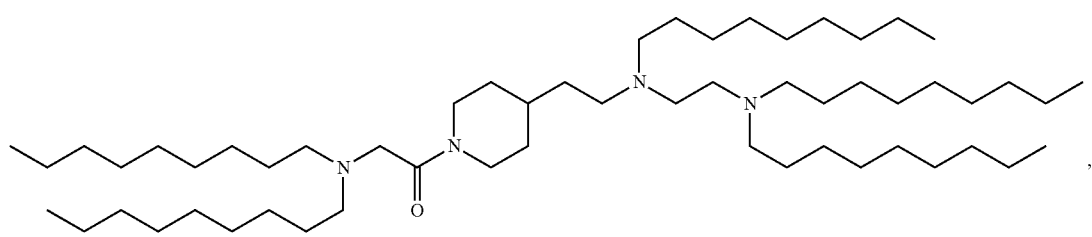
(Compound 51)
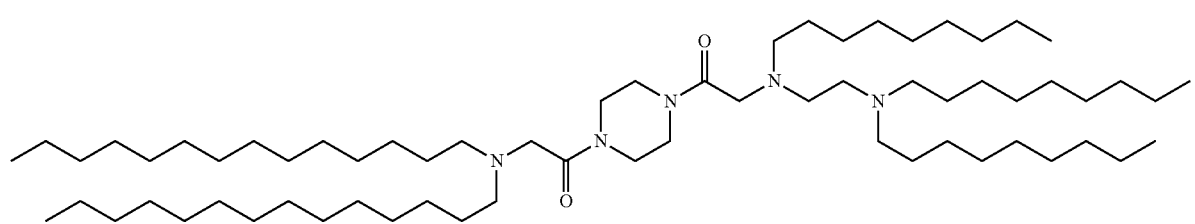
(Compound 52)
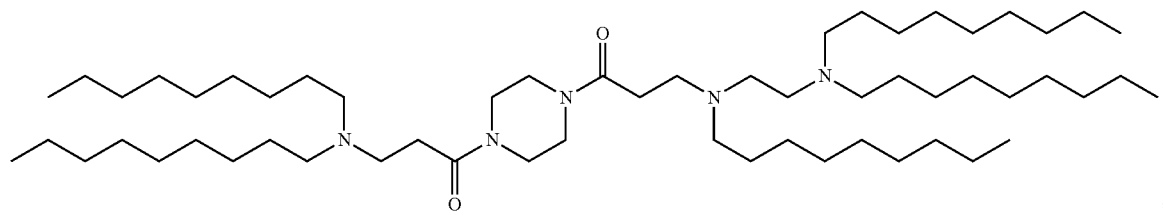
(Compound 53)
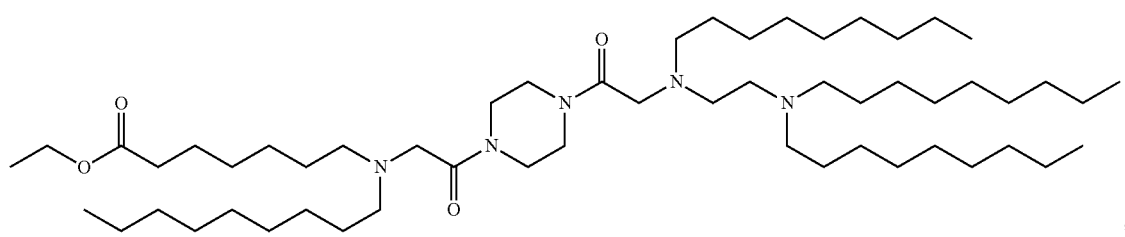
(Compound 54)
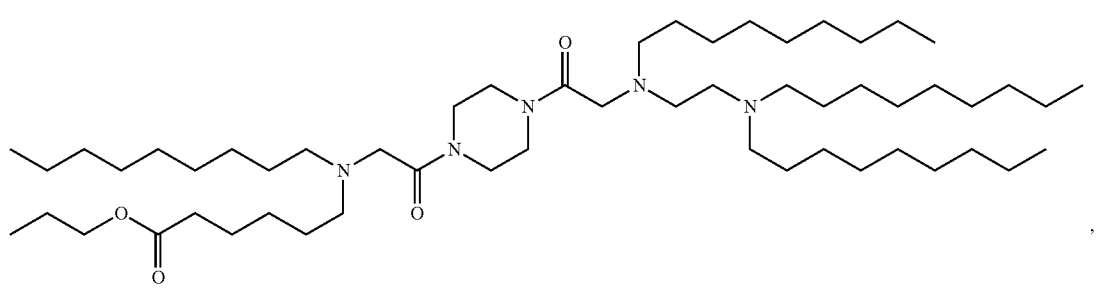

(Compound 55)
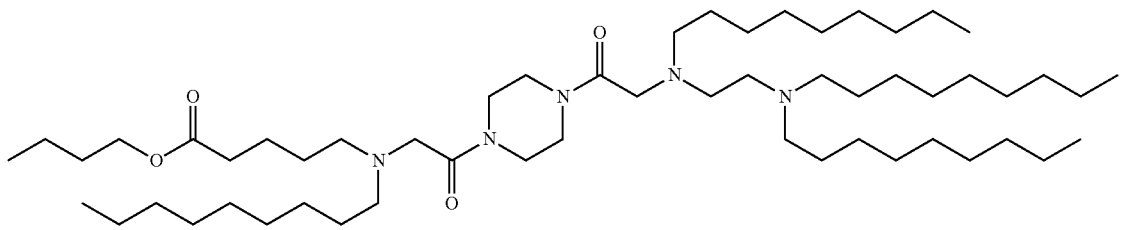
(Compound 56)
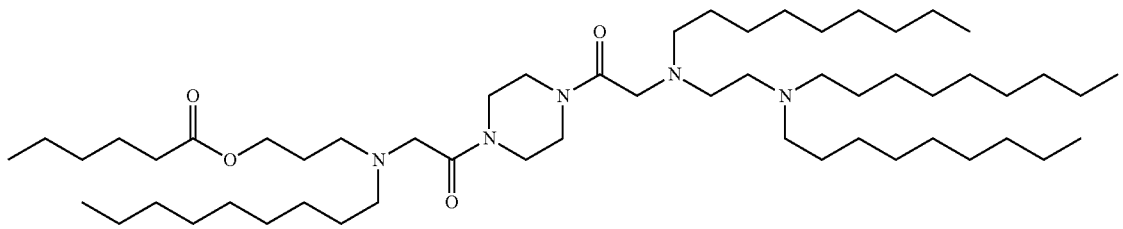
(Compound 57)
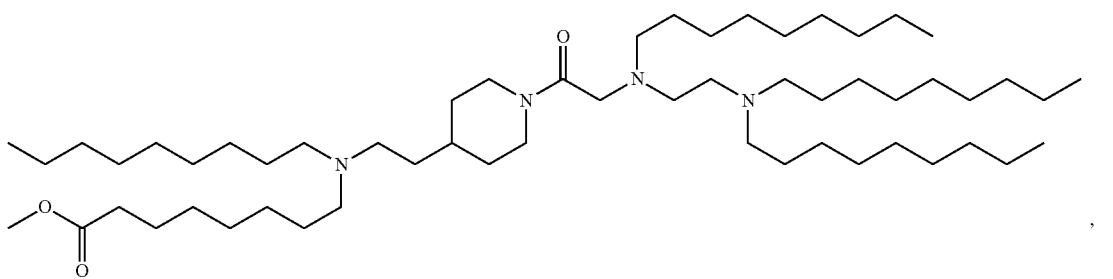
(Compound 58)
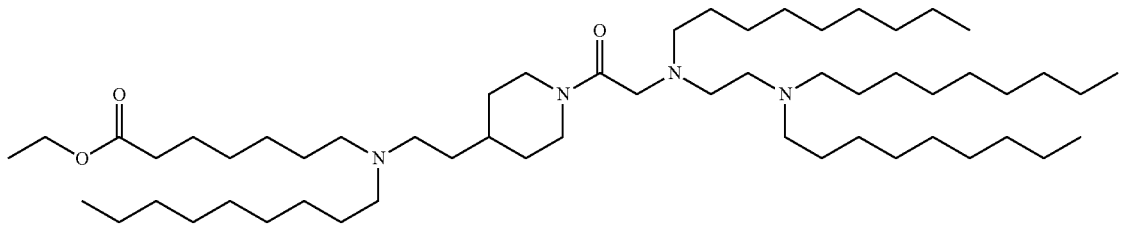
(Compound 59)
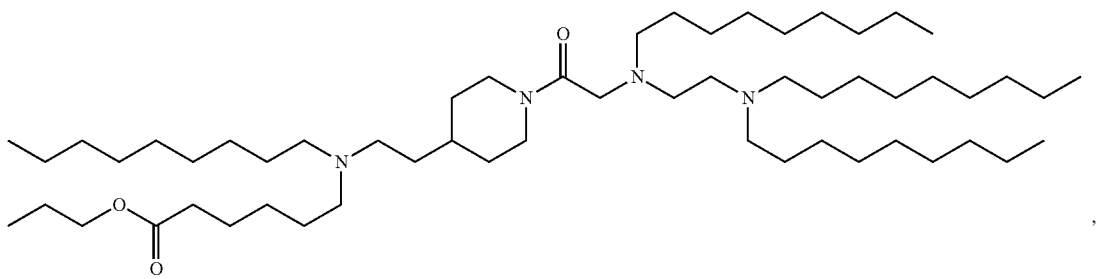
(Compound 60)
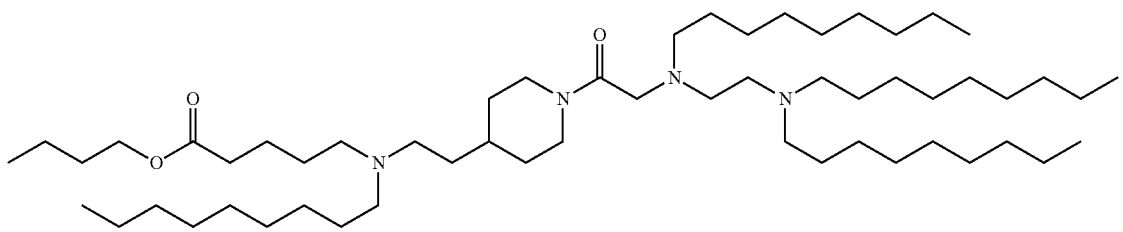

(Compound 61)
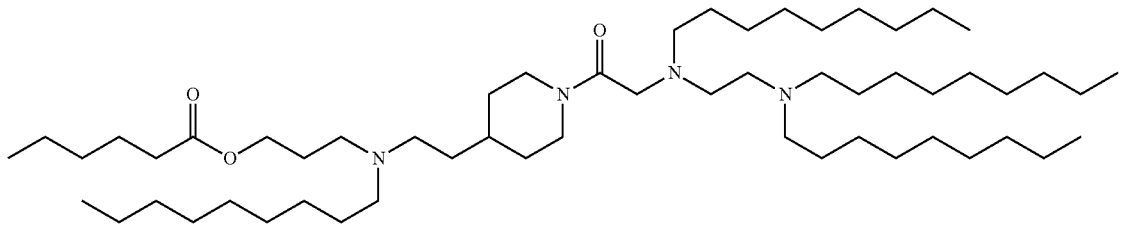
,
(Compound 62)
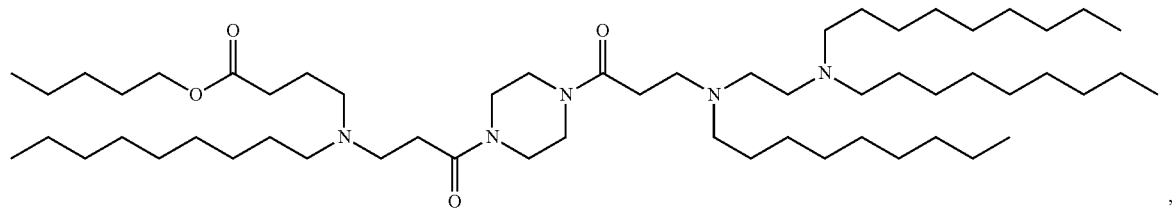
,
(Compound 63)
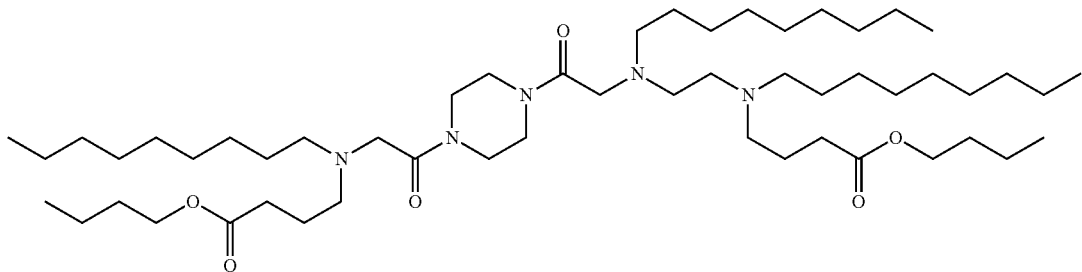
,
(Compound 64)
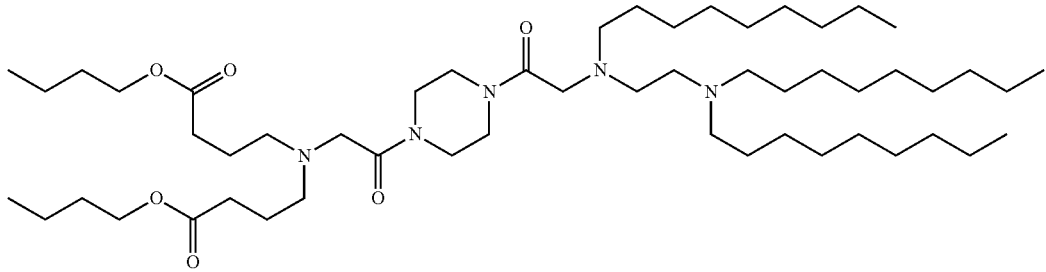
,
(Compound 65)
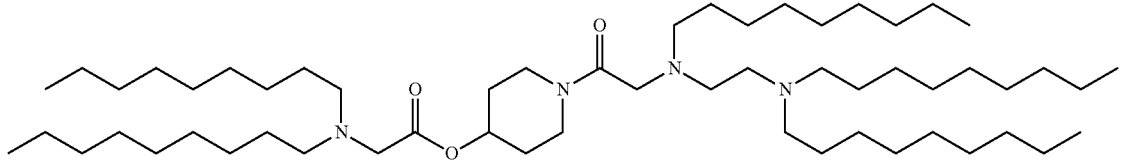
,
(Compound 66)
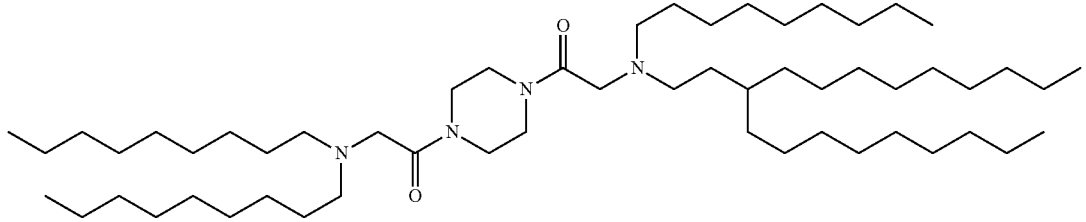
, -continued
(Compound 68)
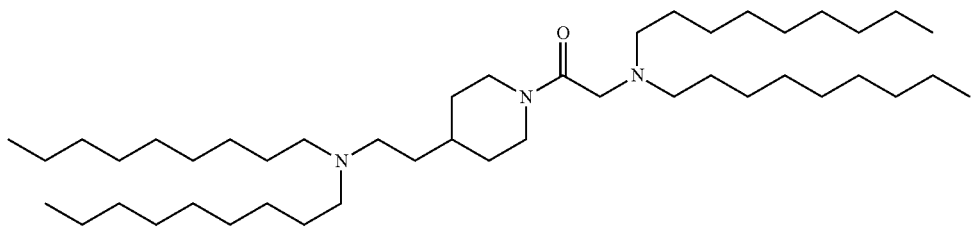
(Compound 69)
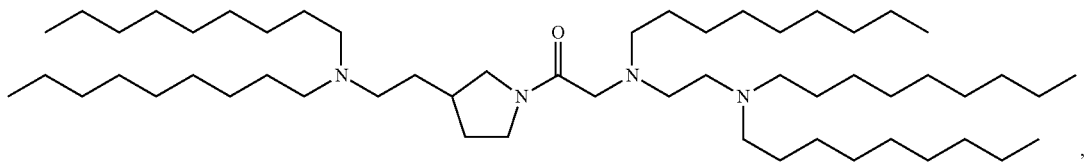
(Compound 70)
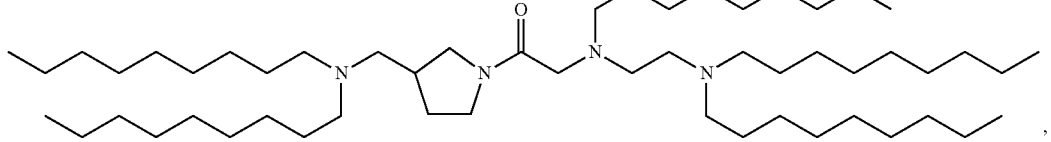
(Compound 71)
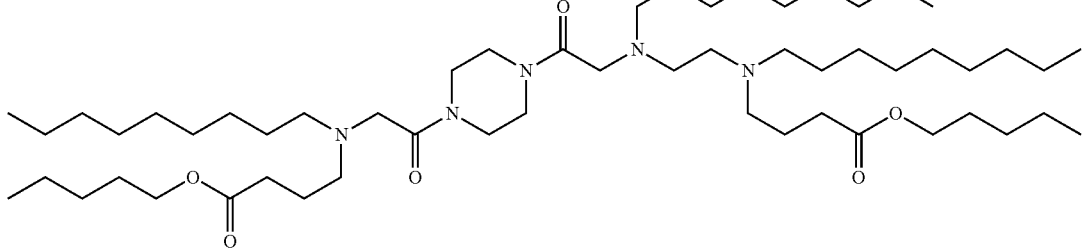
(Compound 72)
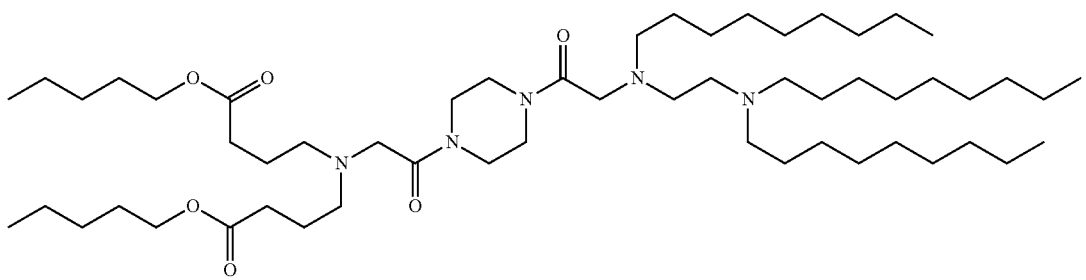
(Compound 73)
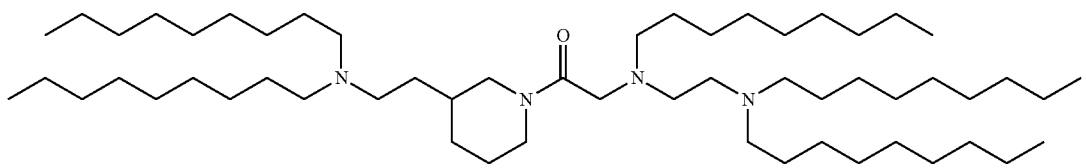

(Compound 74)
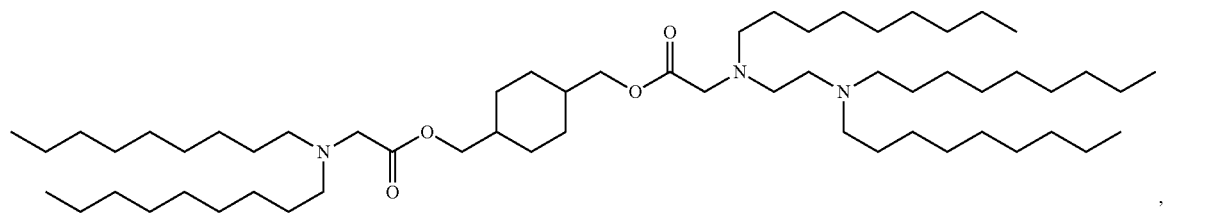
,
(Compound 75)
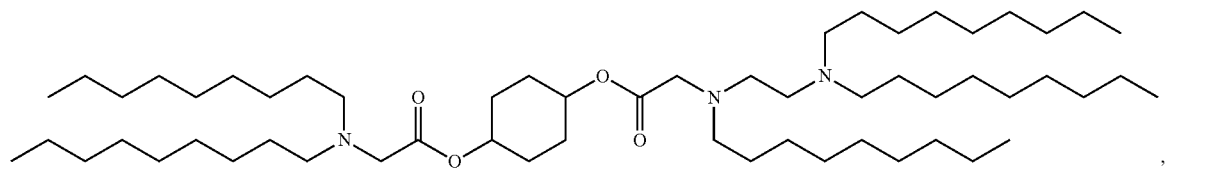
,
(Compound 76)
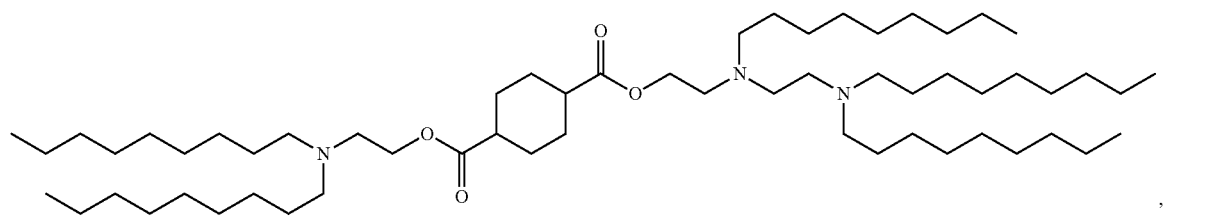
,
(Compound 78)
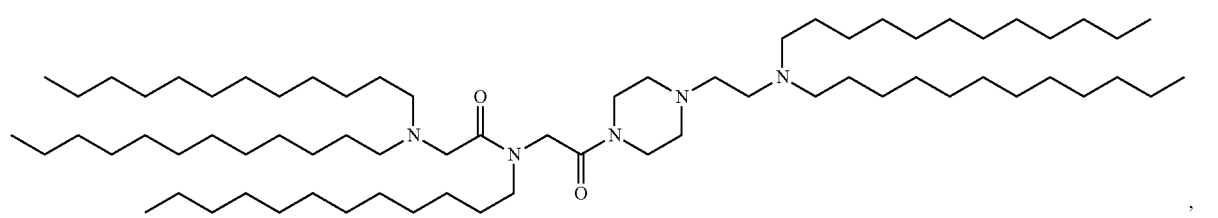
,
(Compound 79)
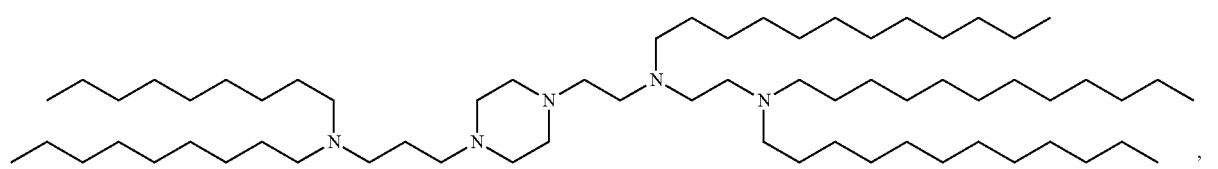
,
(Compound 80)
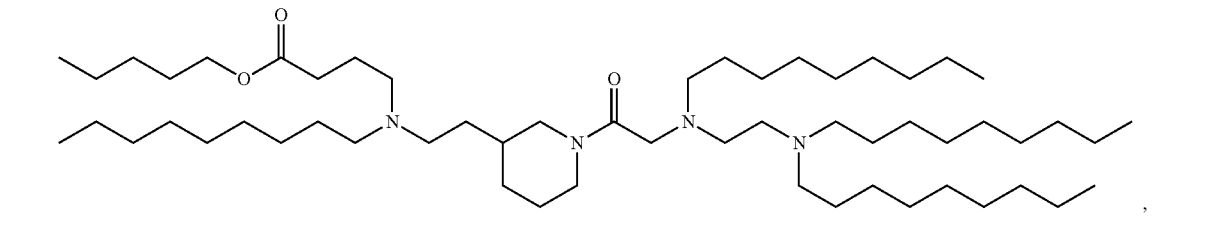
,
(Compound 81)
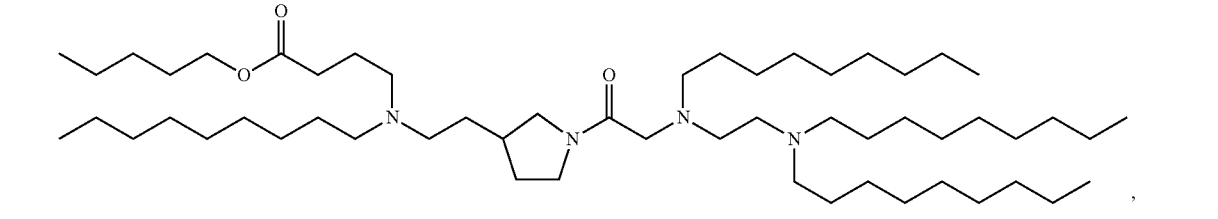
, -continued
(Compound 82)
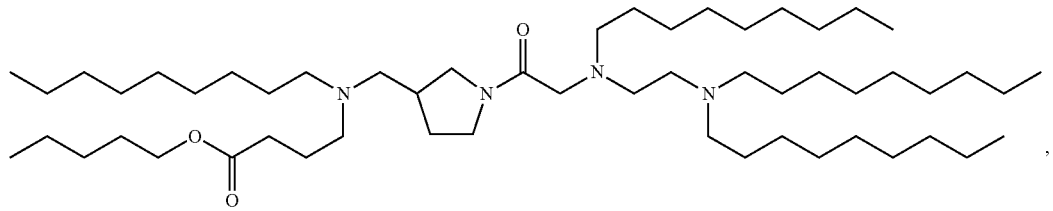
(Compound 83)
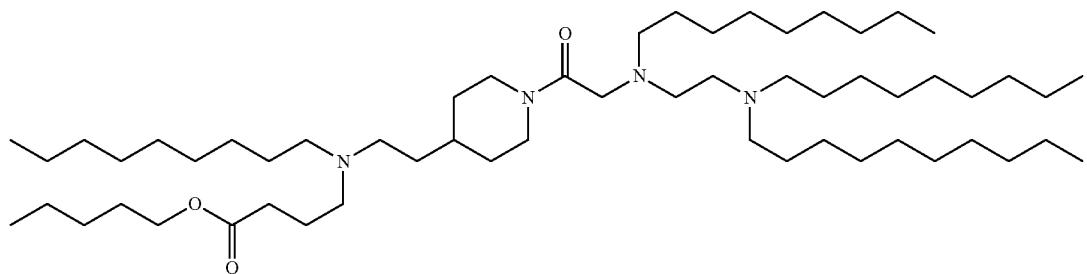
(Compound 84)
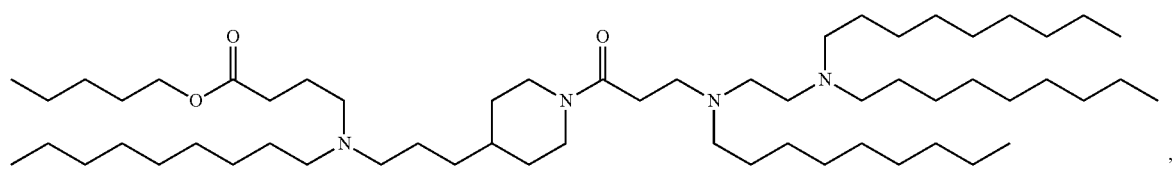
(Compound 85)
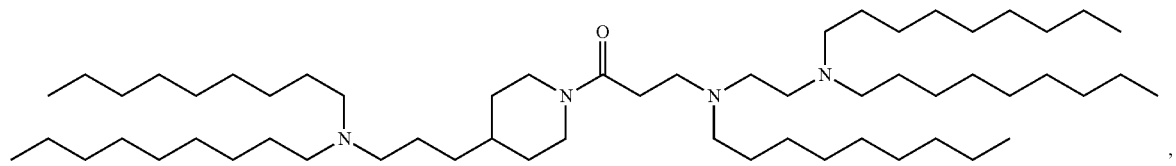
(Compound 86)
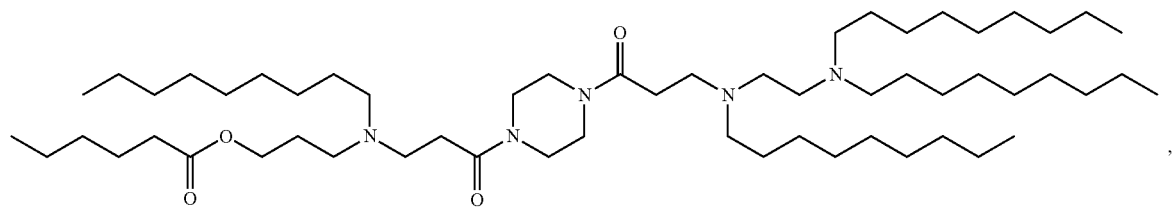
(Compound 87)
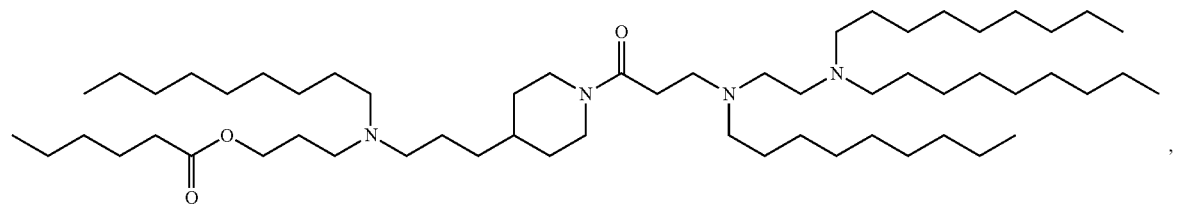

(Compound 88)
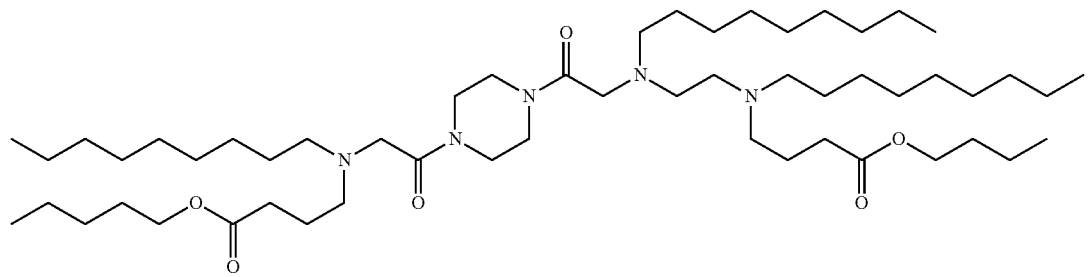
(Compound 89)
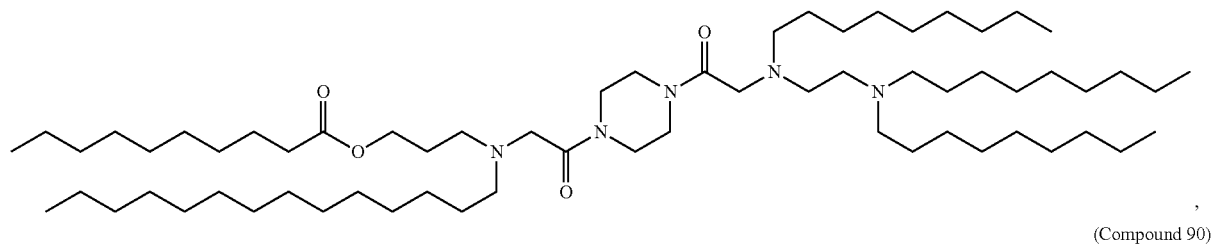
(Compound 90)
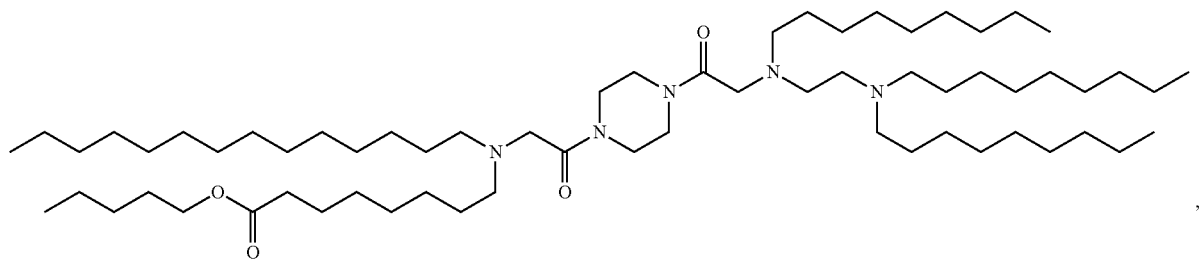
(Compound 91)
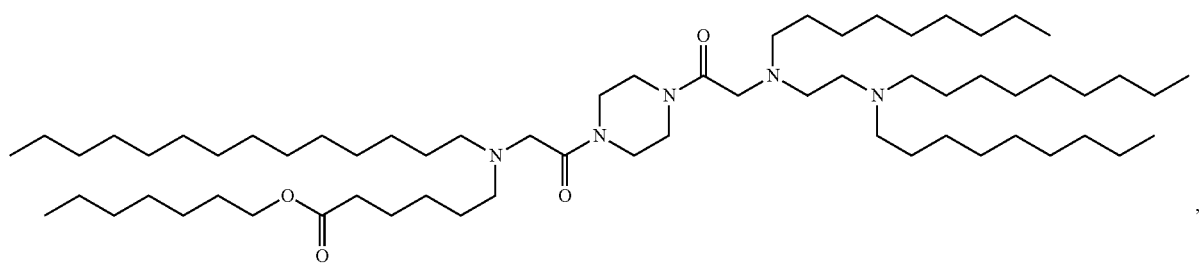
(Compound 92)
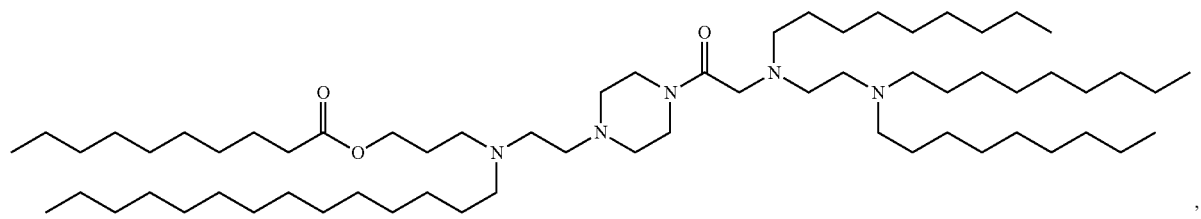
(Compound 93)
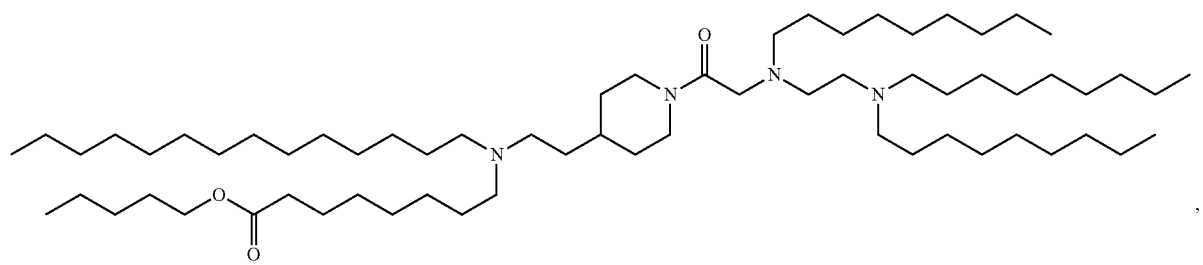

-continued
(Compound 94)
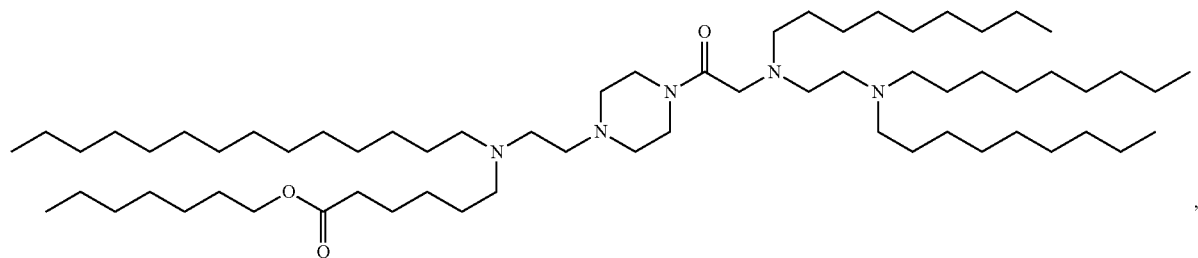
(Compound 95)
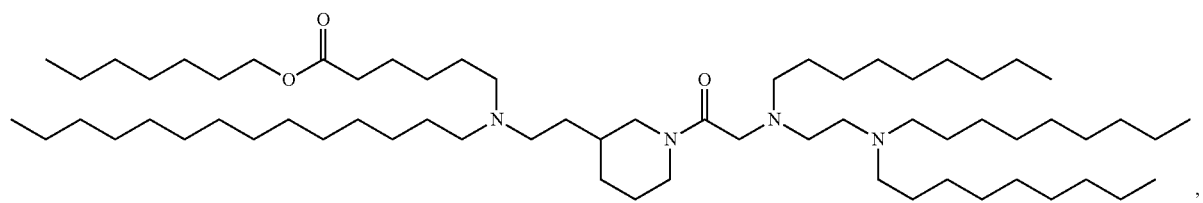
(Compound 96)
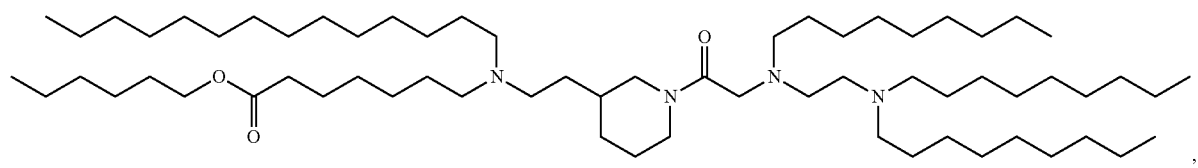
(Compound 97)
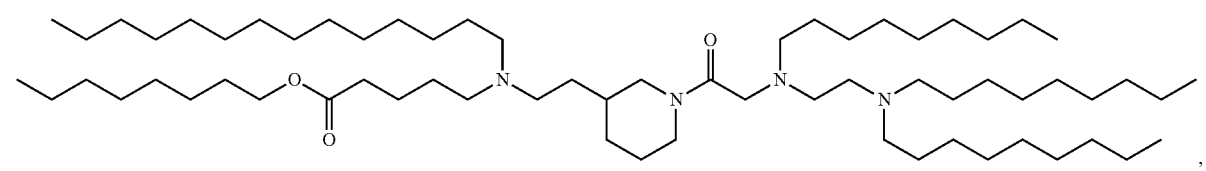
(Compound 98)
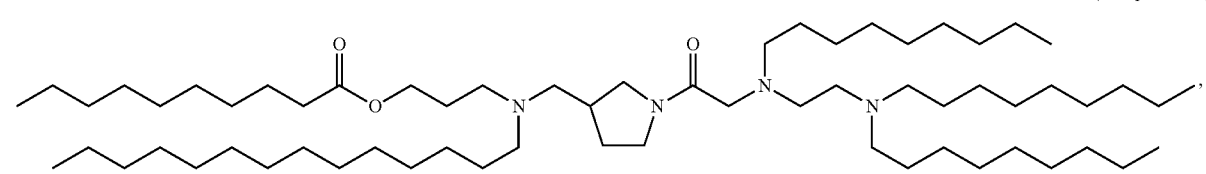
(Compound 99)
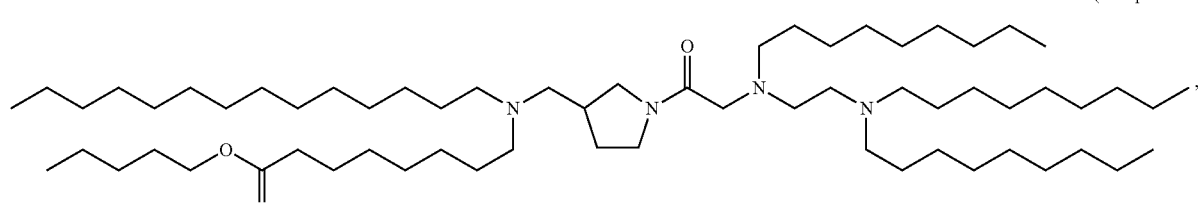
(Compound 100)
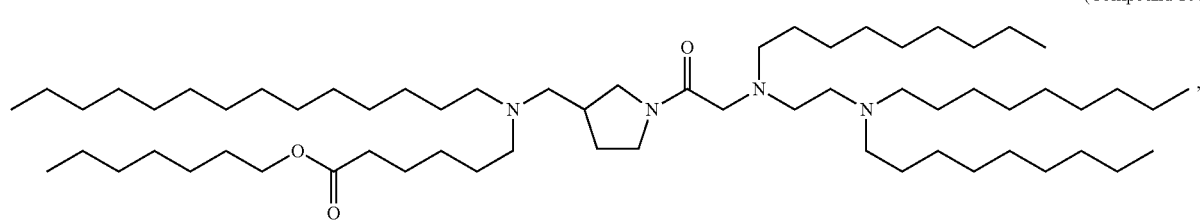

(Compound 101)
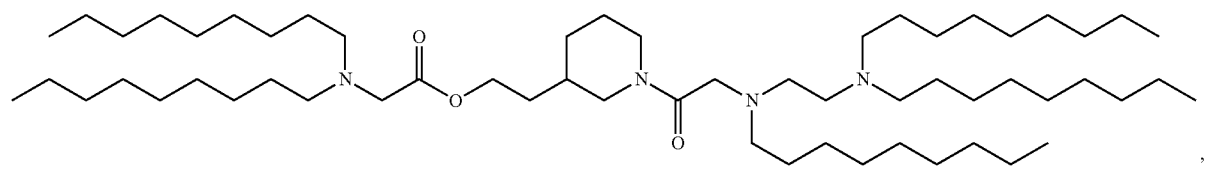
(Compound 102)
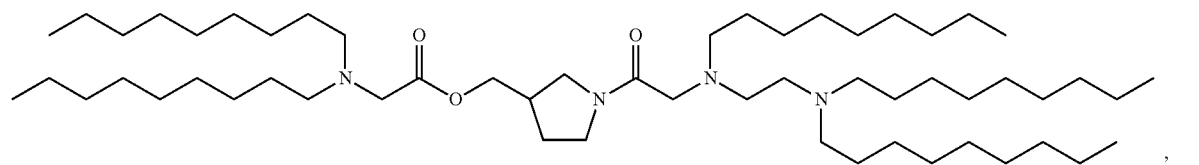
(Compound 103)
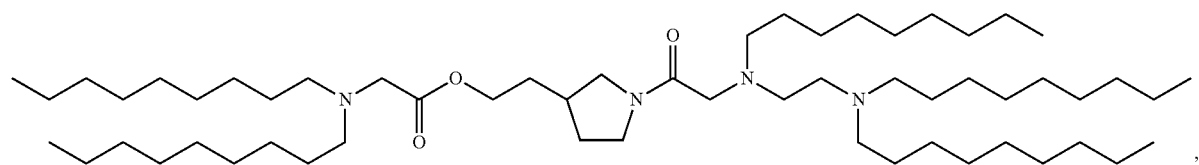
(Compound 104)
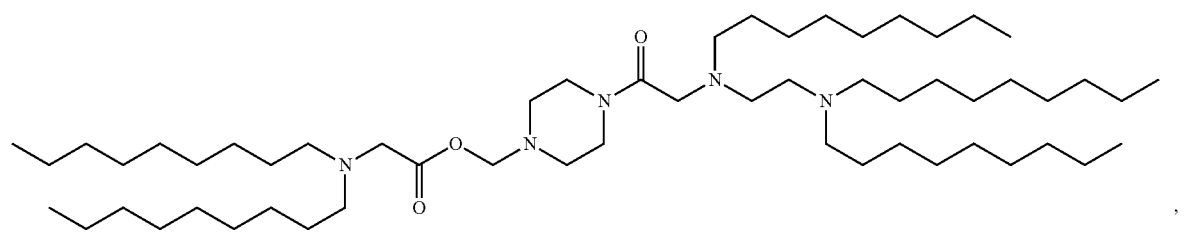
(Compound 105)
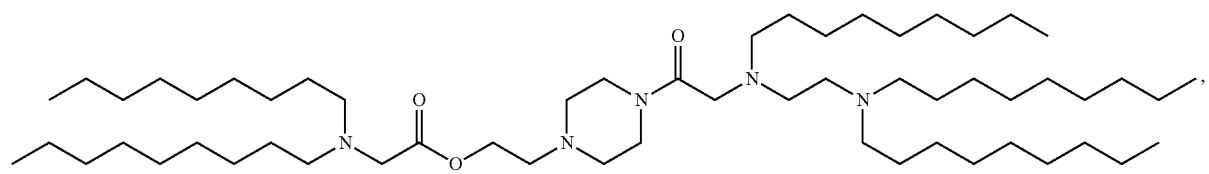
(Compound 106)
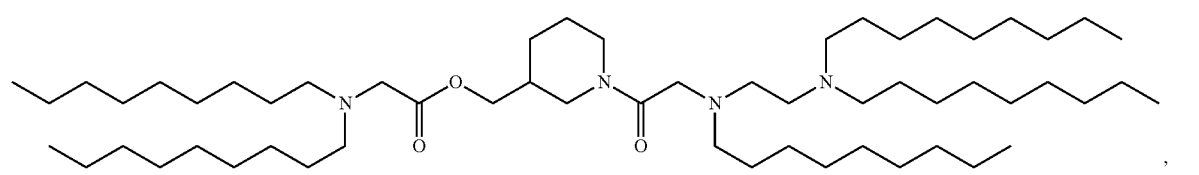
(Compound 107)
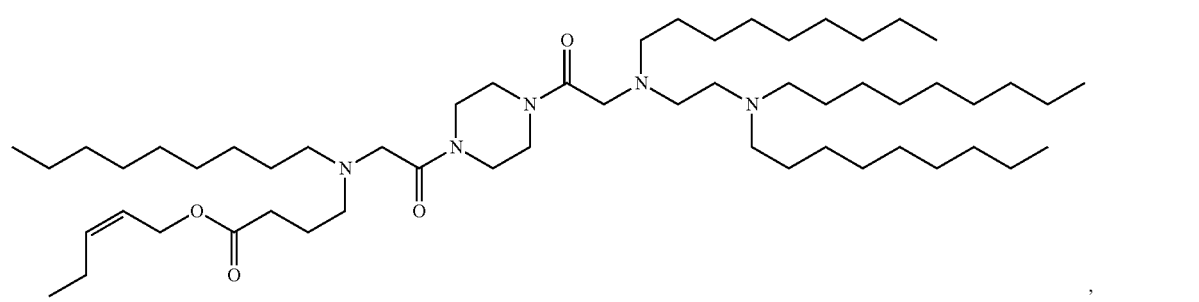

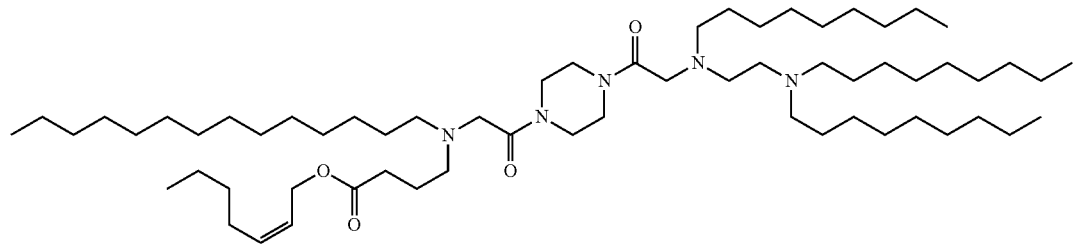
(Compound 108)

, and
(Compound 109)
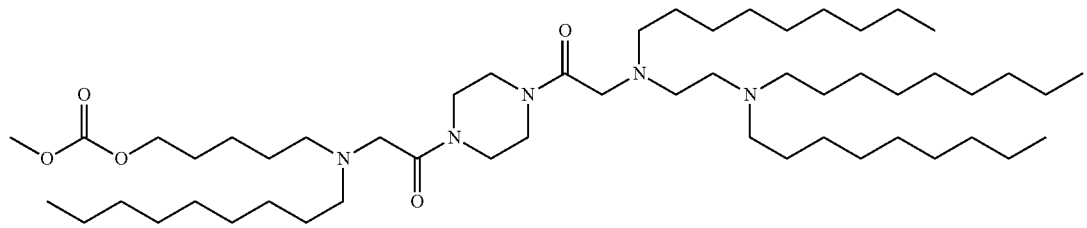

In other embodiments, a lipid has the formula (II)

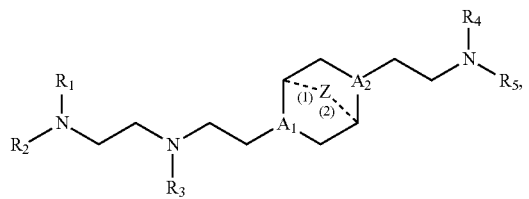

or a salt or isomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is

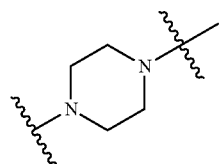

then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of formula (IIa):

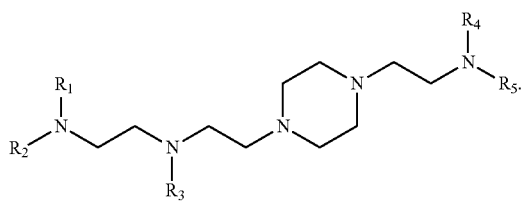

The compounds of Formula (II) or (IIa) include one or more of the following features when applicable.

In some embodiments, Z is $CH_2$.
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:

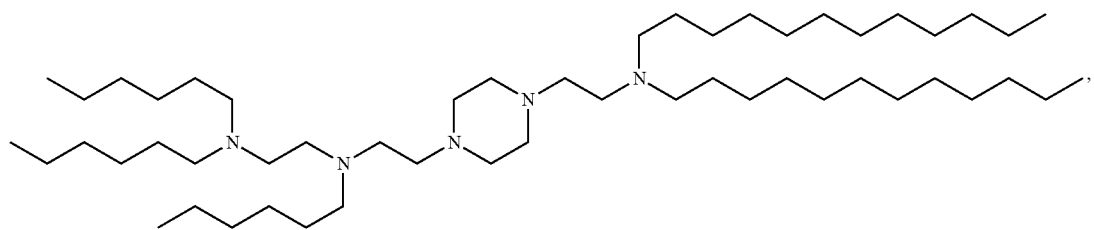
(Compound 17)

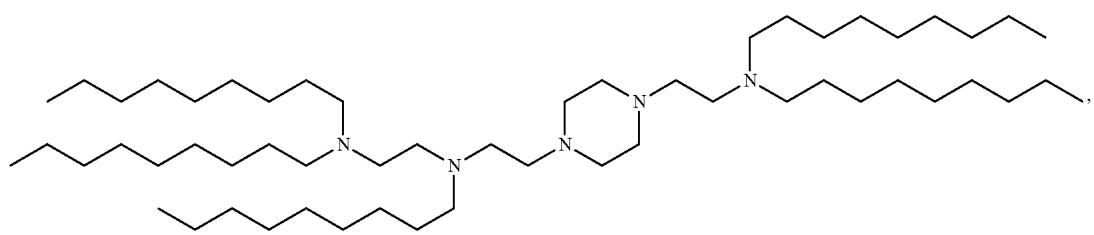
(Compound 18)

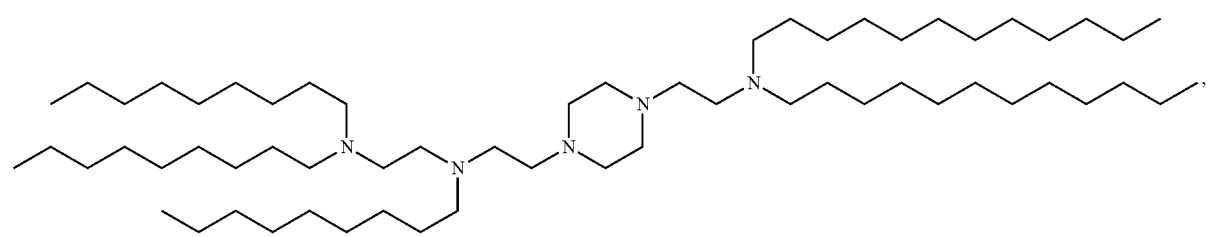
(Compound 19)

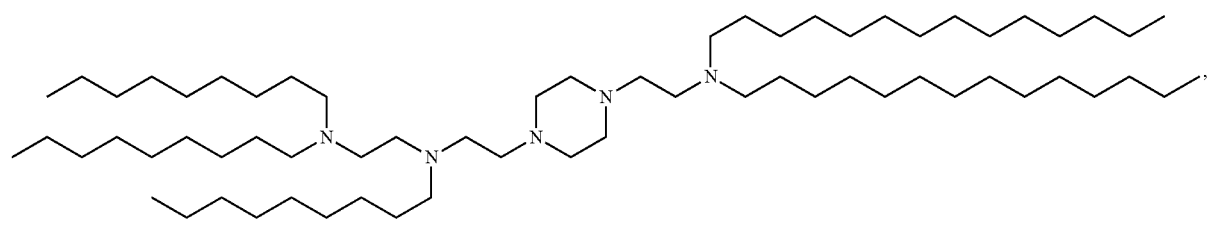
(Compound 20)

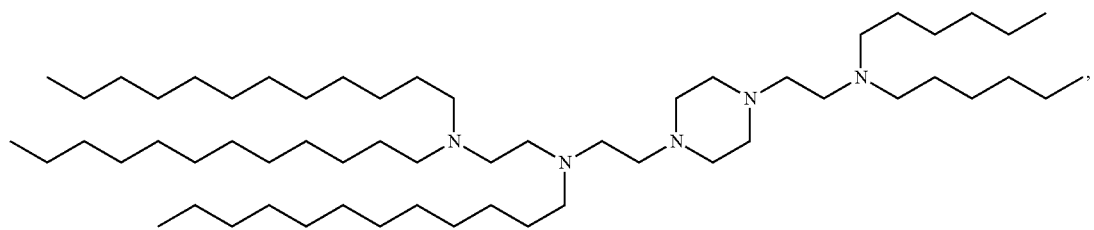
(Compound 21)

-continued
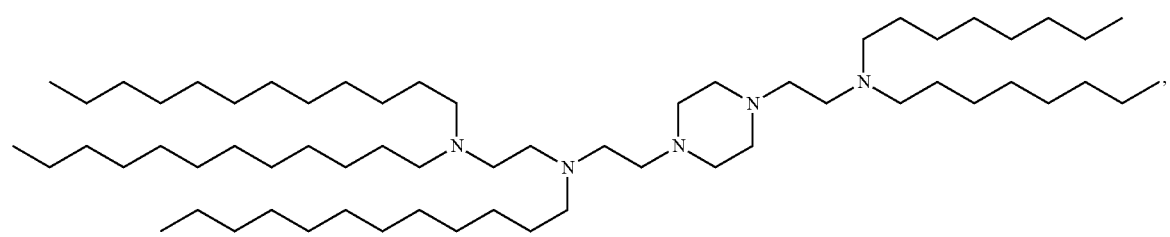
(Compound 22)
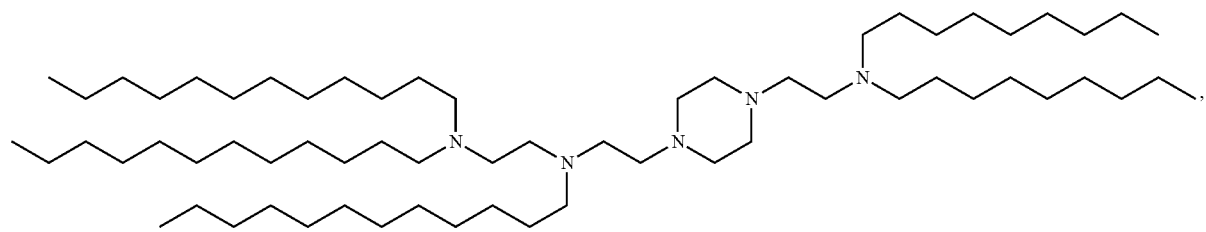
(Compound 23)
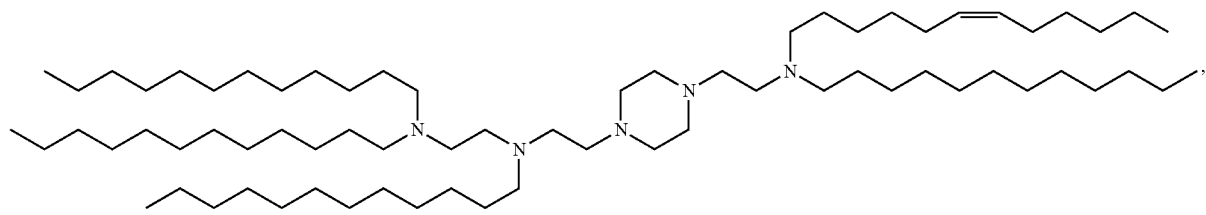
(Compound 24)
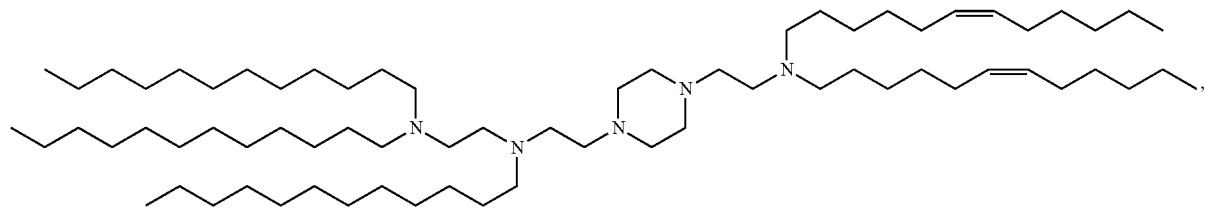
(Compound 25)
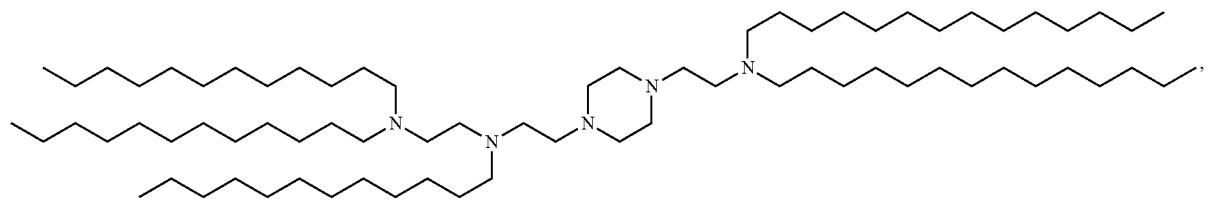
(Compound 26)
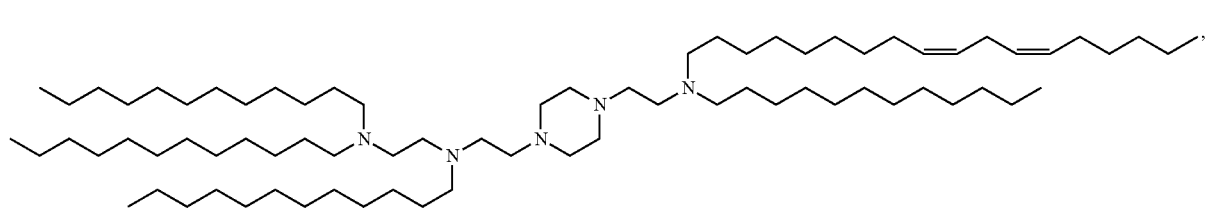
(Compound 27)
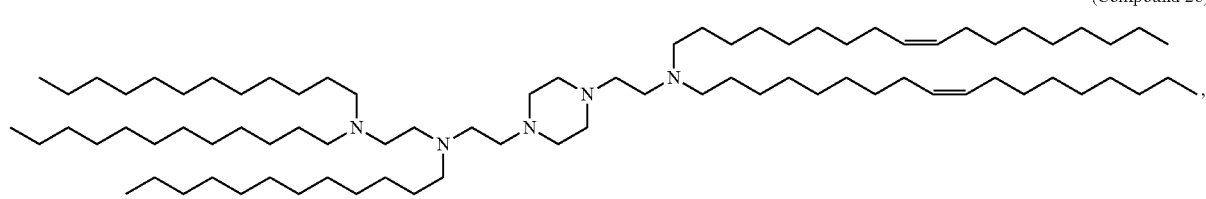
(Compound 28)

-continued (Compound 29)
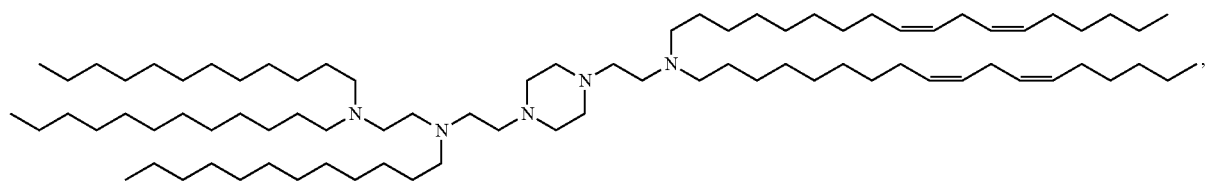

(Compound 30)
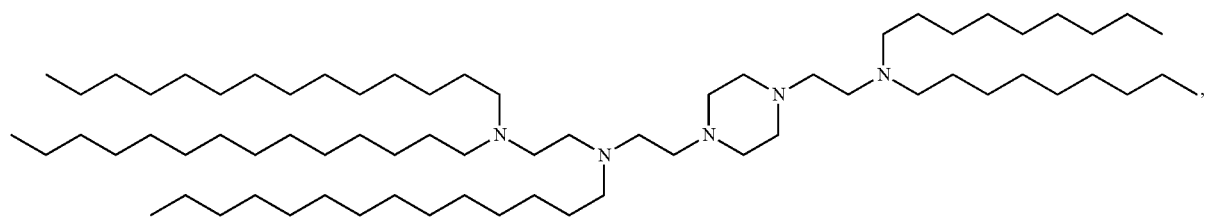

(Compound 31)
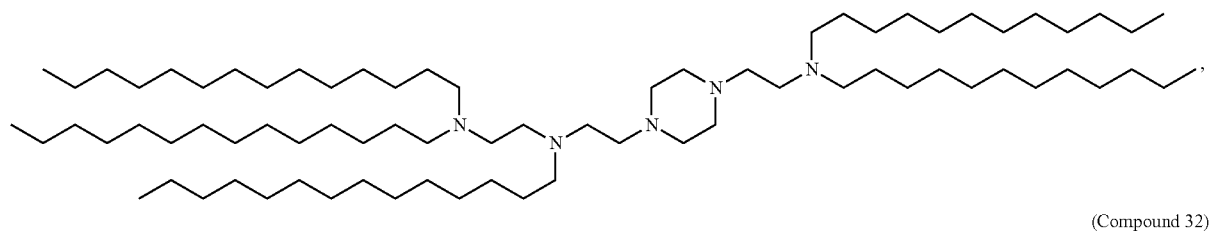

(Compound 32)
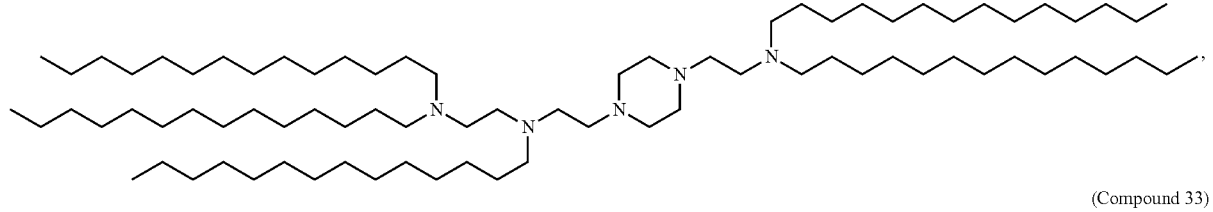

(Compound 33)
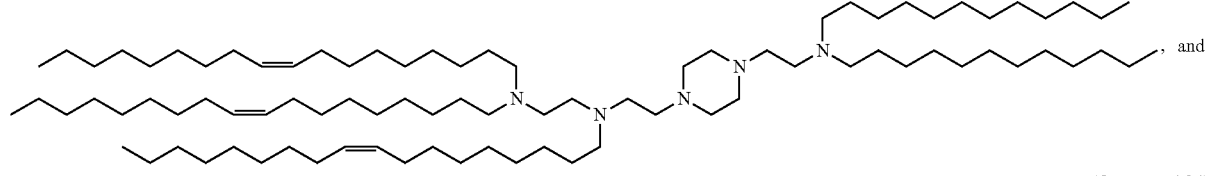, and (Compound 34)
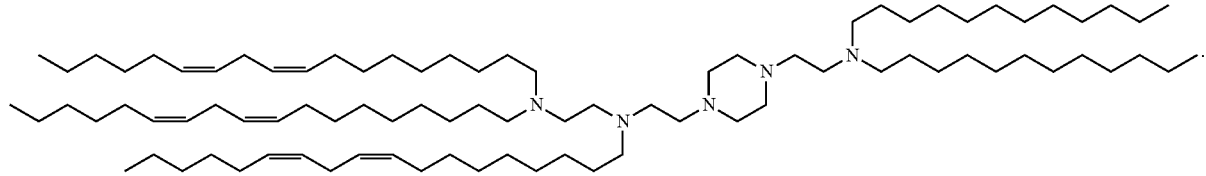.

In other embodiments, the compound has the formula (III)

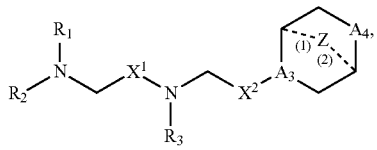

(III)

or a salt or isomer thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$ and $X^2$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H; and
each R" is independently selected from the group consisting of $C_{3-12}$ alkyl and $C_{3-12}$ alkenyl.

In some embodiments, the compound is of formula (IIIa):

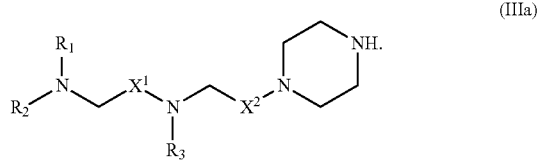

(IIIa)

The compounds of Formula (III) or (IIIa) include one or more of the following features when applicable.

In some embodiments, Z is $CH_2$.
In some embodiments, Z is absent.
In some embodiments, at least one of $A_3$ and $A_4$ is N or NH.
In some embodiments, $A_3$ is N and $A_4$ is NH.
In some embodiments, $A_3$ is N and $A_4$ is $CH_2$.
In some embodiments, $A_3$ is CH and $A_4$ is NH.
In some embodiments, at least one of $X^1$ and $X^2$ is not —$CH_2$—. For example, in certain embodiments, $X^1$ is not —$CH_2$—. In some embodiments, at least one of $X^1$ and $X^2$ is —C(O)—.
In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, the compound is selected from the group consisting of:

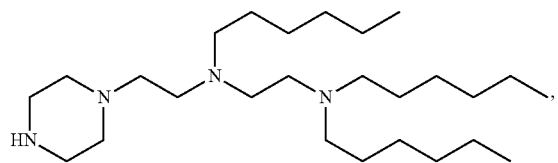

(Compound 35)

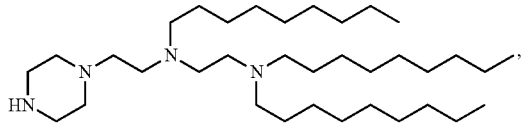

(Compound 36)

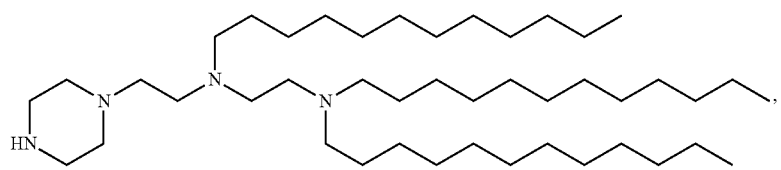

(Compound 37)

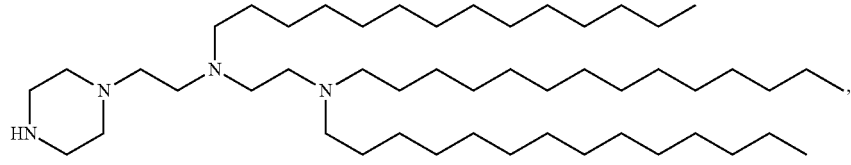

(Compound 38)

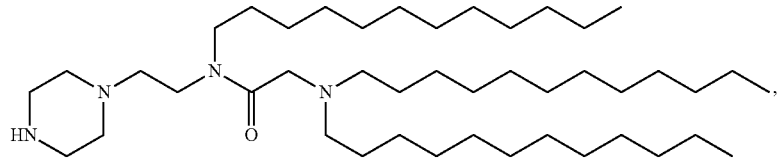

(Compound 39)

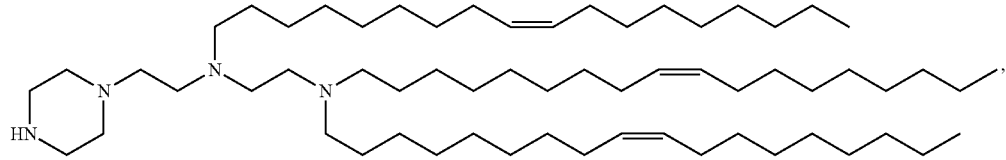

(Compound 40)

(Compound 41)

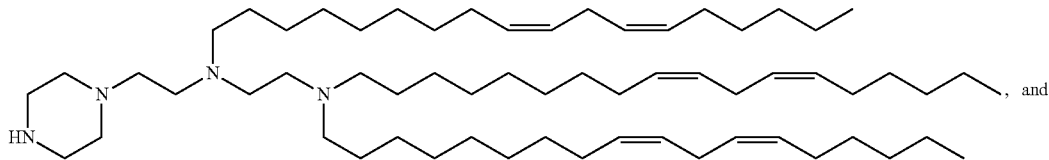

, and (Compound 77)

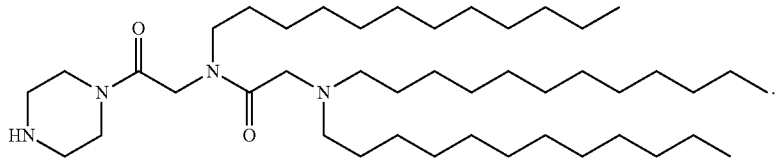

.

In another aspect, the disclosure provides a compound according to formula (Ib):

(Ib)

or a salt or isomer thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

$R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when $A_6$ is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some embodiments, the compound is (Compound 67)

In an embodiment, the compound has the formula (IV)

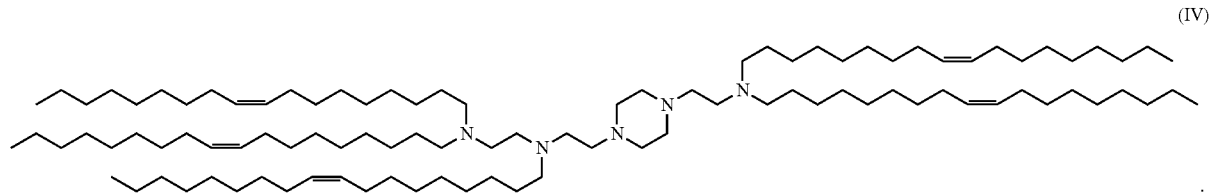 [SMILES: CCCCCCCC/C=C\CCCCCCCCN(CCCCCCCC/C=C\CCCCCCCC)CCN(CCCCCCCC/C=C\CCCCCCCC)CCN1CCN(CCN(CCCCCCCC/C=C\CCCCCCCC)CCCCCCCC/C=C\CCCCCCCC)CC1]

In another aspect, the disclosure provides a compound having the formula (17-I)

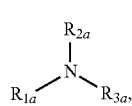

or a salt or isomer thereof, wherein $R_{1a}$ is —$(CH_2)_{n^a}Q^a$, where $Q^a$ is selected from a heterocycle, —$OR^a$, —$O(CH_2)_{n^a}N(R^a)_2$, —$C(O)OR^a$, —$OC(O)R^a$, —$CX^a_3$, —$CX^a_2H$, —$CX^aH_2$, —CN, —$N(R^a)_2$, —$C(O)N(R^a)_2$, —$N(R^a)C(O)R^a$, and —$N(R^a)S(O)_2R^a$ and each $n^a$ is independently selected from 1, 2, 3, 4, and 5;

$R_{2a}$ and $R_{3a}$ are each independently selected from the group consisting of $C_{3-24}$ alkyl, $C_{3-24}$ alkenyl, —$R^{a*}Y^aR^{a\prime\prime\prime}$, —$Y^aR^{a\prime\prime\prime}$, and —$R^{a*}OR^{a\prime\prime\prime}$;

each $Y^a$ is independently a $C_{3-6}$ carbocycle;

each $R^{a*}$ is independently selected from the group consisting of $C_{1-12}$ alkyl and $C_{1-12}$ alkenyl;

each $X^a$ is independently selected from the group consisting of F, Cl, Br, and I;

each $R^a$ is independently selected from the group consisting of $C_{1-3}$ alkyl, $C_{2-3}$ alkenyl, and H; and each $R^{a\prime\prime\prime}$ is selected from the group consisting of $C_{3-12}$ alkyl and $C_{3-12}$ alkenyl;

wherein $R_{2a}$ includes 7 or fewer carbon atoms.

In some embodiments, $Q^a$ is —$OR^a$. In certain embodiments, $R^a$ is H. In other embodiments, $R^a$ is —$CH_3$.

In some embodiments, $n^a$ is 1. In other embodiments, $n^a$ is 2. In other embodiments, n is 3. In other embodiments, $n^a$ is 4. In some embodiments, $n^a$ is 5.

In some embodiments, $R_{3a}$ includes 7 or fewer carbon atoms.

In some embodiments, the compound is selected from the group consisting of:

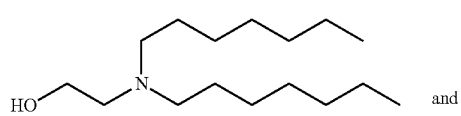

and

In another aspect, the disclosure provides a compound having the formula (17-I)

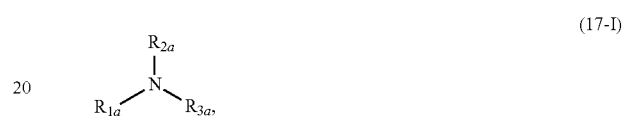

or a salt or isomer thereof, wherein $R_{1a}$ is —$(CH_2)_{n^a}Q^a$, where $Q^a$ is selected from a heterocycle, —$OR^a$, —$O(CH_2)_{n^a}N(R^a)_2$, —$C(O)OR^a$, —$OC(O)R^a$, —$CX^a_3$, —$CX^a_2H$, —$CX^aH_2$, —CN, —$N(R^a)_2$, —$C(O)N(R^a)_2$, —$N(R^a)C(O)R^a$, and —$N(R^a)S(O)_2R^a$ and each $n^a$ is independently selected from 1, 2, 3, 4, and 5;

each $X^a$ is independently selected from the group consisting of F, Cl, Br, and I;

$R_{2a}$ is selected from the group consisting of $C_{8-24}$ alkenyl;

$R_{3a}$ is selected from the group consisting of $C_{8-24}$ alkyl; and each R is independently selected from the group consisting of $C_{1-3}$ alkyl, $C_{2-3}$ alkenyl, and H.

In some embodiments, $Q^a$ is —$OR^a$. In certain embodiments, $R^a$ is H. In other embodiments, $R^a$ is —$CH_3$.

In some embodiments, $n^a$ is 1. In other embodiments, $n^a$ is 2. In other embodiments, $n^a$ is 3. In other embodiments, $n^a$ is 4. In some embodiments, $n^a$ is 5.

In some embodiments, $R_{3a}$ is an alkyl including 9, 12, 14, or 18 carbon atoms.

In some embodiments, $R_{2a}$ is $C_{18}$ alkenyl (e.g., linoleyl).

In some embodiments, the compound is selected from the group consisting of:

(Compound 17-1)

(Compound 17-2)

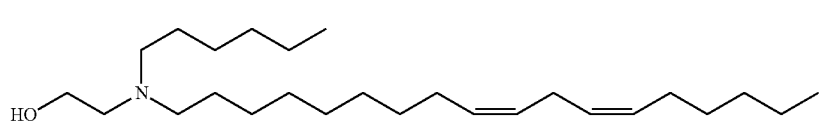

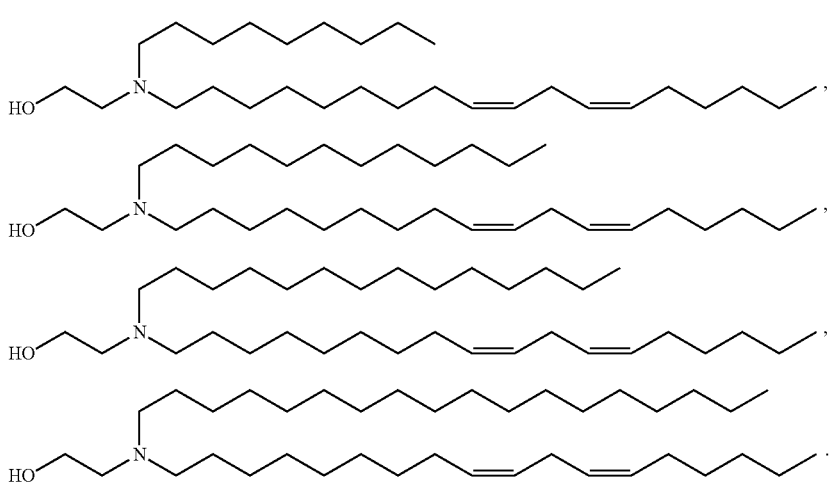

(Compound 17-3), (Compound 17-4), (Compound 17-5), and (Compound 17-6).

In a further aspect, the disclosure provides a compound having the formula (17-I)

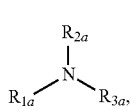

(17-I)

or a salt or isomer thereof, wherein $R_{1a}$ is —$(CH_2)_n{}^aQ^a$, where $Q^a$ is selected from a heterocycle, —$OR^a$, —$O(CH_2)_n{}^aN(R^a)_2$, —$C(O)OR^a$, —$OC(O)R^a$, —$CX^a{}_3$, —$CX^a{}_2H$, —$CX^aH_2$, —CN, —$N(R^a)_2$, —$C(O)N(R^a)_2$, —$N(R^a)C(O)R^a$, and —$N(R^a)S(O)_2R^a$ and each $n^a$ is independently selected from 1, 2, 3, 4, and 5;

each $X^a$ is independently selected from the group consisting of F, Cl, Br, and I;

$R_{2a}$ is selected from the group consisting of $C_{13-20}$ alkyl;

$R_{3a}$ is selected from the group consisting of $C_{8-20}$ alkyl; and each $R^a$ is independently selected from the group consisting of $C_{1-3}$ alkyl, $C_{2-3}$ alkenyl, and H.

In some embodiments, $Q^a$ is —$OR^a$. In certain embodiments, $R^a$ is H. In other embodiments, $R^a$ is —$CH_3$.

In some embodiments, $n^a$ is 1. In other embodiments, $n^a$ is 2. In other embodiments, $n^a$ is 3. In other embodiments, $n^a$ is 4. In some embodiments, $n^a$ is 5.

In some embodiments, $R_{2a}$ and $R_{3a}$ are the same.

In some embodiments, $R_{2a}$ and/or $R_{3a}$ is $C_{14}$ alkyl.

In some embodiments, the compound is (Compound 17-7)

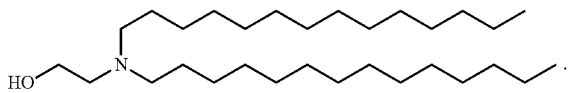

In a further aspect, the disclosure provides a compound having the formula (17-I)

(17-I)

or a salt or isomer thereof, wherein $R_{1a}$ is —$(CH_2)_n{}^aQ^a$, where $Q^a$ is —$OR^a$, $R^a$ is selected from the group consisting of $C_{1-3}$ alkyl, $C_{2-3}$ alkenyl, and H, and $n^a$ is selected from 1, 2, 3, 4, and 5; and $R_{2a}$ and $R_{3a}$ are each independently selected from the group consisting of $C_{8-20}$ alkenyl, wherein iii) $R^a$ is selected from the group consisting of $C_{1-3}$ alkyl and $C_{2-3}$ alkenyl; or iv) $R_{1a}$ is —$(CH_2)_2OH$, and $R_{2a}$ and $R_{3a}$ each include one or fewer double bonds.

In some embodiments, $R^a$ is H. In other embodiments, $R^a$ is —$CH_3$.

In some embodiments, $n^a$ is 1. In other embodiments, $n^a$ is 2. In other embodiments, $n^a$ is 3. In other embodiments, $n^a$ is 4. In some embodiments, $n^a$ is 5.

In certain embodiments, $R_{1a}$ is —$(CH_2)_2OCH_3$. In other embodiments, $R_{1a}$ is —$(CH_2)_2OH$.

In some embodiments, $R_{2a}$ is $C_{18}$ alkenyl (e.g., linoleyl). In certain embodiments, $R_{3a}$ is $C_{18}$ alkenyl (e.g., linoleyl).

In some embodiments, $R_{2a}$ and $R_{3a}$ are the same.

In some embodiments, the compound is selected from the group consisting of

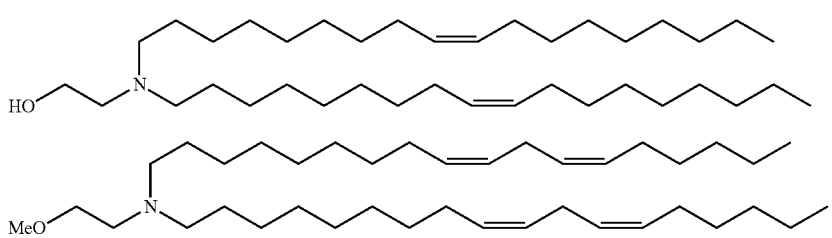

(Compound 17-8)

and (Compound 17-9)

In another aspect, the disclosure provides a compound of formula (17-I)

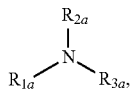

(17-I)

or a salt or isomer thereof, wherein $R_1$ is —$(CH_2)_n{}^a Q^a$, where $Q^a$ is selected from a heterocycle, —$OR^a$, —$O(CH_2)_n{}^a N(R^a)_2$, —$C(O)OR^a$, —$OC(O)R^a$, —$CX^a{}_3$, —$CX^a{}_2H$, —$CX^a H_2$, —CN, —$N(R^a)_2$, —$C(O)N(R^a)_2$, —$N(R^a)C(O)R^a$, and —$N(R^a)S(O)_2 R^a$ and each $n^a$ is independently selected from 1, 2, 3, 4, and 5;

each $X^a$ is independently selected from the group consisting of F, Cl, Br, and I;

$R_{2a}$ is selected from the group consisting of $C_{8-12}$ alkyl;

$R_{3a}$ is selected from the group consisting of $C_{8-20}$ alkyl; and each $R^a$ is independently selected from the group consisting of $C_{1-3}$ alkyl, $C_{2-3}$ alkenyl, and H.

In some embodiments, $Q^a$ is —$OR^a$. In certain embodiments, $R^a$ is H. In other embodiments, $R^a$ is —$CH_3$.

In some embodiments, $n^a$ is 1. In other embodiments, $n^a$ is 2. In other embodiments, n is 3. In other embodiments, $n^a$ is 4. In some embodiments, $n^a$ is 5.

In certain embodiments, $Q^a$ is —$OR^a$ and $n^a$ is selected from 2, 3, and 4.

In some embodiments, $R_{2a}$ is $C_9$ alkyl. In other embodiments, $R_{2a}$ is $C_{12}$ alkyl.

In some embodiments, $R_{2a}$ and $R_{3a}$ are the same.

In some embodiments, the compound is selected from the group consisting of:

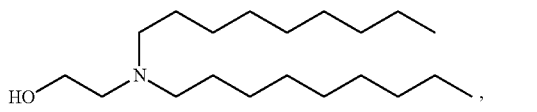

(Compound 17-10)

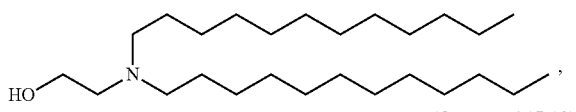

(Compound 17-11)

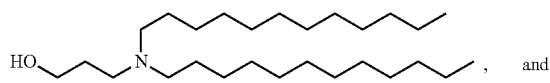

(Compound 17-12)

, and

-continued (Compound 17-13)

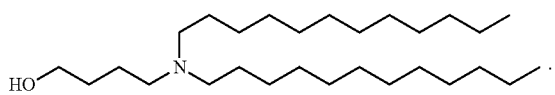

In another aspect, the disclosure provides a compound having the formula (19-I),

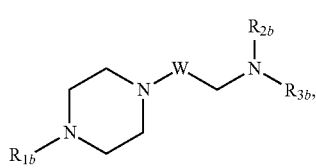

(19-I)

or a salt or isomer thereof, wherein $R_{1b}$ is selected from the group consisting of H, $C_{1-5}$ alkyl, $C_{2-5}$ alkenyl, —$R^{b''}M^b R^{b'}$, a $C_{3-6}$ carbocycle, —$(CH_2)_n Q^b$, and —$(CH_2)_n CHQ^b R^b$, where $Q^b$ is selected from a heterocycle, —$OR^b$, —$O(CH_2)_n N(R^b)_2$, —$C(O)OR^b$, —$OC(O)R^b$, —$CX^b{}_3$, —$CX^b{}_2 H$, —$CX^b H_2$, —CN, —$N(R^b)_2$, —$C(O)N(R^b)_2$, —$N(R^b)C(O)R^b$, and —$N(R^b)S(O)_2 R^b$ and each n is independently selected from 1, 2, 3, 4, and 5;

$R_{2b}$ and $R_{3b}$ are independently selected from the group consisting of $C_{1-20}$ alkyl, $C_{2-20}$ alkenyl, —$R^{b''}MR^{b'}$, —$R^{b*}YR^{b''}$, —$YR^{b''}$, and —$R^{b*}OR^{b''}$;

each $M^b$ is independently selected from the group consisting of —C(O)O—, —OC(O)—, —C(O)N($R^{b'}$)—, —N($R^{b'}$)C(O)—, —C(O)—, —C(S)—, —C(S)S—, —SC(S)—, —CH(OH)—, —P(O)($OR^{b'}$)O—, —$S(O)_2$—, an aryl group, and a heteroaryl group;

W is selected from the group consisting of —$CH_2$—, —$CHR^b$—, —C(O)—, —CH(OH)—, —C(S)—, and —CH(SH)—;

each $X^b$ is independently selected from the group consisting of F, Cl, Br, and I;

each $Y^b$ is independently a $C_{3-6}$ carbocycle;

each $R^{b*}$ is independently selected from the group consisting of $C_{1-12}$ alkyl and $C_{1-12}$ alkenyl;

each $R^b$ is independently selected from the group consisting of $C_{1-3}$ alkyl, a $C_{3-6}$ carbocycle, $C_{2-3}$ alkenyl, and H;

each $R^{b'}$ is independently selected from the group consisting of $C_{1-12}$ alkyl, $C_{2-12}$ alkenyl, and H; and each $R^{b''}$ is independently selected from the group consisting of $C_{3-12}$ alkyl and $C_{3-12}$ alkenyl.

In some embodiments, W is not —$CH_2$—, e.g., W is —C(O)—.

In some embodiments, at least one of $R_{2b}$ and $R_{3b}$ is —$R^{b''}M^b R^{b'}$. In certain embodiments, at least one $M^b$ is —C(O)O—. In some embodiments, at least one $R^{b''}$ is $C_5$ alkyl. In certain embodiments, at least one $R^{b'}$ is $C_5$ alkyl.

In some embodiments, $R_{2b}$ and/or $R_{3b}$ are selected from the group consisting of $C_{1-20}$ alkyl. For example, $R_{2b}$ and/or $R_{3b}$ may be alkyl groups including 9 or 12 carbon atoms. In other embodiments, $R_{2b}$ and/or $R_{3b}$ are selected from the group consisting of $C_{2-20}$ alkenyl. For example, $R_{2b}$ and/or $R_{3b}$ may be alkenyl groups including 18 carbon atoms (e.g., linoleyl groups). In certain embodiments, $R_{2b}$ and $R_{3b}$ are the same.

In some embodiments, $R_{1b}$ is H, while in other embodiments, $R_{1b}$ is selected from $C_{1-5}$ alkyl. For example, $R_{1b}$ may be $C_1$ alkyl.

In certain embodiments, $R_{1b}$ is —$(CH_2)_n Q^b$. In such embodiments, $Q^b$ is a heterocycle such as a phenyl group. For example, $Q^b$ may be a phenyl group with one or more substituents, as described herein.

In certain embodiments, the compound is selected from the group consisting of:

In other embodiments, lipids are compounds of formula (19-II)

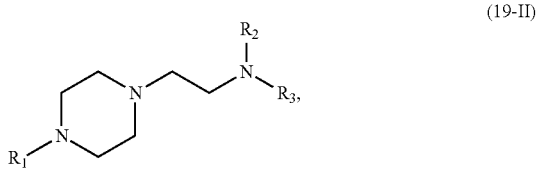

(19-II)

or a salt or isomer thereof, wherein $R_{1b}$ is selected from the group consisting of $C_{6-20}$ alkyl; and $R_{2b}$ and $R_{3b}$ are independently selected from the group consisting of $C_{6-20}$ alkenyl.

In particular embodiments, $R_{1b}$ is $C_{12}$ alkyl.

In some embodiments, $R_{2b}$ and/or $R_{3b}$ are $C_{18}$ alkenyl (e.g., linoleyl).

In certain embodiments, $R_{2b}$ and $R_{3b}$ are both linoleyl.

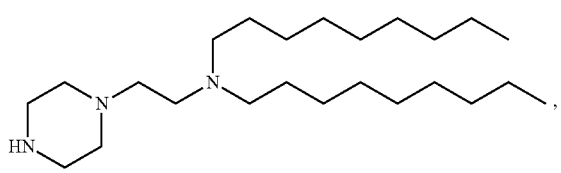

(Compound 19-1)

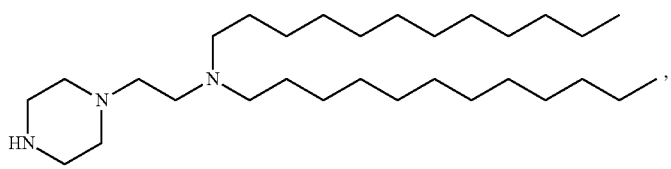

(Compound 19-2)

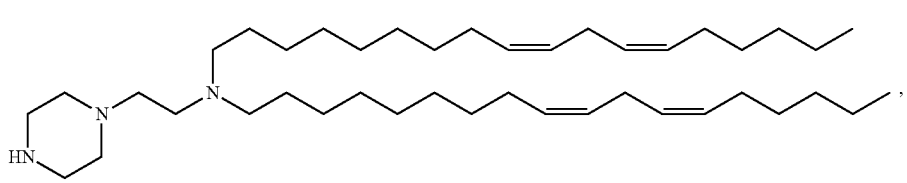

(Compound 19-3)

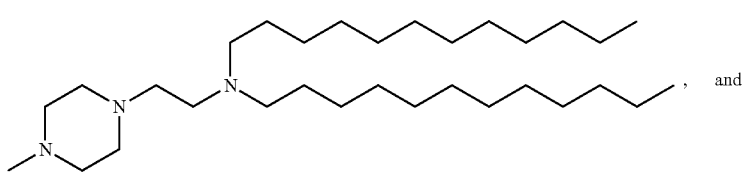

(Compound 19-4) and

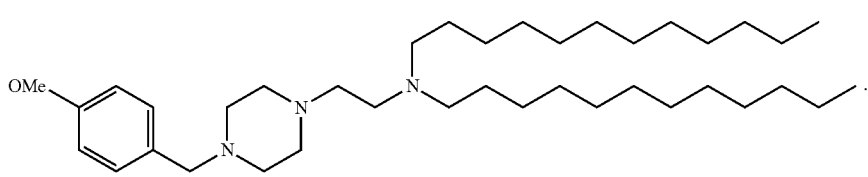

(Compound 19-5)

In one embodiment, the compound is

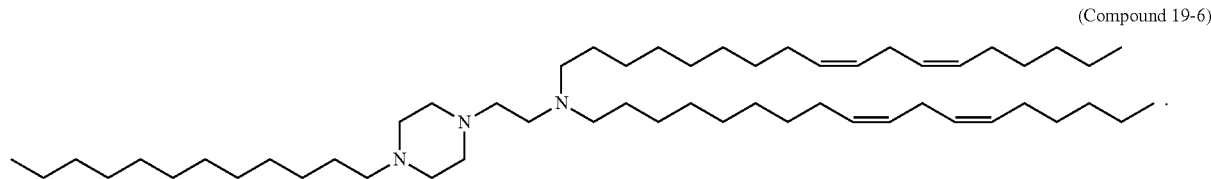 [SMILES: CCCCC/C=C\C/C=C\CCCCCCCCN(CCCCCCCC/C=C\C/C=C\CCCCC)CCN1CCN(CCCCCCCCCCCC)CC1]

(Compound 19-6)

In another aspect, lipids may be compounds of formula (20-I),

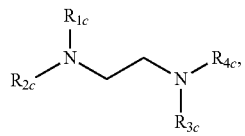

(20-I)

or a salt or isomer thereof, wherein $R_{1c}$ is selected from the group consisting of a $C_{3-6}$ carbocycle, —$(CH_2)_n{}^cQ^c$, —$(CH_2)_n{}^cCHQ^cR^c$, —$CHQ^cR^c$, and —$CQ^c(R^c)_2$, where $Q^c$ is selected from a heterocycle, —$OR^c$, —$O(CH_2)_n{}^cN(R^c)_2$, —$C(O)OR^c$, —$OC(O)R^c$, —$CX^c{}_3$, —$CX^c{}_2H$, —$CX^cH_2$, —CN, —$N(R^c)_2$, —$C(O)N(R^c)_2$, —$N(R^c)C(O)R^c$, and —$N(R^c)S(O)_2R^c$ and each $n^c$ is independently selected from 1, 2, 3, 4, and 5;

$R_{2c}$, $R_{3c}$, and $R_{4c}$ are independently selected from the group consisting of $C_{1-20}$ alkyl, $C_{2-20}$ alkenyl, —$R^{c''}M^cR^{c1}$, —$R^{c*}Y^cR^{c''}$, —$Y^cR^{c''}$, and —$R^{c*}OR^{c''}$;

each $M^c$ is independently selected from the group consisting of —C(O)O—, —OC(O)—, —$C(O)N(R^{c1})$—, —$N(R^{c1})C(O)$—, —C(O)—, —C(S)—, —C(S)S—, —SC(S)—, —CH(OH)—, —$P(O)(OR^{c1})O$—, —$S(O)_2$—, an aryl group, and a heteroaryl group;

each $X^c$ is independently selected from the group consisting of F, Cl, Br, and I;

each $Y^c$ is independently a $C_{3-6}$ carbocycle;

each $R^{c*}$ is independently selected from the group consisting of $C_{1-12}$ alkyl and $C_{1-12}$ alkenyl;

each $R^c$ is independently selected from the group consisting of $C_{1-3}$ alkyl, $C_{2-3}$ alkenyl, and H;

each $R^{c1}$ is independently selected from the group consisting of $C_{1-12}$ alkyl, $C_{2-12}$ alkenyl, and H; and each $R^{c''}$ is independently selected from the group consisting of $C_{3-12}$ alkyl and $C_{3-12}$ alkenyl, wherein i) $R_{1c}$ is selected from the group consisting of a $C_{3-6}$ carbocycle, —$(CH_2)_n{}^cQ^c$, —$(CH_2)_n{}^cCHQ^cR^c$, —$CHQ^cR^c$, and —$CQ^c(R^c)_2$, where $Q^c$ is selected from a heterocycle, —$O(CH_2)_n{}^cN(R^c)_2$, —$C(O)OR^c$, —$OC(O)R^c$, —$CX^c{}_3$, —$CX^c{}_2H$, —$CX^cH_2$, —$C(O)N(R^c)_2$, —$N(R^c)C(O)R^c$, and —$N(R^c)S(O)_2R^c$ and each $n^c$ is independently selected from 1, 2, 3, 4, and 5; and/or ii) at least one of $R_{2c}$, $R_{3c}$, and $R_{4c}$ is —$R^{c''}M^cR^{c1}$.

In some embodiments, $R_{1c}$ is selected from the group consisting of —$(CH_2)_n{}^cQ^c$, —$(CH_2)_n{}^cCHQ^cR^c$, —$CHQ^cR^c$, and —$CQ^c(R^c)_2$, where $Q^c$ is selected from a heterocycle, —$O(CH_2)_n{}^cN(R^c)_2$, —$C(O)OR^c$, —$OC(O)R^c$, —$CX^c{}_3$, —$CX^c{}_2H$, —$CX^cH_2$, —CN, —$C(O)N(R^c)_2$, —$N(R^c)C(O)R^c$, and —$N(R^c)S(O)_2R^c$ and each n is independently selected from 1, 2, 3, 4, and 5. In certain embodiments, $R_{1c}$ is —$(CH_2)_n{}^cQ^c$. In some embodiments, $n^c$ is 2. In some embodiments, $Q^c$ is —$C(O)OR^c$, where $R^c$ is, for example, H.

In some embodiments, at least one of $R_{2c}$, $R_{3c}$, and $R_{4c}$ is —$R^{c''}M^cR^{c1}$. For example, $R_{2c}$, $R_{3c}$, and/or $R_{4c}$ may be —$R^{c''}M^cR^{c1}$. In some embodiments, at least one $M^c$ is —C(O)O—. In certain embodiments, each $M^c$ is —C(O)O—. In some embodiments, at least one $R^{c''}$ is $C_5$ or $C_7$ alkyl. In certain embodiments, each $R^{c''}$ is $C_5$ alkyl. In other embodiments, each $R^{c''}$ is $C_7$ alkyl. In some embodiments, at least one $R^{c1}$ is $C_5$, $C_7$, or $C_9$ alkyl. In certain embodiments, each $R^{c1}$ is $C_5$ alkyl. In other embodiments, each $R^{c1}$ is $C_7$ alkyl. In other embodiments, each $R^{c1}$ is $C_9$ alkyl. In some embodiments, $R^{c1}$ is branched.

In some embodiments, $R_{2c}$, $R_{3c}$, and $R_{4c}$ are selected from the group consisting of $C_{5-20}$ alkyl. In certain embodiments, $R_{2c}$, $R_{3c}$, and $R_{4c}$ are $C_{12}$ alkyl.

In some embodiments, $R_{2c}$ is selected from the group consisting of $C_{5-20}$ alkyl and $C_{5-20}$ alkenyl. For example, $R_{2c}$ may be $C_{12}$ alkyl.

In some embodiments, $R_{3c}$ is selected from the group consisting of $C_{5-20}$ alkyl and $C_{5-20}$ alkenyl. For example, $R_{3c}$ may be $C_6$, $C_9$, or $C_{12}$ alkyl.

In some embodiments, $R_{4c}$ is selected from the group consisting of $C_{5-20}$ alkyl and $C_{5-20}$ alkenyl. For example, $R_{4c}$ may be $C_6$, $C_9$, or $C_{12}$ alkyl.

In some embodiments, $R_{3c}$ and $R_{4c}$ are the same.

In some embodiments, the compound is selected from the group consisting of:

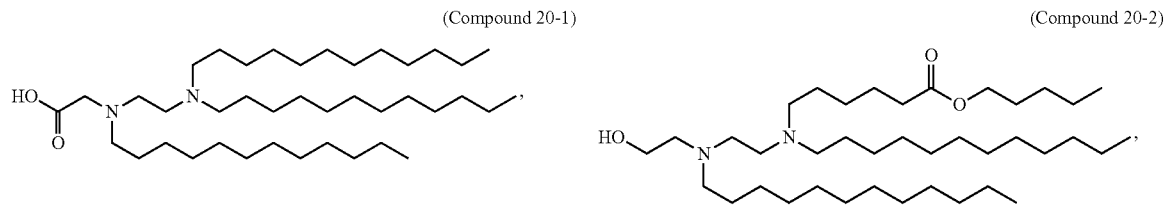

(Compound 20-1)     (Compound 20-2)

-continued
(Compound 20-3)
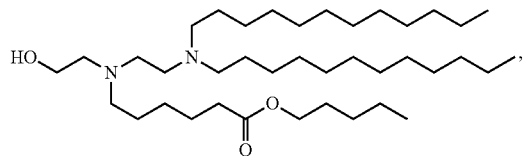
(Compound 20-4)
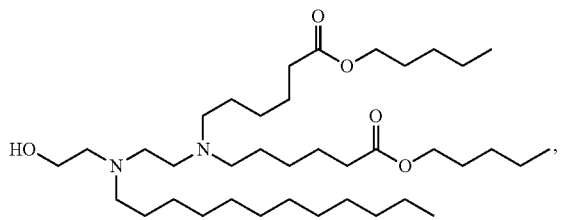
(Compound 20-5)
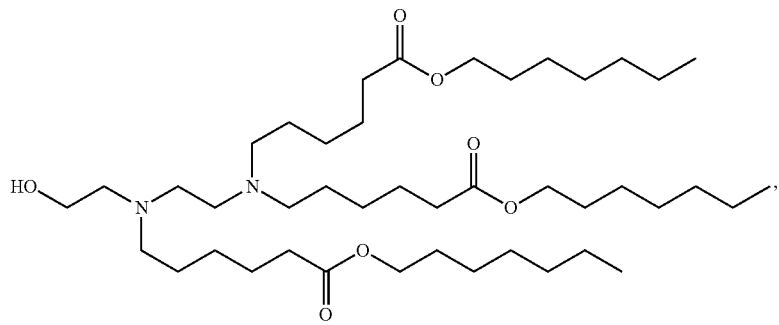
(Compound 20-6)
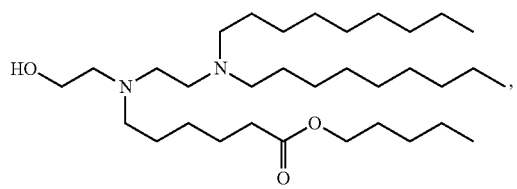
(Compound 20-7)
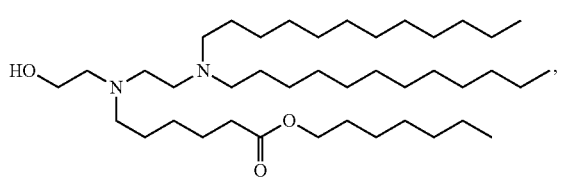
(Compound 20-8)
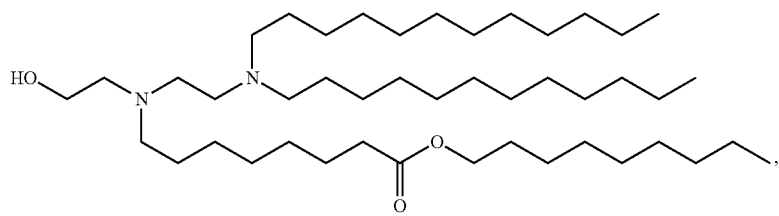
, and
(Compound 20-9)
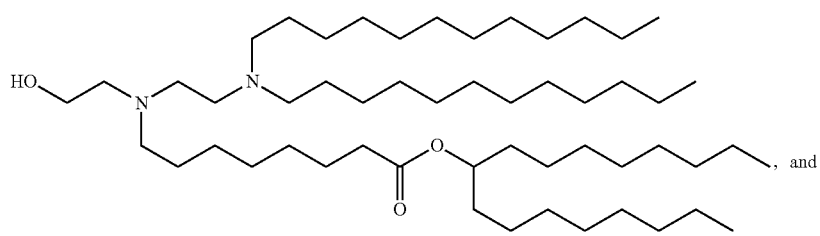
(Compound 20-10)
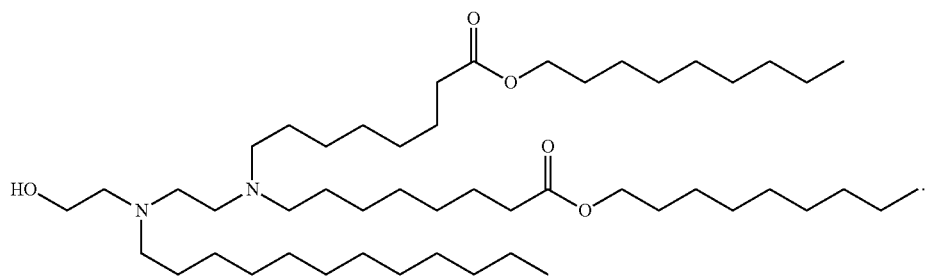

In other embodiments, the lipid is a compound according to formula (20-I)

In some embodiments, the compound is selected from the group consisting of:

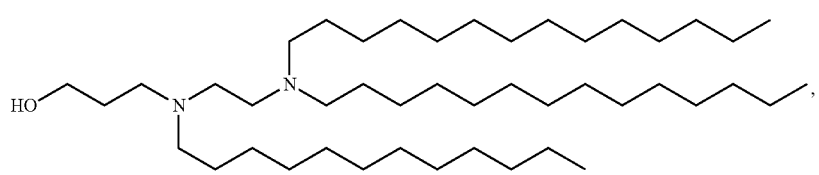

(Compound 20-11)

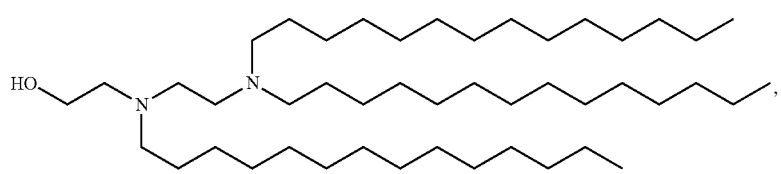

Compound 20-12)

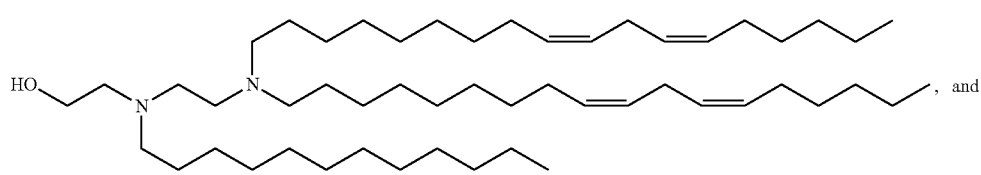

(Compound 20-13), and

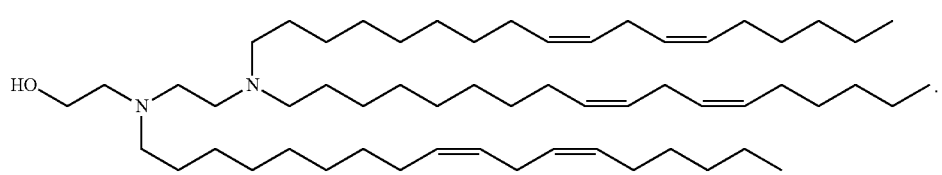

(Compound 20-14).

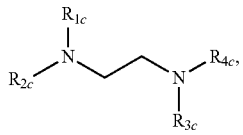

(20-I)

In other embodiments, the lipid is a compound having formula (20-I)

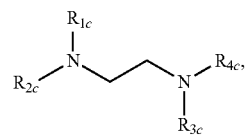

(20-I)

or a salt or isomer thereof, wherein $R_{1c}$ is selected from the group consisting of —$(CH_2)_{n^c}Q^c$, —$(CH_2)_{n^c}CHQ^cR^c$, —$CHQ^cR^c$, and —$CQ^c(R^c)_2$, where $Q^c$ is selected from —$OR^c$, —CN, and —$N(R^c)_2$, and $n^c$ is selected from 1, 2, 3, 4, and 5;

$R_{2c}$ and $R_{3c}$ are independently selected from the group consisting of $C_{6-20}$ alkyl and $C_{6-20}$ alkenyl;

$R_{4c}$ is selected from the group consisting of $C_{13-20}$ alkyl and $C_{5-20}$ alkenyl; and each $R^c$ is independently selected from the group consisting of $C_{1-3}$ alkyl, $C_{2-3}$ alkenyl, and H.

In embodiments, $R_{3c}$ is $C_{14}$ alkyl.
In some embodiments, $R_{4c}$ is $C_{14}$ alkyl.
In some embodiments, $R_{3c}$ is $C_{18}$ alkenyl. For example, $R_{3c}$ may be linoleyl.
In some embodiments, $R_{4c}$ is $C_{18}$ alkenyl. For example, $R_{4c}$ may be linoleyl.
In some embodiments, $R_{2c}$ is $C_{12}$ alkyl. In other embodiments, $R_{2c}$ is $C_{14}$ alkyl. In some embodiments, $R_{2c}$ is $C_{18}$ alkenyl. For example, $R_{2c}$ may be linoleyl.
In some embodiments, $R_{3c}$ and $R_{4c}$ are the same.
In some embodiments, $R_{1c}$ is —$(CH_2)_{n^c}Q^c$. In some embodiments, $Q^c$ is —$OR^c$. For example, $Q^c$ may be —OH. In some embodiments, $n^c$ is 2 or 3.

or a salt or isomer thereof, wherein $R_{1c}$ is selected from the group consisting of —$(CH_2)_{n^c}Q^c$, —$(CH_2)_{n^c}CHQ^cR^c$, —$CHQ^cR^c$, and —$CQ^c(R^c)_2$, where $Q^c$ is selected from —$OR^c$, —CN, and —$N(R^c)_2$, and $n^c$ is selected from 1, 2, 3, 4, and 5;

$R_{2c}$, $R_{3c}$, and $R_{4c}$ are independently selected from the group consisting of $C_{6-20}$ alkyl and $C_{6-20}$ alkenyl; and each $R^c$ is independently selected from the group consisting of $C_{1-3}$ alkyl, $C_{2-3}$ alkenyl, and H;

wherein i) $R_{2c}$ is selected from the group consisting of $C_{1-11}$ alkyl and $C_{2-5}$ alkenyl, and/or ii) $R_{3c}$ is selected from the group consisting of $C_{1-11}$ alkyl and $C_{2-5}$ alkenyl.

In some embodiments, $R_{2c}$ is selected from the group consisting of $C_{1-11}$ alkyl and $C_{2-5}$ alkenyl. For example, $R_{2c}$ may be $C_6$ or $C_9$ alkyl.

In some embodiments, $R_{3c}$ is selected from the group consisting of $C_{1-11}$ alkyl and $C_{2-5}$ alkenyl. For example, $R_{3c}$ may be $C_6$ or $C_9$ alkyl.

In some embodiments, $R_{3c}$ is $C_{12}$ alkyl.
In some embodiments, $R_{2c}$ is $C_{12}$ alkyl.
In some embodiments, $R_{4c}$ is $C_6$, $C_9$, or $C_{12}$ alkyl.

In some embodiments, $R_{1c}$ is —$(CH_2)_n{}^cQ^c$. In certain embodiments, $Q^c$ is —$OR^c$. In some embodiments, $R^c$ is H. In some embodiments, $n^c$ is 2 or 3.

In some embodiments, the compound is selected from the group consisting of:

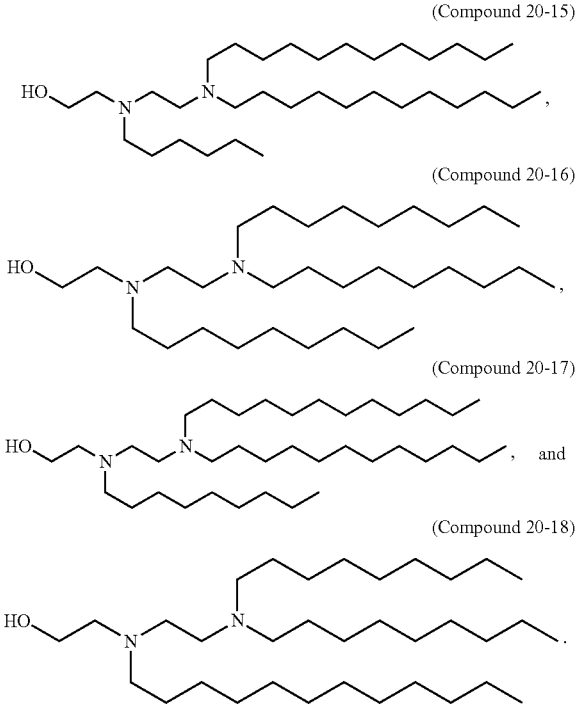

(Compound 20-15)

(Compound 20-16)

(Compound 20-17)

(Compound 20-18)

In other embodiments, the lipid is a compound according to formula (20-I)

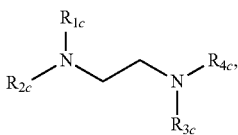

(20-I)

or a salt or isomer thereof, wherein $R_{1c}$ is selected from the group consisting of —$(CH_2)_n{}^cQ^c$, —$(CH_2)_n{}^cCHQ^cR^c$, —$CHQ^cR^c$, and —$CQ^c(R^c)_2$, where $Q^c$ is selected from —$OR^c$, —CN, and —$N(R^c)_2$, and $n^c$ is selected from 1, 2, 3, 4, and 5;

$R_{2c}$ is selected from the group consisting of H, $C_{12-20}$ alkyl, and $C_{6-20}$ alkenyl;

$R_{3c}$ and $R_{4c}$ are $C_{12}$ alkyl; and each $R^c$ is independently selected from the group consisting of $C_{1-3}$ alkyl, $C_{2-3}$ alkenyl, and H.

In some embodiments, $R_{2c}$ is H. In other embodiments, $R_{2c}$ is $C_{12}$ alkyl or alkenyl. In some embodiments, $R_{2c}$ is $C_{14}$ alkyl. In other embodiments, $R_{2c}$ is $C_{18}$ alkenyl. For example, $R_{2c}$ may be linoleyl.

In some embodiments, $R_{1c}$ is —$(CH_2)_n{}^cQ^c$. In certain embodiments, $Q^c$ is —$OR^c$. For example, $Q^c$ may be OH. In some embodiments, $n^c$ is 2, 3, or 4.

In some embodiments, the compound is selected from the group consisting of:

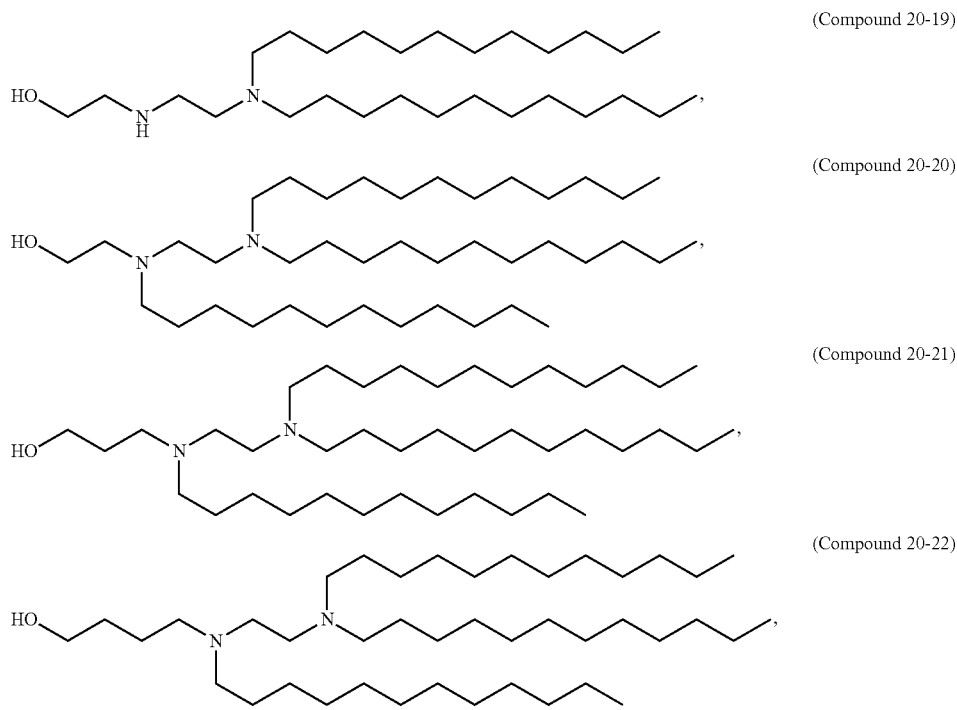

(Compound 20-19)

(Compound 20-20)

(Compound 20-21)

(Compound 20-22)

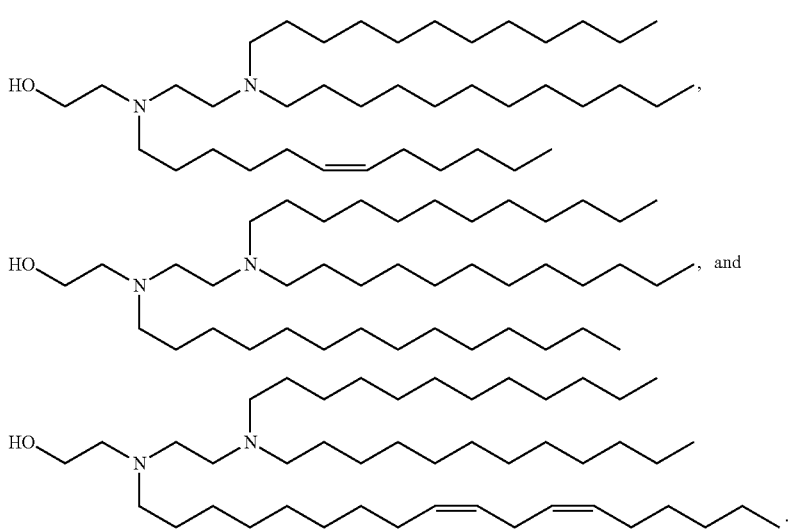

(Compound 20-23)

(Compound 20-24), and (Compound 20-25).

In another aspect, lipids may be compounds of formula (21-I),

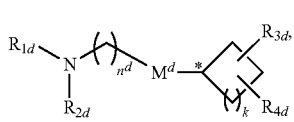

(21-I)

or a salt or isomer thereof, wherein $R_{1d}$ and $R_{2d}$ are independently selected from the group consisting of H, $C_{1-5}$ alkyl, and $C_{2-5}$ alkenyl;

$n^d$ is selected from 1, 2, 3, 4, and 5;

k is selected from 0, 1, 2, and 3;

$R_{3d}$ and $R_{4d}$ are independently selected from the group consisting of $C_{1-20}$ alkyl, $C_{2-20}$ alkenyl, —$R^{d''}M^dR^{d'}$, —$R^{d*}Y^dR^{d''}$, —$Y^dR^{d''}$ and —$R^{d*}OR^{d''}$;

each $M^d$ is independently selected from the group consisting of —C(O)O—, —OC(O)—, —C(O)N($R^{d'}$)—, —N($R^{d'}$)C(O)—, —C(O)—, —C(S)—, —C(S)S—, —SC(S)—, —CH(OH)—, —P(O)(O$R^{d'}$)O—, and —S(O)$_2$—, or is absent;

each $R^{d'}$ is independently selected from the group consisting of $C_{1-12}$ alkyl, $C_{2-12}$ alkenyl, and H; each $Y^d$ is independently a $C_{3-6}$ carbocycle;

each $R^{d*}$ is independently selected from the group consisting of $C_{1-12}$ alkyl and $C_{1-12}$ alkenyl;

each $R^{d'}$ is independently selected from the group consisting of $C_{1-12}$ alkyl, $C_{2-12}$ alkenyl, and H; and each $R^{d''}$ is independently selected from the group consisting of $C_{3-12}$ alkyl and $C_{3-12}$ alkenyl, wherein $R_{3d}$ and $R_{4d}$ are bound to either i) the same carbon atom or ii) adjacent carbon atoms.

In some embodiments, $R_{3d}$ and $R_{4d}$ are bound to the same carbon atom. For example, $R_{3d}$ and $R_{4d}$ may be bound to a carbon atom adjacent to C*. In certain embodiments, $R_{3d}$ and $R_{4d}$ are not bound to a carbon atom adjacent to C*.

In other embodiments, $R_{3d}$ and $R_{4d}$ are bound to adjacent carbon atoms. In certain embodiments, one or both of $R_{3d}$ and $R_{4d}$ are bound to carbon atoms adjacent to C*.

In some embodiments, k is 0. In other embodiments, k is 1, 2, or 3.

In certain embodiments, $M^d$ is absent. In other embodiments, $M^d$ is selected from the group consisting of —C(O)O—, —OC(O)—, —C(O)N($R^{d'}$)—, —N($R^{d'}$)C(O)—, —C(O)—, —C(S)—, —C(S)S—, —SC(S)—, —CH(OH)—, —P(O)(O$R^{d'}$)O—, and —S(O)$_2$—. In particular such embodiments, $M^d$ is —C(O)O—.

In some embodiments, $n^d$ is 1, 2, or 3.

In some embodiments, $R_{1d}$ and/or $R_{2d}$ are selected from $C_{1-5}$ alkyl. In certain embodiments, $R_{1d}$ and/or $R_{2d}$ are $C_1$ alkyl.

In certain embodiments, $R_{3d}$ and/or $R_{4d}$ are selected from $C_{2-20}$ alkenyl. In certain embodiments, $R_{3d}$ and/or $R_{4d}$ are alkenyl groups including 17, 18, or 19 carbon atoms. For example, $R_{3d}$ and/or $R_{4d}$ may be $C_{18}$ alkenyl groups (e.g., linoleyl).

In certain embodiments, the compound is selected from the group consisting of:

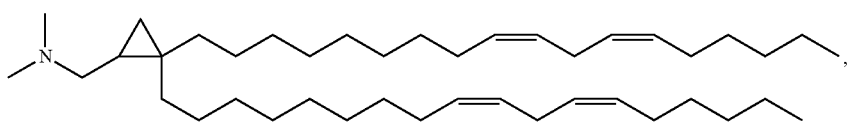

(Compound 21-1)

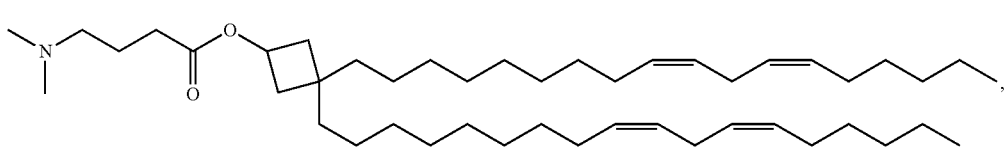

(Compound 21-2)

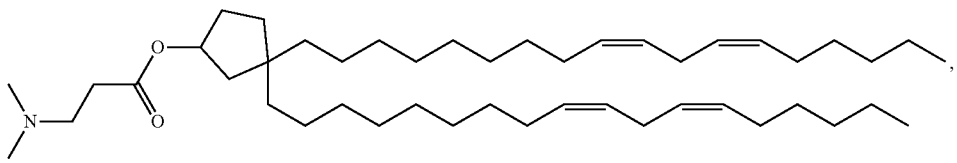

(Compound 21-3)

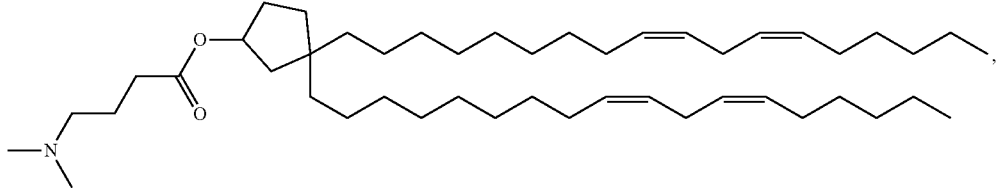

(Compound 21-4)

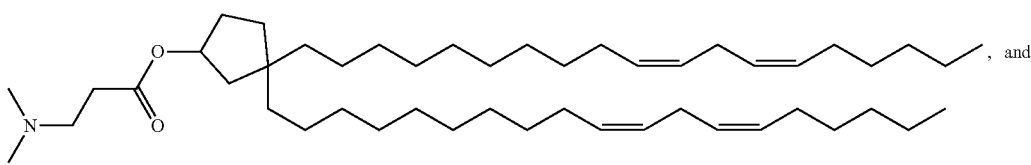

, and (Compound 21-5)

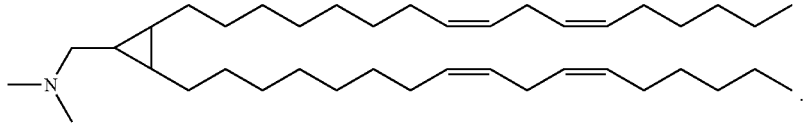

(Compound 21-6)

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. For example, the notation "$C_{1-24}$ alkyl" means an optionally substituted linear or branched, saturated hydrocarbon including 1-24 carbon atoms. An alkyl group described herein refers to both unsubstituted and substituted alkyl group unless otherwise specified.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-24}$ alkenyl" means an optionally substituted linear or branched hydrocarbon including 2 to 24 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. An alkenyl group described herein refers to both unsubstituted and substituted unless otherwise specified.

As used herein, the term "carbocycle" or "carbocyclic group" means an optionally substituted mono- or multi-cyclic system including one or more rings of carbon atoms. Rings may be three, four, five, six, seven, eight, nine, ten, eleven, or twelve membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups).

Examples of carbocycles include cyclopropyl, cyclopentyl, cyclohexyl, phenyl, naphthyl, and 1,2-dihydronaphthyl groups. Carbocycles described herein refers to both unsubstituted and substituted carbocycles unless otherwise specified. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, or twelve membered rings. Heterocycles may include one or more double or triple bonds and may be non-aromatic or aromatic. Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles may be optionally substituted.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group. As used herein, an "aryl group" is a carbocyclic group including one or more aromatic rings. Examples of aryl groups include phenyl and naphthyl groups. As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Aryl and heteroaryl groups may be optionally substituted. For example, each M, $M^b$, $M^c$, or $M^d$ can be independently selected from the non-limiting group consisting of phenyl, oxazole, and thiazole. In the formulae above, each M, $M^b$, $M^c$, or $M^d$ can be independently selected from the list of biodegradable groups above.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C=O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R'''', in which each OR are alkoxy groups that can be the same or different and R'''' is an alkyl or alkenyl group), a phosphate (e.g., P(O)$_4^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., S(O)$_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), a cyclyl (e.g., carbocyclyl or heterocyclyl) group, an alkyl group, and an alkenyl group. In any of the preceding, R is an alkyl or alkenyl group, as defined herein. In some embodiments, the substituent groups themselves may be further substituted with, for example, one, two, three, four, five, or six substituents as defined herein. For example, a $C_{5-20}$ alkyl group may be further substituted with one, two, three, four, five, six, or more substituents as described herein.

An amine moiety of a lipid according to one of formulae (I), (Ia1)-(Ia6), (Ib), (II), (IIa), (III), (IIIa), (IV), (17-I), (19-I), (19-II), (20-I) and (21-I) may be protonated at a physiological pH. Thus, a lipid may have a positive or partial positive charge at physiological pH. Such lipids may be referred to as cationic or ionizable (amino)lipids. Lipids may be zwitterionic, i.e., neutral molecules having both a positive and a negative charge.

Nanoparticle Compositions

The disclosure also features nanoparticle compositions comprising a lipid component comprising a compound according to one of formulae (I), (Ia1)-(Ia6), (Ib), (II), (IIa), (III), (IIIa), (IV), (17-I), (19-I), (19-II), (20-I) and (21-I) as described herein. In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter), e.g., when measured by dynamic light scattering (DLS), transmission electron microscopy, scanning electron microscopy, or another method. Nanoparticle compositions include, for example, lipid nanoparticles (LNPs), liposomes, lipid vesicles, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or crosslinked to one another. Lipid bilayers may include one or more ligands, proteins, or channels.

Nanoparticle compositions comprise a lipid component including at least one lipid, such as a compound according to one of formulae (I), (Ia1)-(Ia6), (Ib), (II), (IIa), (III), (IIIa), (IV), (17-I), (19-I), (19-II), (20-I) and (21-I), as described herein. For example, in some embodiments, a nanoparticle composition may include a lipid component including one of Compounds 1 through 88, Compounds 17-1 through 17-13, Compounds 19-1 through 19-6, Compounds 20-1 through 20-25 and Compounds 21-1 through 21-6. Nanoparticle compositions may also include a variety of other components. For example, the lipid component of a nanoparticle composition may include one or more other lipids in addition to a lipid according to one of formulae (I), (Ia1)-(Ia6), (Ib), (II), (IIa), (III), (IIIa), (IV), (17-I), (19-I), (19-II), (20-I) and (21-I).

Cationic/Ionizable Lipids

A nanoparticle composition may include one or more cationic and/or ionizable lipids (e.g., lipids that may have a positive or partial positive charge at physiological pH) in addition to a lipid according to one of formulae (I), (Ia1)-(Ia6), (Ib), (II), (IIa), (III), (IIIa), (IV), (17-I), (19-I), (19-II), (20-I) and (21-I). Cationic and/or ionizable lipids may be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLinDMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)),

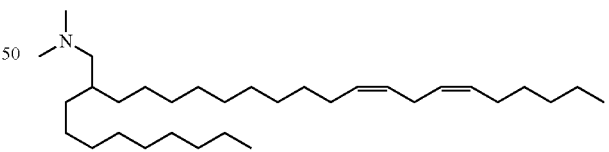

(i.e., (12Z, 15Z)—N,N-dimethyl-2-nonylhenicosa-12,15-dien-1-amine), and

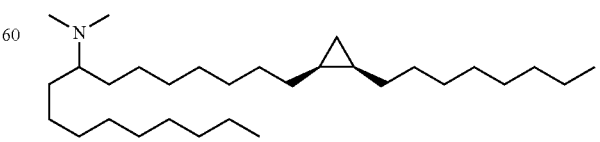

(i.e., N,N-dimethyl-1-{(1S,2R)-2-octylcyclopropyl}heptadecan-8-amine).

In addition to these, a cationic lipid may also be a lipid including a cyclic amine group. Additional cationic and/or ionizable lipids that are suitable for the formulations and methods disclosed herein include those described in WO2015199952, WO2016176330, and WO2015011633, the entire contents of each of which are hereby incorporated by reference in their entireties.

PEG Lipids

The lipid component of a nanoparticle composition may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

Structural Lipids

The lipid component of a nanoparticle composition may include one or more structural lipids. Structural lipids can be selected from the group consisting of, but are not limited to, cholesterol, fecosterol, sitosterol, ergosterol, campesterol, stigmasterol, brassicasterol, tomatidine, tomatine, ursolic acid, alpha-tocopherol, and mixtures thereof. In certain embodiments, the structural lipid is cholesterol. In some embodiments, the structural lipid includes cholesterol and a corticosteroid (such as prednisolone, dexamethasone, prednisone, and hydrocortisone), or a combination thereof.

Phospholipids

The lipid component of a nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties. For example, a phospholipid may be a lipid according to formula (V)

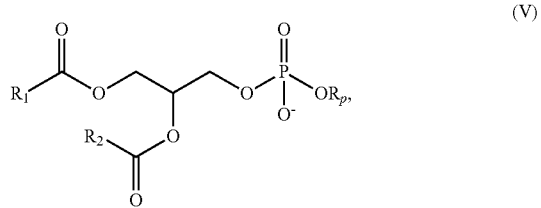

(V)

in which $R_p$ represents a phospholipid moiety and $R_1$ and $R_2$ represent fatty acid moieties with or without unsaturation that may be the same or different. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids useful in the compositions and methods described herein may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In certain embodiments, a nanoparticle composition includes DSPC. In certain embodiments, a nanoparticle composition includes DOPE. In some embodiments, a nanoparticle composition includes both DSPC and DOPE.

Adjuvants

In some embodiments, a nanoparticle composition that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Therapeutic Agents

Nanoparticle compositions may include one or more therapeutic and/or prophylactic agents. The disclosure features methods of delivering a therapeutic and/or prophylactic agent to a mammalian cell or organ, producing a polypeptide of interest in a mammalian cell, and treating a disease or disorder in a mammal in need thereof comprising administering to a mammal and/or contacting a mammalian cell with a nanoparticle composition including a therapeutic and/or prophylactic agent.

Therapeutic and/or prophylactic agents include biologically active substances and are alternately referred to as "active agents." A therapeutic and/or prophylactic agent may be a substance that, once delivered to a cell or organ, brings about a desirable change in the cell, organ, or other bodily tissue or system. Such species may be useful in the treatment of one or more diseases, disorders, or conditions. In some embodiments, a therapeutic and/or prophylactic agent is a small molecule drug useful in the treatment of a particular disease, disorder, or condition. Examples of drugs useful in the nanoparticle compositions described herein include, but are not limited to, antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cytosine arabinoside, anthracyclines, alkylating agents, platinum compounds, antimetabolites, and nucleoside analogs, such as methotrexate and purine and pyrimidine analogs), anti-infective agents, local anesthetics (e.g., dibucaine and chlorpromazine), beta-adrenergic blockers (e.g., propranolol, timolol, and labetalol), antihypertensive agents (e.g., clonidine and hydralazine), anti-depressants (e.g., imipramine, amitriptyline, and doxepin), anti-convulsants (e.g., phenytoin), antihistamines (e.g., diphenhydramine, chlorpheniramine, and promethazine), antibiotic/antibacterial agents (e.g., gentamycin, ciprofloxacin, and cefoxitin), antifungal agents (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma agents, vitamins, narcotics, and imaging agents.

In some embodiments, a therapeutic and/or prophylactic agent is a cytotoxin, a radioactive ion, a chemotherapeutic, a vaccine, a compound that elicits an immune response, and/or another therapeutic and/or prophylactic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol, rachelmycin (CC-1065), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Vaccines include compounds and preparations that are capable of providing immunity against one or more conditions related to infectious diseases such as influenza, measles, human papillomavirus (HPV), rabies, meningitis, whooping cough, tetanus, plague, hepatitis, and tuberculosis and can include mRNAs encoding infectious disease derived antigens and/or epitopes. Vaccines also include compounds and preparations that direct an immune response against cancer cells and can include mRNAs encoding tumor cell derived antigens, epitopes, and/or neoepitopes. Compounds eliciting immune responses may include vaccines, corticosteroids (e.g., dexamethasone), and other species. In some embodiments, a vaccine and/or a compound capable of eliciting an immune response is administered intramuscularly via a composition including a compound according to one of formulae (I), (Ia1)-(Ia6), (Ib), (II), (IIa), (III), (IIIa), (IV), (17-I), (19-I), (19-II), (20-I) and (21-I). Other therapeutic and/or prophylactic agents include, but are not limited to, antimetabolites (e.g., methotrexate, 6-mercaptopurine, 6-thioguanine, cytarabine, 5-fluorouracil, dacarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In other embodiments, a therapeutic and/or prophylactic agent is a protein. Therapeutic proteins useful in the nanoparticles of the disclosure include, but are not limited to, gentamycin, amikacin, insulin, erythropoietin (EPO), granulocyte-colony stimulating factor (G-CSF), granulocyte-macrophage colony stimulating factor (GM-CSF), Factor VIR, luteinizing hormone-releasing hormone (LHRH) analogs, interferons, heparin, Hepatitis B surface antigen, typhoid vaccine, and cholera vaccine.

Polynucleotides and Nucleic Acids

In some embodiments, a therapeutic and/or prophylactic agent is a polynucleotide or nucleic acid (e.g., ribonucleic acid or deoxyribonucleic acid). The term "polynucleotide," in its broadest sense, includes any compound and/or substance that is or can be incorporated into an oligonucleotide chain. Exemplary polynucleotides for use in accordance with the present disclosure include, but are not limited to, one or more of deoxyribonucleic acid (DNA), ribonucleic acid (RNA) including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. In certain embodiments, a therapeutic and/or prophylactic agent is an RNA. RNAs useful in the compositions and methods described herein can be selected from the group consisting of, but are not limited to, shortmers, antagomirs, antisense, ribozymes, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), and mixtures thereof. In certain embodiments, the RNA is an mRNA.

In certain embodiments, a therapeutic and/or prophylactic agent is an mRNA. An mRNA may encode any polypeptide of interest, including any naturally or non-naturally occurring or otherwise modified polypeptide. A polypeptide encoded by an mRNA may be of any size and may have any secondary structure or activity. In some embodiments, a polypeptide encoded by an mRNA may have a therapeutic effect when expressed in a cell.

In other embodiments, a therapeutic and/or prophylactic agent is an siRNA. An siRNA may be capable of selectively knocking down or down regulating expression of a gene of interest. For example, an siRNA could be selected to silence a gene associated with a particular disease, disorder, or condition upon administration to a subject in need thereof of a nanoparticle composition including the siRNA. An siRNA may comprise a sequence that is complementary to an mRNA sequence that encodes a gene or protein of interest. In some embodiments, the siRNA may be an immunomodulatory siRNA.

In some embodiments, a therapeutic and/or prophylactic agent is an shRNA or a vector or plasmid encoding the same. An shRNA may be produced inside a target cell upon delivery of an appropriate construct to the nucleus. Constructs and mechanisms relating to shRNA are well known in the relevant arts.

Nucleic acids and polynucleotides useful in or suitable for the compounds and methods of the disclosure typically include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR), at least one 5'-cap region, and a 3'-stabilizing region. In some embodiments, a nucleic acid or polynucleotide further includes a poly-A region or a Kozak sequence (e.g., in the 5'-UTR). In some cases, polynucleotides may contain one or more intronic nucleotide sequences capable of being excised from the polynucleotide. In some embodiments, a polynucleotide or nucleic acid (e.g., an mRNA) may include a 5' cap structure, a chain terminating nucleotide, a stem loop, a polyA sequence, and/or a polyadenylation signal. Any one of the regions of a nucleic acid may include one or more alternative components (e.g., an alternative nucleoside). For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl-pseudouridine or 1-ethyl-pseudouridine), and/or a 5-substituted cytidine (e.g., 5-methyl-cytidine).

Generally, the shortest length of a polynucleotide can be the length of the polynucleotide sequence that is sufficient to encode for a dipeptide. In another embodiment, the length of the polynucleotide sequence is sufficient to encode for a tripeptide. In another embodiment, the length of the polynucleotide sequence is sufficient to encode for a tetrapeptide. In another embodiment, the length of the polynucleotide sequence is sufficient to encode for a pentapeptide. In another embodiment, the length of the polynucleotide sequence is sufficient to encode for a hexapeptide. In another embodiment, the length of the polynucleotide sequence is sufficient to encode for a heptapeptide. In another embodiment, the length of the polynucleotide sequence is sufficient to encode for an octapeptide. In another embodiment, the length of the polynucleotide sequence is sufficient to encode for a nonapeptide. In another embodiment, the length of the polynucleotide sequence is sufficient to encode for a decapeptide.

Examples of dipeptides that the alternative polynucleotide sequences can encode for include, but are not limited to, carnosine and anserine.

In some cases, a polynucleotide is greater than 30 nucleotides in length. In another embodiment, the polynucleotide molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 50 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

Nucleic acids and polynucleotides may include one or more naturally occurring components, including any of the canonical nucleotides A (adenosine), G (guanosine), C (cytosine), U (uridine), or T (thymidine). In one embodiment, all or substantially all of the nucleotides comprising (a) the 5'-UTR, (b) the open reading frame (ORF), (c) the 3'-UTR, (d) the poly A tail, and any combination of (a, b, c, or d above) comprise naturally occurring canonical nucleotides A (adenosine), G (guanosine), C (cytosine), U (uridine), or T (thymidine).

Nucleic acids and polynucleotides may include one or more alternative components, as described herein, which impart useful properties including increased stability and/or the lack of a substantial induction of the innate immune response of a cell into which the polynucleotide is introduced. For example, an alternative polynucleotide or nucleic acid exhibits reduced degradation in a cell into which the polynucleotide or nucleic acid is introduced, relative to a corresponding unaltered polynucleotide or nucleic acid. These alternative species may enhance the efficiency of protein production, intracellular retention of the polynucleotides, and/or viability of contacted cells, as well as possess reduced immunogenicity.

Polynucleotides and nucleic acids may be naturally or non-naturally occurring. Polynucleotides and nucleic acids may include one or more modified (e.g., altered or alternative) nucleobases, nucleosides, nucleotides, or combinations thereof. The nucleic acids and polynucleotides useful in the nanoparticle compositions described herein can include any useful modification or alteration, such as to the nucleobase, the sugar, or the internucleoside linkage (e.g., to a linking phosphate/to a phosphodiester linkage/to the phosphodiester backbone). In certain embodiments, alterations (e.g., one or more alterations) are present in each of the nucleobase, the sugar, and the internucleoside linkage. Alterations according to the present disclosure may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof. Additional alterations are described herein.

Polynucleotides and nucleic acids may or may not be uniformly altered along the entire length of the molecule. For example, one or more or all types of nucleotide (e.g., purine or pyrimidine, or any one or more or all of A, G, U, C) may or may not be uniformly altered in a polynucleotide or nucleic acid, or in a given predetermined sequence region thereof. In some instances, all nucleotides X in a polynucleotide (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations and/or internucleoside linkages (e.g., backbone structures) may exist at various positions in a polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus. The polynucleotide may contain from about 1% to about 100% alternative nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of a canonical nucleotide (e.g., A, G, U, or C).

Polynucleotides may contain at a minimum zero and at maximum 100% alternative nucleotides, or any intervening percentage, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, polynucleotides may contain an alternative pyrimidine such as an alternative uracil or cytosine. In some embodiments, at least 5%, at least 10%, at least 25%, at least 50%, at least 80%, at least 90% or 100% of the uracil in a polynucleotide is replaced with an alternative uracil (e.g., a 5-substituted uracil). The alternative uracil can be replaced by a compound having a single unique structure, or can be replaced by a plurality of compounds having different structures (e.g., 2, 3, 4 or more unique structures). In some instances, at least 5%, at least 10%, at least 25%, at least 50%, at least 80%, at least 90% or 100% of the cytosine in the polynucleotide is replaced with an alternative cytosine (e.g., a 5-substituted cytosine). The alternative cytosine can be replaced by a compound having a single unique structure, or can be replaced by a plurality of compounds having different structures (e.g., 2, 3, 4 or more unique structures).

In some instances, nucleic acids do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc., and/or 3) termination or reduction in protein translation.

The nucleic acids can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, and vectors). In some embodiments, the nucleic acids may include one or more messenger RNAs (mRNAs) having one or more alternative nucleoside or nucleotides (i.e., alternative mRNA molecules).

In some embodiments, a nucleic acid (e.g. mRNA) molecule, formula, composition or method associated therewith comprises one or more polynucleotides comprising features as described in WO2002/098443, WO2003/051401, WO2008/052770, WO2009127230, WO2006122828, WO2008/083949, WO2010088927, WO2010/037539, WO2004/004743, WO2005/016376, WO2006/024518, WO2007/095976, WO2008/014979, WO2008/077592, WO2009/030481, WO2009/095226, WO2011069586, WO2011026641, WO2011/144358, WO2012019780, WO2012013326, WO2012089338, WO2012113513, WO2012116811, WO2012116810, WO2013113502, WO2013113501, WO2013113736, WO2013143698, WO2013143699, WO2013143700, WO2013/120626, WO2013120627, WO2013120628, WO2013120629, WO2013174409, WO2014127917, WO2015/024669, WO2015/024668, WO2015/024667, WO2015/024665, WO2015/024666, WO2015/024664, WO2015101415, WO2015101414, WO2015024667, WO2015062738, WO2015101416, all of which are incorporated by reference herein.

Nucleobase Alternatives

The alternative nucleosides and nucleotides can include an alternative nucleobase. A nucleobase of a nucleic acid is an organic base such as a purine or pyrimidine or a derivative thereof. A nucleobase may be a canonical base (e.g., adenine, guanine, uracil, thymine, and cytosine). These nucleobases can be altered or wholly replaced to provide polynucleotide molecules having enhanced properties, e.g., increased stability such as resistance to nucleases. Non-canonical or modified bases may include, for example, one or more substitutions or modifications including but not limited to alkyl, aryl, halo, oxo, hydroxyl, alkyloxy, and/or thio substitutions; one or more fused or open rings; oxidation; and/or reduction.

Alternative nucleotide base pairing encompasses not only the standard adenine-thymine, adenine-uracil, or guanine-cytosine base pairs, but also base pairs formed between nucleotides and/or alternative nucleotides including non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenine, cytosine, or uracil.

In some embodiments, the nucleobase is an alternative uracil. Exemplary nucleobases and nucleosides having an alternative uracil include pseudouridine (ψ), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5s^2U$), 5-methylaminomethyl-uracil ($mnm^5U$), 5-methylaminomethyl-2-thio-uracil ($mnm^5s^2U$), 5-methylaminomethyl-2-seleno-uracil ($mnm^5se^2U$), 5-carbamoylmethyl-uracil ($ncm^5U$), 5-carboxymethylaminomethyl-uracil ($cmnm^5U$), 5-carboxymethylaminomethyl-2-thio-uracil ($cmnm^5s^2U$), 5-propynyl-uracil, 1-propynyl-pseudouracil, 5-taurinomethyl-uracil ($τm^5U$), 1-taurinomethyl-pseudouridine, 5-taurinomethyl-2-thio-uracil ($τm^5s^2U$), 1-taurinomethyl-4-thio-pseudouridine, 5-methyl-uracil ($m^5U$, i.e., having the nucleobase deoxythymine), 1-methyl-pseudouridine (m$^1$ψ), 1-ethyl-pseudouridine (Et$^1$ψ), 5-methyl-2-thio-uracil (m$^5$s$^2$U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil (m$^5$D), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil (acp$^3$U), 1-methyl-3-(3-amino-3-carboxypropyl)pseudouridine (acp$^3$ψ), 5-(isopentenylaminomethyl)uracil (inm$^5$U), 5-(isopentenylaminomethyl)-2-thio-uracil (inm$^5$s$^2$U), 5,2'-O-dimethyl-uridine (m$^5$Um), 2-thio-2'-O_methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), and 5-(isopentenylaminomethyl)-2'-O-methyl-uridine (inm$^5$Um), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the nucleobase is an alternative cytosine. Exemplary nucleobases and nucleosides having an alternative cytosine include 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl-adenine (m6t6A), 2-methylthio-N6-threonylcarbamoyl-adenine (ms2g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the nucleobase is an alternative guanine. Exemplary nucleobases and nucleosides having an alternative guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQ0), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

The alternative nucleobase of a nucleotide can be independently a purine, a pyrimidine, a purine or pyrimidine analog. For example, the nucleobase can be an alternative to adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Alterations on the Sugar

Nucleosides include a sugar molecule (e.g., a 5-carbon or 6-carbon sugar, such as pentose, ribose, arabinose, xylose, glucose, galactose, or a deoxy derivative thereof) in combination with a nucleobase, while nucleotides are nucleosides containing a nucleoside and a phosphate group or alternative group (e.g., boranophosphate, thiophosphate, selenophosphate, phosphonate, alkyl group, amidate, and glycerol). A nucleoside or nucleotide may be a canonical species, e.g., a nucleoside or nucleotide including a canonical nucleobase, sugar, and, in the case of nucleotides, a phosphate group, or may be an alternative nucleoside or nucleotide including one or more alternative components. For example, alternative nucleosides and nucleotides can be altered on the sugar of the nucleoside or nucleotide. In some embodiments, the alternative nucleosides or nucleotides include the structure:

Formula VI

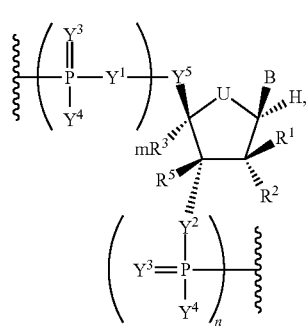

Formula VII

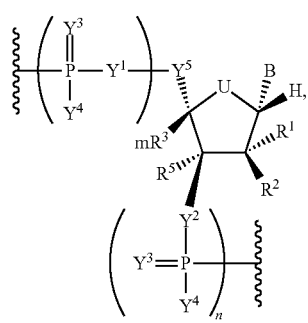

Formula VIII

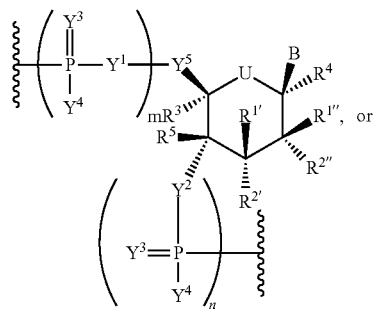

Formula IX

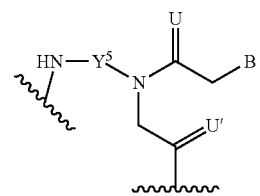

In each of the Formulae VI, VII, VIII, and IX,
each of m and n is independently, an integer from 0 to 5,
each of U and U' independently, is O, S, $N(R^U)_{nu}$, or $C(R^U)_{nu}$, wherein nu is an integer from 0 to 2 and each $R^U$ is, independently, H, halo, or optionally substituted alkyl;
each of $R^{1'}$, $R^{2'}$, $R^{1''}$, $R^{2''}$, $R^1$, $R^2$, $R^3$, $R^4$, and $R^5$ is, independently, if present, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of $R^3$ with one or more of $R^{1'}$, $R^{1''}$, $R^{2'}$, $R^{2''}$, or $R^5$ (e.g., the combination of $R^{1'}$ and $R^3$, the combination of $R^{1''}$ and $R^3$, the combination of $R^{2'}$ and $R^3$, the combination of $R^{2''}$ and $R^3$, or the combination of $R^5$ and $R^3$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); wherein the combination of $R^5$ with one or more of $R^{1'}$, $R^{1''}$, $R^{2'}$, or $R^{2''}$ (e.g., the combination of $R^{1'}$ and $R^5$, the combination of $R^{1''}$ and $R^5$, the combination of $R^{2'}$ and $R^5$, or the combination of $R^{2''}$ and $R^5$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); and wherein the combination of $R^4$ and one or more of $R^{1'}$, $R^{1''}$, $R^{2'}$, $R^{2''}$, $R^3$, or $R^5$ can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); each of m' and m'' is, independently, an integer from 0 to 3 (e.g., from 0 to 2, from 0 to 1, from 1 to 3, or from 1 to 2);
each of $Y^1$, $Y^2$, and $Y^3$, is, independently, O, S, Se, $-NR^{N1}-$, optionally substituted alkylene, or optionally substituted heteroalkylene, wherein $R^{N1}$ is H, optionally substituted alkyl, optionally substituted alkenyl, optionally substituted alkynyl, optionally substituted aryl, or absent;
each $Y^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;
each $Y^5$ is, independently, O, S, Se, optionally substituted alkylene (e.g., methylene), or optionally substituted heteroalkylene; and B is a nucleobase, either modified or unmodified. In some embodiments, the 2'-hydroxy group (OH) can be modified or replaced with a number of different substituents. Exemplary substitutions at the 2'-position include, but are not limited to, H, azido, halo (e.g., fluoro), optionally substituted $C_{1-6}$ alkyl (e.g., methyl); optionally substituted $C_{1-6}$ alkoxy (e.g., methoxy or ethoxy); optionally substituted $C_{6-10}$ aryloxy; optionally substituted $C_{3-8}$ cycloalkyl; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $-O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxy is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein;

aminoalkoxy, as defined herein; amino as defined herein; and amino acid, as defined herein.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a polynucleotide molecule can include nucleotides containing, e.g., arabinose or L-ribose, as the sugar.

In some embodiments, the polynucleotide includes at least one nucleoside wherein the sugar is L-ribose, 2'-O-methyl-ribose, 2'-fluoro-ribose, arabinose, hexitol, an LNA, or a PNA.

Alterations on the Internucleoside Linkage

Alternative nucleotides can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl, and/or methoxy. As a non-limiting example, two non-bridging oxygens at the same position (e.g., the alpha ($\alpha$), beta ($\beta$) or gamma ($\gamma$) position) can be replaced with a sulfur (thio) and a methoxy.

The replacement of one or more of the oxygen atoms at the a position of the phosphate moiety (e.g., α-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present disclosure, including internucleoside linkages which do not contain a phosphorous atom, are described herein.

Internal Ribosome Entry Sites

Polynucleotides may contain an internal ribosome entry site (IRES). An IRES may act as the sole ribosome binding site, or may serve as one of multiple ribosome binding sites of an mRNA. A polynucleotide containing more than one functional ribosome binding site may encode several peptides or polypeptides that are translated independently by the ribosomes (e.g., multicistronic mRNA). When polynucleotides are provided with an IRES, further optionally provided is a second translatable region. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

5'-Cap Structure

A polynucleotide (e.g., an mRNA) may include a 5'-cap structure. The 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly-A binding protein to form the mature cyclic mRNA species. The cap further assists the removal of 5'-proximal introns removal during mRNA splicing.

Endogenous polynucleotide molecules may be 5'-end capped generating a 5'-ppp-5'-triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-O-methylated. 5'-decapping through hydrolysis and cleavage of the guanylate cap structure may target a polynucleotide molecule, such as an mRNA molecule, for degradation.

Alterations to polynucleotides may generate a non-hydrolyzable cap structure preventing decapping and thus increasing polynucleotide half-life. Because cap structure hydrolysis requires cleavage of 5'-ppp-5' phosphorodiester linkages, alternative nucleotides may be used during the capping reaction. For example, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional alternative guanosine nucleotides may be used such as α-methyl-phosphonate and selenophosphate nucleotides.

Additional alterations include, but are not limited to, 2'-O-methylation of the ribose sugars of 5'-terminal and/or 5'-anteterminal nucleotides of the polynucleotide (as mentioned above) on the 2'-hydroxy group of the sugar. Multiple distinct 5'-cap structures can be used to generate the 5'-cap of a polynucleotide, such as an mRNA molecule.

5'-Cap structures include those described in International Patent Publication Nos. WO2008127688, WO 2008016473, and WO 2011015347, the cap structures of each of which are incorporated herein by reference.

Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide.

For example, the Anti-Reverse Cap Analog (ARCA) cap contains two guanosines linked by a 5'-5'-triphosphate group, wherein one guanosine contains an N7-methyl group as well as a 3'-O-methyl group (i.e., N7,3'-O-dimethyl-guanosine-5'-triphosphate-5'-guanosine, $m^7$G-3'mppp-G, which may equivalently be designated 3' O-Me-m7G(5')ppp(5')G). The 3'-O atom of the other, unaltered, guanosine becomes linked to the 5'-terminal nucleotide of the capped polynucleotide (e.g., an mRNA). The N7- and 3'-O-methylated guanosine provides the terminal moiety of the capped polynucleotide (e.g., mRNA).

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

A cap may be a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the cap structures of which are herein incorporated by reference.

Alternatively, a cap analog may be a N7-(4-chlorophenoxyethyl) substituted dinucleotide cap analog known in the art and/or described herein. Non-limiting examples of N7-(4-chlorophenoxyethyl) substituted dinucleotide cap analogs include a N7-(4-chlorophenoxyethyl)-G(5')ppp(5')G and a N7-(4-chlorophenoxyethyl)-m3'-OG(5')ppp(5')G cap analog (see, e.g., the various cap analogs and the methods of synthesizing cap analogs described in Kore et al. Bioorganic & Medicinal Chemistry 2013 21:4570-4574; the cap structures of which are herein incorporated by reference). In other instances, a cap analog useful in the polynucleotides of the present disclosure is a 4-chloro/bromophenoxyethyl analog.

While cap analogs allow for the concomitant capping of a polynucleotide in an in vitro transcription reaction, up to 20% of transcripts remain uncapped. This, as well as the structural differences of a cap analog from endogenous 5'-cap structures of polynucleotides produced by the endogenous, cellular transcription machinery, may lead to reduced translational competency and reduced cellular stability.

Alternative polynucleotides may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects. Non-limiting examples of more authentic 5'-cap structures useful in the polynucleotides of the present disclosure are those which, among other things, have enhanced binding of cap binding proteins, increased half-life, reduced susceptibility to 5'-endonucleases, and/or reduced 5'-decapping, as compared to synthetic 5'-cap structures known in the art (or to a wild-type, natural or physiological 5'-cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-O-methyl. Such a structure is termed the Cap1 structure. This cap results in a higher translational-competency, cellular stability, and a reduced activation of cellular pro-inflammatory cytokines, as compared, e.g., to other 5' cap analog structures known in the art. Other exemplary cap structures include 7mG(5')ppp(5')N,pN2p (Cap 0), 7mG(5')ppp(5')NlmpNp (Cap 1), 7mG(5')-ppp(5')NlmpN2mp (Cap 2), and m(7)Gpppm(3)(6,6,2')Apm(2')Apm(2')Cpm(2)(3,2')Up (Cap 4).

Because the alternative polynucleotides may be capped post-transcriptionally, and because this process is more efficient, nearly 100% of the alternative polynucleotides may be capped. This is in contrast to ~80% when a cap analog is linked to an polynucleotide in the course of an in vitro transcription reaction.

5'-terminal caps may include endogenous caps or cap analogs. A 5'-terminal cap may include a guanosine analog. Useful guanosine analogs include inosine, N1-methyl-guanosine, 2'-fluoro-guanosine, 7-deaza-guanosine, 8-oxo-guanosine, 2-amino-guanosine, LNA-guanosine, and 2-azido-guanosine.

In some cases, a polynucleotide contains a modified 5'-cap. A modification on the 5'-cap may increase the stability of polynucleotide, increase the half-life of the polynucleotide, and could increase the polynucleotide translational efficiency. The modified 5'-cap may include, but is not limited to, one or more of the following modifications: modification at the 2'- and/or 3'-position of a capped guanosine triphosphate (GTP), a replacement of the sugar ring oxygen (that produced the carbocyclic ring) with a methylene moiety ($CH_2$), a modification at the triphosphate bridge moiety of the cap structure, or a modification at the nucleobase (G) moiety.

5'-UTRs

A 5'-UTR may be provided as a flanking region to polynucleotides (e.g., mRNAs). A 5'-UTR may be homologous or heterologous to the coding region found in a polynucleotide. Multiple 5'-UTRs may be included in the flanking region and may be the same or of different sequences. Any portion of the flanking regions, including none, may be codon optimized and any may independently contain one or more different structural or chemical alterations, before and/or after codon optimization.

Shown in Table 21 in U.S. Provisional Application No. 61/775,509, and in Table 21 and in Table 22 in U.S. Provisional Application No. 61/829,372, of which are incorporated herein by reference, is a listing of the start and stop site of alternative polynucleotides (e.g., mRNA). In Table 21 each 5'-UTR (5'-UTR-005 to 5'-UTR 68511) is identified by its start and stop site relative to its native or wild type (homologous) transcript (ENST; the identifier used in the ENSEMBL database).

To alter one or more properties of a polynucleotide (e.g., mRNA), 5'-UTRs which are heterologous to the coding region of an alternative polynucleotide (e.g., mRNA) may be engineered. The polynucleotides (e.g., mRNA) may then be administered to cells, tissue or organisms and outcomes such as protein level, localization, and/or half-life may be measured to evaluate the beneficial effects the heterologous 5'-UTR may have on the alternative polynucleotides (mRNA). Variants of the 5'-UTRs may be utilized wherein one or more nucleotides are added or removed to the termini, including A, T, C or G. 5'-UTRs may also be codon-optimized, or altered in any manner described herein.

5'-UTRs, 3'-UTRs, and Translation Enhancer Elements (TEEs)

The 5'-UTR of a polynucleotides (e.g., mRNA) may include at least one translation enhancer element. The term "translational enhancer element" refers to sequences that increase the amount of polypeptide or protein produced from a polynucleotide. As a non-limiting example, the TEE may be located between the transcription promoter and the start codon. The polynucleotides (e.g., mRNA) with at least one TEE in the 5'-UTR may include a cap at the 5'-UTR. Further, at least one TEE may be located in the 5'-UTR of polynucleotides (e.g., mRNA) undergoing cap-dependent or cap-independent translation.

In one aspect, TEEs are conserved elements in the UTR which can promote translational activity of a polynucleotide such as, but not limited to, cap-dependent or cap-independent translation. The conservation of these sequences has been previously shown by Panek et al. (Nucleic Acids Research, 2013, 1-10) across 14 species including humans.

In one non-limiting example, the TEEs known may be in the 5'-leader of the Gtx homeodomain protein (Chappell et al., Proc. Natl. Acad. Sci. USA 101:9590-9594, 2004, the TEEs of which are incorporated herein by reference).

In another non-limiting example, TEEs are disclosed in US Patent Publication Nos. 2009/0226470 and 2013/0177581, International Patent Publication Nos. WO2009/075886, WO2012/009644, and WO1999/024595, U.S. Pat. Nos. 6,310,197 and 6,849,405, the TEE sequences disclosed in each of which are incorporated herein by reference.

In yet another non-limiting example, the TEE may be an internal ribosome entry site (IRES), HCV-IRES or an IRES element such as, but not limited to, those described in U.S. Pat. No. 7,468,275, US Patent Publication Nos. 2007/0048776 and 2011/0124100 and International Patent Publication Nos. WO2007/025008 and WO2001/055369, the IRES sequences of each of which are incorporated herein by reference. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102:6273-6278, 2005) and in US Patent Publication Nos. 2007/0048776 and 2011/0124100 and International Patent Publication No. WO2007/025008, the IRES sequences of each of which are incorporated herein by reference.

"Translational enhancer polynucleotides" are polynucleotides which include one or more of the specific TEE exemplified herein and/or disclosed in the art (see e.g., U.S. Pat. Nos. 6,310,197, 6,849,405, 7,456,273, 7,183,395, U.S. Patent Publication Nos. 20090/226470, 2007/0048776, 2011/0124100, 2009/0093049, 2013/0177581, International Patent Publication Nos. WO2009/075886, WO2007/025008, WO2012/009644, WO2001/055371, WO1999/024595, and European Patent Nos. 2610341 and 2610340; the TEE sequences of each of which are incorporated herein by reference) or their variants, homologs or functional derivatives. One or multiple copies of a specific TEE can be present in a polynucleotide (e.g., mRNA). The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

A polynucleotide (e.g., mRNA) may include at least one TEE that is described in International Patent Publication Nos. WO1999/024595, WO2012/009644, WO2009/075886, WO2007/025008, WO1999/024595, European Patent Publication Nos. 2610341 and 2610340, U.S. Pat. Nos. 6,310,197, 6,849,405, 7,456,273, 7,183,395, and US Patent Publication Nos. 2009/0226470, 2011/0124100, 2007/0048776, 2009/0093049, and 2013/0177581 the TEE sequences of each of which are incorporated herein by reference. The TEE may be located in the 5'-UTR of the polynucleotides (e.g., mRNA).

A polynucleotide (e.g., mRNA) may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. 2009/0226470, 2007/0048776, 2013/0177581 and 2011/0124100, International Patent Publication Nos. WO 1999/024595, WO2012/009644, WO2009/075886 and WO2007/025008, European Patent Publication Nos. 2610341 and 2610340, U.S. Pat. Nos. 6,310,197, 6,849,405, 7,456,273, 7,183,395, the TEE sequences of each of which are incorporated herein by reference.

The 5'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'-UTR of a polynucleotide (e.g., mRNA) may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In some cases, the 5'-UTR may include a spacer to separate two TEE sequences. As a non-limiting example, the spacer may be a 15 nucleotide spacer and/or other spacers known in the art. As another non-limiting example, the 5'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 5'-UTR.

In other instances, the spacer separating two TEE sequences may include other sequences known in the art which may regulate the translation of the polynucleotides (e.g., mRNA) of the present disclosure such as, but not limited to, miR sequences (e.g., miR binding sites and miR seeds). As a non-limiting example, each spacer used to separate two TEE sequences may include a different miR sequence or component of a miR sequence (e.g., miR seed sequence).

In some instances, the TEE in the 5'-UTR of a polynucleotide (e.g., mRNA) may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. 2009/0226470, 2007/0048776, 2013/0177581 and 2011/0124100, International Patent Publication Nos. WO1999/024595, WO2012/009644, WO2009/

075886 and WO2007/025008, European Patent Publication Nos. 2610341 and 2610340, and U.S. Pat. Nos. 6,310,197, 6,849,405, 7,456,273, and 7,183,395 the TEE sequences of each of which are incorporated herein by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. 2009/0226470, 2007/0048776, 2013/0177581 and 2011/0124100, International Patent Publication Nos. WO 1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395; the TEE sequences of each of which are incorporated herein by reference.

In certain cases, the TEE in the 5'-UTR of the polynucleotides (e.g., mRNA) of the present disclosure may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102: 6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/ NMETH.2522); the TEE sequences of each of which are herein incorporated by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); the TEE sequences of each of which is incorporated herein by reference.

In some cases, the TEE used in the 5'-UTR of a polynucleotide (e.g., mRNA) is an IRES sequence such as, but not limited to, those described in U.S. Pat. No. 7,468,275 and International Patent Publication No. WO2001/055369, the TEE sequences of each of which are incorporated herein by reference.

In some instances, the TEEs used in the 5'-UTR of a polynucleotide (e.g., mRNA) may be identified by the methods described in US Patent Publication Nos. 2007/0048776 and 2011/0124100 and International Patent Publication Nos. WO2007/025008 and WO2012/009644, the methods of each of which are incorporated herein by reference.

In some cases, the TEEs used in the 5'-UTR of a polynucleotide (e.g., mRNA) of the present disclosure may be a transcription regulatory element described in U.S. Pat. Nos. 7,456,273 and 7,183,395, US Patent Publication No. 2009/0093049, and International Publication No. WO2001/055371, the TEE sequences of each of which is incorporated herein by reference. The transcription regulatory elements may be identified by methods known in the art, such as, but not limited to, the methods described in U.S. Pat. Nos. 7,456,273 and 7,183,395 US Patent Publication No. 2009/ 0093049, and International Publication No. WO2001/ 055371, the methods of each of which is incorporated herein by reference.

In yet other instances, the TEE used in the 5'-UTR of a polynucleotide (e.g., mRNA) is a polynucleotide or portion thereof as described in U.S. Pat. Nos. 7,456,273 and 7,183, 395, US Patent Publication No. 2009/0093049, and International Publication No. WO2001/055371, the TEE sequences of each of which are incorporated herein by reference.

The 5'-UTR including at least one TEE described herein may be incorporated in a monocistronic sequence such as, but not limited to, a vector system or a polynucleotide vector. As a non-limiting example, the vector systems and polynucleotide vectors may include those described in U.S. Pat. Nos. 7,456,273 and 7,183,395, US Patent Publication Nos. 2007/0048776, 2009/0093049 and 2011/0124100, and International Patent Publication Nos. WO2007/025008 and WO2001/055371, the TEE sequences of each of which are incorporated herein by reference.

The TEEs described herein may be located in the 5'-UTR and/or the 3'-UTR of the polynucleotides (e.g., mRNA). The TEEs located in the 3'-UTR may be the same and/or different than the TEEs located in and/or described for incorporation in the 5'-UTR.

In some cases, the 3'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'-UTR of the polynucleotides (e.g., mRNA) of the present disclosure may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In one instance, the 3'-UTR may include a spacer to separate two TEE sequences. As a non-limiting example, the spacer may be a 15 nucleotide spacer and/or other spacers known in the art. As another non-limiting example, the 3'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 3'-UTR.

In other cases, the spacer separating two TEE sequences may include other sequences known in the art which may regulate the translation of the polynucleotides (e.g., mRNA) of the present disclosure such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In yet other cases, the incorporation of a miR sequence and/or a TEE sequence changes the shape of the stem loop region which may increase and/or decrease translation. (see e.g., Kedde et al. A Pumilio-induced RNA structure switch in p27-3'UTR controls miR-221 and miR-22 accessibility. Nature Cell Biology. 2010).

Stem Loops

Polynucleotides (e.g., mRNAs) may include a stem loop such as, but not limited to, a histone stem loop. The stem loop may be a nucleotide sequence that is about 25 or about 26 nucleotides in length such as, but not limited to, those as described in International Patent Publication No. WO2013/103659, which is incorporated herein by reference. The histone stem loop may be located 3'-relative to the coding region (e.g., at the 3'-terminus of the coding region). As a non-limiting example, the stem loop may be located at the 3'-end of a polynucleotide described herein. In some cases, a polynucleotide (e.g., an mRNA) includes more than one stem loop (e.g., two stem loops). Examples of stem loop sequences are described in International Patent Publication Nos. WO2012/019780 and WO201502667, the stem loop sequences of which are herein incorporated by reference. In some instances, a polynucleotide includes the stem loop sequence CAAAGGCTCTTTTCAGAGCCACCA (SEQ ID NO: 1). In others, a polynucleotide includes the stem loop sequence CAAAGGCUCUUUUCAGAGCCACCA (SEQ ID NO: 2).

A stem loop may be located in a second terminal region of a polynucleotide. As a non-limiting example, the stem loop may be located within an untranslated region (e.g., 3'-UTR) in a second terminal region.

In some cases, a polynucleotide such as, but not limited to mRNA, which includes the histone stem loop may be stabilized by the addition of a 3'-stabilizing region (e.g., a 3'-stabilizing region including at least one chain terminating nucleoside). Not wishing to be bound by theory, the addition of at least one chain terminating nucleoside may slow the degradation of a polynucleotide and thus can increase the half-life of the polynucleotide.

In other cases, a polynucleotide such as, but not limited to mRNA, which includes the histone stem loop may be stabilized by an alteration to the 3'-region of the polynucleotide that can prevent and/or inhibit the addition of oligo(U) (see e.g., International Patent Publication No. WO2013/103659).

In yet other cases, a polynucleotide such as, but not limited to mRNA, which includes the histone stem loop may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

In some instances, the polynucleotides of the present disclosure may include a histone stem loop, a poly-A region, and/or a 5'-cap structure. The histone stem loop may be before and/or after the poly-A region. The polynucleotides including the histone stem loop and a poly-A region sequence may include a chain terminating nucleoside described herein.

In other instances, the polynucleotides of the present disclosure may include a histone stem loop and a 5'-cap structure. The 5'-cap structure may include, but is not limited to, those described herein and/or known in the art.

In some cases, the conserved stem loop region may include a miR sequence described herein. As a non-limiting example, the stem loop region may include the seed sequence of a miR sequence described herein. In another non-limiting example, the stem loop region may include a miR-122 seed sequence.

In certain instances, the conserved stem loop region may include a miR sequence described herein and may also include a TEE sequence.

In some cases, the incorporation of a miR sequence and/or a TEE sequence changes the shape of the stem loop region which may increase and/or decrease translation. (see e.g., Kedde et al. A Pumilio-induced RNA structure switch in p27-3'UTR controls miR-221 and miR-22 accessibility. Nature Cell Biology. 2010, herein incorporated by reference in its entirety).

Polynucleotides may include at least one histone stem-loop and a poly-A region or polyadenylation signal. Non-limiting examples of polynucleotide sequences encoding for at least one histone stem-loop and a poly-A region or a polyadenylation signal are described in International Patent Publication No. WO2013/120497, WO2013/120629, WO2013/120500, WO2013/120627, WO2013/120498, WO2013/120626, WO2013/120499 and WO2013/120628, the sequences of each of which are incorporated herein by reference. In certain cases, the polynucleotide encoding for a histone stem loop and a poly-A region or a polyadenylation signal may code for a pathogen antigen or fragment thereof such as the polynucleotide sequences described in International Patent Publication No WO2013/120499 and WO2013/120628, the sequences of both of which are incorporated herein by reference. In other cases, the polynucleotide encoding for a histone stem loop and a poly-A region or a polyadenylation signal may code for a therapeutic protein such as the polynucleotide sequences described in International Patent Publication No WO2013/120497 and WO2013/120629, the sequences of both of which are incorporated herein by reference. In some cases, the polynucleotide encoding for a histone stem loop and a poly-A region or a polyadenylation signal may code for a tumor antigen or fragment thereof such as the polynucleotide sequences described in International Patent Publication No WO2013/120500 and WO2013/120627, the sequences of both of which are incorporated herein by reference. In other cases, the polynucleotide encoding for a histone stem loop and a poly-A region or a polyadenylation signal may code for a allergenic antigen or an autoimmune self-antigen such as the polynucleotide sequences described in International Patent Publication No WO2013/120498 and WO2013/120626, the sequences of both of which are incorporated herein by reference.

Poly-A Regions

A polynucleotide or nucleic acid (e.g., an mRNA) may include a polyA sequence and/or polyadenylation signal. A polyA sequence may be comprised entirely or mostly of adenine nucleotides or analogs or derivatives thereof. A polyA sequence may be a tail located adjacent to a 3' untranslated region of a nucleic acid.

During RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long.

Unique poly-A region lengths may provide certain advantages to the alternative polynucleotides of the present disclosure.

Generally, the length of a poly-A region of polynucleotides of the present disclosure is at least 30 nucleotides in length. In another embodiment, the poly-A region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In some instances, the poly-A region may be 80 nucleotides, 120 nucleotides, 160 nucleotides in length on an alternative polynucleotide molecule described herein.

In other instances, the poly-A region may be 20, 40, 80, 100, 120, 140 or 160 nucleotides in length on an alternative polynucleotide molecule described herein.

In some cases, the poly-A region is designed relative to the length of the overall alternative polynucleotide. This design may be based on the length of the coding region of the alternative polynucleotide, the length of a particular feature or region of the alternative polynucleotide, or based on the length of the ultimate product expressed from the alternative polynucleotide. When relative to any feature of the alternative polynucleotide (e.g., other than the mRNA portion which includes the poly-A region) the poly-A region may be 10, 20, 30, 40, 50, 60, 70, 80, 90 or 100% greater in length than the additional feature. The poly-A region may also be designed as a fraction of the alternative polynucleotide to which it belongs. In this context, the poly-A region may be 10, 20, 30, 40, 50, 60, 70, 80, or 90% or more of the total length of the construct or the total length of the construct minus the poly-A region.

In certain cases, engineered binding sites and/or the conjugation of polynucleotides (e.g., mRNA) for poly-A binding protein may be used to enhance expression. The engineered binding sites may be sensor sequences which can operate as binding sites for ligands of the local microenvironment of the polynucleotides (e.g., mRNA). As a non-limiting example, the polynucleotides (e.g., mRNA) may include at least one engineered binding site to alter the binding affinity of poly-A binding protein (PABP) and analogs thereof. The incorporation of at least one engineered binding site may increase the binding affinity of the PABP and analogs thereof.

Additionally, multiple distinct polynucleotides (e.g., mRNA) may be linked together to the PABP (poly-A binding protein) through the 3'-end using alternative nucleotides at the 3'-terminus of the poly-A region. Transfection experiments can be conducted in relevant cell lines at and protein production can be assayed by ELISA at 12 hours, 24 hours, 48 hours, 72 hours, and day 7 post-transfection. As a non-limiting example, the transfection experiments may be used to evaluate the effect on PABP or analogs thereof binding affinity as a result of the addition of at least one engineered binding site.

In certain cases, a poly-A region may be used to modulate translation initiation. While not wishing to be bound by theory, the poly-A region recruits PABP which in turn can interact with translation initiation complex and thus may be essential for protein synthesis.

In some cases, a poly-A region may also be used in the present disclosure to protect against 3'-5'-exonuclease digestion.

In some instances, a polynucleotide (e.g., mRNA) may include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the polyA-G quartet results in protein production equivalent to at least 75% of that seen using a poly-A region of 120 nucleotides alone.

In some cases, a polynucleotide (e.g., mRNA) may include a poly-A region and may be stabilized by the addition of a 3'-stabilizing region. The polynucleotides (e.g., mRNA) with a poly-A region may further include a 5'-cap structure.

In other cases, a polynucleotide (e.g., mRNA) may include a poly-A-G Quartet. The polynucleotides (e.g., mRNA) with a poly-A-G Quartet may further include a 5'-cap structure.

In some cases, the 3'-stabilizing region which may be used to stabilize a polynucleotide (e.g., mRNA) including a poly-A region or poly-A-G Quartet may be, but is not limited to, those described in International Patent Publication No. WO2013/103659, the poly-A regions and poly-A-G Quartets of which are incorporated herein by reference. In other cases, the 3'-stabilizing region which may be used with the polynucleotides of the present disclosure include a chain termination nucleoside such as 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside.

In other cases, a polynucleotide such as, but not limited to mRNA, which includes a polyA region or a poly-A-G Quartet may be stabilized by an alteration to the 3'-region of the polynucleotide that can prevent and/or inhibit the addition of oligio(U) (see e.g., International Patent Publication No. WO2013/103659).

In yet other instances, a polynucleotide such as, but not limited to mRNA, which includes a poly-A region or a poly-A-G Quartet may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

Chain Terminating Nucleosides

A nucleic acid may include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine.

Other Components

A nanoparticle composition may include one or more components in addition to those described in the preceding sections. For example, a nanoparticle composition may include one or more small hydrophobic molecules such as a vitamin (e.g., vitamin A or vitamin E) or a sterol.

Nanoparticle compositions may also include one or more permeability enhancer molecules, carbohydrates, polymers, surface altering agents, or other components. A permeability enhancer molecule may be a molecule described by U.S. patent application publication No. 2005/0222064, for example. Carbohydrates may include simple sugars (e.g., glucose) and polysaccharides (e.g., glycogen and derivatives and analogs thereof).

A polymer may be included in and/or used to encapsulate or partially encapsulate a nanoparticle composition. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone (PVP), polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl (meth)acrylate), poly(butyl(meth)acrylate), poly(isobutyl (meth)acrylate), poly(hexyl(meth)acrylate), poly(isodecyl (meth)acrylate), poly(lauryl(meth)acrylate), poly(phenyl (meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, polyoxamines, poly (ortho)esters, poly(butyric acid), poly(valeric acid), poly (lactide-co-caprolactone), trimethylene carbonate, poly(N-acryloylmorpholine) (PAcM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin $\beta 4$, dornase alfa, neltenexine, and erdosteine), and DNases (e.g., rhDNase). A surface altering agent may be disposed within a nanoparticle and/or on the surface of a nanoparticle composition (e.g., by coating, adsorption, covalent linkage, or other process).

A nanoparticle composition may also comprise one or more functionalized lipids. For example, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a nanoparticle composition may also be conjugated with one or more useful antibodies. Functional groups and conjugates useful in targeted cell delivery, imaging, and membrane permeation are well known in the art.

In addition to these components, nanoparticle compositions may include any substance useful in pharmaceutical compositions. For example, the nanoparticle composition may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's *The Science and Practice of Pharmacy*, 21$^{st}$ Edition, A. R. Gennaro; Lippincott, Williams & Wilkins, Baltimore, Md., 2006).

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN® 60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinylpyrrolidone), diethylene glycol monolaurate, triethanolamine oleate, sodium oleate, potassium oleate, ethyl oleate, oleic acid, ethyl laurate, sodium lauryl sulfate, PLURONIC® F 68, POLOXAMER® 188, cetrimonium bromide, cetylpyridinium chloride, benzalkonium chloride, docusate sodium, and/or combinations thereof.

A binding agent may be starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g. HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Formulations

Nanoparticle compositions may include a lipid component and one or more additional components, such as a therapeutic and/or prophylactic agent. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, a lipid according to one of formulae (I), (Ia1)-(Ia6), (Ib), (II), (IIa), (III), (IIIa), (IV), (17-I), (19-I), (19-II), (20-I) and (21-I), a phospholipid (such as an unsaturated lipid, e.g., DOPE or DSPC), a PEG lipid, and a structural lipid. The elements of the lipid component may be provided in specific fractions.

In some embodiments, the lipid component of a nanoparticle composition includes a lipid according to one of formulae (I), (Ia1)-(Ia6), (Ib), (II), (IIa), (III), (IIIa), (IV), (17-I), (19-I), (19-II), (20-I) and (21-I), a phospholipid, a PEG lipid, and a structural lipid. In certain embodiments, the lipid component of the nanoparticle composition includes about 30 mol % to about 60 mol % compound according to one of formulae (I), (Ia1)-(Ia6), (Ib), (II), (IIa), (III), (IIIa), (IV), (17-I), (19-I), (19-II), (20-I) and (21-I), about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the nanoparticle composition includes about 35 mol % to about 55 mol % compound according to one of formulae (I), (Ia1)-(Ia6), (Ib), (II), (IIa), (III), (IIIa), (IV), (17-I), (19-I), (19-II), (20-I) and (21-I), about 5 mol % to about 25 mol % phospholipid, about 30 mol % to about 40 mol % structural lipid, and about 0 mol % to about 10 mol % of PEG lipid. In certain embodiments, the lipid component includes about 50 mol % said compound, about 10 mol % phospholipid, about 38.5 mol % structural lipid, and about 1.5 mol % of PEG lipid. In other embodiments, the lipid component includes about 40 mol % said compound, about 20 mol % phospholipid, about 38.5 mol % structural lipid, and about 1.5 mol % of PEG lipid. In some embodiments, the phospholipid may be DOPE or DSPC. In other embodiments, the PEG lipid may be PEG-DMG and/or the structural lipid may be cholesterol.

Nanoparticle compositions may be designed for one or more specific applications or targets. For example, a nanoparticle composition may be designed to deliver a therapeutic and/or prophylactic agent such as an RNA to a particular cell, tissue, organ, or system or group thereof in a mammal's body. Physiochemical properties of nanoparticle compositions may be altered in order to increase selectivity for particular bodily targets. For instance, particle sizes may be adjusted based on the fenestration sizes of different organs. The therapeutic and/or prophylactic agent included in a nanoparticle composition may also be selected based on the desired delivery target or targets. For example, a therapeutic and/or prophylactic agent may be selected for a particular indication, condition, disease, or disorder and/or for delivery to a particular cell, tissue, organ, or system or group thereof (e.g., localized or specific delivery). In certain embodiments, a nanoparticle composition may include an mRNA encoding a polypeptide of interest capable of being translated within a cell to produce the polypeptide of interest. Such a composition may be designed to be specifically delivered to a particular organ. In certain embodiments, a composition may be designed to be specifically delivered to a mammalian liver.

The amount of a therapeutic and/or prophylactic agent in a nanoparticle composition may depend on the size, composition, desired target and/or application, or other properties of the nanoparticle composition as well as on the properties of the therapeutic and/or prophylactic agent. For example, the amount of an RNA useful in a nanoparticle composition may depend on the size, sequence, and other characteristics of the RNA. The relative amounts of a therapeutic and/or prophylactic agent and other elements (e.g., lipids) in a nanoparticle composition may also vary. In some embodiments, the wt/wt ratio of the lipid component to a therapeutic and/or prophylactic agent in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic agent may be from about 10:1 to about 40:1. In certain embodiments, the wt/wt ratio is about 20:1. The amount of a therapeutic and/or prophylactic agent in a nanoparticle composition may, for example, be measured using absorption spectroscopy (e.g., ultraviolet-visible spectroscopy).

In some embodiments, a nanoparticle composition includes one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

Physical Properties

The characteristics of a nanoparticle composition may depend on the components thereof. For example, a nanoparticle composition including cholesterol as a structural lipid may have different characteristics than a nanoparticle composition that includes a different structural lipid. Similarly, the characteristics of a nanoparticle composition may depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes.

Instruments such as the Zetasizer Nano ZS (Malvern Instruments Ltd, Malvern, Worcestershire, UK) may also be used to measure multiple characteristics of a nanoparticle composition, such as particle size, polydispersity index, and zeta potential.

The mean size of a nanoparticle composition may be between 10s of nm and 100s of nm. For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a nanoparticle composition may be from about 70 nm to about 100 nm. In some embodiments, the mean size may be about 80 nm. In other embodiments, the mean size may be about 100 nm.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic agent describes the amount of therapeutic and/or prophylactic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic and/or prophylactic agent in a solution containing the nanoparticle composition before and after breaking up the nanoparticle composition with one or more organic solvents or detergents. Fluorescence may be used to measure the amount of free therapeutic and/or prophylactic agent (e.g., RNA) in a solution. For the nanoparticle compositions described herein, the encapsulation efficiency of a therapeutic and/or prophylactic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

A nanoparticle composition may optionally comprise one or more coatings. For example, a nanoparticle composition may be formulated in a capsule, film, or tablet having a coating. A capsule, film, or tablet including a composition described herein may have any useful size, tensile strength, hardness, or density.

Pharmaceutical Compositions

Nanoparticle compositions may be formulated in whole or in part as pharmaceutical compositions. Pharmaceutical compositions may include one or more nanoparticle compositions. For example, a pharmaceutical composition may include one or more nanoparticle compositions including one or more different therapeutic and/or prophylactic agents. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy*, 21$^{st}$ Edition, A. R. Gennaro; Lippincott, Williams & Wilkins, Baltimore, Md., 2006. Conventional excipients and accessory ingredients may be used in any pharmaceutical composition, except insofar as any conventional excipient or accessory ingredient may be incompatible with one or more components of a nanoparticle composition. An excipient or accessory ingredient may be incompatible with a component of a nanoparticle composition if its combination with the component may result in any undesirable biological effect or otherwise deleterious effect.

In some embodiments, one or more excipients or accessory ingredients may make up greater than 50% of the total mass or volume of a pharmaceutical composition including a nanoparticle composition. For example, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more nanoparticle compositions, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition may comprise between 0.1% and 100% (wt/wt) of one or more nanoparticle compositions.

In certain embodiments, the nanoparticle compositions and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising a compound of any of Formulae (I)-(IV) is a solution that is refrigerated for storage and/or shipment at, for example, about −20° C., −30° C., −40° C., −50° C., −60° C., −70° C., or −80° C. In certain embodiments, the disclosure also relates to a method of increasing stability of the nanoparticle compositions and/or pharmaceutical compositions comprising a compound of any of formulae (I), (Ia1)-(Ia6), (Ib), (II), (IIa), (III), (IIIa), (IV), (17-I), (19-I), (19-II), (20-I) and (21-I) by storing the nanoparticle compositions and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the nanoparticle compositions and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one embodiment, the formulation is stabilized for at least 4 weeks at about 4° C. In certain embodiments, the pharmaceutical composition of the disclosure comprises a nanoparticle composition disclosed herein and a pharmaceutically acceptable carrier selected from one or more of Tris, an acetate (e.g., sodium acetate), an citrate (e.g., sodium citrate), saline, PBS, and sucrose. In certain embodiments, the pharmaceutical composition of the disclosure has a pH value between about 7 and 8 (e.g., 6.8, 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a nanoparticle composition disclosed herein, Tris, saline and sucrose, and has a pH of about 7.5-8, which is suitable for storage and/or shipment at, for example, about −20° C. For example, a pharmaceutical composition of the disclosure comprises a nanoparticle composition disclosed herein and PBS and has a pH of about 7-7.8, suitable for storage and/or shipment at, for example, about 4° C. or lower. "Stability," "stabilized," and "stable" in the context of the present disclosure refers to the resistance of nanoparticle compositions and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

Nanoparticle compositions and/or pharmaceutical compositions including one or more nanoparticle compositions may be administered to any patient or subject, including those patients or subjects that may benefit from a therapeutic effect provided by the delivery of a therapeutic and/or prophylactic agent to one or more particular cells, tissues, organs, or systems or groups thereof, such as the renal system. Although the descriptions provided herein of nanoparticle compositions and pharmaceutical compositions including nanoparticle compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition including one or more nanoparticle compositions may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage.

Pharmaceutical compositions may be prepared in a variety of forms suitable for a variety of routes and methods of administration. For example, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutic and/or prophylactic agents, additional agents such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, films, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay, silicates), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants, and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (wt/wt) of the composition, and active ingredient may constitute 0.1% to 20% (wt/wt) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (wt/wt) and as much as 100% (wt/wt) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (wt/wt) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (wt/wt) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this present disclosure.

Methods of Producing Polypeptides in Cells

The present disclosure provides methods of producing a polypeptide of interest in a mammalian cell. Methods of producing polypeptides involve contacting a cell with a nanoparticle composition including an mRNA encoding the polypeptide of interest. Upon contacting the cell with the nanoparticle composition, the mRNA may be taken up and translated in the cell to produce the polypeptide of interest.

In general, the step of contacting a mammalian cell with a nanoparticle composition including an mRNA encoding a polypeptide of interest may be performed in vivo, ex vivo, in culture, or in vitro. The amount of nanoparticle composition contacted with a cell, and/or the amount of mRNA therein, may depend on the type of cell or tissue being contacted, the means of administration, the physiochemical characteristics of the nanoparticle composition and the mRNA (e.g., size, charge, and chemical composition) therein, and other factors. In general, an effective amount of the nanoparticle composition will allow for efficient polypeptide production in the cell. Metrics for efficiency may include polypeptide translation (indicated by polypeptide expression), level of mRNA degradation, and immune response indicators.

The step of contacting a nanoparticle composition including an mRNA with a cell may involve or cause transfection. A phospholipid including in the lipid component of a nanoparticle composition may facilitate transfection and/or increase transfection efficiency, for example, by interacting and/or fusing with a cellular or intracellular membrane. Transfection may allow for the translation of the mRNA within the cell.

In some embodiments, the nanoparticle compositions described herein may be used therapeutically. For example, an mRNA included in a nanoparticle composition may encode a therapeutic polypeptide (e.g., in a translatable region) and produce the therapeutic polypeptide upon contacting and/or entry (e.g., transfection) into a cell. In other embodiments, an mRNA included in a nanoparticle composition may encode a polypeptide that may improve or increase the immunity of a subject. For example, an mRNA may encode a granulocyte-colony stimulating factor or trastuzumab.

In certain embodiments, an mRNA included in a nanoparticle composition may encode a recombinant polypeptide that may replace one or more polypeptides that may be substantially absent in a cell contacted with the nanoparticle composition. The one or more substantially absent polypeptides may be lacking due to a genetic mutation of the encoding gene or a regulatory pathway thereof. Alternatively, a recombinant polypeptide produced by translation of the mRNA may antagonize the activity of an endogenous protein present in, on the surface of, or secreted from the cell. An antagonistic recombinant polypeptide may be desirable to combat deleterious effects caused by activities of the endogenous protein, such as altered activities or localization caused by mutation. In another alternative, a recombinant polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Recombinant polypeptides produced by translation of the mRNA may be engineered for localization within the cell, such as within a specific compartment such as the nucleus, or may be engineered for secretion from the cell or for translocation to the plasma membrane of the cell.

In some embodiments, contacting a cell with a nanoparticle composition including an mRNA may reduce the innate immune response of a cell to an exogenous nucleic acid. A cell may be contacted with a first nanoparticle composition including a first amount of a first exogenous mRNA including a translatable region and the level of the innate immune response of the cell to the first exogenous mRNA may be determined. Subsequently, the cell may be contacted with a second composition including a second amount of the first exogenous mRNA, the second amount being a lesser amount of the first exogenous mRNA compared to the first amount. Alternatively, the second composition may include a first amount of a second exogenous mRNA that is different from the first exogenous mRNA. The steps of contacting the cell with the first and second compositions may be repeated one or more times. Additionally, efficiency of polypeptide production (e.g., translation) in the cell may be optionally determined, and the cell may be re-contacted with the first and/or second composition repeatedly until a target protein production efficiency is achieved.

In some embodiments, a method of producing a polypeptide of interest in a mammalian cell involves contacting the cell with a nanoparticle composition including (i) a lipid component including a phospholipid, a structural lipid, a PEG lipid, and a compound of one of formulae (I), (Ia1)-(Ia6), (Ib), (II), (IIa), (III), (IIIa), (IV), (17-I), (19-I), (19-II), (20-I) and (21-I), as described herein; and (ii) an mRNA encoding the polypeptide of interest, whereby the mRNA is capable of being translated in the cell to produce the polypeptide of interest.

Methods of Delivering Therapeutic Agents to Cells and Organs

The present disclosure provides methods of delivering a therapeutic and/or prophylactic agent to a mammalian cell or organ. Delivery of a therapeutic and/or prophylactic agent to a cell involves administering a nanoparticle composition including the therapeutic and/or prophylactic agent to a subject, where administration of the composition involves contacting the cell with the composition. For example, a protein, cytotoxic agent, radioactive ion, chemotherapeutic agent, or nucleic acid (such as an RNA, e.g., mRNA) may be delivered to a cell or organ. In the instance that a therapeutic and/or prophylactic agent is an mRNA, upon contacting a cell with the nanoparticle composition, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some embodiments, a nanoparticle composition may target a particular type or class of cells (e.g., cells of a particular organ or system thereof). For example, a nanoparticle composition including a therapeutic and/or prophylactic agent of interest may be specifically delivered to a mammalian liver, kidney, spleen, femur, or lung. Specific delivery to a particular class of cells, an organ, or a system or group thereof implies that a higher proportion of nanoparticle compositions including a therapeutic and/or prophylactic agent are delivered to the destination (e.g., tissue) of interest relative to other destinations, e.g., upon administration of a nanoparticle composition to a mammal. In some embodiments, specific delivery may result in a greater than 2 fold, 5 fold, 10 fold, 15 fold, or 20 fold increase in the amount of therapeutic and/or prophylactic agent per 1 g of tissue of the targeted destination (e.g., tissue of interest, such as a liver) as compared to another destination (e.g., the spleen). In certain embodiments, the tissue of interest is selected from the group consisting of a liver, kidney, a lung, a spleen, a femur, vascular endothelium in vessels (e.g., intra-coronary or intra-femoral) or kidney, and tumor tissue (e.g., via intratumoral injection).

As another example of targeted or specific delivery, an mRNA that encodes a protein-binding partner (e.g., an antibody or functional fragment thereof, a scaffold protein, or a peptide) or a receptor on a cell surface may be included in a nanoparticle composition. An mRNA may additionally or instead be used to direct the synthesis and extracellular localization of lipids, carbohydrates, or other biological moieties. Alternatively, other therapeutic and/or prophylactic agents or elements (e.g., lipids or ligands) of a nanoparticle composition may be selected based on their affinity for particular receptors (e.g., low density lipoprotein receptors) such that a nanoparticle composition may more readily interact with a target cell population including the receptors. For example, ligands may include, but are not limited to, members of a specific binding pair, antibodies, monoclonal antibodies, Fv fragments, single chain Fv (scFv) fragments, Fab' fragments, F(ab')$_2$ fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tridobdies, or tetrabodies; and aptamers, receptors, and fusion proteins.

In some embodiments, a ligand may be a surface-bound antibody, which can permit tuning of cell targeting specificity. This is especially useful since highly specific antibodies can be raised against an epitope of interest for the desired targeting site. In one embodiment, multiple antibodies are expressed on the surface of a cell, and each antibody can have a different specificity for a desired target. Such approaches can increase the avidity and specificity of targeting interactions.

A ligand can be selected, e.g., by a person skilled in the biological arts, based on the desired localization or function of the cell. For example an estrogen receptor ligand, such as tamoxifen, can target cells to estrogen-dependent breast cancer cells that have an increased number of estrogen receptors on the cell surface. Other non-limiting examples of ligand/receptor interactions include CCR1 (e.g., for treatment of inflamed joint tissues or brain in rheumatoid arthritis, and/or multiple sclerosis), CCR7, CCR8 (e.g., targeting to lymph node tissue), CCR6, CCR9, CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), and VLA-4NCAM-1 (e.g., targeting to endothelium). In general, any receptor involved in targeting (e.g., cancer metastasis) can be harnessed for use in the methods and compositions described herein.

Targeted cells may include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In certain embodiments, a nanoparticle composition may target hepatocytes. Apolipoproteins such as apolipoprotein E (apoE) have been shown to associate with neutral or near neutral lipid-containing nanoparticle compositions in the body, and are known to associate with receptors such as low-density lipoprotein receptors (LDLRs) found on the surface of hepatocytes. See, e.g., Akinc, A. et al., *Mol. Ther.* 2010, 18, 1357-1364 and Dong, Y. et al., *PNAS* 2014, 111, 3955-3960, the contents of each of which are incorporated herein by reference in their entireties. Thus, a nanoparticle composition including a lipid component with a neutral or near neutral charge that is administered to a subject may acquire apoE in a subject's body and may subsequently deliver a therapeutic and/or prophylactic agent (e.g., an RNA) to hepatocytes including LDLRs in a targeted manner.

In certain embodiments, cell uptake of a compound of one of formulae (I), (Ia1)-(Ia6), (Ib), (II), (IIa), (III), (IIIa), and (IV) as described herein or a nanoparticle composition comprising the compound may be dependent on levels and/or activities of LDLRs, or cell uptake of the nanoparticle composition is LDLR-dependent. For example, if the cell is LDLR-deficient (e.g., having an aberrant LDLR activity and/or an abnormally low level of LDLRs), the cell uptake of the compound or nanoparticle composition may decrease as compared to the uptake by a normal cell.

In certain embodiments, cell uptake of a compound of one of formulae (I), (Ia1)-(Ia6), (Ib), (II), (IIa), (III), (IIIa), and (IV) as described herein or a nanoparticle composition comprising the compound may be independent on levels and/or activities of LDLRs, or cell uptake of the nanoparticle composition is LDLR-independent. For example, if the cell is LDLR-deficient (e.g., having an aberrant LDLR activity and/or an abnormally low level of LDLRs), the cell uptake of the compound or nanoparticle composition is substantively the same as the uptake by a normal cell.

In certain embodiments, cell uptake of a compound of one of formulae (I), (Ia1)-(Ia6), (Ib), (II), (IIa), (III), (IIIa), and (IV)=as described herein or a nanoparticle composition comprising the compound may be dependent on levels and/or activities of apoE, or cell uptake of the nanoparticle composition is apoE-dependent. For example, if the cell is apoE-deficient (e.g., having an aberrant apoE activity and/or an abnormally low level of apoE), the cell uptake of the compound or nanoparticle composition may decrease as compared to the uptake by a normal cell.

In certain embodiments, cell uptake of a compound of one of formulae (I), (Ia1)-(Ia6), (Ib), (II), (IIa), (III), (IIIa), and (IV) as described herein or a nanoparticle composition comprising the compound may be independent on levels and/or activities of apoE, or cell uptake of the nanoparticle composition is apoE-independent. For example, if the cell is apoE-deficient (e.g., having an aberrant apoE activity and/or an abnormally low level of apoE), the cell uptake of the compound or nanoparticle composition is substantively the same as the uptake by a normal cell.

In certain embodiments, cell uptake of the compound or nanoparticle composition disclosed herein may be both LDLR-dependent and apoE-dependent.

In certain embodiments, cell uptake of the compound or nanoparticle composition disclosed herein may be dependent on the interaction of LDLR and apoE. For example, if the interaction of LDLR and apoE is abnormal (e.g., leading to an abnormally low level of downstream signaling), the cell uptake of the compound or nanoparticle composition may decrease as compared to the uptake by a normal cell.

In certain embodiments, cell uptake of the compound or nanoparticle composition disclosed herein may be both LDLR-independent and apoE-independent.

In certain embodiments, cell uptake of the compound or nanoparticle composition disclosed herein may be independent on the interaction of LDLR and apoE. For example, if the interaction of LDLR and apoE is abnormal (e.g., leading to an abnormally low level of downstream signaling), the cell uptake of the compound or nanoparticle composition is substantively the same as the uptake by a normal cell.

In certain embodiments, the apoE is apoE3.

In some embodiments, a method of delivering a therapeutic and/or prophylactic agent to a mammalian cell involves administering to a subject a nanoparticle composition including (i) a lipid component including a phospholipid, a structural lipid, a PEG lipid, and a compound of one of formulae (I), (Ia1)-(Ia6), (Ib), (II), (IIa), (III), (IIIa), (IV), (17-I), (19-I), (19-II), (20-I) and (21-I), as described herein; and (ii) a therapeutic and/or prophylactic agent (e.g., an mRNA), where administering involves contacting the cell with the nanoparticle composition, whereby the therapeutic and/or prophylactic agent is delivered to the cell.

In further embodiments, a method of specifically delivering a therapeutic and/or prophylactic agent to a mammalian organ involves administering to a mammal a nanoparticle composition including (i) a lipid component including a phospholipid, a structural lipid, a PEG lipid, and a compound of one of formulae (I), (Ia1)-(Ia6), (Ib), (II), (IIa), (III), (IIIa), (IV), (17-I), (19-I), (19-II), (20-I) and (21-I), as described herein; and (ii) a therapeutic and/or prophylactic agent (e.g., an mRNA), where administering involves contacting the mammalian organ with the nanoparticle composition, whereby the therapeutic and/or prophylactic agent is delivered to the organ.

In certain embodiments, the delivery efficiency of the therapeutic and/or prophylactic agent is LDLR-independent or apoE-independent, or both. In certain embodiments, the delivery efficiency of the therapeutic and/or prophylactic agent is LDLR-dependent or apoE-dependent, or both. In certain embodiments, the delivery efficiency of the therapeutic and/or prophylactic agent is independent of LDLR-apoE interaction. In certain embodiments, the delivery efficiency of the therapeutic and/or prophylactic agent is dependent on LDLR-apoE interaction.

Methods of Treating Diseases and Disorders

Nanoparticle compositions may be useful for treating a disease, disorder, or condition. In particular, such compositions may be useful in treating a disease, disorder, or condition characterized by missing or aberrant protein or polypeptide activity. For example, a nanoparticle composition comprising an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic agent included in a nanoparticle composition may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases (e.g., cystic fibrosis), autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene, which produce a dysfunctional protein variant of CFTR protein, which causes cystic fibrosis. The present disclosure provides a method for treating such diseases, disorders, and/or conditions in a subject by administering a nanoparticle composition including an RNA and a lipid component including a lipid according to one of formulae (I), (Ia1)-(Ia6), (Ib), (II), (IIa), (III), (IIIa), (IV), (17-1), (19-1), (19-II), (20-I) and (21-1), a phospholipid (optionally unsaturated), a PEG lipid, and a structural lipid, wherein the RNA may be an mRNA encoding a polypeptide that antagonizes or otherwise overcomes an aberrant protein activity present in the cell of the subject.

In some embodiments, a method of treating a disease or disorder in a mammal in need involves administering to the mammal a therapeutically effective amount of a nanoparticle composition including (i) a lipid component including a phospholipid, a structural lipid, a PEG lipid, and a compound of formula (I), (Ia1)-(Ia6), (Ib), (II), (IIa), (III), (IIIa), (IV), (17-I), (19-I), (19-II), or (20-I), as described herein; and (ii) a therapeutic and/or prophylactic agent (e.g., an mRNA).

The disclosure provides methods involving administering nanoparticle compositions including one or more therapeutic and/or prophylactic agents and pharmaceutical compositions including the same. The terms therapeutic and prophylactic can be used interchangeably herein with respect to features and embodiments of the present disclosure. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject; the purpose of the administration; the particular composition; the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutic and/or prophylactic agents employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

A nanoparticle composition including one or more therapeutic and/or prophylactic agents may be administered by any route. In some embodiments, compositions, including prophylactic, diagnostic, or imaging compositions including one or more nanoparticle compositions described herein, are administered by one or more of a variety of routes, including oral, intravenous, intramuscular, intra-arterial, intramedullary, intrathecal, subcutaneous, intraventricular, trans- or intra-dermal, interdermal, rectal, intravaginal, intraperitoneal, intraocular, subretinal, intravitreal, topical (e.g. by powders, ointments, creams, gels, lotions, and/or drops), mucosal, nasal, buccal, enteral, vitreal, intratumoral, sublingual, intranasal; by intratracheal instillation, bronchial instillation, and/or inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, intraocular, subretinal, intravitreal, or by inhalation. However, the present disclosure encompasses the delivery or administration of compositions by any appropriate route taking into consideration likely advances in the sciences of drug delivery. In general, the most appropriate route of administration will depend upon a variety of factors including the nature of the nanoparticle composition including one or more therapeutic and/or prophylactic agents (e.g., its stability in various bodily environments such as the bloodstream and gastrointestinal tract), the condition of the patient (e.g., whether the patient is able to tolerate particular routes of administration), etc.

In certain embodiments, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic and/or prophylactic agent (e.g., an mRNA) in a given dose, where a dose of 1 mg/kg (mpk) provides 1 mg of a therapeutic and/or prophylactic agent per 1 kg of subject body weight. In certain embodiments, a dose of about 0.001 mg/kg to about 10 mg/kg of a therapeutic and/or prophylactic agent (e.g., mRNA) of a nanoparticle composition may be administered. In other embodiments, a dose of about 0.005 mg/kg to about 2.5 mg/kg of a therapeutic and/or prophylactic agent may be administered. In certain embodiments, a dose of about 0.1 mg/kg to about 1 mg/kg may be administered. In other embodiments, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect. The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition.

Nanoparticle compositions including one or more therapeutic and/or prophylactic agents may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more nanoparticle compositions including one or more different therapeutic and/or prophylactic agents may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A nanoparticle composition may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an S1P1 agonist, a glucocorticoid receptor modulator (GRM), or an anti-histamine. In some embodiments, a nanoparticle composition may be used in combination with dexamethasone, methotrexate, acetaminophen, an H1 receptor blocker, or an H2 receptor blocker. In certain embodiments, a method of treating a subject in need thereof or of delivering a therapeutic and/or prophylactic agent to a subject (e.g., a mammal) may involve pre-treating the subject with one or more agents prior to administering a nanoparticle composition. For example, a subject may be pre-treated with a useful amount (e.g., 10 mg, 20 mg, 30 mg, 40 mg, 50 mg, 60 mg, 70 mg, 80 mg, 90 mg, 100 mg, or any other useful amount) of dexamethasone, methotrexate, acetaminophen, an H1 receptor blocker, or an H2 receptor blocker. Pre-treatment may occur 24 or fewer hours (e.g., 24 hours, 20 hours, 16 hours, 12 hours, 8 hours, 4 hours, 2 hours, 1 hour, 50 minutes, 40 minutes, 30 minutes, 20 minutes, or 10 minutes) before administration of the nanoparticle composition and may occur one, two, or more times in, for example, increasing dosage amounts.

In any method or use described herein, in certain embodiments, the subject in need thereof is LDLR-deficient or apoE-deficient or both. In certain embodiments, the subject in need thereof is not LDLR-deficient or has normal LDLR levels and/or activities. In certain embodiments, the subject in need thereof is not apoE-deficient or has normal apoE levels and/or activities. In certain embodiments, the subject in need thereof has an abnormal interaction of LDLR and apoE. In certain embodiments, the subject in need thereof has a normal interaction of LDLR and apoE.

About, Approximately: As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean +/−10% of the recited value. For instance, a nanoparticle composition including a lipid component having about 40% of a given compound may include 30-50% of the compound.

Compound: As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

Delivering: As used herein, the term "delivering" means providing an entity to a destination. For example, delivering a therapeutic and/or prophylactic agent to a subject may involve administering a nanoparticle composition including the therapeutic and/or prophylactic agent to the subject (e.g., by an intravenous, intramuscular, intradermal, or subcutaneous route). Administration of a nanoparticle composition to a mammal or mammalian cell may involve contacting one or more cells with the nanoparticle composition.

Enhanced delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic agent by a nanoparticle to a target tissue of interest (e.g., mammalian liver) compared to the level of delivery of a therapeutic and/or prophylactic agent by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of therapeutic and/or prophylactic agent in a tissue to the weight of said tissue, comparing the amount of protein produced in a tissue to the amount of total protein in said tissue, or comparing the amount of therapeutic and/or prophylactic agent in a tissue to the amount of total therapeutic and/or prophylactic agent in said tissue. It will be understood that the enhanced delivery of a nanoparticle to a target tissue need not be determined in a subject being treated, it may be determined in a surrogate such as an animal model (e.g., a rat model).

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic agent by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of therapeutic and/or prophylactic agent in a tissue to the weight of said tissue, comparing the amount of protein produced in a tissue to the amount of total protein in said tissue, or comparing the amount of therapeutic and/or prophylactic agent in a tissue to the amount of total therapeutic and/or prophylactic agent in said tissue. For example, for renovascular targeting, a therapeutic and/or prophylactic agent is specifically provided to a mammalian kidney as compared to the liver and spleen if 1.5, 2-fold, 3-fold, 5-fold, 10-fold, 15 fold, or 20 fold more therapeutic and/or prophylactic agent per 1 g of tissue is delivered to a kidney compared to that delivered to the liver or spleen following systemic administration of the therapeutic and/or prophylactic agent. It will be understood that the ability of a nanoparticle to specifically deliver to a target tissue need not be determined in a subject being treated, it may be determined in a surrogate such as an animal model (e.g., a rat model).

Encapsulation efficiency: As used herein, "encapsulation efficiency" refers to the amount of a therapeutic and/or prophylactic agent that becomes part of a nanoparticle composition, relative to the initial total amount of therapeutic and/or prophylactic agent used in the preparation of a nanoparticle composition. For example, if 97 mg of therapeutic and/or prophylactic agent are encapsulated in a nanoparticle composition out of a total 100 mg of therapeutic and/or prophylactic agent initially provided to the composition, the encapsulation efficiency may be given as 97%. As used herein, "encapsulation" may refer to complete, substantial, or partial enclosure, confinement, surrounding, or encasement.

Expression: As used herein, "expression" of a nucleic acid sequence refers to translation of an mRNA into a polypeptide or protein and/or post-translational modification of a polypeptide or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Ex vivo: As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

Isomer: As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

Lipid component: As used herein, a "lipid component" is that component of a nanoparticle composition that includes one or more lipids. For example, the lipid component may include one or more cationic/ionizable, PEGylated, structural, or other lipids, such as phospholipids.

Linker: As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. For example, two nucleosides of a cap analog may be linked at their 5' positions by a triphosphate group or by a chain including two phosphate moieties and a boranophosphate moiety.

Methods of administration: As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

Modified: As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

N:P ratio: As used herein, the "N:P ratio" is the molar ratio of ionizable (in the physiological pH range) nitrogen atoms in a lipid to phosphate groups in an RNA, e.g., in a nanoparticle composition including a lipid component and an RNA.

Nanoparticle composition: As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

Naturally occurring: As used herein, "naturally occurring" means existing in nature without artificial aid.

Patient: As used herein, "patient" refers to a subject who may seek or be in need of treatment, requires treatment, is receiving treatment, will receive treatment, or a subject who is under care by a trained professional for a particular disease or condition.

PEG lipid: As used herein, a "PEG lipid" or "PEGylated lipid" refers to a lipid comprising a polyethylene glycol component.

Pharmaceutically acceptable: The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipient: The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Pharmaceutically acceptable salts: Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

Phospholipid: As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

Polydispersity index: As used herein, the "polydispersity index" is a ratio that describes the homogeneity of the particle size distribution of a system. A small value, e.g., less than 0.3, indicates a narrow particle size distribution.

Polypeptide: As used herein, the term "polypeptide" or "polypeptide of interest" refers to a polymer of amino acid residues typically joined by peptide bonds that can be produced naturally (e.g., isolated or purified) or synthetically.

RNA: As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the non-liming group consisting of small interfering RNA (siRNA), asymmetrical interfering RNA (aiRNA), microRNA (miRNA), Dicer-substrate RNA (dsRNA), small hairpin RNA (shRNA), mRNA, and mixtures thereof.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Total daily dose: As used herein, a "total daily dose" is an amount given or prescribed in 24 hour period. It may be administered as a single unit dose.

Size: As used herein, "size" or "mean size" in the context of nanoparticle compositions refers to the mean diameter of a nanoparticle composition.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

Targeted cells: As used herein, "targeted cells" refers to any one or more cells of interest. The cells may be found in vitro, in vivo, in situ, or in the tissue or organ of an organism. The organism may be an animal, preferably a mammal, more preferably a human and most preferably a patient.

Target tissue: As used herein "target tissue" refers to any one or more tissue types of interest in which the delivery of a therapeutic and/or prophylactic agent would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

Therapeutic and/or prophylactic agent: The term "therapeutic agent" refers to any agent that, when administered to a subject, has a therapeutic and/or diagnostic effect and/or elicits a desired biological and/or pharmacological effect. The term "prophylactic agent" refers to any agent that, when administered to a subject, has a prophylactic effect. Therapeutic and/or prophylactic agents are also referred to as "actives" or "active agents." Such agents include, but are not limited to, cytotoxins, radioactive ions, chemotherapeutic agents, small molecule drugs, proteins, and nucleic acids.

Therapeutically effective amount: As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Transfection: As used herein, "transfection" refers to the introduction of a species (e.g., an RNA) into a cell. Transfection may occur, for example, in vitro, ex vivo, or in vivo.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Zeta potential: As used herein, the "zeta potential" is the electrokinetic potential of a lipid e.g., in a particle composition.

Those skilled in the art will recognize, or be able to ascertain using no more than routine experimentation, many equivalents to the specific embodiments in accordance with the present disclosure. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all, of the group members are present in, employed in, or otherwise relevant to a given product or process. As used herein, the expressions "one or more of A, B, or C," "one or more A, B, or C," "one or more of A, B, and C," "one or more A, B, and C", "selected from A, B, and C," "selected from the group consisting of A, B, and C," and the like are used interchangeably and all refer to a selection from a group consisting of A, B, and/or C, i.e., one or more As, one or more Bs, one or more Cs, or any combination thereof, unless otherwise specified.

It is also noted that the term "comprising" is intended to be open and permits but does not require the inclusion of additional elements or steps. When the term "comprising" is used herein, the terms "consisting essentially of" and "consisting of" are thus also encompassed and disclosed. Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5th edition, John Wiley & Sons: New York, 2001; Greene, T. W., Wuts, P. G. M., *Protective Groups in Organic Synthesis,* 3rd edition, John Wiley & Sons: New York, 1999; R. Larock, *Comprehensive Organic Transformations,* VCH Publishers (1989); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

The compounds of this disclosure having any of the formulae described herein may be prepared according to the procedures illustrated in Schemes 1-3 below, from commercially available starting materials or starting materials which can be prepared using literature procedures. The variables in the Schemes (e.g., $R_1$, $R_2$, $R_3$, $R_4$, and $R_5$) are as defined herein, e.g., $R_1$, $R_2$, $R_3$, $R_4$, and $R_5$ are each independently alkyl. One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3rd edition, John Wiley & Sons: New York, 1999. Preferred protecting groups include, but are not limited to:

For a hydroxyl moiety: TBS, benzyl, THP, Ac;
For carboxylic acids: benzyl ester, methyl ester, ethyl ester, allyl ester;
For amines: Fmoc, Cbz, BOC, DMB, Ac, Bn, Tr, Ts, trifluoroacetyl, phthalimide, benzylideneamine;
For diols: Ac (×2) TBS (×2), or when taken together acetonides;
For thiols: Ac;
For benzimidazoles: SEM, benzyl, PMB, DMB;
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

Scheme 1

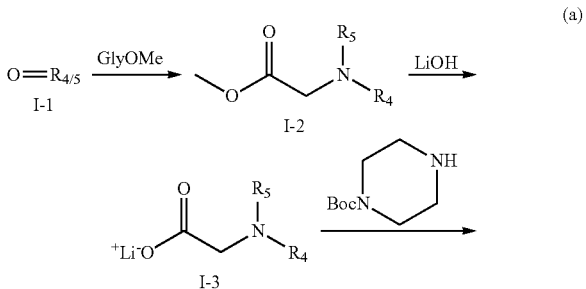

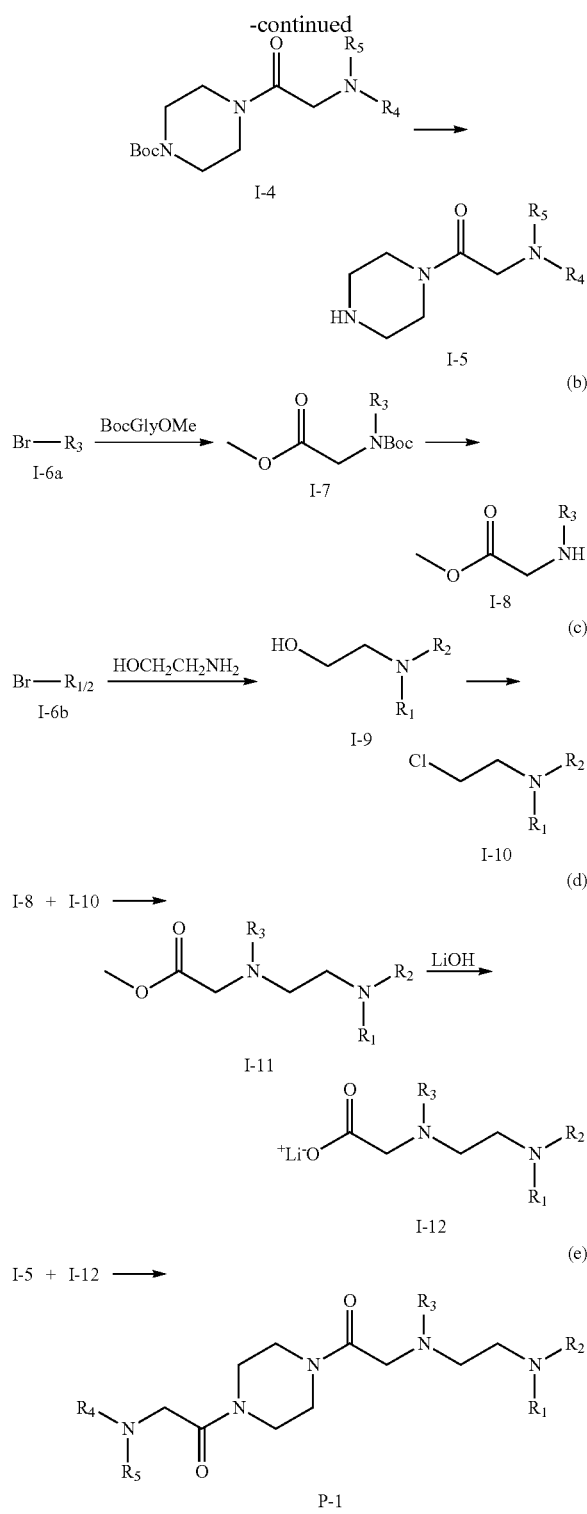

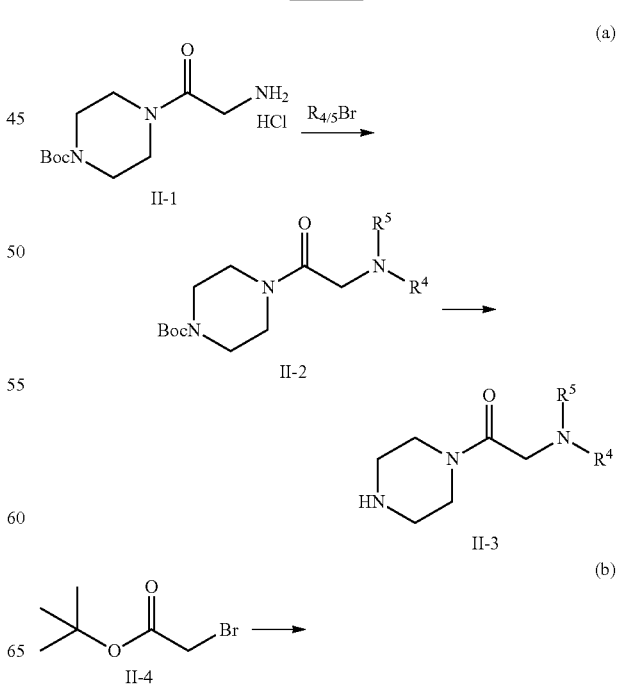

A solution of (I-3), e.g. in THF, is reacted with 1-tert-butyl-piperazine in the presence of a base, e.g. diisopropylethylamine (DIPEA), and a coupling agent, e.g. propylphosphonic acid anhydride, to form tert-butyl 4-(alkyl)piperazine-1-carboxylate (I-4), which is then deprotected, using e.g. trifluoroacetic acid (TFA), to yield 2-(alkyl)-1-(piperazine-1-yl)ethan-1-one (I-5). This reaction can take place in an organic solvent, e.g. dichloromethane (DCM). (b) Bromoalkane (I-6) is reacted with tert-butyl-methyl alkyl glycinate in the presence of a strong base, e.g. NaH, and in an appropriate solvent, e.g. dimethylformamide (DMF), to form methyl N-(tert-butyl)-N-alkylycinate (I-7), which is then deprotected, using e.g. TFA, to yield methyl alkylglycinate (I-8). The deprotection reaction can take place in an organic solvent, e.g. dichloromethane. (c) Bromoalkane (I-6) is reacted with ethanol-1-amine under alkaline conditions (e.g. $K_2CO_3$) and in the presence of a catalyst, e.g. KI in an appropriate solvent (e.g. acetonitrile), to form 2-(dialkylamino)ethanol (I-9), which is converted to N-(2-chloroethyl)-N-alkylalkan-1-amine (I-10) using a suitable reagent, e.g. mesylchloride in the presence of a base, e.g. triethylamine, and an appropriate solvent, e.g. DCM. (d) methyl alkylglycinate (I-8), obtained according to (b) and N-(2-chloroethyl)-N-alkylalkan-1-amine (I-10) obtained according to (c) are coupled in the presence of a base, e.g. $K_2CO_3$ and a nucleophilic catalyst, e.g. KI in an appropriate solvent (e.g. acetonitrile), to form the methyl glycinate intermediate (I-11), which is then hydrolyzed using lithium hydroxide in an appropriate solvent, e.g. tetrahydrofuran (THF), to yield the lithium glycinate compound (I-12). (e) 2-(alkyl)-1-(piperazine-1-yl)ethan-1-one (I-5) obtained according to (a) and compound (I-12) obtained according to (d) are reacted in the presence of a base, e.g. diisopropylethylamine (DIPEA), and a coupling agent, e.g. propylphosphonic acid anhydride, to yield the product (P-1). This reaction can take place in an organic solvent, e.g. THF.

Scheme 1 above illustrates an 11-step procedure for the synthesis of lipids of the disclosure. (a) Aldehyde (I-1) is reacted with glycine methyl ester hydrochloride in the presence of a reducing agent, e.g. $NaBH(OAc)_3$, and a base, e.g. $NEt_3$, in an appropriate solvent, e.g. AcOH, to yield methyl dialkylglycinate (I-2). This reaction can take place in an organic solvent, e.g. dichloroethane. Methyl dialkylglycinate (I-2) is hydrolyzed using lithium hydroxide, e.g. in THF, to produce the respective lithium alkyl glycinate (I-3).

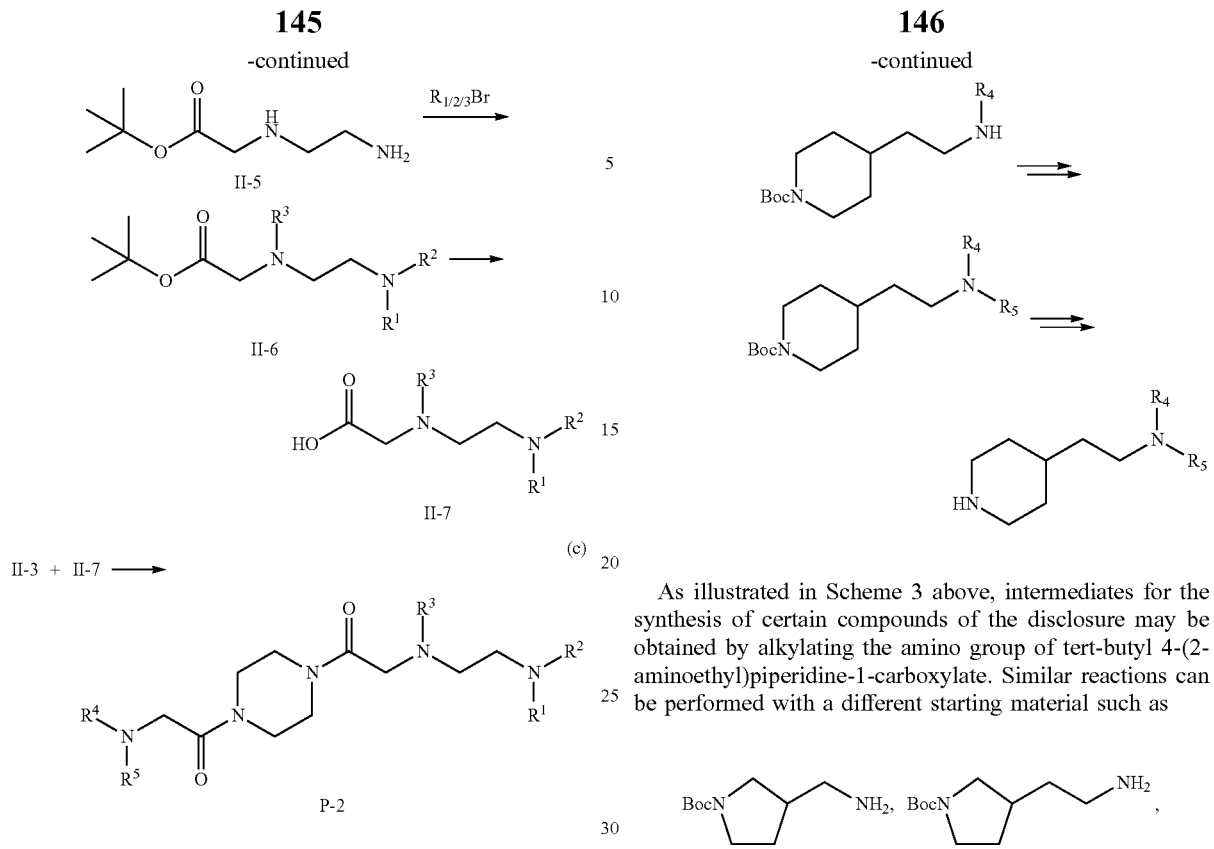

Scheme 2 above illustrates a 6-step procedure for the synthesis of lipids of the disclosure. (a) Commercially available tert-butyl 4-glycylpiperazine-1-carboxylate hydrochloride (II-1) is reacted with bromoalkane in the presence of a base, e.g. $K_2CO_3$ and a nucleophilic catalyst, e.g. KI in an appropriate solvent, e.g. cyclopentyl methyl ether/acetonitrile, and deprotected using, e.g. trifluoroacetic (TFA) to yield 2-(dialkylamino)-1-(piperazin-1-yl)ethan-1-one. The deprotection step can take place in an organic solvent, e.g. dichloromethane (DCM) (b) tert-Butyl 2-bromoacetate (II-4) is reacted with 1,2-diamino ethane, in an appropriate solvent, e.g. DCM to yield tert-butyl (2-aminoethyl)glycinate (II-5) which is coupled with bromoalkane in the presence of a base, e.g. $K_2CO_3$ and a nucleophilic catalyst, e.g. KI in an appropriate solvent, e.g. acetonitrile, to yield tert-butyl N-(2-(dialkylamino)ethyl)-N-alkylglycinate (II-6). Deprotection of II-6, using e.g. TFA, yields the corresponding glycine compound (II-7). (c) The reaction of (II-3), obtained according to (a), and (II-7), obtained according to (b), in the presence of a base, e.g. diisopropylethylamine (DIPEA), and a coupling agent, e.g. propylphosphonic acid anhydride, yields the product (P-2). This reaction can take place in an organic solvent, e.g. 2-methyltetrahydrofuran.

Scheme 3

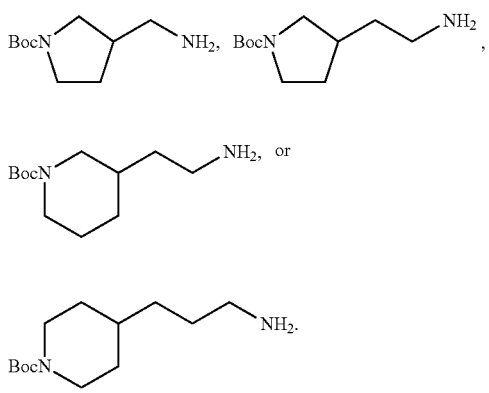

As illustrated in Scheme 3 above, intermediates for the synthesis of certain compounds of the disclosure may be obtained by alkylating the amino group of tert-butyl 4-(2-aminoethyl)piperidine-1-carboxylate. Similar reactions can be performed with a different starting material such as In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein.

All cited sources, for example, references, publications, databases, database entries, and art cited herein, are incorporated into this application by reference, even if not expressly stated in the citation. In case of conflicting statements of a cited source and the instant application, the statement in the instant application shall control. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1: Synthesis of Compounds According to One of Formulae (I), (Ia1)-(Ia6), (Ib), (II), (IIa), (III), (IIIa), (IV), (17-I), (19-I), (19-II), (20-I) and (21-I)

A. General Considerations

All solvents and reagents used were obtained commercially and used as such unless noted otherwise. $^1$H NMR spectra were recorded in CDCl$_3$, at 300 K using a Bruker Ultrashield 300 MHz instrument or a Varian Unity Inova 400 MHz Instrument. Chemical shifts are reported as parts per million (ppm) relative to TMS (0.00) for $^1$H. Silica gel chromatographies were performed on ISCO CombiFlash Rf+ Lumen Instruments using ISCO RediSep Rf Gold Flash Cartridges (particle size: 20-40 microns). Reverse phase chromatographies were performed on ISCO CombiFlash Rf+ Lumen Instruments using RediSep Rf Gold C18 High Performance columns. All final compounds were determined to be greater than 85% pure via analysis by reverse phase UPLC-MS (retention times, RT, in minutes) using Waters Acquity UPLC instrument with DAD and ELSD and a ZORBAX Rapid Resolution High Definition (RRHD) SB-C18 LC column, 2.1 mm, 50 mm, 1.8 m, and a gradient of 65 to 100% acetonitrile in water with 0.1% TFA over 5 minutes at 1.2 mL/min. Injection volume was 5 µL and the column temperature was 80° C. Detection was based on electrospray ionization (ESI) in positive mode using Waters SQD mass spectrometer (Milford, Mass., USA) and evaporative light scattering detector.

The procedures described for the synthesis of Compounds 12 and 19 are applicable to the synthesis of compounds according to formulae (I), (Ia1)-(Ia6), (Ib), (II), (IIa), (III), (IIIa), (IV), (17-I), (19-I), (19-II), (20-I) and (21-I) generally.

The following abbreviations are employed herein:
rt: Room Temperature
MeOH: Methanol
DCM: Dichloromethane
DCE: Dichloroethane
DMAP: 4-Dimethylaminopyridine
DMF: N,N-Dimethylformamide
EtOAc: Ethylacetate
MeCN: Acetonitrile
THF: Tetrahydrofuran
EDC.HCl: N-(3-Dimethylaminopropyl)-N'-ethylcarbodiimide hydrochloride B. Compound 1: 2-(Didodecylamino)-N-(2-(4-(2-(didodecylamino)ethyl)piperazin-1-yl)ethyl)-N-dodecylacetamide Step 1: tert-Butyl 4-(2-(dodecylamino)ethyl)piperazine-1-carboxylate Chemical Formula: C$_{23}$H$_{47}$N$_3$O$_2$
Moleucular Weight: 397.65

In the same manner as Step 3 for Compound 18, tert-butyl 4-(2-(dodecylamino)ethyl)piperazine-1-carboxylate was synthesized from 1-bromododecane (3.3 g, 13.1 mmol), 4-(2-aminoethyl)-1-boc-piperazine (3.0 g, 13.1 mmol), K$_2$CO$_3$ (3.62 g, 26.2 mmol), and KI (217 mg, 1.31 mmol) in MeCN (60 mL). Yield (1.42 g, 27%).

UPLC/ELSD: RT=1.18 min. MS (ES): m/z (MH$^+$) 398.56 for C$_{23}$H$_{47}$N$_3$O$_2$ $^1$H-NMR (300 MHz, CDCl$_3$) δ: ppm 3.45 (br. m, 4H); 2.75 (br. m, 2H); 2.65 (br. m, 2H); 2.55 (br. m, 2H); 2.42 (br. m, 4H); 1.60-1.22 (br. m, 29H); 0.91 (br. m, 3H).

Step 2: tert-Butyl 4-(2-(2-(didodecylamino)-N-dodecylacetamido)ethyl)piperazine-1-carboxylate Chemical Formula: C$_{49}$H$_{98}$N$_4$O$_3$
Molecular Weight: 791.35

In the same manner as Step 3 for Compound 11, tert-butyl 4-(2-(2-(didodecylamino)-N-dodecylacetamido)ethyl)piperazine-1-carboxylate was synthesized from tert-butyl 4-(2-(dodecylamino)ethyl)piperazine-1-carboxylate (100 mg, 0.25 mmol), lithium didodecylglycine (0.10 g, 0.25 mmol), propylphosphonic acid anhydride (50% EtOAc solution, 0.45 mL, 0.75 mmol), and i-Pr$_2$EtN (0.044 mL, 0.25 mmol) in THF (2 mL). Yield (0.12 g, 63%).

UPLC/ELSD: RT=3.36 min. MS (ES): m/z (MH$^+$) 792.082 for C$_{49}$H$_{98}$N$_4$O$_3$ Step 3: 2-(Didodecylamino)-N-dodecyl-N-(2-(piperazin-1-yl)ethyl)acetamide Chemical Formula: C$_{44}$H$_{90}$N$_4$O
Molecular Weight: 691.23

In the same manner as Step 4 for Compound 11, 2-(didodecylamino)-N-dodecyl-N-(2-(piperazin-1-yl)ethyl)acetamide was synthesized from tert-butyl 4-(2-(2-(didodecylamino)-N-dodecylacetamido)ethyl)piperazine-1-carboxylate (0.12 g, 0.16 mmol) and TFA (0.25 mL, 3.2 mmol) in 0.25 mL DCM.

UPLC/ELSD: RT=3.06 min. MS (ES): m/z (MH$^+$) 692.984 for C$_{44}$H$_{90}$N$_4$O Step 4: Compound 1: 2-(Didodecylamino)-N-(2-(4-(2-(didodecylamino)ethyl)piperazin-1-yl)ethyl)-N-dodecylacetamide

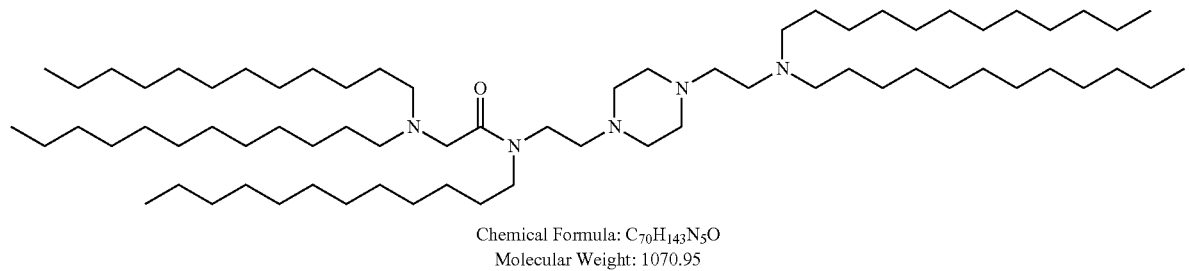 [SMILES: CCCCCCCCCCCCN(CCCCCCCCCCCC)CCN1CCN(CCN(CCCCCCCCCCCC)C(=O)CN(CCCCCCCCCCCC)CCCCCCCCCCCC)CC1]

Chemical Formula: C₇₀H₁₄₃N₅O
Molecular Weight: 1070.95

In the same manner as Step 6 for Compound 18, 2-(didodecylamino)-N-(2-(4-(2-(didodecylamino)ethyl)piperazin-1-yl)ethyl)-N-dodecylacetamide was synthesized from 2-(didodecylamino)-N-dodecyl-N-(2-(piperazin-1-yl)ethyl)acetamide (65 mg, 0.094 mmol), N-(2-chloroethyl)-N-dodecyldodecan-1-amine (42 mg, 0.10 mmol), K₂CO₃ (13 mg, 0.094 mmol) and KI (2 mg, 0.0094 mmol) in 0.5 mL MeCN to afford 58.5 mg for 58% yield.

UPLC/ELSD: RT=3.75 min. MS (ES): m/z (MH⁺) 1072.585 for $C_{70}H_{143}N_5O$

¹H NMR (300 MHz, CDCl₃) δ: ppm 3.82-3.23 (br. m. 8H); 3.04-2.90 (br. m., 2H); 2.47 (m, 18H); 1.24 (m, 100H); 0.96 (m, 15H).

C. Compound 2: 2-((2-(Didodecylamino)ethyl)(dodecyl)amino)-1-(4-(2-(didodecylamino)ethyl)piperazin-1-yl)ethan-1-one Step 1: tert-Butyl 4-(2-(didodecylamino)ethyl)piperazine-1-carboxylate

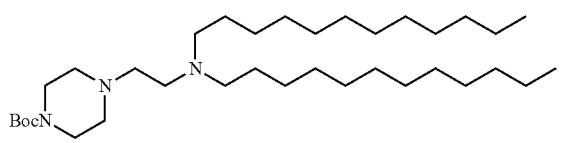

Chemical Formula: C₃₅H₇₁N₃O₂
Molecular Weight: 565.97

A mixture of 1-bromododecane (1.1 mL, 4.6 mmol), 4-(2-aminoethyl)-1-boc-piperazine (1.0 g, 4.4 mmol), K₂CO₃ (0.61 g, 4.4 mmol), in 10 mL MeCN was allowed to stir at rt for 12 h. After this time the reaction was filtered and concentrated. The crude material was purified by silica gel chromatography (0-20% MeOH in DCM with 1% NH₄OH to afford tert-butyl 4-(2-(didodecylamino)ethyl)piperazine-1-carboxylate (450 mg, 0.80 mmol, 18%).

UPLC/ELSD: RT=2.87 min. MS (ES): m/z (MH⁺) 566.655 for $C_{35}H_{71}N_3O_2$

¹H NMR (400 MHz, CDCl₃) δ: ppm 3.40 (m, 4H); 2.56 (m, 2H); 2.40 (m, 10H); 1.44 (s, 9H); 1.40-1.24 (m, 40H); 0.86 (t, 6H).

Step 2: N-Dodecyl-N-(2-(piperazin-1-yl)ethyl)dodecan-1-amine

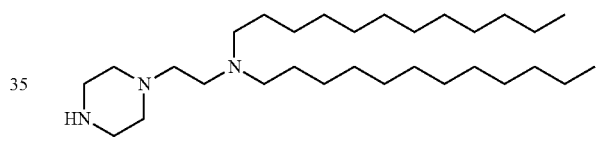

Chemical Formula: C₃₀H₆₃N₃
Molecular Weight: 465.86

In the same manner as Step 5 for Compound 18, N-dodecyl-N-(2-(piperazin-1-yl)ethyl)dodecan-1-amine was synthesized from tert-butyl 4-(2-(didodecylamino)ethyl)piperazine-1-carboxylate (0.92 g, 1.63 mmol), TFA (6.2 mL, 82 mmol) in 6 mL DCM to afford 490 mg for 65% yield.

UPLC/ELSD: RT=2.10 min. MS (ES): m/z (MH⁺) 466.379 for $C_{30}H_{63}N_3$

¹H NMR (400 MHz, CDCl₃) δ: ppm 2.88 (t, 4H); 2.61 (m, 2H); 2.45 (m, 10H); 1.43-1.24 (m, 40H); 0.86 (t, 6H).

Step 3: Compound 2: 2-((2-(Didodecylamino)ethyl)(dodecyl)amino)-1-(4-(2-(didodecylamino)ethyl)piperazin-1-yl)ethan-1-one

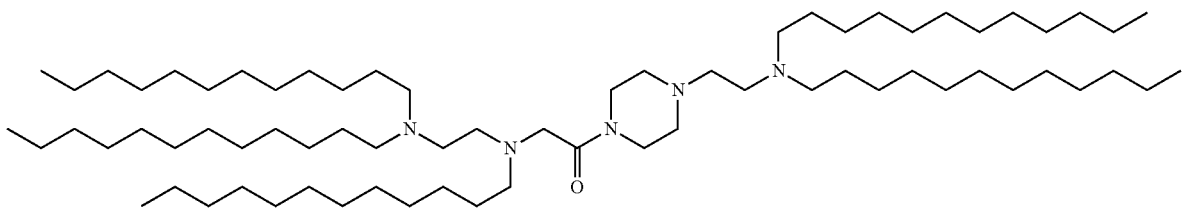

Chemical Formula: C₇₀H₁₄₃N₅O
Molecular Weight: 1070.95

In the same manner as Step 11 for Compound 11, 2-((2-(didodecylamino)ethyl)(dodecyl)amino)-1-(4-(2-(didodecylamino)ethyl)piperazin-1-yl)ethan-1-one was synthesized from N-dodecyl-N-(2-(piperazin-1-yl)ethyl)dodecan-1-amine (32 mg, 0.069 mmol), N-(2-(didodecylamino)ethyl)-N-dodecylglycine (43 mg, 0.069 mmol), propylphosphonic acid anhydride (50% EtOAc solution, 0.12 mL, 0.21 mmol) and i-Pr$_2$EtN (0.024 mL, 0.14 mmol) in 0.5 mL THF to provide 17.7 mg (17%).

UPLC: RT=3.90 min. MS (ES): m/z (MH$^+$) 1071.475 for C$_{70}$H$_{143}$N$_5$O $^1$H NMR (400 MHz, CDCl$_3$) δ: ppm 3.65 (m, 2H); 3.57 (m, 2H); 3.26 (s, 2H); 2.33-2.57 (n, 22H); 1.24-1.39 (m, 100H); 0.88 (t, 15H).

D. Compound 3: 2-(Didodecylamino)-1-(4-(2-((2-(didodecylamino)ethyl)(dodecyl)amino)ethyl)piperazin-1-yl)ethan-1-one Step 1: tert-Butyl 4-(2-((2-(didodecylamino)ethyl)(dodecyl)amino)ethyl)piperazine-1-carboxylate

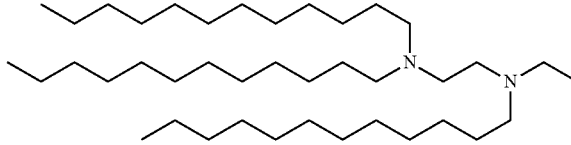

Chemical Formula: C$_{49}$H$_{100}$N$_4$O$_2$
Molecular Weight: 777.37

In the same manner as Step 4 for Compound 18, tert-butyl 4-(2-((2-(didodecylamino)ethyl)(dodecyl)amino)ethyl)piperazine-1-carboxylate was synthesized from tert-butyl 4-(2-(dodecylamino)ethyl)piperazine-1-carboxylate (700 mg, 1.76 mmol), N-(2-chloroethyl)-N-dodecyldodecan-1-amine (806 mg, 1.93 mmol), K$_2$CO$_3$ (486 mg, 3.52 mmol), and KI (29 mg, 0.176 mmol) in THF (15 mL). Yield (683 mg, 50%).

UPLC/ELSD: RT=3.35 min. MS (ES): m/z (MH$^+$) 778.16 for C$_{49}$H$_{100}$N$_4$O$_2$ $^1$H-NMR (300 MHz, CDCl$_3$) δ: ppm 3.44 (t, 4H); 3.11-2.86 (br. m, 4H); 2.78-2.32 (br. m, 14H); 1.80-1.05 (br. m, 69H); 0.91 (t, 9H).

Step 2: N$^1$,N$^1$,N$^2$-Tridodecyl-N$^2$-(2-(piperazin-1-yl)ethyl)ethane-1,2-diamine

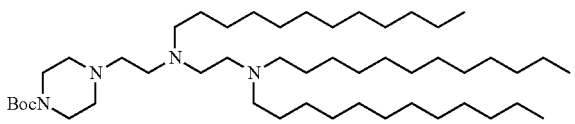

Chemical Formula: C$_{44}$H$_{92}$N$_4$
Molecular Weight: 677.25

In the same manner as Step 5 for Compound 18, N$^1$,N1,N$^2$-tridodecyl-N$^2$-(2-(piperazin-1-yl)ethyl)ethane-1,2-diamine was synthesized from tert-butyl 4-(2-((2-(didodecylamino)ethyl)(dodecyl)amino)ethyl)piperazine-1-carboxylate (683 mg, 0.879 mmol), and TFA (3.4 mL, 43.9 mmol) in DCM (3.4 mL). Yield (595 mg, 99%).

UPLC/ELSD: RT=2.94 min. MS (ES): m/z (MH$^+$) 678.16 for C$_{44}$H$_{92}$N$_4$

Step 3: Compound 3: 2-(Didodecylamino)-1-(4-(2-((2-(didodecylamino)ethyl)(dodecyl)amino)ethyl)piperazin-1-yl)ethan-1-one

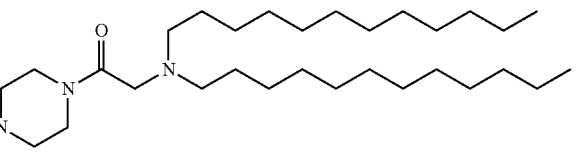

Chemical Formula: C$_{70}$H$_{143}$N$_5$O
Molecular Weight: 1070.95

In the same manner as Step 11 for Compound 11, 2-(didodecylamino)-1-(4-(2-((2-(didodecylamino)ethyl)(dodecyl)amino)ethyl)piperazin-1-yl)ethan-1-one was from N$^1$,N$^1$,N$^2$-tridodecyl-N$^2$-(2-(piperazin-1-yl)ethyl)ethane-1,2-diamine (50 mg, 0.074 mmol), lithium didodecylglycine (33 mg, 0.078 mmol), propylphosphonic acid anhydride (50% in EtOAc, 0.13 mL, 0.22 mmol) and i-Pr$_2$EtN (0.026 mL) in 0.5 mL THF to afford 33.9 mg (43%).

UPLC: RT=3.90 min. MS (ES): m/z (MH$^+$) 1071.475 for C$_{70}$H$_{143}$N$_5$O $^1$H NMR (400 MHz, CDCl$_3$) δ: ppm 3.65 (m, 2H); 3.57 (m, 2H); 3.26 (s, 2H); 2.33-2.57 (n, 22H); 1.24-1.39 (m, 100H); 0.88 (t, 15H).

E. Compound 4: 2-(Dinonylamino)-1-(4-(N-(2-(dinonylamino)ethyl)-N-nonylglycyl)piperazin-1-yl)ethan-1-one Step 1: Methyl Dinonylglycinate

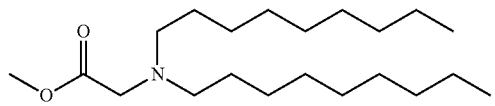

Chemical Formula: C$_{21}$H$_{43}$NO$_2$
Molecular Weight: 341.58

In the same manner as Step 1 for Compound 11, methyl dinonylglycinate was synthesized from glycine methyl ester hydrochloride (5.0 g, 39.8 mmol), triethylamine (8.3 mL, 59.7 mmol), 95% nonanal (15.0 g, 99.6 mmol), sodium triacetoxyborohydride (21.1 g, 99.6 mmol), and acetic acid (5.7 mL, 99.6 mmol) in DCE (50 mL). Yield (3.5 g, 26%).

UPLC/ELSD: RT=1.82 min. MS (ES): m/z (MH$^+$) 343.62 for C$_{21}$H$_{43}$NO$_2$ $^1$H-NMR (300 MHz, CDCl$_3$) δ: ppm 3.72 (s, 3H); 3.35 (s, 2H); 2.57 (t, 4H); 1.46 (br. m, 4H); 1.29 (br. m, 24H); 0.90 (t, 6H).

Step 2: Lithium Dinonylglycinate

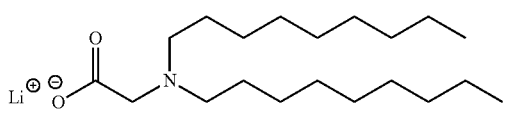

Chemical Formula: C₂₀H₄₀LiNO₂
Molecular Weight: 333.49

In the same manner as Step 2 for Compound 11, lithium dinonylglycinate was synthesized from methyl dinonylglycinate (3.5 g, 10.2 mmol) and 1M LiOH (50 mL, 50 mmol) in THF (50 mL). Yield (3.0 g, 88%).
UPLC/ELSD: RT=1.71 min. MS (ES): m/z (MH⁺) 328.37 for C₂₀H₄₁NO₂
¹H-NMR (300 MHz, CD₃OD) δ: ppm 3.13 (s, 2H); 2.59 (t, 4H); 1.51 (br. m, 4H); 1.32 (br. m, 24H); 0.92 (t, 6H).

Step 3: tert-Butyl 4-(dinonylglycyl)piperazine-1-carboxylate

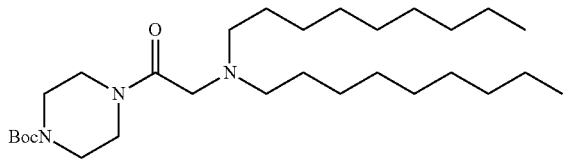

Chemical Formula: C₂₉H₅₇N₃O₂
Molecular Weight: 495.79

In the same manner as Step 3 for Compound 11, tert-butyl 4-(dinonylglycyl)piperazine-1-carboxylate was synthesized from lithium dinonylglycinate (2.0 g, 6.00 mmol), 1-boc-piperazine (1.23 g, 6.58 mmol), i-Pr₂EtN (2.3 mL, 13.2 mmol), and propylphosphonic acid anhydride (50% EtOAc solution, 10.7 mL, 17.9 mmol). Yield (824 mg, 28%).
UPLC/ELSD: RT=2.19 min. MS (ES): m/z (MH⁺) 496.72 for C₂₉H₅₇N₃O₃

Step 4: 2-(Dinonylamino)-1-(piperazin-1-yl)ethan-1-one

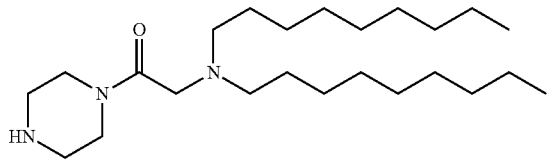

Chemical Formula: C₂₄H₄₉N₃O
Molecular Weight: 395.68

In the same manner as Step 4 for Compound 11, 2-(dinonylamino)-1-(piperazin-1-yl)ethan-1-one was synthesized from tert-butyl 4-(dinonylglycyl)piperazine-1-carboxylate (824 mg, 1.66 mmol) and TFA (6.4 mL, 83.1 mmol) in DCM (6.4 mL). Yield (246 mg, 37%).
UPLC/ELSD: RT=1.25 min. MS (ES): m/z (MH⁺) 396.68 for C₂₄H₄₉N₃O
¹H-NMR (300 MHz, CDCl₃) δ: ppm 3.63 (br. m, 4H); 3.28 (s, 2H); 2.89 (br. m, 4H); 2.48 (t, 4H); 1.45 (br. m, 4H); 1.28 (br. m, 24H); 0.90 (t, 6H).

Step 5: Methyl N-(tert-butoxycarbonyl)-N-nonylglycinate

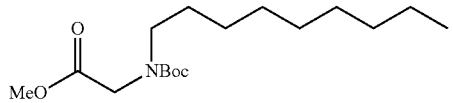

Chemical Formula: C₁₇H₃₃NO₄
Molecular Weight: 315.45

In the same manner as Step 5 for Compound 11, methyl N-(tert-butoxycarbonyl)-N-nonylglycinate was synthesized from N-(tert-butoxycarbonyl)glycine methyl ester (7.7 g, 40.7 mmol) and NaH (60%, 1.71 g, 42.7 mmol) in DMF (100 mL). Yield (3.32 g, 26%).
¹H-NMR (300 MHz, CDCl₃) δ: ppm 4.02-3.84 (br. m, 2H); 3.75 (s, 3H); 3.26 (br. m, 2H); 1.65-1.39 (br. m, 11H); 1.28 (br. m, 12H); 0.90 (t, 3H).

Step 6: Methyl Nonylglycinate

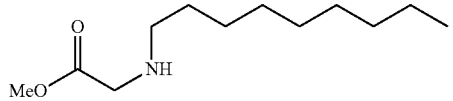

Chemical Formula: C₁₂H₂₅NO₂
Molecular Weight: 215.34

In the same manner as Step 6 for Compound 11, methyl nonylglycinate was synthesized from methyl N-(tert-butoxycarbonyl)-N-nonylglycinate (3.32 g, 10.5 mmol) and TFA (16 mL, 210 mmol) in DCM (16 mL). Yield (2.23 g, 98%).
¹H-NMR (300 MHz, CDCl₃) δ: ppm 3.75 (s, 3H); 3.44 (s, 2H); 2.61 (t, 2H); 1.69 (br. m, 1H); 1.51 (br. m, 2H); 1.28 (br. m, 12H); 0.90 (t, 3H).

Step 7: Methyl N-(2-(dinonylamino)ethyl)-N-nonylglycinate

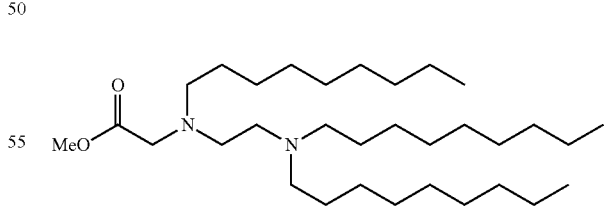

Chemical Formula: C₃₂H₆₆N₂O₂
Molecular Weight: 510.89

In the same manner as Step 9 for Compound 11, methyl N-(2-(dinonylamino)ethyl)-N-nonylglycinate was synthesized from methyl nonylglycinate (449 mg, 2.08 mmol), N-(2-chloroethyl)-N-nonylnonan-1-amine (830 mg, 2.50 mmol), K₂CO₃ (576 mg, 4.16 mmol), and KI (35 mg, 0.208 mmol) in MeCN (13 mL). Yield (958 mg, 90%).

UPLC/ELSD: RT=3.11 min. MS (ES): m/z (MH⁺) 511.97 for $C_{32}H_{66}N_2O_2$

¹H-NMR (300 MHz, CDCl₃) δ: ppm 3.72 (s, 3H); 3.42 (s, 2H); 2.95-2.15 (br. m, 10H); 1.85-1.00 (br. m, 42H); 0.90 (t, 9H).

Step 8: N-(2-(Dinonylamino)ethyl)-N-nonylglycine

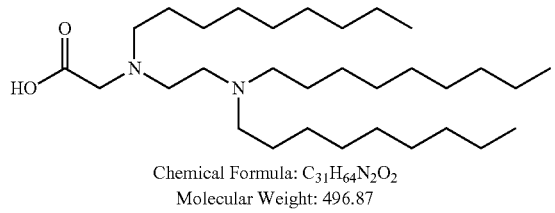 [SMILES: CCCCCCCCCN(CCCCCCCCC)CCN(CCCCCCCCC)CC(=O)O]

Chemical Formula: $C_{31}H_{64}N_2O_2$
Molecular Weight: 496.87

In the same manner as Step 10 for Compound 11, N-(2-(dinonylamino)ethyl)-N-nonylglycine was synthesized from methyl N-(2-(dinonylamino)ethyl)-N-nonylglycinate (958 mg, 1.88 mmol), and 1M LiOH (10 mL, 10 mmol) in THF (10 mL). Yield (514 mg, 55%).

UPLC/ELSD: RT=2.75 min. MS (ES): m/z (MH⁺) 497.95 for $C_{31}H_{64}N_2O_2$

¹H-NMR (300 MHz, CDCl₃) δ: ppm 3.92 (br. m, 6H); 3.14 (br. m, 6H); 1.77 (br. m, 6H); 1.45-1.13 (br. m, 36H); 0.90 (t, 9H).

Step 9: Compound 4: 2-(Dinonylamino)-1-(4-(N-(2-(dinonylamino)ethyl)-N-nonylglycyl)piperazin-1-yl)ethan-1-one

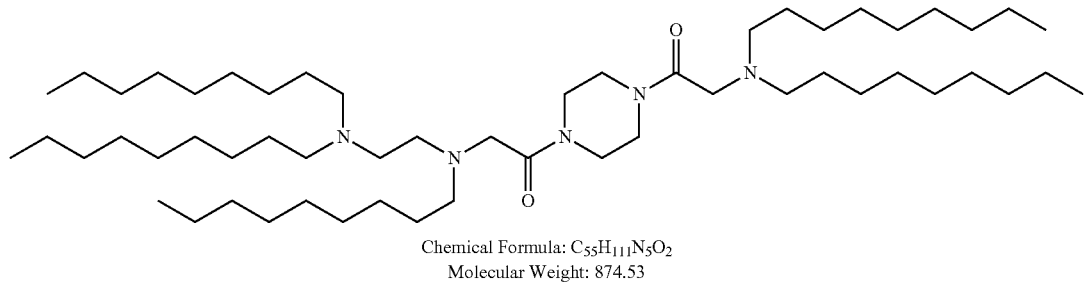 [SMILES: CCCCCCCCCN(CCCCCCCCC)CCN(CCCCCCCCC)CC(=O)N1CCN(C(=O)CN(CCCCCCCCC)CCCCCCCCC)CC1]

Chemical Formula: $C_{55}H_{111}N_5O_2$
Molecular Weight: 874.53

In the same manner as Step 11 for Compound 11, 2-(dinonylamino)-1-(4-(N-(2-(dinonylamino)ethyl)-N-nonylglycyl)piperazin-1-yl)ethan-1-one was synthesized from 2-(dinonylamino)-1-(piperazin-1-yl)ethan-1-one (61.5 mg, 0.155 mmol), N-(2-(dinonylamino)ethyl)-N-nonylglycine (85 mg, 0.171 mmol), i-Pr₂EtN (60 µL, 0.342 mmol), and propylphosphonic acid anhydride (50% EtOAc solution, 0.278 mL, 0.466 mmol). Yield (38 mg, 28%).

UPLC/ELSD: RT=3.13 min. MS (ES): m/z (MH⁺) 875.76 for $C_{55}H_{111}N_5O_2$

¹H-NMR (300 MHz, CDCl₃) δ: ppm 3.82-3.49 (br. m, 8H); 3.33 (s, 2H); 3.27 (s, 2H); 2.68-2.18 (br. m, 14H); 1.82-1.02 (br. m, 70H); 0.90 (t, 15H).

F. Compound 5: 2-(Dinonylamino)-1-(4-(N-(2-(dinonylamino)ethyl)-N-dodecylglycyl)piperazin-1-yl)ethan-1-one Step 1: Methyl N-(2-(dinonylamino)ethyl)-N-dodecylglycinate

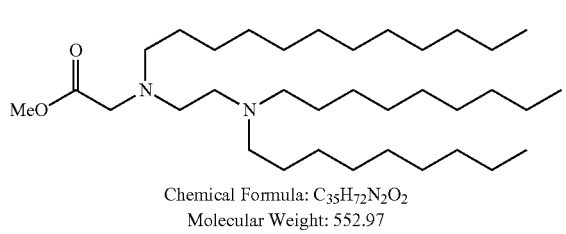 [SMILES: CCCCCCCCCCCCN(CCN(CCCCCCCCC)CCCCCCCCC)CC(=O)OC]

Chemical Formula: $C_{35}H_{72}N_2O_2$
Molecular Weight: 552.97

In the same manner as Step 9 for Compound 11, methyl N-(2-(dinonylamino)ethyl)-N-dodecylglycinate was synthesized from methyl dodecylglycinate (535 mg, 2.08 mmol), N-(2-chloroethyl)-N-nonylnonan-1-amine (830 mg, 2.50 mmol), K₂CO₃ (576 mg, 4.16 mmol), and KI (35 mg, 0.208 mmol) in MeCN (13 mL). Yield (385 mg, 34%).

UPLC/ELSD: RT=3.34 min. MS (ES): m/z (MH⁺) 553.96 for $C_{35}H_{72}N_2O_2$

¹H-NMR (300 MHz, CDCl₃) δ: ppm 3.72 (s, 3H); 3.41 (s, 2H); 2.90-2.20 (br. m, 10H); 1.85-1.05 (br. m, 48H); 0.90 (t, 9H).

Step 2: N-(2-(Dinonylamino)ethyl)-N-dodecylglycine

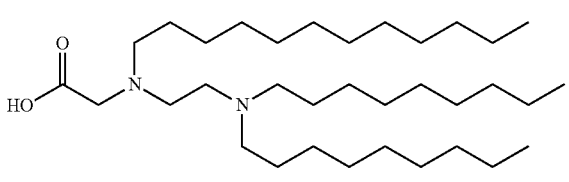

Chemical Formula: $C_{34}H_{70}N_2O_2$
Molecular Weight: 538.95

In the same manner as Step 10 for Compound 11, N-(2-(dinonylamino)ethyl)-N-dodecylglycine was synthesized from methyl N-(2-(dinonylamino)ethyl)-N-dodecylglycinate (385 mg, 0.696 mmol), and 1M LiOH (3.5 mL, 3.5 mmol) in THF (3.5 mL). Yield (225 mg, 60%).

UPLC/ELSD: RT=3.13 min. MS (ES): m/z (MH$^+$) 539.93 for $C_{34}H_{70}N_2O_2$ $^1$H-NMR (300 MHz, CDCl$_3$) δ: ppm 3.73 (s, 2H); 3.62-3.39 (br. m, 4H); 3.09 (br. m, 6H); 1.76 (br. m, 6H); 1.28 (br, 42H); 0.90 (t, 9H).

Step 3: Compound 5: 2-(Dinonylamino)-1-(4-(N-(2-(dinonylamino)ethyl)-N-dodecylglycyl)piperazin-1-yl)ethan-1-one

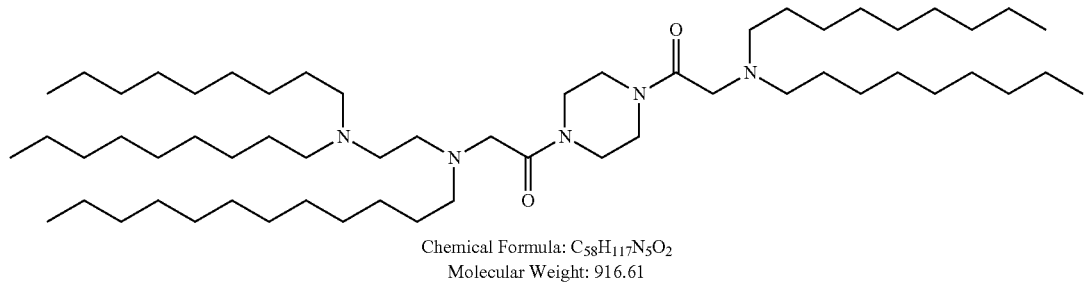 [SMILES: CCCCCCCCCCCCN(CCN(CCCCCCCCC)CCCCCCCCC)CC(=O)N1CCN(C(=O)CN(CCCCCCCCC)CCCCCCCCC)CC1]

Chemical Formula: $C_{58}H_{117}N_5O_2$
Molecular Weight: 916.61

In the same manner as Step 11 for Compound 11, 2-(dinonylamino)-1-(4-(N-(2-(dinonylamino)ethyl)-N-dodecylglycyl)piperazin-1-yl)ethan-1-one was synthesized from 2-(dinonylamino)-1-(piperazin-1-yl)ethan-1-one (62 mg, 0.155 mmol), N-(2-(dinonylamino)ethyl)-N-dodecylglycine (92 mg, 0.171 mmol), i-Pr$_2$EtN (60 µL, 0.342 mmol), and propylphosphonic acid anhydride (50% EtOAc solution, 0.278 mL, 0.466 mmol). Yield (38 mg, 26%).

UPLC/ELSD: RT=3.32 min. MS (ES): m/z (MH$^+$) 917.67 for $C_{58}H_{117}N_5O_2$ $^1$H-NMR (300 MHz, CDCl$_3$) δ: ppm 3.86-3.45 (br. m, 8H); 3.33 (s, 2H); 3.28 (s, 2H); 2.73-2.27 (br. m, 14H); 1.86-1.00 (76H); 0.91 (t, 15H).

G. Compound 6: 2-((2-(Didodecylamino)ethyl)(nonyl)amino)-1-(4-(dinonylglycyl)piperazin-1-yl)ethan-1-one Step 1: Methyl N-(2-(didodecylamino)ethyl)-N-nonylglycinate

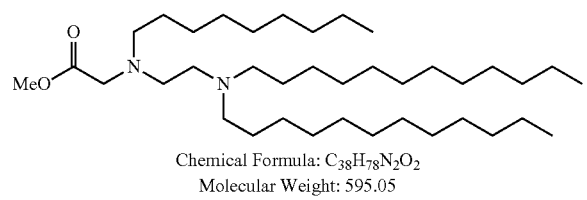 [SMILES: CCCCCCCCCCCCN(CCCCCCCCCCCC)CCN(CCCCCCCCC)CC(=O)OC]

Chemical Formula: $C_{38}H_{78}N_2O_2$
Molecular Weight: 595.05

In the same manner as Step 9 for Compound 11, methyl N-(2-(didodecylamino)ethyl)-N-nonylglycinate was synthesized from methyl nonylglycinate (355 mg, 1.65 mmol), N-(2-chloroethyl)-N-dodecyldodecan-1-amine (825 mg, 1.98 mmol), K$_2$CO$_3$ (457 mg, 3.30 mmol), and KI (27 mg, 0.165 mmol) in MeCN (10 mL). Yield (460 mg, 47%).

UPLC/ELSD: RT=3.62 min. MS (ES): m/z (MH$^+$) 596.03 for $C_{38}H_{78}N_2O_2$ $^1$H-NMR (300 MHz, CDCl$_3$) δ: ppm 3.72 (s, 3H); 3.42 (s, 2H); 2.80-2.24 (br. m, 10H); 1.56-1.00 (br. m, 54H); 0.90 (t, 9H).

Step 2: N-(2-(Didodecylamino)ethyl)-N-nonylglycine

Chemical Formula: $C_{37}H_{76}N_2O_2$
Molecular Weight: 581.03

In the same manner as Step 10 for Compound 11, N-(2-(didodecylamino)ethyl)-N-nonylglycine was synthesized from methyl N-(2-(didodecylamino)ethyl)-N-nonylglycinate (460 mg, 0.773 mmol), and 1M LiOH (3.9 mL, 3.9 mmol) in THF (3.9 mL). Yield (323 mg, 72%).

UPLC/ELSD: RT=3.37 min. MS (ES): m/z (MH$^+$) 582.00 for $C_{37}H_{76}N_2O_2$ $^1$H-NMR (300 MHz, CDCl$_3$) δ: ppm 4.17 (s, 2H); 4.00 (br. m, 2H); 3.84 (br. m, 2H); 3.34 (br. m, 2H); 3.18 (br. m, 4H); 1.82 (br. m, 6H); 1.27 (br. m, 48H); 0.91 (t, 9H).

Step 3: Compound 6: 2-((2-(Didodecylamino)ethyl)(nonyl)amino)-1-(4-(dinonylglycyl)piperazin-1-yl)ethan-1-one

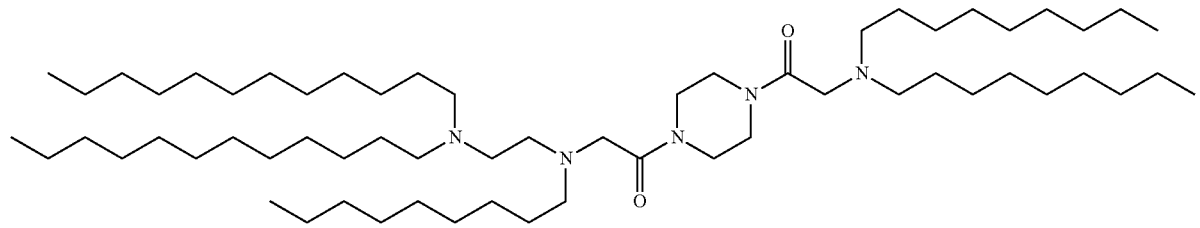

Chemical Formula: C₆₁H₁₂₃N₅O₂
Molecular Weight: 958.69

In the same manner as Step 11 for Compound 11, 2-((2-(didodecylamino)ethyl)(nonyl)amino)-1-(4-(dinonylglycyl)piperazin-1-yl)ethan-1-one was synthesized from 2-(dinonylamino)-1-(piperazin-1-yl)ethan-1-one (62 mg, 0.155 mmol), N-(2-(didodecylamino)ethyl)-N-nonylglycine (99 mg, 0.171 mmol), i-Pr₂EtN (60 µL, 0.342 mmol), and propylphosphonic acid anhydride (50% EtOAc solution, 0.278 mL, 0.466 mmol). Yield (45 mg, 30%).

UPLC/ELSD: RT=3.46 min. MS (ES): m/z (MH⁺) 959.98 for $C_{61}H_{123}N_5O_2$

¹H-NMR (300 MHz, CDCl₃) δ: ppm 3.81-3.49 (br. m, 8H); 3.33 (s, 2H); 3.27 (s, 2H); 2.70-2.25 (br. m, 14H); 1.90-1.00 (br. m, 82H); 0.90 (t, 15H).

H. Compound 7: 2-((2-(Didodecylamino)ethyl)(dodecyl)amino)-1-(4-(dinonylglycyl)piperazin-1-yl)ethan-1-one

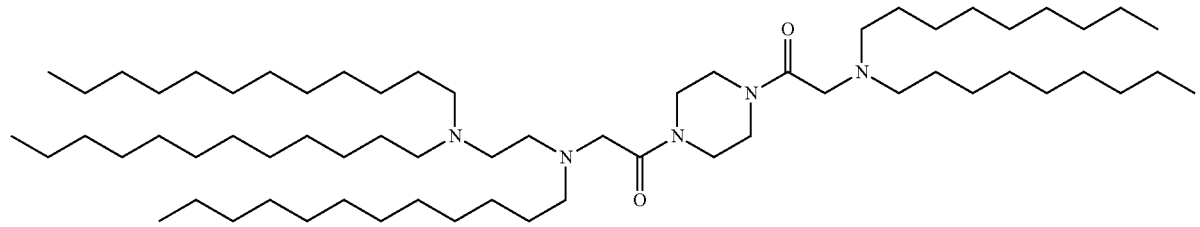

Chemical Formula: C₆₄H₁₂₉N₅O₂
Molecular Weight: 1000.77

In the same manner as Step 11 for Compound 11, 2-((2-(didodecylamino)ethyl)(dodecyl)amino)-1-(4-(dinonylglycyl)piperazin-1-yl)ethan-1-one was synthesized from 2-(dinonylamino)-1-(piperazin-1-yl)ethan-1-one (62 mg, 0.155 mmol), N-(2-(didodecylamino)ethyl)-N-dodecylglycine (107 mg, 0.171 mmol), i-Pr₂EtN (60 µL, 0.342 mmol), and propylphosphonic acid anhydride (50% EtOAc solution, 0.278 mL, 0.466 mmol). Yield (34 mg, 20%).

UPLC/ELSD: RT=3.60 min. MS (ES): m/z (MH⁺) 1001.97 for $C_{64}H_{129}N_5O_2$

¹H-NMR (300 MHz, CDCl₃) δ: ppm 3.85-2.18 (br. m, 26H); 1.91-1.00 (br. m, 88H); 0.90 (t, 15H).

I. Compound 8: 2-(Didodecylamino)-1-(4-(N-(2-(dinonylamino)ethyl)-N-nonylglycyl)piperazin-1-yl)ethan-1-one

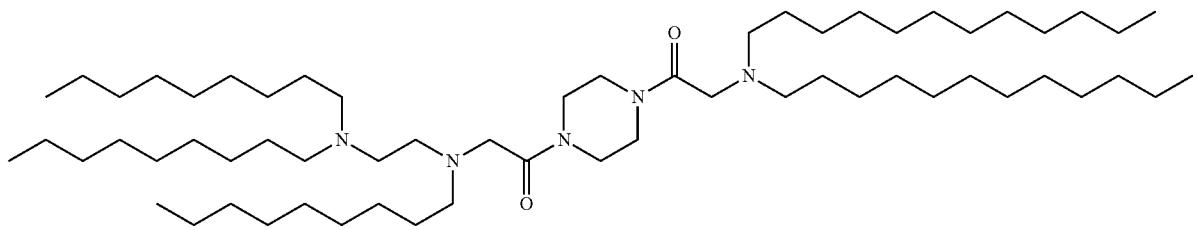

Chemical Formula: $C_{61}H_{123}N_5O_2$
Molecular Weight: 958.69

In the same manner as Step 11 for Compound 11, 2-(didodecylamino)-1-(4-(N-(2-(dinonylamino)ethyl)-N-nonylglycyl)piperazin-1-yl)ethan-1-one was synthesized from 2-(didodecylamino)-1-(piperazin-1-yl)ethan-1-one (202 mg, 0.421 mmol), N-(2-(dinonylamino)ethyl)-N-nonylglycine (230 mg, 0.463 mmol), i-Pr$_2$EtN (0.162 mL, 0.926 mmol), and propylphosphonic acid anhydride (50% EtOAc solution, 0.752 mL, 1.26 mmol). Yield (148 mg, 37%).

UPLC/ELSD: RT=3.41 min. MS (ES): m/z (MH$^+$) 959.74 for $C_{61}H_{123}N_5O_2$ $^1$H-NMR (300 MHz, CDCl$_3$) δ: ppm 3.82-3.49 (br. m, 8H); 3.33 (s, 2H); 3.27 (s, 2H); 2.66-2.30 (br. m, 14H); 1.85-1.02 (br. m, 82H), 0.90 (t, 15H).

J. Compound 9: 2-(Didodecylamino)-1-(4-(N-(2-(dinonylamino)ethyl)-N-dodecylglycyl)piperazin-1-yl)ethan-1-one

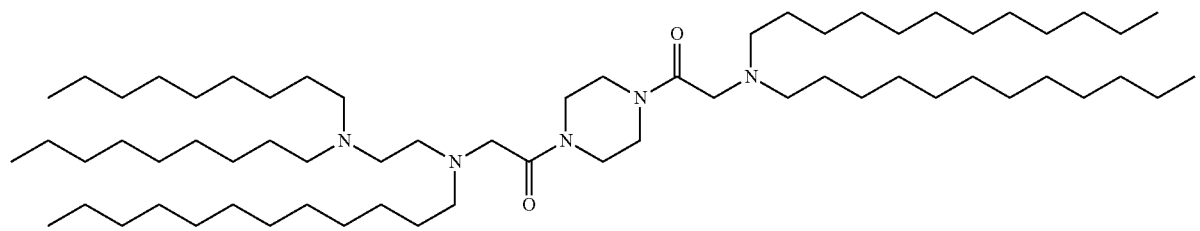

Chemical Formula: $C_{64}H_{129}N_5O_2$
Molecular Weight: 1000.77

In the same manner as Step 11 for Compound 11, 2-(didodecylamino)-1-(4-(N-(2-(dinonylamino)ethyl)-N-dodecylglycyl)piperazin-1-yl)ethan-1-one was synthesized from (76 mg, 0.157 mmol), (93 mg, 0.173 mmol), i-Pr$_2$EtN (60 μL, 0.342 mmol), and propylphosphonic acid anhydride (50% EtOAc solution, 0.278 mL, 0.466 mmol). Yield (59 mg, 37%).

UPLC/ELSD: RT=3.57 min. MS (ES): m/z (MH$^+$) 1001.65 for $C_{64}H_{129}N_5O_2$ $^1$H-NMR (300 MHz, CDCl$_3$) δ: ppm 3.95-2.23 (br. m, 26H); 2.05-1.00 (br. m, 88H); 0.90 (t, 15H).

K. Compound 10: 2-(Didodecylamino)-1-(4-(N-(2-(didodecylamino)ethyl)-N-nonylglycyl)piperazin-1-yl)ethan-1-one

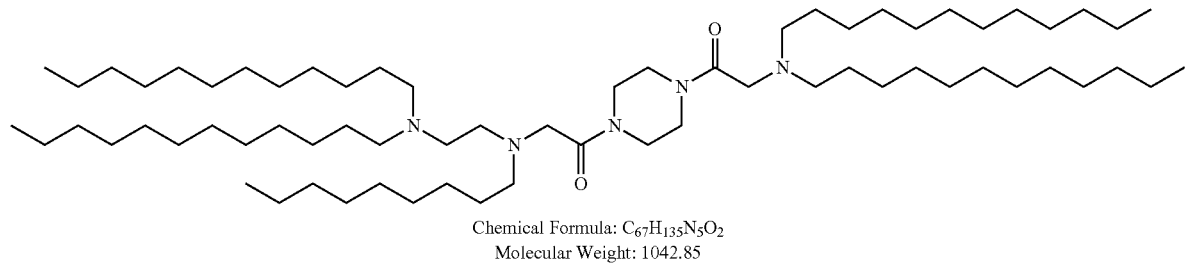 [SMILES: CCCCCCCCCCCCN(CCCCCCCCCCCC)CCN(CCCCCCCCC)CC(=O)N1CCN(C(=O)CN(CCCCCCCCCCCC)CCCCCCCCCCCC)CC1]

Chemical Formula: C₆₇H₁₃₅N₅O₂
Molecular Weight: 1042.85

In the same manner as Step 11 for Compound 11, 2-(didodecylamino)-1-(4-(N-(2-(didodecylamino)ethyl)-N-nonylglycyl)piperazin-1-yl)ethan-1-one was synthesized from 2-(didodecylamino)-1-(piperazin-1-yl)ethan-1-one (76 mg, 0.157 mmol), N-(2-(didodecylamino)ethyl)-N-nonylglycine (101 mg, 0.173 mmol), i-Pr₂EtN (60 µL, 0.342 mmol), and propylphosphonic acid anhydride (50% EtOAc solution, 0.278 mL, 0.466 mmol). Yield (56 mg, 34%).

UPLC/ELSD: RT=3.72 min. MS (ES): m/z (MH⁺) 1043.88 for C₆₇H₁₃₅N₅O₂

¹H-NMR (300 MHz, CDCl₃) δ: ppm 3.95-2.15 (br. m, 26H); 1.90-1.05 (br. m, 94H); 0.90 (t, 15H).

L. Compound 11: 2-(Didodecylamino)-1-(4-(N-(2-(didodecylamino)ethyl)-N-dodecylglycyl)piperazin-1-yl)ethan-1-one

Step 1: Methyl Didodecylglycinate

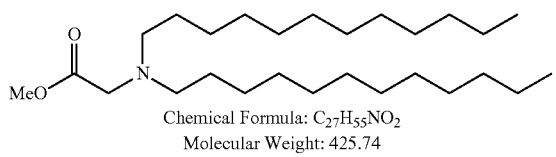 [SMILES: CCCCCCCCCCCCN(CCCCCCCCCCCC)CC(=O)OC]

Chemical Formula: C₂₇H₅₅NO₂
Molecular Weight: 425.74

A solution of glycine methyl ester hydrochloride (5.0 g, 39.8 mmol) and triethylamine (8.3 mL, 59.7 mmol) in DCE (50 mL) was allowed to stir at room temperature for 15 minutes. A solution of 92% dodecanol (20.0 g, 99.6 mmol) in DCE (50 mL) was added and the mixture was cooled to 0° C. Sodium triacetoxyborohydride (21.1 g, 99.6 mmol) and acetic acid (5.7 mL, 99.6 mmol) were added and the reaction was allowed to return to room temperature and stir for 16 hours. The reaction was quenched by slow addition of saturated sodium bicarbonate and extracted with DCM. The combined extracts were washed with brine, dried over anhydrous Na₂SO₄, filtered, and concentrated in vacuo. Purification by ISCO silica flash chromatography (0-30% EtOAc/hexanes) provided methyl didodecylglycinate (7.7 g, 45%).

UPLC/ELSD: RT=2.82 min. MS (ES): m/z (MH⁺) 426.69 for C₂₇H₅₅NO₂

¹H-NMR (300 MHz, CDCl₃) δ: ppm 3.72 (s, 3H); 3.35 (s, 2H); 2.57 (t, 4H); 1.46 (m, 4H); 1.28 (br. m, 36H); 0.91 (t, 6H).

Step 2: Lithium Didodecylglycinate

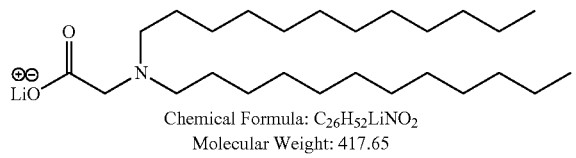

Chemical Formula: C₂₆H₅₂LiNO₂
Molecular Weight: 417.65

A solution of methyl didodecylglycinate (7.7 g, 18.1 mmol) in THF (100 mL) and 1M LiOH (90.4 mL, 90.4 mmol) was allowed to stir at 65° C. for 16 hours. The reaction was cooled to room temperature and concentrated to a white powder. The powder was suspended in water, filtered, washed with water and diethyl ether, and dried under vacuum to provide lithium didodecylglycinate (7.0 g, 93%).

UPLC/ELSD: RT=2.74 min. MS (ES): m/z (MH⁺) 412.83 for C₂₆H₅₃NO₂

¹H-NMR (300 MHz, CD₃OD) δ: ppm 3.14 (s, 2H); 2.60 (t, 4H); 1.51 (m, 4H); 1.31 (br. m, 36H); 0.92 (t, 6H).

Step 3: tert-Butyl 4-didodecylglycyl)piperazine-1-carboxylate

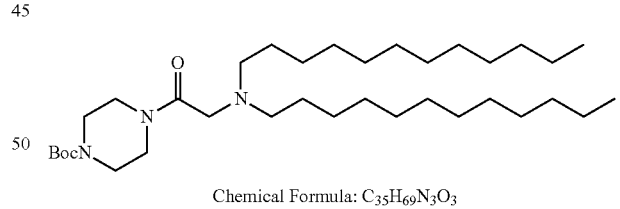

Chemical Formula: C₃₅H₆₉N₃O₃
Molecular Weight: 579.96

A solution of lithium didodecylglycinate (2.0 g, 4.79 mmol), 1-boc-piperazine (978 mg, 5.25 mmol), i-Pr₂EtN (1.84 mL, 10.5 mmol), and propylphosphonic acid anhydride (50% EtOAc solution, 8.53 mL, 14.3 mmol) in THF (24 mL) was allowed to stir at room temperature for 48 hours. The reaction was diluted with water and extracted with EtOAc. The organics were washed with brine, dried over anhydrous Na₂SO₄, filtered, and concentrated in vacuo. Purification by ISCO silica flash chromatography (0-20% MeOH/DCM) provided tert-butyl 4-(didodecylglycyl)piperazine-1-carboxylate (983 mg, 35%).

UPLC/ELSD: RT=3.06 min. MS (ES): m/z (MH⁺) 581.02 for C₃₅H₆₉N₃O₃

Step 4: 2-(Didodecylamino)-1-(piperazin-1-yl)ethan-1-one

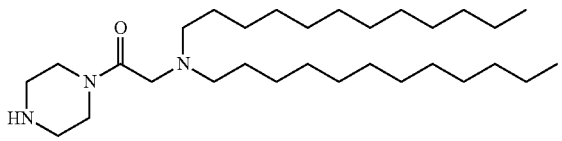

Chemical Formula: C$_{30}$H$_{61}$N$_3$O
Molecular Weight: 479.84

To a 0° C. solution of tert-butyl 4-(didodecylglycyl)piperazine-1-carboxylate (983 mg, 1.69 mmol) in DCM (6.5 mL) was added dropwise TFA (6.5 mL, 84.7 mmol). The reaction was allowed to return to room temperature and stir for 16 hours. The reaction mixture was concentrated in vacuo and the crude material was dissolved in CHCl$_3$. The solution was washed with 5% Na$_2$CO$_3$, brine, dried over anhydrous Na$_2$SO$_4$, filtered, and concentrated in vacuo to provide 2-(didodecylamino)-1-(piperazin-1-yl)ethan-1-one (163 mg, 20%).

UPLC/ELSD: RT=2.07 min. MS (ES): m/z (MH$^+$) 480.89 for C$_{30}$H$_{61}$N$_3$O $^1$H-NMR (300 MHz, CDCl$_3$) δ: ppm 3.67 (br. m, 4H); 3.32 (s, 2H); 2.92 (br. m, 4H); 2.53 (br. m, 4H); 1.48 (br. m, 4H); 1.28 (br. m, 36H); 0.91 (t, 6H).

Step 5: Methyl N-(tert-butoxycarbonyl)-N-dodecylglycinate

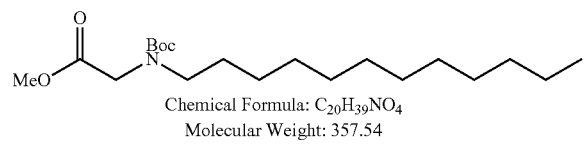 [SMILES: CCCCCCCCCCCCN(CC(=O)OC)C(=O)OC(C)(C)C]

Chemical Formula: C$_{20}$H$_{39}$NO$_4$
Molecular Weight: 357.54

A 0° C. solution of N-(tert-butoxycarbonyl)glycine methyl ester (7.7 g, 40.7 mmol) in DMF (100 mL) was treated with NaH (60%, 1.71 g, 42.7 mmol) and the mixture was allowed to stir for 30 minutes. The solution was allowed to return to room temperature before 1-bromododecane (15.2 g, 61.0 mmol) was added. The reaction was quenched with water and extracted with EtOAc. The organics were washed with brine, dried over anhydrous Na$_2$SO$_4$, filtered, and concentrated in vacuo. Purification by ISCO silica flash chromatography (0-20% EtOAc/hexanes) provided methyl N-(tert-butoxycarbonyl)-N-dodecylglycinate (4.03 g, 28%).

$^1$H-NMR (300 MHz, CDCl$_3$) δ: ppm 4.01-3.84 (br. m, 2H); 3.75 (s, 3H); 3.27 (br. m, 2H); 1.67-1.39 (br. m, 11H); 1.28 (br. m, 18H); 0.90 (t, 3H).

Step 6: Methyl Dodecylglycinate

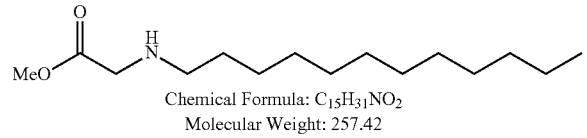 [SMILES: CCCCCCCCCCCCNCC(=O)OC]

Chemical Formula: C$_{15}$H$_{31}$NO$_2$
Molecular Weight: 257.42

To a 0° C. solution of methyl N-(tert-butoxycarbonyl)-N-dodecylglycinate (4.03 g, 11.3 mmol) in DCM (17 mL) was added dropwise TFA (17 mL, 226 mmol). The reaction was allowed to return to room temperature and stir for 6 hours. The reaction mixture was concentrated in vacuo and the crude material was dissolved in DCM. The solution was washed with 10% NaOH, brine, dried over anhydrous Na2SO4, filtered, and concentrated in vacuo to provide methyl dodecylglycinate (2.84 g, 98%).

$^1$H-NMR (300 MHz, CDCl$_3$) δ: ppm 3.75 (s, 3H); 3.44 (s, 2H); 2.62 (t, 2H); 1.70 (br, 1H); 1.51 (m, 2H); 1.29 (br. m, 18H); 0.90 (t, 3H).

Step 7: 2-(Didodecylamino)ethan-1-ol

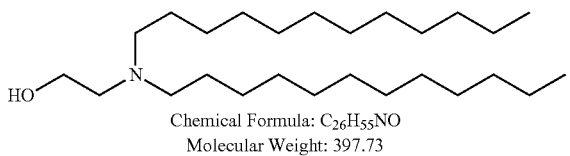 [SMILES: CCCCCCCCCCCCN(CCO)CCCCCCCCCCCC]

Chemical Formula: C$_{26}$H$_{55}$NO
Molecular Weight: 397.73

In the same manner as Step 1 for Compound 18, 2-(didodecylamino)ethan-1-ol was synthesized from 1-bromododecane (10 g, 40.1 mmol), ethanolamine (1.10 mL, 18.2 mmol), K$_2$CO$_3$ (11.1 g, 80.1 mmol), and KI (302 mg, 1.82 mmol) in MeCN (84 mL). Yield (3.87 g, 53%).

UPLC/ELSD: RT=2.69 min. MS (ES): m/z (MH$^+$) 398.56 for C$_{26}$H$_{55}$NO $^1$H-NMR (300 MHz, CDCl$_3$) δ: ppm 3.57 (t, 2H); 2.63 (t, 2H); 2.49 (br. m, 4H); 1.48 (br. m, 4H); 1.29 (br. m, 36H); 0.91 (t, 6H).

Step 8: N-(2-Chloroethyl)-N-dodecyldodecan-1-amine

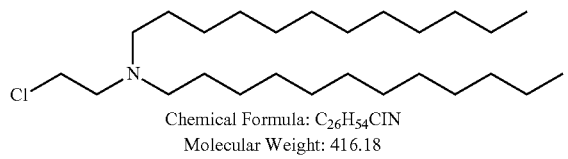 [SMILES: CCCCCCCCCCCCN(CCCl)CCCCCCCCCCCC]

Chemical Formula: C$_{26}$H$_{54}$ClN
Molecular Weight: 416.18

In the same manner as Step 2 for Compound 18, N-(2-chloroethyl)-N-dodecyldodecan-1-amine was synthesized from 2-(didodecylamino)ethan-1-ol (3.87 g, 9.73 mmol), triethylamine (1.76 mL, 12.6 mmol), and methanesulfonyl chloride (0.941 mL, 12.2 mmol) in DCM (50 mL). Yield (1.92 g, 47%).

$^1$H-NMR (300 MHz, CDCl$_3$) δ: ppm 3.51 (t, 2H); 2.78 (t, 2H); 2.47 (br. m, 4H); 1.44 (br. m, 4H); 1.28 (br. m, 36H); 0.90 (t, 6H).

Step 9: Methyl N-(2-(didodecylamino)ethyl)-N-dodecylglycinate

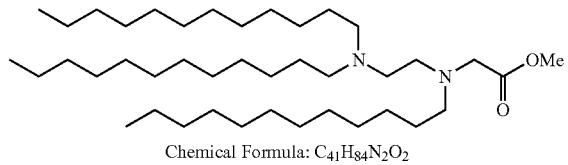

Chemical Formula: C$_{41}$H$_{84}$N$_2$O$_2$
Molecular Weight: 637.14

To a solution of methyl dodecylglycinate (425 mg, 1.65 mmol) in MeCN (10 mL) was added N-(2-chloroethyl)-N-dodecyldodecan-1-amine (825 mg, 1.98 mmol), $K_2CO_3$ (457 mg, 3.30 mmol), and KI (27 mg, 0.165 mmol). The reaction was allowed to stir at 82° C. for 72 hours. The reaction mixture was filtered and the solids were washed with hexanes. The filtrate was concentrated in vacuo to provide the crude product. Purification by ISCO silica flash chromatography (0-20% MeOH/DCM) provided methyl N-(2-(didodecylamino)ethyl)-N-dodecylglycinate (652 mg, 62%).

UPLC/ELSD: RT=3.77 min. MS (ES): m/z (MH$^+$) 638.18 for $C_{41}H_{84}N_2O_2$ $^1$H-NMR (300 MHz, CDCl$_3$) δ: ppm 3.72 (s, 3H); 3.41 (s, 2H); 2.90-2.20 (br. m, 10H); 1.60-1.00 (br. m, 60H); 0.90 (t, 9H).

Step 10:
N-(2-(Didodecylamino)ethyl)-N-dodecylglycine

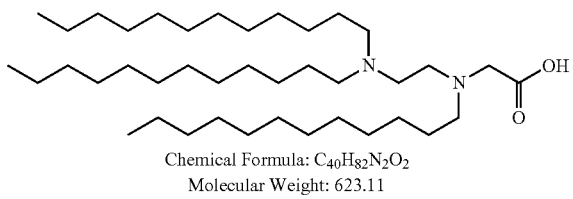 [SMILES: CCCCCCCCCCCCN(CCCCCCCCCCCC)CCN(CCCCCCCCCCCC)CC(=O)O]

Chemical Formula: $C_{40}H_{82}N_2O_2$
Molecular Weight: 623.11

A solution of methyl N-(2-(didodecylamino)ethyl)-N-dodecylglycinate (652 mg, 1.02 mmol) in THF (6 mL) and 1M LiOH (5 mL, 5 mmol) was allowed to stir at 65° C. for 16 hours. The reaction was cooled to room temperature and acidified with 10% HCl. The mixture was extracted with chloroform, and the organics were washed with brine, dried over anhydrous $Na_2SO_4$, filtered, and concentrated in vacuo. Purification by ISCO silica flash chromatography (0-20% MeOH/DCM) provided N-(2-(didodecylamino)ethyl)-N-dodecylglycine (153 mg, 24%).

UPLC/ELSD: RT=3.60 min. MS (ES): m/z (MH$^+$) 624.07 for $C_{40}H_{82}N_2O_2$ $^1$H-NMR (300 MHz, CDCl$_3$) δ: ppm 4.02-3.40 (br. m, 6H); 3.16 (br. m, 6H); 1.78 (br. m, 6H); 1.46-1.01 (br. m, 54H); 0.90 (t, 9H).

Step 11: Compound 11: 2-(Didodecylamino)-1-(4-(N-(2-(didodecylamino)ethyl)-N-dodecylglycyl) piperazin-1-yl)ethan-1-one To a solution of N-(2-(didodecylamino)ethyl)-N-dodecylglycine (212 mg, 0.340 mmol) and 2-(didodecylamino)-1-(piperazin-1-yl)ethan-1-one (163 mg, 0.340 mmol) in THF (4 mL) was added i-Pr$_2$EtN (0.119 mL, 0.680 mmol), and propylphosphonic acid anhydride (50% EtOAc solution, 0.606 mL, 1.02 mmol). The reaction was allowed to stir at room temperature overnight. The reaction mixture was diluted with water and extracted with EtOAc. The organics were washed with brine, dried over anhydrous $Na_2SO_4$, and concentrated in vacuo. Purification by ISCO silica flash chromatography (0-100% [DCM, 20% MeOH, 1% $NH_4OH$]/MeOH) provided 2-(didodecylamino)-1-(4-(N-(2-(didodecylamino)ethyl)-N-dodecylglycyl)piperazin-1-yl) ethan-1-one (148 mg, 37%).

UPLC/ELSD: RT=3.81 min. MS (ES): m/z (MH$^+$) 1086.94 for $C_{70}H_{141}N_5O_2$ $^1$H-NMR (300 MHz, CDCl$_3$) δ: ppm 4.00-2.20 (br. m, 26H); 1.77 (br. m, 6H); 1.54-1.02 (br. m, 94H); 0.90 (t, 15H).

M. Compound 12: Pentyl 6-((2-(4-(2-((2-(didodecylamino)ethyl)(dodecyl)amino)ethyl)piperazin-1-yl) ethyl)(dodecyl)amino)hexanoate Step 1: Pentyl 6-bromohexanoate

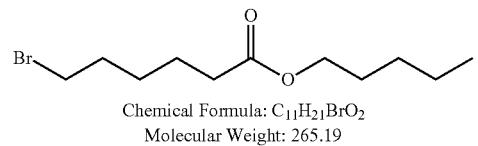

Chemical Formula: $C_{11}H_{21}BrO_2$
Molecular Weight: 265.19

To a solution of 6-bromohexanoic acid (2 g, 10.3 mmol) and pentan-1-ol (2.2 mL, 20.5 mmol) in 26 mL DCM, EDC.HCl (1.97 g, 10.3 mmol) and DMAP (0.26 g, 2.1 mmol) were added. The solution was allowed to stir at rt overnight. After this time the reaction was quenched by the addition of water. The mixture was extracted three times with DCM. The organics were pooled and washed with saturated NaHCO$_3$, 10% citric acid and brine. The organics were then dried over MgSO4, filtered and concentrated in vacuo. The crude material was purified via silica gel chromatography (0-30% EtOAc in hexanes) to afford the desired product (2.3 g, 8.67 mmol).

$^1$H NMR (400 MHz, CDCl$_3$) δ: ppm 4.06 (t, 2H); 3.39 (t, 2H); 2.30 (t, 2H); 1.84 (m, 2H); 1.62 (m, 4H); 1.46 (m, 2H); 1.31 (m, 4H); 0.88 (t, 3H).

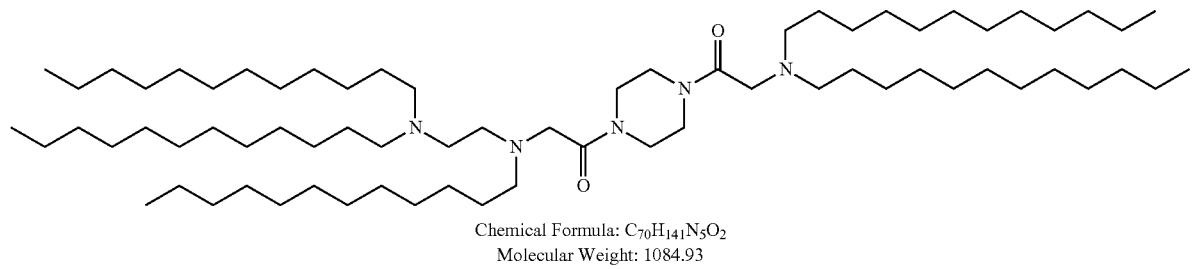 [SMILES: CCCCCCCCCCCCN(CCCCCCCCCCCC)CCN(CCCCCCCCCCCC)CC(=O)N1CCN(C(=O)CN(CCCCCCCCCCCC)CCCCCCCCCCCC)CC1]

Chemical Formula: $C_{70}H_{141}N_5O_2$
Molecular Weight: 1084.93

Step 2: 2-(Dodecylamino)ethan-1-ol

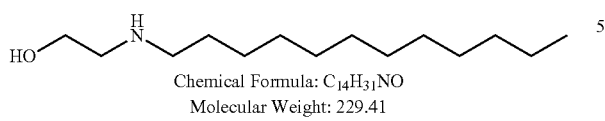

Chemical Formula: $C_{14}H_{31}NO$
Molecular Weight: 229.41

Methyl dodecylglycinate (3.4 g, 13.2 mmol) was dissolved in 2 mL THF under $N_2$ atmosphere and the reaction flask was allowed to cool in an ice bath. To the solution $LiAlH_4$ (0.55 g, 14.5 mmol) was slowly added. The reaction was allowed to stir at the same temperature for 1 h. After this time the reaction was quenched by the subsequent addition of 0.55 mL $H_2O$, 0.55 mL 10% NaOH and then 1.65 mL of $H_2O$. The reaction was then filtered and the filtrate was concentrated in vacuo. The crude material was purified via silica gel chromatography (0-20% MeOH in DCM, with 1% NaOH) to afford the desired alcohol (1.9 g, 8.28 mmol, 63% yield).

$^1$H NMR (400 MHz, $CDCl_3$) δ: ppm 3.63 (t, 2H); 2.78 (t, 2H); 2.63 (t, 2H); 1.48 (m, 2H); 2.14 (m, 18H); 0.88 (t, 3H).

Step 3: Pentyl 6-(dodecyl(2-hydroxyethyl)amino)hexanoate

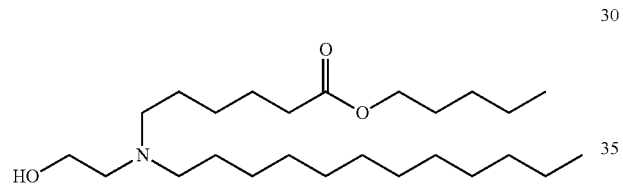

Chemical Formula: $C_{25}H_{51}NO_3$
Molecular Weight: 413.69

In the same manner as Step 1 for Compound 18, pentyl 6-(dodecyl(2-hydroxyethyl)amino)hexanoate was synthesized from pentyl 6-bromohexanoate (0.87 g, 3.27 mmol), 2-(dodecylamino)ethan-1-ol (0.50 g, 2.18 mmol), $K_2CO_3$ (0.60 g, 4.36 mmol) and KI (36 mg, 0.22 mmol) in 10 mL THF to afford 0.30 g of the desired product (33%).

$^1$H NMR (400 MHz, $CDCl_3$) δ: ppm 4.04 (t, 2H); 3.51 (m, 2H); 2.56 (m, 2H); 2.42 (m, 4H); 2.28 (t, 2H); 1.60 (m, 4H); 1.42 (m, 4H); 1.30-1.24 (m, 24); 0.87 (m, 6H).

Step 4: Pentyl 6-((2-chloroethyl)(dodecyl)amino)hexanoate

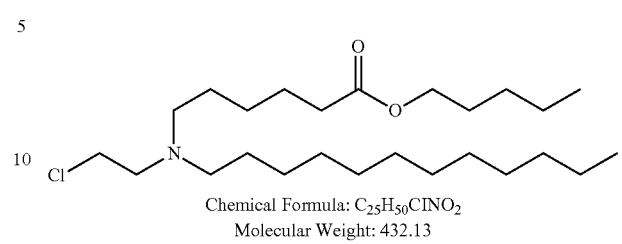

Chemical Formula: $C_{25}H_{50}ClNO_2$
Molecular Weight: 432.13

In the same manner as Step 2 for Compound 18, pentyl 6-((2-chloroethyl)(dodecyl)amino)hexanoate was synthesized from pentyl 6-(dodecyl(2-hydroxyethyl)amino) hexanoate (300 mg, 0.73 mmol), methanesulfonyl chloride (0.062 mL, 0.80 mmol) and triethylamine (0.13 mL, 1.3 mmol) in 2 mL DCM to afford 285 mg of the desired product (66%).

$^1$H NMR (400 MHz, $CDCl_3$) δ: ppm 4.04 (t, 2H); 3.45 (t, 2H); 2.74 (t, 2H); 2.43 (m, 4H); 2.28 (t, 2H); 1.65-1.59 (m, 4H); 1.31-1.24 (m, 32H); 0.88 (m, 6H).

Step 5: Compound 12: Pentyl 6-((2-(4-(2-((2-(didodecylamino)ethyl)(dodecyl)amino)ethyl)piperazin-1-yl)ethyl)(dodecyl)amino)hexanoate

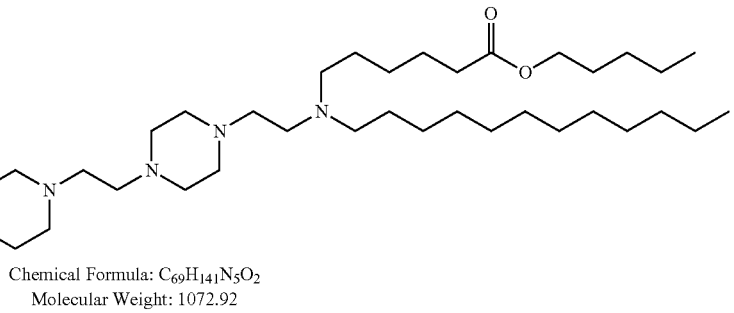

Chemical Formula: $C_{69}H_{141}N_5O_2$
Molecular Weight: 1072.92

In the same manner as Step 6 for Compound 18, pentyl 6-((2-(4-(2-((2-(didodecylamino)ethyl)(dodecyl)amino) ethyl)piperazin-1-yl)ethyl)(dodecyl)amino)hexanoate was synthesized from pentyl 6-((2-chloroethyl)(dodecyl)amino) hexanoate (75 mg, 0.17 mmol), $N^1,N^1,N^2$-tridodecyl-$N^2$-(2-(piperazin-1-yl)ethyl)ethane-1,2-diamine (107 mg, 0.16 mmol), $K_2CO_3$ (23 mg, 0.17 mmol) and KI (2.7 mg, 0.1 mmol) in 1 mL MeCN to afford 99 mg of the desired product (58%).

UPLC: RT=3.53 min. MS (ES): m/z (MH$^+$) 1073.325 for $C_{69}H_{141}N_5O_2$

¹H NMR (400 MHz, CDCl₃) δ: ppm 4.03 (t, 2H); 2.56-2.37 (br. m., 30H); 2.27 (t, 2H); 1.61 (m, 4H); 1.40-1.23 (br. m.; 90H); 0.87 (m, 15H).

N. Compound 13: Pentyl 6-((2-(4-(2-((2-(ditetradecylamino)ethyl)(tetradecyl)amino)ethyl)piperazin-1-yl)ethyl)(dodecyl)amino)hexanoate Step 1: 2-(Ditetradecylamino)ethan-1-ol

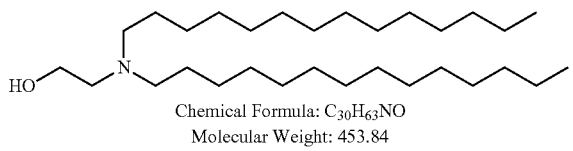 [SMILES: CCCCCCCCCCCCCCN(CCO)CCCCCCCCCCCCCC]

Chemical Formula: C₃₀H₆₃NO
Molecular Weight: 453.84

In the same manner as Step 1 for Compound 18, 2-(ditetradecylamino)ethan-1-ol was synthesized from 1-bromotetradecane (21.6 mL, 72.8 mmol), ethanolamine (2 mL, 33.1 mmol), K2CO3 (20 g, 145.5 mmol), and KI (549 mg, 3.31 mmol) in MeCN (165 mL). Yield (12 g, 81%).

UPLC/ELSD: RT=3.30 min. MS (ES): m/z (MH⁺) 454.46 for C₃₀H₆₃NO

¹H-NMR (300 MHz, CDCl₃) δ: ppm 3.54 (br. m, 2H); 2.59 (br. m, 2H); 2.46 (br. m, 4H); 1.56-1.17 (br. m, 48H); 0.90 (br. m, 6H).

Step 2: N-(2-Chloroethyl)-N-tetradecyltetradecan-1-amine

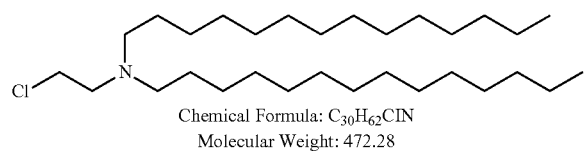 [SMILES: CCCCCCCCCCCCCCN(CCCl)CCCCCCCCCCCCCC]

Chemical Formula: C₃₀H₆₂ClN
Molecular Weight: 472.28

In the same manner as Step 2 for Compound 18, N-(2-chloroethyl)-N-tetradecyltetradecan-1-amine was synthesized from 2-(ditetradecylamino)ethan-1-ol (10 g, 22.0 mmol), triethylamine (4.0 mL, 28.6 mmol), and methanesulfonyl chloride (2.75 mL, 27.5 mmol) in DCM (110 mL). Crude material was carried onto next step without purification. Yield (10.2 g, 98%).

UPLC/ELSD: RT=3.37 min. MS (ES): m/z (MH⁺) 472.45 for C₃₀H₆₂ClN

¹H-NMR (300 MHz, CDCl₃) δ: ppm 4.27-2.20 (br. m, 8H); 1.96-1.17 (br. m, 48H); 0.90 (br. m, 6H).

Step 3: tert-Butyl 4-(2-(tetradecylamino)ethyl)piperazine-1-carboxylate

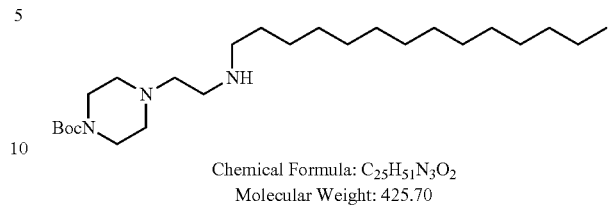

Chemical Formula: C₂₅H₅₁N₃O₂
Molecular Weight: 425.70

In the same manner as Step 3 for Compound 18, tert-butyl 4-(2-(tetradecylamino)ethyl)piperazine-1-carboxylate was synthesized from 1-bromotetradecane (3.63 g, 13.1 mmol), 4-(2-aminoethyl)-1-boc-piperazine (3.0 g, 13.1 mmol), K₂CO₃ (3.62 g, 26.2 mmol), and KI (217 mg, 1.31 mmol) in MeCN (60 mL). Yield (1.42 g, 27%).

UPLC/ELSD: RT=1.58 min. MS (ES): m/z (MH⁺) 426.61 for C₂₅H₅₁N₃O₂

¹H-NMR (300 MHz, CDCl₃) δ: ppm 3.45 (t, 4H); 2.75 (t, 2H) 2.65 (t, 2H); 2.54 (t, 2H); 2.42 (t, 4H); 1.61-1.41 (br. m, 11H); 1.40-1.20 (br. m, 22H); 0.90 (t, 3H).

Step 4: tert-Butyl 4-(2-((2-(ditetradecylamino)ethyl)(tetradecyl)amino)ethyl)piperazine-1-carboxylate

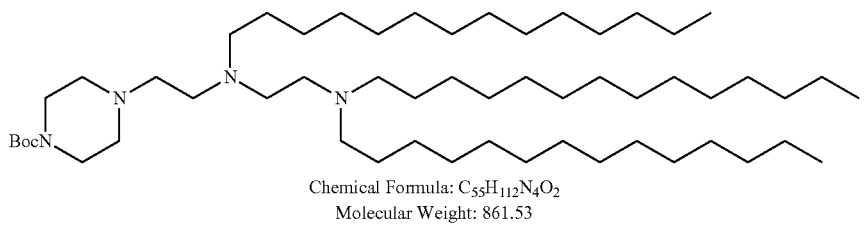 [SMILES: CCCCCCCCCCCCCCN(CCCCCCCCCCCCCC)CCN(CCCCCCCCCCCCCC)CCN1CCN(C(=O)OC(C)(C)C)CC1]

Chemical Formula: C₅₅H₁₁₂N₄O₂
Molecular Weight: 861.53

In the same manner as Step 4 for Compound 18, tert-butyl 4-(2-((2-(ditetradecylamino)ethyl)(tetradecyl)amino)ethyl)piperazine-1-carboxylate was synthesized from tert-butyl 4-(2-(tetradecylamino)ethyl)piperazine-1-carboxylate (700 mg, 1.64 mmol), N-(2-chloroethyl)-N-tetradecyltetradecan-1-amine (1.01 g, 2.14 mmol), K₂CO₃ (455 mg, 3.29 mmol), and KI (27 mg, 0.164 mmol) in THF (15 mL). Yield (740 mg, 52%).

UPLC/ELSD: RT=3.81 min. MS (ES): m/z (MH⁺) 862.47 for C₅₅H₁₁₂N₄O₂

¹H-NMR (300 MHz, CDCl₃) δ: ppm 3.45 (br. m, 4H); 3.10-2.83 (br. m, 4H); 2.74-2.34 (br. m, 14H); 1.75-1.20 (br. m, 81H); 0.91 (t, 9H).

Step 5: $N^1$-(2-(Piperazin-1-yl)ethyl)-$N^1,N^2,N^2$-tritetradecylethane-1,2-diamine

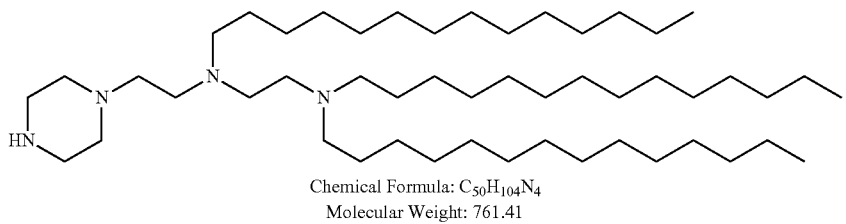 [SMILES: CCCCCCCCCCCCCCN(CCCCCCCCCCCCCC)CCN(CCCCCCCCCCCCCC)CCN1CCNCC1]

Chemical Formula: $C_{50}H_{104}N_4$
Molecular Weight: 761.41

In the same manner as Step 5 for Compound 18, $N^1$-(2-(piperazin-1-yl)ethyl)-$N^1,N^2,N^2$-tritetradecylethane-1,2-diamine was synthesized from tert-butyl 4-(2-((2-(ditetradecylamino)ethyl)(tetradecyl)amino)ethyl)piperazine-1-carboxylate (740 mg, 0.859 mmol), and TFA (3.3 mL, 42.9 mmol) in DCM (3.3 mL). Yield (661 mg, 99%).

UPLC/ELSD: RT=3.38 min. MS (ES): m/z (MH$^+$) 762.42 for $C_{50}H_{104}N_4$ $^1$H-NMR (300 MHz, CDCl$_3$) δ: ppm 2.92 (t, 4H); 2.70-2.30 (br. m, 18H); 1.46 (br. m, 6H); 1.37-1.20 (br. m, 66H); 0.90 (t, 9H).

Step 6: Compound 13: Pentyl 6-((2-(4-(2-((2-(ditetradecylamino)ethyl)(tetradecyl)amino)ethyl)piperazin-1-yl)ethyl)(dodecyl)amino)hexanoate

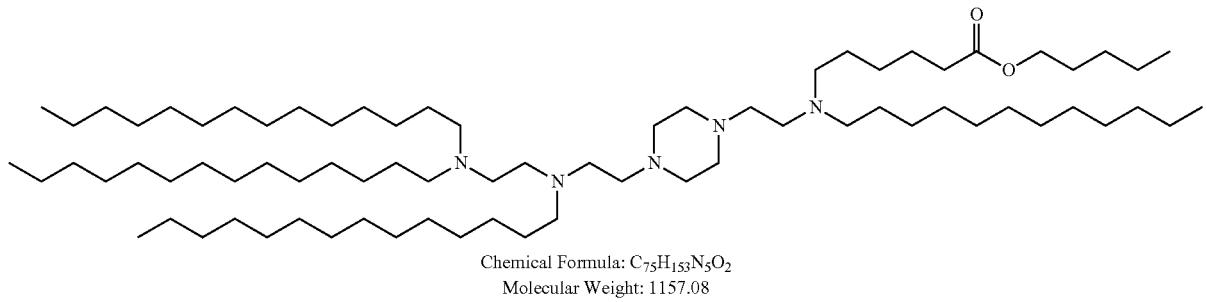 [SMILES: CCCCCCCCCCCCCCN(CCCCCCCCCCCCCC)CCN(CCCCCCCCCCCCCC)CCN1CCN(CCN(CCCCCCCCCCCC)CCCCCC(=O)OCCCCC)CC1]

Chemical Formula: $C_{75}H_{153}N_5O_2$
Molecular Weight: 1157.08

In the same manner as Step 6 for Compound 18, pentyl 6-((2-(4-(2-((2-(ditetradecylamino)ethyl)(tetradecyl)amino)ethyl)piperazin-1-yl)ethyl)(dodecyl)amino)hexanoate was synthesized from $N^1$-(2-(piperazin-1-yl)ethyl)-$N^1,N^2,N^2$-tritetradecylethane-1,2-diamine (66 mg, 0.087 mmol), pentyl 6-((2-chloroethyl)(dodecyl)amino)hexanoate (42 mg, 0.095 mmol) K$_2$CO$_3$ (24 mg, 0.17 mmol), and KI (2 mg, 0.012 mmol) in THF (2 mL). Yield (38 mg, 38%).

UPLC/ELSD: RT=3.81 min. MS (ES): m/z (MH$^+$) 1157.70 for $C_{75}H_{153}N_5O_2$ $^1$H-NMR (300 MHz, CDCl$_3$) δ: ppm 4.08 (m, 2H); 3.16-2.15 (br. m, 32H); 1.65 (br. m, 4H); 1.54-1.00 (br. m, 100H); 0.91 (br. m, 15H).

O. Compound 14: Dipentyl 6,6'-((2-(4-(2-((2-(didodecylamino)ethyl)(dodecyl)amino)ethyl)piperazin-1-yl)ethyl)azanediyl)dihexanoate Step 1: Dipentyl 6,6'-((2-hydroxyethyl)azanediyl)dihexanoate

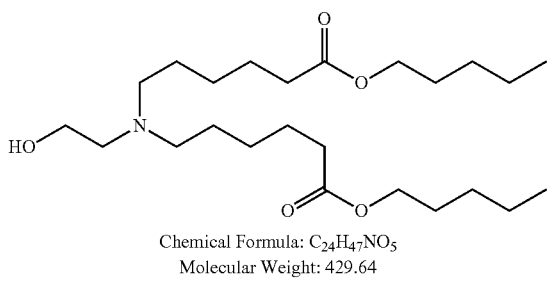 [SMILES: CCCCCOC(=O)CCCCCN(CCO)CCCCCC(=O)OCCCCC]

Chemical Formula: $C_{24}H_{47}NO_5$
Molecular Weight: 429.64

In the same manner as Step 1 for Compound 18, dipentyl 6,6'-((2-hydroxyethyl)azanediyl)dihexanoate was synthesized from pentyl 6-bromohexanoate (0.50 g, 1.89 mmol), ethanolamine (0.052 mL, 0.86 mmol), K2C03 (0.52 g, 3.77 mmol) and KI (14 mg, 0.098 mmol) in 4 mL MeCN to provide 234 mg (55%).

$^1$H NMR (400 MHz, CDCl$_3$) δ: ppm 4.08 (t, 4H); 3.62 (m, 2H); 2.68-2.56 (br. m., 6H); 2.33 (t, 4H); 1.64-1.54 (m, 13H); 1.35 (m, 12H); 0.93 (t, 6H).

Step 2: Dipentyl 6,6'-((2-chloroethyl)azanediyl)dihexanoate

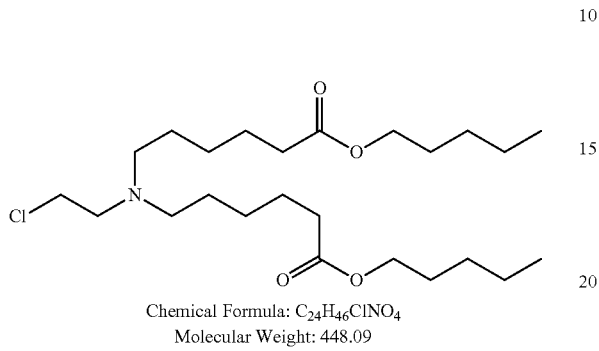

Chemical Formula: C$_{24}$H$_{46}$ClNO$_4$
Molecular Weight: 448.09

In the same manner as Step 2 for Compound 18, dipentyl 6,6'-((2-chloroethyl)azanediyl)dihexanoate was synthesized from dipentyl 6,6'-((2-hydroxyethyl)azanediyl)dihexanoate (124 mg, 0.29 mmol), methanesulfonyl chloride (0.025 mL, 0.32 mmol) and triethylamine (0.060 mL, 0.44 mmol) in 1.5 mL DCM to provide 84 mg (65%).

$^1$H NMR (400 MHz, CDCl$_3$) δ: ppm 4.04 (t, 4H); 3.46 (t, 2H); 2.73 (t, 2H); 2.43 (t, 4H); 2.28 (t, 4H); 1.60 (m, 8H); 1.40 (m, 4H); 1.29 (m, 12H); 0.89 (t, 6H).

Step 3: Compound 14: Dipentyl 6,6'-((2-(4-(2-((2-(didodecylamino)ethyl)(dodecyl)amino)ethyl)piperazin-1-yl)ethyl)azanediyl)dihexanoate

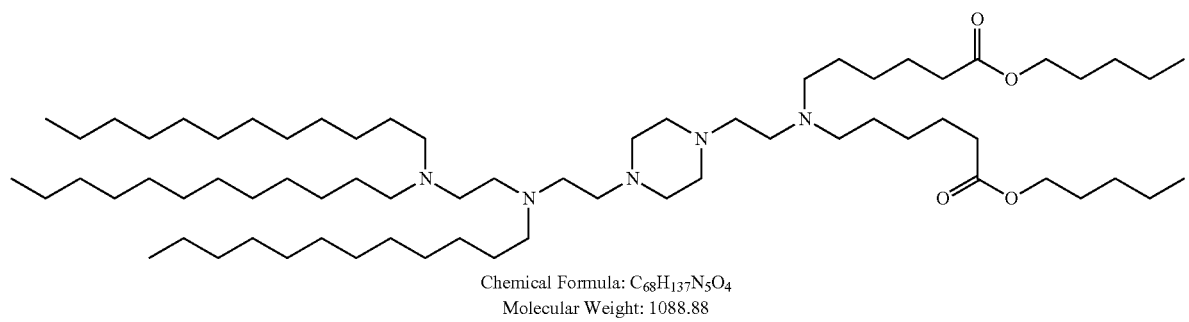 [SMILES: CCCCCCCCCCCCN(CCCCCCCCCCCC)CCN(CCCCCCCCCCCC)CCN1CCN(CCN(CCCCCC(=O)OCCCCC)CCCCCC(=O)OCCCCC)CC1]

Chemical Formula: C$_{68}$H$_{137}$N$_5$O$_4$
Molecular Weight: 1088.88

In the same manner as Step 6 for Compound 18, dipentyl 6,6'-((2-(4-(2-((2-(didodecylamino)ethyl)(dodecyl)amino)ethyl)piperazin-1-yl)ethyl)azanediyl)dihexanoate was synthesized from N$^1$,N$^1$,N$^2$-tridodecyl-N$^2$-(2-(piperazin-1-yl)ethyl)ethane-1,2-diamine (105 mg, 0.16 mmol), dipentyl 6,6'-((2-chloroethyl)azanediyl)dihexanoate (84 mg, 0.19 mmol) and K$_2$CO$_3$ (22 mg, 0.16 mmol) in 1 mL MeCN. Yield (53 mg, 0.049 mmol, 30%).

UPLC: RT=3.47 min. MS (ES): m/z (MH$^+$) 1089.53 for C$_{68}$H$_{137}$N$_5$O$_4$ $^1$H NMR (400 MHz, CDCl$_3$) δ: ppm 4.04 (t, 4H); 2.89-2.98 (m, 4H); 2.39-2.68 (m, 26H); 2.27 (t, 4H); 1.57-1.71 (m, 10H); 1.35 (m, 4H); 1.28-1.35 (m, 74H); 0.90 (m, 15H).

P. Compound 15: Methyl 12-((2-(4-(2-((2-(didodecylamino)ethyl)(dodecyl)amino)ethyl)piperazin-1-yl)ethyl)(dodecyl)amino)dodecanoate Step 1: Methyl 12-bromododecanoate

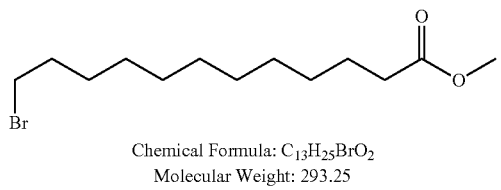 [SMILES: COC(=O)CCCCCCCCCCCBr]

Chemical Formula: C$_{13}$H$_{25}$BrO$_2$
Molecular Weight: 293.25

To a solution of 12-bromododecanoic acid (2.5 g, 8.95 mmol) in THF (7 mL) was added methanol (7.2 mL, 179 mmol). Sulfuric acid (0.50 mL, 8.95 mmol) was added dropwise and the reaction was allowed to stir at 65° C. for two hours. The reaction mixture was washed with 5% NaHCO$_3$ and brine. The organic layer was dried over anhydrous Na$_2$SO$_4$, filtered, and concentrated in vacuo. Purification by ISCO silica flash chromatography (0-20% EtOAc/hexanes) provided methyl 12-bromododecanoate (2.40 g, 92%).

$^1$H-NMR (300 MHz, CDCl$_3$) δ: ppm 3.69 (s, 3H); 3.44 (t, 2H); 2.33 (t, 2H); 1.88 (br. m, 2H); 1.64 (br. m, 2H); 1.45 (br. m, 2H); 1.31 (br. m, 12H).

Step 2: Methyl 12-(dodecyl(2-hydroxyethyl)amino)dodecanoate

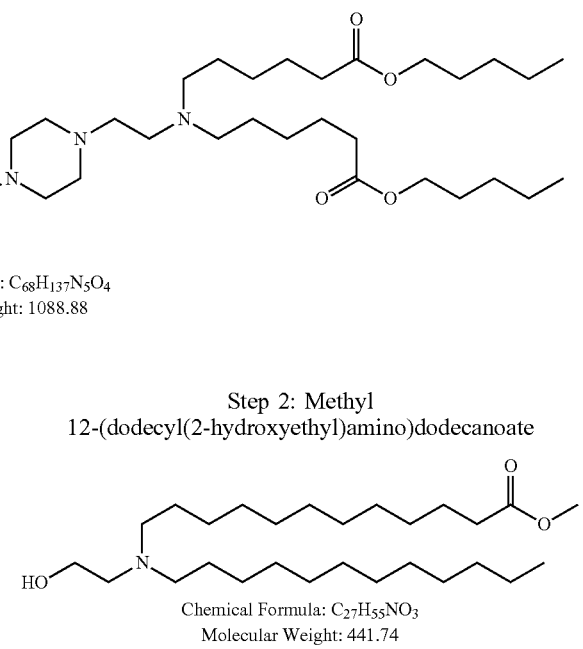

Chemical Formula: C$_{27}$H$_{55}$NO$_3$
Molecular Weight: 441.74

To a solution of methyl 12-((2-hydroxyethyl)amino)dodecanoate (413 mg, 1.51 mmol) in MeCN (5 mL) was added 1-bromododecane (452 mg, 1.81 mmol), K$_2$CO$_3$ (418 mg, 3.02 mmol), and KI (25 mg, 0.151 mmol). The reaction was allowed to stir at 82° C. for 16 hours. The reaction mixture was cooled to room temperature, diluted with $H_2O$, and extracted with EtOAc. The combined organic layers were washed with brine, dried over anhydrous $Na_2SO_4$, filtered, and concentrated in vacuo. Purification by ISCO silica flash chromatography (0-100% [DCM, 20% MeOH, 1% $NH_4OH$]/MeOH) provided methyl 12-(dodecyl(2-hydroxyethyl)amino)dodecanoate (409 mg, 61%).

UPLC/ELSD: RT=2.39 min. MS (ES): m/z (MH$^+$) 442.60 for $C_{27}H_{55}NO_3$ $^1$H-NMR (300 MHz, $CDCl_3$) δ: ppm 3.69 (s, 3H); 3.61 (t, 2H); 2.68 (t, 2H); 2.54 (t, 4H); 2.32 (t, 2H); 1.64 (m, 2H); 1.50 (br. m, 4H); 1.28 (br. m, 32H); 0.90 (t, 3H).

Step 3: Methyl 12-((2-chloroethyl)(dodecyl)amino)dodecanoate

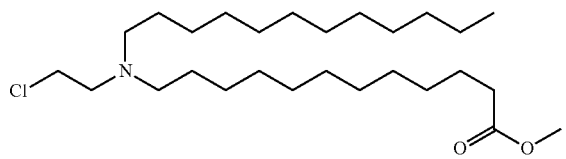

Chemical Formula: $C_{27}H_{54}ClNO_2$
Molecular Weight: 460.18

In the same manner as Step 2 for Compound 18, methyl 12-((2-chloroethyl)(dodecyl)amino)dodecanoate was synthesized from methyl 12-((2-hydroxyethyl)amino)dodecanoate (409 mg, 0.926 mmol), triethylamine (0.168 mL, 1.20 mmol), and methanesulfonyl chloride (0.090 mL, 1.16 mmol) in DCM (5 mL). Yield (307 mg, 72%).

UPLC/ELSD: RT=4.30 min. MS (ES): m/z (MH$^+$) 460.80 for $C_{27}H_{54}ClNO_2$ $^1$H-NMR (300 MHz, $CDCl_3$) δ: ppm 3.59 (s, 3H); 3.42 (br. m, 2H); 2.70 (br. m, 2H); 2.38 (br. m, 4H); 2.30 (t, 2H); 1.55 (m, 2H); 1.36 (br. m, 4H); 1.27-0.96 (br. m, 32H); 0.81 (t, 3H).

Step 4: Compound 15: Methyl 12-((2-(4-(2-((2-(didodecylamino)ethyl)(dodecyl)amino)ethyl)piperazin-1-yl)ethyl)(dodecyl)amino)dodecanoate In the same manner as Step 6 for Compound 18, methyl 12-((2-(4-(2-((2-(didodecylamino)ethyl)(dodecyl)amino)ethyl)piperazin-1-yl)ethyl)(dodecyl)amino)dodecanoate was synthesized from $N^1,N^1,N^2$-tridodecyl-$N^2$-(2-(piperazin-1-yl)ethyl)ethane-1,2-diamine (150 mg, 0.221 mmol), methyl 12-((2-chloroethyl)(dodecyl)amino)dodecanoate (134 mg, 0.266 mmol) $K_2CO_3$ (61 mg, 0.443 mmol), and KI (4 mg, 0.024 mmol) in THF (5 mL). Yield (32 mg, 15%).

UPLC/ELSD: RT=4.83 min. MS (ES): m/z (MH$^+$) 1102.11 for $C_{71}H_{145}N_5O_2$ $^1$H-NMR (300 MHz, $CDCl_3$) δ: ppm 3.69 (s, 3H); 2.75-2.24 (br. m, 32H); 1.64 (m, 2H); 1.52-1.00 (br. m, 96H); 0.90 (t, 12H).

Q. Compound 16: Dimethyl 12,12'-((2-(4-(2-((2-(didodecylamino)ethyl)(dodecyl)amino)ethyl)piperazin-1-yl)ethyl)azanediyl)didodecanoate

Step 1: Dimethyl 12,12'-((2-hydroxyethyl)azanediyl)didodecanoate

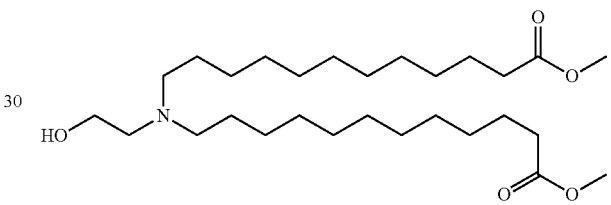

Chemical Formula: $C_{28}H_{55}NO_5$
Molecular Weight: 485.75

In the same manner as Step 1 for Compound 18, dimethyl 12,12'-((2-hydroxyethyl)azanediyl)didodecanoate was synthesized from methyl 12-bromododecanoate (1.5 g, 5.12 mmol), ethanolamine (0.310 mL, 5.12 mmol), $K_2CO_3$ (1.42 g, 10.2 mmol), and KI (85 mg, 0.512 mmol) in MeCN (11 mL). Yield (563 mg, 45%).

UPLC/ELSD: RT=1.81 min. MS (ES): m/z (MH$^+$) 486.63 for $C_{28}H_{55}NO_5$ $^1$H-NMR (300 MHz, $CDCl_3$) δ: ppm 3.69 (s, 6H); 3.59 (br. m, 2H); 2.75-2.40 (br. m, 6H); 2.32 (t, 4H); 1.64 (m, 4H); 1.48 (br. m, 4H); 1.29 (br. m, 28H).

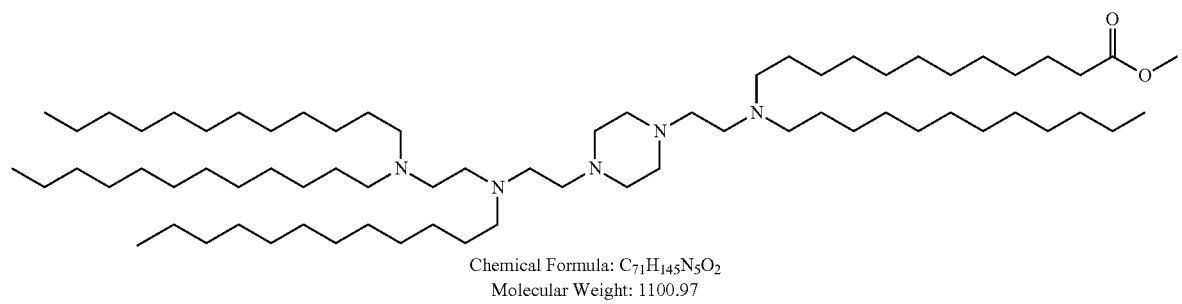 [SMILES: CCCCCCCCCCCCN(CCCCCCCCCCCC)CCN(CCCCCCCCCCCC)CCN1CCN(CCN(CCCCCCCCCCCC)CCCCCCCCCCCC(=O)OC)CC1]

Chemical Formula: $C_{71}H_{145}N_5O_2$
Molecular Weight: 1100.97

Step 2: Dimethyl 12,12'-((2-chloroethyl)azanediyl)didodecanoate

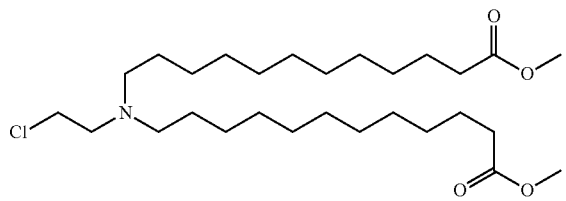

Chemical Formula: $C_{28}H_{54}ClNO_4$
Molecular Weight: 504.19

In the same manner as Step 2 for Compound 18, dimethyl 12,12'-((2-chloroethyl)azanediyl)didodecanoate was synthesized from dimethyl 12,12'-((2-hydroxyethyl)azanediyl)didodecanoate (518 mg, 1.07 mmol), triethylamine (0.193 mL, 1.39 mmol), and methanesulfonyl chloride (0.103 mL, 1.33 mmol) in DCM (5.5 mL). Yield (376 mg, 70%).

UPLC/ELSD: RT=2.17 min. MS (ES): m/z (MH$^+$) 504.75 for $C_{28}H_{54}ClNO_4$

Step 3: Compound 16: Dimethyl 12,12'-((2-(4-(2-((2-(didodecylamino)ethyl)(dodecyl)amino)ethyl)piperazin-1-yl)ethyl)azanediyl)didodecanoate

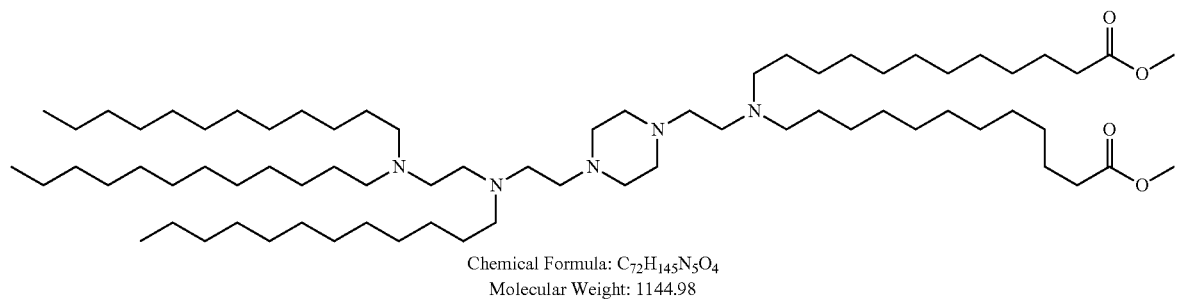 [SMILES: CCCCCCCCCCCCN(CCCCCCCCCCCC)CCN(CCCCCCCCCCCC)CCN1CCN(CCN(CCCCCCCCCCCC(=O)OC)CCCCCCCCCCCC(=O)OC)CC1]

Chemical Formula: $C_{72}H_{145}N_5O_4$
Molecular Weight: 1144.98

In the same manner as Step 6 for Compound 18, dimethyl 12,12'-((2-(4-(2-((2-(didodecylamino)ethyl)(dodecyl)amino)ethyl)piperazin-1-yl)ethyl)azanediyl)didodecanoate was synthesized from $N^1,N^1,N^2$-tridodecyl-$N^2$-(2-(piperazin-1-yl)ethyl)ethane-1,2-diamine (150 mg, 0.221 mmol), dimethyl 12,12'-((2-chloroethyl)azanediyl)didodecanoate (134 mg, 0.266 mmol) $K_2CO_3$ (61 mg, 0.443 mmol), and KI (4 mg, 0.024 mmol) in THF (5 mL). Yield (32 mg, 15%).

UPLC/ELSD: RT=3.46 min. MS (ES): m/z (MH$^+$) 1146.07 for $C_{72}H_{145}N_5O_4$ $^1$H-NMR (300 MHz, CDCl$_3$) δ: ppm 3.69 (s, 6H); 2.75-2.24 (br. m, 34H); 1.64 (m, 4H); 1.52-1.00 (br. m, 92H); 0.90 (t, 9H).

R. Compound 17: $N^1$-(2-(4-(2-(Didodecylamino)ethyl)piperazin-1-yl)ethyl)-$N^1,N^2,N^2$-trihexylethane-1,2-diamine Step 1: 2-(Dihexylamino)ethan-1-ol

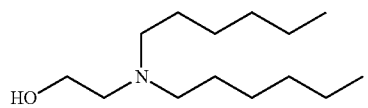

Chemical Formula: $C_{14}H_{31}NO$
Molecular Weight: 229.41

In the same manner as Step 1 for Compound 18, 2-(dihexylamino)ethan-1-ol was synthesized from 1-bromohexane (5 g, 82 mmol), ethanolamine (11.5 mL, 82 mmol), $K_2CO_3$ (22.7 g, 164 mmol), and KI (1.36 g, 8.2 mmol) in MeCN (380 mL). Yield (2.58 g, 14%).

UPLC/ELSD: RT=0.41 min. MS (ES): m/z (MH$^+$) 229.95 for $C_{14}H_{31}NO$ $^1$H-NMR (300 MHz, CDCl$_3$) δ: ppm 3.62 (t, 2H); 2.70 (t, 2H), 2.57 (t, 4H); 1.50 (br. m, 4H); 1.30 (br, 12H); 0.91 (t, 6H).

Step 2: N-(2-Chloroethyl)-N-hexylhexan-1-amine

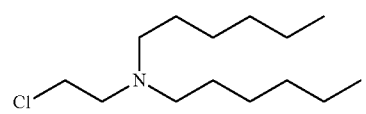

Chemical Formula: $C_{14}H_{30}ClN$
Molecular Weight: 247.85

In the same manner as Step 2 for Compound 18, N-(2-chloroethyl)-N-hexylhexan-1-amine was synthesized from 2-(dihexylamino)ethan-1-ol (2.50 g, 10.9 mmol), triethylamine (2.0 mL, 14.2 mmol), and methanesulfonyl chloride (1.0 mL, 13.6 mmol) in DCM (56 mL). Yield (1.93 g, 71%).

UPLC/ELSD: RT=0.42 min. MS (ES): m/z (MH$^+$) 247.86 for $C_{14}H_{30}ClN$ $^1$H-NMR (300 MHz, CDCl$_3$) δ: ppm 3.50 (t, 2H); 2.77 (t, 2H); 2.51 (t, 4H); 1.42 (br. m, 4H); 1.27 (br, 12H); 0.89 (t, 6H).

Step 3: tert-Butyl 4-(2-(hexyamino)ethyl)piperazine-1-carboxylate

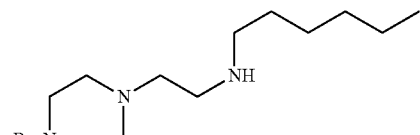

Chemical Formula: $C_{17}H_{35}N_3O_2$
Molecular Weight: 313.49

In the same manner as Step 3 for Compound 18, tert-butyl 4-(2-(hexylamino)ethyl)piperazine-1-carboxylate was synthesized from 1-bromohexane (1.44 g, 8.72 mmol), 4-(2- aminoethyl)-1-boc-piperazine (2.0 g, 8.72 mmol), K$_2$CO$_3$ (2.4 g, 17.4 mmol), and KI (145 mg, 0.872 mmol). Yield (446 mg, 16%).

$^1$H-NMR (300 MHz, CDCl$_3$) δ: ppm 3.44 (br. m, 4H); 2.75 (br. m, 2H); 2.65 (br. m, 2H); 2.54 (br. m, 2H); 2.42 (br. m, 4H); 1.60-1.43 (br. m, 11H); 1.40-1.05 (br. m, 6H); 0.91 (br. m, 3H).

Step 4: tert-Butyl 4-(2-((2-(dihexylamino)ethyl)(hexyl)amino)ethyl)piperazine-1-carboxylate

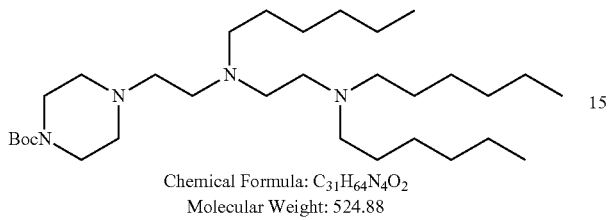

Chemical Formula: C$_{31}$H$_{64}$N$_4$O$_2$
Molecular Weight: 524.88

In the same manner as Step 4 for Compound 18, tert-butyl 4-(2-((2-(dihexylamino)ethyl)(hexyl)amino)ethyl)piperazine-1-carboxylate was synthesized from tert-butyl 4-(2-(hexylamino)ethyl)piperazine-1-carboxylate (250 mg, 0.797 mmol), N-(2-chloroethyl)-N-hexylhexan-1-amine (217 mg, 0.877 mmol), K$_2$CO$_3$ (220 mg, 1.59 mmol), and KI (13 mg, 0.0797 mmol) in THF (5 mL). Yield 308 mg, 74%).

UPLC/ELSD: RT=1.40 min. MS (ES): m/z (MH$^+$) 525.83 for C$_{31}$H$_{64}$N$_4$O$_2$ $^1$H-NMR (300 MHz, CDCl$_3$) δ: ppm 3.45 (br. m, 4H); 3.15-2.15 (br. m, 18H); 1.85-1.00 (br. m, 33H); 0.91 (9H).

Step 5: N$^1$,N$^1$,N$^2$-Trihexyl-N$^2$-(2-(piperazin-1-yl)ethyl)ethane-1,2-diamine

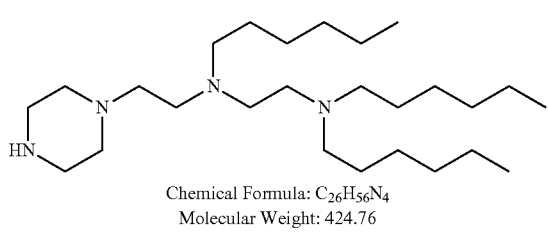 [SMILES: CCCCCCN(CCCCCC)CCN(CCCCCC)CCN1CCNCC1]

Chemical Formula: C$_{26}$H$_{56}$N$_4$
Molecular Weight: 424.76

In the same manner as Step 5 for Compound 18, N$^1$N1, N$^2$-trihexyl-N$^2$-(2-(piperazin-1-yl)ethyl)ethane-1,2-diamine was synthesized from tert-butyl 4-(2-((2-(dihexylamino)ethyl)(hexyl)amino)ethyl)piperazine-1-carboxylate (308 mg, 0.587 mmol), and TFA (2.25 ml, 29.3 mmol) in DCM (2.5 mL). Yield (220 mg, 88%).

$^1$H-NMR (300 MHz, CDCl$_3$) δ: ppm 2.92 (br. m, 4H); 2.70-2.20 (br. m, 18H), 1.54-1.22 (br. m, 24H); 0.91 (br. m, 9H).

Step 6: Compound 17: N$^1$-(2-(4-(2-(Didodecylamino)ethyl)piperazin-1-yl)ethyl)-N$^1$,N$^2$,N$^2$-trihexylethane-1,2-diamine

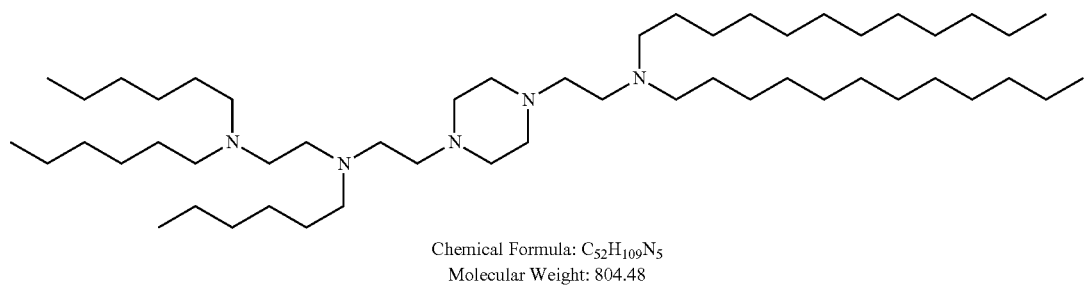 [SMILES: CCCCCCCCCCCCN(CCCCCCCCCCCC)CCN1CCN(CCN(CCCCCC)CCN(CCCCCC)CCCCCC)CC1]

Chemical Formula: C$_{52}$H$_{109}$N$_5$
Molecular Weight: 804.48

In the same manner as Step 6 for Compound 18, N$^1$-(2-(4-(2-(didodecylamino)ethyl)piperazin-1-yl)ethyl)-N$^1$,N$^2$, N$^2$-trihexylethane-1,2-diamine was synthesized from N$^1$,N$^1$, N$^2$-trihexyl-N$^2$-(2-(piperazin-1-yl)ethyl)ethane-1,2-diamine (110 mg, 0.259 mmol), N-(2-chloroethyl)-N-dodecyldodecan-1-amine (162 mg, 0.388 mmol), K$_2$CO$_3$ (72 mg, 0.518 mmol), and KI (5 mg, 0.0259 mmol) in THF (6 mL). Yield (81 mg, 39%).

UPLC/ELSD: RT=2.79 min. MS (ES): m/z (MH$^+$) 806.30 for C$_{52}$H$_{109}$N$_5$ $^1$H-NMR (300 MHz, CDCl$_3$) δ: ppm 3.05-2.10 (br. m, 30H); 1.80-1.05 (br. m, 64H); 0.91 (br. m, 15H).

S: Compound 18: N$^1$-(2-(4-(2-(Dinonylamino)ethyl)piperazin-1-yl)ethyl)-N$^1$,N$^2$,N$^2$-trinonylethane-1,2-diamine Step 1: 2-(Dinonylamino)ethan-1-ol

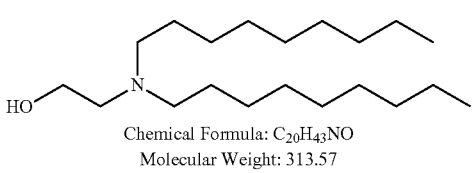 [SMILES: CCCCCCCCCN(CCO)CCCCCCCCC]

Chemical Formula: C$_{20}$H$_{43}$NO
Molecular Weight: 313.57

To a solution of 1-bromononane (8.31 g, 40.1 mmol) in MeCN (84 mL) was added ethanolamine (1.10 mL, 18.2 mmol), K$_2$CO$_3$ (11.1 g, 80.1 mmol), and KI (302 mg, 1.82 mmol). The reaction was allowed to stir at 82° C. for 48 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-20% MeOH/DCM) provided 2-(dinonylamino)ethan-1-ol (4.06 g, 71%).

$^1$H-NMR (300 MHz, CDCl$_3$) δ: ppm 3.57 (t, 2H); 2.63 (t, 2H); 2.49 (br. m, 4H); 1.48 (br. m, 4H); 1.29 (br. m, 24H); 0.91 (t, 6H).

Step 2: N-(2-Chloroethyl)-N-nonylnonan-1-amine

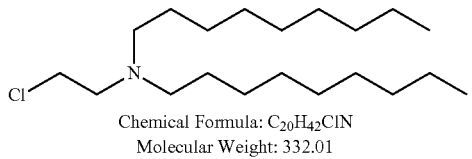 [SMILES: CCCCCCCCCN(CCCl)CCCCCCCCC]

Chemical Formula: C$_{20}$H$_{42}$ClN
Molecular Weight: 332.01

To a 0° C. solution of 2-(dinonylamino)ethan-1-ol (4.06 g, 12.9 mmol) and triethylamine (2.35 ml, 16.8 mmol) in DCM (65 mL) was added dropwise a solution of methanesulfonyl chloride (1.25 mL, 16.18 mmol) in DCM (5 mL). The reaction was allowed to return to room temperature and stir for 16 hours. The mixture was quenched by the addition of water and extracted with DCM. The organic layer was washed with saturated NaHCO$_3$, brine, dried over anhydrous Na$_2$SO$_4$, filtered, and concentrated in vacuo. Purification by ISCO silica flash chromatography (0-10% EtOAc/hexanes) provided N-(2-chloroethyl)-N-nonylnonan-1-amine (2.58 g, 60%).

$^1$H-NMR (300 MHz, CDCl$_3$) δ: ppm 3.51 (t, 2H); 2.78 (t, 2H); 2.47 (br. m, 4H); 1.44 (br. m, 4H); 1.28 (br. m, 24H); 0.90 (t, 6H).

Step 3: tert-Butyl 4-(2-(nonylamino)ethyl)piperazine-1-carboxylate

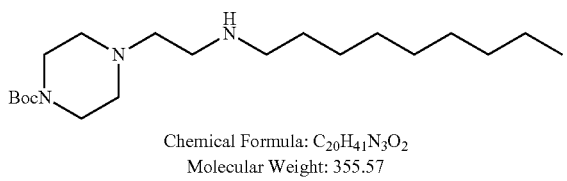 [SMILES: CCCCCCCCCNCCN1CCN(C(=O)OC(C)(C)C)CC1]

Chemical Formula: C$_{20}$H$_{41}$N$_3$O$_2$
Molecular Weight: 355.57

To a solution of 1-bromononane (1.81 g, 8.72 mmol) in MeCN (44 mL) was added 4-(2-aminoethyl)-1-boc-piperazine (2.0 g, 8.72 mmol), K$_2$CO$_3$ (2.4 g, 17.4 mmol), and KI (145 mg, 0.872 mmol). The reaction was allowed to stir at 65° C. for 16 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-20% MeOH/DCM) provided tert-butyl 4-(2-(nonylamino)ethyl)piperazine-1-carboxylate (775 mg, 25%).

UPLC/ELSD: RT=0.47 min. MS (ES): m/z (MH$^+$) 356.41 for C$_{20}$H$_{41}$N$_3$O$_2$ $^1$H-NMR (300 MHz, CDCl$_3$) δ: ppm 3.44 (br. m, 4H); 2.74 (t, 2H); 2.63 (t, 2H); 2.53 (t, 2H); 2.41 (br. m, 4H); 1.48 (br. m, 9H); 1.30 (br. m, 14H); 0.90 (t, 3H).

Step 4: tert-Butyl 4-(2-((2-(dinonylamino)ethyl)(nonyl)amino)ethyl)piperazine-1-carboxylate

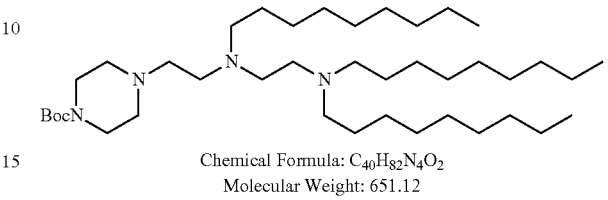

Chemical Formula: C$_{40}$H$_{82}$N$_4$O$_2$
Molecular Weight: 651.12

To a solution of tert-butyl 4-(2-(nonylamino)ethyl)piperazine-1-carboxylate (500 mg, 1.41 mmol) in THF (9 mL) was added N-(2-chloroethyl)-N-nonylnonan-1-amine (514 mg, 1.55 mmol), K$_2$CO$_3$ (390 mg, 2.82 mmol), and KI (23 mg, 0.141 mmol). The reaction was allowed to stir at 65° C. for 72 hours. The reaction mixture was cooled to room temperature, diluted with water, and extracted with EtOAc. The combined extracts were washed with brine, dried over anhydrous Na$_2$SO$_4$, filtered, and concentrated in vacuo. Purification by ISCO silica flash chromatography (0-15% MeOH/DCM) provided tert-butyl 4-(2-((2-(dinonylamino)ethyl)(nonyl)amino)ethyl)piperazine-1-carboxylate (763 mg, 83%).

UPLC/ELSD: RT=2.61 min. MS (ES): m/z (MH$^+$) 651.91 for C$_{40}$H$_{82}$N$_4$O$_2$ $^1$H-NMR (300 MHz, CDCl$_3$) δ: ppm 3.45 (br. m, 4H); 2.75-2.30 (br. m, 18H); 1.55-1.20 (br. m, 51H); 0.91 (br. m, 9H).

Step 5: N$^1$,N$^1$,N$^2$-Trinonyl-N$^2$-(2-(piperazin-1-yl)ethyl)ethane-1,2-diamine

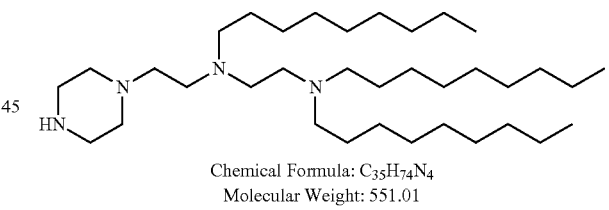

Chemical Formula: C$_{35}$H$_{74}$N$_4$
Molecular Weight: 551.01

To a 0° C. solution of tert-Butyl 4-(2-((2-(dinonylamino)ethyl)(nonyl)amino)ethyl)piperazine-1-carboxylate (763 mg, 1.17 mmol) in DCM (4.5 mL) was added dropwise TFA (4.5 mL, 58.5 mmol). The reaction was allowed to return to room temperature and stir for 16 hours. The reaction mixture was concentrated in vacuo and the crude material was dissolved in CHCl$_3$. The solution was washed with 5% Na$_2$CO$_3$, brine, dried over anhydrous Na$_2$SO$_4$, filtered, and concentrated in vacuo. Purification by ISCO silica flash chromatography (0-100% [DCM, 20% MeOH, 1% NH$_4$OH]/MeOH) provided N$^1$,N$^1$,N$^2$-trinonyl-N$^2$-(2-(piperazin-1-yl)ethyl)ethane-1,2-diamine (218 mg, 34%).

UPLC/ELSD: RT=1.81 min. MS (ES): m/z (MH$^+$) 551.78 for C$_{35}$H$_{74}$N$_4$ $^1$H-NMR (300 MHz, CDCl$_3$) δ: ppm 2.91 (br. m, 4H); 2.70-2.35 (br. m, 18H); 1.46 (br. m, 6H); 1.29 (br. m, 36H); 0.91 (br. m, 9H)

Step 6: Compound 18: $N^1$-(2-(4-(2-(Dinonylamino)ethyl)piperazin-1-yl)ethyl)-$N^1$,$N^2$,$N^2$-trinonylethane-1,2-diamine

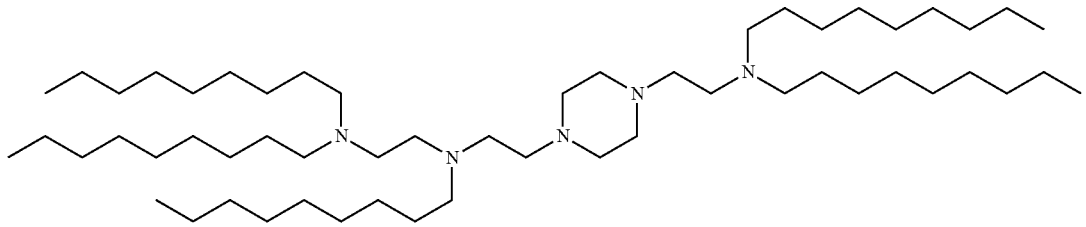

Chemical Formula: $C_{55}H_{115}N_5$
Molecular Weight: 846.56

To a solution of $N^1$,$N^1$,$N^2$-trinonyl-$N^2$-(2-(piperazin-1-yl)ethyl)ethane-1,2-diamine (74 mg, 0.134 mmol) and N-(2-chloroethyl)-N-nonylnonan-1-amine (58 mg, 0.175 mmol) in THF (4 mL) was added $K_2CO_3$ (37 mg, 0.269 mmol), and KI (3 mg, 0.0134 mmol). The reaction allowed to stir at 65° C. for 48 hours. The reaction mixture was cooled to room temperature, diluted with water, and extracted with EtOAc. The combined extracts were washed with brine, dried over anhydrous $Na_2SO_4$, filtered, and concentrated in vacuo. Purification by ISCO C18 flash chromatography (50-100% [MeCN 0.1% TFA]/[$H_2O$ 0.1% TFA]) afforded the desired product as a TFA salt. The salt was dissolved in $CHCl_3$ and the solution was washed with 5% $Na_2CO_3$, brine, dried over anhydrous $Na_2SO_4$, filtered, and concentrated in vacuo to provide $N^1$-(2-(4-(2-(dinonylamino)ethyl)piperazin-1-yl)ethyl)-$N^1$,$N^2$,$N^2$-trinonylethane-1,2-diamine (66 mg, 58%).

UPLC/ELSD: RT=2.91 min. MS (ES): m/z (MH$^+$) 847.30 for $C_{55}H_{115}N_5$ $^1$H-NMR (300 MHz, $CDCl_3$) δ: ppm 3.10-2.25 (br. m, 30H); 1.90-1.35 (br. m, 10H); 1.29 (br. m, 60H); 0.91 (br. m, 15H).

T: Compound 19: $N^1$-(2-(4-(2-(Didodecylamino)ethyl)piperazin-1-yl)ethyl)-$N^1$,$N^2$,$N^2$-trinonylethane-1,2-diamine

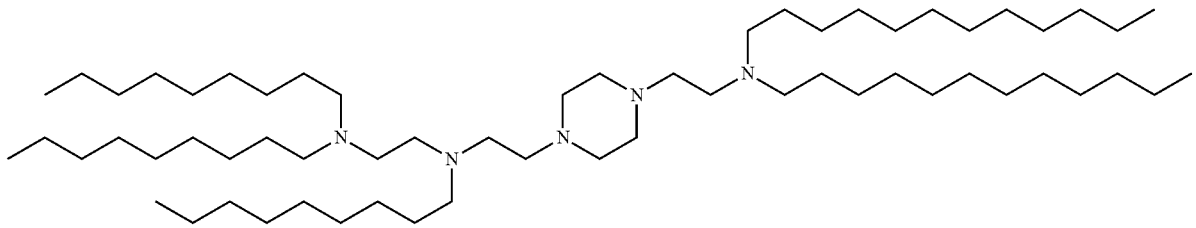

Chemical Formula: $C_{61}H_{127}N_5$
Molecular Weight: 930.72

In the same manner as Step 6 for Compound 18, $N^1$-(2-(4-(2-(didodecylamino)ethyl)piperazin-1-yl)ethyl)-$N^1$,$N^2$,$N^2$-trinonylethane-1,2-diamine was synthesized from $N^1$,$N^1$,$N^2$-trinonyl-$N^2$-(2-(piperazin-1-yl)ethyl)ethane-1,2-diamine (70 mg, 0.127 mmol), N-(2-chloroethyl)-N-dodecyldodecan-1-amine (79 mg, 0.191 mmol), $K_2CO_3$ (35 mg, 0.254 mmol), and KI (2 mg, 0.0127 mmol) in THF (3 mL). Yield (52 mg, 44%).

UPLC/ELSD: RT=3.35 min. MS (ES): m/z (MH$^+$) 931.61 for $C_{61}H_{127}N_5$ $^1$H-NMR (300 MHz, $CDCl_3$) δ: ppm 2.70 (br. m, 30H); 1.56-1.02 (br. m, 82H); 0.90 (t, 15H).

U: Compound 20: $N^1$-(2-(4-(2-(Ditetradecylamino)ethyl)piperazin-1-yl)ethyl)-$N^1,N^2,N^2$-trinonylethane-1,2-diamine

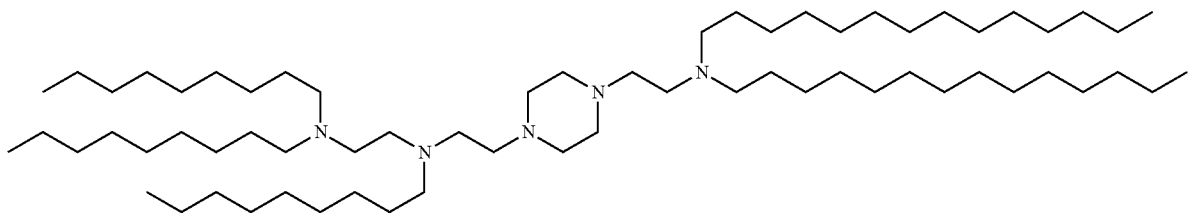

Chemical Formula: $C_{65}H_{135}N_5$
Molecular Weight: 986.83

In the same manner as Step 6 for Compound 18, $N^1$-(2-(4-(2-(ditetradecylamino)ethyl)piperazin-1-yl)ethyl)-$N^1,N^2,N^2$-trinonylethane-1,2-diamine was synthesized from $N^1,N^1,N^2$-trinonyl-$N^2$-(2-(piperazin-1-yl)ethyl)ethane-1,2-diamine (74 mg, 0.134 mmol), N-(2-chloroethyl)-N-tetradecyltetradecan-11-amine (95 mg, 0.201 mmol), $K_2CO_3$ (37 mg, 0.269 mmol), and KI (3 mg, 0.0134 mmol) in THF (2 mL). Yield (50 mg, 38%)

UPLC/ELSD: RT=3.55 min. MS (ES): m/z ($MH^+$) 987.87 for $C_{65}H_{135}N_5$ $^1$H-NMR (300 MHz, $CDCl_3$) δ: ppm 3.20-2.25 (br. m, 30H); 1.85-1.00 (br. m, 90H); 0.91 (t, 15H).

V: Compound 21: $N^1$-(2-(4-(2-(Dihexylamino)ethyl)piperazin-1-yl)ethyl)-$N^1,N^2,N^2$-tridodecylethane-1,2-diamine

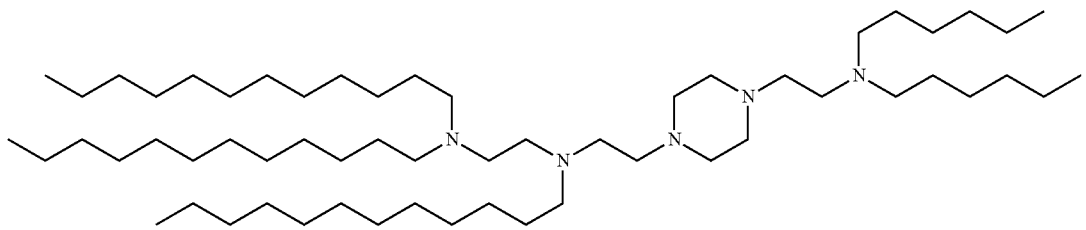

Chemical Formula: $C_{58}H_{121}N_5$
Molecular Weight: 888.64

In the same manner Step 6 for Compound 18, $N^1$-(2-(4-(2-(dihexylamino)ethyl)piperazin-1-yl)ethyl)-$N^1,N^2,N^2$-tridodecylethane-1,2-diamine was synthesized from $N^1,N^1,N^2$-tridodecyl-$N^2$-(2-(piperazin-1-yl)ethyl)ethane-1,2-diamine (67 mg, 0.099 mmol), N-(2-chloroethyl)-N-hexylhexan-1-amine (32 mg, 0.129 mmol), $K_2CO_3$ (28 mg, 0.198 mmol), and KI (2 mg, 0.0099 mmol) in THF (2 mL). Yield (30 mg, 34%).

UPLC/ELSD: RT=3.24 min. MS (ES): m/z ($MH^+$) 890.58 for $C_{58}H_{121}N_5$ $^1$H-NMR (300 MHz, $CDCl_3$) δ: ppm 3.15-2.20 (br. m, 30H); 1.85-1.00 (br. m, 76H); 0.91 (br. m, 15H).

W: Compound 22: $N^1$-(2-(4-(2-(Dioctylamino)ethyl)piperazin-1-yl)ethyl)-$N^1,N^2,N^2$-tridodecylethane-1,2-diamine Step 1: 2-(Dioctylamino)ethan-1-ol

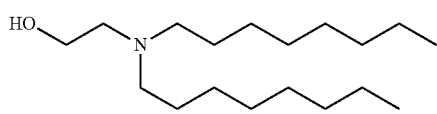

Chemical Formula: $C_{18}H_{39}NO$
Molecular Weight: 285.52

In the same manner as Step 1 for Compound 18, compound was synthesized from ethanolamine (5 g, 82 mmol), 1-bromooctane (14 mL, 82 mmol), and K$_2$CO$_3$ (11 g, 82 mmol) in 200 mL MeCN. Yield (3.13 g, 11 mmol, 13%).

UPLC/ELSD: RT=1.78 min. MS (ES): m/z (MH$^+$) 286.22 for C$_{18}$H$_{39}$NO $^1$H-NMR (300 MHz, CDCl$_3$) δ: ppm 3.54 (m, 2H); 2.60-2.47 (m, 6H); 1.44 (m, 4H); 1.26 (m, 21H); 0.86 (t, 6H).

Step 2: N-(2-Chloroethyl)-N-octyloctan-1-amine

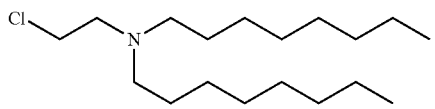

Chemical Formula: C$_{18}$H$_{38}$ClN
Molecular Weight: 303.96

In the same manner as Step 2 for Compound 18, N-(2-chloroethyl)-N-octyloctan-1-amine was synthesized from 2-(dioctylamino)ethan-1-ol (3.13 g, 11 mmol), methanesulfonyl chloride (0.85 mL, 11 mmol) and Et$_3$N (1.5 mL, 11 mmol) in 30 mL DCM. Yield (1.55 g, 5.1 mmol, 46%).

UPLC/ELSD: RT=3.86 min. MS (ES): m/z (MH$^+$) 304.43 for C$_{18}$H$_{38}$ClN $^1$H-NMR (300 MHz, CDCl$_3$) δ: ppm 3.48 (2, 2H); 2.75 (t, 2H); 2.43 (t, 4H); 1.40-1.25 (m, 24H); 0.86 (t, 6H).

Step 3: Compound 22: N$^1$-(2-(4-(2-(Dioctylamino)ethyl)piperazin-1-yl)ethyl)-N$^1$,N$^2$,N$^2$-tridodecylethane-1,2-diamine

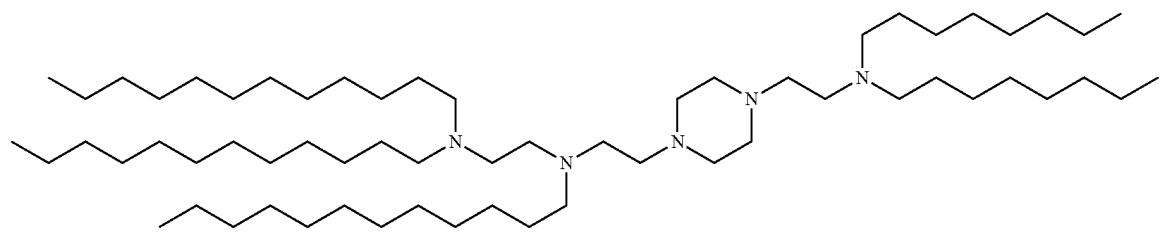

Chemical Formula: C$_{62}$H$_{129}$N$_5$
Molecular Weight: 944.75

In the same manner as Step 6 for Compound 18, N$^1$-(2-(4-(2-(dioctylamino)ethyl)piperazin-1-yl)ethyl)-N$^1$,N$^2$,N$^2$-tridodecylethane-1,2-diamine was synthesized from N$^1$,N$^1$,N$^2$-tridodecyl-N$^2$-(2-(piperazin-1-yl)ethyl)ethane-1,2-diamine (150 mg, 0.221 mmol), N-(2-chloroethyl)-N-octyloctan-1-amine 54 (81 mg, 0.266 mmol), K$_2$CO$_3$ (61 mg, 0.443 mmol), and KI (4 mg, 0.024 mmol) in THF (5 mL). Yield (200 mg, 96%).

UPLC/ELSD: RT=3.41 min. MS (ES): m/z (MH) 945.96 for C$_{62}$H$_{129}$N$_5$ $^1$H-NMR (300 MHz, CDCl$_3$) δ: ppm 2.76-2.10 (br. m, 30H); 1.56-1.00 (br. m, 84H); 0.90 (t, 15H).

X: Compound 23: N$^1$-(2-(4-(2-(Dinonylamino)ethyl)piperazin-1-yl)ethyl)-N$^1$,N$^2$,N$^2$-tridodecylethane-1,2-diamine

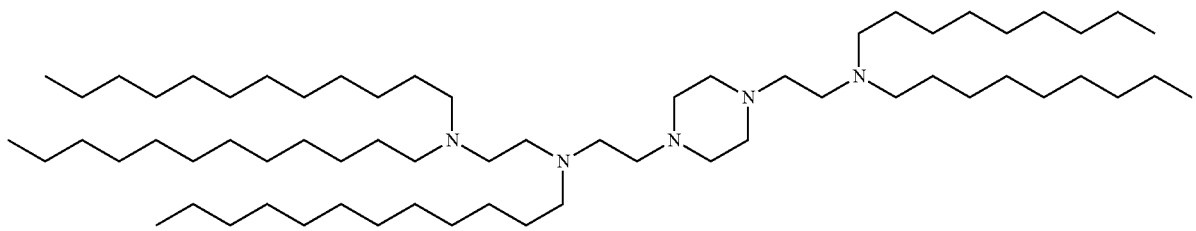

Chemical Formula: C$_{64}$H$_{133}$N$_5$
Molecular Weight: 972.80

In the same manner as Step 6 for Compound 18, $N^1$-(2-(4-(2-(dinonylamino)ethyl)piperazin-1-yl)ethyl)-$N^1,N^2,N^2$-tridodecylethane-1,2-diamine was synthesized from $N^1,N^1,N^2$-tridodecyl-$N^2$-(2-(piperazin-1-yl)ethyl)ethane-1,2-diamine (595 mg, 0.879 mg), N-(2-chloroethyl)-N-nonylnonan-1-amine (350 mg, 1.05 mmol), $K_2CO_3$ (243 mg, 1.76 mmol), and KI (15 mg, 0.0879 mmol) in THF (13 mL). Yield (534 mg, 62%).

UPLC/ELSD: RT=3.50 min. MS (ES): m/z (MH$^+$) 973.60 for $C_{64}H_{133}N_5$.

$^1$H-NMR (300 MHz, CDCl$_3$) δ: ppm 2.70-2.30 (br. m, 30H); 1.56-1.37 (br. m, 10H); 1.28 (br. m, 78H); 0.90 (t, 15H).

Y: Compound 24: (Z)—$N^1$-(2-(4-(2-(Dodec-6-en-1-yl(dodecyl)amino)ethyl)piperazin-1-yl)ethyl)-$N^1,N^2,N^2$-tridodecylethane-1,2-diamine Step 1: (6-Hydroxyhexyl)triphenylphosphonium Bromide

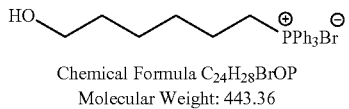

Chemical Formula $C_{24}H_{28}BrOP$
Molecular Weight: 443.36

6-Bromo-1-hexanol (4.89 g, 27 mmol) and triphenylphosphine (7.87 g, 30 mmol) and 50 mL MeCN were combined in a round bottomed flask. The flask was fitted with a condenser and placed in a heating mantel and the reaction was allowed to stir at 82° C. for 48 h. After this time the reaction was allowed to cool to rt and the solution was cannulated into 200 mL Et$_2$O, producing a white precipitate. The solids were allowed to settle and the solvent was decanted off. 20 mL DCM was added to dissolve the solids and then 100 mL Et$_2$O was slowly added to afford a white precipitate. The solvent was then removed in vacuo to afford clean (6-hydroxyhexyl)triphenylphosphonium bromide (9.4 g, 21.2 mmol, for 78% yield).

$^1$H-NMR (300 MHz, CDCl$_3$) δ: ppm 7.80 (m, 15H); 3.80 (m, 2H); 3.65 (m, 2H); 2.23 (m, 2H); 1.68 (m, 4H); 1.52 (m, 4H).

Step 2: (Z)-Dodec-6-en-1-ol

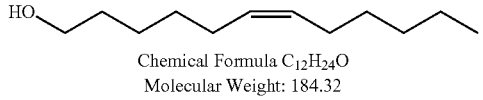

Chemical Formula $C_{12}H_{24}O$
Molecular Weight: 184.32

A solution of (6-hydroxyhexyl)triphenylphosphonium bromide (3.0 g, 6.77 mmol) in 25 mL THF was allowed to cool in a −78° C. dry ice/acetone bath. Once cool n-BuLi (2.5 M in hexanes) (5.7 mL, 14.2 mmol) was added dropwise. After 1 h, an additional 10 mL THF and n-BuLi (1.35 mL) were added and stirring was continued at the same temperature for 1 h. After this time 1-hexanal (1.6 mL, 13.5 mmol) was added and the reaction was allowed to warm to rt and stir for 3 h. After this time the reaction was quenched by addition of excess saturated NH$_4$Cl. The solution was extracted three times with EtOAc. The pooled organics were washed with brine, dried over MgSO$_4$, filtered and concentrated. The crude material was purified by silica gel chromatography (0-50% EtOAc in hexanes) to afford the desired product as a clear oil (0.76 g, 4.1 mmol, 61%).

$^1$H-NMR (300 MHz, CDCl$_3$) δ: ppm 5.34 (m, 2H); 3.62 (t, 2H); 2.01 (m, 4H); 1.56 (m, 2H); 1.35-1.27 (m, 11H); 0.87 (t, 3H).

Step 3: (Z)-Dodec-6-en-1-yl Methanesulfonate

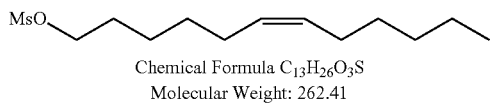 [SMILES: CCCCC/C=C\CCCCCOS(C)(=O)=O]

Chemical Formula $C_{13}H_{26}O_3S$
Molecular Weight: 262.41

To a 0° C. solution of (Z)-dodec-6-en-1-ol (1.81 g, 9.3 mmol) in 20 mL DCM, was added Et$_3$N (1.7 mL, 12.1 mmol) and methanesulfonyl chloride (0.80 mL, 10.2 mmol). The reaction was allowed to slowly warm to rt and stir overnight. The reaction was quenched by the addition of water and the mixture was extracted two times with DCM. The organics were pooled, washed with brine, dried over MgSO$_4$, filtered and concentrated. The crude material was purified by silica gel chromatography (0-30% EtOAc in hexanes) to afford clean desired product (2.2 g, 8.4 mmol, 90%).

$^1$H-NMR (300 MHz, CDCl$_3$) δ: ppm 5.34 (m, 2H); 4.20 (t, 2H); 2.98 (s, 3H); 2.01 (m, 4H); 1.74 (m, 2H); 1.38-1.27 (m, 10H); 0.87 (t, 3H).

Step 4: (Z)-1-Bromododec-6-ene

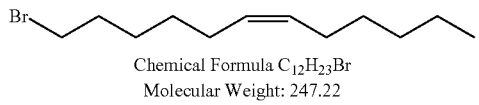

Chemical Formula $C_{12}H_{23}Br$
Molecular Weight: 247.22

In a round bottomed flask, under N$_2$, (Z)-dodec-6-en-1-yl methanesulfonate (2.2 g, 8.3 mmol) was dissolved in 40 mL Et$_2$O. MgBr$_2$.Et$_2$O (6.5 g, 25 mmol) was added and the reaction was allowed to stir for 48 h. After this time the reaction was quenched by the addition of ice. The mixture was then extracted with Et$_2$O three times. The pooled organics were washed with brine, dried over MgSO$_4$, filtered and concentrated. The crude material was purified by silica gel chromatography (0-30% EtOAc in hexanes) to afford the desired product (1.8 g, 7.28 mmol, 88%).

$^1$H-NMR (300 MHz, CDCl$_3$) δ: ppm 5.34 (m, 2H); 3.39 (t, 2H); 2.01-1.84 (m, 6H); 1.28 (m, 10H); 0.87 (t, 3H).

Step 5: (Z)-2-(Dodec-6-en-1-yl(dodecyl)amino)ethan-1-ol

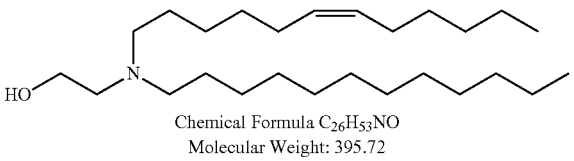 [SMILES: CCCCC/C=C\CCCCCN(CCO)CCCCCCCCCCCC]

Chemical Formula $C_{26}H_{53}NO$
Molecular Weight: 395.72

In the same manner as Step 1 for Compound 18, (Z)-2-(Dodec-6-en-1-yl(dodecyl)amino)ethan-1-ol was synthesized from (Z)-1-bromododec-6-ene (0.25 g, 1.0 mmol), 2-(dodecylamino)ethan-1-ol (0.23 g, 1.0 mmol), $K_2CO_3$ (0.14 g, 1.0 mmol) and KI (2 mg, 0.01 mmol) in 5 mL MeCN.

$^1$H-NMR (300 MHz, $CDCl_3$) δ: ppm 5.34 (m, 2H); 3.65 (br. m., 2H); 2.64 (br. m, 6H); 2.00 (m, 4H); 1.55 (m, 6H); 1.24 (m, 26H); 0.86 (t, 6H).

Step 6: (Z)—N-(2-Chloroethyl)-N-dodecyldodec-6-en-1-amine

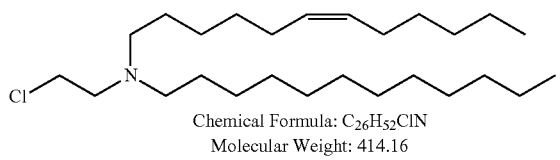 [SMILES: CCCCC/C=C\CCCCCN(CCCl)CCCCCCCCCCCC]

Chemical Formula: $C_{26}H_{52}ClN$
Molecular Weight: 414.16

In the same manner as Step 2 for Compound 18, (Z)—N-(2-chloroethyl)-N-dodecyldodec-6-en-1-amine was synthesized from (Z)-2-(dodec-6-en-1-yl(dodecyl)amino)ethan-1-ol (35 mg, 0.088 mmol), methanesulfonyl chloride (0.008 mL, 0.097 mmol) and triethylamine (0.018 mL, 0.13 mmol) in 0.5 mL DCM. Yield (17.3 mg, 47%).

$^1$H-NMR (300 MHz, $CDCl_3$) δ: ppm 5.34 (m, 2H); 3.47 (t, 2H); 2.74 (t, 2H); 2.43 (t, 4H); 2.0 (m, 4H); 1.24 (m, 32H); 0.86 (t, 6H).

Step 7: Compound 24: (Z)—$N^1$-(2-(4-(2-(Dodec-6-en-1-yl(dodecyl)amino)ethyl)piperazin-1-yl)ethyl)-$N^1,N^2,N^2$-tridodecylethane-1,2-diamine

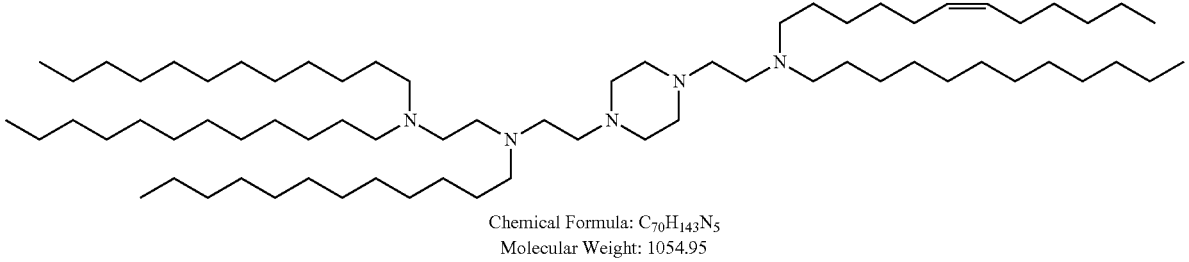 [SMILES: CCCCC/C=C\CCCCCN(CCCCCCCCCCCC)CCN1CCN(CCN(CCCCCCCCCCCC)CCN(CCCCCCCCCCCC)CCCCCCCCCCCC)CC1]

Chemical Formula: $C_{70}H_{143}N_5$
Molecular Weight: 1054.95

In the same manner as Step 6 for Compound 18, (Z)—$N^1$-(2-(4-(2-(dodec-6-en-1-yl(dodecyl)amino)ethyl)piperazin-1-yl)ethyl)-$N^1,N^2,N^2$-tridodecylethane-1,2-diamine was synthesized from $N^1,N^1,N^2$-tridodecyl-$N^2$-(2-(piperazin-1-yl)ethyl)ethane-1,2-diamine (27 mg, 0.040 mmol) and (Z)—N-(2-chloroethyl)-N-dodecyldodec-6-en-1-amine (17.3 mg, 0.042 mmol), $K_2CO_3$ (6 mg, 0.040 mmol) in 0.5 mL DCM. Yield (24 mg, 0.023 mmol, 57%).

UPLC: RT=3.78 min. MS (ES): m/z (MH$^+$) 1056.376 for $C_{70}H_{143}N_5$ $^1$H NMR (400 MHz, $CDCl_3$) δ: ppm 5.36 (m, 2H); 2.53-2.35 (m, 30H); 2.00 (m, 4H); 1.39-1.24 (m, 92H); 0.86 (m, 15H).

Z: Compound 25: $N^1$-(2-(4-(2-(Di((Z)-dodec-6-en-1-yl)amino)ethyl)piperazin-1-yl)ethyl)-$N^1,N^2,N^2$-tridodecylethane-1,2-diamine Step 1: 2-(Di((Z)-dodec-6-en-1-yl)amino)ethan-1-ol

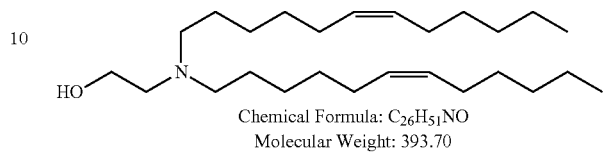

Chemical Formula: $C_{26}H_{51}NO$
Molecular Weight: 393.70

In the same manner as Step 1 for Compound 18, 2-(di((Z)-dodec-6-en-1-yl)amino)ethan-1-ol was synthesized from ethanolamine (60 mg, 1.0 mmol), (Z)-1-bromododec-6-ene (0.51 g, 2.1 mmol) and $K_2CO_3$ (0.14 g, 1.0 mmol) in 5 mL DCM. Yield (0.22 g, 0.56 mmol, 56%).

$^1$H NMR (400 MHz, $CDCl_3$) δ: ppm 5.34 (m, 4H); 3.59 (m, 2H); 2.65-2.53 (m, 6H); 2.00 (m, 9H); 1.49 (m, 4H); 1.23 (m, 20H); 0.86 (t, 6H).

Step 2: (Z)—N-(2-Chloroethyl)-N—((Z)-dodec-6-en-1-yl)dodec-6-en-1-amine

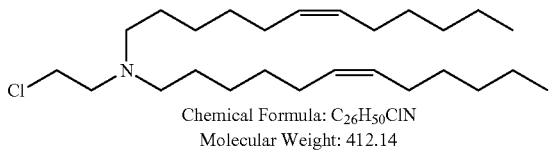 [SMILES: CCCCC/C=C\CCCCCN(CCCl)CCCCC/C=C\CCCCC]

Chemical Formula: $C_{26}H_{50}ClN$
Molecular Weight: 412.14

In the same manner as Step 2 for Compound 18, (Z)—N-(2-chloroethyl)-N—((Z)-dodec-6-en-1-yl)dodec-6-en-1-amine was synthesized from 2-(di((Z)-dodec-6-en-1-yl)amino)ethan-1-ol (0.22 g, 0.56 mmol), methanesulfonyl chloride (0.047 mL, 0.61 mmol) and triethylamine (0.12 mL, 0.84 mmol) in 3 mL DCM. (Yield (150 mg, 0.36 mmol, 65%).

$^1$H NMR (400 MHz, $CDCl_3$) δ: ppm 5.34 (m, 4H); 3.47 (t, 2H); 2.74 (t, 2H); 2.43 (t, 4H); 2.00 (m, 8H); 1.41-1.27 (m, 24H); 0.87 (m, 6H).

Step 3: Compound 25: N¹-(2-(4-(2-(Di((Z)-dodec-6-en-1-yl)amino)ethyl)piperazin-1-yl)ethyl)-N¹,N²,N²-tridodecylethane-1,2-diamine

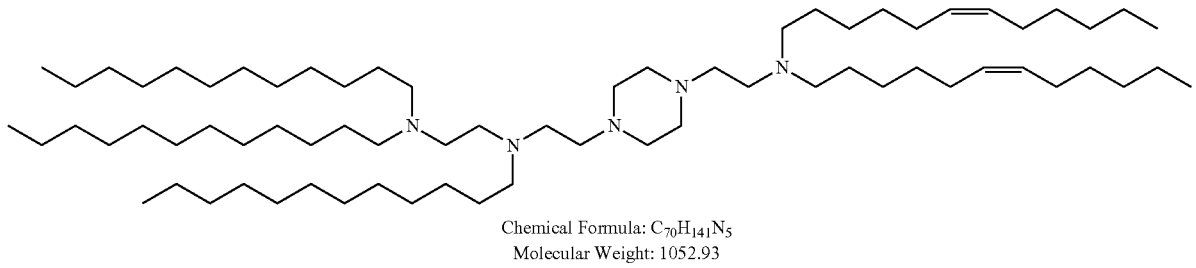 [SMILES: CCCCC/C=C\CCCCCN(CCCCC/C=C\CCCCC)CCN1CCN(CCN(CCCCCCCCCCCC)CCN(CCCCCCCCCCCC)CCCCCCCCCCCC)CC1]

Chemical Formula: $C_{70}H_{141}N_5$
Molecular Weight: 1052.93

In the same manner as Step 6 for Compound 18, N¹-(2-(4-(2-(di((Z)-dodec-6-en-1-yl)amino)ethyl)piperazin-1-yl)ethyl)-N¹,N²,N²-tridodecylethane-1,2-diamine was synthesized from (Z)—N-(2-chloroethyl)-N—((Z)-dodec-6-en-1-yl)dodec-6-en-1-amine (56 mg, 0.14 mmol), N¹,N¹,N²-tridodecyl-N²-(2-(piperazin-1-yl)ethyl)ethane-1,2-diamine (84 mg, 0.12 mmol) and K₂CO₃ (17 mg, 0.12 mmol) in 1 mL MeCN. Yield (41.9 mg, 0.040 mmol, 33%).

UPLC: RT=3.74 min. MS (ES): m/z (MH⁺) 1053.564 for $C_{70}H_{141}N_5$
¹H NMR (400 MHz, CDCl₃) δ: ppm 5.33 (m, 4H); 2.55-2.35 (br. m, 30H); 1.98 (m, 8H); 1.32-1.24 (m, 84H); 0.86 (m, 15H).

AA: Compound 26: N¹-(2-(4-(2-(Ditetradecylamino)ethyl)piperazin-1-yl)ethyl)-N¹,N²,N²-tridodecylethane-1,2-diamine

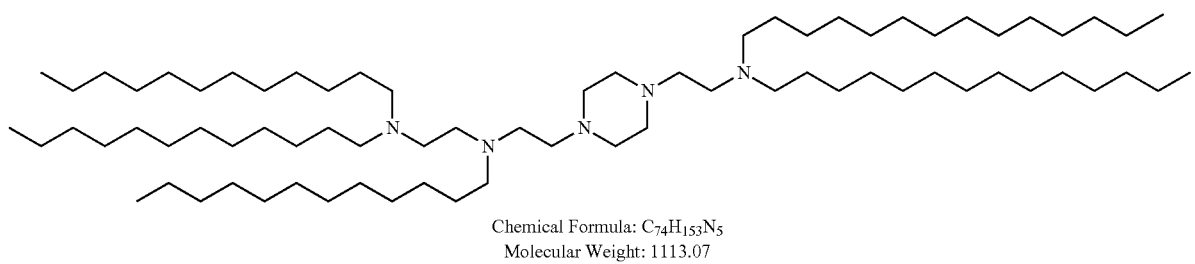 [SMILES: CCCCCCCCCCCCCCN(CCCCCCCCCCCCCC)CCN1CCN(CCN(CCCCCCCCCCCC)CCN(CCCCCCCCCCCC)CCCCCCCCCCCC)CC1]

Chemical Formula: $C_{74}H_{153}N_5$
Molecular Weight: 1113.07

In the same manner as Step 6 for Compound 18, N¹-(2-(4-(2-(ditetradecylamino)ethyl)piperazin-1-yl)ethyl)-N¹,N²,N²-tridodecylethane-1,2-diamine was synthesized from N¹,N¹,N²-tridodecyl-N²-(2-(piperazin-1-yl)ethyl)ethane-1,2-diamine (75 mg, 0.111 mmol), N-(2-chloroethyl)-N-tetradecyltetradecan-1l-amine (58 mg, 0.122 mmol), K₂CO₃ (31 mg, 0.221 mmol), and KI (3 mg, 0.0181 mmol) in THF (4 mL). Yield (17 mg, 7%).

UPLC/ELSD: RT=3.88 min. MS (ES): m/z (MH⁺) 1113.59 for $C_{74}H_{153}N_5$
¹H-NMR (300 MHz, CDCl₃) δ: ppm 3.15-2.00 (br. m, 30H); 1.75-0.90 (br. m, 108H); 0.81 (t, 15H).

AB: Compound 27: N¹,N¹,N²-Tridodecyl-N²-(2-(4-(2-(dodecyl((9Z,12Z)-octadeca-9,12-dien-1-yl)amino)ethyl)piperazin-1-yl)ethyl)ethane-1,2-diamine Step 1:
(6Z,9Z)-18-(Methylsulfonyl)octadeca-6,9-diene

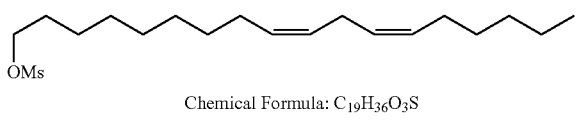

Chemical Formula: $C_{19}H_{36}O_3S$
Molecular Weight: 344.55

To a 0° C. solution of linoleyl alcohol (10 mL, 31.2 mmol) and triethylamine (5.68 mL, 40.5 mmol)) in DCM (50 mL) was added dropwise a solution of methanesulfonyl chloride (2.66 mL, 34.3 mmol) in DCM (20 mL). The reaction was allowed to return to room temperature and let stir for 4 hours. The mixture was quenched by the addition of water and extracted with DCM. The organic layer was washed with saturated NaHCO₃, brine, dried over anhydrous Na₂SO₄, filtered, and concentrated in vacuo. Purification by ISCO silica flash chromatography (0-40% EtOAc/hexanes) provided (6Z,9Z)-18-(methylsulfonyl)octadeca-6,9-diene (10.0 g, 93%).

¹H-NMR (300 MHz, CDCl₃) δ: ppm 5.35 (m, 4H); 4.22 (t, 2H); 2.99 (s, 3H); 2.77 (t, 2H); 2.04 (q, 4H); 1.74 (m, 2H); 1.30 (br. m, 16H); 0.89 (t, 3H).

Step 2: (6Z,9Z)-18-Bromooctadeca-6,9-diene

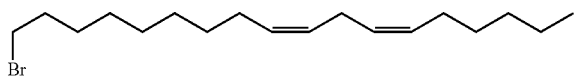

Chemical Formula: $C_{18}H_{33}Br$
Molecular Weight: 329.37

To a solution of (6Z,9Z)-18-(methylsulfonyl)octadeca-6,9-diene (10.0 g, 29.0 mmol) in diethyl ether (372 mL) was added magnesium bromide ethyl etherate (22.5 g, 87.1 mmol). The reaction was let stir at room temperature for 16 hours. The mixture was quenched by the addition of water and extracted with diethyl ether. The combined organic layers were washed with 1% $K_2CO_3$, brine, dried over anhydrous $Na_2SO_4$, filtered, and concentrated in vacuo. Purification by ISCO silica flash chromatography provided (6Z,9Z)-18-bromooctadeca-6,9-diene (8.9 g, 93%).

$^1$H-NMR (300 MHz, $CDCl_3$) δ: ppm 5.36 (m, 4H); 3.41 (t, 2H); 2.77 (t, 2H); 2.05 (q, 4H); 1.86 (m, 2H); 1.48-1.22 (br. m, 16H); 0.89 (t, 3H).

Step 3: Methyl N-dodecyl-N-((9Z,12Z)-octadeca-9,12-dien-1-yl)glycinate

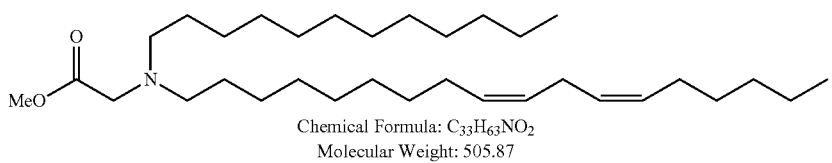 [SMILES: CCCCC/C=C\C/C=C\CCCCCCCCN(CCCCCCCCCCCC)CC(=O)OC]

Chemical Formula: $C_{33}H_{63}NO_2$
Molecular Weight: 505.87

To a solution of methyl dodecylglycinate.HCl (1 g, 3.4 mmol) in 8.5 mL DMF, (Z)-1-bromooctadec-9-ene (1.68 g, 5.1 mmol) and $K_2CO_3$ (1.4 g, 10.2 mmol) were added. The reaction was then allowed to stir at 85° C. for 12 h. After this time the reaction was allowed to cool to rt and was quenched by the addition of excess $H_2O$. The mixture was extracted 3 times with EtOAc. The organics were pooled and washed with brine, dried over $MgSO_4$, filtered and concentrated. The crude material was purified by silica gel chromatography (0-10% EtOAc in hexanes) to afford the desired product (0.87 g, 1.72 mmol, 50%).

$^1$H-NMR (300 MHz, $CDCl_3$) δ: ppm 5.33 (m, 4H); 3.68 (s, 3H); 3.30 (s, 2H); 2.74 (t, 2H); 2.52 (m, 4H); 2.02 (m, 4H); 1.23 (m, 38H); 0.86 (m, 6H).

Step 4: 2-(Dodecyl((9Z,12Z)-octadeca-9,12-dien-1-yl)amino)ethan-1-ol

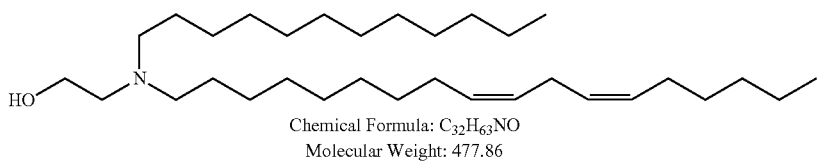 [SMILES: CCCCC/C=C\C/C=C\CCCCCCCCN(CCO)CCCCCCCCCCCC]

Chemical Formula: $C_{32}H_{63}NO$
Molecular Weight: 477.86

To a 0° C. solution of methyl N-dodecyl-N-((9Z,12Z)-octadeca-9,12-dien-1-yl)glycinate (980 mg, 1.94 mmol) in THF (10 mL) was added dropwise lithium aluminum hydride (184 mg, 4.85 mmol). The reaction was allowed to return to room temperature and let stir for 3 hours. The mixture was slowly quenched by the stepwise addition of water (0.184 mL), 10% NaOH (0.552 mL) and water (0.184 mL). The reaction mixture was filtered, washed with THF and concentrated in vacuo. Purification by ISCO silica flash chromatography (0-100% [DCM, 20% MeOH, 1% $NH_4OH$]/MeOH) provided 2-(dodecyl((9Z,12Z)-octadeca-9,12-dien-1-yl)amino)ethan-1-ol (660 mg, 71%).

UPLC/ELSD: RT=3.13 min. MS (ES): m/z (MH$^+$) 478.52 for $C_{32}H_{63}NO$ $^1$H-NMR (300 MHz, $CDCl_3$) δ: ppm 5.39 (br. m, 4H); 3.56 (br. m, 2H); 2.80 (br. m, 2H); 2.61 (br. m, 2H); 2.48 (br. m, 4H); 2.09 (br. m, 4H); 1.57-1.17 (br. m, 38H); 0.91 (br. m, 6H).

Step 5: (9Z,12Z)—N-(2-Chloroethyl)-N-dodecyloc-
tadeca-9,12-dien-1-amine

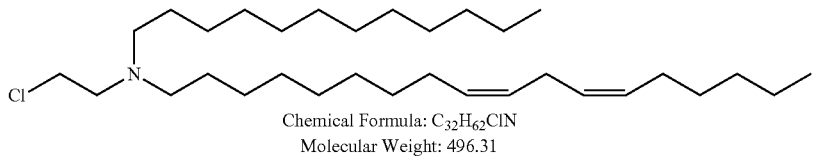 [SMILES: CCCCC/C=C\C/C=C\CCCCCCCCN(CCCl)CCCCCCCCCCCC]

Chemical Formula: $C_{32}H_{62}ClN$
Molecular Weight: 496.31

In a same manner as Step 2 for Compound 18, (9Z,12Z)—N-(2-chloroethyl)-N-dodecyloctadeca-9,12-dien-1-amine was synthesized from 2-(dodecyl((9Z,12Z)-octadeca-9,12-dien-1-yl)amino)ethan-1-ol (660 mg, 1.38 mmol), triethylamine (0.249 mL, 1.80 mmol), and methanesulfonyl chloride (0.172 mL, 1.73 mmol) in DCM (7 mL). Yield (123 mg, 18%).

UPLC/ELSD: RT=3.23 min. MS (ES): m/z (MH$^+$) 496.72 for $C_{32}H_{62}ClN$ $^1$H-NMR (300 MHz, CDCl$_3$) δ: ppm 5.29 (br. m, 4H); 3.43 (br. m, 2H); 2.71 (br. m, 4H); 2.38 (br. m, 4H); 1.98 (br. m, 4H); 1.45-1.07 (br. m, 38H); 0.82 (br. m, 6H).

Step 6: Compound 27: $N^1,N^1,N^2$-Tridodecyl-$N^2$-(2-(4-(2-(dodecyl((9Z,12Z)-octadeca-9,12-dien-1-yl)amino)ethyl)piperazin-1-yl)ethyl)ethane-1,2-diamine

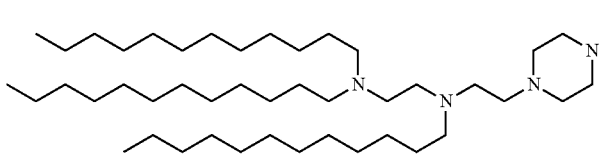

(Chemical Formula: $C_{76}H_{153}N_5$
Molecular Weight: 1137.10

In the same manner as Step 6 for Compound 18, $N^1N1,N^2$-tridodecyl-$N^2$-(2-(4-(2-(dodecyl((9Z,12Z)-octadeca-9,12-dien-1-yl)amino)ethyl)piperazin-1-yl)ethyl)ethane-1,2-diamine was synthesized from $N^1,N^1,N^2$-tridodecyl-$N^2$-(2-(piperazin-1-yl)ethyl)ethane-1,2-diamine (67 mg, 0.099 mmol), (9Z,12Z)—N-(2-chloroethyl)-N-dodecyloctadeca-9,12-dien-1-amine (64 mg, 0.129 mmol) K$_2$CO$_3$ (28 mg, 0.198 mmol), and KI (2 mg, 0.012 mmol) in THF (2 mL). Yield (48 mg, 43%).

UPLC/ELSD: RT=3.90 min. MS (ES): m/z (MH$^+$) 1137.95 for $C_{76}H_{153}N_5$ $^1$H-NMR (300 MHz, CDCl$_3$) δ: ppm 5.48-5.29 (m, 4H); 3.15-2.15 (br. m, 32H); 2.07 (br. m, 4H); 1.83-1.00 (br. m, 98H); 0.91 (br. m, 15H).

AC: Compound 28: $N^1$-(2-(4-(2-(Di((Z)-octadec-9-en-1-yl)amino)ethyl)piperazin-1-yl)ethyl)-$N^1,N^2,N^2$-tridodecylethane-1,2-diamine Step 1: (Z)-1-(Methylsulfonyl)octadec-9-ene

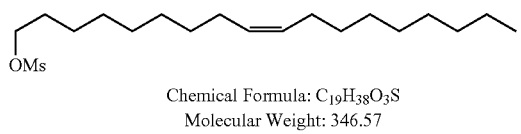 [SMILES: CCCCCCCC/C=C\CCCCCCCCOS(C)(=O)=O]

Chemical Formula: $C_{19}H_{38}O_3S$
Molecular Weight: 346.57

In the same manner as Step 1 for Compound 27, (Z)-1-(methylsulfonyl)octadec-9-ene was synthesized from oleyl alcohol (10 mL, 31.7 mmol), triethylamine (5.74 mL, 41.2 mmol), and methanesulfonyl chloride (2.70 mL, 34.9 mmol) in DCM (50 mL). Yield (8.55 g, 78%).

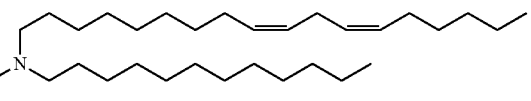

$^1$H-NMR (300 MHz, CDCl$_3$) δ: ppm 5.33 (m, 2H); 4.20 (t, 2H); 2.98 (s, 3H); 2.00 (m, 4H); 1.73 (m, 2H); 1.44-1.16 (br. m, 22H); 0.87 (t, 3H).

Step 2: (Z)-1-Bromooctadec-9-ene

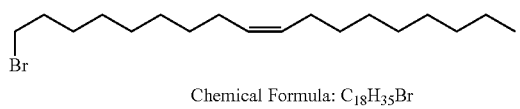

Chemical Formula: $C_{18}H_{35}Br$
Molecular Weight: 331.38

In the same manner as Step 2 for Compound 27, (Z)-1-bromooctadec-9-ene was synthesized from (Z)-1-(methylsulfonyl)octadec-9-ene (8.55 g, 24.7 mmol), and magnesium bromide ethyl etherate (19.1 g, 74.1 mmol) in diethyl ether (317 mL). Yield (7.42 g, 91%).

$^1$H-NMR (300 MHz, CDCl$_3$) δ: ppm 5.35 (m, 2H); 3.41 (t, 2H); 2.01 (m, 4H); 1.85 (m, 2H); 1.48-1.14 (br. m, 22H); 0.88 (t, 3H).

Step 3: 2-(Di((Z)-octadec-9-en-1-yl)amino)ethan-1-ol

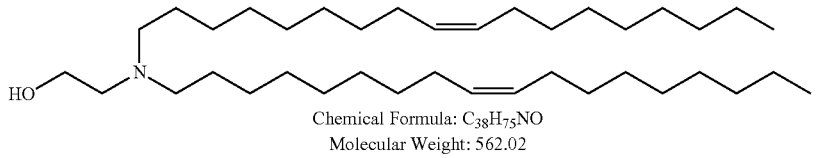 [SMILES: CCCCCCCC/C=C\CCCCCCCCN(CCO)CCCCCCCC/C=C\CCCCCCCC]

Chemical Formula: $C_{38}H_{75}NO$
Molecular Weight: 562.02

In the same manner as Step 1 for Compound 18, 2-(di((Z)-octadec-9-en-1-yl)amino)ethan-1-ol was synthesized from (Z)-1-bromooctadec-9-ene (5 g, 15.1 mmol), ethanolamine, (0.414 mL, 6.86 mmol), $K_2CO_3$ (4.17 g, 30.2 mmol), and KI (114 mg, 0.686 mmol) in MeCN (32 mL). Yield (3.2 g, 83%).

UPLC/ELSD: RT=7.325 min. MS (ES): m/z (MH$^+$) 562.60 for $C_{38}H_{75}NO$ $^1$H-NMR (300 MHz, CDCl$_3$) δ: ppm 5.34 (m, 4H); 3.53 (t, 2H); 2.58 (t, 2H); 2.45 (t, 4H); 2.01 (m, 8H); 1.44 (m, 4H); 1.38-1.18 (br. m, 44H); 0.88 (t, 6H).

Step 4: (Z)—N-(2-Chloroethyl)-N—((Z)-octadec-9-en-1-yl)octadec-9-en-1-amine

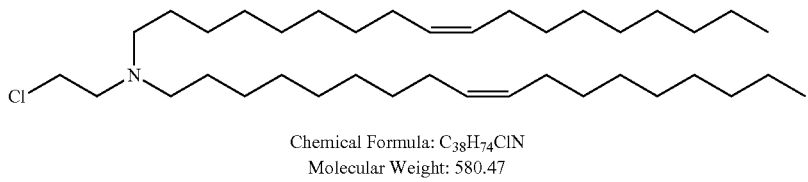 [SMILES: CCCCCCCC/C=C\CCCCCCCCN(CCCl)CCCCCCCC/C=C\CCCCCCCC]

Chemical Formula: $C_{38}H_{74}ClN$
Molecular Weight: 580.47

In the same manner as Step 2 for Compound 18, (Z)—N-(2-chloroethyl)-N—((Z)-octadec-9-en-1-yl)octadec-9-en-1-amine was synthesized from 2-(di((Z)-octadec-9-en-1-yl)amino)ethan-1-ol (1.64 g, 2.92 mmol) triethylamine (0.529 mL, 3.79 mmol), and methanesulfonyl chloride (0.282 mL, 3.65 mmol) in DCM (15 mL). Yield (1.47 g, 87%).

UPLC/ELSD: RT=3.75 min. MS (ES): m/z (MH$^+$) 580.64 for $C_{38}H_{74}ClN$ $^1$H-NMR (300 MHz, CDCl$_3$) δ: ppm 5.35 (m, 4H); 3.48 (br. m, 2H); 2.77 (br. m, 2H); 2.45 (br. m, 4H); 2.02 (br. m, 8H); 1.62-1.05 (br. m, 48H); 0.89 (t, 6H).

Step 5: Compound 28: N$^1$-(2-(4-(2-(Di((Z)-octadec-9-en-1-yl)amino)ethyl)piperazin-1-yl)ethyl)-N$^1$,N$^2$,N$^2$-tridodecylethane-1,2-diamine

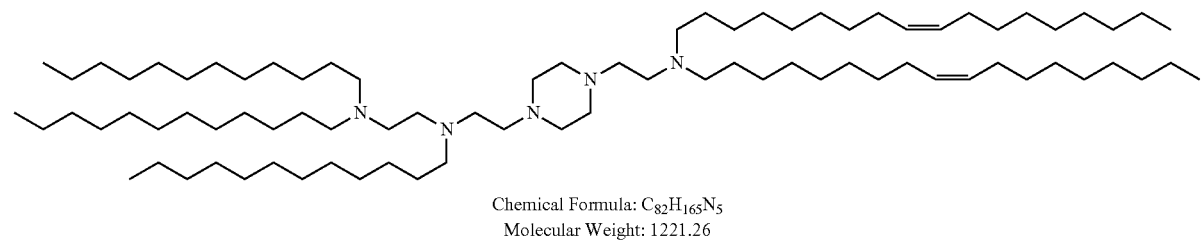 [SMILES: CCCCCCCC/C=C\CCCCCCCCN(CCCCCCCC/C=C\CCCCCCCC)CCN1CCN(CCN(CCCCCCCCCCCC)CCN(CCCCCCCCCCCC)CCCCCCCCCCCC)CC1]

Chemical Formula: $C_{82}H_{165}N_5$
Molecular Weight: 1221.26

In the same manner as Step 6 for Compound 18, $N^1$-(2-(4-(2-(di((Z)-octadec-9-en-1-yl)amino)ethyl)piperazin-1-yl)ethyl)-$N^1,N^2,N^2$-tridodecylethane-1,2-diamine was synthesized from $N^1,N^1,N^2$-tridodecyl-$N^2$-(2-(piperazin-1-yl)ethyl)ethane-1,2-diamine (75 mg, 0.111 mmol), (Z)—N-(2-chloroethyl)-N—((Z)-octadec-9-en-1-yl)octadec-9-en-1-amine (71 mg, 0.122 mmol) $K_2CO_3$ (31 mg, 0.222 mmol), and KI (3 mg, 0.018 mmol) in THF (1.5 mL). Yield (20 mg, 15%).

UPLC/ELSD: RT=4.05 min. MS (ES): m/z (MH$^+$) 1221.72 for $C_{82}H_{165}N_5$ $^1$H-NMR (300 MHz, CDCl$_3$) δ: ppm 5.29-5.14 (br. m, 4H); 2.95-2.00 (br. m, 30H); 1.96-1.77 (br. m, 8H); 1.60-0.85 (br. m, 108H); 0.76 (br. m, 15H).

AD: Compound 29: $N^1$-(2-(4-(2-(Di((9Z,12Z)-octadeca-9,12-dien-1-yl)amino)ethyl)piperazin-1-yl)ethyl)-$N^1,N^2,N^2$-tridodecylethane-1,2-diamine Step 1: 2-(Di((9Z,12Z)-octadeca-9,12-dien-1-yl)amino)ethan-1-ol

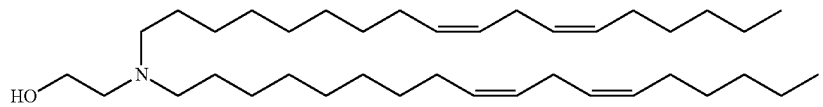

Chemical Formula: $C_{38}H_{71}NO$
Molecular Weight: 557.99

In the same manner as Step 1 for Compound 18, 2-(di((9Z,12Z)-octadeca-9,12-dien-1-yl)amino)ethan-1-ol was synthesized from (6Z,9Z)-18-bromooctadeca-6,9-diene (4 g, 12.1 mmol), ethanolamine, (0.334 mL, 5.52 mmol), $K_2CO_3$ (3.36 g, 24.3 mmol), and KI (92 mg, 0.552 mmol) in MeCN (26 mL). Yield (1.9 g, 62%).

UPLC/ELSD: RT=6.80 min. MS (ES): m/z (MH$^+$) 557.94 for $C_{38}H_{71}NO$ $^1$H-NMR (300 MHz, CDCl$_3$) δ: ppm 5.35 (m, 8H); 3.52 (t, 2H); 2.77 (t, 4H); 2.57 (t, 2H); 2.43 (t, 4H); 2.04 (q, 8H); 1.48-1.18 (br. m, 36H); 0.89 (t, 6H).

Step 2: (9Z,12Z)—N-(2-Chloroethyl)-N-((9Z,12Z)-octadeca-9,12-dien-1-yl)octadeca-9,12-dien-1-amine

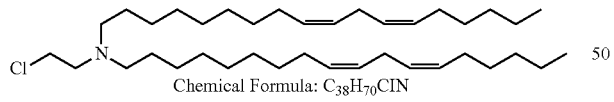

Chemical Formula: $C_{38}H_{70}ClN$
Molecular Weight: 576.44

In a same manner as Step 2 for Compound 18, (9Z,12Z)—N-(2-chloroethyl)-N-((9Z,12Z)-octadeca-9,12-dien-1-yl)octadeca-9,12-dien-1-amine was synthesized from 2-(di((9Z,12Z)-octadeca-9,12-dien-1-yl)amino)ethan-1-ol (250 mg, 0.45 mmol), triethylamine (81 μL, 0.58 mmol), and methanesulfonyl chloride (38 μL, 0.49 mmol) in DCM (2 mL). Yield (134 mg, 52%).

$^1$H-NMR (300 MHz, CDCl$_3$) δ: ppm 5.36 (m, 8H); 3.49 (t, 2H); 2.78 (m, 6H); 2.45 (t, 4H); 2.05 (q, 8H); 1.48-1.18 (br. m, 36H); 0.89 (t, 6H).

Step 3: Compound 29: $N^1$-(2-(4-(2-(Di((9Z,12Z)-octadeca-9,12-dien-1-yl)amino)ethyl)piperazin-1-yl)ethyl)-$N^1,N^2,N^2$-tridodecylethane-1,2-diamine

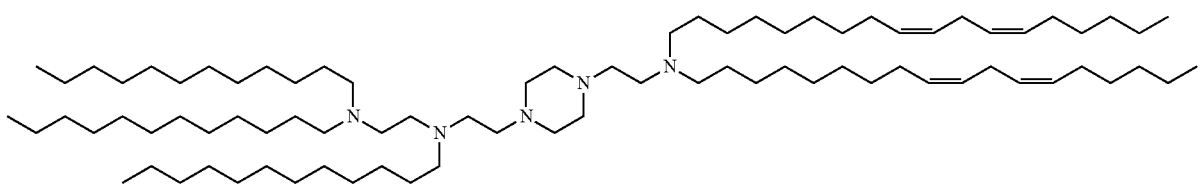

Chemical Formula: $C_{82}H_{161}N_5$
Molecular Weight: 1217.23

In the same manner as Step 6 for Compound 18, $N^1$-(2-(4-(2-(di((9Z,12Z)-octadeca-9,12-dien-1-yl)amino)ethyl)piperazin-1-yl)ethyl)-$N^1$,$N^2$,$N^2$-tridodecylethane-1,2-diamine was synthesized from $N^1$,$N^1$,$N^2$-tridodecyl-$N^2$-(2-(piperazin-1-yl)ethyl)ethane-1,2-diamine (75 mg, 0.111 mmol), (9Z,12Z)—N-(2-chloroethyl)-N-((9Z,12Z)-octadeca-9,12-dien-1-yl)octadeca-9,12-dien-1-amine (71 mg, 0.122) $K_2CO_3$ (31 mg, 0.222 mmol), and KI (3 mg, 0.018 mmol) in THF (3 mL). Yield (20 mg, 15%)

UPLC/ELSD: RT=3.97 min. MS (ES): m/z (MH$^+$) 1217.95 for $C_{82}H_{161}N_5$ $^1$H-NMR (300 MHz, CDCl$_3$) δ: ppm 5.48-5.28 (m, 12H); 3.30-2.20 (br. m, 36H); 2.17-1.92 (br. m, 12H); 1.90-1.00 (br. m, 94H); 0.87 (br. m, 15H).

AE: Compound 30: $N^1$-(2-(4-(2-(Dinonylamino)ethyl)piperazin-1-yl)ethyl)-$N^1$,$N^2$,$N^2$-tritetradecylethane-1,2-diamine

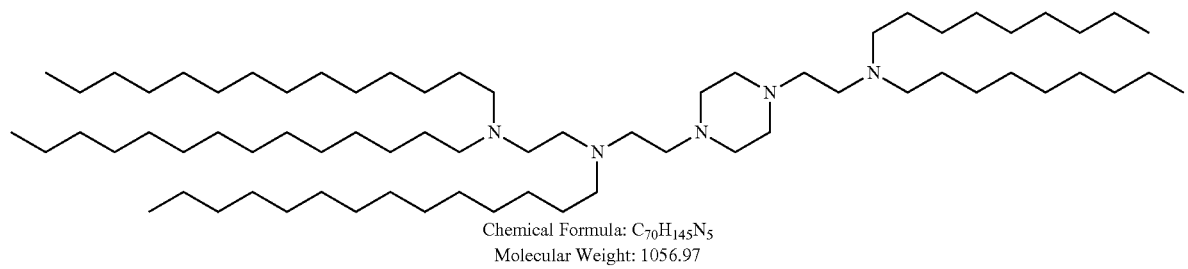 [SMILES: CCCCCCCCCCCCCCN(CCCCCCCCCCCCCC)CCN(CCCCCCCCCCCCCC)CCN1CCN(CCN(CCCCCCCCC)CCCCCCCCC)CC1]

Chemical Formula: $C_{70}H_{145}N_5$
Molecular Weight: 1056.97

In the same manner as Step 6 for Compound 18, $N^1$-(2-(4-(2-(dinonylamino)ethyl)piperazin-1-yl)ethyl)-$N^1$,$N^2$,$N^2$-tritetradecylethane-1,2-diamine was synthesized from $N^1$-(2-(piperazin-1-yl)ethyl)-$N^1$,$N^2$,$N^2$-tritetradecylethane-1,2-diamine (150 mg, 0.197 mmol), N-(2-chloroethyl)-N-nonylnonan-1-amine (79 mg, 0.236 mmol), $K_2CO_3$ (54 mg, 0.394 mmol), and KI (3 mg, 0.0134 mmol) in THF (4 mL). Yield (50 mg, 24%).

UPLC/ELSD: RT=3.79 min. MS (ES): m/z (MH$^+$) 1057.74 for $C_{70}H_{145}N_5$ $^1$H-NMR (300 MHz, CDCl$_3$) δ: ppm 3.15-2.20 (br. m, 30H); 1.90-1.00 (br. m, 100H); 0.90 (t, 15H).

AF: Compound 31: $N^1$-(2-(4-(2-(Didodecylamino)ethyl)piperazin-1-yl)ethyl)-$N^1$,$N^2$,$N^2$-tritetradecylethane-1,2-diamine

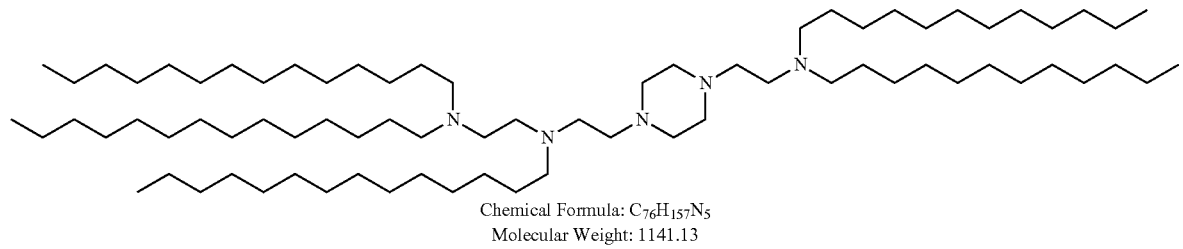 [SMILES: CCCCCCCCCCCCCCN(CCCCCCCCCCCCCC)CCN(CCCCCCCCCCCCCC)CCN1CCN(CCN(CCCCCCCCCCCC)CCCCCCCCCCCC)CC1]

Chemical Formula: $C_{76}H_{157}N_5$
Molecular Weight: 1141.13

In the same manner as Step 6 for Compound 18, $N^1$-(2-(4-(2-(Didodecylamino)ethyl)piperazin-1-yl)ethyl)-$N^1$,$N^2$,$N^2$-tritetradecylethane-1,2-diamine was synthesized from $N^1$-(2-(piperazin-1-yl)ethyl)-$N^1$,$N^2$,$N^2$-tritetradecylethane-1,2-diamine (150 mg, 0.197 mmol), N-(2-chloroethyl)-N-dodecyldodecan-1-amine (98 mg, 0.236 mmol), $K_2CO_3$ (54 mg, 0.394 mmol), and KI (3 mg, 0.0134 mmol) in THF (4 mL). Yield (42 mg, 19%).

UPLC/ELSD: RT=3.98 min. MS (ES): m/z (MH$^+$) 1142.14 for $C_{76}H_{157}N_5$ $^1$H-NMR (300 MHz, CDCl$_3$) δ: ppm 3.20-2.20 (br. m, 30H); 1.90-1.00 (br. m, 112H); 0.90 (t, 15H).

AG: Compound 32: $N^1$-(2-(4-(2-(Ditetradecylamino)ethyl)piperazin-1-yl)ethyl)-$N^1$,$N^2$,$N^2$-tritetradecylethane-1,2-diamine

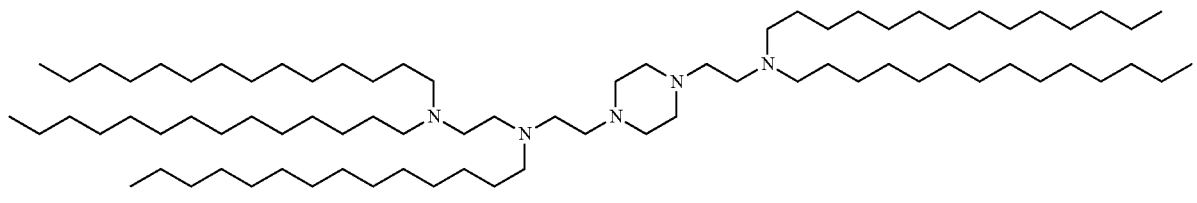

Chemical Formula: $C_{80}H_{165}N_5$
Molecular Weight: 1197.24

In the same manner as Step 6 for Compound 18, $N^1$-(2-(4-(2-(ditetradecylamino)ethyl)piperazin-1-yl)ethyl)-$N^1$,$N^2$,$N^2$-tritetradecylethane-1,2-diamine was synthesized from $N^1$-(2-(piperazin-1-yl)ethyl)-$N^1$,$N^2$,$N^2$-tritetradecylethane-1,2-diamine (150 mg, 0.197 mmol), N-(2-chloroethyl)-N-tetradecyltetradecan-1-amine (130 mg, 0.276 mmol), $K_2CO_3$ (54 mg, 0.394 mmol), and KI (3 mg, 0.0134 mmol) in THF (4 mL). Yield (17 mg, 7%).

UPLC/ELSD: RT=4.11 min. MS (ES): m/z (MH$^+$) 1198.32 for $C_{80}H_{165}N_5$ $^1$H-NMR (300 MHz, CDCl$_3$) δ: ppm 3.20-2.15 (br. m, 30H); 1.90-1.00 (br. m, 120H); 0.90 (t, 15H).

AH: Compound 33: $N^1$-(2-(4-(2-(Didodecylamino)ethyl)piperazin-1-yl)ethyl)-$N^1$,$N^2$,$N^2$-tri((Z)-octadec-9-en-1-yl)ethane-1,2-diamine Step 1: tert-Butyl (Z)-4-(2-(octadec-9-en-1-ylamino)ethyl)piperazine-1-carboxylate

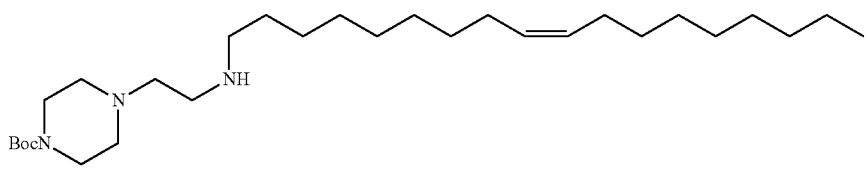

Chemical Formula: $C_{29}H_{57}N_3O_2$
Molecular Weight: 479.79

In the same manner as Step 3 for Compound 18, tert-butyl (Z)-4-(2-(octadec-9-en-1-ylamino)ethyl)piperazine-1-carboxylate was synthesized from (Z)-1-bromooctadec-9-ene (1.95 g, 11.8 mmol), 4-(2-aminoethyl)-1-boc-piperazine (1.35 g, 5.89 mmol), $K_2CO_3$ (1.60 g, 11.8 mmol), and KI (98 mg, 0.689 mmol) in MeCN (30 mL). Yield (790 mg, 28%).

$^1$H-NMR (300 MHz, $CDCl_3$) δ: ppm 5.32 (m, 2H); 3.45 (br, 4H); 2.75 (t, 2H); 2.65 (t, 2H); 2.57 (t, 2H); 2.40 (br, 4H); 2.09 (br, 4H); 1.48 (br. m, 11H); 1.41-1.10 (br, 22H); 0.89 (t, 3H).

Step 2: tert-Butyl 4-(2-((2-(di((Z)-octadec-9-en-1-yl)amino)ethyl)((Z)-octadec-9-en-1-yl)amino)ethyl)piperazine-1-carboxylate

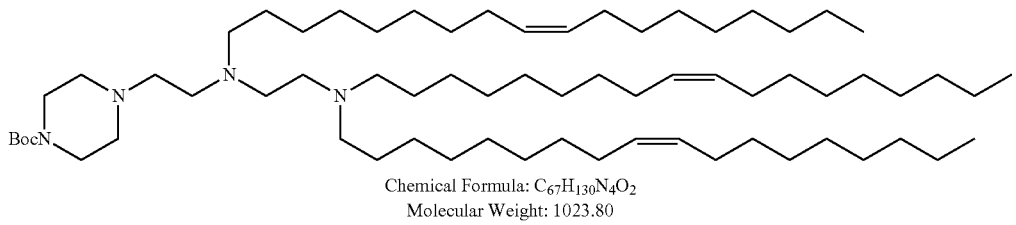 [SMILES: CCCCCCCC/C=C\CCCCCCCCN(CCCCCCCC/C=C\CCCCCCCC)CCN(CCCCCCCC/C=C\CCCCCCCC)CCN1CCN(C(=O)OC(C)(C)C)CC1]

Chemical Formula: $C_{67}H_{130}N_4O_2$
Molecular Weight: 1023.80

In the same manner as Step 4 for Compound 18, tert-butyl 4-(2-((2-(di((Z)-octadec-9-en-1-yl)amino)ethyl)((Z)-octadec-9-en-1-yl)amino)ethyl)piperazine-1-carboxylate was synthesized from tert-butyl (Z)-4-(2-(octadec-9-en-1-ylamino)ethyl)piperazine-1-carboxylate (573 mg, 1.19 mmol), (Z)—N-(2-chloroethyl)-N—((Z)-octadec-9-en-1-yl)octadec-9-en-1-amine (693 mg, 1.19 mmol), $K_2CO_3$ (329 mg, 2.38 mmol), and KI (20 mg, 0.119 mmol) in THF (6 mL). Yield (918 mg, 75%).

$^1$H-NMR (300 MHz, $CDCl_3$) δ: ppm 5.37 (m, 6H); 3.45 (br. m, 4H); 2.72-2.18 (br. m, 18H); 2.04 (br. m, 12H); 1.65-1.05 (br. m, 81H) 0.91 (br. m, 9H).

Step 3: $N^1,N^1,N^2$-Tri((Z)-octadec-9-en-1-yl)-$N^2$-(2-(piperazin-1-yl)ethyl)ethane-1,2-diamine

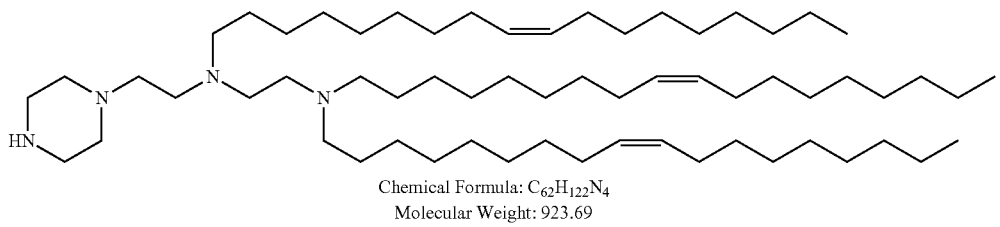 [SMILES: CCCCCCCC/C=C\CCCCCCCCN(CCCCCCCC/C=C\CCCCCCCC)CCN(CCCCCCCC/C=C\CCCCCCCC)CCN1CCNCC1]

Chemical Formula: $C_{62}H_{122}N_4$
Molecular Weight: 923.69

In the same manner as Step 5 for Compound 18, $N^1,N^1,N^2$-tri((Z)-octadec-9-en-1-yl)-$N^2$-(2-(piperazin-1-yl)ethyl)ethane-1,2-diamine was synthesized from, tert-butyl 4-(2-((2-(di((Z)-octadec-9-en-1-yl)amino)ethyl)((Z)-octadec-9-en-1-yl)amino)ethyl)piperazine-1-carboxylate (740 mg, 0.859 mmol), and TFA (3.3 mL, 42.9 mmol) in DCM (3.3 mL). Yield (115 mg, 14%).

$^1$H-NMR (300 MHz, $CDCl_3$) δ: ppm 5.36 (m, 6H); 2.91 (br, 4H); 2.74-2.34 (br. m, 18H); 2.03 (br. m, 12H); 1.54-1.04 (br. m, 72H); 0.90 (br. m, 9H).

Step 4: Compound 33: $N^1$-(2-(4-(2-(Didodecy-lamino)ethyl)piperazin-1-yl)ethyl)-$N^1,N^2,N^2$-tri((Z)-octadec-9-en-1-yl)ethane-1,2-diamine

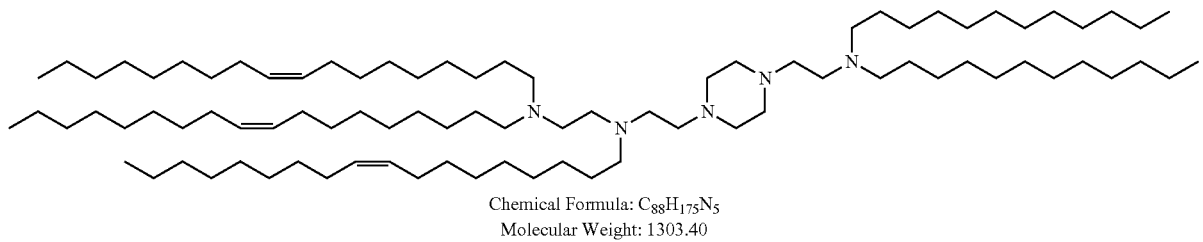 [SMILES: CCCCCCCC/C=C\CCCCCCCCN(CCCCCCCC/C=C\CCCCCCCC)CCN(CCCCCCCC/C=C\CCCCCCCC)CCN1CCN(CCN(CCCCCCCCCCCC)CCCCCCCCCCCC)CC1]

Chemical Formula: $C_{88}H_{175}N_5$
Molecular Weight: 1303.40

In the same manner as Step 6 for Compound 18, $N^1$-(2-(4-(2-(didodecylamino)ethyl)piperazin-1-yl)ethyl)-$N^1,N^2,N^2$-tri((Z)-octadec-9-en-1-yl)ethane-1,2-diamine was synthesized from $N^1,N^1,N^2$-tri((Z)-octadec-9-en-1-yl)-$N^2$-(2-(piperazin-1-yl)ethyl)ethane-1,2-diamine (58 mg, 0.063 mmol), N-(2-chloroethyl)-N-dodecyldodecan-1-amine (31 mg, 0.075 mmol), $K_2CO_3$ (17 mg, 0.13 mmol), and KI (1 mg, 0.006 mmol) in THF (1.5 mL). Yield (30 mg, 37%).

UPLC/ELSD: RT=4.16 min. MS (ES): m/z ($MH^+$) 1304.03 for $C_{88}H_{175}N_5$ $^1$H-NMR (300 MHz, $CDCl_3$) δ: ppm 5.36-5.24 (br. m, 6H); 2.66-2.08 (br. m, 30H); 2.04-1.82 (br. m, 12H); 1.57-0.87 (br. m, 112H); 0.81 (br. m, 15H).

AI: Compound 34: $N^1$-(2-(4-(2-(Didodecylamino) ethyl)piperazin-1-yl)ethyl)-$N^1,N^2,N^2$-tri((9Z,12Z)-octadeca-9,12-dien-1-yl)ethane-1,2-diamine Step 1: tert-Butyl 4-(2-(((9Z,12Z)-octadeca-9,12-dien-1-yl)amino)ethyl)piperazine-1-carboxylate

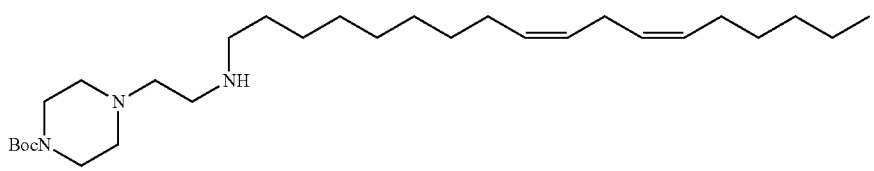

Chemical Formula: $C_{29}H_{55}N_3O_2$
Molecular Weight: 477.78

In the same manner as Step 3 for Compound 18, tert-butyl 4-(2-(((9Z,12Z)-octadeca-9,12-dien-1-yl)amino)ethyl)piperazine-1-carboxylate was synthesized from (6Z,9Z)-18-bromooctadeca-6,9-diene (3.0 g, 9.11 mmol), 4-(2-aminoethyl)-1-boc-piperazine (2.09 g, 9.11 mmol), $K_2CO_3$ (2.52 g, 18.22 mmol), and KI (151 mg, 0.911 mmol) in MeCN (44 mL). Yield (1.20 g, 27%).

$^1$H-NMR (300 MHz, $CDCl_3$) δ: ppm 5.35 (m, 4H); 3.42 (t, 4H); 2.77 (t, 2H); 2.73 (t, 2H); 2.62 (t, 2H); 2.51 (t, 2H); 2.38 (t, 4H); 2.04 (q, 4H); 1.60-1.20 (br. m, 27H); 0.89 (t, 3H).

Step 2: tert-Butyl 4-(2-((2-(di((9Z,12Z)-octadeca-9,12-dien-1-yl)amino)ethyl)((9Z,12Z)-octadeca-9,12-dien-1-yl)amino)ethyl)piperazine-1-carboxylate

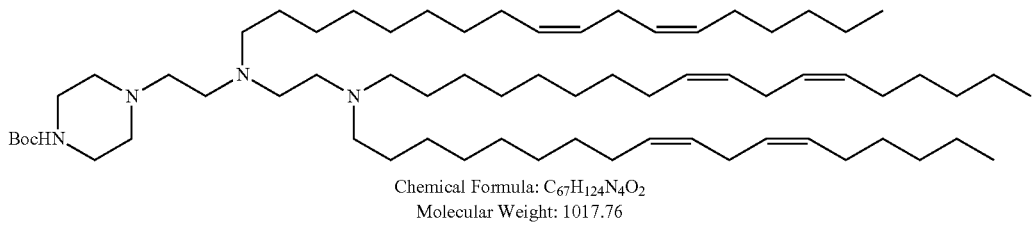

Chemical Formula: C₆₇H₁₂₄N₄O₂
Molecular Weight: 1017.76

In the same manner as Step 4 for Compound 18, tert-butyl 4-(2-((2-(di((9Z,12Z)-octadeca-9,12-dien-1-yl)amino)ethyl)((9Z,12Z)-octadeca-9,12-dien-1-yl)amino)ethyl)piperazine-1-carboxylate was synthesized from tert-butyl 4-(2-(((9Z,12Z)-octadeca-9,12-dien-1-yl)amino)ethyl)piperazine-1-carboxylate (600 mg, 1.26 mmol), (9Z,12Z)—N-(2-chloroethyl)-N-((9Z,12Z)-octadeca-9,12-dien-1-yl)octadeca-9,12-dien-1-amine (796 mg, 1.38 mmol), K$_2$CO$_3$ (347 mg, 2.51 mmol), and KI (21 mg, 0.126 mmol) in THF (8 mL). Yield (793 mg, 62%).

UPLC/ELSD: RT=3.95 min. MS (ES): m/z (MH$^+$) 1018.19 for C$_{67}$H$_{124}$N$_4$O$_2$ Step 3: N$^1$,N$^1$,N$^2$-Tri((9Z,12Z)-octadeca-9,12-dien-1-yl)-N$^2$-(2-(piperazin-1-yl)ethyl)ethane-1,2-diamine

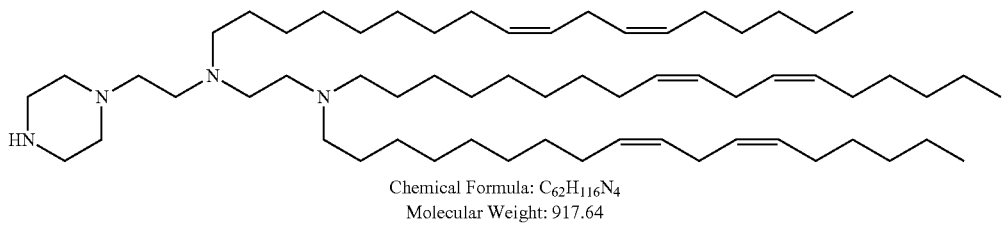 [SMILES: CCCCC/C=C\C/C=C\CCCCCCCCN(CCCCCCCC/C=C\C/C=C\CCCCC)CCN(CCCCCCCC/C=C\C/C=C\CCCCC)CCN1CCNCC1]

Chemical Formula: C₆₂H₁₁₆N₄
Molecular Weight: 917.64

In the same manner as Step 5 for Compound 18, N$^1$,N$^1$,N$^2$-tri((9Z,12Z)-octadeca-9,12-dien-1-yl)-N$^2$-(2-(piperazin-1-yl)ethyl)ethane-1,2-diamine was synthesized from tert-butyl 4-(2-((2-(di((9Z,12Z)-octadeca-9,12-dien-1-yl)amino)ethyl)((9Z,12Z)-octadeca-9,12-dien-1-yl)amino)ethyl)piperazine-1-carboxylate (793 mg, 0.779 mmol), and TFA (3.0 mL, 39.0 mmol) in DCM (3.0 mL). Yield (374 mg, 52%).

UPLC/ELSD: RT=3.68 min. MS (ES): m/z (MH$^+$) 918.84 for C$_{62}$H$_{116}$N$_4$ $^1$H-NMR (300 MHz, CDCl$_3$) δ: ppm 5.36 (m, 12H); 4.12 (m, 6H); 3.30-2.55 (22H); 2.04 (q, 12H); 1.80-1.00 (br. m, 54H); 0.89 (t, 9H).

Step 4: N$^1$-(2-(4-(2-(Didodecylamino)ethyl)piperazin-1-yl)ethyl)-N$^1$,N$^2$,N$^2$-tri((9Z,12Z)-octadeca-9,12-dien-1-yl)ethane-1,2-diamine

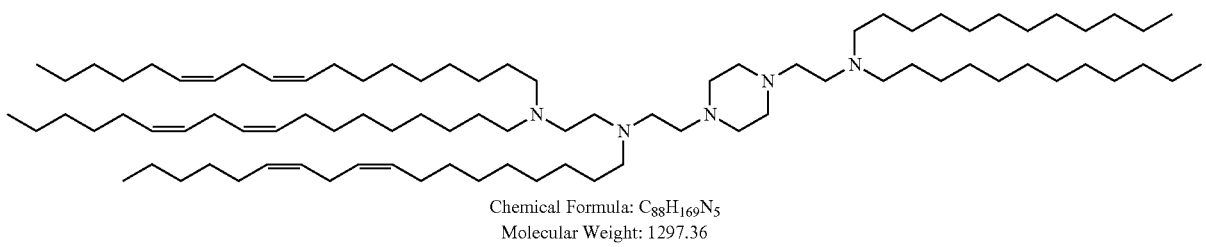 [SMILES: CCCCC/C=C\C/C=C\CCCCCCCCN(CCCCCCCC/C=C\C/C=C\CCCCC)CCN(CCCCCCCC/C=C\C/C=C\CCCCC)CCN1CCN(CCN(CCCCCCCCCCCC)CCCCCCCCCCCC)CC1]

Chemical Formula: C₈₈H₁₆₉N₅
Molecular Weight: 1297.36

In the same manner as Step 6 for Compound 18, $N^1$-(2-(4-(2-(didodecylamino)ethyl)piperazin-1-yl)ethyl)-$N^1$,$N^2$,$N^2$-tri((9Z,12Z)-octadeca-9,12-dien-1-yl)ethane-1,2-diamine was synthesized from $N^1$,$N^1$,$N^2$-tri((9Z,12Z)-octadeca-9,12-dien-1-yl)-$N^2$-(2-(piperazin-1-yl)ethyl)ethane-1,2-diamine (75 mg, 0.082 mmol), N-(2-chloroethyl)-N-dodecyldodecan-1-amine (37 mg, 0.090) $K_2CO_3$ (23 mg, 0.163 mmol), and KI (2 mg, 0.012 mmol) in THF (3 mL). Yield (20 mg, 15%).

UPLC/ELSD: RT=4.00 min. MS (ES): m/z (MH$^+$) 1297.88 for $C_{88}H_{169}N_5$ $^1$H-NMR (300 MHz, CDCl$_3$) δ: ppm 5.48-5.28 (Br, 12H); 3.30-2.20 (br. m, 36H); 2.17-1.92 (br. m, 12H); 1.90-1.00 (br. m, 94H); 0.87 (br. m., 15H).

AJ: Compound 35: $N^1$,$N^1$,$N^2$-Trihexyl-$N^2$-(2-(piperazin-1-yl)ethyl)ethane-1,2-diamine Compound 35 was synthesized according to Steps 1-5 for Compound 17.

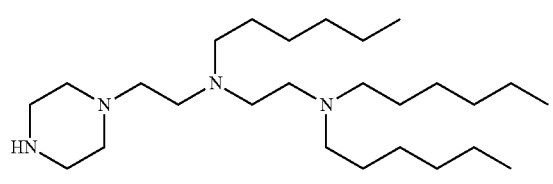

Chemical Formula: $C_{26}H_{56}N_4$
Molecular Weight: 424.76

AK: Compound 36: $N^1$,$N^1$,$N^2$-Trinonyl-$N^2$-(2-(piperazin-1-yl)ethyl)ethane-1,2-diamine Compound 36 was synthesized according to Steps 1-5 outlined for Compound 18.

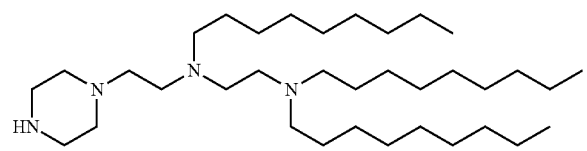

Chemical Formula: $C_{35}H_{74}N_4$
Molecular Weight: 551.01

AL: Compound 37: $N^1$,$N^1$,$N^2$-Tridodecyl-$N^2$-(2-(piperazin-1-yl)ethyl)ethane-1,2-diamine Compound 37 was synthesized according to Steps 1 and 2 for Compound 3.

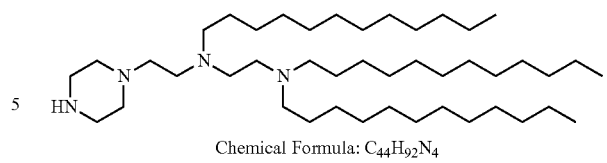

Chemical Formula: $C_{44}H_{92}N_4$
Molecular Weight: 677.25

AM: Compound 38: $N^1$-(2-(Piperazin-1-yl)ethyl)-$N^1$,$N^2$,$N^2$-tritetradecylethane-1,2-diamine Compound 38 was synthesized according to Steps 1-5 for Compound 13.

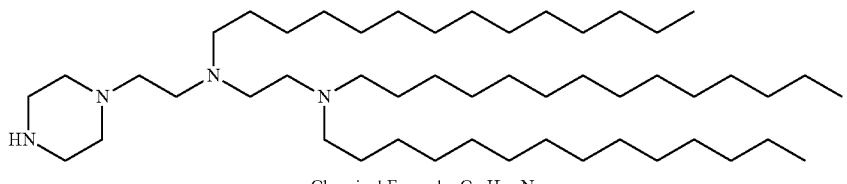

Chemical Formula: $C_{50}H_{104}N_4$
Molecular Weight: 761.41

AN: Compound 39: 2-(Didodecylamino)-N-dodecyl-N-(2-(piperazin-1-yl)ethyl)acetamide Compound 39 was synthesized according to Steps 1-3 for Compound 1.

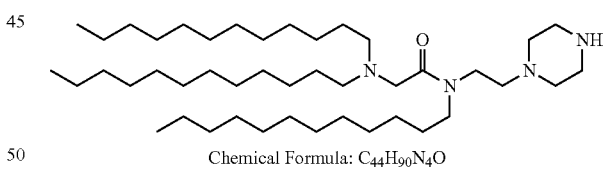

Chemical Formula: $C_{44}H_{90}N_4O$
Molecular Weight: 691.23

AO: Compound 40: $N^1$,$N^1$,$N^2$-Tri((Z)-octadec-9-en-1-yl)-$N^2$-(2-(piperazin-1-yl)ethyl)ethane-1,2-diamine Compound 40 was synthesized according to Steps 1-3 for Compound 33.

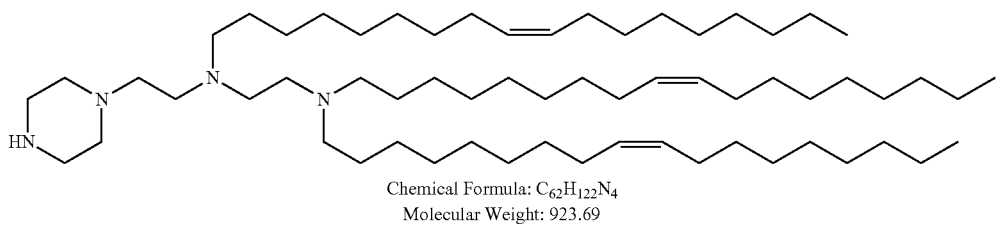 [SMILES: CCCCCCCC/C=C\CCCCCCCCN(CCCCCCCC/C=C\CCCCCCCC)CCN(CCCCCCCC/C=C\CCCCCCCC)CCN1CCNCC1]

Chemical Formula: $C_{62}H_{122}N_4$
Molecular Weight: 923.69

AP: Compound 41: $N^1,N^1,N^2$-Tri((9Z,12Z)-octa-deca-9,12-dien-1-yl)-$N^2$-(2-(piperazin-1-yl)ethyl)ethane-1,2-diamine Compound 41 was synthesized according to Steps 1-3 for Compound 34.

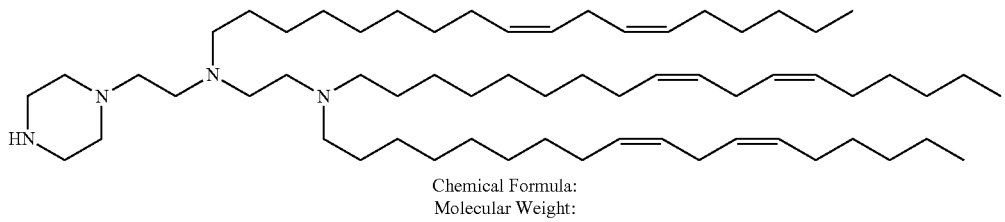 [SMILES: CCCCC/C=C\C/C=C\CCCCCCCCN(CCCCCCCC/C=C\C/C=C\CCCCC)CCN(CCCCCCCC/C=C\C/C=C\CCCCC)CCN1CCNCC1]

Chemical Formula:
Molecular Weight:

AQ: Compound According to Formula (IV): $N^1$-(2-(4-(2-(Di((Z)-octadec-9-en-1-yl)amino)ethyl)piperazin-1-yl)ethyl)-$N^1,N^2,N^2$-tri((Z)-octadec-9-en-1-yl)ethane-1,2-diamine

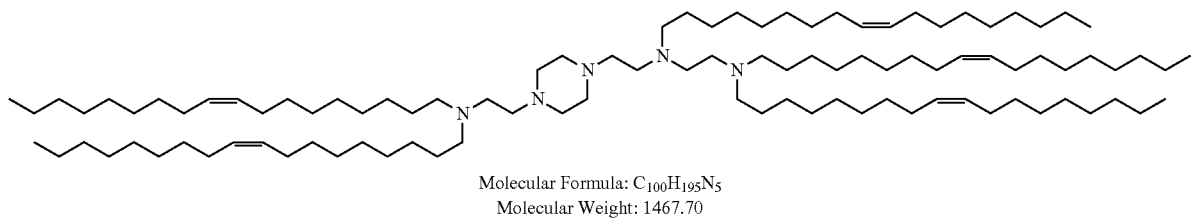 [SMILES: CCCCCCCC/C=C\CCCCCCCCN(CCCCCCCC/C=C\CCCCCCCC)CCN(CCCCCCCC/C=C\CCCCCCCC)CCN1CCN(CCN(CCCCCCCC/C=C\CCCCCCCC)CCCCCCCC/C=C\CCCCCCCC)CC1]

Molecular Formula: $C_{100}H_{195}N_5$
Molecular Weight: 1467.70

In the same manner as Step 6 for Compound 18, $N^1$-(2-(4-(2-(di((Z)-octadec-9-en-1-yl)amino)ethyl)piperazin-1-yl)ethyl)-$N^1,N^2,N^2$-tri((Z)-octadec-9-en-1-yl)ethane-1,2-diamine was synthesized from $N^1,N^1,N^2$-tri((Z)-octadec-9-en-1-yl)-$N^2$-(2-(piperazin-1-yl)ethyl)ethane-1,2-diamine (75 mg, 0.0812 mmol), (Z)—N-(2-chloroethyl)-N—((Z)-octadec-9-en-1-yl)octadec-9-en-1-amine (57 mg, 0.0974 mmol) $K_2CO_3$ (22 mg, 0.162 mmol), and KI (2 mg, 0.012 mmol) in THF (1.5 mL). Yield (30 mg, 25%)

UPLC/ELSD: RT=4.41 min. MS (ES): m/z (MH$^+$) 1469.08 for $C_{100}H_{195}N_5$ $^1$H-NMR (300 MHz, CDCl$_3$) δ: ppm 5.40-5.27 (br. m, 10H); 3.18-2.22 (br. m, 30H); 2.06-1.89 (m, 20H); 1.80-0.97 (br. m, 120H); 0.88 (t, 15H).

AR: Compound 42: 2-(Dinonylamino)-1-(5-(N-(2-(dinonylamino)ethyl)-N-nonylglycyl)-2,5-diazabicyclo[2.2.1]heptan-2-yl)ethan-1-one Step 1: tert-Butyl 5-(dinonylglycyl)-2,5-diazabicyclo[2.2.1]heptane-2-carboxylate

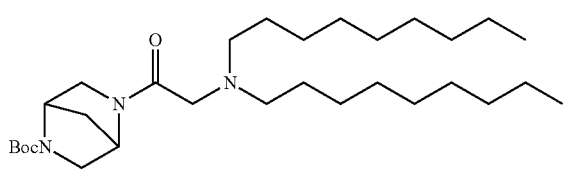

Chemical Formula: $C_{30}H_{57}N_3O_3$
Molecular Weight: 507.80

In the same manner as Step 3 for Compound 11, tert-butyl 5-(dinonylglycyl)-2,5-diazabicyclo[2.2.1]heptane-2-carboxylate was synthesized from lithium dinonylglycinate (500 mg, 1.50 mmol), tert-butyl 2,5-diazabicyclo[2.2.1]heptane-2-carboxylate (357 mg, 1.80 mmol), iPr$_2$EtN (628 µL, 3.60 mmol), and T3P (50% EtOAc solution, 2.68 mL, 4.50 mmol) in THF (15 mL). Yield (710 mg, 78%).

UPLC/ELSD: RT=0.87 min. MS (ES): m/z (MH$^+$) 508.44 for C$_{30}$H$_{57}$N$_3$O$_3$ $^1$H-NMR (300 MHz, CDCl$_3$) δ: ppm 4.98-4.46 (br. m, 2H); 4.30-3.15 (br. m, 10H); 2.14-1.60 (br. m, 6H); 1.49 (s, 9H); 1.40-1.00 (br. m, 24H); 0.89 (t, 6H).

Step 2: 1-(2,5-Diazabicyclo[2.2.1]heptan-2-yl)-2-(dinonylamino)ethan-1-one

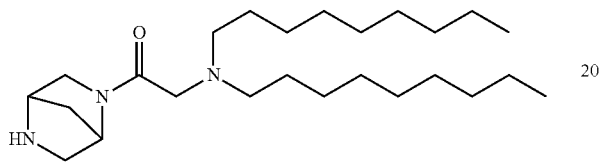

Chemical Formula: C$_{25}$H$_{49}$N$_3$O
Molecular Weight: 407.69

In the same manner as Step 4 for Compound 11, 1-(2,5-diazabicyclo[2.2.1]heptan-2-yl)-2-(dinonylamino)ethan-1-one was synthesized from tert-butyl 5-(dinonylglycyl)-2,5-diazabicyclo[2.2.1]heptane-2-carboxylate (710 mg, 1.40 mmol) and TFA (5.4 mL, 70 mmol) in DCM (5 mL). Yield (446 mg, 78%)

UPLC/ELSD: RT=0.67 min. MS (ES): m/z (MH$^+$) 408.64 for C$_{25}$H$_{49}$N$_3$O $^1$H-NMR (300 MHz, CDCl$_3$) δ: ppm 4.90-3.00 (br. m, 8H); 2.49 (br. m, 4H); 1.79 (br. m, 2H); 1.58-1.08 (br. m, 28H); 0.90 (t, 6H).

Step 3: 2-(Dinonylamino)-1-(5-(N-(2-(dinonylamino)ethyl)-N-nonylglycyl)-2,5-diazabicyclo[2.2.1]heptan-2-yl)ethan-1-one

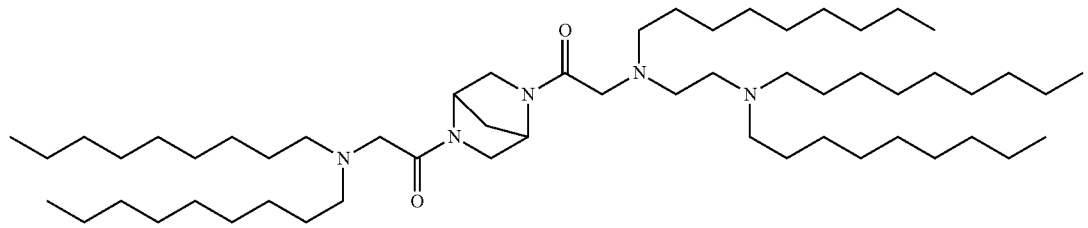

Chemical Formula: C$_{56}$H$_{111}$N$_5$O$_2$
Molecular Weight: 886.54

In the same manner as Step 11 for Compound 11, 2-(dinonylamino)-1-(5-(N-(2-(dinonylamino)ethyl)-N-nonylglycyl)-2,5-diazabicyclo[2.2.1]heptan-2-yl)ethan-1-one was synthesized from 1-(2,5-diazabicyclo[2.2.1]heptan-2-yl)-2-(dinonylamino)ethan-1-one (100 mg, 0.25 mmol), N-(2-(dinonylamino)ethyl)-N-nonylglycine (134 mg, 0.27 mmol), iPr$_2$EtN (94 µL, 0.54 mmol), and T3P (50% EtOAc solution, 438 µL, 0.74 mmol) in THF (20 mL). Yield (50 mg, 23%).

UPLC/ELSD: RT=3.60 min. MS (ES): m/z (MH$^+$) 887.12 for C$_{56}$H$_{111}$N$_5$O$_2$ $^1$H-NMR (300 MHz, CDCl$_3$) δ: ppm 5.15-2.28 (br. m, 26H); 2.16-1.00 (br. m, 70H); 0.90 (t, 15H).

AS: Compound 43: 2-((2-(Didodecylamino)ethyl)(dodecyl)amino)-1-(5-(dinonylglycyl)-2,5-diazabicyclo[2.2.1]heptan-2-yl)ethan-1-one 3

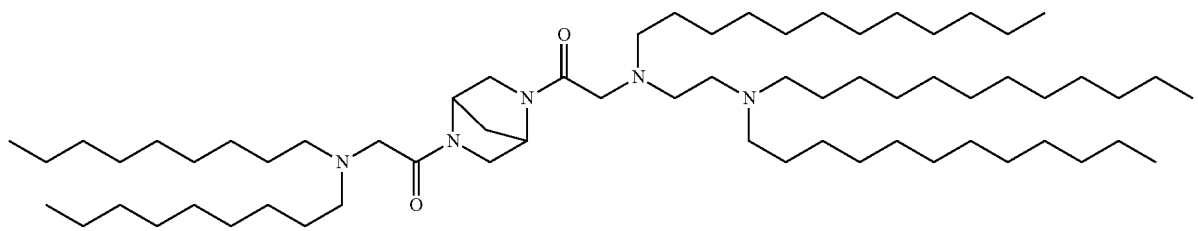

Chemical Formula: $C_{65}H_{129}N_5O_2$
Molecular Weight: 1012.78

In the same manner as Step 11 for Compound 11, 2-((2-(didodecylamino)ethyl)(dodecyl)amino)-1-(5-(dinonylglycyl)-2,5-diazabicyclo[2.2.1]heptan-2-yl)ethan-1-one was synthesized from 1-(2,5-diazabicyclo[2.2.1]heptan-2-yl)-2-(dinonylamino)ethan-1-one (100 mg, 0.25 mmol), N-(2-(didodecylamino)ethyl)-N-dodecylglycine (168 mg, 0.27 mmol), iPr$_2$EtN (94 µL, 0.54 mmol), and T3P (50% EtOAc solution, 438 µL, 0.74 mmol) in THF (20 mL). Yield (150 mg, 60%).

UPLC/ELSD: RT=3.60 min. MS (ES): m/z (MH$^+$) 1013.24 for $C_{65}H_{129}N_5O_2$ $^1$H-NMR (300 MHz, CDCl$_3$) δ: ppm 5.15-2.26 (br. m, 24H); 2.13-1.09 (br. m, 90H); 0.90 (t, 15H).

AT: Compound 44: Methyl 8-((2-(4-(N-(2-(dinonylamino)ethyl)-N-nonylglycyl)piperazin-1-yl)-2-oxoethyl)(nonyl)amino)octanoate Step 1: Tert-Butyl Nonylglycinate

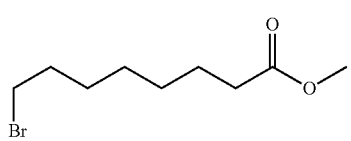

Chemical Formula: $C_{15}H_{31}NO_2$
Molecular Weight: 257.42

To a mixture of tert-butyl glycine (3.0 g, 23 mmol) and 1-bromononane (2.4 g, 11.5 mmol) in MeCN (100 mL) was added K$_2$CO$_3$ (3.2 g, 23 mmol) and KI (190 mg, 1.1 mmol) and the mixture was allowed to stir at 82° C. for 24 hours. The suspension was cooled to RT and filtered through a celite plug, rinsing with hexanes. The MeCN was extracted 3× with hexanes, and the combined extracts were concentrated in vacuo. Purification by ISCO silica flash chromatography (0-15% MeOH/DCM) provided tert-butyl nonylglycinate as a clear colorless oil (848 mg, 29%).

$^1$H-NMR (300 MHz, CDCl$_3$) δ: ppm 3.31 (s, 2H); 2.60 (t, 2H); 1.82-1.63 (br, 1H); 1.56-1.20 (br. m, 23H); 0.90 (t, 3H).

Step 2: Methyl 8-bromooctanoate

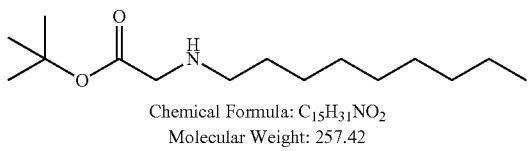 [SMILES: CCCCCCCCCNCC(=O)OC(C)(C)C]

Chemical Formula: $C_9H_{17}BrO_2$
Molecular Weight: 237.14

In the same manner as Step 1 for Compound 15, methyl 8-bromooctanoate was synthesized from 8-bromooctanoic acid (5.0 g, 22 mmol), methanol (20 mL, 450 mmol), and H$_2$SO$_4$ (1.2 mL, 22 mmol) in THF (20 mL). Yield (5.0 g, 95%).

$^1$H-NMR (300 MHz, CDCl$_3$) δ: ppm 3.69 (s, 3H); 3.42 (t, 2H); 2.33 (t, 2H); 1.88 (quint, 2H); 1.65 (quint, 2H); 1.54-1.27 (br. m, 6H).

Step 3: Methyl 8-((2-(tert-butoxy)-2-oxoethyl)(nonyl)amino)octanoate

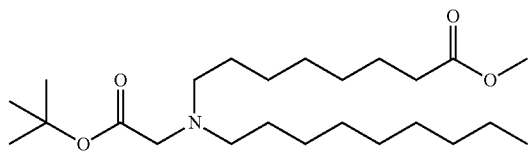

Chemical Formula: $C_{24}H_{47}NO_4$
Molecular Weight: 413.64

To a mixture of tert-butyl nonylglycinate (300 mg, 1.17 mmol) and methyl 8-bromooctanoate (290 mg, 1.22 mmol) in MeCN (12 mL) was added K$_2$CO$_3$ (341 mg, 2.45 mmol) and KI (19 mg, 0.12 mmol) and the mixture was allowed to stir at 82° C. for 12 hours. The suspension was cooled to RT and filtered through a celite plug, rinsing with hexanes. The MeCN was extracted 3× with hexanes, and the combined extracts were concentrated in vacuo. Purification by ISCO silica flash chromatography (0-10% EtOAc/Hexanes) provided methyl 8-((2-(tert-butoxy)-2-oxoethyl)(nonyl)amino)octanoate (353 mg, 73%).

UPLC/ELSD: RT=1.60 min. MS (ES): m/z (MH$^+$) 414.51 for $C_{24}H_{47}NO_4$ $^1$H-NMR (300 MHz, CDCl$_3$) δ: ppm 3.69 (s, 3H); 3.23 (s, 2H); 2.57 (t, 4H); 2.32 (t, 2H); 1.70-1.18 (br. m, 33H); 0.90 (t, 3H).

Step 4: N-(8-Methoxy-8-oxooctyl)-N-nonylglycine

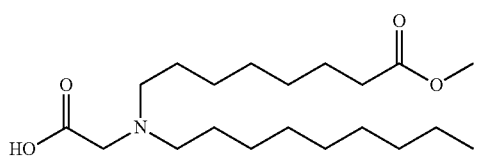

Chemical Formula: $C_{20}H_{39}NO_4$
Molecular Weight: 357.54

To a solution of methyl 8-((2-(tert-butoxy)-2-oxoethyl)(nonyl)amino)octanoate (353 mg, 0.85 mmol) in DCM (4 mL) was added TFA (3.3 mL, 43 mmol) and the solution was allowed to stir at RT for 4 hours. The solution was concentrated in vacuo, taken up in DCM, and washed with 5% Na$_2$CO$_3$ and brine, dried over Na$_2$SO$_4$, filtered, and concentrated in vacuo to provide N-(8-methoxy-8-oxooctyl)-N-nonylglycine (305 mg, 99%).

$^1$H-NMR (300 MHz, CDCl$_3$) δ: ppm 3.69 (s, 3H); 3.49 (s, 2H); 3.06 (t, 4H); 2.32 (t, 2H); 1.79-1.14 (br. m, 24H); 0.90 (t, 3H).

Step 5: tert-Butyl 4-(N-(2-(dinonylamino)ethyl)-N-nonylglycyl)piperazine-1-carboxylate

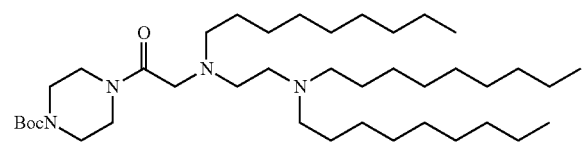

Chemical Formula: C$_{40}$H$_{80}$N$_4$O$_3$
Molecular Weight: 665.11

To a solution of N-(2-(dinonylamino)ethyl)-N-nonylglycine (1.0 g, 2.0 mmol) and 1-boc-piperazine (412 mg, 2.2 mmol) in THF (20 mL) was added iPr$_2$EtN (773 μL, 4.4 mmol) and T3P (50% EtOAc solution, 3.6 mL, 6.0 mmol) and the solution was allowed to stir at RT for 12 hours. The reaction was quenched with water and extracted 3× with EtOAc. The combined organics were washed with brine, dried over Na$_2$SO$_4$, filtered, and concentrated in vacuo. Purification by ISCO silica flash chromatography (0-20% MeOH/DCM) provided tert-butyl 4-(N-(2-(dinonylamino)ethyl)-N-nonylglycyl)piperazine-1-carboxylate (961 mg, 72%).

UPLC/ELSD: RT=3.27 min. MS (ES): m/z (MH$^+$) 665.79 for C$_{40}$H$_{80}$N$_4$O$_3$ $^1$H-NMR (300 MHz, CDCl$_3$) δ: ppm 4.43-2.90 (br. m, 20H); 2.04-0.99 (br. m, 51H); 0.90 (t, 9H).

Step 6: 2-((2-(Dinonylamino)ethyl)(nonyl)amino)-1-(piperazin-1-yl)ethan-1-one

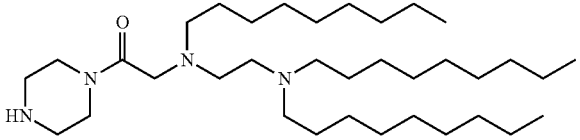

Chemical Formula: C$_{35}$H$_{72}$N$_4$O
Molecular Weight: 564.99

To a solution of tert-butyl 4-(N-(2-(dinonylamino)ethyl)-N-nonylglycyl)piperazine-1-carboxylate (961 mg, 1.44 mmol) in DCM (6 mL) was added TFA (5.5 mL, 72 mmol) and the solution was allowed to stir for 4 hours. The solution was concentrated in vacuo, taken up in DCM, and washed with 5% Na$_2$CO$_3$, brine, dried over Na$_2$SO$_4$, filtered, and concentrated in vacuo to provide 2-((2-(dinonylamino)ethyl)(nonyl)amino)-1-(piperazin-1-yl)ethan-1-one (743 mg, 91%).

UPLC/ELSD: RT=2.14 min. MS (ES): m/z (MH$^+$) 565.82 for C$_{35}$H$_{72}$N$_4$O $^1$H-NMR (300 MHz, CDCl$_3$) δ: ppm 3.59 (br, 4H); 3.36 (br, 2H); 2.99-2.03 (br. m, 14H); 1.74-1.01 (br. m, 42H); 0.90 (t, 9H).

Step 7: Methyl 8-((2-(4-(N-(2-(dinonylamino)ethyl)-N-nonylglycyl)piperazin-1-yl)-2-oxoethyl)(nonyl)amino)octanoate

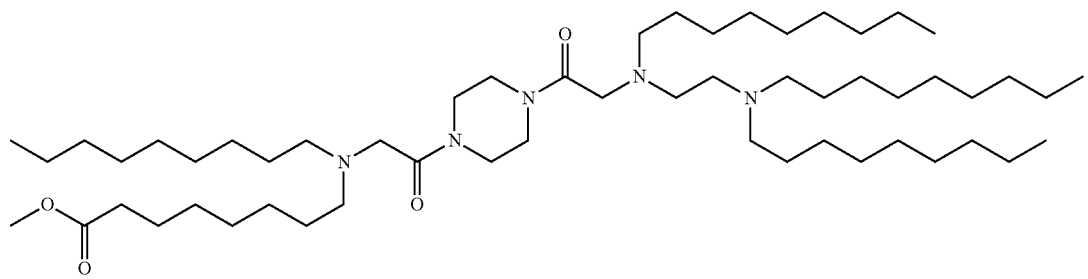

Chemical Formula: C$_{55}$H$_{109}$N$_5$O$_4$
Molecular Weight: 904.51

To a solution of N-(8-methoxy-8-oxooctyl)-N-nonylglycine (100 mg, 0.28 mmol) and 2-((2-(dinonylamino)ethyl)(nonyl)amino)-1-(piperazin-1-yl)ethan-1-one (174 mg, 0.31 mmol) in THF (25 mL) was added), iPr$_2$EtN (107 μL, 0.62 mmol), and T3P (50% EtOAc solution, 0.50 mL, 0.84 mmol) and the reaction was allowed to stir at room temperature overnight. The reaction mixture was diluted with water and extracted with EtOAc. The organics were dried over anhydrous Na$_2$SO$_4$, filtered, and concentrated in vacuo. Purification by ISCO silica flash chromatography (0-100% DCM/[DCM 20% MeOH 1% NH$_4$OH]) provided methyl 8-((2-(4-(N-(2-(dinonylamino)ethyl)-N-nonylglycyl)piperazin-1-yl)-2-oxoethyl)(nonyl)amino)octanoate (121 mg, 48%).

UPLC/ELSD: RT=2.88 min. MS (ES): m/z (MH$^+$) 905 for C$_{55}$H$_{109}$N$_5$O$_4$ $^1$H-NMR (300 MHz, CDCl$_3$) δ: ppm 3.64-3.36 (br. m, 11H); 3.18 (s, 2H); 3.13 (s, 2H); 2.54-2.09 (br. m, 16H); 1.55-0.88 (br. m, 66H); 0.76 (t, 12H).

AU: Compound 45: Pentyl 4-((2-(4-(N-(2-(dinonylamino)ethyl)-N-nonylglycyl)piperazin-1-yl)-2-oxoethyl)(nonyl)amino)butanoate

Step 1: Pentyl 4-bromobutanoate

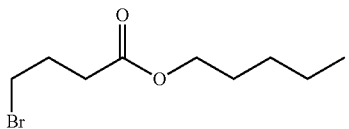

Chemical Formula: $C_9H_{17}BrO_2$
Molecular Weight: 237.14

In the same manner as Step 1 for Compound 15, pentyl 4-bromobutanoate was synthesized from 4-bromobutanoic acid (2.0 g, 12 mmol), pentanol (1.7 mL, 15.6 mmol), and $H_2SO_4$ (0.65 mL, 12 mmol) in THF (20 mL). Yield (1.26 g, 44%).
$^1$H-NMR (300 MHz, $CDCl_3$) δ: ppm 4.10 (t, 2H); 3.49 (t, 2H); 2.52 (t, 2H); 2.20 (quint, 2H); 1.65 (quint, 2H); 1.35 (m, 4H); 0.93 (t, 3H).

Step 2: Pentyl 4-((2-(tert-butoxy)-2-oxoethyl)(nonyl)amino)butanoate

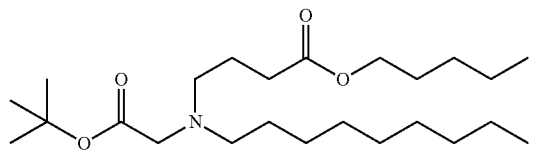

Chemical Formula: $C_{24}H_{47}NO_4$
Molecular Weight: 413.64

In the same manner as Step 3 for Compound 44, pentyl 4-((2-(tert-butoxy)-2-oxoethyl)(nonyl)amino)butanoate was synthesized from tert-butyl nonylglycinate (300 mg, 1.17 mmol) and pentyl 4-bromobutanoate (290 mg, 1.22 mmol) in MeCN (12 mL) was added $K_2CO_3$ (341 mg, 2.45 mmol) and KI (19 mg, 0.12 mmol). Yield (343 mg, 71%).
UPLC/ELSD: RT=1.81 min. MS (ES): m/z (MH$^+$) 415 for $C_{24}H_{47}NO_4$ $^1$H-NMR (300 MHz, $CDCl_3$) δ: ppm 4.08 (t, 2H); 3.23 (s, 2H); 2.60 (br. m, 4H); 2.37 (t, 2H); 1.78 (m, 2H); 1.64 (m, 2H); 1.52-1.20 (br. m, 27H); 0.90 (m, 6H).

Step 3: N-Nonyl-N-(4-oxo-4-(pentyloxy)butyl)glycine

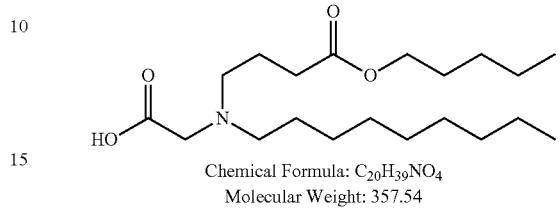

Chemical Formula: $C_{20}H_{39}NO_4$
Molecular Weight: 357.54

In the same manner as Step 4 for Compound 44, N-nonyl-N-(4-oxo-4-(pentyloxy)butyl)glycine was synthesized from pentyl 4-((2-(tert-butoxy)-2-oxoethyl)(nonyl)amino)butanoate (343 mg, 0.83 mmol) and TFA (3.17 mL, 41.5 mmol) in DCM (4 mL). Yield (296 mg, 99%).
UPLC/ELSD: RT=1.29 min. MS (ES): m/z (MH$^+$) 358 for $C_{20}H_{39}NO_4$
$^1$H-NMR (300 MHz, $CDCl_3$) δ: ppm 4.08 (t, 2H); 3.43 (br, 2H); 2.94 (br, 4H); 2.41 (t, 2H); 1.98 (br. m, 2H); 1.74-1.54 (br. m, 4H); 1.40-1.16 (br. m, 16H); 0.91 (m, 6H).

Step 4: Pentyl 4-((2-(4-(N-(2-(dinonylamino)ethyl)-N-nonylglycyl)piperazin-1-yl)-2-oxoethyl)(nonyl)amino)butanoate

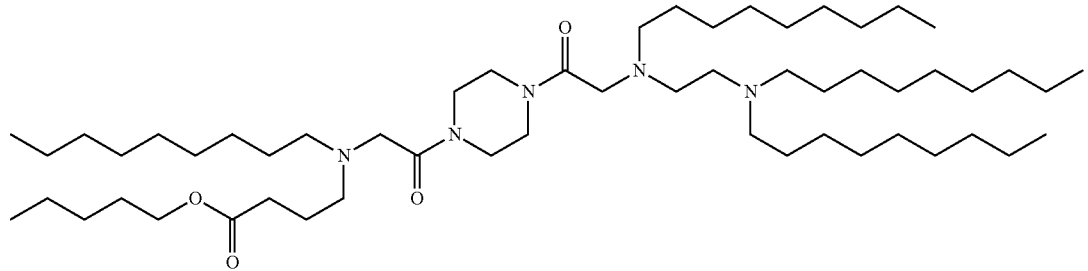

Chemical Formula: $C_{55}H_{109}N_5O_4$
Molecular Weight: 904.51

In the same manner as Step 7 for Compound 44, pentyl 4-((2-(4-(N-(2-(dinonylamino)ethyl)-N-nonylglycyl)piperazin-1-yl)-2-oxoethyl)(nonyl)amino)butanoate was synthesized from N-nonyl-N-(4-oxo-4-(pentyloxy)butyl)glycine (100 mg, 0.28 mmol), 2-((2-(dinonylamino)ethyl)(nonyl)amino)-1-(piperazin-1-yl)ethan-1-one (174 mg, 0.31 mmol), $iPr_2EtN$ (107 μL, 0.62 mmol), and T3P (50% EtOAc solution, 0.50 mL, 0.84 mmol) in THF (25 mL). Yield (121 mg, 48%).

UPLC/ELSD: RT=3.01 min. MS (ES): m/z (MH$^+$) 905 for C$_{55}$H$_{109}$N$_5$O$_4$ $^1$H-NMR (300 MHz, CDCl$_3$) δ: ppm 3.93 (t, 2H); 3.61-3.31 (br. m, 8H); 3.17 (m, 4H); 2.55-2.08 (br. m, 16H); 1.71-0.90 (br. m, 64H); 0.75 (m, 15H).

AV: Compound 46: Methyl 8-((2-((2-(4-(dinonylglycyl)piperazin-1-yl)-2-oxoethyl)(nonyl)amino) ethyl)(nonyl)amino)octanoate Step 1: 2-(Nonylamino)ethan-1-ol

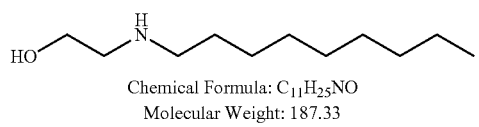

Chemical Formula: C$_{11}$H$_{25}$NO
Molecular Weight: 187.33

To a mixture of ethanolamine (4.4 mL, 72 mmol) and 1-bromononane (3.0 g, 14.5 mmol) in MeCN (150 mL) was added K$_2$CO$_3$ (4.0 g, 29 mmol) and KI (240 mg, 1.5 mmol) and the mixture was allowed to stir at 82° C. for 12 hours. The suspension was cooled to RT and filtered over a pad of celite, rinsing with hexanes. The MeCN was extracted with hexanes 3×, and the combined hexanes were concentrated. Purification by ISCO silica flash chromatography (0-100% DCM/[DCM 20% MeOH 1% NH$_4$OH]) provided 2-(nonylamino)ethan-1-ol (1.0 g, 38%)

$^1$H-NMR (300 MHz, CDCl$_3$) δ: ppm 3.66 (t, 2H); 2.80 (t, 2H); 2.62 (t, 2H); 1.96 (br. m, 2H); 1.50 (br. m, 2H); 1.28 (br. m, 12H); 0.90 (t, 3H).

Step 2: Methyl 8-((2-hydroxyethyl)(nonyl)amino)octanoate

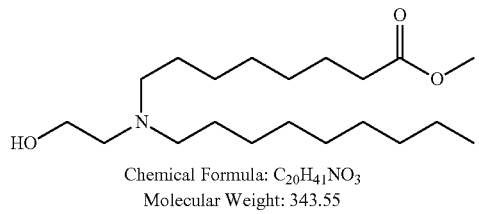 [SMILES: CCCCCCCCCN(CCO)CCCCCCCC(=O)OC]

Chemical Formula: C$_{20}$H$_{41}$NO$_3$
Molecular Weight: 343.55

In the same manner as Step 1 for Compound 18, methyl 8-((2-hydroxyethyl)(nonyl)amino)octanoate was synthesized from 2-(nonylamino)ethan-1-ol (500 mg, 2.67 mmol), methyl 8-bromooctanoate (665 mg, 2.8 mmol), K$_2$CO$_3$ (780 mg, 5.6 mmol), and KI (44 mg, 0.27 mmol) in MeCN (30 mL). Yield (578 mg, 63%).

UPLC/ELSD: RT=1.01 min. MS (ES): m/z (MH$^+$) 344.31 for C$_{20}$H$_{41}$NO$_3$ $^1$H-NMR (300 MHz, CDCl$_3$) δ: ppm 3.69 (s, 3H); 3.59 (t, 2H), 2.65 (br, 2H); 2.51 (t, 4H); 2.32 (t, 2H); 1.65 (br. m, 2H); 1.49 (br. m, 4H); 1.30 (br. m, 18H); 0.90 (t, 3H).

Step 3: Methyl 8-((2-chloroethyl)(nonyl)amino)octanoate

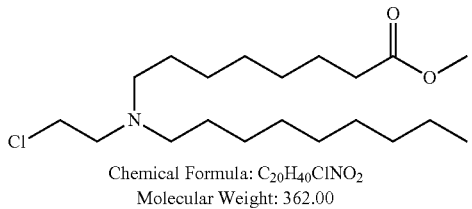 [SMILES: CCCCCCCCCN(CCCl)CCCCCCCC(=O)OC]

Chemical Formula: C$_{20}$H$_{40}$ClNO$_2$
Molecular Weight: 362.00

In the same manner as Step 2 for Compound 18, methyl 8-((2-chloroethyl)(nonyl)amino)octanoate was synthesized from methyl 8-((2-hydroxyethyl)(nonyl)amino)octanoate (578 mg, 1.68 mmol), methanesulfonyl chloride (163 μL, 2.10 mmol) and trimethylamine (305 μL, 2.20 mmol) in DCM (10 mL). Yield (418 mg, 69%).

UPLC/ELSD: RT=1.21 min. MS (ES): m/z (MH$^+$) 363 for C$_{20}$H$_{40}$ClNO$_2$ $^1$H-NMR (300 MHz, CDCl$_3$) δ: ppm 3.69 (br, 3H); 3.51 (br, 2H), 2.78 (br. m, 2H); 2.47 (br. m, 4H); 2.33 (t, 2H); 1.72-1.20 (br. m, 24H); 0.91 (t, 3H).

Step 4: Methyl 8-((2-((2-(tert-butoxy)-2-oxoethyl) (nonyl)amino)ethyl)(nonyl)amino)octanoate

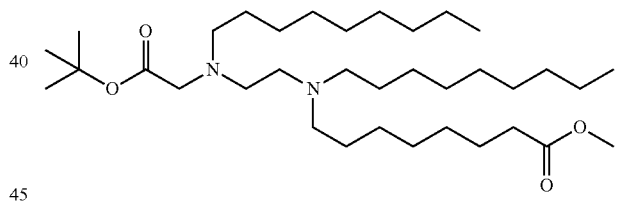

Chemical Formula: C$_{35}$H$_{70}$N$_2$O$_4$
Molecular Weight: 582.96

To a mixture of tert-butyl nonylglycinate (218 mg, 0.85 mmol) and methyl 8-((2-chloroethyl)(nonyl)amino)octanoate (337 mg, 0.93 mmol) in MeCN (10 mL) was added K$_2$CO$_3$ (236 mg, 1.69 mmol) and KI (14 mg, 0.08 mmol) and the mixture was allowed to stir at 82° C. for 12 hours. The suspension was cooled to RT and filtered through a pad of celite, rinsing with hexanes. The mixture was extracted with hexanes 3× and the combined hexanes were concentrated. Purification by ISCO silica flash chromatography (0-10% MeOH/DCM) provided methyl 8-((2-((2-(tert-butoxy)-2-oxoethyl)(nonyl)amino)ethyl)(nonyl)amino)octanoate (283 mg, 57%).

UPLC/ELSD: RT=2.92 min. MS (ES): m/z (MH$^+$) 584 for C$_{35}$H$_{70}$N$_2$O$_4$ $^1$H-NMR (300 MHz, CDCl$_3$) δ: ppm 3.69 (s, 3H); 3.28 (s, 2H); 2.80-2.20 (br. m, 12H); 1.85-1.10 (br. m, 47H); 0.91 (t, 6H).

Step 5: N-(2-((8-Methoxy-8-oxooctyl)(nonyl)amino)ethyl)-N-nonylglycine

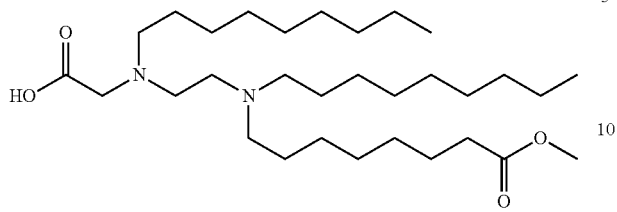

Chemical Formula: $C_{31}H_{62}N_2O_4$
Molecular Weight: 526.85

In the same manner as Step 4 for Compound 44, N-(2-((8-methoxy-8-oxooctyl)(nonyl)amino)ethyl)-N-nonylglycine was synthesized from methyl 8-((2-((2-(tert-butoxy)-2-oxoethyl)(nonyl)amino)ethyl)(nonyl)amino)octanoate (283 mg, 0.49 mmol) and TFA (1.86 mL, 24.3 mmol) in DCM (2 mL). Yield (255 mg, 99%).

UPLC/ELSD: RT=2.18 min. MS (ES): m/z (MH$^+$) 528 for $C_{31}H_{62}N_2O_4$ $^1$H-NMR (300 MHz, CDCl$_3$) δ: ppm 3.69 (s, 3H), 3.26 (s, 2H), 2.79 (br. m, 8H), 2.59 (t, 2H), 2.33 (t, 2H), 1.76-1.08 (br. m, 38H); 0.90 (t, 6H).

Step 6: Methyl 8-((2-((2-(4-(dinonylglycyl)piperazin-1-yl)-2-oxoethyl)(nonyl)amino)ethyl)(nonyl)amino)octanoate

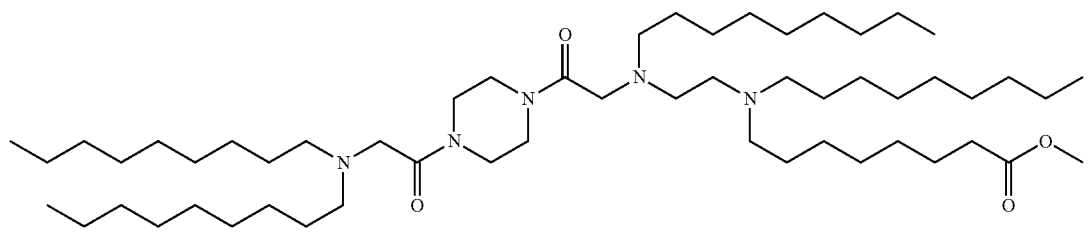

Chemical Formula: $C_{55}H_{109}N_5O_4$
Molecular Weight: 904.51

In the same manner as Step 11 for Compound 11, methyl 8-((2-((2-(4-(dinonylglycyl)piperazin-1-yl)-2-oxoethyl)(nonyl)amino)ethyl)(nonyl)amino)octanoate was synthesized from 2-(dinonylamino)-1-(piperazin-1-yl)ethan-1-one (75 mg, 0.20 mmol), N-(2-((8-methoxy-8-oxooctyl)(nonyl)amino)ethyl)-N-nonylglycine (150 mg, 0.28 mmol), iPr$_2$EtN (88 μL, 0.50 mmol) and T3P (50% EtOAc solution, 409 μL, 0.69 mmol). Yield (57 mg, 32%).

UPLC/ELSD: RT=2.88 min. MS (ES): m/z (MH$^+$) 905 for $C_{55}H_{109}N_5O_4$ $^1$H-NMR (300 MHz, CDCl$_3$) δ: ppm 3.82-2.87 (br. m, 27H); 2.64 (m, 2H); 2.33 (t, 2H); 1.80-1.15 (br. m, 66H); 0.90 (t, 12H).

AW: Compound 47: Methyl 8-((2-(dinonylamino)ethyl)(2-(4-(dinonylglycyl)piperazin-1-yl)-2-oxoethyl)amino)octanoate

Step 1: Methyl 8-((2-(tert-butoxy)-2-oxoethyl)amino)octanoate

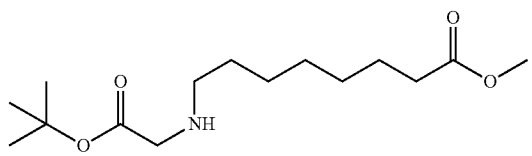

Chemical Formula: $C_{15}H_{29}NO_4$
Molecular Weight: 287.40

In the same manner as Step 1 for Compound 44, methyl 8-((2-(tert-butoxy)-2-oxoethyl)amino)octanoate was synthesized from tert-butyl glycine (2.0 g, 12 mmol), methyl 8-bromooctanoate (2.8 g, 12 mmol), K$_2$CO$_3$ (3.3 g, 24 mmol), and KI (198 mg, 1.2 mmol) in MeCN (100 mL). Yield (1.16 g, 34%).

$^1$H-NMR (300 MHz, CDCl$_3$) δ: ppm 3.69 (s, 3H); 3.33 (s, 2H); 2.62 (t, 2H); 2.32 (s, 2H); 2.16-1.80 (br, 1H); 1.72-1.42 (br. m, 13H); 1.34 (br. m, 6H).

Step 2: Methyl 8-((2-(tert-butoxy)-2-oxoethyl)(2-(dinonylamino)ethyl)amino)octanoate

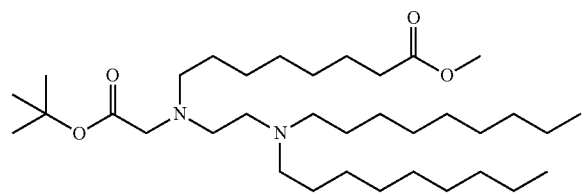

Chemical Formula: $C_{35}H_{70}N_2O_4$
Molecular Weight: 582.96

In the same manner as Step 4 for Compound 46, methyl 8-((2-(tert-butoxy)-2-oxoethyl)(2-(dinonylamino)ethyl)

amino)octanoate was synthesized from methyl 8-((2-(tert-butoxy)-2-oxoethyl)amino)octanoate (300 mg, 1.0 mmol), N-(2-chloroethyl)-N-nonylnonan-1-amine (381 mg, 1.15 mmol), K₂CO₃ (320 mg, 2.3 mmol), and KI (17 mg, 0.10 mmol) in MeCN (10 mL). Yield (285 mg, 47%).

UPLC/ELSD: RT=2.89 min. MS (ES): m/z (MH⁺) 584 for C$_{35}$H$_{70}$N$_2$O$_4$

¹H-NMR (300 MHz, CDCl₃) δ: ppm 3.69 (s, 3H); 3.29 (s, 2H); 3.10 (br. m, 8H); 2.59 (t, 2H); 2.32 (t, 2H); 1.82 (br. m, 4H); 1.74-1.16 (br. m, 43H); 0.91 (t, 6H).

Step 3: N-(2-(dinonylamino)ethyl)-N-(8-methoxy-8-oxooctyl)glycine

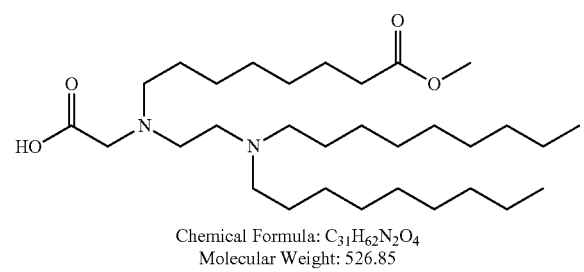 [SMILES: CCCCCCCCCN(CCCCCCCCC)CCN(CCCCCCCC(=O)OC)CC(=O)O]

Chemical Formula: C$_{31}$H$_{62}$N$_2$O$_4$
Molecular Weight: 526.85

In the same manner as Step 5 for Compound 46, N-(2-(dinonylamino)ethyl)-N-(8-methoxy-8-oxooctyl)glycine was synthesized from methyl 8-((2-(tert-butoxy)-2-oxoethyl)(2-(dinonylamino)ethyl)amino)octanoate (285 mg, 0.50 mmol), and TFA (1.87 mL, 24.4 mmol) in DCM (2 mL). Yield (254 mg, 98%).

UPLC/ELSD: RT=2.16 min. MS (ES): m/z (MH⁺) 528 for C$_{31}$H$_{62}$N$_2$O$_4$

¹H-NMR (300 MHz, CDCl₃) δ: ppm 3.69 (s, 3H); 3.25 (s, 2H); 2.90-2.72 (br. m, 8H); 2.59 (t, 2H); 2.32 (t, 2H); 1.66 (br. m, 6H); 1.48 (br. m, 2H); 1.40-1.20 (br. m, 30H); 0.91 (t, 6H).

Step 4: Methyl 8-((2-(dinonylamino)ethyl)(2-(4-(dinonylglycyl)piperazin-1-yl)-2-oxoethyl)amino)octanoate oxooctyl)glycine (150 mg, 0.28 mmol), iPr₂EtN (88 μL, 0.50 mmol) and T3P (50% EtOAc solution, 409 μL, 0.69 mmol). Yield (80 mg, 39%).

UPLC/ELSD: RT=2.87 min. MS (ES): m/z (MH⁺) 905 for C$_{55}$H$_{109}$N$_5$O$_4$

¹H-NMR (300 MHz, CDCl₃) δ: ppm 3.81-2.21 (br. m, 31H); 1.89-1.05 (br. m, 66H); 0.90 (t, 12H).

AX: Compound 48: Methyl 8-((2-(4-(dinonylglycyl)piperazin-1-yl)-2-oxoethyl)(2-((8-methoxy-8-oxooctyl)(nonyl)amino)ethyl)amino)octanoate Step 1: Methyl 8-((2-(tert-butoxy)-2-oxoethyl)(2-((8-methoxy-8-oxooctyl)(nonyl)amino)ethyl)amino)octanoate

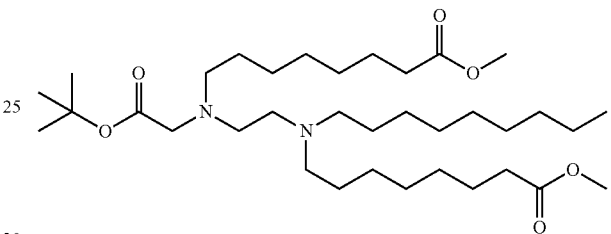

Chemical Formula: C$_{35}$H$_{68}$N$_2$O$_6$
Molecular Weight: 612.94

In the same manner as Step 4 for Compound 46, methyl 8-((2-(tert-butoxy)-2-oxoethyl)(2-((8-methoxy-8-oxooctyl)(nonyl)amino)ethyl)amino)octanoate was synthesized from methyl 8-((2-(tert-butoxy)-2-oxoethyl)amino)octanoate (65 mg, 0.23 mmol), methyl 8-((2-chloroethyl)(nonyl)amino)octanoate (86 mg, 0.24 mmol), K₂CO₃ (69 mg, 0.50 mmol), and KI (4 mg, 0.02 mmol) in MeCN (4 mL). Yield (60 mg, 43%).

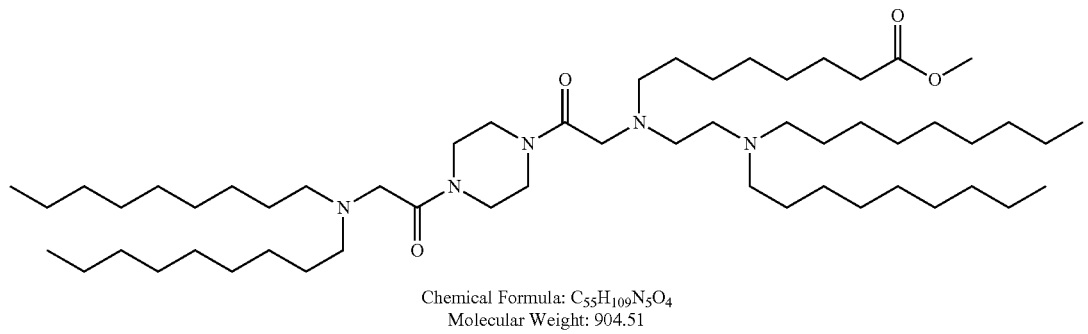 [SMILES: CCCCCCCCCN(CCCCCCCCC)CCN(CCCCCCCC(=O)OC)CC(=O)N1CCN(C(=O)CN(CCCCCCCCC)CCCCCCCCC)CC1]

Chemical Formula: C$_{55}$H$_{109}$N$_5$O$_4$
Molecular Weight: 904.51

In the same manner as Step 11 for Compound 11, methyl 8-((2-(dinonylamino)ethyl)(2-(4-(dinonylglycyl)piperazin-1-yl)-2-oxoethyl)amino)octanoate was synthesized from 2-(dinonylamino)-1-(piperazin-1-yl)ethan-1-one (75 mg, 0.20 mmol), N-(2-(dinonylamino)ethyl)-N-(8-methoxy-8-

UPLC/ELSD: RT=2.42 min. MS (ES): m/z (MH⁺) 614 for C$_{35}$H$_{68}$N$_2$O$_6$

¹H-NMR (300 MHz, CDCl₃) δ: ppm 3.66 (s, 6H); 3.25 (s, 2H); 2.66 (m, 2H); 2.54 (m, 4H); 2.38 (m, 4H); 2.28 (t, 4H); 1.61 (m, 4H); 1.54-1.10 (br. m, 39H); 0.87 (t, 3H).

Step 2: N-(8-methoxy-8-oxooctyl)-N-(2-((8-methoxy-8-oxooctyl)(nonyl)amino)ethyl)glycine

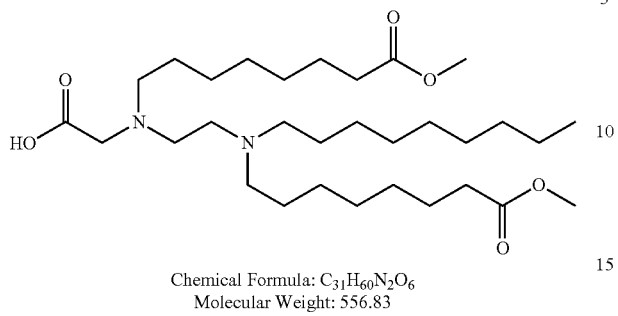

Chemical Formula: $C_{31}H_{60}N_2O_6$
Molecular Weight: 556.83

In the same manner as Step 5 for Compound 46, N-(8-methoxy-8-oxooctyl)-N-(2-((8-methoxy-8-oxooctyl)(nonyl)amino)ethyl)glycine was synthesized from methyl 8-((2-(tert-butoxy)-2-oxoethyl)(2-((8-methoxy-8-oxooctyl)(nonyl)amino)ethyl)amino)octanoate (60 mg, 0.10 mmol), and TFA (0.37 mL, 4.9 mmol) in DCM (1 mL). Yield (54 mg, 99%).

$^1$H-NMR (300 MHz, CDCl$_3$) δ: ppm 3.60 (s, 6H); 3.15 (s, 2H); 2.72 (br. m, 8H); 2.50 (t, 2H); 2.22 (t, 4H); 1.70-1.05 (br. m, 34H); 0.81 (t, 3H).

Step 3: Methyl 8-((2-(4-(dinonylglycyl)piperazin-1-yl)-2-oxoethyl)(2-((8-methoxy-8-oxooctyl)(nonyl)amino)ethyl)amino)octanoate

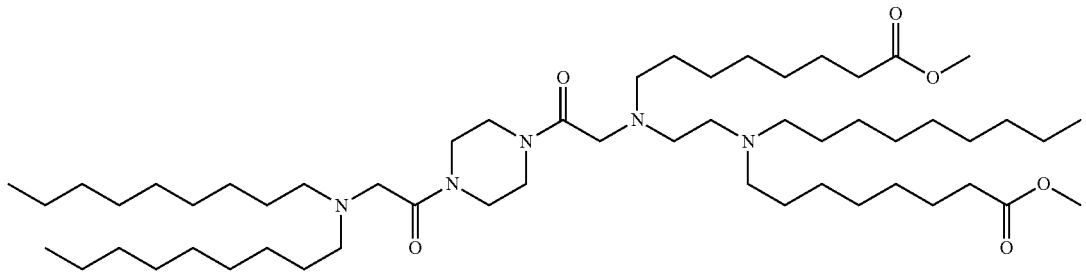

Chemical Formula: $C_{55}H_{107}N_5O_6$
Molecular Weight: 934.49

In the same manner as Step 11 for Compound 11, methyl 8-((2-(4-(dinonylglycyl)piperazin-1-yl)-2-oxoethyl)(2-((8-methoxy-8-oxooctyl)(nonyl)amino)ethyl)amino)octanoate was synthesized from 2-(dinonylamino)-1-(piperazin-1-yl)ethan-1-one (26 mg, 0.07 mmol), N-(8-methoxy-8-oxooctyl)-N-(2-((8-methoxy-8-oxooctyl)(nonyl)amino)ethyl)glycine (54 mg, 0.10 mmol), iPr$_2$EtN (30 μL, 0.17 mmol) and T3P (50% EtOAc solution, 140 μL, 0.24 mmol). Yield (20 mg, 27%).

UPLC/ELSD: RT=2.56 min. MS (ES): m/z (MH$^+$) 935 for $C_{55}H_{107}N_5O_6$ $^1$H-NMR (300 MHz, CDCl$_3$) δ: ppm 3.70-3.00 (br. m, 18H); 2.55-2.05 (br. m, 18H); 1.70-0.95 (br. m, 62H); 0.76 (t, 9H).

AY: Compound 49: 2-((2-(Dinonylamino)ethyl)(nonyl)amino)-1-(4-(2-(dinonylamino)ethyl)piperidin-1-yl)ethan-1-one

Step 1: tert-Butyl 4-(2-(dinonylamino)ethyl)piperidine-1-carboxylate

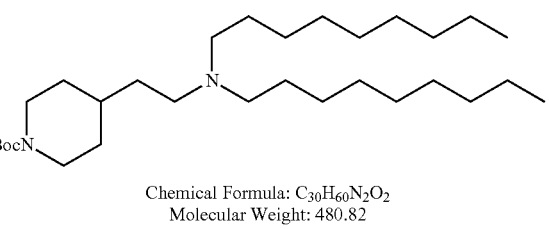

Chemical Formula: $C_{30}H_{60}N_2O_2$
Molecular Weight: 480.82

To a mixture of tert-butyl 4-(2-aminoethyl)piperidine-1-carboxylate (1.50 g, 6.6 mmol) and 1-bromononane (1.36 g, 6.57 mmol) in MeCN (100 mL) was added K$_2$CO$_3$ (1.83 g, 13.1 mmol) and KI (109 mg, 0.66 mmol) and the mixture was allowed to stir at 82° C. for 12 hours. The suspension was cooled to RT, filtered over a pad of celite rinsing with hexanes, and concentrated in vacuo. Purification by ISCO silica flash chromatography (0-100% DCM/[DCM 20% MeOH 1% NH$_4$OH]) provided tert-butyl 4-(2-(dinonylamino)ethyl)piperidine-1-carboxylate (602 mg, 19%).

UPLC/ELSD: RT=2.41 min. MS (ES): m/z (MH$^+$) 482 for $C_{30}H_{60}N_2O_2$ $^1$H-NMR (300 MHz, CDCl$_3$) δ: ppm 4.20-2.26 (br. m, 10H); 1.77-1.10 (br. m, 44H); 0.91 (t, 6H).

Step 2: N-Nonyl-N-(2-(piperidin-4-yl)ethyl)nonan-1-amine

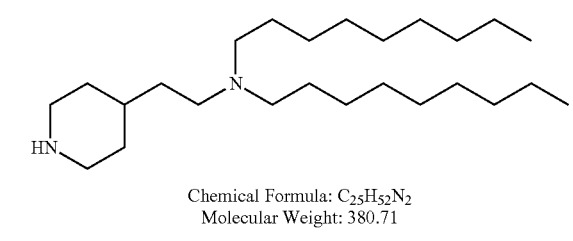 [SMILES: CCCCCCCCCN(CCCCCCCCC)CCC1CCNCC1]

Chemical Formula: $C_{25}H_{52}N_2$
Molecular Weight: 380.71

In the same manner as Step 4 for Compound 11, N-nonyl-N-(2-(piperidin-4-yl)ethyl)nonan-1-amine was synthesized from tert-butyl 4-(2-(dinonylamino)ethyl)piperidine-1-carboxylate (602 mg, 1.25 mmol) and TFA (4.8 mL, 63 mmol) in DCM (5 mL). Yield (406 mg, 85%).

UPLC/ELSD: RT=1.27 min. MS (ES): m/z (MH⁺) 382 for $C_{25}H_{52}N_2$

¹H-NMR (300 MHz, CDCl₃) δ: ppm 3.15 (br. m, 2H); 2.65 (br. m, 2H); 2.42 (br. m, 6H); 1.83-1.04 (br. m, 35H); 0.90 (t, 6H).

Step 3: 2-((2-(Dinonylamino)ethyl)(nonyl)amino)-1-(4-(2-(dinonylamino)ethyl)piperidin-1-yl)ethan-1-one

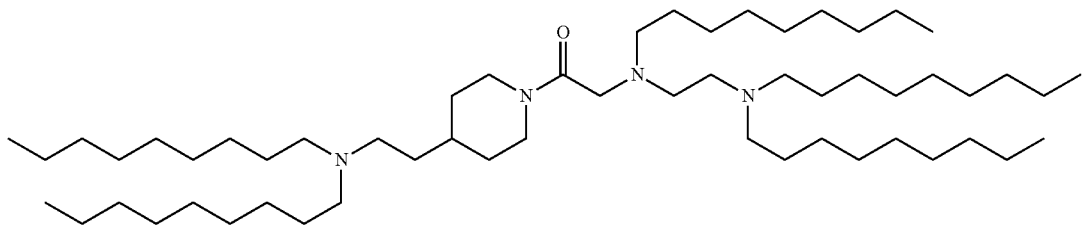

Chemical Formula: $C_{56}H_{114}N_4O$
Molecular Weight: 859.56

In the same manner as Step 11 for Compound 11, 2-((2-(dinonylamino)ethyl)(nonyl)amino)-1-(4-(2-(dinonylamino)ethyl)piperidin-1-yl)ethan-1-one was synthesized from N-nonyl-N-(2-(piperidin-4-yl)ethyl)nonan-1-amine (200 mg, 0.53 mmol), N-(2-(dinonylamino)ethyl)-N-nonylglycine (287 mg, 0.58 mmol), iPr₂EtN (201 μL, 1.2 mmol), and T3P (50% EtOAc solution, 938 μL, 1.6 mmol) in THF (10 mL). Yield (90 mg, 20%).

UPLC/ELSD: RT=3.26 min. MS (ES): m/z (MH⁺) 860 for $C_{56}H_{114}N_4O$

¹H-NMR (300 MHz, CDCl₃) δ: ppm 4.62-4.09 (br. m, 2H); 3.55-2.21 (br. m, 20H); 1.94-1.00 (br. m, 77H); 0.91 (t, 15H).

AZ: Compound 50: 2-(Dinonylamino)-1-(4-(2-((2-(dinonylamino)ethyl)(nonyl)amino)ethyl)piperidin-1-yl)ethan-1-one Step 1: tert-Butyl 4-(2-(nonylamino)ethyl)piperidine-1-carboxylate

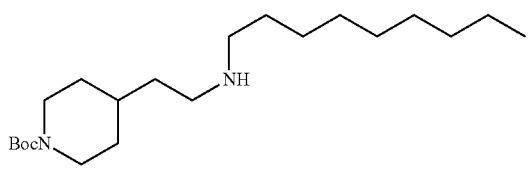

Chemical Formula: $C_{21}H_{42}N_2O_2$
Molecular Weight: 354.58

In the same manner as Step 1 for Compound 49, tert-butyl 4-(2-(nonylamino)ethyl)piperidine-1-carboxylate was synthesized from tert-butyl 4-(2-aminoethyl)piperidine-1-carboxylate (1.50 g, 6.6 mmol), 1-bromononane (1.36 g, 6.57 mmol), K₂CO₃ (1.83 g, 13.1 mmol), and KI (109 mg, 0.66 mmol) in MeCN (100 mL). Yield (288 mg, 13%).

UPLC/ELSD: RT=1.23 min. MS (ES): m/z (MH⁺) 356 for $C_{21}H_{42}N_2O_2$

¹H-NMR (300 MHz, CDCl₃) δ: ppm 4.08 (br. m, 2H); 2.67 (br. m, 6H); 1.80-0.98 (br. m, 30H); 0.90 (t, 3H).

Step 2: tert-Butyl 4-(2-((2-(dinonylamino)ethyl)(nonyl)amino)ethyl)piperidine-1-carboxylate

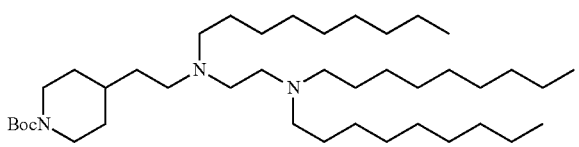

Chemical Formula: $C_{41}H_{83}N_3O_2$
Molecular Weight: 650.13

To a mixture of tert-butyl 4-(2-(nonylamino)ethyl)piperidine-1-carboxylate (288 mg, 0.81 mmol) and N-(2-chloroethyl)-N-nonylnonan-1-amine (297 mg, 0.89 mmol) in MeCN (20 mL) was added K₂CO₃ (249 mg, 1.79 mmol), and KI (13 mg, 0.08 mmol) and the mixture was allowed to stir at 82° C. for 12 hours. The suspension was cooled to RT and filtered over a pad of celite rinsing with hexanes, and concentrated. Purification by ISCO silica flash chromatography (0-100% DCM/[DCM 20% MeOH 1% NH₄OH]) provided tert-butyl 4-(2-((2-(dinonylamino)ethyl)(nonyl)amino)ethyl)piperidine-1-carboxylate (216 mg, 41%)

UPLC/ELSD: RT=2.72 min. MS (ES): m/z (MH⁺) 651 for $C_{41}H_{83}N_3O_2$

¹H-NMR (300 MHz, CDCl₃) δ: ppm 4.08 (br, 2H); 2.83-2.29 (br. m, 14H); 1.75-1.00 (br. m, 58H); 0.90 (t, 9H).

Step 3: N¹,N¹,N²-Trinonyl-N²-(2-(piperidin-4-yl)ethyl)ethane-1,2-diamine

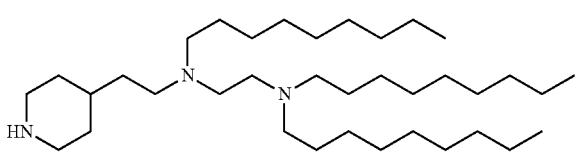

Chemical Formula: $C_{36}H_{75}N_3$
Molecular Weight: 550.02

In the same manner as Step 6 for Compound 44, $N^1,N^1,N^2$-trinonyl-$N^2$-(2-(piperidin-4-yl)ethyl)ethane-1,2-diamine was synthesized from tert-butyl 4-(2-((2-(dinonylamino)ethyl)(nonyl)amino)ethyl)piperidine-1-carboxylate (216 mg, 0.33 mmol) and TFA (1.27 mL, 16.6 mmol) in DCM (2 mL). Yield (178 mg, 97%).

UPLC/ELSD: RT=1.84 min. MS (ES): m/z (MH$^+$) 551 for $C_{36}H_{75}N_3$ $^1$H-NMR (300 MHz, CDCl$_3$) δ: ppm 3.08 (br. m, 2H); 2.70-2.25 (br. m, 14H); 2.0 (br, 1H); 1.80-1.02 (br. m, 49H); 0.90 (t, 9H).

Step 4: 2-(Dinonylamino)-1-(4-(2-((2-(dinonylamino)ethyl)(nonyl)amino)ethyl)piperidin-1-yl)ethan-1-one

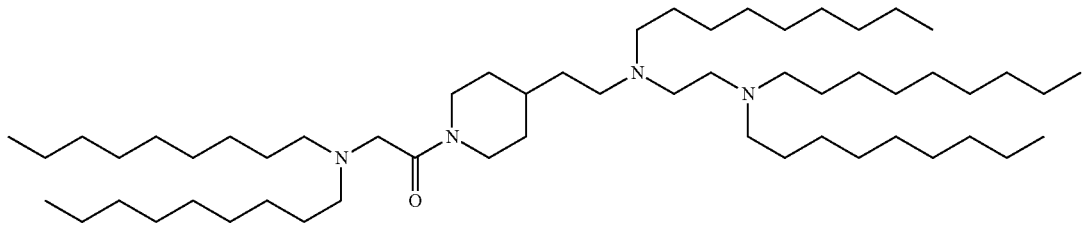

Chemical Formula: $C_{56}H_{114}N_4O$
Molecular Weight: 859.56

In the same manner as Step 7 for Compound 44, 2-(dinonylamino)-1-(4-(2-((2-(dinonylamino)ethyl)(nonyl)amino)ethyl)piperidin-1-yl)ethan-1-one was synthesized from dinonylglycine (96 mg, 0.29 mmol), $N^1,N^1,N^2$-trinonyl-$N^2$-(2-(piperidin-4-yl)ethyl)ethane-1,2-diamine (178 mg, 0.32 mmol), iPr$_2$EtN (112 µL, 0.65 mmol), and T3P (50% EtOAc solution, 525 µL, 0.88 mmol) in THF (6 mL). Yield (121 mg, 48%).

UPLC/ELSD: RT=2.96 min. MS (ES): m/z (MH$^+$) 860 for $C_{56}H_{114}N_4O$ $^1$H-NMR (300 MHz, CDCl$_3$) δ: ppm 4.63-4.08 (br. m, 4H); 3.34-2.25 (br. m, 18H); 1.90-1.01 (br. m, 77H); 0.91 (t, 15H).

BA: Compound 51: 2-((2-(Dinonylamino)ethyl)(nonyl)amino)-1-(4-(ditetradecylglycyl)piperazin-1-yl)ethan-1-one

Step 1: Methyl Ditetradecylglycinate

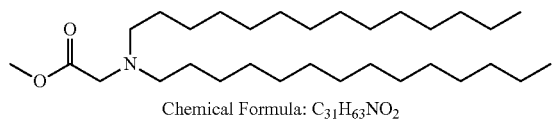

Chemical Formula: $C_{31}H_{63}NO_2$
Molecular Weight: 481.85

In the same manner as Step 1 from Compound 11, methyl 3-(ditetradecylamino)propanoate was synthesized from glycine methyl ester hydrochloride (564 mg, 4.49 mmol), tetradecanal (2.1 g, 9.89 mmol), sodium triacetoxyborohydride (2.1 g, 9.89 mmol), acetic acid (0.6 mL, 9.89 mmol), trimethylamine (0.93 mL, 6.74 mmol), in DCE (22 mL). Yield (1.93 g, 89%).

$^1$H-NMR (300 MHz, CDCl$_3$) δ: ppm 3.72 (s, 3H); 3.34 (s, 2H); 1.56 (t, 4H); 1.60-1.03 (br. m, 48H); 0.91 (t, 6H).

Step 2: Lithium Ditetradecylglycinate

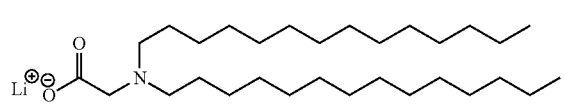

Chemical Formula: $C_{30}H_{60}LiNO_2$
Molecular Weight: 473.76

In the same manner as Step 2 from Compound 11, lithium ditetradecylglycinate was synthesized from methyl ditetradecylglycinate (1.93 g, 4.0 mmol) and 1M LiOH (20 mL, 20 mmol) in THF (20 mL). Yield (1.81 g, 97%).

$^1$H-NMR (300 MHz, CDCl$_3$) δ: ppm 3.17 (s, 2H); 2.64 (t, 4H); 1.52 (br. m, 4H); 1.31 (br. m, 44H); 0.93 (t, 6H).

Step 3: 2-((2-(Dinonylamino)ethyl)(nonyl)amino)-1-(4-(ditetradecylglycyl)piperazin-1-yl)ethan-1-one

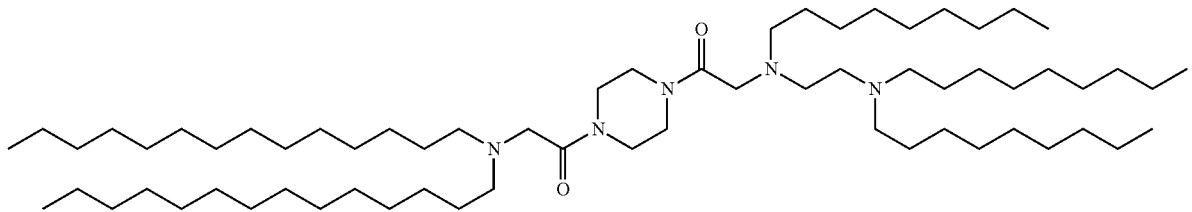

Chemical Formula: C$_{65}$H$_{131}$N$_5$O$_2$
Molecular Weight: 1014.80

In the same manner as Step 7 for Compound 44, 2-((2-(dinonylamino)ethyl)(nonyl)amino)-1-(4-(ditetradecylglycyl)piperazin-1-yl)ethan-1-one was synthesized from lithium ditetradecylglycinate (126 mg, 0.26 mmol), 2-((2-(dinonylamino)ethyl)(nonyl)amino)-1-(piperazin-1-yl)ethan-1-one (134 mg, 0.24 mmol), iPr$_2$EtN (91 μL, 0.52 mmol), and T3P (50% EtOAc solution, 424 μL, 0.71 mmol) in THF (4 mL)

UPLC/ELSD: RT=3.64 min. MS (ES): m/z (MH$^+$) 1016 for C$_{65}$H$_{131}$N$_5$O$_2$ $^1$H-NMR (300 MHz, CDCl$_3$) δ: ppm 3.84-2.34 (br. m, 26H); 1.88-0.99 (br. m, 90H); 0.90 (t, 15H).

BB: Compound 52: 3-(Dinonylamino)-1-(4-(3-((2-(dinonylamino)ethyl)(nonyl)amino)propanoyl)piperazin-1-yl)propan-1-one Step 1: Methyl 3-(dinonylamino)propanoate

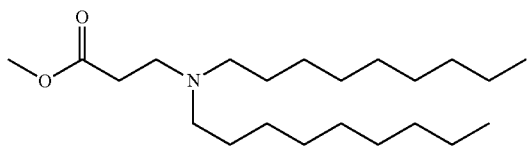

Chemical Formula: C$_{22}$H$_{45}$NO$_2$
Molecular Weight: 355.61

To a mixture of methyl 3-aminopropanoate hydrochloride (2.0 g, 14 mmol) and 1-bromononane (2.7 mL, 14 mmol) in MeCN (100 mL) was added K$_2$CO$_3$ (4.0 g, 29 mmol) and KI (238 mg, 1.4 mmol) and the mixture was allowed to stir at 82° C. for 12 hours. The suspension was cooled to RT and filtered over a pad of celite washing with hexanes, and concentrated in vacuo. Purification by ISCO silica flash chromatography (0-10% MeOH/DCM) provided methyl 3-(dinonylamino)propanoate (663 mg, 13%).

$^1$H-NMR (300 MHz, CDCl$_3$) δ: ppm 3.69 (s, 3H); 2.80 (t, 2H); 2.41 (br. m, 6H); 1.70-1.10 (br. m, 28H); 0.90 (t, 6H).

Step 2: Lithium 3-(dinonylamino)propanoate

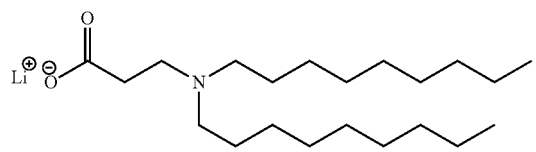

Chemical Formula: C$_{21}$H$_{42}$LiNO$_2$
Molecular Weight: 347.51

In the same manner as Step 2 from Compound 11, lithium 3-(dinonylamino)propanoate was synthesized from methyl 3-(dinonylamino)propanoate (663 mg, 1.86 mmol) and 1M LiOH (9.32 mL, 9.32 mmol) in THF (10 mL). Yield (636 mg, 99%).

$^1$H-NMR (300 MHz, CDCl$_3$) δ: ppm 2.94-1.65 (br. m, 8H); 1.65-1.04 (br. m, 28H); 0.90 (t, 6H).

tert-Butyl 4-(3-(dinonylamino)propanoyl)piperazine-1-carboxylate

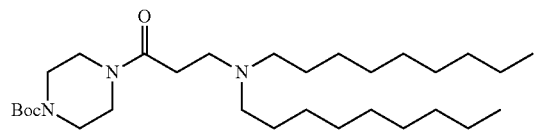

Chemical Formula: C$_{30}$H$_{59}$N$_3$O$_3$
Molecular Weight: 509.82

In the same manner as Step 3 for Compound 11, tert-butyl 4-(3-(dinonylamino)propanoyl)piperazine-1-carboxylate was synthesized from lithium 3-(dinonylamino)propanoate (636 mg, 1.83 mmol), 1-boc-piperazine (388 mg, 2.08 mmol), iPr$_2$EtN (726 μL, 4.17 mmol), and T3P (50% EtOAc solution, 3.4 mL, 5.68 mmol) in THF (20 mL). Yield (839 mg, 87%).

UPLC/ELSD: RT=2.26 min. MS (ES): m/z (MH$^+$) 511 for C$_{30}$H$_{59}$N$_3$O$_3$ $^1$H-NMR (300 MHz, CDCl$_3$) δ: ppm 3.71-2.21 (br. m, 16H); 1.92-0.98 (br. m, 37H); 0.90 (t, 6H).

Step 3: 3-(Dinonylamino)-1-(piperazin-1-yl)propan-1-one

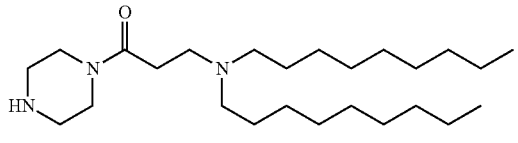

Chemical Formula: $C_{25}H_{51}N_3O$
Molecular Weight: 409.70

In the same manner as Step 4 for Compound 11, 3-(dinonylamino)-1-(piperazin-1-yl)propan-1-one was synthesized from tert-butyl 4-(3-(dinonylamino)propanoyl)piperazine-1-carboxylate (839 mg, 1.65 mmol), and TFA (6.3 mL, 83 mmol) in DCM (7 mL). Yield (501 mg, 74%).

UPLC/ELSD: RT=1.19 min. MS (ES): m/z (MH$^+$) 411 for $C_{25}H_{51}N_3O$ $^1$H-NMR (300 MHz, CDCl$_3$) δ: ppm 3.61 (t, 2H); 3.47 (t, 2H); 2.86 (br. m, 6H); 2.46 (br. m, 6H); 1.80 (br, 1H); 1.56-1.08 (br. m, 28H); 0.90 (t, 6H).

Step 4: Methyl 3-(nonylamino)propanoate

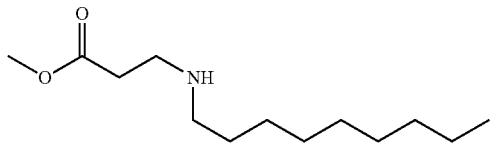

Chemical Formula: $C_{13}H_{27}NO_2$
Molecular Weight: 229.36

In the same manner as Step 1 for Compound 52, methyl 3-(nonylamino)propanoate was synthesized from methyl 3-aminopropanoate hydrochloride (2.0 g, 14 mmol), 1-bromononane (2.7 mL, 14 mmol), K$_2$CO$_3$ (4.0 g, 29 mmol) and KI (238 mg, 1.4 mmol) in MeCN (100 mL). Yield (300 mg, 9%)

$^1$H-NMR (300 MHz, CDCl$_3$) δ: ppm 3.70 (s, 3H); 2.91 (t, 2H); 2.60 (br. m, 4H); 1.90 (br, 1H); 1.58-1.02 (br. m, 14H); 0.90 (t, 3H).

Step 5: Methyl 3-((2-(dinonylamino)ethyl)(nonyl)amino)propanoate

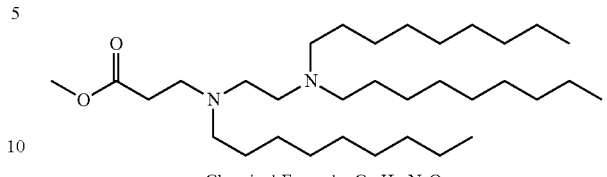

Chemical Formula: $C_{33}H_{68}N_2O_2$
Molecular Weight: 524.92

In the same manner as Step 9 from Compound 10, methyl 3-((2-(dinonylamino)ethyl)(nonyl)amino)propanoate was synthesized from methyl 3-(nonylamino)propanoate (300 mg, 1.31 mmol), N-(2-chloroethyl)-N-nonylnonan-1-amine (478 mg, 1.44 mmol), K$_2$CO$_3$ (400 mg, 2.88 mmol), and KI (22 mg, 0.13 mmol) in MeCN (20 mL). Yield (348 mg, 51%).

UPLC/ELSD: RT=2.66 min. MS (ES): m/z (MH$^+$) 526 for $C_{33}H_{68}N_2O_2$ $^1$H-NMR (300 MHz, CDCl$_3$) δ: ppm 3.69 (s, 3H); 2.82 (t, 2H); 2.44 (br. m, 12H); 1.85-1.05 (br. m, 42H); 0.90 (t, 9H).

Step 6: 3-((2-(Dinonylamino)ethyl)(nonyl)amino)propanoic Acid

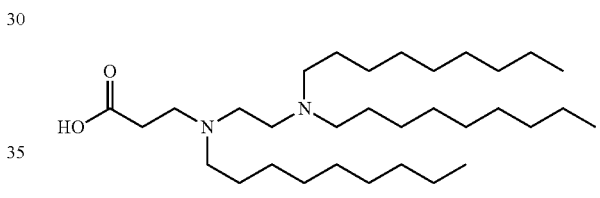

Chemical Formula: $C_{32}H_{66}N_2O_2$
Molecular Weight: 510.89

In the same manner as Step 10 from Compound 10, 3-((2-(dinonylamino)ethyl)(nonyl)amino)propanoic acid was synthesized from methyl 3-((2-(dinonylamino)ethyl)(nonyl)amino)propanoate (348 mg, 0.66 mmol) and 1M LiOH (3.3 mL, 3.3 mmol) in THF (3.3 mL). Yield (338 mg, 99%).

UPLC/ELSD: RT=2.29 min. MS (ES): m/z (MH$^+$) 512 for $C_{32}H_{66}N_2O_2$

Step 7: 3-(Dinonylamino)-1-(4-(3-((2-(dinonylamino)ethyl)(nonyl)amino)propanoyl)piperazin-1-yl)propan-1-one

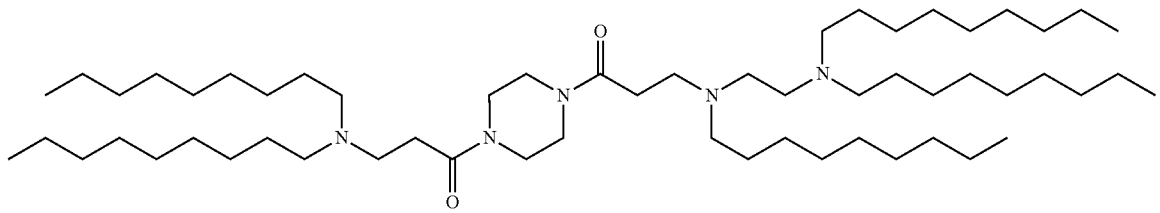

Chemical Formula: $C_{57}H_{115}N_5O_2$
Molecular Weight: 902.58

In the same manner as Step 11 for Compound 11, 3-(dinonylamino)-1-(4-(3-((2-(dinonylamino)ethyl)(nonyl)amino)propanoyl)piperazin-1-yl)propan-1-one was synthesized from 3-(dinonylamino)-1-(piperazin-1-yl)propan-1-one (298 mg, 0.73 mmol), 3-((2-(dinonylamino)ethyl)(nonyl)amino)propanoic acid (338 mg, 0.68 mmol), iPr$_2$EtN (254 µL, 1.46 mmol), and T3P (50% EtOAc solution, 1.18 mL, 1.98 mmol) in THF (10 mL). Yield (218 mg, 37%).

UPLC/ELSD: RT=2.89 min. MS (ES): m/z (MH$^+$) 903 for C$_{57}$H$_{115}$N$_5$O$_2$ $^1$H-NMR (300 MHz, CDCl$_3$) δ: ppm 3.65 (br. m, 4H); 3.50 (br. m, 4H); 2.82 (br. m, 4H); 2.66-2.30 (br. m, 18H); 1.61-1.02 (br. m, 70H); 0.90 (t, 15H).

BC: Compound 53: Ethyl 7-((2-(4-(N-(2-(dinonylamino)ethyl)-N-nonylglycyl)piperazin-1-yl)-2-oxoethyl)(nonyl)amino)heptanoate Step 1: Ethyl 7-bromoheptanoate

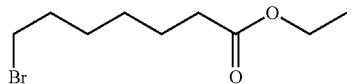

Chemical Formula: C$_9$H$_{17}$BrO$_2$
Molecular Weight: 237.14

In the same manner as Step 1 for Compound 15, ethyl 7-bromoheptanoate was synthesized from 7-bromoheptanoic acid (1.0 g, 4.8 mmol), ethanol (5.6 mL, 96 mmol), and H$_2$SO$_4$ (0.25 mL, 4.8 mmol) in THF (6 mL). Yield (911 mg, 80%).

$^1$H-NMR (300 MHz, CDCl$_3$) δ: ppm 4.15 (q, 2H); 3.42 (t, 2H); 2.33 (t, 2H); 1.87 (m, 2H); 1.66 (m, 2H); 1.57-1.14 (br. m, 7H).

Step 2: Ethyl 7-((2-(tert-butoxy)-2-oxoethyl)(nonyl)amino)heptanoate

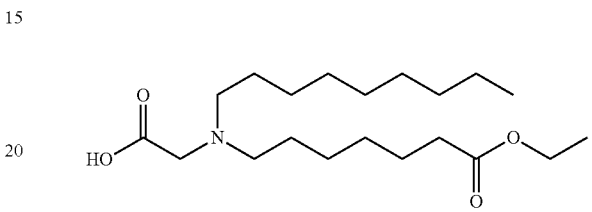

Chemical Formula: C$_{24}$H$_{47}$NO$_4$
Molecular Weight: 413.64

In the same manner as Step 3 for Compound 44, ethyl 7-((2-(tert-butoxy)-2-oxoethyl)(nonyl)amino)heptanoate was synthesized from tert-butyl nonylglycinate (250 mg, 0.97 mmol), ethyl 7-bromoheptanoate (253 mg, 1.07 mmol), K$_2$CO$_3$ (270 mg, 1.94 mmol), and KI (16 mg, 0.10 mmol) in MeCN (10 mL). Yield (298 mg, 74%).

UPLC/ELSD: RT=1.60 min. MS (ES): m/z (MH$^+$) 414.68 for C$_{24}$H$_{47}$NO$_4$ $^1$H-NMR (300 MHz, CDCl$_3$) δ: ppm 4.14 (q, 2H); 3.23 (s, 2H); 2.57 (t, 4H); 2.31 (t, 2H); 1.74-1.12 (br. m, 34H); 0.90 (t, 3H).

Step 3: N-(7-Ethoxy-7-oxoheptyl)-N-nonylglycine

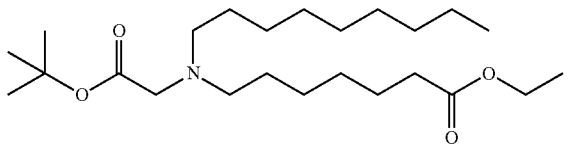

Chemical Formula: C$_{20}$H$_{39}$NO$_4$
Molecular Weight: 357.54

In the same manner as Step 4 for Compound 44, N-(7-ethoxy-7-oxoheptyl)-N-nonylglycine was synthesized from ethyl 7-((2-(tert-butoxy)-2-oxoethyl)(nonyl)amino)heptanoate (298 mg, 0.72 mmol), and TFA (2.8 mL, 36 mmol) in DCM (3 mL). Yield (244 mg, 95%).

UPLC/ELSD: RT=1.07 min. MS (ES): m/z (MH$^+$) 358.50 for C$_{20}$H$_{39}$NO$_4$ $^1$H-NMR (300 MHz, CDCl$_3$) δ: ppm 4.15 (q, 2H); 3.46 (br, 2H); 3.01 (br, 4H); 2.31 (t, 2H); 1.86-1.10 (br. m, 25H); 0.91 (t, 3H).

Step 4: Ethyl 7-((2-(4-(N-(2-(dinonylamino)ethyl)-N-nonylglycyl)piperazin-1-yl)-2-oxoethyl)(nonyl)amino)heptanoate

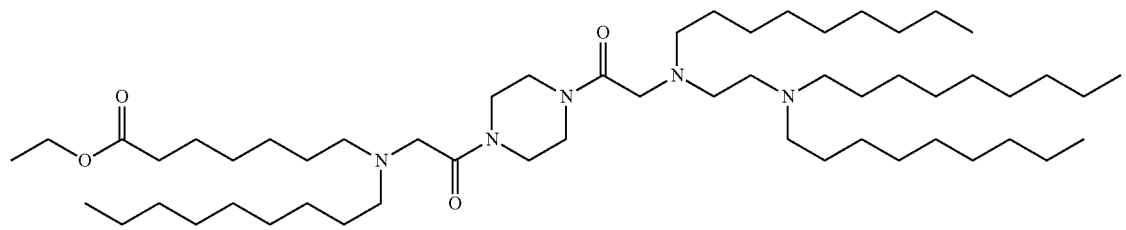

Chemical Formula: C$_{55}$H$_{109}$N$_5$O$_4$
Moleuclar Weight: 904.51

In the same manner as Step 7 for Compound 44, ethyl 7-((2-(4-(N-(2-(dinonylamino)ethyl)-N-nonylglycyl)piperazin-1-yl)-2-oxoethyl)(nonyl)amino)heptanoate was synthesized from N-(7-ethoxy-7-oxoheptyl)-N-nonylglycine (111 mg, 0.31 mmol), 2-((2-(dinonylamino)ethyl)(nonyl)amino)-1-(piperazin-1-yl)ethan-1-one (160 mg, 0.28 mmol), iPr₂EtN (109 μL, 0.62 mmol), and T3P (50% EtOAc solution, 0.51 mL, 0.81 mmol) in THF (10 mL). Yield (70 mg, 27%).

UPLC/ELSD: RT=2.88 min. MS (ES): m z (MH⁺) 905.33 for $C_{55}H_{109}N_5O_4$

¹H-NMR (300 MHz, CDCl₃) δ: ppm 4.00 (q, 2H); 3.65-3.34 (br. m, 8H); 3.19 (s, 2H); 3.13 (s, 2H); 2.50-2.10 (br. m, 16H); 1.65-0.90 (br. m, 67H); 0.75 (t, 12H).

BD: Compound 54: Propyl 6-((2-(4-(N-(2-(dinonylamino)ethyl)-N-nonylglycyl)piperazin-1-yl)-2-oxoethyl)(nonyl)amino)hexanoate Step 1: Propyl 6-bromohexanoate

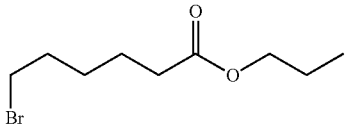

Chemical Formula: $C_9H_{17}BrO_2$
Molecular Weight: 237.14

In the same manner as Step 1 for Compound 15, propyl 6-bromohexanoate was synthesized from 6-bromohexanoic acid (1.0 g, 5.1 mmol), 1-propanol (1.5 g, 26 mmol), and H₂SO₄ (0.27 mL, 5.1 mmol) in THF (5 mL). Yield (1.14 g, 94%).

¹H-NMR (300 MHz, CDCl₃) δ: ppm 4.05 (t, 2H); 3.43 (t, 2H); 2.34 (t, 2H); 1.90 (m, 2H); 1.68 (m, 4H); 1.50 (m, 2H); 0.96 (t, 3H).

Step 2: Propyl 6-((2-(tert-butoxy)-2-oxoethyl)(nonyl)amino)hexanoate

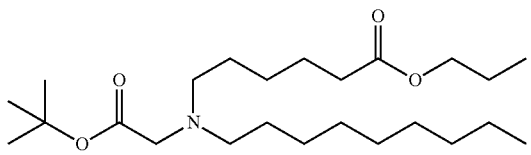

Chemical Formula: $C_{24}H_{47}NO_4$
Molecular Weight: 413.64

In the same manner as Step 3 for Compound 44, propyl 6-((2-(tert-butoxy)-2-oxoethyl)(nonyl)amino)hexanoate was synthesized from tert-butyl nonylglycinate (250 mg, 0.97 mmol), propyl 6-bromohexanoate (253 mg, 1.07 mmol), K₂CO₃ (270 mg, 1.94 mmol), and KI (16 mg, 0.10 mmol) in MeCN (10 mL). Yield (258 mg, 64%).

UPLC/ELSD: RT=1.62 min. MS (ES): m/z (MH⁺) 414.59 for $C_{24}H_{47}NO_4$

¹H-NMR (300 MHz, CDCl₃) δ: ppm 4.05 (t, 2H); 3.23 (s, 2H); 2.58 (br. m, 4H); 2.33 (t, 2H); 1.75-1.15 (br. m, 31H); 0.91 (m, 6H).

Step 3: N-Nonyl-N-(6-oxo-6-propoxyhexyl)glycine

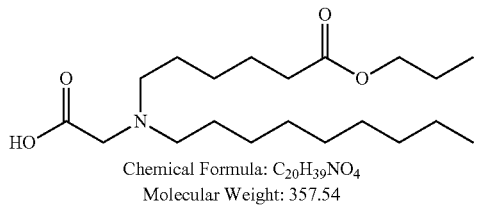 [SMILES: CCCCCCCCCN(CCCCCC(=O)OCCC)CC(=O)O]

Chemical Formula: $C_{20}H_{39}NO_4$
Molecular Weight: 357.54

In the same manner as Step 4 for Compound 44, N-nonyl-N-(6-oxo-6-propoxyhexyl)glycine was synthesized from propyl 6-((2-(tert-butoxy)-2-oxoethyl)(nonyl)amino)hexanoate (258 mg, 0.62 mmol), and TFA (2.4 mL, 31 mmol) in DCM (3 mL). Yield (223 mg, 99%).

UPLC/ELSD: RT=1.13 min. MS (ES): m/z (MH⁺) 358.50 for $C_{20}H_{39}NO_4$

¹H-NMR (300 MHz, CDCl₃) δ: ppm 4.09 (t, 2H); 3.34 (s, 2H); 2.87 (br. m, 4H); 2.36 (t, 2H); 1.77-1.10 (br. m, 22H); 0.92 (m, 6H).

Step 4: Propyl 6-((2-(4-(N-(2-(dinonylamino)ethyl)-N-nonylglycyl)piperazin-1-yl)-2-oxoethyl)(nonyl)amino)hexanoate

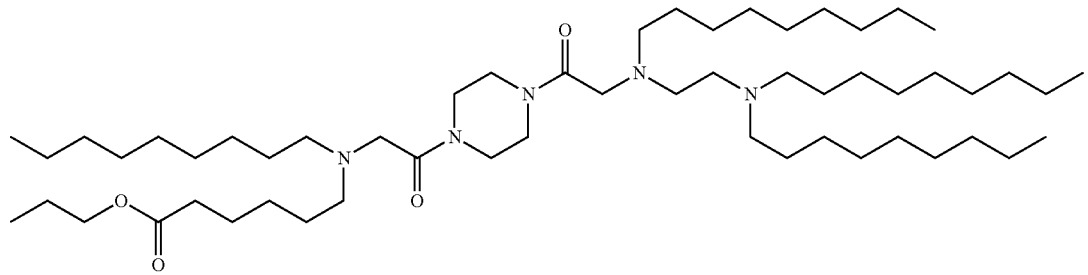

Chemical Formula: $C_{55}H_{109}N_5O_4$
Molecular Weight: 904.51

In the same manner as Step 7 for Compound 44, propyl 6-((2-(4-(N-(2-(dinonylamino)ethyl)-N-nonylglycyl)piperazin-1-yl)-2-oxoethyl)(nonyl)amino)hexanoate was synthesized from N-nonyl-N-(6-oxo-6-propoxyhexyl)glycine (111 mg, 0.31 mmol), 2-((2-(dinonylamino)ethyl)(nonyl)amino)-1-(piperazin-1-yl)ethan-1-one (160 mg, 0.28 mmol), iPr$_2$EtN (109 μL, 0.62 mmol), and T3P (50% EtOAc solution, 0.51 mL, 0.81 mmol) in THF (10 mL). Yield (72 mg, 28%).

UPLC/ELSD: RT=2.91 min. MS (ES): m/z (MH$^+$) 905.33 for C$_{55}$H$_{109}$N$_5$O$_4$ $^1$H-NMR (300 MHz, CDCl$_3$) δ: ppm 4.09 (t, 2H); 3.78-3.46 (br. m, 8H); 3.34 (s, 2H); 3.28 (s, 2H); 2.68-2.24 (br. m, 16H); 1.85-1.10 (br. m, 64H); 0.92 (m, 15H).

BE: Compound 55: Butyl 5-((2-(4-(N-(2-(dinonylamino)ethyl)-N-nonylglycyl)piperazin-1-yl)-2-oxoethyl)(nonyl)amino)pentanoate Step 1: Butyl 5-bromopentanoate

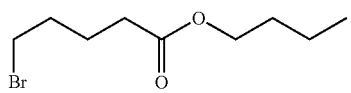

Chemical Formula: C$_9$H$_{17}$BrO$_2$
Molecular Weight: 237.14

In the same manner as Step 1 for Compound 15, butyl 5-bromopentanoate was synthesized from 5-bromopentanoic acid (1.47 g, 8.1 mmol), 1-butanol (0.50 g, 6.8 mmol), and H$_2$SO$_4$ (0.36 mL, 6.8 mmol) in THF (7 mL). Yield (1.42 g, 0.89%).

$^1$H-NMR (300 MHz, CDCl$_3$) δ: ppm 4.10 (t, 2H); 4.34 (t, 2H); 2.36 (t, 2H); 1.93 (m, 2H); 1.80 (m, 2H); 1.62 (m, 2H); 1.40 (m, 2H); 0.96 (t, 3H).

Step 2: Butyl 5-((2-(tert-butoxy)-2-oxoethyl)(nonyl)amino)pentanoate

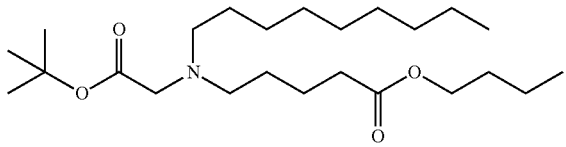

Chemical Formula: C$_{24}$H$_{47}$NO$_4$
Molecular Weight: 413.64

In the same manner as Step 3 for Compound 44, butyl 5-((2-(tert-butoxy)-2-oxoethyl)(nonyl)amino)pentanoate was synthesized from tert-butyl nonylglycinate (250 mg, 0.97 mmol), butyl 5-bromopentanoate (253 mg, 1.07 mmol), K$_2$CO$_3$ (270 mg, 1.94 mmol), and KI (16 mg, 0.10 mmol) in MeCN (10 mL). Yield (284 mg, 71%).

UPLC/ELSD: RT=1.67 min. MS (ES): m/z (MH$^+$) 414.59 for C$_{24}$H$_{47}$NO$_4$ $^1$H-NMR (300 MHz, CDCl$_3$) δ: ppm 4.09 (t, 2H); 3.23 (s, 2H); 2.58 (m, 4H); 2.34 (t, 2H); 1.74-1.20 (br. m, 31H); 0.93 (m, 6H).

Step 3: N-(5-butoxy-5-oxopentyl)-N-nonylglycine

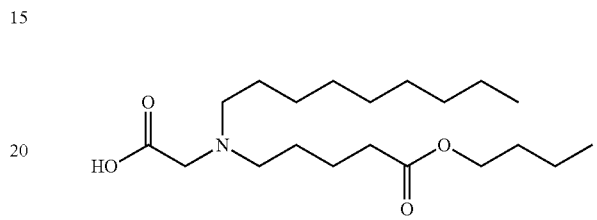

Chemical Formula: C$_{20}$H$_{39}$NO$_4$
Molecular Weight: 357.54

In the same manner as Step 4 for Compound 44, N-(5-butoxy-5-oxopentyl)-N-nonylglycine was synthesized from butyl 5-((2-(tert-butoxy)-2-oxoethyl)(nonyl)amino)pentanoate (284 mg, 0.69 mmol), and TFA (2.6 mL, 34 mmol) in DCM (3 mL). Yield (245 mg, 99%).

UPLC/ELSD: RT=1.09 min. MS (ES): m/z (MH$^+$) 358.50 for C$_{20}$H$_{39}$NO$_4$ $^1$H-NMR (300 MHz, CDCl$_3$) δ: ppm 4.05 (t, 2H); 3.48 (s, 2H); 3.03 (br. m, 4H); 2.34 (t, 2H); 1.85-1.15 (br. m, 22H); 0.93 (m, 6H).

Step 4: Butyl 5-((2-(4-(N-(2-(dinonylamino)ethyl)-N-nonylglycyl)piperazin-1-yl)-2-oxoethyl)(nonyl)amino)pentanoate

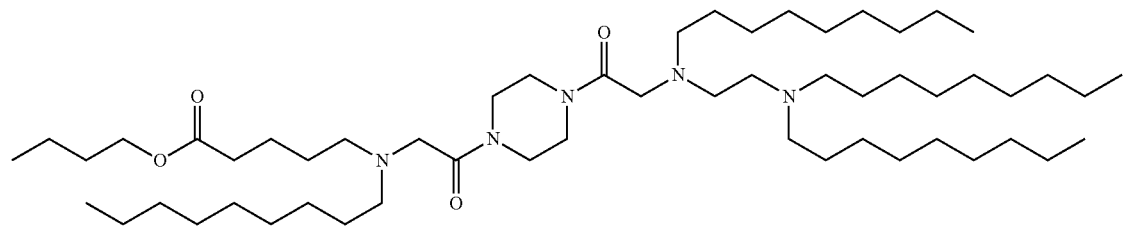

Chemical Formula: C$_{55}$H$_{109}$N$_5$O$_4$
Moleuclar Weight: 904.51

In the same manner as Step 7 for Compound 44, butyl 5-((2-(4-(N-(2-(dinonylamino)ethyl)-N-nonylglycyl)piperazin-1-yl)-2-oxoethyl)(nonyl)amino)pentanoate was synthesized from N-(5-butoxy-5-oxopentyl)-N-nonylglycine (111 mg, 0.31 mmol), 2-((2-(dinonylamino)ethyl)(nonyl)amino)-1-(piperazin-1-yl)ethan-1-one (160 mg, 0.28 mmol), iPr₂EtN (109 µL, 0.62 mmol), and T3P (50% EtOAc solution, 0.51 mL, 0.81 mmol) in THF (10 mL). Yield (92 mg, 36%).

UPLC/ELSD: RT=2.88 min. MS (ES): m/z (MH⁺) 905.33 for $C_{55}H_{109}N_5O_4$

¹H-NMR (300 MHz, CDCl₃) δ: ppm 3.90 (t, 2H); 3.65-3.35 (br. m, 8H); 3.19 (s, 2H); 3.13 (t, 2H); 2.52-2.06 (br. m, 16H); 1.65-0.95 (br. m, 64H); 0.77 (m, 15H).

BF: Compound 56: 3-((2-(4-(N-(2-(Dinonylamino) ethyl)-N-nonylglycyl)piperazin-1-yl)-2-oxoethyl) (nonyl)amino)propyl Hexanoate Step 1: 3-Bromopropyl Hexanoate

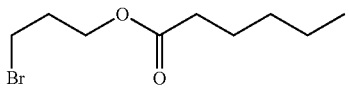

Chemical Formula: $C_9H_{17}BrO_2$
Molecular Weight: 237.14

In the same manner as Step 1 for Compound 15, 3-bromopropyl hexanoate was synthesized from 3-bromopropan-1-ol (0.87 mL, 9.6 mmol), hexanoic acid (1.0 mL, 8.0 mmol), and H₂SO₄ (1.0 mL, 8.0 mmol) in THF (10 mL). Yield (823 mg, 44%).

¹H-NMR (300 MHz, CDCl₃) δ: ppm 4.23 (t, 2H); 3.49 (t, 2H), 2.33 (t, 2H); 2.20 (m, 2H); 1.65 (m, 2H); 1.34 (m, 4H), 0.91 (t, 3H).

Step 2: 3-((2-(tert-Butoxy 2-oxoethyl)(nonyl)amino) propyl Hexanoate

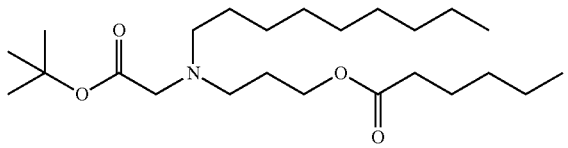

Chemical Formula: $C_{24}H_{47}NO_4$
Molecular Weight: 413.64

In the same manner as Step 3 for Compound 44, 3-((2-(tert-butoxy)-2-oxoethyl)(nonyl)amino)propyl hexanoate was synthesized from tert-butyl nonylglycinate (250 mg, 0.97 mmol), 3-bromopropyl hexanoate (253 mg, 1.07 mmol), K₂CO₃ (270 mg, 1.94 mmol), and KI (16 mg, 0.10 mmol) in MeCN (10 mL). Yield (335 mg, 83%).

UPLC/ELSD: RT=1.78 min. MS (ES): m/z (MH⁺) 414.59 for $C_{24}H_{47}NO_4$

¹H-NMR (300 MHz, CDCl₃) δ: ppm 4.14 (t, 2H); 3.23 (s, 2H); 2.68 (t, 2H); 2.58 (t, 2H); 2.30 (t, 2H); 1.79 (m, 2H); 1.64 (m, 2H); 1.55-1.20 (br. m, 27H); 0.91 (m, 6H).

Step 3: N-(3-(Hexanoyloxy)propyl)-N-nonylglycine

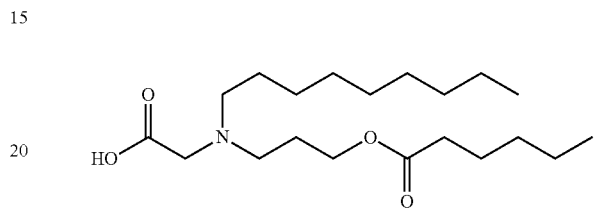

Chemical Formula: $C_{20}H_{39}NO_4$
Molecular Weight: 357.54

In the same manner as Step 4 for Compound 44, N-(3-(hexanoyloxy)propyl)-N-nonylglycine was synthesized from 3-((2-(tert-butoxy)-2-oxoethyl)(nonyl)amino)propyl hexanoate (335 mg, 0.81 mmol), and TFA (3.1 mL, 40 mmol) in DCM (4 mL). Yield (284 mg, 98%).

¹H-NMR (300 MHz, CDCl₃) δ: ppm 4.11 (t, 2H); 3.17 (s, 2H); 2.68 (br. m, 4H); 2.30 (t, 2H); 1.87 (m, 2H); 1.63 (m, 2H); 1.48 (m, 2H); 1.28 (br. m, 16H); 0.91 (m, 6H).

Step 4: 3-((2-(4-(N-(2-(Dinonylamino)ethyl)-N-nonylglycyl)piperazin-1-yl)-2-oxoethyl)(nonyl) amino)propyl Hexanoate

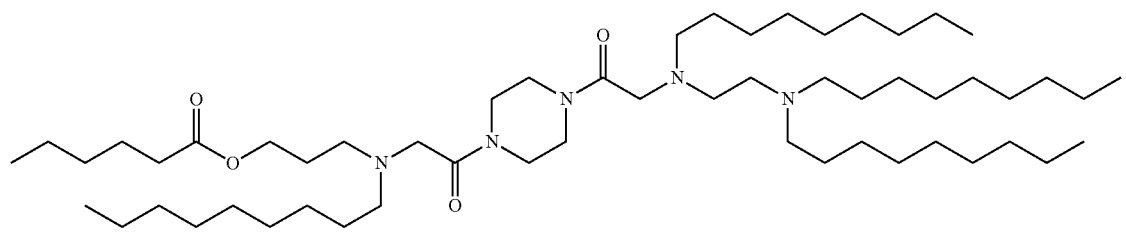

Chemical Formula: $C_{55}H_{109}N_5O_4$
Moleuclar Weight: 904.51

In the same manner as Step 7 for Compound 44, 3-((2-(4-(N-(2-(dinonylamino)ethyl)-N-nonylglycyl)piperazin-1-yl)-2-oxoethyl)(nonyl)amino)propyl hexanoate was synthesized from N-(3-(hexanoyloxy)propyl)-N-nonylglycine (111 mg, 0.31 mmol), 2-((2-(dinonylamino)ethyl)(nonyl)amino)-1-(piperazin-1-yl)ethan-1-one (160 mg, 0.28 mmol), iPr$_2$EtN (109 µL, 0.62 mmol), and T3P (50% EtOAc solution, 0.51 mL, 0.81 mmol) in THF (10 mL). Yield (55 mg, 21%).

UPLC/ELSD: RT=2.94 min. MS (ES): m/z (MH$^+$) 905.25 for C$_{55}$H$_{109}$N$_5$O$_4$ $^1$H-NMR (300 MHz, CDCl$_3$) δ: ppm 4.01 (t, 2H); 3.77-3.43 (br. m, 8H), 3.23 (m, 4H); 2.64-2.15 (m, 16H); 1.70 (m, 2H); 1.54 (m, 2H); 1.50-0.96 (br. m, 60H); 0.81 (m, 15H).

BG: Compound 57: Methyl 8-((2-(1-(N-(2-(dinonylamino)ethyl)-N-nonylglycyl)piperidin-4-yl)ethyl)(nonyl)amino)octanoate Step 1: tert-Butyl 4-(2-((8-methoxy-8-oxooctyl)(nonyl)amino)ethyl)piperidine-1-carboxylate

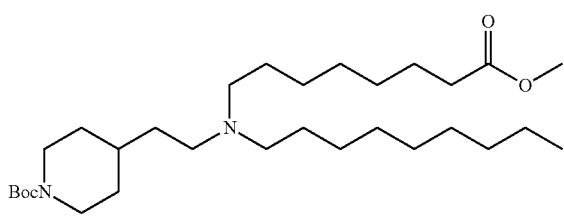

Chemical Formula: C$_{30}$H$_{58}$N$_2$O$_4$
Molecular Weight: 510.80

To a mixture of tert-butyl 4-(2-(nonylamino)ethyl)piperidine-1-carboxylate (239 mg, 0.67 mmol) and methyl 8-bromooctanoate (192 mg, 0.81 mmol) in MeCN (10 mL) was added K$_2$CO$_3$ (188 mg, 1.35 mmol) and KI (11 mg, 0.07 mmol) and the mixture was allowed to stir at 82° C. for 12 hours. The suspension was cooled to RT and filtered over a pad of celite rinsing with EtOAc, and concentrated in vacuo. Purification by ISCO silica flash chromatography (0-80% EtOAc/hexanes) provided tert-butyl 4-(2-((8-methoxy-8-oxooctyl)(nonyl)amino)ethyl)piperidine-1-carboxylate (241 mg, 70%).

UPLC/ELSD: RT=1.87 min. MS (ES): m/z (MH$^+$) 512.76 for C$_{30}$H$_{58}$N$_2$O$_4$ $^1$H-NMR (300 MHz, CDCl$_3$) δ: ppm 4.07 (br. m, 2H); 3.69 (s, 3H); 2.70 (m, 2H); 2.37 (br. m, 8H); 1.75-1.00 (br. m, 40H); 0.90 (t, 3H).

Step 2: Methyl 8-(nonyl(2-(piperidin-4-yl)ethyl)amino)octanoate

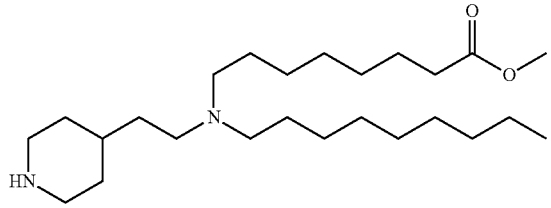

Chemical Formula: C$_{25}$H$_{50}$N$_2$O$_2$
Molecular Weight: 410.69

In the same manner as Step 4 for Compound 11, methyl 8-(nonyl(2-(piperidin-4-yl)ethyl)amino)octanoate was synthesized from tert-butyl 4-(2-((8-methoxy-8-oxooctyl)(nonyl)amino)ethyl)piperidine-1-carboxylate (241 mg, 0.47 mmol), and TFA (1.8 mL, 24 mmol) in DCM (2 mL). Yield (193 mg, 99%).

$^1$H-NMR (300 MHz, CDCl$_3$) δ: ppm 3.69 (s, 3H); 3.08 (m, 2H); 2.60 (m, 2H); 2.49-2.24 (br. m, 8H); 2.06 (br, 1H); 1.78-1.02 (br. m, 31H); 0.90 (t, 3H).

Step 3: Methyl 8-((2-(1-(N-(2-(dinonylamino)ethyl)-N-nonylglycyl)piperidin-4-yl)ethyl)(nonyl)amino)octanoate

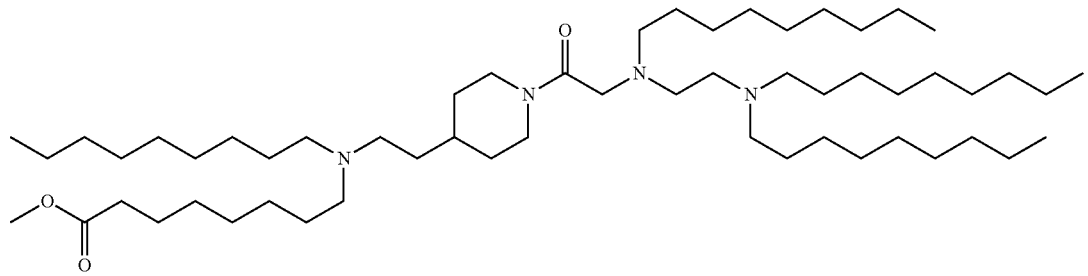

Chemical Formula: C$_{56}$H$_{112}$N$_4$O$_3$
Moleuclar Weight: 889.54

In the same manner as Step 11 for Compound 11, methyl 8-((2-(1-(N-(2-(dinonylamino)ethyl)-N-nonylglycyl)piperidin-4-yl)ethyl)(nonyl)amino)octanoate was synthesized from methyl 8-(nonyl(2-(piperidin-4-yl)ethyl)amino)octanoate (141 mg, 0.34 mmol), N-(2-(dinonylamino)ethyl)-N-nonylglycine (188 mg, 0.38 mmol), iPr$_2$EtN (132 µL, 0.76 mmol), and T3P (50% EtOAc solution, 614 µL, 1.03 mmol) in THF (10 mL). Yield (70 mg, 23%).

UPLC/ELSD: RT=2.97 min. MS (ES): m/z (MH$^+$) 890.24 for C$_{56}$H$_{112}$N$_4$O$_3$ $^1$H-NMR (300 MHz, CDCl$_3$) δ: ppm 4.64-4.09 (br. m, 2H); 3.69 (s, 3H); 3.42-2.83 (br. m, 3H); 2.69-2.24 (br. m, 19H); 1.81-0.99 (br. m, 73H); 0.90 (t, 12H).

BH: Compound 58: Ethyl 7-((2-(1-(N-(2-(dinon-ylamino)ethyl)-N-nonylglycyl)piperidin-4-yl)ethyl)(nonyl)amino)heptanoate Step 1: tert-Butyl 4-(2-((7-ethoxy-7-oxoheptyl)(nonyl)amino)ethyl)piperidine-1-carboxylate

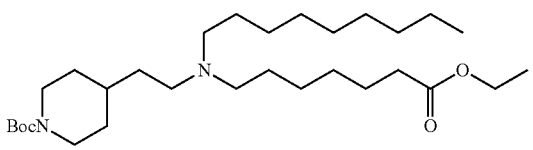

Chemical Formula: $C_{30}H_{58}N_2O_4$
Molecular Weight: 510.80

In the same manner as Step 1 for Compound 57, tert-butyl 4-(2-((7-ethoxy-7-oxoheptyl)(nonyl)amino)ethyl)piperidine-1-carboxylate was synthesized from tert-butyl 4-(2-(nonylamino)ethyl)piperidine-1-carboxylate (239 mg, 0.67 mmol), ethyl 7-bromoheptanoate (192 mg, 0.81 mmol), $K_2CO_3$ (188 mg, 1.35 mmol) and KI (11 mg, 0.07 mmol) in MeCN (10 mL). Yield (247 mg, 72%).

UPLC/ELSD: RT=1.91 min. MS (ES): m/z (MH$^+$) 511.62 for $C_{30}H_{58}N_2O_4$ $^1$H-NMR (300 MHz, CDCl$_3$) δ: ppm 4.12 (br. m, 4H); 2.80-2.15 (br. m, 10H); 1.75-1.00 (br. m, 41H); 0.90 (t, 3H).

Step 2: Ethyl 7-(nonyl(2-(piperidin-4-yl)ethyl)amino)heptanoate

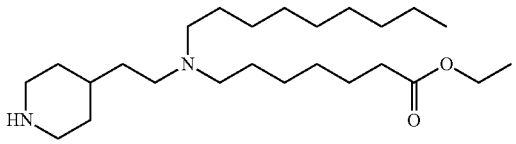

Chemical Formula: $C_{25}H_{50}N_2O_2$
Molecular Weight: 410.69

In the same manner as Step 4 for Compound 11, ethyl 7-(nonyl(2-(piperidin-4-yl)ethyl)amino)heptanoate was synthesized from tert-butyl 4-(2-((7-ethoxy-7-oxoheptyl)(nonyl)amino)ethyl)piperidine-1-carboxylate (247 mg, 0.48 mmol), and TFA (1.9 mL, 24 mmol) in DCM (2 mL). Yield (194 mg, 98%).

$^1$H-NMR (300 MHz, CDCl$_3$) δ: ppm 4.14 (t, 2H); 3.08 (m, 2H); 2.60 (m, 2H); 2.52-2.24 (br. m, 8H); 2.12 (br, 1H); 1.77-1.05 (br. m, 32H); 0.90 (t, 3H).

Ethyl 7-((2-(1-(N-(2-(dinonylamino)ethyl)-N-nonylglycyl)piperidin-4-yl)ethyl)(nonyl)amino)heptanoate In the same manner as Step 11 for Compound 11, ethyl 7-((2-(1-(N-(2-(dinonylamino)ethyl)-N-nonylglycyl)piperidin-4-yl)ethyl)(nonyl)amino)heptanoate was synthesized from ethyl 7-(nonyl(2-(piperidin-4-yl)ethyl)amino)heptanoate (141 mg, 0.34 mmol), N-(2-(dinonylamino)ethyl)-N-nonylglycine (188 mg, 0.38 mmol), iPr$_2$EtN (132 µL, 0.76 mmol), and T3P (50% EtOAc solution, 614 µL, 1.03 mmol) in THF (10 mL). Yield (42 mg, 14%). UPLC/ELSD: RT=3.00 min. MS (ES): m/z (MH$^+$) 890.32 for $C_{56}H_{112}N_4O_3$ $^1$H-NMR (300 MHz, CDCl$_3$) δ: ppm 4.55-3.95 (br. m, 4H); 3.38-2.72 (br. m, 4H); 2.66-2.10 (br. m, 18H); 1.72-0.91 (br. m, 74H); 0.81 (t, 12H).

BI: Compound 59: Propyl 6-((2-(1-(N-(2-(dinon-ylamino)ethyl)-N-nonylglycyl)piperidin-4-yl)ethyl)(nonyl)amino)hexanoate Step 1: tert-Butyl 4-(2-(nonyl(6-oxo-6-propoxyhexyl)amino)ethyl)piperidine-1-carboxylate

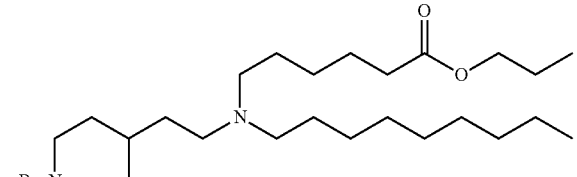

Chemical Formula: $C_{30}H_{58}N_2O_4$
Molecular Weight: 510.80

In the same manner as Step 1 for Compound 57, tert-butyl 4-(2-(nonyl(6-oxo-6-propoxyhexyl)amino)ethyl)piperidine-1-carboxylate was synthesized from tert-butyl 4-(2-(nonylamino)ethyl)piperidine-1-carboxylate (239 mg, 0.67 mmol), propyl 6-bromohexanoate (192 mg, 0.81 mmol), $K_2CO_3$ (188 mg, 1.35 mmol) and KI (11 mg, 0.07 mmol) in MeCN (10 mL). Yield (240 mg, 70%).

UPLC/ELSD: RT=1.93 min. MS (ES): m/z (MH$^+$) 511.78 for $C_{30}H_{58}N_2O_4$ $^1$H-NMR (300 MHz, CDCl$_3$) δ: ppm 4.05 (br. m, 4H); 2.80-2.20 (br. m, 10H); 1.85-1.04 (br. m, 38H); 0.92 (t, 6H).

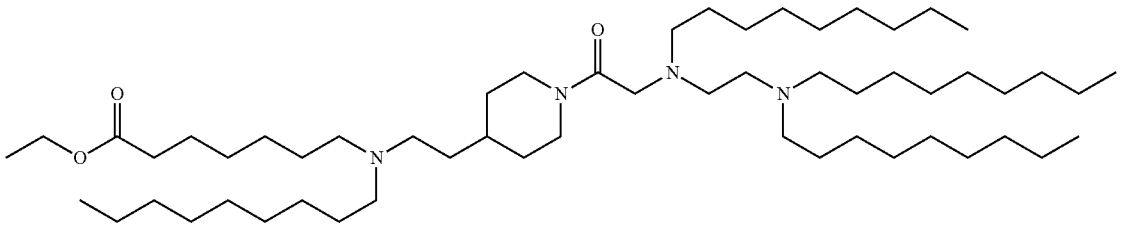

Chemical Formula: $C_{56}H_{112}N_4O_3$
Molecular Weight: 889.54

Step 2: Propyl 6-(nonyl(2-(piperidin-4-yl)ethyl)amino)hexanoate

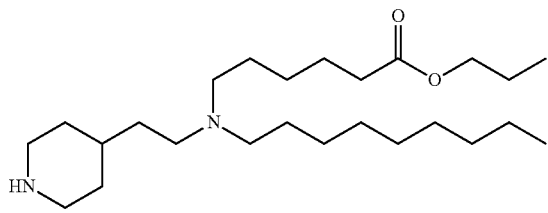

Chemical Formula: C₂₅H₅₀N₂O₂
Molecular Weight: 410.69

In the same manner as Step 4 for Compound 11, propyl 6-(nonyl(2-(piperidin-4-yl)ethyl)amino)hexanoate was synthesized from tert-butyl 4-(2-(nonyl(6-oxo-6-propoxyhexyl)amino)ethyl)piperidine-1-carboxylate (240 mg, 0.47 mmol), and TFA (1.8 mL, 23 mmol) in DCM (2 mL). Yield (183 mg, 95%).

¹H-NMR (300 MHz, CDCl₃) δ: ppm 4.04 (t, 2H); 3.08 (m, 2H); 2.60 (m, 2H); 2.35 (br. m, 8H); 1.95 (br, 1H); 1.75-1.00 (br. m, 29H); 0.92 (m, 6H).

Step 3: Propyl 6-((2-(1-(N-(2-(dinonylamino)ethyl)-N-nonylglycyl)piperidin-4-yl)ethyl)(nonyl)amino) hexanoate

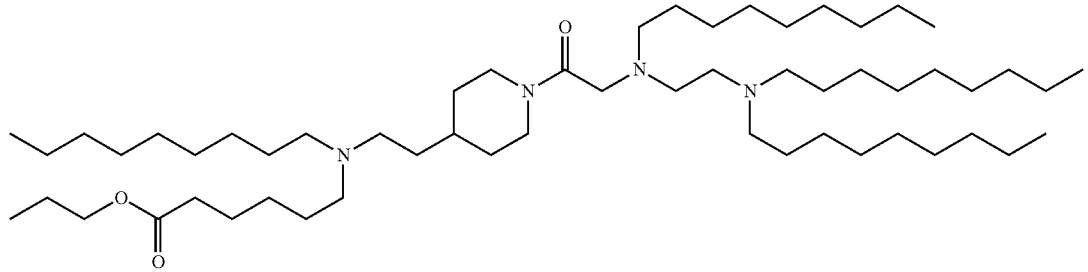

Chemical Formula: C₅₆H₁₁₂N₄O₃
Molecular Weight: 889.54

In the same manner as Step 11 for Compound 11, propyl 6-((2-(1-(N-(2-(dinonylamino)ethyl)-N-nonylglycyl)piperidin-4-yl)ethyl)(nonyl)amino)hexanoate was synthesized from propyl 6-(nonyl(2-(piperidin-4-yl)ethyl)amino) hexanoate (141 mg, 0.34 mmol), N-(2-(dinonylamino) ethyl)-N-nonylglycine (188 mg, 0.38 mmol), iPr₂EtN (132 μL, 0.76 mmol), and T3P (50% EtOAc solution, 614 μL, 1.03 mmol) in THF (10 mL). Yield (67 mg, 22%).

UPLC/ELSD: RT=3.02 min. MS (ES): m/z (MH⁺) 890.32 for C₅₆H₁₁₂N₄O₃

¹H-NMR (300 MHz, CDCl₃) δ: ppm 4.65-4.13 (br. m, 2H); 4.05 (t, 2H); 3.50-2.81 (br. m, 4H); 2.69-2.18 (br. m, 18H); 1.98-1.02 (br. m, 71H); 0.92 (br. m, 15H).

BJ: Compound 60: Butyl 5-((2-(1-(N-(2-(dinonylamino)ethyl)-N-nonylglycyl)piperidin-4-yl)ethyl)(nonyl)amino)pentanoate

Step 1: tert-Butyl 4-(2-((5-butoxy-5-oxopentyl)(nonyl)amino)ethyl)piperidine-1-carboxylate

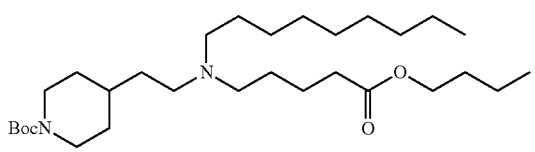

Chemical Formula: C₃₀H₅₈N₂O₄
Molecular Weight: 510.80

In the same manner as Step 1 for Compound 57, tert-butyl 4-(2-((5-butoxy-5-oxopentyl)(nonyl)amino)ethyl)piperidine-1-carboxylate was synthesized from tert-butyl 4-(2-(nonylamino)ethyl)piperidine-1-carboxylate (239 mg, 0.67 mmol), butyl 5-bromopentanoate (192 mg, 0.81 mmol), K₂CO₃ (188 mg, 1.35 mmol) and KI (11 mg, 0.07 mmol) in MeCN (10 mL). Yield (211 mg, 61%).

UPLC/ELSD: RT=1.95 min. MS (ES): m/z (MH⁺) 511.78 for C₃₀H₅₈N₂O₄

¹H-NMR (300 MHz, CDCl₃) δ: ppm 4.09 (br. m, 4H); 2.70 (br. m, 2H); 2.38 (br. m, 8H); 1.73-1.02 (br. m, 38H); 0.93 (br. m, 6H).

Step 2: Butyl 5-(nonyl(2-(piperidin-4-yl)ethyl)amino)pentanoate

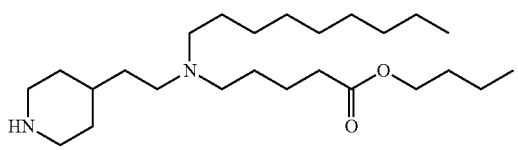

Chemical Formula: C₂₅H₅₀N₂O₂
Molecular Weight: 410.69

In the same manner as Step 4 for Compound 11, butyl 5-(nonyl(2-(piperidin-4-yl)ethyl)amino)pentanoate was synthesized from tert-butyl 4-(2-((5-butoxy-5-oxopentyl)(nonyl)amino)ethyl)piperidine-1-carboxylate (211 mg, 0.41 mmol), and TFA (1.6 mL, 21 mmol) in DCM (2 mL). Yield (169 mg, 99%).

$^1$H-NMR (300 MHz, CDCl$_3$) δ: ppm 4.09 (t, 2H); 3.07 (m, 2H); 2.60 (m, 2H); 2.37 (br. m, 8H); 1.83 (br, 1H); 1.76-1.04 (br. m, 29H); 0.93 (br. m, 6H).

Step 3: Butyl 5-((2-(1-(N-(2-(dinonylamino)ethyl)-N-nonylglycyl)piperidin-4-yl)ethyl)(nonyl)amino) pentanoate

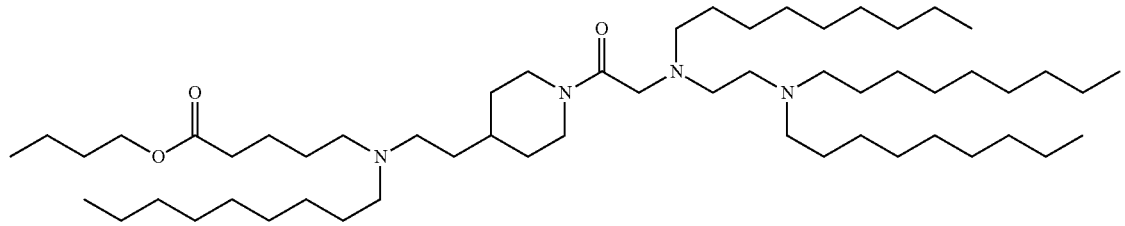

Chemical Formula: C$_{56}$H$_{112}$N$_4$O$_3$
Molecular Weight: 889.54

In the same manner as Step 11 for Compound 11, butyl 5-((2-(1-(N-(2-(dinonylamino)ethyl)-N-nonylglycyl)piperidin-4-yl)ethyl)(nonyl)amino)pentanoate was synthesized from butyl 5-(nonyl(2-(piperidin-4-yl)ethyl)amino)pentanoate (141 mg, 0.34 mmol), N-(2-(dinonylamino)ethyl)-N-nonylglycine (188 mg, 0.38 mmol), iPr$_2$EtN (132 μL, 0.76 mmol), and T3P (50% EtOAc solution, 614 μL, 1.03 mmol) in THF (10 mL). Yield (46 mg, 15%).

UPLC/ELSD: RT=3.03 min. MS (ES): m/z (MH$^+$) 890.32 for C$_{56}$H$_{112}$N$_4$O$_3$ $^1$H-NMR (300 MHz, CDCl$_3$) δ: ppm 4.62-4.13 (br. m, 2H); 4.09 (t, 2H); 3.41-2.84 (br. m, 4H); 2.72-2.25 (br. m, 18H); 1.82-1.02 (br. m, 71H); 0.91 (br. m, 15H).

BK: Compound 61: 3-((2-(1-(N-(2-(Dinonylamino) ethyl)-N-nonylglycyl)piperidin-4-yl)ethyl)(nonyl) amino)propyl hexanoate Step 1: tert-Butyl 4-(2-((3-(hexanoyloxy)propyl) (nonyl)amino)ethyl)piperidine-1-carboxylate

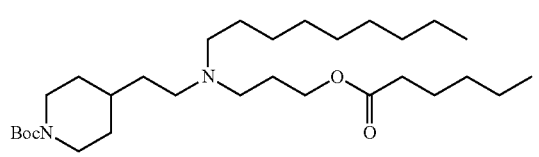

Chemical Formula: C$_{30}$H$_{58}$N$_2$O$_4$
Molecular Weight: 510.80

In the same manner as Step 1 for Compound 57, tert-butyl 4-(2-((3-(hexanoyloxy)propyl)(nonyl)amino)ethyl)piperidine-1-carboxylate was synthesized from tert-butyl 4-(2-(nonylamino)ethyl)piperidine-1-carboxylate (239 mg, 0.67 mmol), 3-bromopropyl hexanoate (192 mg, 0.81 mmol), K$_2$CO$_3$ (188 mg, 1.35 mmol) and KI (11 mg, 0.07 mmol) in MeCN (10 mL). Yield (195 mg, 57%).

UPLC/ELSD: RT=1.97 min. MS (ES): m/z (MH$^+$) 511.86 for C$_{30}$H$_{58}$N$_2$O$_4$ $^1$H-NMR (300 MHz, CDCl$_3$) δ: ppm 4.11 (br. m, 4H); 2.69 (m, 2H); 2.56-2.22 (br. m, 8H); 1.76 (m, 2H); 1.65 (m, 4H); 1.55-1.05 (br. m, 32H); 0.91 (m, 6H).

Step 2:
3-(Nonyl(2-(piperidin-4-yl)ethyl)amino)propyl Hexanoate

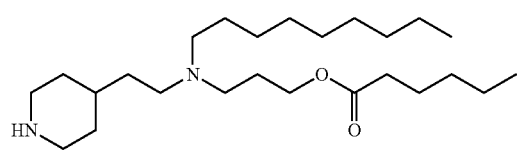

Chemical Formula: C$_{25}$H$_{50}$N$_2$O$_2$
Molecular Weight: 410.69

In the same manner as Step 4 for Compound 11, 3-(nonyl (2-(piperidin-4-yl)ethyl)amino)propyl hexanoate was synthesized from tert-butyl 4-(2-((3-(hexanoyloxy)propyl) (nonyl)amino)ethyl)piperidine-1-carboxylate (195 mg, 0.38 mmol), and TFA (1.5 mL, 19 mmol) in DCM (2 mL). Yield (149 mg, 95%).

$^1$H-NMR (300 MHz, CDCl$_3$) δ: ppm 4.12 (t, 2H); 3.08 (m, 2H); 2.70-2.22 (br. m, 10H); 2.07 (br, 1H); 1.70 (br. m, 6H); 1.48-1.00 (br. m, 23H); 0.91 (m, 6H).

Step 3: 3-((2-(1-(N-(2-(Dinonylamino)ethyl)-N-nonylglycyl)piperidin-4-yl)ethyl)(nonyl)amino)propyl Hexanoate

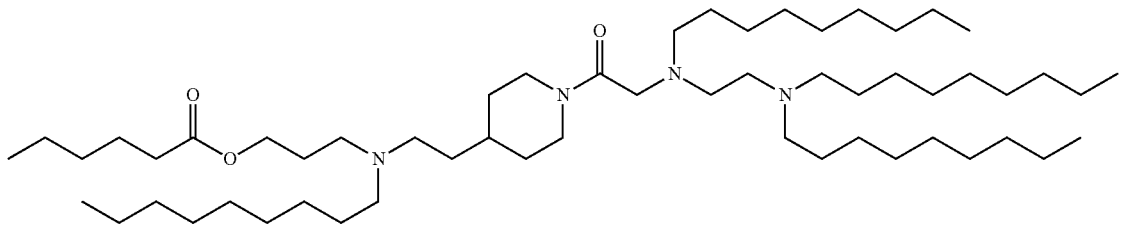

Chemical Formula: $C_{56}H_{112}N_4O_3$
Molecular Weight: 889.54

In the same manner as Step 11 for Compound 11, 3-((2-(1-(N-(2-(dinonylamino)ethyl)-N-nonylglycyl)piperidin-4-yl)ethyl)(nonyl)amino)propyl hexanoate was synthesized from 3-(nonyl(2-(piperidin-4-yl)ethyl)amino)propyl hexanoate (141 mg, 0.34 mmol), N-(2-(dinonylamino)ethyl)-N-nonylglycine (188 mg, 0.38 mmol), iPr$_2$EtN (132 µL, 0.76 mmol), and T3P (50% EtOAc solution, 614 µL, 1.03 mmol) in THF (10 mL). Yield (64 mg, 21%).

UPLC/ELSD: RT=3.02 min. MS (ES): m/z (MH$^+$) 890.41 for $C_{56}H_{112}N_4O_3$ $^1$H-NMR (300 MHz, CDCl$_3$) δ: ppm 4.67 (br. m, 4H); 3.42-2.81 (br. m, 3H); 2.73-2.23 (br. m, 19H); 1.87-1.00 (br. m, 71H); 0.90 (t, 15H).

BL: Compound 62: Pentyl 4-((3-(4-(3-((2-(dinonylamino)ethyl)(nonyl)amino)propanoyl)piperazin-1-yl)-3-oxopropyl)(nonyl)amino)butanoate Step 1: tert-Butyl 3-(nonylamino)propanoate Chemical Formula: $C_{16}H_{33}NO_2$
Molecular Weight: 271.45

In the same manner as Step 1 for Compound 44, tert-butyl 3-(nonylamino)propanoate was synthesized from tert-butyl 3-aminopropanoate hydrochloride (2.8 g, 15 mmol), 1-bromononane (3.2 g, 15 mmol), K$_2$CO$_3$ (4.3 g, 31 mmol), and KI (256 mg, 1.54 mmol) in MeCN (200 mL). Yield (1.74 g, 42%).

$^1$H-NMR (300 MHz, CDCl$_3$) δ: ppm 2.86 (t, 2H); 2.63 (t, 2H); 2.46 (t, 2H); 1.65 (br, 1H); 1.47 (br. m, 11H); 1.29 (br. m, 12H); 0.90 (t, 3H).

Step 2: Pentyl 4-((3-(tert-butoxy)-3-oxopropyl)(nonyl)amino)butanoate

Chemical Formula: $C_{25}H_{49}NO_4$
Molecular Weight: 427.67

In the same manner as Step 3 for Compound 44, pentyl 4-((3-(tert-butoxy)-3-oxopropyl)(nonyl)amino)butanoate was synthesized from tert-butyl 3-(nonylamino)propanoate (750 mg, 2.76 mmol), pentyl 4-bromobutanoate (786 mg, 3.31 mmol), K$_2$CO$_3$ (764 mg, 5.52 mmol), and KI (46 mg, 0.28 mmol) in MeCN (30 mL). Yield (934 mg, 79%).

UPLC/ELSD: RT=1.82 min. MS (ES): m/z (MH$^+$) 428.62 for $C_{25}H_{49}NO_4$ $^1$H-NMR (300 MHz, CDCl$_3$) δ: ppm 4.08 (t, 2H); 2.74 (t, 2H); 2.50-2.28 (br. m, 8H); 1.76 (m, 2H); 1.64 (m, 2H); 1.50-1.14 (br. m, 27H); 0.91 (m, 6H).

Step 3: 3-(Nonyl(4-oxo-4-(pentyloxy)butyl)amino)propanoic Acid

Chemical Formula: $C_{21}H_{41}NO_4$
Molecular Weight: 371.56

In the same manner as Step 4 for Compound 44, 3-(nonyl (4-oxo-4-(pentyloxy)butyl)amino)propanoic acid was synthesized from pentyl 4-((3-(tert-butoxy)-3-oxopropyl)(nonyl)amino)butanoate (934 mg, 2.18 mmol), and TFA (8.4 mL, 109 mmol) in DCM (10 mL). Yield (793 mg, 98%).

UPLC/ELSD: RT=1.23 min. MS (ES): m/z (MH$^+$) 372.52 for $C_{21}H_{41}NO_4$ $^1$H-NMR (300 MHz, CDCl$_3$) δ: ppm 4.10 (t, 2H); 2.88 (t, 2H); 2.70 (br. m, 4H); 2.52 (t, 2H); 2.38 (t, 2H); 1.90 (m, 2H); 1.73-1.49 (br. m, 4H); 1.47-1.17 (br. m, 16H); 0.92 (m, 6H).

Step 4: tert-Butyl 4-(3-(nonyl(4-oxo-4-(pentyloxy)butyl)amino)propanoyl)piperazine-1-carboxylate

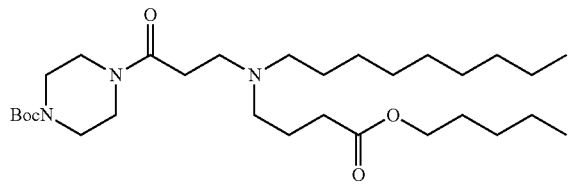

Chemical Formula: $C_{30}H_{57}N_3O_5$
Molecular Weight: 539.80

In the same manner as Step 3 for Compound 11, tert-butyl 4-(3-(nonyl(4-oxo-4-(pentyloxy)butyl)amino)propanoyl)piperazine-1-carboxylate was synthesized from 3-(nonyl(4-oxo-4-(pentyloxy)butyl)amino)propanoic acid (793 mg, 2.13 mmol), 1-boc-piperazine (477 mg, 2.56 mmol), iPr$_2$EtN (0.82 mL, 4.7 mmol), and T3P (50% EtOAc solution, 3.8 mL, 6.4 mmol). Yield (1.15 g, 99%).

UPLC/ELSD: RT=1.86 min. MS (ES): m/z (MH$^+$) 540.65 for $C_{30}H_{57}N_3O_5$

Step 5: Pentyl 4-(nonyl(3-oxo-3-(piperazin-1-yl)propyl)amino)butanoate

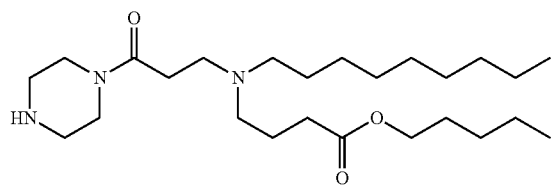

Chemical Formula: $C_{25}H_{49}N_3O_3$
Molecular Weight: 439.69

In the same manner as Step 4 for Compound 44, pentyl 4-(nonyl(3-oxo-3-(piperazin-1-yl)propyl)amino)butanoate was synthesized from tert-butyl 4-(3-(nonyl(4-oxo-4-(pentyloxy)butyl)amino)propanoyl)piperazine-1-carboxylate (1.15 g, 2.13 mmol), and TFA (8.2 mL, 106 mmol) in DCM (10 mL). Yield (901 mg, 96%).

UPLC/ELSD: RT=0.75 min. MS (ES): m/z (MH$^+$) 440.47 for $C_{25}H_{49}N_3O_3$ $^1$H-NMR (300 MHz, CDCl$_3$) δ: ppm 4.08 (t, 2H); 3.70-3.40 (br. m, 4H); 2.88 (br. m, 6H); 2.57 (br. m, 6H); 2.36 (t, 2H); 1.83 (m, 2H); 1.64 (m, 2H); 1.49 (m, 2H); 1.41-1.18 (br. m, 17H); 0.91 (m, 6H).

Step 6: tert-Butyl 3-((2-(dinonylamino)ethyl)(nonyl)amino)propanoate

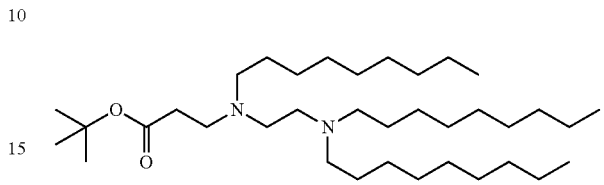

Chemical Formula: $C_{36}H_{74}N_2O_2$
Molecular Weight: 567.00

In the same manner as Step 4 for Compound 46, tert-butyl 3-((2-(dinonylamino)ethyl)(nonyl)amino)propanoate was synthesized from tert-butyl 3-(nonylamino)propanoate (1.13 mg, 4.14 mol), N-(2-chloroethyl)-N-nonylnonan-1-amine (1.65 g, 4.97 mmol), K$_2$CO$_3$ (1.15 g, 8.33 mmol), and KI (138 mg, 0.83 mmol) in MeCN (100 mL). Yield (1.41 g, 60%).

UPLC/ELSD: RT=2.90 min. MS (ES): m/z (MH$^+$) 567.79 for $C_{36}H_{74}N_2O_2$ $^1$H-NMR (300 MHz, CDCl$_3$) δ: ppm 2.78 (t, 2H); 2.69-2.29 (br. m, 12H); 1.55-1.15 (br. m, 51H); 0.90 (t, 9H).

Step 7: 3-((2-(dinonylamino)ethyl)(nonyl)amino)propanoic Acid

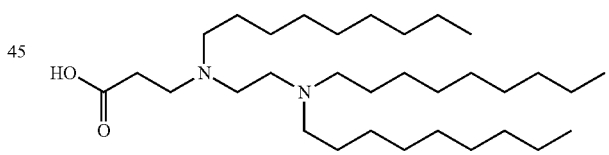

Chemical Formula: $C_{36}H_{66}N_2O_2$
Molecular Weight: 510.89

In the same manner as Step 4 for Compound 44, 3-((2-(dinonylamino)ethyl)(nonyl)amino)propanoic acid was synthesized from tert-butyl 3-((2-(dinonylamino)ethyl)(nonyl)amino)propanoate (1.41 g, 2.49 mmol), and TFA (9.6 mL, 124 mmol) in DCM (10 mL). Yield (924 mg, 73%).

UPLC/ELSD: RT=2.26 min. MS (ES): m/z (MH$^+$) 511.78 for $C_{32}H_{66}N_2O_2$ $^1$H-NMR (300 MHz, CDCl$_3$) δ: ppm 2.76 (br. m, 6H); 2.61 (br. m, 6H); 2.47 (t, 2H); 1.52 (br. m, 6H); 1.40-1.10 (br. m, 36H); 0.90 (t, 9H).

Step 8: Pentyl 4-((3-(4-(3-((2-(dinonylamino)ethyl)(nonyl)amino)propanoyl)piperazin-1-yl)-3-oxopropyl)(nonyl)amino)butanoate

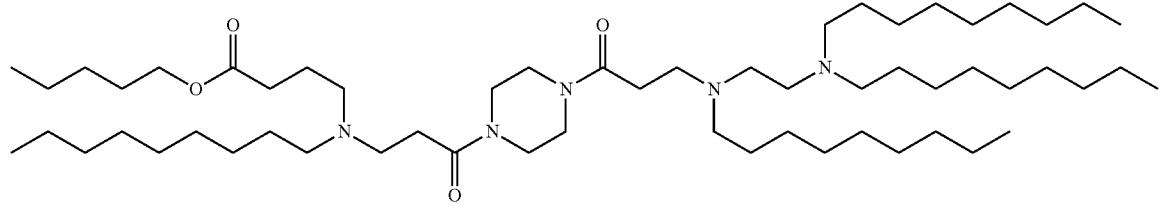

Chemical Formula: C₅₇H₁₁₃N₅O₄
Molecular Weight: 932.56

In the same manner as Step 11 for Compound 11, pentyl 4-((3-(4-(3-((2-(dinonylamino)ethyl)(nonyl)amino)propanoyl)piperazin-1-yl)-3-oxopropyl)(nonyl)amino)butanoate was synthesized from pentyl 4-(nonyl(3-oxo-3-(piperazin-1-yl)propyl)amino)butanoate (268 mg, 0.61 mmol), 3-((2-(dinonylamino)ethyl)(nonyl)amino)propanoic acid (343 mg, 0.67 mmol), iPr₂EtN (234 µL, 1.34 mmol), and T3P (50% EtOAc solution, 1.09 mL, 1.83 mmol) in THF (20 mL). Yield (243 mg, 43%).

UPLC/ELSD: RT=2.26 min. MS (ES): m/z (MH⁺) 933.10 for C₅₇H₁₁₃N₅O₄

¹H-NMR (300 MHz, CDCl₃) δ: ppm 4.07 (t, 2H); 3.72-3.40 (br. m, 8H); 2.81 (m, 4H); 2.66-2.28 (br. m, 20H); 1.77 (m, 2H); 1.64 (m, 2H); 1.54-1.08 (br. m, 60H); 0.90 (t, 15H).

BM: Compound 69: 2-((2-(Dinonylamino)ethyl)(nonyl)amino)-1-(3-(2-(dinonylamino)ethyl)pyrrolidin-1-yl)ethan-1-one Step 1: tert-Butyl 3-(2-(dinonylamino)ethyl)pyrrolidine-1-carboxylate

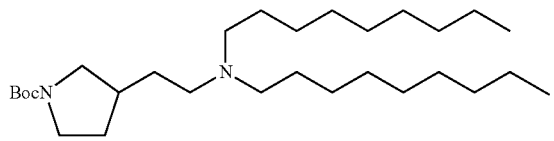

Chemical Formula: C₂₉H₅₈N₂O₂
Molecular Weight: 466.80

In the same manner as Step 1 for Compound 49, tert-butyl 3-(2-(dinonylamino)ethyl)pyrrolidine-1-carboxylate was synthesized from tert-butyl 3-(2-aminoethyl)pyrrolidine-1-carboxylate (1.25 g, 5.47 mmol), 1-bromononane (1.13 g, 5.47 mmol), K₂CO₃ (757 mg, 5.47 mmol), and KI (91 mg, 0.55 mmol) in MeCN (100 mL). Yield (710 mg, 28%).

UPLC/ELSD: RT=2.23 min. MS (ES): m/z (MH⁺) 467.74 for C₂₉H₅₈N₂O₂

¹H-NMR (300 MHz, CDCl₃) δ: ppm 3.67-3.34 (br. m, 2H); 3.34-2.75 (br. m 2H); 2.52-1.89 (br. m, 8H); 1.70-1.03 (br. m, 40H); 0.90 (t, 6H).

Step 2: N-Nonyl-N-(2-(pyrrolidin-3-yl)ethyl)nonan-1-amine

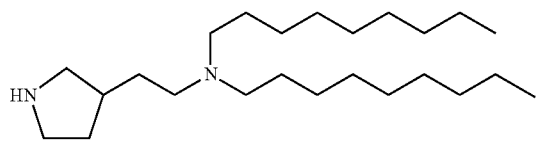

Chemical Formula: C₂₄H₅₀N₂
Molecular Weight: 366.68

In the same manner as Step 4 for Compound 11, N-nonyl-N-(2-(pyrrolidin-3-yl)ethyl)nonan-1-amine was synthesized from tert-butyl 3-(2-(dinonylamino)ethyl)pyrrolidine-1-carboxylate (710 mg, 1.52 mmol), and TFA (5.8 mL, 76 mmol) in DCM (6 mL). Yield (541 mg, 97%).

UPLC/ELSD: RT=1.23 min. MS (ES): m/z (MH⁺) 367.70 for C₂₄H₅₀N₂

¹H-NMR (300 MHz, CDCl₃) δ: ppm 3.32-1.90 (br. m, 11H); 1.66-1.14 (br. m, 33H); 0.90 (t, 6H).

Step 3: 2-((2-(Dinonylamino)ethyl)(nonyl)amino)-1-(3-(2-(dinonylamino)ethyl)pyrrolidin-1-yl)ethan-1-one

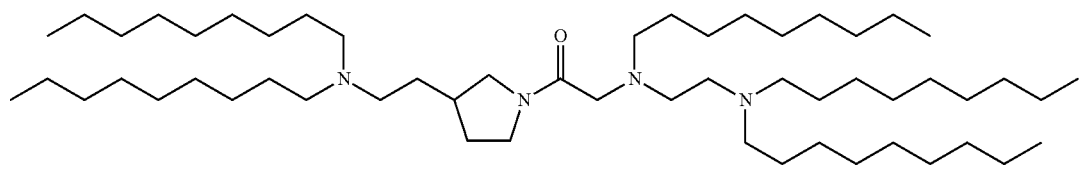

Chemical Formula: C₅₅H₁₁₂N₄O
Molecular Weight: 845.53

In the same manner as Step 11 for Compound 11, 2-((2-(dinonylamino)ethyl)(nonyl)amino)-1-(3-(2-(dinonylamino)ethyl)pyrrolidin-1-yl)ethan-1-one was synthesized from N-nonyl-N-(2-(pyrrolidin-3-yl)ethyl)nonan-1-amine (250 mg, 0.68 mmol), N-(2-(dinonylamino)ethyl)-N-nonylglycine (308 mg, 0.62 mmol), iPr$_2$EtN (0.24 mL, 1.4 mmol), and T3P (50% EtOAc solution, 1.1 mL, 1.9 mmol) in THF (10 mL). Yield (100 mg, 19%).

UPLC/ELSD: RT=3.17 min. MS (ES): m/z (MH$^+$) 846.20 for C$_{55}$H$_{112}$N$_4$O $^1$H-NMR (300 MHz, CDCl$_3$) δ: ppm 3.82-2.90 (br. m, 6H); 2.74-1.94 (br. m, 16H); 1.83-1.00 (br. m, 75H); 0.90 (t, 15H).

BN: Compound 70: 2-((2-(Dinonylamino)ethyl)(nonyl)amino)-1-(3-((dinonylamino)methyl)pyrrolidin-1-yl)ethan-1-one Step 1: tert-Butyl 3-((dinonylamino)methyl)pyrrolidine-1-carboxylate

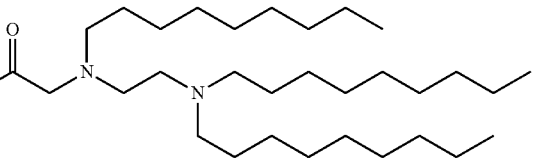

Chemical Formula: C$_{28}$H$_{56}$N$_2$O$_2$
Molecular Weight: 452.77

In the same manner as Step 1 for Compound 49, tert-butyl 3-((dinonylamino)methyl)pyrrolidine-1-carboxylate was synthesized from tert-butyl 3-(aminomethyl)pyrrolidine-1-carboxylate (2.0 g, 10.0 mmol), 1-bromononane (2.07 g, 10.0 mmol), K$_2$CO$_3$ (1.39 g, 10.0 mmol), and KI (166 mg, 1.00 mmol) in MeCN (100 mL). Yield (1.16 g, 26%).

UPLC/ELSD: RT=2.17 min. MS (ES): m/z (MH$^+$) 453.72 for C$_{29}$H$_{58}$N$_2$O$_2$ $^1$H-NMR (300 MHz, CDCl$_3$) δ: ppm 3.72-2.90 (br. m, 4H); 2.36 (br. m, 6H); 2.04-1.04 (br. m, 40H); 0.90 (t, 6H).

Step 2: N-Nonyl-N-(pyrrolidin-3-ylmethyl)nonan-1-amine

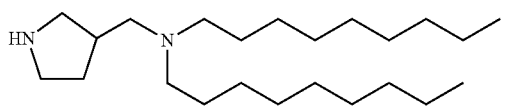

Chemical Formula: C$_{23}$H$_{48}$N$_2$
Molecular Weight: 352.65

In the same manner as Step 4 for Compound 11, N-nonyl-N-(pyrrolidin-3-ylmethyl)nonan-1-amine was synthesized from tert-butyl 3-((dinonylamino)methyl)pyrrolidine-1-carboxylate (1.16 g, 2.56 mmol), and TFA (9.8 mL, 128 mmol) in DCM (10 mL). Yield (900 mg, 99%).

UPLC/ELSD: RT=1.17 min. MS (ES): m/z (MH$^+$) 353.66 for C$_{23}$H$_{48}$N$_2$ $^1$H-NMR (300 MHz, CDCl$_3$) δ: ppm 3.33-2.23 (br. m, 10H); 1.99 (br, 1H); 1.65-1.00 (br. m, 31H); 0.90 (t, 6H).

Step 3: 2-((2-(Dinonylamino)ethyl)(nonyl)amino)-1-(3-((dinonylamino)methyl)pyrrolidin-1-yl)ethan-1-one

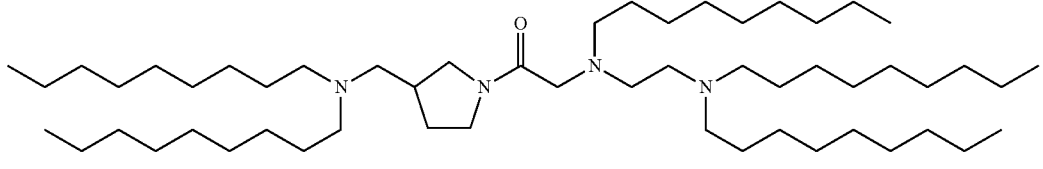

Chemical Formula: C$_{54}$H$_{110}$N$_4$O
Molecular Weight: 831.50

In the same manner as Step 11 for Compound 11, 2-((2-(dinonylamino)ethyl)(nonyl)amino)-1-(3-((dinonylamino)methyl)pyrrolidin-1-yl)ethan-1-one was synthesized from N-nonyl-N-(pyrrolidin-3-ylmethyl)nonan-1-amine (200 mg, 0.57 mmol), N-(2-(dinonylamino)ethyl)-N-nonylglycine (256 mg, 0.52 mmol), iPr$_2$EtN (0.198 mL, 1.14 mmol), and T3P (50% EtOAc solution, 0.92 mL, 1.56 mmol). Yield (114 mg, 27%).

UPLC/ELSD: RT=3.22 min. MS (ES): m/z (MH$^+$) 832.26 for C$_{54}$H$_{110}$N$_4$O $^1$H-NMR (300 MHz, CDCl$_3$) δ: ppm 3.79-2.96 (br. m, 6H); 2.75-2.18 (br. m, 16H); 2.12-1.01 (br. m, 73H); 0.90 (t, 15H).

BO: Compound 72: Dipentyl 4,4'-((2-(4-(N-(2-(dinonylamino)ethyl)-N-nonylglycyl)piperazin-1-yl)-2-oxoethyl)azanediyl)dibutyrate Step 1: Dipentyl 4,4'-((2-(tert-butoxy)-2-oxoethyl)azanediyl)dibutyrate

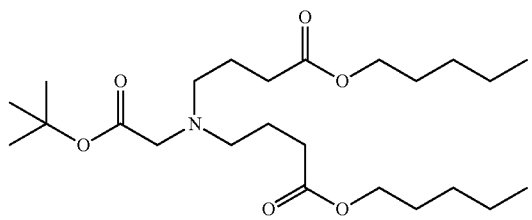

Chemical Formula: C$_{24}$H$_{45}$NO$_6$
Molecular Weight: 443.63

To a mixture of tert-butyl glycine (200 mg, 1.52 mmol) and pentyl 4-bromobutanoate (759 mg, 3.2 mmol) in MeCN (30 mL) was added K$_2$CO$_3$ (637 mg, 4.6 mmol) and KI (51 mg, 0.30 mmol) and the mixture was allowed to stir at 82°

C. for 12 hours. The suspension was cooled to RT, filtered over a pad of celite rinsing with EtOAc, and concentrated in vacuo. Purification by ISCO silica flash chromatography (0-20% EtOAc/hexanes) provided dipentyl 4,4'-((2-(tert-butoxy)-2-oxoethyl)azanediyl)dibutyrate (230 mg, 34%).

UPLC/ELSD: RT=1.54 min. MS (ES): m/z (MH$^+$) 444.61 for $C_{24}H_{45}NO_6$ $^1$H-NMR (300 MHz, CDCl$_3$) δ: ppm 4.07 (t, 4H); 3.22 (s, 2H); 2.63 (t, 4H); 2.36 (t, 4H); 1.77 (m, 4H); 1.64 (m, 4H); 1.47 (s, 9H); 1.35 (br. m, 8H); 0.93 (t, 6H).

Step 2: Bis(4-oxo-4-(pentyloxy)butyl)glycine

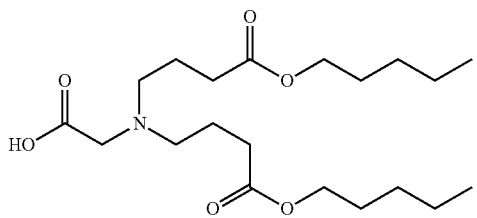

Chemical Formula: $C_{20}H_{37}NO_6$
Molecular Weight: 387.52

In the same manner as Step 4 for Compound 44, bis(4-oxo-4-(pentyloxy)butyl)glycine was synthesized from dipentyl 4,4'-((2-(tert-butoxy)-2-oxoethyl)azanediyl)dibutyrate (230 mg, 0.52 mmol), and TFA (2 mL, 26 mmol) in DCM (2 mL). Yield (200 mg, 99%).

UPLC/ELSD: RT=0.80 min. MS (ES): m/z (MH$^+$) 388.51 for $C_{20}H_{37}NO_6$ $^1$H-NMR (300 MHz, CDCl$_3$) δ: ppm 4.05 (t, 4H); 3.10 (s, 2H); 2.58 (m, 4H); 2.32 (t, 4H); 1.80 (br. m, 4H); 1.63 (br. m, 4H); 1.32 (br. m, 8H); 0.92 (t, 6H).

Step 3: Dipentyl 4,4'-((2-(4-(N-(2-(dinonylamino)ethyl)-N-nonylglycyl)piperazin-1-yl)-2-oxoethyl)azanediyl)dibutyrate

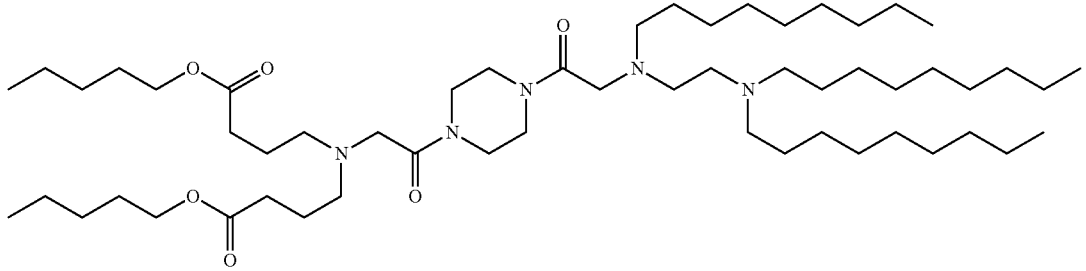

Chemical Formula: $C_{55}H_{107}N_5O_6$
Molecular Weight: 934.49

In the same manner as Step 7 for Compound 44, dipentyl 4,4'-((2-(4-(N-(2-(dinonylamino)ethyl)-N-nonylglycyl)piperazin-1-yl)-2-oxoethyl)azanediyl)dibutyrate was synthesized from bis(4-oxo-4-(pentyloxy)butyl)glycine (200 mg, 0.52 mmol), 2-((2-(dinonylamino)ethyl)(nonyl)amino)-1-(piperazin-1-yl)ethan-1-one (265 mg, 0.47 mmol), iPr$_2$EtN (180 μL, 1.03 mmol) and T3P (50% EtOAc solution, 838 μL, 1.41 mmol) in THF (10 mL). Yield (250 mg, 57%).

UPLC/ELSD: RT=2.85 min. MS (ES): m/z (MH$^+$) 935.26 for $C_{55}H_{107}N_5O_6$ $^1$H-NMR (300 MHz, CDCl$_3$) δ: ppm 4.08 (t, 4H); 3.78-3.46 (br. m, 8H); 3.34 (br. m, 4H); 2.72-2.24 (br. m, 18H); 1.78 (m, 4H); 1.64 (m, 4H); 1.50-1.16 (br. m, 50H); 0.91 (m, 15H).

BP: Compound 73: 2-((2-(Dinonylamino)ethyl) (nonyl)amino)-1-(3-(2-(dinonylamino)ethyl)piperidin-1-yl)ethan-1-one Step 1: tert-Butyl 3-(2-(dinonylamino)ethyl)piperidine-1-carboxylate

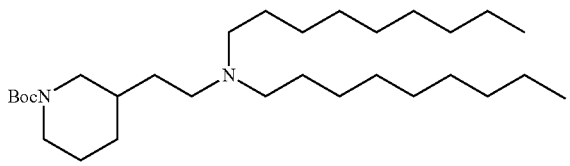

Chemical Formula: $C_{30}H_{60}N_2O_2$
Molecular Weight: 480.82

In the same manner as Step 1 for Compound 49, tert-butyl 3-(2-(dinonylamino)ethyl)piperidine-1-carboxylate was synthesized from tert-butyl 3-(2-aminoethyl)piperidine-1-carboxylate (1.00 g, 4.38 mmol), 1-bromononane (907 mg, 4.38 mmol), K$_2$CO$_3$ (610 mg, 4.38 mmol), and KI (73 mg, 0.44 mmol) in MeCN (50 mL). Yield (514 mg, 24%).

$^1$H-NMR (300 MHz, CDCl$_3$) δ: ppm 4.12-2.24 (br. m, 10H); 1.92-1.00 (br. m, 44H); 0.90 (t, 6H).

N-Nonyl-N-(2-(piperidin-3-yl)ethyl)nonan-1-amine

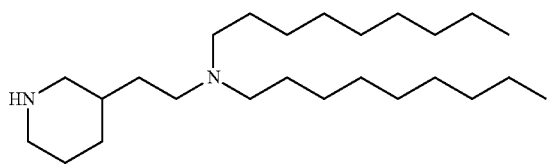

Chemical Formula: C₂₅H₅₂N₂
Molecular Weight: 380.71

In the same manner as Step 4 for Compound 11, N-nonyl-N-(2-(piperidin-3-yl)ethyl)nonan-1-amine was synthesized from tert-butyl 3-(2-(dinonylamino)ethyl)piperidine-1-carboxylate (514 mg, 1.07 mmol), and TFA (4.1 mL, 53 mmol) in DCM (4 mL). Yield (378 mg, 93%).

UPLC/ELSD: RT=1.27 min. MS (ES): m/z (MH⁺) 381.62 for C₂₅H₅₂N₂

¹H-NMR (300 MHz, CDCl₃) δ: ppm 3.12-1.95 (br. m, 11H); 1.93-0.98 (br. m, 35H); 0.90 (t, 6H).

2-((2-(Dinonylamino)ethyl)(nonyl)amino)-1-(3-(2-(dinonylamino)ethyl)piperidin-1-yl)ethan-1-one

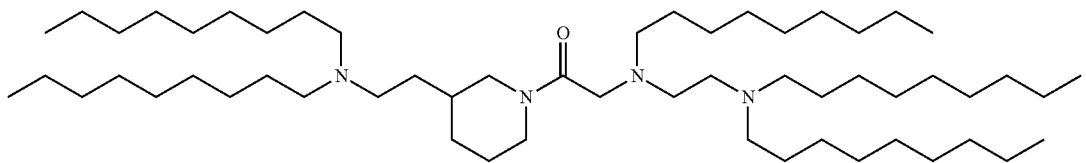

Chemical Formula: C₅₆H₁₁₄N₄O
Molecular Weight: 859.56

In the same manner as Step 11 for Compound 11, 2-((2-(dinonylamino)ethyl)(nonyl)amino)-1-(3-(2-(dinonylamino)ethyl)piperidin-1-yl)ethan-1-one was synthesized from N-nonyl-N-(2-(piperidin-3-yl)ethyl)nonan-1-amine (250 mg, 0.66 mmol), N-(2-(dinonylamino)ethyl)-N-nonyl-glycine (297 mg, 0.60 mmol), iPr₂EtN (0.23 mL, 1.3 mmol), and T3P (50% EtOAc solution, 1.06 mL, 1.8 mmol) in THF (10 mL). Yield (136 mg, 27%).

UPLC/ELSD: RT=3.22 min. MS (ES): m/z (MH⁺) 860.39 for C₅₆H₁₁₄N₄O

¹H-NMR (300 MHz, CDCl₃) δ: ppm 4.56-4.01 (br. m, 2H); 3.48-2.20 (br. m, 20H), 1.99-1.00 (br. m, 77H); 0.90 (t. 15H).

BQ: Compound 71: Pentyl 4-(nonyl(2-(4-(N-nonyl-N-(2-(nonyl(4-oxo-4-(pentyloxy)butyl)amino)ethyl)glycyl)piperazin-1-yl)-2-oxoethyl)amino)butanoate Step 1: tert-Butyl 4-(N-nonyl-N-(4-oxo-4-(pentyloxy)butyl)glycyl)piperazine-1-carboxylate

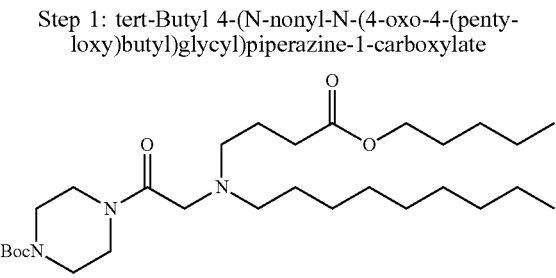

Chemical Formula: C₂₉H₅₅N₃O₅
Molecular Weight: 525.78

In the same manner as Step 3 for Compound 11, tert-butyl 4-(N-nonyl-N-(4-oxo-4-(pentyloxy)butyl)glycyl)piperazine-1-carboxylate was synthesized from N-nonyl-N-(4-oxo-4-(pentyloxy)butyl)glycine (480 mg, 1.34 mmol), 1-boc-piperazine (275 mg, 1.48 mmol), iPr₂EtN (5.14 µL, 2.95 mmol) and T3P (50% EtOAc solution, 2.40 mL, 4.03 mmol) in THF (15 mL). Yield (700 mg, 99%).

UPLC/ELSD: RT=1.90 min. MS (ES): m/z (MH⁺) 526.79 for C₂₉H₅₅N₃O₅

¹H-NMR (300 MHz, CDCl₃) δ: ppm 4.08 (t, 2H); 3.70-3.10 (br. m, 14H); 2.45 (t, 2H); 2.13 (br. m, 2H); 2.00-1.00 (br. m, 29H); 0.91 (br. m, 6H).

Step 2: Pentyl 4-(nonyl(2-oxo-2-(piperazin-1-yl)ethyl)amino)butanoate

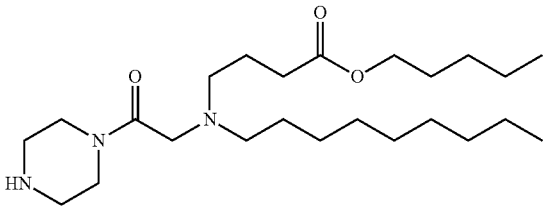

Chemical Formula: C₂₄H₄₇N₃O₃
Molecular Weight: 425.66

In the same manner as Step 4 for Compound 11, pentyl 4-(nonyl(2-oxo-2-(piperazin-1-yl)ethyl)amino)butanoate was synthesized from tert-butyl 4-(N-nonyl-N-(4-oxo-4-(pentyloxy)butyl)glycyl)piperazine-1-carboxylate (700 mg, 1.33 mmol), and TFA (5.1 mL, 66.6 mmol) in DCM (5 mL). Yield (560 mg, 99%).

UPLC/ELSD: RT=0.77 min. MS (ES): m/z (MH⁺) 426.65 for C₂₄H₄₇N₃O₃

¹H-NMR (300 MHz, CDCl₃) δ: ppm 4.07 (t, 2H); 3.59 (br. m, 4H); 3.28 (s, 2H); 2.86 (br. m, 4H); 2.50 (br. m, 4H); 2.33 (t, 2H); 2.05 (br, 1H); 1.77 (m, 2H); 1.63 (m, 2H); 1.30 (br. m, 18H); 0.91 (m, 6H).

Step 3: Pentyl 4-((2-hydroxyethyl)(nonyl)amino)butanoate

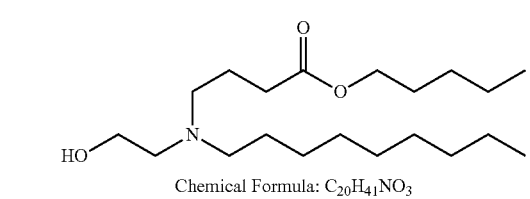

Chemical Formula: C₂₀H₄₁NO₃
Molecular Weight: 343.55

In the same manner as Step 1 for Compound 18, pentyl 4-((2-hydroxyethyl)(nonyl)amino)butanoate was synthesized from 2-(nonylamino)ethan-1-ol (350 mg, 1.87 mmol), pentyl 4-bromobutanoate (487 mg, 2.06 mmol), K$_2$CO$_3$ (572 mg, 4.11 mmol), and KI (31 mg, 0.19 mmol) in MeCN (40 mL). Yield (427 mg, 66%).

UPLC/ELSD: RT=1.25 min. MS (ES): m/z (MH$^+$) 344.55 for C$_{20}$H$_{41}$NO$_3$ $^1$H-NMR (300 MHz, CDCl$_3$) δ: ppm 4.09 (t, 2H); 3.61 (t, 2H); 2.67 (t, 2H); 2.56 (m, 4H); 2.36 (t, 2H); 1.85 (m, 2H); 1.65 (m, 2H); 1.49 (m, 2H); 1.42-1.18 (br. m, 16H); 0.91 (m, 6H).

Step 4: Pentyl 4-((2-chloroethyl)(nonyl)amino)butanoate

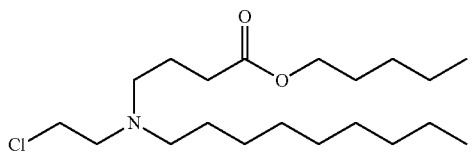

Chemical Formula: C$_{20}$H$_{40}$ClNO$_2$
Molecular Weight: 362.00

In the same manner as Step 2 for Compound 18, pentyl 4-((2-chloroethyl)(nonyl)amino)butanoate was synthesized from pentyl 4-((2-hydroxyethyl)(nonyl)amino)butanoate (427 mg, 1.27 mmol), methanesulfonyl chloride (120 μL, 1.55 mmol), and triethylamine (225 μL, 1.62 mmol) in DCM (8 mL). Yield (448 mg, 99%).

UPLC/ELSD: RT=1.52 min. MS (ES): m/z (MH$^+$) 362.51 for C$_{20}$H$_{40}$ClNO$_2$ $^1$H-NMR (300 MHz, CDCl$_3$) δ: ppm 4.07-3.71 (br. m, 4H); 3.45-2.76 (br. m, 6H); 2.30 (br. m, 2H); 2.24-1.05 (br. m, 22H); 0.82 (br. m, 6H).

Step 5: Pentyl 4-((2-((2-(tert-butoxy)-2-oxoethyl)(nonyl)amino)ethyl)(nonyl)amino)butanoate

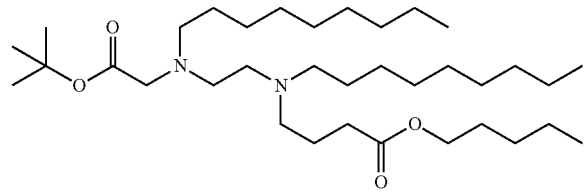

Chemical Formula: C$_{35}$H$_{70}$N$_2$O$_4$
Molecular Weight: 582.96

In the same manner as Step 4 for Compound 46, pentyl 4-((2-((2-(tert-butoxy)-2-oxoethyl)(nonyl)amino)ethyl)(nonyl)amino)butanoate was synthesized from tert-butyl nonylglycinate (338 mg, 1.31 mmol), pentyl 4-((2-chloroethyl)(nonyl)amino)butanoate (527 mg, 1.46 mmol), K$_2$CO$_3$ (402 mg, 2.89 mmol), and KI (22 mg, 0.13 mmol) in MeCN (30 mL). Yield (200 mg, 26%).

UPLC/ELSD: RT=3.03 min. MS (ES): m/z (MH$^+$) 583.95 for C$_{35}$H$_{70}$N$_2$O$_4$ $^1$H-NMR (300 MHz, CDCl$_3$) δ: ppm 4.07 (t, 2H); 3.27 (s, 2H); 2.76-2.24 (br. m, 12H); 1.85-1.10 (br. m, 45H); 0.90 (m, 9H).

Step 6: N-Nonyl-N-(2-(nonyl(4-oxo-4-(pentyloxy)butyl)amino)ethyl)glycine

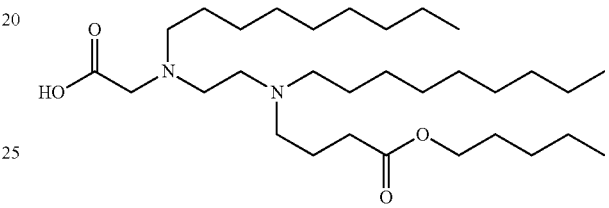

Chemical Formula: C$_{31}$H$_{62}$N$_2$O$_4$
Molecular Weight: 526.85

In the same manner as Step 5 for Compound 46, N-nonyl-N-(2-(nonyl(4-oxo-4-(pentyloxy)butyl)amino)ethyl)glycine was synthesized from pentyl 4-((2-((2-(tert-butoxy)-2-oxoethyl)(nonyl)amino)ethyl)(nonyl)amino)butanoate (200 mg, 0.34 mmol), and TFA (1.31 mL, 17.2 mmol), in DCM (2 mL). Yield (160 mg, 89%).

UPLC/ELSD: RT=2.39 min. MS (ES): m/z (MH$^+$) 527.77 for C$_{31}$H$_{62}$N$_2$O$_4$ $^1$H-NMR (300 MHz, CDCl$_3$) δ: ppm 4.09 (t, 2H); 3.27 (s, 2H); 2.94-2.74 (br. m, 6H); 2.61 (t, 2H); 2.37 (m, 2H); 2.15-1.90 (br. m, 2H); 1.80-1.05 (br. m, 36H); 0.90 (m, 9H).

Step 7: Pentyl 4-(nonyl(2-(4-(N-nonyl-N-(2-(nonyl(4-oxo-4-(pentyloxy)butyl)amino)ethyl)glycyl)piperazin-1-yl)-2-oxoethyl)amino)butanoate

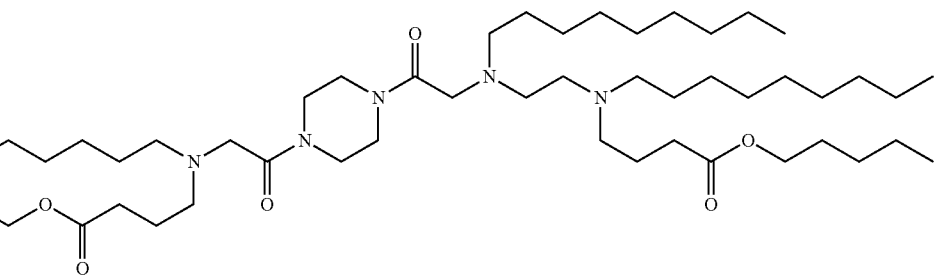

Chemical Formula: C$_{55}$H$_{107}$N$_5$O$_6$
Molecular Weight: 934.49

In the same manner as Step 11 for Compound 11, pentyl 4-(nonyl(2-(4-(N-nonyl-N-(2-(nonyl(4-oxo-4-(pentyloxy)butyl)amino)ethyl)glycyl)piperazin-1-yl)-2-oxoethyl)amino)butanoate was synthesized from pentyl 4-(nonyl(2-oxo-2-(piperazin-1-yl)ethyl)amino)butanoate (142 mg, 0.33 mmol), N-nonyl-N-(2-(nonyl(4-oxo-4-(pentyloxy)butyl)amino)ethyl)glycine (160 mg, 0.30 mmol), iPr$_2$EtN (116 μL, 0.67 mmol), and T3P (50% EtOAc solution, 542 μL, 0.91 mmol). Yield (53 mg, 19%).

UPLC/ELSD: RT=2.79 min. MS (ES): m/z (MH$^+$) 935.34 for C$_{55}$H$_{107}$N$_5$O$_6$ $^1$H-NMR (300 MHz, CDCl$_3$) δ: ppm 4.08 (t, 4H); 3.78-3.53 (br. m, 8H); 3.32 (br. m, 4H); 2.76-2.24 (br. m, 18H); 1.87-1.10 (br. m, 58H); 0.91 (br. m, 15H).

BR: Compound 80: Pentyl 4-((2-(1-(N-(2-(dinonylamino)ethyl)-N-nonylglycyl)piperidin-3-yl)ethyl)(nonyl)amino)butanoate Step 1: tert-butyl 3-(2-(nonylamino)ethyl)piperidine-1-carboxylate

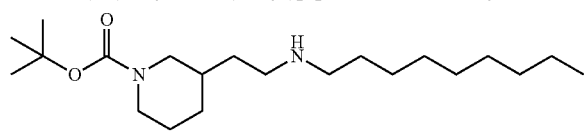

Chemical Formula: C$_{21}$H$_{42}$N$_2$O$_2$
Molecular Weight: 354.58

In the same manner as Step 1 for Compound 49, tert-butyl 3-(2-(nonylamino)ethyl)piperidine-1-carboxylate was synthesized from tert-butyl 3-(2-aminoethyl)piperidine-1-carboxylate (1.00 g, 4.38 mmol), 1-bromononane (907 mg, 4.38 mmol), K$_2$CO$_3$ (610 mg, 4.38 mmol), and KI (73 mg, 0.44 mmol) in MeCN (50 mL). Yield (474 mg, 31%).

UPLC/ELSD: RT=1.23 min. MS (ES): m/z (MH$^+$) 355.58 for C$_{21}$H$_{42}$N$_2$O$_2$ $^1$H-NMR (300 MHz, CDCl$_3$) δ: ppm 3.88 (br, 2H); 3.00-2.43 (br. m, 6H); 1.92-0.97 (br. m, 30H), 0.90 (t, 3H).

Step 2: tert-Butyl 3-(2-(nonyl(4-oxo-4-(pentyloxy)butyl)amino)ethyl)piperidine-1-carboxylate

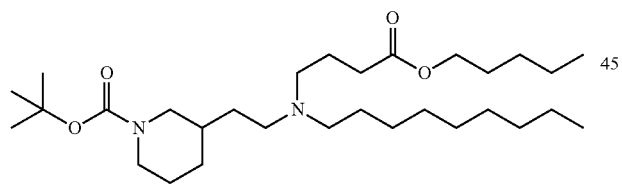

Chemical Formula: C$_{30}$H$_{58}$N$_2$O$_4$
Molecular Weight: 510.80

In the same manner as Step 1 for Compound 57, tert-butyl 3-(2-(nonyl(4-oxo-4-(pentyloxy)butyl)amino)ethyl)piperidine-1-carboxylate was synthesized from tert-butyl 3-(2-(nonylamino)ethyl)piperidine-1-carboxylate (474 mg, 1.34 mmol), pentyl 4-bromobutanoate (380 mg, 1.6 mmol), K$_2$CO$_3$ (223 mg, 1.60 mmol) and KI (44 mg, 0.27 mmol) in MeCN (15 mL). Yield (492 mg, 72%).

UPLC/ELSD: RT=2.09 min. MS (ES): m/z (MH$^+$) 511.70 for C$_{30}$H$_{58}$N$_2$O$_4$ $^1$H-NMR (300 MHz, CDCl$_3$) δ: ppm 4.08 (t, 2H); 3.90 (br. m, 2H); 2.87-2.22 (br. m, 10H); 1.91-1.00 (br. m, 38H); 0.91 (m, 6H).

Step 3: Pentyl 4-(nonyl(2-(piperidin-3-yl)ethyl)amino)butanoate

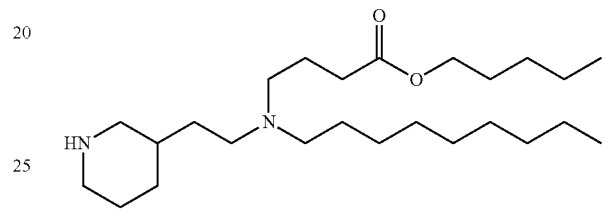

Chemical Formula: C$_{25}$H$_{50}$N$_2$O$_2$
Molecular Weight: 410.69

In the same manner as Step 4 for Compound 11, pentyl 4-(nonyl(2-(piperidin-3-yl)ethyl)amino)butanoate was synthesized from tert-butyl 3-(2-(nonyl(4-oxo-4-(pentyloxy)butyl)amino)ethyl)piperidine-1-carboxylate (492 mg, 0.96 mmol), and TFA (3.7 mL, 48 mmol) in DCM (4 mL). Yield (390 mg, 99%).

UPLC/ELSD: RT=0.85 min. MS (ES): m/z (MH$^+$) 411.72 for C$_{25}$H$_{50}$N$_2$O$_2$ $^1$H-NMR (300 MHz, CDCl$_3$) δ: ppm 4.08 (t, 2H); 3.03 (br. m, 2H); 2.66-2.18 (br. m, 10H); 2.18-0.98 (br. m, 30H); 0.91 (m, 6H).

Step 4: Pentyl 4-((2-(1-(N-(2-(dinonylamino)ethyl)-N-nonylglycyl)piperidin-3-yl)ethyl)(nonyl)amino)butanoate

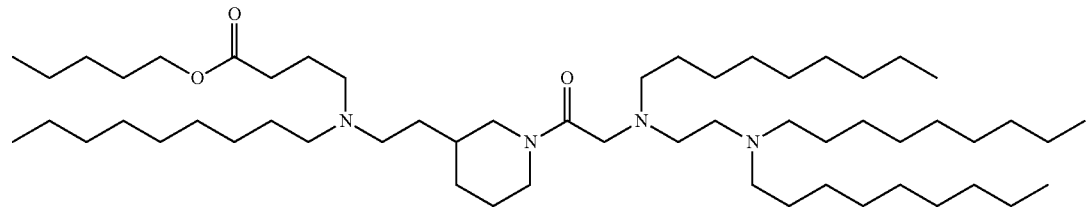

Chemical Formula: C$_{56}$H$_{112}$N$_4$O$_3$
Molecular Weight: 889.54

In the same manner as Step 11 for Compound 11, pentyl 4-((2-(1-(N-(2-(dinonylamino)ethyl)-N-nonylglycyl)piperidin-3-yl)ethyl)(nonyl)amino)butanoate was synthesized from pentyl 4-(nonyl(2-(piperidin-3-yl)ethyl)amino)butanoate (250 mg, 0.61 mmol), N-(2-(dinonylamino)ethyl)-N-nonylglycine (275 mg, 0.55 mmol), iPr$_2$EtN (0.21 mL, 1.2 mmol), and T3P (50% EtOAc solution, 0.98 mL, 1.7 mmol). Yield (96 mg, 20%).

UPLC/ELSD: RT=3.08 min. MS (ES): m/z (MH$^+$) 890.32 for C$_{56}$H$_{112}$N$_4$O$_3$ $^1$H-NMR (300 MHz, CDCl$_3$) δ: ppm 4.55-4.01 (br. m, 4H); 3.48-2.21 (br. m, 22H); 1.95-1.00 (br. m, 71H); 0.90 (m, 15H).

BS: Compound 81: Pentyl 4-((2-(1-(N-(2-(dinonylamino)ethyl)-N-nonylglycyl)pyrrolidin-3-yl)ethyl)(nonyl)amino)butanoate Step 1: tert-Butyl 3-(2-(nonylamino)ethyl)pyrrolidine-1-carboxylate

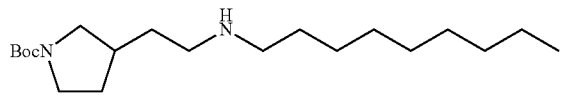

Chemical Formula: C$_{20}$H$_{40}$N$_2$O$_2$
Molecular Weight: 340.55

In the same manner as Step 1 for Compound 49, tert-butyl 3-(2-(nonylamino)ethyl)pyrrolidine-1-carboxylate was synthesized from tert-butyl 3-(2-aminoethyl)pyrrolidine-1-carboxylate (1.25 g, 5.47 mmol), 1-bromononane (1.13 g, 5.47 mmol), K$_2$CO$_3$ (757 mg, 5.47 mmol), and KI (91 mg, 0.55 mmol) in MeCN (100 mL). Yield (420 mg, 23%).

UPLC/ELSD: RT=1.08 min. MS (ES): m/z (MH$^+$) 341.52 for C$_{20}$H$_{40}$N$_2$O$_2$ $^1$H-NMR (300 MHz, CDCl$_3$) δ: ppm 3.68-1.91 (br. m, 9H); 1.71-1.12 (br. m, 28H); 0.90 (t, 3H).

Step 2: tert-Butyl 3-(2-(nonyl(4-oxo-4-(pentyloxy)butyl)amino)ethyl)pyrrolidine-1-carboxylate

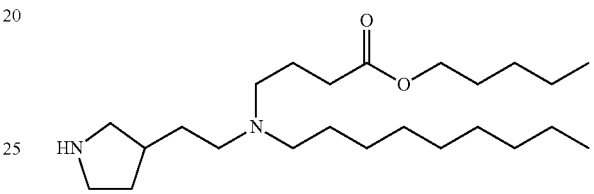

Chemical Formula: C$_{29}$H$_{56}$N$_2$O$_4$
Molecular Weight: 496.78

In the same manner as Step 1 for Compound 57, tert-butyl 3-(2-(nonyl(4-oxo-4-(pentyloxy)butyl)amino)ethyl)pyrrolidine-1-carboxylate was synthesized from tert-butyl 3-(2-(nonylamino)ethyl)pyrrolidine-1-carboxylate (420 mg, 1.23 mmol), pentyl 4-bromobutanoate (321 mg, 1.36 mmol), K$_2$CO$_3$ (187 mg, 1.36 mmol), and KI (41 mg, 0.25 mmol). Yield (390 mg, 64%).

UPLC/ELSD: RT=1.98 min. MS (ES): m/z (MH$^+$) 497.67 for C$_{29}$H$_{56}$N$_2$O$_4$ $^1$H-NMR (300 MHz, CDCl$_3$) δ: ppm 4.08 (t, 2H); 3.50 (br. m, 2H); 3.34-2.76 (br. m, 2H); 2.52-1.87 (br. m, 10H); 1.87-1.02 (br. m, 34H); 0.91 (t, 6H).

Step 3: Pentyl 4-(nonyl(2-(pyrrolidin-3-yl)ethyl)amino)butanoate

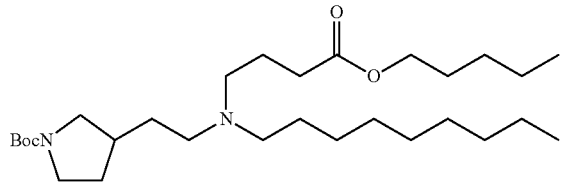

Chemical Formula: C$_{24}$H$_{48}$N$_2$O$_2$
Molecular Weight: 396.66

In the same manner as Step 4 for Compound 11, pentyl 4-(nonyl(2-(pyrrolidin-3-yl)ethyl)amino)butanoate was synthesized from tert-butyl 3-(2-(nonyl(4-oxo-4-(pentyloxy)butyl)amino)ethyl)pyrrolidine-1l-carboxylate (390 mg, 0.79 mmol), and TFA (3.0 mL, 40 mmol) in DCM (3 mL). Yield (298 mg, 96%).

UPLC/ELSD: RT=0.81 min. MS (ES): m/z (MH$^+$) 397.62 for C$_{24}$H$_{48}$N$_2$O$_2$ $^1$H-NMR (300 MHz, CDCl$_3$) δ: ppm 4.08 (t, 2H); 3.20-2.82 (br. m, 4H); 2.58-2.24 (br. m, 8H); 2.11-1.11 (br. m, 28H); 0.91 (m, 6H).

Step 4: Pentyl 4-((2-(1-(N-(2-(dinonylamino)ethyl)-N-nonylglycyl)pyrrolidin-3-yl)ethyl)(nonyl)amino)butanoate

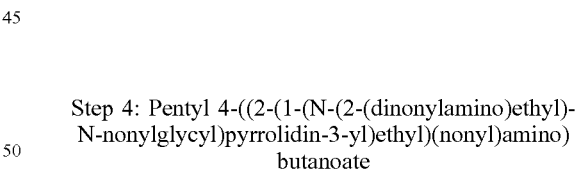

Chemical Formula: C$_{55}$H$_{110}$N$_4$O$_3$
Molecular Weight: 875.51

In the same manner as Step 11 for Compound 11, pentyl 4-((2-(1-(N-(2-(dinonylamino)ethyl)-N-nonylglycyl)pyrrolidin-3-yl)ethyl)(nonyl)amino)butanoate was synthesized from pentyl 4-(nonyl(2-(pyrrolidin-3-yl)ethyl)amino)butanoate (202 mg, 0.51 mmol), N-(2-(dinonylamino)ethyl)-N-nonylglycine (230 mg, 0.46 mmol), iPr$_2$EtN (0.177 mL, 1.0 mmol), and T3P (50% EtOAc solution, 0.82 mL, 1.4 mmol) in THF (10 mL). Yield (109 mg, 27%).

UPLC/ELSD: RT=3.06 min. MS (ES): m/z (MH$^+$) 876.30 for $C_{55}H_{110}N_4O_3$ $^1$H-NMR (300 MHz, CDCl$_3$) δ: ppm 4.08 (t, 2H); 3.83-2.85 (br. m, 7H); 2.78-1.88 (br. m, 19H); 1.83-1.14 (br. m, 67H); 0.90 (m, 15H).

BT: Compound 82: Pentyl 4-(((1-(N-(2-(dinonylamino)ethyl)-N-nonylglycyl)pyrrolidin-3-yl)methyl)(nonyl)amino)butanoate Step 1: tert-Butyl 3-((nonylamino)methyl)pyrrolidine-1-carboxylate

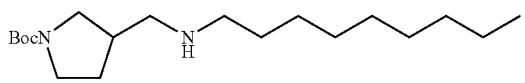

Chemical Formula: $C_{19}H_{38}N_2O_2$
Molecular Weight: 326.53

In the same manner as Step 1 for Compound 49, tert-butyl 3-((nonylamino)methyl)pyrrolidine-1-carboxylate was synthesized from tert-butyl 3-((aminomethyl)pyrrolidine-1-carboxylate (2.0 g, 10.0 mmol), 1-bromononane (2.07 g, 10.0 mmol), K$_2$CO$_3$ (1.39 g, 10.0 mmol), and KI (166 mg, 1.00 mmol) in MeCN (100 mL). Yield (1.53 g, 47%).

UPLC/ELSD: RT=0.92 min. MS (ES): m/z (MH$^+$) 327.54 for $C_{19}H_{38}N_2O_2$ $^1$H-NMR (300 MHz, CDCl$_3$) δ: ppm 3.69-1.79 (br. m, 9H); 1.74-1.13 (br. m, 26H); 0.89 (t, 3H).

Step 2: tert-Butyl 3-((nonyl(4-oxo-4-(pentyloxy)butyl)amino)methyl)pyrrolidine-1-carboxylate

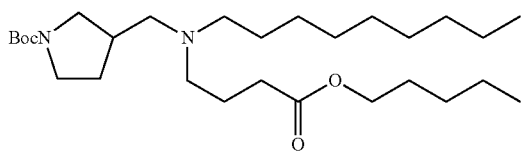

Chemical Formula: $C_{28}H_{54}N_2O_4$
Molecular Weight: 482.75

In the same manner as Step 1 for Compound 57, tert-butyl 3-((nonyl(4-oxo-4-(pentyloxy)butyl)amino)methyl)pyrrolidine-1-carboxylate was synthesized from tert-butyl 3-((nonylamino)methyl)pyrrolidine-1-carboxylate (500 mg, 1.53 mmol), pentyl 4-bromobutanoate (400 mg, 1.68 mmol), K$_2$CO$_3$ (423 mg, 3.07 mmol), and KI (51 mg, 0.31 mmol) in MeCN (100 mL). Yield (233 mg, 32%).

UPLC/ELSD: RT=1.85 min. MS (ES): m/z (MH$^+$) 483.65 for $C_{28}H_{54}N_2O_4$ $^1$H-NMR (300 MHz, CDCl$_3$) δ: ppm 4.08 (t, 2H); 3.59-2.91 (br. m, 4H); 2.49-1.83 (br. m, 10H); 1.83-1.13 (br. m, 32H); 0.91 (m, 6H).

Step 3: Pentyl 4-(nonyl(pyrrolidin-3-ylmethyl)amino)butanoate

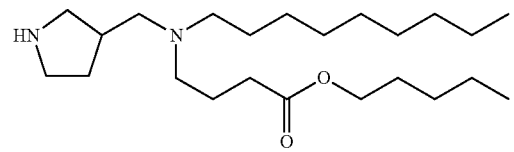

Chemical Formula: $C_{23}H_{46}N_2O_2$
Molecular Weight: 382.63

In the same manner as Step 4 for Compound 11, pentyl 4-(nonyl(pyrrolidin-3-ylmethyl)amino)butanoate was synthesized from tert-butyl 3-((nonyl(4-oxo-4-(pentyloxy)butyl)amino)methyl)pyrrolidine-1-carboxylate (233 mg, 0.48 mmol), and TFA (1.84 mL, 24 mmol) in DCM (2 mL). Yield (179 mg, 97%).

UPLC/ELSD: RT=0.70 min. MS (ES): m/z (MH$^+$) 383.51 for $C_{23}H_{46}N_2O_2$ $^1$H-NMR (300 MHz, CDCl$_3$) δ: ppm 4.08 (t, 2H); 3.11-2.81 (br. m, 3H); 2.67-1.51 (br. m, 16H); 1.51-1.03 (br. m, 19H); 0.91 (m, 6H).

Step 4: Pentyl 4-(((1-(N-(2-(dinonylamino)ethyl)-N-nonylglycyl)pyrrolidin-3-yl)methyl)(nonyl)amino)butanoate

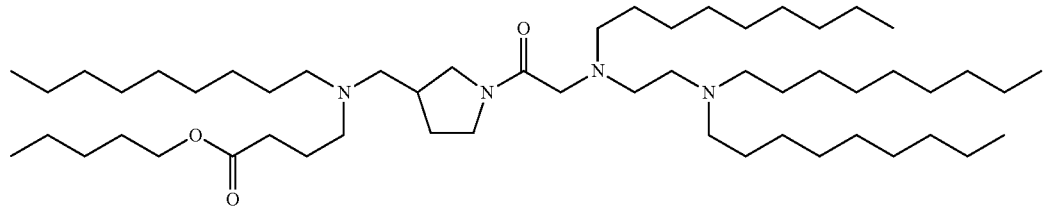

Chemical Formula: $C_{54}H_{108}N_4O_3$
Molecular Weight: 861.48

In the same manner as Step 11 for Compound 11, pentyl 4-(((1-(N-(2-(dinonylamino)ethyl)-N-nonylglycyl)pyrrolidin-3-yl)methyl)(nonyl)amino)butanoate was synthesized from pentyl 4-(nonyl(pyrrolidin-3-ylmethyl)amino)butanoate (179 mg, 0.47 mmol), N-(2-(dinonylamino)ethyl)-N-nonylglycine (211 mg, 0.43 mmol), iPr₂EtN (163 μL, 0.95 mmol), and T3P (50% EtOAc solution, 0.76 mL, 1.1 mmol). Yield (88 mg, 24%).

UPLC/ELSD: RT=3.05 min. MS (ES): m/z (MH⁺) 862.28 for $C_{54}H_{108}N_4O_3$

¹H-NMR (300 MHz, CDCl₃) δ: ppm 4.08 (t, 2H); 3.76-2.17 (br. m, 24H); 2.12-1.05 (br. m, 67H); 0.90 (m, 15H).

BU: Compound 83: Pentyl 4-((2-(1-(N-(2-(dinonylamino)ethyl)-N-nonylglycyl)piperidin-4-yl)ethyl)(nonyl)amino)butanoate Step 1: tert-Butyl 4-(2-(nonyl(4-oxo-4-(pentyloxy)butyl)amino)ethyl)piperidine-1-carboxylate

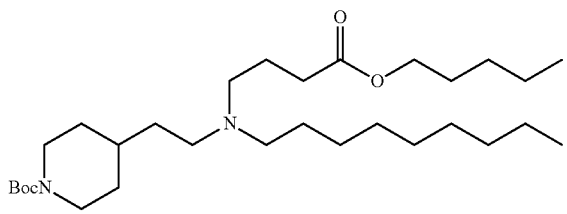

Chemical Formula: $C_{30}H_{58}N_2O_4$
Molecular Weight: 510.80

In the same manner as Step 1 for Compound 57, tert-butyl 4-(2-(nonyl(4-oxo-4-(pentyloxy)butyl)amino)ethyl)piperidine-1-carboxylate was synthesized from tert-butyl 4-(2-(nonylamino)ethyl)piperidine-1-carboxylate (500 mg, 1.41 mmol), pentyl 4-bromobutanoate (368 mg, 1.55 mmol), K₂CO₃ (390 mg, 2.82 mmol), and KI (23 mg, 0.14 mmol) in MeCN (100 mL). Yield (487 mg, 68%).

UPLC/ELSD: RT=2.03 min. MS (ES): m/z (MH⁺) 511.57 for $C_{30}H_{58}N_2O_4$

¹H-NMR (300 MHz, CDCl₃) δ: ppm 4.08 (m, 4H); 2.69 (m, 2H); 2.51-2.25 (br. m, 8H); 1.83-1.55 (br. m, 6H); 1.53-1.02 (br. m, 32H); 0.91 (m, 6H).

Step 2: Pentyl 4-(nonyl(2-(piperidin-4-yl)ethyl)amino)butanoate

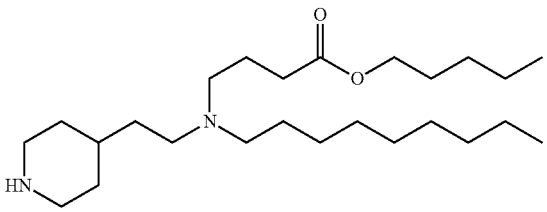

Chemical Formula: $C_{25}H_{50}N_2O_2$
Molecular Weight: 410.69

In the same manner as Step 4 for Compound 11, pentyl 4-(nonyl(2-(piperidin-4-yl)ethyl)amino)butanoate was synthesized from tert-butyl 4-(2-(nonyl(4-oxo-4-(pentyloxy)butyl)amino)ethyl)piperidine-1-carboxylate (487 mg, 0.953 mmol), and TFA (3.6 mL, 48 mmol) in DCM (4 mL). Yield (386 mg, 98%).

UPLC/ELSD: RT=0.87 min. MS (ES): m/z (MH⁺) 411.43 for $C_{25}H_{50}N_2O_2$

¹H-NMR (300 MHz, CDCl₃) δ: ppm 4.08 (t, 2H); 3.07 (m, 2H); 2.60 (m, 2H); 2.50-2.28 (br. m, 8H); 2.03 (br, 1H); 1.86-1.55 (br. m, 6H); 1.52-1.02 (br. m, 23H); 0.91 (m, 6H).

Step 3: Pentyl 4-((2-(1-(N-(2-(dinonylamino)ethyl)-N-nonylglycyl)piperidin-4-yl)ethyl)(nonyl)amino)butanoate

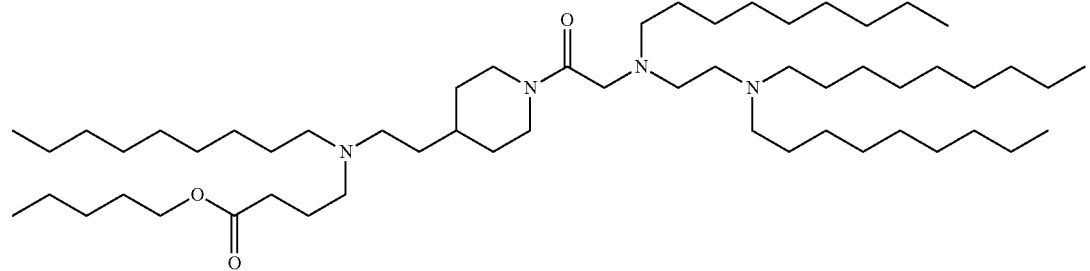

Chemical Formula: $C_{56}H_{112}N_4O_3$
Molecular Weight: 889.54

In the same manner as Step 11 for Compound 11, pentyl 4-((2-(1-(N-(2-(dinonylamino)ethyl)-N-nonylglycyl)piperidin-4-yl)ethyl)(nonyl)amino)butanoate was synthesized from pentyl 4-(nonyl(2-(piperidin-4-yl)ethyl)amino)butanoate (351 mg, 0.855 mmol), N-(2-(dinonylamino)ethyl)-N-nonylglycine (467 mg, 0.941 mmol), iPr₂EtN (328 μL, 1.88 mmol), and T3P (50% EtOAc solution, 1.53 mL, 2.56 mmol) in THF (15 mL). Yield (192 mg, 25%).

UPLC/ELSD: RT=3.00 min. MS (ES): m/z (MH⁺) 890.13 for $C_{56}H_{112}N_4O_3$

¹H-NMR (300 MHz, CDCl₃) δ: ppm 4.61-4.14 (br. m, 2H); 4.08 (t, 2H); 3.40-2.24 (br. m, 22H); 1.86-0.99 (br. m, 71H); 0.90 (m, 15H).

BV: Compound 84: Pentyl 4-((3-(1-(3-((2-(dinonylamino)ethyl)(nonyl)amino)propanoyl)piperidin-4-yl)propyl)(nonyl)amino)butanoate Step 1: tert-Butyl 4-(3-(nonylamino)propyl)piperidine-1-carboxylate

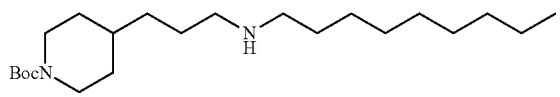

Chemical Formula: $C_{22}H_{44}N_2O_2$
Molecular Weight: 368.61

In the same manner as Step 1 for Compound 49, tert-butyl 4-(3-(nonylamino)propyl)piperidine-1-carboxylate was synthesized from tert-butyl 4-(3-aminopropyl)piperidine-1-carboxylate (2.50 g, 10.3 mmol), 1-bromononane (2.14 g, 10.3 mmol), $K_2CO_3$ (2.85 g, 20.6 mmol), and KI (171 mg, 0.10 mmol) in MeCN (200 mL). Yield (1.27 g, 33%).

$^1$H-NMR (300 MHz, CDCl$_3$) δ: ppm 4.08 (m, 2H), 2.69 (br. m, 6H); 1.79-0.98 (br. m, 32H); 0.89 (t, 3H).

Step 2: tert-Butyl 4-(3-(nonyl(4-oxo-4-(pentyloxy)butyl)amino)propyl)piperidine-1-carboxylate

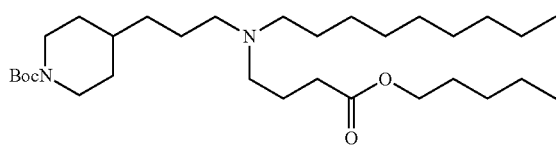

Chemical Formula: $C_{31}H_{60}N_2O_4$
Molecular Weight: 524.83

In the same manner as Step 1 for Compound 57, tert-butyl 4-(3-(nonyl(4-oxo-4-(pentyloxy)butyl)amino)propyl)piperidine-1-carboxylate was synthesized from tert-butyl 4-(3-(nonylamino)propyl)piperidine-1-carboxylate (500 mg, 1.36 mmol), pentyl 4-bromobutanoate (354 mg, 1.49 mmol), $K_2CO_3$ (375 mg, 2.71 mmol), and KI (23 mg, 0.14 mmol) in MeCN (20 mL). Yield (624 mg, 88%).

UPLC/ELSD: RT=2.12 min. MS (ES): m/z (MH$^+$) 525.60 for $C_{31}H_{60}N_2O_4$ $^1$H-NMR (300 MHz, CDCl$_3$) δ: ppm 4.08 (br. m, 4H); 2.69 (m, 2H); 2.38 (br. m, 8H); 1.85-1.55 (br. m, 6H); 1.54-1.00 (br. m, 34H); 0.91 (m, 6H).

Step 3: Pentyl 4-(nonyl(3-(piperidin-4-yl)propyl)amino)butanoate

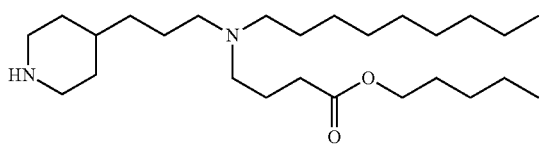

Chemical Formula: $C_{26}H_{52}N_2O_2$
Molecular Weight: 424.71

In the same manner as Step 4 for Compound 44, pentyl 4-(nonyl(3-(piperidin-4-yl)propyl)amino)butanoate was synthesized from tert-butyl 4-(3-(nonyl(4-oxo-4-(pentyloxy)butyl)amino)propyl)piperidine-1l-carboxylate (624 mg, 1.19 mmol), and TFA (4.5 mL, 60 mmol) in DCM (5 mL). Yield (467 mg, 92%).

UPLC/ELSD: RT=0.94 min. MS (ES): m/z (MH$^+$) 424.62 for $C_{26}H_{52}N_2O_2$ $^1$H-NMR (300 MHz, CDCl$_3$) δ: ppm 4.08 (t, 2H); 3.16 (m, 2H); 2.65 (m, 2H); 2.39 (br. m, 8H); 1.84-1.57 (br. m, 6H); 1.52-1.04 (br. m, 26H); 0.91 (m, 6H).

Step 4: Pentyl 4-((3-(1-(3-((2-(dinonylamino)ethyl)(nonyl)amino)propanoyl)piperidin-4-yl)propyl)(nonyl)amino)butanoate

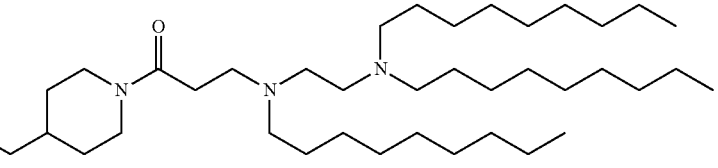

Chemical Formula: $C_{58}H_{116}N_4O_3$
Molecular Weight: 917.59

In the same manner as Step 11 for Compound 11, pentyl 4-((3-(1-(3-((2-(dinonylamino)ethyl)(nonyl)amino)propanoyl)piperidin-4-yl)propyl)(nonyl)amino)butanoate was synthesized from pentyl 4-(nonyl(3-(piperidin-4-yl)propyl)amino)butanoate (259 mg, 0.61 mmol), 3-((2-(dinonylamino)ethyl)(nonyl)amino)propanoic acid (343 mg, 0.67 mmol), iPr$_2$EtN (234 μL, 1.34 mmol), and T3P (50% EtOAc solution, 1.09 mL, 1.83 mmol) in THF (20 mL). Yield (270 mg, 48%).

UPLC/ELSD: RT=2.85 min. MS (ES): m/z (MH$^+$) 918.18 for $C_{58}H_{116}N_4O_3$ $^1$H-NMR (300 MHz, CDCl$_3$) δ: ppm 4.61 (m, 1H); 4.08 (t, 2H); 4.08 (m, 1H); 3.08-2.72 (br. m, 4H); 2.63-2.26 (br. m, 20H); 1.87-1.57 (br. m, 6H); 1.54-1.00 (br. m, 67H); 0.90 (m, 15H).

BW: Compound 85: 3-((2-(Dinonylamino)ethyl)(nonyl)amino)-1-(4-(3-(dinonylamino)propyl)piperidin-1-yl)propan-1-one Step 1: tert-Butyl 4-(3-(dinonylamino)propyl)piperidine-1-carboxylate

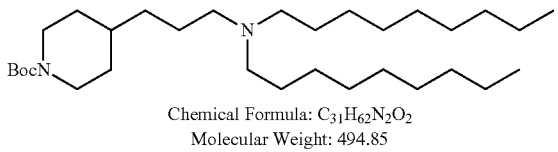 [SMILES: CCCCCCCCCN(CCCCCCCCC)CCCC1CCN(C(=O)OC(C)(C)C)CC1]

Chemical Formula: C₃₁H₆₂N₂O₂
Molecular Weight: 494.85

In the same manner as Step 1 for Compound 49 tert-butyl 4-(3-(dinonylamino)propyl)piperidine-1-carboxylate was synthesized from tert-butyl 4-(3-aminopropyl)piperidine-1-carboxylate (2.50 g, 10.3 mmol), 1-bromononane (2.14 g, 10.3 mmol), K₂CO₃ (2.85 g, 20.6 mmol), and KI (171 mg, 0.10 mmol) in MeCN (200 mL). Yield (1.03 g, 20%).

UPLC/ELSD: RT=2.46 min. MS (ES): m/z (MH⁺) 495.66 for C₃₁H₆₂N₂O₂

¹H-NMR (300 MHz, CDCl₃) δ: ppm 4.09 (br. m, 2H); 2.69 (br. m, 2H); 2.39 (br. m, 6H); 1.75-1.00 (br. m, 46H); 0.90 (t, 6H).

Step 2: N-Nonyl-N-(3-(piperidin-4-yl)propyl)nonan-1-amine

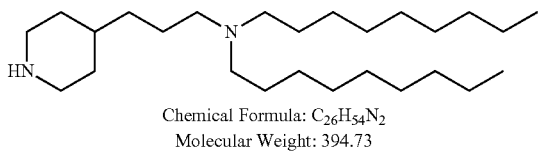 [SMILES: CCCCCCCCCN(CCCCCCCCC)CCCC1CCNCC1]

Chemical Formula: C₂₆H₅₄N₂
Molecular Weight: 394.73

In the same manner as Step 4 for Compound 11, N-nonyl-N-(3-(piperidin-4-yl)propyl)nonan-1-amine was synthesized from tert-butyl 4-(3-(dinonylamino)propyl)piperidine-1-carboxylate (1.03 g, 2.08 mmol), and TFA (8.0 mL, 104 mmol) in DCM (10 mL). Yield (778 mg, 95%).

UPLC/ELSD: RT=1.31 min. MS (ES): m/z (MH⁺) 395.61 for C₂₆H₅₄N₂

¹H-NMR (300 MHz, CDCl₃) δ: ppm 3.18-2.50 (br. m, 4H); 2.40 (br. m, 6H); 1.70 (m, 2H); 1.58-1.03 (br. m, 36H); 0.90 (t, 6H).

Step 3: 3-((2-(Dinonylamino)ethyl)(nonyl)amino)-1-(4-(3-(dinonylamino)propyl)piperidin-1-yl)propan-1-one In the same manner as Step 11 for Compound 11, 3-((2-(dinonylamino)ethyl)(nonyl)amino)-1-(4-(3-(dinonylamino)propyl)piperidin-1-yl)propan-1-one was synthesized from N-nonyl-N-(3-(piperidin-4-yl)propyl)nonan-1-amine (247 mg, 0.63 mmol), 3-((2-(dinonylamino)ethyl)(nonyl)amino)propanoic acid (352 mg, 0.69 mmol), iPr₂EtN (240 µL, 1.4 mmol), and T3P (50% EtOAc solution, 1.1 mL, 1.9 mmol) in THF (20 mL). Yield (293 mg, 53%).

UPLC/ELSD: RT=3.01 min. MS (ES): m/z (MH⁺) 888.08 for C₅₈H₁₁₈N₄O

¹H-NMR (300 MHz, CDCl₃) δ: ppm 4.61 (m, 1H); 3.86 (m, 1H); 2.99 (m, 1H); 2.82 (m, 2H); 2.61-2.29 (br. m, 19H); 1.75 (m, 2H); 1.60-1.00 (br. m, 77H); 0.89 (t, 15H).

BX: Compound 86: 3-((3-(4-(3-((2-(Dinonylamino)ethyl)(nonyl)amino)propanoyl)piperazin-1-yl)-3-oxopropyl)(nonyl)amino)propyl Hexanoate Step 1: 3-((3-(tert-Butoxy)-3-oxopropyl)(nonyl)amino)propyl Hexanoate

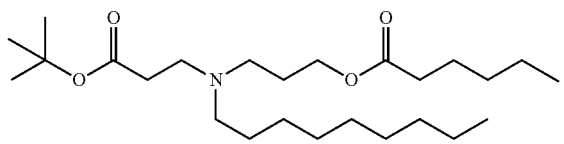

Chemical Formula: C₂₅H₄₉NO₄
Molecular Weight: 427.67

In the same manner as Step 3 for Compound 44, 2-((3-(tert-butoxy)-3-oxopropyl)(nonyl)amino)ethyl heptanoate was synthesized from tert-butyl 3-(nonylamino)propanoate (750 mg, 2.76 mmol), 3-bromopropyl hexanoate (786 mg, 3.32 mmol), K₂CO₃ (764 mg, 5.53 mmol), and KI (46 mg, 0.28 mmol) in MeCN (100 mL). Yield (661 mg, 56%).

UPLC/ELSD: RT=1.80 min. MS (ES): m/z (MH⁺) 428.49 for C₂₅H₄₉NO₄

¹H-NMR (300 MHz, CDCl₃) δ: ppm 4.12 (t, 2H); 2.73 (t, 2H); 2.56-2.24 (br. m, 8H); 1.77 (m, 2H); 1.64 (m, 2H); 1.55-1.10 (br. m, 27H); 0.91 (m, 6H).

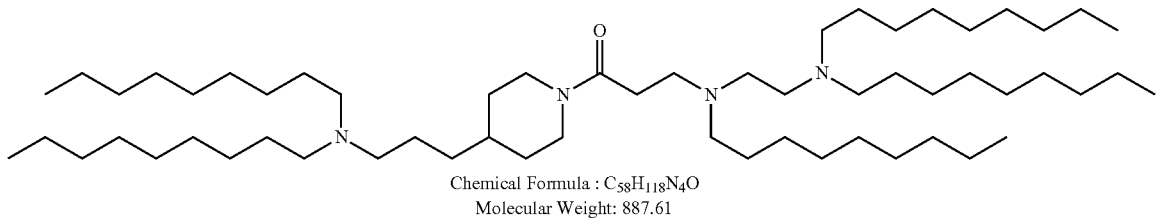 [SMILES: CCCCCCCCCN(CCCCCCCCC)CCCC1CCN(C(=O)CCN(CCCCCCCCC)CCN(CCCCCCCCC)CCCCCCCCC)CC1]

Chemical Formula: C₅₈H₁₁₈N₄O
Molecular Weight: 887.61

Step 2: 3-((3-(Hexanoyloxy)propyl)(nonyl)amino)propanoic Acid

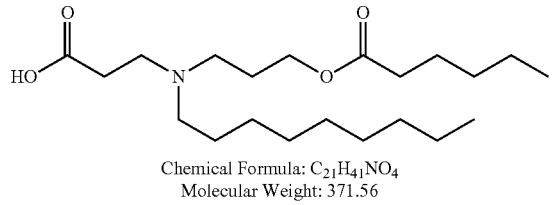 [SMILES: CCCCCCCCCN(CCCOC(=O)CCCCC)CCC(=O)O]

Chemical Formula: C_{21}H_{41}NO_4
Molecular Weight: 371.56

In the same manner as Step 4 for Compound 44, 3-((3-(hexanoyloxy)propyl)(nonyl)amino)propanoic acid was synthesized from 3-((3-(tert-butoxy)-3-oxopropyl)(nonyl)amino)propyl hexanoate (661 mg, 1.55 mmol), and TFA (5.9 mL, 77 mmol) in DCM (6 mL). Yield (556 mg, 97%).

UPLC/ELSD: RT=1.14 min. MS (ES): m/z (MH$^+$) 372.31 for C$_{21}$H$_{41}$NO$_4$ $^1$H-NMR (300 MHz, CDCl$_3$) δ: ppm 4.13 (t, 2H); 2.84 (t, 2H); 2.72 (t, 2H); 2.62 (t, 2H); 2.46 (t, 2H); 2.31 (t, 2H); 1.90 (m, 2H); 1.72-1.10 (br. m, 20H); 0.90 (M, 6H).

Step 3: tert-Butyl 4-(3-((3-(hexanoyloxy)propyl)(nonyl)amino)propanoyl)piperazine-1-carboxylate

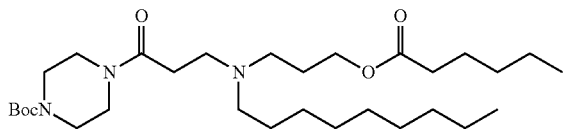

Chemical Formula: C$_{30}$H$_{57}$N$_3$O$_5$
Molecular Weight: 539.80

In the same manner as Step 3 for Compound 11, tert-butyl 4-(3-((3-(hexanoyloxy)propyl)(nonyl)amino)propanoyl)piperazine-1-carboxylate was synthesized from 3-((3-(hexanoyloxy)propyl)(nonyl)amino)propanoic acid (570 mg, 1.49 mmol), 1-boc-piperazine (334 mg, 1.80 mmol), iPr$_2$EtN (573 μL, 3.29 mmol), and T3P (50% EtOAc solution, 2.67 mL, 4.49 mmol) in THF (20 mL). Yield (635 mg, 79%).

UPLC/ELSD: RT=1.85 min. MS (ES): m/z (MH$^+$) 540.52 for C$_{30}$H$_{57}$N$_3$O$_5$ $^1$H-NMR (300 MHz, CDCl$_3$) δ: ppm 4.12 (t, 2H); 3.60 (m, 2H); 3.46 (br. m, 6H); 2.80 (m, 2H); 2.58-2.37 (br. m, 6H); 2.30 (t, 2H); 1.78 (m, 2H); 1.63 (m, 2H); 1.54-1.10 (br. m, 27H); 0.90 (m, 6H).

Step 4: 3-(Nonyl(3-oxo-3-(piperazin-1-yl)propyl)amino)propyl hexanoate

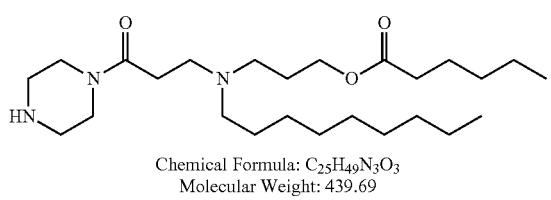 [SMILES: CCCCCCCCCN(CCCOC(=O)CCCCC)CCC(=O)N1CCNCC1]

Chemical Formula: C$_{25}$H$_{49}$N$_3$O$_3$
Molecular Weight: 439.69

In the same manner as Step 4 for Compound 11, 3-(nonyl (3-oxo-3-(piperazin-1-yl)propyl)amino)propyl hexanoate was synthesized from tert-butyl 4-(3-((3-(hexanoyloxy)propyl)(nonyl)amino)propanoyl)piperazine-1-carboxylate (635 mg, 1.18 mmol), and TFA (4.5 mL, 59 mmol) in DCM (5 mL). Yield (510 mg, 99%).

UPLC/ELSD: RT=0.72 min. MS (ES): m/z (MH$^+$) 440.47 for C$_{25}$H$_{49}$N$_3$O$_3$ $^1$H-NMR (300 MHz, CDCl$_3$) δ: ppm 4.12 (t, 2H); 3.60 (m, 2H) 3.46 (m, 2H); 2.85 (br. m, 6H); 2.49 (br. m, 6H); 2.30 (t, 2H); 1.80 (m, 2H); 1.64 (m, 2H); 1.52-1.10 (br. m, 19H); 0.91 (m, 6H).

Step 5: 3-((3-(4-(3-((2-(Dinonylamino)ethyl)(nonyl)amino)propanoyl)piperazin-1-yl)-3-oxopropyl)(nonyl)amino)propyl Hexanoate

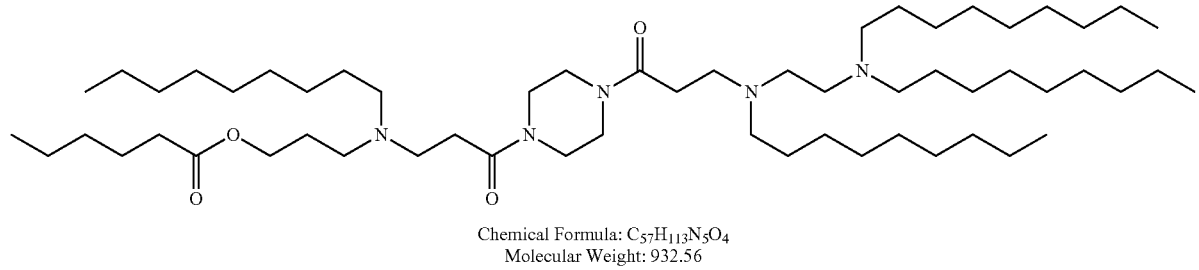 [SMILES: CCCCCCCCCN(CCCOC(=O)CCCCC)CCC(=O)N1CCN(C(=O)CCN(CCCCCCCCC)CCN(CCCCCCCCC)CCCCCCCCC)CC1]

Chemical Formula: C$_{57}$H$_{113}$N$_5$O$_4$
Molecular Weight: 932.56

In the same manner as Step 11 for Compound 11, 3-((3-(4-(3-((2-(dinonylamino)ethyl)(nonyl)amino)propanoyl) piperazin-1-yl)-3-oxopropyl)(nonyl)amino)propyl hexanoate was synthesized from 3-(nonyl(3-oxo-3-(piperazin-1-yl) propyl)amino)propyl hexanoate (154 mg, 0.351 mmol), 3-((2-(dinonylamino)ethyl)(nonyl)amino)propanoic acid (197 mg, 0.386 mmol), iPr$_2$EtN (134 μL, 0.77 mmol), and T3P (50% EtOAc solution, 616 μL, 1.05 mmol) in THF (10 mL). Yield (69 mg, 21%).

UPLC/ELSD: RT=2.70 min. MS (ES): m/z (MH$^+$) 933.10 for C$_{57}$H$_{113}$N$_5$O$_4$ ¹H-NMR (300 MHz, CDCl₃) δ: ppm 4.12 (t, 2H); 3.72-3.40 (br. m, 8H); 2.81 (br. m, 4H); 2.61-2.36 (br. m, 18H); 2.30 (t, 2H); 1.78 (m, 2H); 1.64 (m, 2H); 1.54-1.06 (br. m, 60H); 0.90 (m, 15H).

BY: Compound 87: 3-((3-(1-(3-((2-(Dinonylamino) ethyl)(nonyl)amino)propanoyl)piperidin-4-yl)propyl) (nonyl)amino)propyl Hexanoate Step 1: tert-Butyl 4-(3-((3-(hexanoyloxy)propyl) (nonyl)amino)propyl)piperidine-1-carboxylate

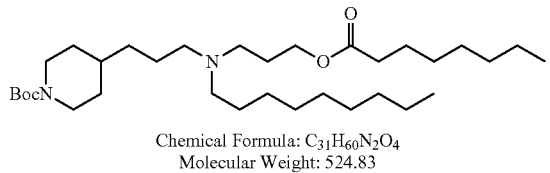 [SMILES: CCCCCCCCCN(CCCOC(=O)CCCCCCC)CCCC1CCN(C(=O)OC(C)(C)C)CC1]

Chemical Formula: C₃₁H₆₀N₂O₄
Molecular Weight: 524.83

In the same manner as Step 1 for Compound 57, tert-butyl 4-(3-((3-(hexanoyloxy)propyl)(nonyl)amino)propyl)piperidine-1-carboxylate was synthesized from tert-butyl 4-(3-(nonylamino)propyl)piperidine-1-carboxylate (500 mg, 1.36 mmol), 3-bromopropyl hexanoate (386 mg, 1.63 mmol), K₂CO₃ (375 mg, 2.71 mmol), and KI (45 mg, 0.27 mmol) in MeCN (100 mL). Yield (322 mg, 45%).

UPLC/ELSD: RT=2.09 min. MS (ES): m/z (MH⁺) 525.60 for C₃₁H₆₀N₂O₄

¹H-NMR (300 MHz, CDCl₃) δ: ppm 4.12 (br. m, 4H); 2.67 (m, 2H); 2.56-2.24 (br. m, 8H); 1.90-1.00 (br. m, 40H); 0.91 (m, 6H).

Step 2:
3-(nonyl(3-(piperidin-4-yl)propyl)amino)propyl Hexanoate

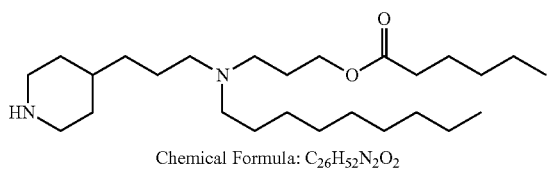

Chemical Formula: C₂₆H₅₂N₂O₂
Molecular Weight: 424.71

In the same manner as Step 4 for Compound 11, 3-(nonyl (3-(piperidin-4-yl)propyl)amino)propyl hexanoate was synthesized from tert-butyl 4-(3-((3-(hexanoyloxy)propyl) (nonyl)amino)propyl)piperidine-1-carboxylate (322 mg, 0.614 mmol), and TFA (2.3 mL, 31 mmol) in DCM (2.5 mL). Yield (260 mg, 99%).

UPLC/ELSD: RT=0.89 min. MS (ES): m/z (MH⁺) 425.54 for C₂₆H₅₂N₂O₂

¹H-NMR (300 MHz, CDCl₃) δ: ppm 4.12 (t, 2H); 3.12 (m, 2H); 2.75-2.24 (br. m, 10H); 1.84-1.54 (br. m, 6H); 1.54-1.02 (br. m, 26H); 0.90 (m, 6H).

Step 3: 3-((3-(1-(3-((2-(Dinonylamino)ethyl)(nonyl) amino)propanoyl)piperidin-4-yl)propyl)(nonyl) amino)propyl Hexanoate

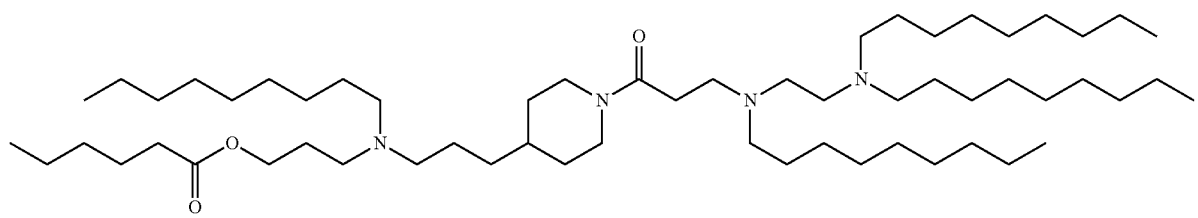

Chemical Formula: C₅₈H₁₁₆N₄O₃
Molecular Weight: 917.59

In the same manner as Step 11 for Compound 11, 3-((3-(1-(3-((2-(dinonylamino)ethyl)(nonyl)amino)propanoyl)piperidin-4-yl)propyl)(nonyl)amino)propyl hexanoate was synthesized from 3-(nonyl(3-(piperidin-4-yl)propyl)amino) propyl hexanoate (149 mg, 0.351 mmol), 3-((2-(dinonylamino)ethyl)(nonyl)amino)propanoic acid (197 mg, 0.386 mmol), iPr₂EtN (134 μL, 0.77 mmol), and T3P (50% EtOAc solution, 616 μL, 1.05 mmol) in THF (10 mL). Yield (39 mg, 12%).

UPLC/ELSD: RT=2.83 min. MS (ES): m/z (MH⁺) 918.01 for C₅₈H₁₁₆N₄O₃

¹H-NMR (300 MHz, CDCl₃) δ: ppm 4.61 (m, 1H); 4.12 (t, 2H); 3.87 (m, 1H); 3.08-2.74 (br. m, 4H); 2.70-2.23 (br. m, 20H); 1.82-1.56 (br. m, 6H); 1.56-1.00 (br. m, 67H); 0.90 (m, 15H).

BZ. Compound 17-1: 2-(Dihexylamino)ethan-1-ol (Compound 17-1)

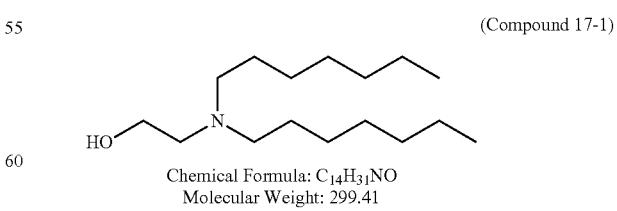

Chemical Formula: C₁₄H₃₁NO
Molecular Weight: 299.41

To a solution of 1-bromohexane (5 g, 82 mmol) in MeCN (380 mL) was added ethanolamine (11.5 mL, 82 mmol), K₂CO₃ (22.7 g, 164 mmol), and KI (1.36 g, 8.2 mmol). The reaction was allowed to stir at 82° C. for 48 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-20% MeOH/DCM) provided 2-(dihexylamino)ethan-1-ol (2.58 g, 14%).

UPLC/ELSD: RT=0.41 min. MS (ES): m/z (MH$^+$) 229.95 for $C_{14}H_{31}NO$ $^1$H NMR (300 MHz, CDCl$_3$) δ: ppm 3.62 (t, 2H); 2.70 (t, 2H), 2.57 (t, 4H); 1.50 (br. m, 4H); 1.30 (br, 12H); 0.91 (t, 6H).

CA. Compound 17-2: 2-(Hexyl((9Z,12Z)-octadeca-9,12-dien-1-yl)amino)ethan-1-ol Step 1: 2-(Hexylamino)ethan-1-ol 2-(Hexylamino)ethan-1-ol was isolated from the same reaction that produced with Compound 1, 2-(dihexylamino)ethan-1-ol.

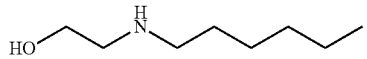

Chemical Formula: $C_8H_{19}NO$
Molecular Weight: 145.25

$^1$H-NMR (300 MHz, CDCl$_3$) δ: ppm 3.62 (t, 2H); 2.78 (t, 2H); 2.62 (t, 2H); 2.10-1.80 (br. m, 2H); 1.49 (m, 2H); 1.30 (br. m, 6H); 0.89 (t, 3H).

Step 2: 2-(Hexyl((9Z,12Z)-octadeca-9,12-dien-1-yl)amino)ethan-1-ol (Compound 17-2)

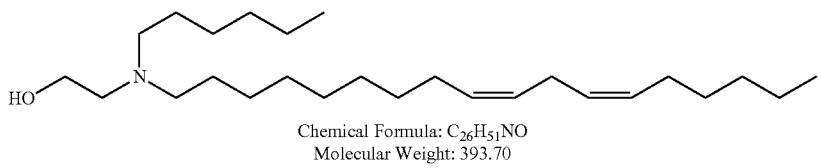

Chemical Formula: $C_{26}H_{51}NO$
Molecular Weight: 393.70

To a solution of (6Z,9Z)-18-bromooctadeca-6,9-diene (0.2 g, 0.61 mmol) in MeCN (3.5 mL) was added 2-(hexylamino)ethan-1-ol (80 mg, 0.55 mmol), K$_2$CO$_3$ (76 mg, 0.55 mmol), and KI (9 mg, 0.06 mmol). The reaction was allowed to stir at room temperature for 18 hours. The reaction mixture was cooled to room temperature, added ethyl acetate and extracted with water. The combined extracts were dried with Na$_2$SO$_4$, filtered and concentrated in vacuo. Purification by ISCO silica flash chromatography (0-10% MeOH/DCM) provided 2-(Hexyl((9Z,12Z)-octadeca-9,12-dien-1-yl)amino)ethan-1-ol (23 mg, 11%).

LC/ELSD: RT=2.47 min. MS (ES): m/z (MH$^+$) 394.60 for $C_{26}H_{51}NO$ $^1$H NMR (300 MHz, CDCl$_3$) δ: ppm 5.36 (m, 4H); 4.07 (m, 2H); 3.23-3.13 (m, 6H); 2.77 (m, 2H); 2.04 (m, 4H); 1.86 (m, 4H); 1.34 (m, 23H); 0.89 (m, 6H)

CB. Compound 17-3: 2-(Nonyl((9Z,12Z)-octadeca-9,12-dien-1-yl)amino)ethan-1-ol Compound 17-3 was synthesized according to the same procedure as Compound 17-2.

(Compound 17-3)

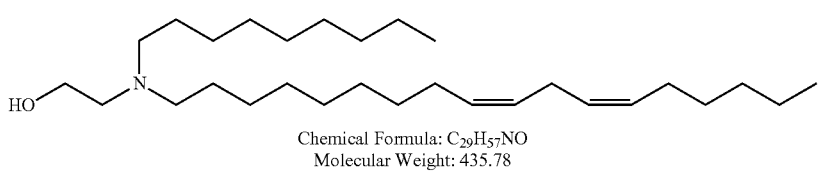

Chemical Formula: $C_{29}H_{57}NO$
Molecular Weight: 435.78

LC/ELSD: RT=2.72 min. MS (ES): m/z (MH⁺) 436.63 for $C_{29}H_{57}NO$
¹H NMR (300 MHz, CDCl₃) δ: ppm 5.36 (m, 4H); 3.55 (t, 2H); 2.77 (t, 2H); 2.60 (t, 2H); 2.47 (m, 4H); 2.04 (m, 4H); 1.55-1.18 (br. m, 33H); 0.87 (m, 6H).

CD. Compound 17-4: 2-(Dodecyl((9Z,12Z)-octadeca-9,12-dien-1-yl)amino)ethan-1-ol Compound 17-4 was synthesized according to the same procedure as Compound 17-2.

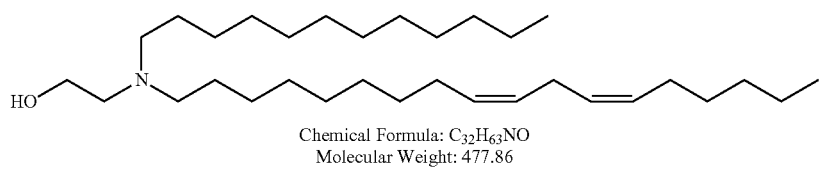

(Compound 17-4)

Chemical Formula: $C_{32}H_{63}NO$
Molecular Weight: 477.86

UPLC: RT=3.18 min. MS (ES): m/z (MH⁺) 478.516 for $C_{32}H_{63}NO$
¹H NMR (400 MHz, CDCl₃) δ: ppm 5.33 (m, 4H); 3.53 (s, 2H); 2.75 (t, 2H); 2.58 (m, 2H); 2.45 (m, 4H); 2.03 (dt, 4H); 1.43 (m, 4H); 1.24 (m, 34H); 0.86 (n, 6H).

CE. Compound 17-5: 2-(((9Z,12Z)—Octadeca-9,12-dien-1-yl)(tetradecyl)amino)ethan-1-ol Compound 17-5 was synthesized according to the same procedure as Compound 17-2.

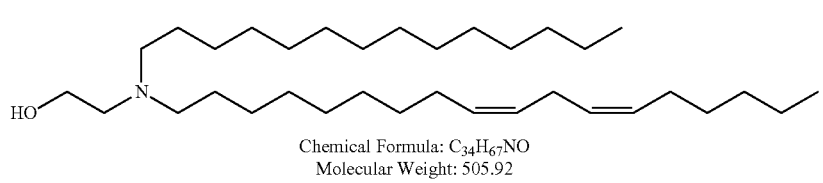

(Compound 17-5)

Chemical Formula: $C_{34}H_{67}NO$
Molecular Weight: 505.92

LC/ELSD: RT=3.39 min. MS (ES): m/z (MH⁺) 506.56 for $C_{34}H_{67}NO$
¹H NMR (300 MHz, CDCl₃) δ: ppm 5.37 (m, 4H); 3.58 (m, 2H); 2.80 (m, 2H); 2.69-2.42 (br. m, 5H); 2.07 (m, 4H); 1.56-1.18 (br. m, 44H); 0.91 (m, 6H).

CF. Compound 17-6: 2-(((9Z,12Z)—Octadeca-9,12-dien-1-yl)(octadecyl)amino)ethan-1-ol Compound 17-6 was synthesized according to the same procedure as Compound 17-2.

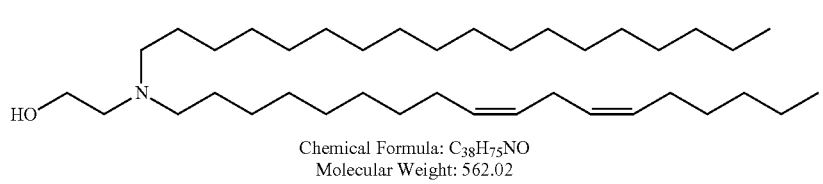

(Compound 17-6)

Chemical Formula: $C_{38}H_{75}NO$
Molecular Weight: 562.02

LC/ELSD: RT=3.68 min. MS (ES): m/z (MH⁺) 562.58 for $C_{38}H_{75}NO$
¹H NMR (300 MHz, CDCl₃) δ: ppm 5.39 (m, 4H); 3.58 (m, 2H); 2.80 (m, 2H); 2.68-2.44 (br. m, 5H); 2.07 (m, 4H); 1.57-1.20 (br. m, 52H); 0.91 (m, 6H).

CG. Compound 17-7: 2-(Ditetradecylamino)ethan-1-ol

Compound 17-7 was synthesized according to the same procedure as Compound 17-1.

(Compound 17-7)

Chemical Formula: $C_{30}H_{63}NO$
Molecular Weight: 453.84

UPLC/ELSD: RT=3.30 min. MS (ES): m/z (MH⁺) 454.46 for $C_{30}H_{63}NO$
¹H-NMR (300 MHz, CDCl₃) δ: ppm 3.54 (br. m, 2H); 2.59 (br. m, 2H); 2.46 (br. m, 4H); 1.56-1.17 (br. m, 48H); 0.90 (br. m, 6H).

CG. Compound 17-8: 2-(Di((Z)-octadec-9-en-1-yl)amino)ethan-1-ol

Compound 17-8 was synthesized according to the same procedure as Compound 17-1.

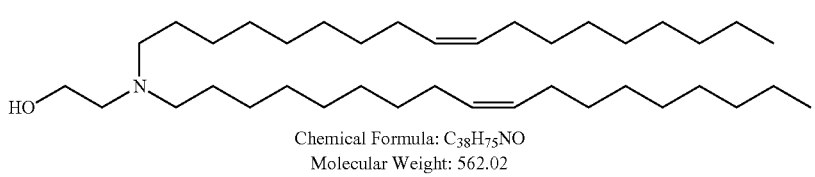

(Compound 17-8)

Chemical Formula: $C_{38}H_{75}NO$
Molecular Weight: 562.02

UPLC/ELSD: RT=7.325 min. MS (ES): m/z (MH$^+$) 562.60 for $C_{38}H_{75}NO$
$^1$H-NMR (300 MHz, CDCl$_3$) δ: ppm 5.34 (m, 4H); 3.53 (t, 2H); 2.58 (t, 2H); 2.45 (t, 4H); 2.01 (m, 8H); 1.44 (m, 4H); 1.38-1.18 (br. m, 44H); 0.88 (t, 6H).

CH. Compound 17-9: (9Z,12Z)—N-(2-Methoxyethyl)-N-((9Z,12Z)-octadeca-9,12-dien-1-yl)octadeca-9,12-dien-1-amine Compound 17-9 was synthesized according to the same procedure as Compound 17-1.

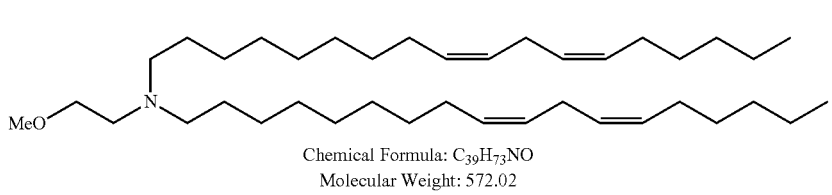

(Compound 17-9)

Chemical Formula: $C_{39}H_{73}NO$
Molecular Weight: 572.02

LC/ELSD: RT=3.53 min. MS (ES): m/z (MH$^+$) 572.72 for $C_{39}H_{73}NO$
$^1$H NMR (300 MHz, CDCl$_3$) δ: ppm 5.39 (m, 8H); 3.47 (m, 2H); 3.37 (s, 3H); 2.80 (m, 4H); 2.5 (m, 2H); 2.46 (m, 4H); 2.09 (m, 8H); 1.50-1.22 (m, 36H); 0.92 (m, 6H).

CI. Compound 17-10: 2-(Dinonylamino)ethan-1-ol

Compound 17-10 was synthesized according to the same procedure as Compound 17-1.

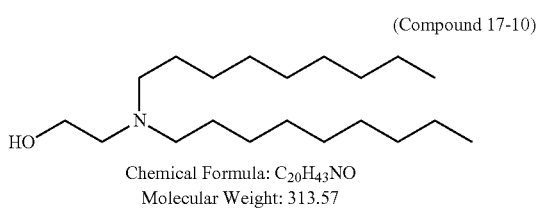 [SMILES: CCCCCCCCCN(CCO)CCCCCCCCC]

(Compound 17-10)

Chemical Formula: $C_{20}H_{43}NO$
Molecular Weight: 313.57

$^1$H-NMR (300 MHz, CDCl$_3$) δ: ppm 3.57 (t, 2H); 2.63 (t, 2H); 2.49 (br. m, 4H); 1.48 (br. m, 4H); 1.29 (br. m, 24H); 0.91 (t, 6H).

CJ: Compound 17-11: 2-(Didodecylamino)ethan-1-ol

Compound 17-11 was synthesized according to the same procedure as Compound 17-1.

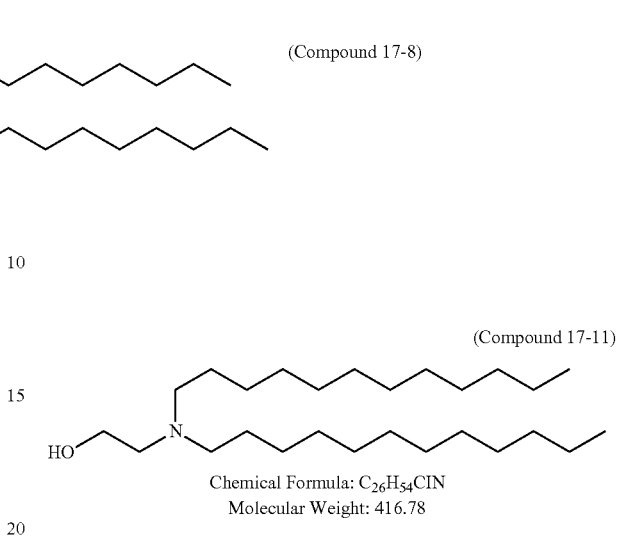

(Compound 17-11)

Chemical Formula: $C_{26}H_{54}ClN$
Molecular Weight: 416.78

UPLC/ELSD: RT=2.69 min. MS (ES): m/z (MH$^+$) 398.56 for $C_{26}H_{55}NO$
$^1$H-NMR (300 MHz, CDCl$_3$) δ: ppm 3.57 (t, 2H); 2.63 (t, 2H); 2.49 (br. m, 4H); 1.48 (br. m, 4H); 1.29 (br. m, 36H); 0.91 (t, 6H).

CK. Compound 17-12: 3-(Didodecylamino)propan-1-ol

Compound 17-12 was synthesized according to the same procedure as Compound 1.

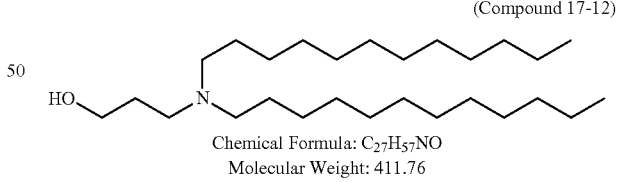

(Compound 17-12)

Chemical Formula: $C_{27}H_{57}NO$
Molecular Weight: 411.76

UPLC/ELSD: RT=2.75 min. MS (ES): m/z (MH$^+$) 412.36 for $C_{27}H_{57}NO$
$^1$H-NMR (300 MHz, CDCl$_3$) δ: ppm 3.79 (t, 2H); 2.66 (t, 2H); 2.43 (br. m, 4H); 1.69 (br. m, 2H); 1.47 (br. m, 4H) 1.25 (br. m, 36H); 0.87 (t, 6H).

CL. Compound 17-13: 4-(Didodecylamino)butan-1-ol

Compound 17-13 was synthesized according to the same procedure as Compound 17-1.

(Compound 17-13)

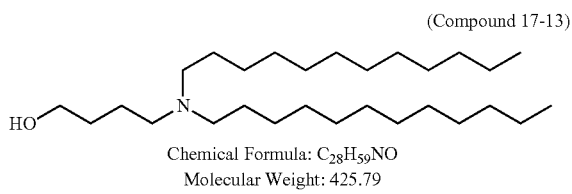 [SMILES: CCCCCCCCCCCCN(CCCCO)CCCCCCCCCCCC]

Chemical Formula: $C_{28}H_{59}NO$
Molecular Weight: 425.79

UPLC/ELSD: RT=2.80 min. MS (ES): m/z (MH$^+$) 426.42 for $C_{28}H_{59}NO$ $^1$H-NMR (300 MHz, CDCl$_3$) δ: ppm 3.56 (br. m, 2H); 2.46 (br. m, 6H); 1.66 (br. m, 4H); 1.48 (br. m, 4H); 1.26 (br. m, 36H); 0.88 (t, 6H).

CM. Compound 19-1: N-Nonyl-N-(2-(piperazin-1-yl)ethyl)nonan-1-amine

Step 1: tert-Butyl 4-(2-(dinonylamino)ethyl)piperazine-1-carboxylate

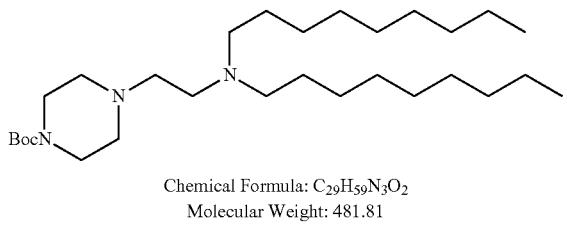 [SMILES: CCCCCCCCCN(CCCCCCCCC)CCN1CCN(C(=O)OC(C)(C)C)CC1]

Chemical Formula: $C_{29}H_{59}N_3O_2$
Molecular Weight: 481.81

A mixture of 1-bromononane (1.81 g, 8.72 mmol), 4-(2-aminoethyl)-1-boc-piperazine (2.0 g, 8.72 mmol), K$_2$CO$_3$ (2.4 g, 17.4 mmol), KI (145 mg, 0.872 mmol) in 44 mL MeCN was allowed to stir at 65° C. for 16 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-20% MeOH/DCM) provided tert-butyl 4-(2-(dinonylamino)ethyl)piperazine-1-carboxylate (924 mg, 1.92 mmol, 44%).

UPLC/ELSD: RT=1.99 min. MS (ES): m/z (MH$^+$) 482.36 for $C_{29}H_{59}N_3O_2$ $^1$H NMR (400 MHz, CDCl$_3$) δ: ppm 3.45 (br. m, 4H); 3.10 (br. m, 2H); 2.59 (br. m, 2H); 2.44 (br. m, 8H); 1.60-1.00 (br. m, 37H); 0.91 (t, 6H).

Step 2: Compound 19-1: N-Nonyl-N-(2-(piperazin-1-yl)ethyl)nonan-1-amine

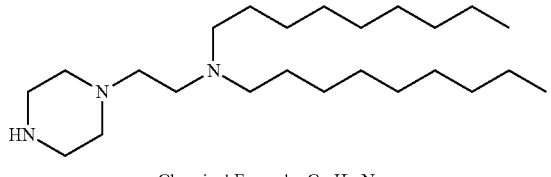

Chemical Formula: $C_{24}H_{51}N_3$
Molecular Weight: 381.69

A solution of tert-butyl 4-(2-(dinonylamino)ethyl)piperazine-1-carboxylate (924 mg, 1.92 mmol) in 8 mL DCM was treated with TFA (7.4 mL, 96 mmol). The reaction was allowed to stir at room temperature for 16 hours. The reaction was concentrated, and the crude residue was taken up in chloroform and washed with 5% Na$_2$CO$_3$ and brine, dried over anhydrous Na$_2$SO$_4$, filtered, and concentrated in vacuo. Purification by ISCO silica flash chromatography (0-100% DCM/[DCM, 20% MeOH, 1% NH$_4$OH]) provided N-nonyl-N-(2-(piperazin-1-yl)ethyl)nonan-1-amine (563 mg, 1.48 mmol, 77%).

UPLC/ELSD: RT=1.27 min. MS (ES): m/z (MH$^+$) 382.54 for $C_{24}H_{51}N_3$ $^1$H NMR (400 MHz, CDCl$_3$) δ: ppm 2.92 (br. m, 4H); 2.62 (br. m, 2H); 2.48 (br. m, 10H); 2.40-1.88 (br. m, 1H); 1.46 (br. m, 4H); 1.29 (br. m, 24H); 0.91 (t, 6H).

CN. Compound 19-2: N-Dodecyl-N-(2-(piperazin-1-yl)ethyl)dodecan-1-amine

Step 1: tert-Butyl 4-(2-(didodecylamino)ethyl)piperazine-1-carboxylate

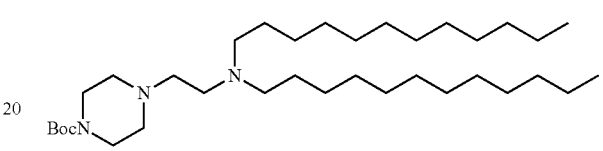

Chemical Formula: $C_{35}H_{71}N_3O_2$
Molecular Weight: 565.97

A mixture of 1-bromododecane (1.1 mL, 4.6 mmol), 4-(2-aminoethyl)-1-boc-piperazine (1.0 g, 4.4 mmol), K$_2$CO$_3$ (0.61 g, 4.4 mmol), in 10 mL MeCN was allowed to stir at room temperature for 12 h. After this time the reaction was filtered and concentrated. The crude material was purified by silica gel chromatography (0-20% MeOH in DCM with 1% NH$_4$OH to afford tert-butyl 4-(2-(didodecylamino)ethyl)piperazine-1-carboxylate (450 mg, 0.80 mmol, 18%).

UPLC/ELSD: RT=2.87 min. MS (ES): m/z (MH$^+$) 566.655 for $C_{35}H_{71}N_3O_2$ $^1$H NMR (400 MHz, CDCl$_3$) δ: ppm 3.40 (m, 4H); 2.56 (m, 2H); 2.40 (m, 10H); 1.44 (s, 9H); 1.40-1.24 (m, 40H); 0.86 (t, 6H).

Step 2: Compound 19-2: N-Dodecyl-N-(2-(piperazin-1-yl)ethyl)dodecan-1-amine

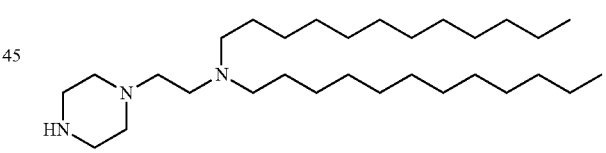

Chemical Formula: $C_{30}H_{63}N_3$
Molecular Weight: 465.86

A solution of tert-butyl 4-(2-(didodecylamino)ethyl)piperazine-1-carboxylate (154 mg, 0.27 mmol) in 1 mL DCM was treated with TFA (0.21 mL, 2.7 mmol). The reaction was allowed to stir overnight. After this time addition TFA (0.1 mL, 1.3 mmol) was added. After an additional 3 h the reaction was concentrated. The crude residue was taken up in DCM and washed with 5% K$_2$CO$_3$ and brine, dried over Na$_2$SO$_4$, filtered and concentrated. The crude material was purified by silica gel chromatography (0-20% MeOH in DCM with 1% NH$_4$OH) to provide N-dodecyl-N-(2-(piperazin-1-yl)ethyl)dodecan-1-amine (109 mg, 87%).

UPLC/ELSD: RT=2.10 min. MS (ES): m/z (MH$^+$) 466.379 for $C_{30}H_{63}N_3$ $^1$H NMR (400 MHz, CDCl$_3$) δ: ppm 2.88 (t, 4H); 2.61 (m, 2H); 2.45 (m, 10H); 1.43-1.24 (m, 40H); 0.86 (t, 6H).

CO. Compound 19-3: (9Z,12Z)—N-((9Z,12Z)—
Octadeca-9,12-dien-1-yl)-N-(2-(piperazin-1-yl)
ethyl)octadeca-9,12-dien-1-amine Step 1: (9Z,12Z)—Octadeca-9,12-dien-1-yl
Methanesulfonate

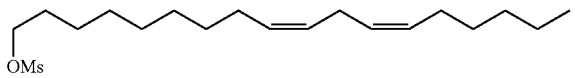

Chemical Formula: C₁₉H₃₆O₃S
Molecular Weight: 344.55

To a 0° C. solution of linoleyl alcohol (10 mL, 31.2 mmol) and trimethylamine (5.68 mL, 40.5 mmol)) in DCM (50 mL) was added dropwise a solution of methanesulfonyl chloride (2.66 mL, 34.3 mmol) in DCM (20 mL). The reaction was allowed to return to room temperature and let stir for 4 hours. The mixture was quenched by the addition of water and extracted with DCM. The organic layer was washed with saturated NaHCO₃, brine, dried over anhydrous Na₂SO₄, filtered, and concentrated in vacuo. Purification by ISCO silica flash chromatography (0-40% EtOAc/hexanes) provided (9Z,12Z)-octadeca-9,12-dien-1-yl methanesulfonate (10.0 g, 93%).

¹H-NMR (300 MHz, CDCl₃) δ: ppm 5.35 (m, 4H); 4.22 (t, 2H); 2.99 (s, 3H); 2.77 (t, 2H); 2.04 (q, 4H); 1.74 (m, 2H); 1.30 (br. m, 16H); 0.89 (t, 3H).

Step 2: (6Z,9Z)-18-Bromooctadeca-6,9-diene

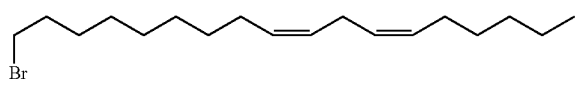

Chemical Formula: C₁₈H₃₃Br
Molecular Weight: 329.37

To a solution of (9Z,12Z)-octadeca-9,12-dien-1-yl methanesulfonate (10.0 g, 29.0 mmol) in diethyl ether (372 mL) was added magnesium bromide ethyl etherate (22.5 g, 87.1 mmol). The reaction was let stir at room temperature for 16 hours. The mixture was quenched by the addition of water and extracted with diethyl ether. The combined organic layers were washed with 1% K₂CO₃, brine, dried over anhydrous Na₂SO₄, filtered, and concentrated in vacuo. Purification by ISCO silica flash chromatography provided (6Z,9Z)-18-bromooctadeca-6,9-diene (8.9 g, 93%).

¹H-NMR (300 MHz, CDCl₃) δ: ppm 5.36 (m, 4H); 3.41 (t, 2H); 2.77 (t, 2H); 2.05 (q, 4H); 1.86 (m, 2H); 1.48-1.22 (br. m, 16H); 0.89 (t, 3H).

Step 3: tert-Butyl 4-(2-(di((9Z,12Z)-octadeca-9,12-dien-1-yl)amino)ethyl)piperazine-1-carboxylate

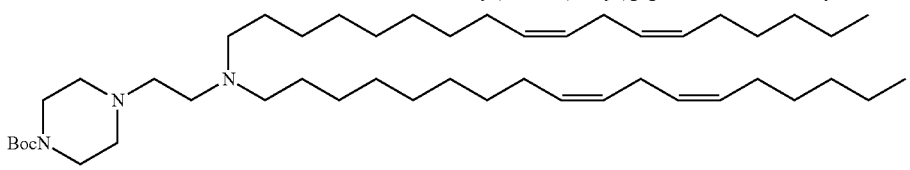

Chemical Formula: C₄₇H₈₇N₃O₂
Molecular Weight: 726.23

A mixture of (6Z,9Z)-18-bromooctadeca-6,9-diene (1.5 g, 4.55 mmol), 4-(2-aminoethyl)-1-boc-piperazine (1.04 g, 4.54 mmol), K₂CO₃ (1.27 g, 9.10 mmol), KI (75 mg, 0.452 mmol), in 22 mL MeCN was allowed to stir at room temperature for 48 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-50% DCM/[DCM, 20% MeOH, 1% NH₄OH]) provided tert-butyl 4-(2-(di((9Z,12Z)-octadeca-9,12-dien-1-yl)amino)ethyl)piperazine-1-carboxylate (1.08 g, 1.49 mmol, 65%).

¹H NMR (400 MHz, CDCl₃) δ: ppm 5.43-5.26 (br. m, 8H); 3.42 (t, 4H); 2.77 (m, 4H); 2.57 (m, 2H); 2.41 (br. m, 10H); 2.04 (br. m, 8H); 1.60-1.00 (br. m, 45H); 0.89 (t, 6H).

Step 4: Compound 19-3: (9Z,12Z)—N-((9Z,12Z)-Octadeca-9,12-dien-1-yl)-N-(2-(piperazin-1-yl)ethyl)octadeca-9,12-dien-1-amine

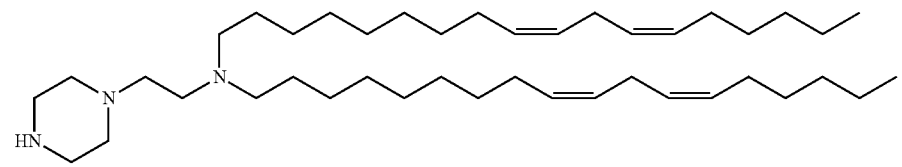

Chemical Formula: C₄₂H₇₉N₃
Molecular Weight: 626.12

A solution of tert-butyl 4-(2-(di((9Z,12Z)-octadeca-9,12-dien-1-yl)amino)ethyl)piperazine-1-carboxylate (1.06 g, 1.46 mmol) in 6 mL DCM was treated with TFA (5.6 mL, 73 mmol). After 4 hours the mixture was concentrated. The crude residue was taken up in chloroform, washed with 5% $Na_2CO_3$, brine, dried over anhydrous $Na_2SO_4$ and concentrated in vacuo. The residue was purification by ISCO silica flash chromatography (0-100% DCM/[DCM, 20% MeOH, 1% $NH_4OH$]) and ISCO $C_{18}$ flash chromatography (50-100% [MeCN 1% TFA]/[$H_2O$ 1% TFA]). The desired fractions were washed with 5% $Na_2CO_3$ and extracted with hexanes. The hexanes were washed with brine, dried over anhydrous $Na_2SO_4$, and concentrated in vacuo to provide (9Z,12Z)—N-((9Z,12Z)-octadeca-9,12-dien-1-yl)-N-(2-(piperazin-1-yl)ethyl)octadeca-9,12-dien-1-amine (108 mg, 12%).

UPLC/ELSD: RT=2.98 min. MS (ES): m/z (MH$^+$) 626.75 for $C_{42}H_{79}N_3$ $^1$H NMR (400 MHz, CDCl$_3$) δ: ppm 5.47-5.25 (br. m, 8H); 2.92 (m, 4H); 2.76 (m, 4H); 2.66 (br. m, 2H); 2.50 (br. m, 10H); 2.05 (m, 8H); 1.60-1.10 (br. m, 36H), 0.89 (t, 6H).

CP. Compound 19-4: N-Dodecyl-N-(2-(4-methylpiperazin-1-yl)ethyl)dodecan-1-amine

Intermediate 1: 2-(Didodecylamino)ethan-1-ol

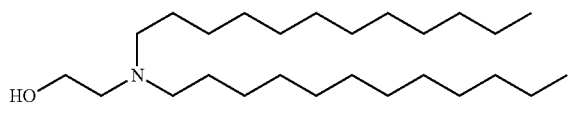

Chemical Formula: $C_{26}H_{55}NO$
Molecular Weight: 397.73

To a solution of 1-bromododecane (10 g, 40.1 mmol) in MeCN (84 mL) was added ethanolamine (1.10 mL, 18.2 mmol), $K_2CO_3$ (11.1 g, 80.1 mmol), and KI (302 mg, 1.82 mmol). The reaction was allowed to stir at 82° C. for 48 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-20% MeOH/DCM) provided 2-(didodecylamino)ethan-1-ol (3.87 g, 53%).

UPLC/ELSD: RT=2.69 min. MS (ES): m/z (MH$^+$) 398.56 for $C_{26}H_{55}NO$ $^1$H-NMR (300 MHz, CDCl$_3$) δ: ppm 3.57 (t, 2H); 2.63 (t, 2H); 2.49 (br. m, 4H); 1.48 (br. m, 4H); 1.29 (br. m, 36H); 0.91 (t, 6H).

Step 2:
N-(2-Chloroethyl)-N-dodecyldodecan-1-amine

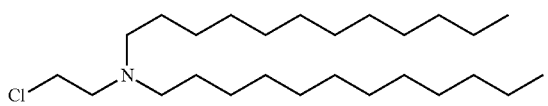

Chemical Formula: $C_{26}H_{54}ClN$
Molecular Weight: 416.18

To a 0° C. solution of 2-(didodecylamino)ethan-1-ol (3.87 g, 9.73 mmol) triethylamine (1.76 mL, 12.6 mmol) in DCM (50 mL) was added dropwise a solution of methanesulfonyl chloride (0.941 mL, 12.2 mmol) in DCM (5 mL). The reaction was allowed to return to room temperature and stir for 16 hours. The mixture was quenched by the addition of water and extracted with DCM. The organic layer was washed with saturated NaHCO$_3$, brine, dried over anhydrous Na$_2$SO$_4$, filtered, and concentrated in vacuo. Purification by ISCO silica flash chromatography (0-10% EtOAc/hexanes) provided N-(2-chloroethyl)-N-dodecyldodecan-1-amine (1.92 g, 47%).

$^1$H-NMR (300 MHz, CDCl$_3$) δ: ppm 3.51 (t, 2H); 2.78 (t, 2H); 2.47 (br. m, 4H); 1.44 (br. m, 4H); 1.28 (br. m, 36H); 0.90 (t, 6H).

Step 3: Compound 19-4: N-Dodecyl-N-(2-(4-methylpiperazin-1-yl)ethyl)dodecan-1-amine

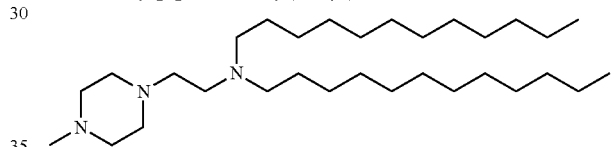

Chemical Formula: $C_{31}H_{65}N_3$
Molecular Weight: 479.88

A mixture of N-methylpiperazine (40 µL, 0.36 mmol), N-(2-chloroethyl)-N-dodecyldodecan-1-amine (166 mg, 0.4 mmol), and K$_2$CO$_3$ (50 mg, 0.36 mmol) in 2 mL MeCN was allowed to stir at 82° C. for 12 h. The reaction was allowed to cool room temperature, was filtered and concentrated. The crude material was purified by silica gel chromatography (0-20% MeOH in DCM with 1% NH$_4$OH) to provide N-dodecyl-N-(2-(4-methylpiperazin-1-yl)ethyl)dodecan-1-amine (87.9 mg, 51%).

UPLC: RT=2.24 min. MS (ES): m/z (MH$^+$) 480.662 for $C_{31}H_{65}N_3$ $^1$H NMR (400 MHz, CDCl$_3$) δ: ppm 2.49 (m, 16H); 2.36 (s, 3H); 1.50 (m, 4H); 1.34 (m, 36H); 0.96 (t, 6H).

CQ. Compound 19-5: N-Dodecyl-N-(2-(4-(4-methoxybenzyl)piperazin-1-yl)ethyl)dodecan-1-amine

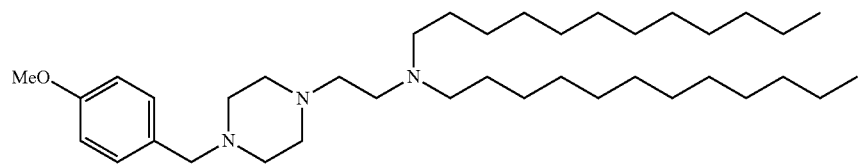

Chemical Formula: $C_{38}H_{71}N_3O$
Molecular Weight: 586.01

A mixture of 1-(4-methoxybenzyl)piperazine (206 mg, 1.0 mmol), N-(2-chloroethyl)-N-dodecyldodecan-1-amine (289 mg, 0.69 mmol), K₂CO₃ (286 mg, 2.07 mmol) and KI (11 mg, 0.069 mmol) in 3.5 mL MeCN was allowed to stir at 80 C for 2 h. After this time the reaction was allowed to cool to room temperature and was quenched with water. The mixture was extracted with EtOAc three times. The pooled organics were washed with brine, dried over MgSO₄, filtered and concentrated. The crude material was purified by silica gel chromatography (0-20% MeOH in DCM) for provide N-dodecyl-N-(2-(4-(4-methoxybenzyl)piperazin-1-yl)ethyl) dodecan-1-amine (0.24 g, 59%).

UPLC: RT=2.30 min. MS (ES): m/z (MH⁺) 586.92 for $C_{38}H_{71}N_3O$

¹H NMR (400 MHz, CDCl₃) δ: ppm 7.19 (d, 2H); 6.83 (d, 2H); 3.78 (s, 3H); 3.42 (s, 2H); 2.99-2.45 (br. m, 16H); 1.71-1.24 (br. m, 40H); 0.86 (t, 6H).

CR. Compound 19-6: (9Z,12Z)—N-(2-(4-Dodecylpiperazin-1-yl)ethyl)-N-((9Z,12Z)-octadeca-9,12-dien-1-yl)octadeca-9,12-dien-1-amine

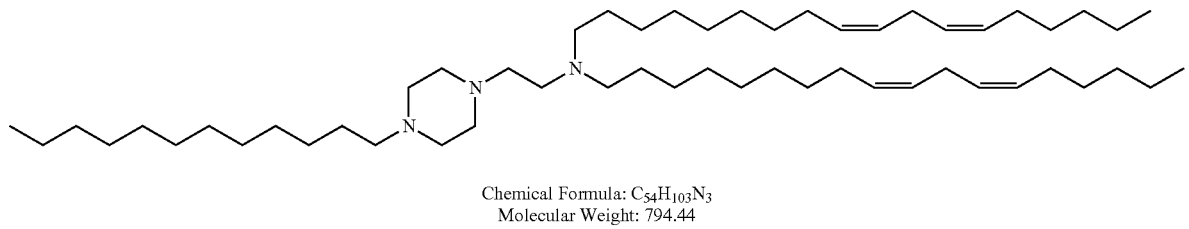 [SMILES: CCCCC/C=C\C/C=C\CCCCCCCCN(CCCCCCCC/C=C\C/C=C\CCCCC)CCN1CCN(CCCCCCCCCCCC)CC1]

Chemical Formula: $C_{54}H_{103}N_3$
Molecular Weight: 794.44

A mixture of (9Z,12Z)—N-((9Z,12Z)—Octadeca-9,12-dien-1-yl)-N-(2-(piperazin-1-yl)ethyl)octadeca-9,12-dien-1-amine (54 mg, 0.086 mmol), 1-bromododecane (24 mg, 0.095 mmol), K₂CO₃ (24 mg, 0.172 mmol), KI (2 mg, 0.012 mmol), in 1.5 mL THF was allowed to stir at 65° C. for 16 hours. The reaction was cooled to room temperature, diluted with H₂O, and extracted with EtOAc. The organics were washed with brine, dried over anhydrous MgSO₄, filtered, and concentrated in vacuo. Purification by ISCO silica flash chromatography (0-100% DCM/[DCM 20% MeOH 1% Et₃N]) provided (9Z,12Z)—N-(2-(4-dodecylpiperazin-1-yl)ethyl)-N-((9Z,12Z)-octadeca-9,12-dien-1-yl)octadeca-9,12-dien-1-amine (51 mg, 0.064 mmol, 74%).

UPLC: RT=3.40 min. MS (ES): m/z (MH⁺) 795.12 for $C_{54}H_{103}N_3$.

CS. Compound 20-1:
N-(2-(Didodecylamino)ethyl)-N-dodecylglycine

Step 1: Methyl
N-(tert-butoxycarbonyl)-N-dodecylglycinate

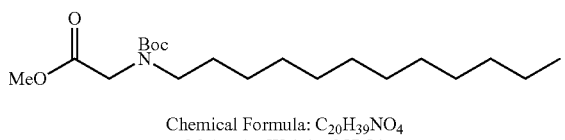

Chemical Formula: $C_{20}H_{39}NO_4$
Molecular Weight: 357.54

A 0° C. solution of N-(tert-butoxycarbonyl)glycine methyl ester (7.7 g, 40.7 mmol) in DMF (100 mL) was treated with NaH (60%, 1.71 g, 42.7 mmol) and the mixture was allowed to stir for 30 minutes. The solution was allowed to return to room temperature before 1-bromododecane (15.2 g, 61.0 mmol) was added and the reaction was allowed to stir overnight. The reaction was quenched with water and extracted with EtOAc. The organics were washed with brine, dried over anhydrous Na₂SO₄, filtered, and concentrated in vacuo. Purification by ISCO silica flash chromatography (0-20% EtOAc/hexanes) provided methyl N-(tert-butoxycarbonyl)-N-dodecylglycinate (4.03 g, 28%).

¹H-NMR (300 MHz, CDCl₃) δ: ppm 4.01-3.84 (br. m, 2H); 3.75 (s, 3H); 3.27 (br. m, 2H); 1.67-1.39 (br. m, 11H); 1.28 (br, 18H); 0.90 (t, 3H).

Step 2: Methyl Dodecylglycinate

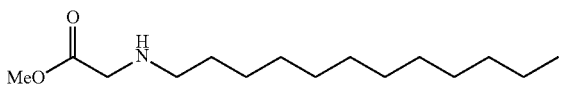

Chemical Formula: $C_{15}H_{31}NO_2$
Molecular Weight: 257.42

To a 0° C. solution of methyl N-(tert-butoxycarbonyl)-N-dodecylglycinate (4.03 g, 11.3 mmol) in DCM (17 mL) was added dropwise TFA (17 mL, 226 mmol). The reaction was allowed to return to room temperature and stir for 6 hours. The reaction mixture was concentrated in vacuo and the crude material was dissolved in DCM. The solution was washed with 10% NaOH, brine, dried over anhydrous Na₂SO₄, filtered, and concentrated in vacuo to provide methyl dodecylglycinate (2.84 g, 98%).

¹H-NMR (300 MHz, CDCl₃) δ: ppm 3.75 (s, 3H); 3.44 (s, 2H); 2.62 (t, 2H); 1.70 (br, 1H); 1.51 (m, 2H); 1.29 (br, 18H); 0.90 (t, 3H).

Step 3: 2-(Didodecylamino)ethan-1-ol

Chemical Formula: $C_{26}H_{55}NO$
Molecular Weight: 397.73

To a solution of 1-bromododecane (10 g, 40.1 mmol) in MeCN (84 mL) was added ethanolamine (1.10 mL, 18.2 mmol), K₂CO₃ (11.1 g, 80.1 mmol), and KI (302 mg, 1.82 mmol). The reaction was allowed to stir at 82° C. for 48 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-20% MeOH/DCM) provided 2-(didodecylamino)ethan-1-ol (3.87 g, 53%).

UPLC/ELSD: RT=2.69 min. MS (ES): m/z (MH⁺) 398.56 for $C_{26}H_{55}NO$ $^1$H-NMR (300 MHz, CDCl$_3$) δ: ppm 3.57 (t, 2H); 2.63 (t, 2H); 2.49 (br. m, 4H); 1.48 (br. m, 4H); 1.29 (br, 36H); 0.91 (t, 6H).

Step 4:
N-(2-Chloroethyl)-N-dodecyldodecan-1-amine

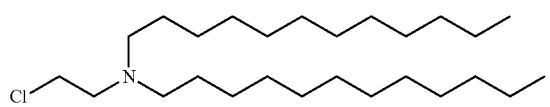

Chemical Formula: $C_{26}H_{54}ClN$
Molecular Weight: 416.18

To a 0° C. solution of 2-(didodecylamino)ethan-1-ol (3.87 g, 9.73 mmol) and triethylamine (1.76 mL, 12.6 mmol) in DCM (50 mL) was added dropwise a solution of methanesulfonyl chloride (0.941 mL, 12.2 mmol) in DCM (5 mL). The reaction was allowed to return to room temperature and stir for 16 hours. The mixture was quenched by the addition of water and extracted with DCM. The organic layer was washed with saturated NaHCO$_3$, brine, dried over anhydrous Na$_2$SO$_4$, filtered, and concentrated in vacuo. Purification by ISCO silica flash chromatography (0-10% EtOAc/hexanes) provided N-(2-chloroethyl)-N-dodecyldodecan-1-amine (1.92 g, 47%).

$^1$H-NMR (300 MHz, CDCl$_3$) δ: ppm 3.51 (t, 2H); 2.78 (t, 2H); 2.47 (br. m, 4H); 1.44 (br. m, 4H); 1.28 (br, 36H); 0.90 (t, 6H).

Step 5: Methyl
N-(2-(didodecylamino)ethyl)-N-dodecylglycinate

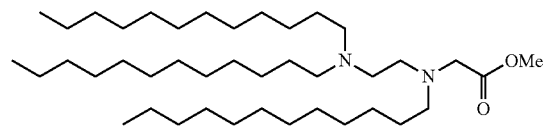

Chemical Formula: $C_{41}H_{84}N_2O_2$
Molecular Weight: 637.14

To a solution of methyl dodecylglycinate (425 mg, 1.65 mmol) in MeCN (10 mL) was added N-(2-chloroethyl)-N-dodecyldodecan-1-amine (825 mg, 1.98 mmol), K$_2$CO$_3$ (457 mg, 3.30 mmol), and KI (27 mg, 0.165 mmol). The reaction was allowed to stir at 82° C. for 72 hours. The reaction mixture was filtered and the solids were washed with hexanes. The filtrate was concentrated in vacuo to provide the crude product. Purification by ISCO silica flash chromatography (0-20% MeOH/DCM) provided methyl N-(2-(didodecylamino)ethyl)-N-dodecylglycinate (652 mg, 62%).

UPLC/ELSD: RT=3.77 min. MS (ES): m/z (MH⁺) 638.18 for $C_{41}H_{84}N_2O_2$ $^1$H-NMR (300 MHz, CDCl$_3$) δ: ppm 3.72 (s, 3H); 3.41 (s, 2H); 2.90-2.20 (br. m, 10H); 1.60-1.00 (br. m, 60H); 0.90 (t, 9H).

Step 6:
N-(2-(Didodecylamino)ethyl)-N-dodecylglycine

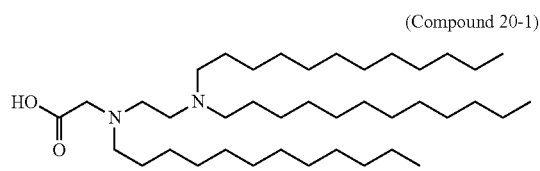

(Compound 20-1)

Chemical Formula: $C_{40}H_{82}N_2O_2$
Molecular Weight: 623.11

A solution of methyl N-(2-(didodecylamino)ethyl)-N-dodecylglycinate (652 mg, 1.02 mmol) in THF (6 mL) and 1M LiOH (5 mL, 5 mmol) was allowed to stir at 65° C. for 16 hours. The reaction was cooled to room temperature and acidified with 10% HCl. The mixture was extracted with chloroform, and the organics were washed with brine, dried over anhydrous Na$_2$SO$_4$, filtered, and concentrated in vacuo. Purification by ISCO silica flash chromatography (0-20% MeOH/DCM) provided N-(2-(didodecylamino)ethyl)-N-dodecylglycine (153 mg, 24%).

UPLC/ELSD: RT=3.60 min. MS (ES): m/z (MH⁺) 624.07 for $C_{40}H_{82}N_2O_2$ $^1$H-NMR (300 MHz, CDCl$_3$) δ: ppm 4.02-3.40 (br. m, 6H); 3.16 (br, 6H); 1.78 (br, 6H); 1.46-1.01 (br. m, 54H); 0.90 (t, 9H).

CT. Compound 20-2: Pentyl 6-(dodecyl(2-(dodecyl (2-hydroxyethyl)amino)ethyl)amino)hexanoate Step 1: 2-(Dodecylamino)ethan-1-ol

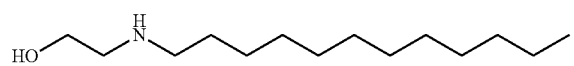

Chemical Formula: $C_{14}H_{31}NO$
Molecular Weight: 229.41

Methyl dodecylglycinate (3.4 g, 13.2 mmol) was dissolved in 2 mL THF under N$_2$ atmosphere and the reaction flask was allowed to cool in an ice bath. To the solution LiAlH$_4$ (0.55 g, 14.5 mmol) was slowly added. The reaction was allowed to stir at the same temperature for 1 h. After this time the reaction was quenched by the subsequent addition of 0.55 mL H$_2$O, 0.55 mL 10% NaOH and then 1.65 mL of H$_2$O. The reaction was then filtered and the filtrate was concentrated in vacuo. The crude material was purified via silica gel chromatography (0-20% MeOH in DCM, with 1% NH$_4$OH) to afford 2-(dodecylamino)ethan-1-ol (1.9 g, 8.28 mmol, 63% yield).

$^1$H NMR (400 MHz, CDCl$_3$) δ: ppm 3.63 (t, 2H); 2.78 (t, 2H); 2.63 (t, 2H); 1.48 (m, 2H); 2.14 (m, 18H); 0.88 (t, 3H).

Step 2: Pentyl 6-bromohexanoate

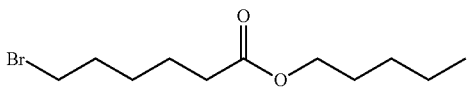

Chemical Formula: $C_{11}H_{21}BrO_2$
Molecular Weight: 265.19

To a solution of 6-bromohexanoic acid (2 g, 10.3 mmol) and pentan-1-ol (2.2 mL, 20.5 mmol) in 26 mL DCM, EDC.HCl (1.97 g, 10.3 mmol) and DMAP (0.26 g, 2.1 mmol) were added. The solution was allowed to stir at room temperature overnight. After this time the reaction was quenched by the addition of water. The mixture was extracted three times with DCM. The organics were pooled and washed with saturated NaHCO$_3$, 10% citric acid and brine. The organics were then dried over MgSO$_4$, filtered and concentrated in vacuo. The crude material was purified via silica gel chromatography (0-30% EtOAc in hexanes) to afford the desired product (2.3 g, 8.67 mmol).

$^1$H NMR (400 MHz, CDCl$_3$) δ: ppm 4.06 (t, 2H); 3.39 (t, 2H); 2.30 (t, 2H); 1.84 (m, 2H); 1.62 (m, 4H); 1.46 (m, 2H); 1.31 (m, 4H); 0.88 (t, 3H).

Step 3: Pentyl 6-(dodecyl(2-hydroxyethyl)amino)hexanoate

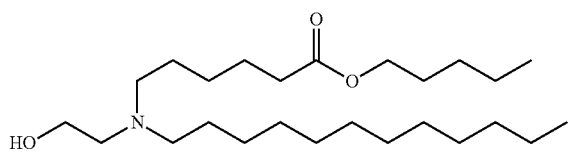

Chemical Formula: $C_{25}H_{51}NO_3$
Molecular Weight: 413.69

To a solution of 2-(dodecylamino)ethan-1-ol (0.50 g, 2.18 mmol) in 10 mL THF, pentyl 6-bromohexanoate (0.87 g, 3.27 mmol) was added followed by K$_2$CO$_3$ (0.60 g, 4.36 mmol) and KI (36 mg, 0.22 mmol). The reaction was allowed to stir under N$_2$ at 65° C. for 24 h. After this time the reaction was allowed to cool to room temperature and the reaction was diluted with water. The mixture was extracted three times with EtOAc. The pooled organics were washed with brine, dried over MgSO$_4$, filtered and concentrated. The crude material was purified by silica gel chromatography (0-20% EtOAc in hexanes) to afford pentyl 6-(dodecyl(2-hydroxyethyl)amino)hexanoate (300 mg, 33%).

$^1$H NMR (400 MHz, CDCl$_3$) δ: ppm 4.04 (t, 2H); 3.51 (m, 2H); 2.56 (m, 2H); 2.42 (m, 4H); 2.28 (t, 2H); 1.60 (m, 4H); 1.42 (m, 4H); 1.30-1.24 (m, 24); 0.87 (m, 6H).

Step 4: Pentyl 6-((2-chloroethyl)(dodecyl)amino)hexanoate

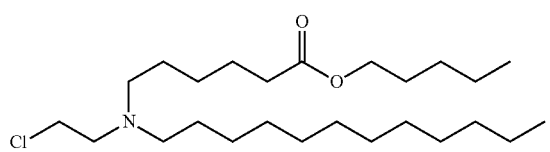

Chemical Formula: $C_{25}H_{50}ClNO_2$
Molecular Weight: 432.13

To a 0° C. solution of pentyl 6-(dodecyl(2-hydroxyethyl)amino)hexanoate (300 mg, 0.73 mmol) in 2 mL DCM, methanesulfonyl chloride (0.062 mL, 0.80 mmol) was added, followed by triethylamine (0.13 mL, 1.3 mmol). The reaction was allowed to slowly warm to room temperature and stir for 12 h under N$_2$. The reaction was quenched by the addition of water and was extracted with DCM. The pooled organics were dried over MgSO$_4$, filtered and concentrated. The aqueous layer was re-extracted with EtOAc three times. The organics were pooled and washed with brine, dried over MgSO$_4$, filtered and concentrated. The crude material was combined and purification by silica gel chromatography (0-30% EtOAc in hexanes) afforded pentyl 6-((2-chloroethyl)(dodecyl)amino)hexanoate (285 mg, 66%).

$^1$H NMR (400 MHz, CDCl$_3$) δ: ppm 4.04 (t, 2H); 3.45 (t, 2H); 2.74 (t, 2H); 2.43 (m, 4H); 2.28 (t, 2H); 1.65-1.59 (m, 4H); 1.31-1.24 (m, 32H); 0.88 (m, 6H).

Step 5: Pentyl 6-(dodecyl(2-(dodecyl(2-hydroxyethyl)amino)ethyl)amino)hexanoate (Compound 20-2)

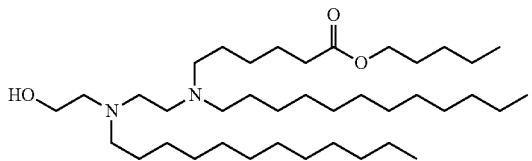

Chemical Formula: $C_{39}H_{80}N_2O_3$
Molecular Weight: 625.08

To a solution of pentyl 6-((2-chloroethyl)(dodecyl)amino) hexanoate (94 mg, 0.22 mmol) in MeCN (2 mL) and THF (2 mL) was added 2-(dodecylamino)ethan-1-ol (50 mg, 0.22 mmol), K$_2$CO$_3$ (60 mg, 0.44 mmol), and KI (4 mg, 0.022 mmol). The reaction was allowed to stir at 65° C. for 18 hours. The reaction mixture was cooled to room temperature, filtered, and the solids were washed with hexanes and EtOAc. The filtrate was extracted with EtOAc three times. The pooled organics were washed with water and brine, dried over Na$_2$SO$_4$, filtered and concentrated in vacuo. Purification by ISCO silica flash chromatography (0-100% DCM, [20% MeOH, 1% NH$_4$OH]/DCM) provided pentyl 6-(dodecyl(2-(dodecyl(2-hydroxyethyl)amino)ethyl)amino) hexanoate (21 mg, 15%).

UPLC/ELSD: RT=2.86 min. MS (ES): m/z (MH$^+$) 625.86 for $C_{39}H_{80}N_2O_3$ $^1$H NMR (300 MHz, CDCl$_3$) δ: ppm 4.07-4.05 (m, 2H); 3.53 (m, 2H), 2.60-2.43 (br. m, 12H); 2.33-2.29 (m, 2H); 1.65-1.64 (m, 4H); 1.46 (m, 6H); 1.34-1.28 (br. m, 42H); 0.92-0.90 (m, 9H).

CU. Compound 20-3: Pentyl 6-((2-(didodecylamino)ethyl)(2-hydroxyethyl)amino)hexanoate

Step 1: Pentyl 6-((2-hydroxyethyl)amino)hexanoate

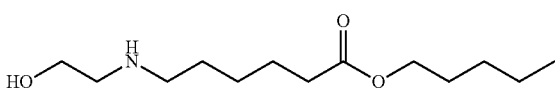

Chemical Formula: $C_{13}H_{27}NO_3$
Molecular Weight: 245.36

To a solution of pentyl 6-bromohexanoate (4.65 g, 17.5 mmol) in MeCN (88 mL) was added ethanolamine (1.10 mL, 17.5 mmol), K$_2$CO$_3$ (4.85 g, 35.1 mmol), and KI (291 mg, 1.75 mmol). The reaction was allowed to stir at 82° C. for 48 hours. The reaction mixture was cooled to room temperature, filtered, and the solids were washed with hexanes and EtOAc. The filtrate was extracted with EtOAc three times. The pooled organics were washed with water and brine, dried over Na$_2$SO$_4$, filtered and concentrated in vacuo. Purification by ISCO silica flash chromatography (0-100% DCM, [20% MeOH, 1% NH$_4$OH]/DCM) provided pentyl 6-((2-hydroxyethyl)amino)hexanoate (1.74 g, 41%).

UPLC/ELSD: RT=0.30 min. MS (ES): m/z (MH$^+$) 246.21 for C$_{13}$H$_{27}$NO$_3$ $^1$H NMR (300 MHz, CDCl$_3$) δ: ppm 4.08 (t, 2H); 3.69 (t, 2H), 2.82 (t, 2H); 2.68 (t, 2H); 2.35-2.31 (m, 4H); 1.72-1.52 (br. m, 6H); 1.39-1.32 (br. m, 6H); 0.93 (t, 3H).

Step 2: Pentyl 6-((2-(didodecylamino)ethyl)(2-hydroxyethyl)amino)hexanoate

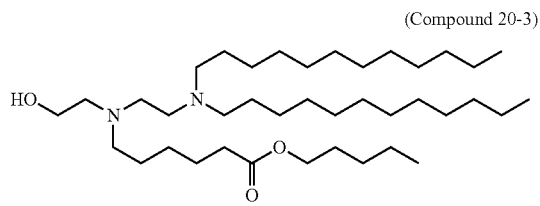

(Compound 20-3)

Chemical Formula: C$_{39}$H$_{80}$N$_2$O$_3$
Molecular Weight: 625.08

In the same manner as pentyl 6-(dodecyl(2-(dodecyl(2-hydroxyethyl)amino)ethyl)amino)hexanoate, pentyl 6-((2-(didodecylamino)ethyl)(2-hydroxyethyl)amino)hexanoate was synthesized from pentyl 6-((2-hydroxyethyl)amino)hexanoate (108 mg, 0.44 mmol), N-(2-chloroethyl)-N-dodecyldodecan-1-amine (183 mg, 0.44 mmol), K$_2$CO$_3$ (122 mg, 0.88 mmol), and KI (7.3 mg, 0.044 mmol) in MeCN (1 mL) and THF (1 mL). Yield (88 mg, 32%).

UPLC/ELSD: RT=2.92 min. MS (ES): m/z (MH$^+$) 626.0 for C$_{39}$H$_{80}$N$_2$O$_3$ $^1$H NMR (300 MHz, CDCl$_3$) δ: ppm 4.07 (t, 2H); 3.53 (t, 2H), 2.62-2.40 (br. m, 12H); 2.31 (t, 2H); 1.70-1.60 (m, 4H); 1.53-1.43 (m, 6H); 1.27 (br. m, 42H); 0.91 (m, 9H).

CV. Compound 20-4: Dipentyl 6,6'-((2-(dodecyl(2-hydroxyethyl)amino)ethyl)azanediyl)dihexanoate

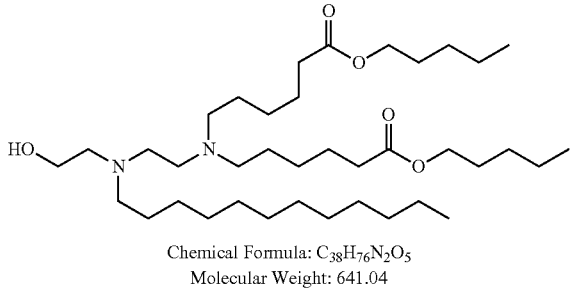

(Compound 20-4)

Chemical Formula: C$_{38}$H$_{76}$N$_2$O$_5$
Molecular Weight: 641.04

In the same manner as pentyl-(dodecyl(2-(dodecyl(2-hydroxyethyl)amino)ethyl)amino)hexanoate, dipentyl 6,6'-((2-(dodecyl(2-hydroxyethyl)amino)ethyl)azanediyl)dihexanoate was synthesized from 2-(dodecylamino)ethan-1-ol (60 mg, 0.26 mmol), dipentyl 6,6'-((2-chloroethyl)azanediyl)dihexanoate (118 mg, 0.26 mmol), K$_2$CO$_3$ (73 mg, 0.53 mmol), and KI (5 mg, 0.026 mmol) in MeCN (1 mL) and THF (1 mL). Yield (60 mg, 36%).

UPLC/ELSD: RT=2.37 min. MS (ES): m/z (MH$^+$) 641.95 for C$_{38}$H$_{76}$N$_2$O$_5$ $^1$H NMR (300 MHz, CDCl$_3$) δ: ppm 4.08 (t, 4H); 3.57 (m, 2H), 2.64-2.53 (br. m, 12H); 2.32 (t, 4H); 1.72-1.60 (m, 8H); 1.50 (m, 6H); 1.38-1.28 (br. m, 30H); 0.95-0.88 (m, 9H).

CW. Compound 20-5: Diheptyl 6,6'-((2-((6-(heptyloxy)-6-oxohexyl)(2hydroxyethyl)amino)ethyl)azanediyl)dihexanoate

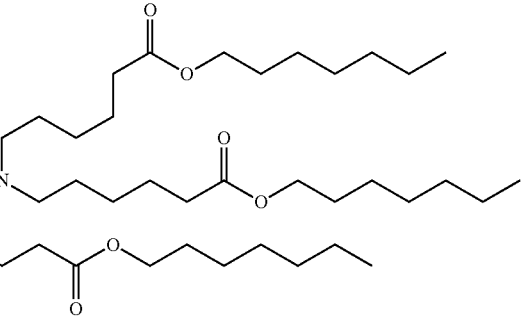

(Compound 20-5)

Chemical Formula: C$_{43}$H$_{84}$N$_2$O$_7$
Molecular Weight: 741.15

In the same manner as pentyl 6-(dodecyl(2-(dodecyl(2-hydroxyethyl)amino)ethyl)amino)hexanoate, diheptyl 6,6'-((2-((6-(heptyloxy)-6-oxohexyl)(2-hydroxyethyl)amino)ethyl)azanediyl)dihexanoate was synthesized from heptyl 6-((2-hydroxyethyl)amino)hexanoate (100 mg, 0.37 mmol), diheptyl 6,6'-((2-chloroethyl)azanediyl)dihexanoate (184 mg, 0.37 mmol), K$_2$CO$_3$ (101 mg, 0.73 mmol), and KI (6 mg, 0.037 mmol) in MeCN (2 mL) and THF (2 mL). Yield (91 mg, 34%).

UPLC/ELSD: RT=3.33 min. MS (ES): m/z (MH$^+$) 742.08 for C$_{43}$H$_{84}$N$_2$O$_7$ ¹H NMR (300 MHz, CDCl₃) δ: ppm 4.08 (t, 6H); 3.66 (m, 2H), 3.23-2.53 (br. m, 12H); 2.37-2.30 (m, 6H); 1.74-1.31 (br. m, 48H); 0.93-0.89 (m, 9H).

CX. Compound 20-6: Pentyl 6-((2-(dinonylamino) ethyl)(2-hydroxyethyl)amino)hexanoate

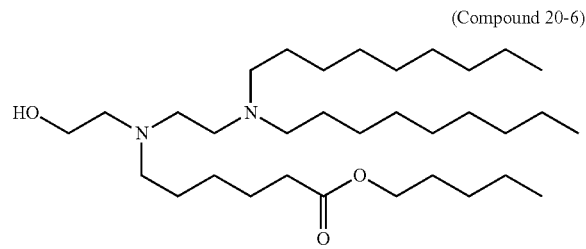

(Compound 20-6)

Chemical Formula: C₃₃H₆₈N₂O₃
Molecular Weight: 540.92

In the same manner as pentyl 6-(dodecyl(2-(dodecyl(2-hydroxyethyl)amino)ethyl)amino)hexanoate, pentyl 6-((2-(dinonylamino)ethyl)(2-hydroxyethyl)amino)hexanoate was synthesized from pentyl 6-((2-hydroxyethyl)amino) hexanoate (100 mg, 0.41 mmol), N-(2-chloroethyl)-N-nonylnonan-1-amine (101 mg, 0.41 mmol), K₂CO₃ (108 mg, 0.82 mmol), and KI (7 mg, 0.041 mmol) in MeCN (1 mL) and THF (1 mL). Yield (25 mg, 13%).
UPLC/ELSD: RT=3.37 min. MS (ES): m/z (MH⁺) 541.90 for C₃₃H₆₈N₂O₃
¹H NMR (300 MHz, CDCl₃) δ: ppm 4.08 (t, 2H); 3.54 (t, 2H), 2.63-2.42 (br. m, 12H); 2.32 (t, 2H); 1.71-1.61 (m, 4H); 1.51-1.46 (m, 6H); 1.35-1.29 (br. m, 30H); 0.95-0.88 (m, 9H).

CX. Compound 20-7: Heptyl 6-(dodecyl(2-(dodecyl (2-hydroxyethyl)amino)ethyl)amino)hexanoate (Compound 20-7)

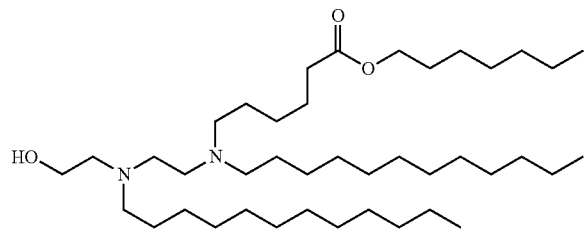

Chemical Formula: C₄₁H₈₄N₂O₃
Molecular Weight: 653.13

In the same manner as pentyl 6-(dodecyl(2-(dodecyl(2-hydroxyethyl)amino)ethyl)amino)hexanoate, heptyl 6-(dodecyl(2-(dodecyl(2-hydroxyethyl)amino)ethyl)amino) hexanoate was synthesized from 2-(dodecylamino)ethan-1-ol (100 mg, 0.37 mmol), heptyl 6-((2-chloroethyl)(dodecyl) amino)hexanoate (152 mg, 0.37 mmol), K₂CO₃ (101 mg, 0.73 mmol), and KI (6 mg, 0.037 mmol) in MeCN (2 mL) and THF (2 mL). Yield (41 mg, 17%).
UPLC/ELSD: RT=3.14 min. MS (ES): m/z (MH⁺) 654.0 for C₄₁H₈₄N₂O₃
¹H NMR (300 MHz, CDCl₃) δ: ppm 4.08 (t, 2H); 3.55 (t, 2H), 2.63-2.45 (br. m, 12H); 2.32 (t, 2H); 1.71-1.59 (m, 4H); 1.54-1.28 (br. m, 52H); 0.92-0.88 (m, 9H).

CY. Compound 20-8: Nonyl 8-((2-(didodecylamino)ethyl)(2-hydroxyethyl)amino)octanoate

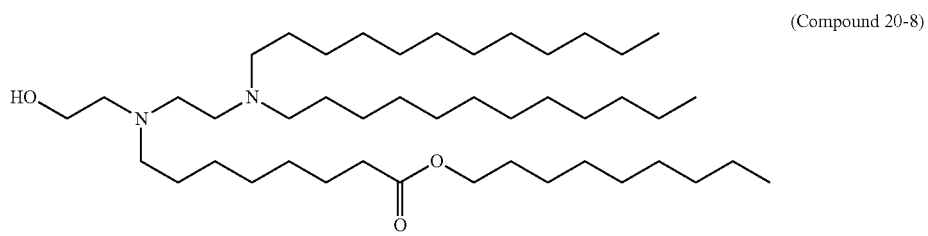

(Compound 20-8)

Chemical Formula: C₄₅H₉₂N₂O₃
Molecular Weight: 709.24

In the same manner as pentyl 6-(dodecyl(2-(dodecyl(2-hydroxyethyl)amino)ethyl)amino)hexanoate, nonyl 8-((2-(didodecylamino)ethyl)(2-hydroxyethyl)amino)octanoate was synthesized from nonyl 8-((2-hydroxyethyl)amino)octanoate (240 mg, 0.73 mmol), N-(2-chloroethyl)-N-dodecyldodecan-1-amine (335 mg, 0.80 mmol), K₂CO₃ (121 mg, 0.88 mmol), and KI (12 mg, 0.072 mmol) in MeCN (1.5 mL) and THF (1.5 mL). Yield (122 mg, 24%).
UPLC/ELSD: RT=3.41 min. MS (ES): m/z (MH⁺) 709.93 for C₄₅H₉₂N₂O₃
¹H NMR (300 MHz, CDCl₃) δ: ppm 4.08 (t, 2H); 3.56 (m, 2H), 2.91-2.37 (br. m, 12H); 2.31 (m, 2H); 1.64 (br. m, 4H); 1.55-1.20 (br. m, 60H); 0.91 (m, 9H).

CZ: Compound 20-9: Heptadecan-9-yl 8-((2-(didodecylamino)ethyl)(2-hydroxyethyl)amino)octanoate Step 1: Heptadecan-9-yl 8-bromooctanoate

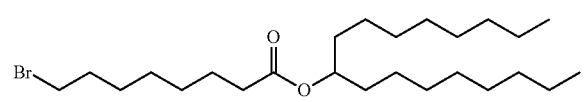 [SMILES: CCCCCCCCC(CCCCCCCC)OC(=O)CCCCCCCBr]

To a solution of 8-bromooctanoic acid (1.04 g, 4.6 mmol) and heptadecan-9-ol (1.5 g, 5.8 mmol) in dichloromethane (20 mL) was added N-(3-dimethylaminopropyl)-N'-ethylcarbodiimide hydrochloride (1.1 g, 5.8 mmol), N,N-diisopropylethylamine (3.3 mL, 18.7 mmol) and DMAP (114 mg, 0.9 mmol). The reaction was allowed to stir at room temperature for 18 h. The reaction was diluted with dichloromethane and extracted with saturated sodium bicarbonate. The organic layer was separated, washed with brine and dried over MgSO$_4$. The organic layer was filtered and the filtrate was evaporated in vacuo. The residue was purified by silica gel chromatography (0-10% ethyl acetate in hexanes) to obtain heptadecan-9-yl 8-bromooctanoate (875 mg, 1.9 mmol, 41%).

$^1$H NMR (300 MHz, CDCl$_3$) δ: ppm 4.89 (m, 1H); 3.42 (m, 2H); 2.31 (m, 2H); 1.89 (m, 2H); 1.73-1.18 (br. m, 36H); 0.88 (m, 6H).

Step 2: Heptadecan-9-yl 8-((2-(didodecylamino)ethyl)(2-hydroxyethyl)amino)octanoate

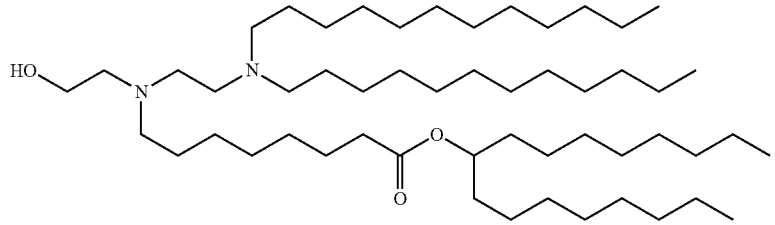

(Compound 20-9)

Chemical Formula: C$_{53}$H$_{108}$N$_2$O$_3$
Molecular Weight: 821.46

In the same manner as pentyl 6-(dodecyl(2-(dodecyl(2-hydroxyethyl)amino)ethyl)amino)hexanoate, heptadecan-9-yl 8-((2-(didodecylamino)ethyl)(2-hydroxyethyl)amino)octanoate was synthesized from heptadecan-9-yl 8-((2-hydroxyethyl)amino)octanoate (100 mg, 0.23 mmol), N-(2-chloroethyl)-N-dodecyldodecan-1-amine (94 mg, 0.23 mmol), K$_2$CO$_3$ (63 mg, 0.45 mmol), and KI (4 mg, 0.023 mmol) in MeCN (1 mL) and THF (1 mL). Yield (107 mg, 57%).

UPLC/ELSD: RT=3.91 min. MS (ES): m/z (MH$^+$) 822.3 for C$_{53}$H$_{108}$N$_2$O$_3$ $^1$H NMR (300 MHz, CDCl$_3$) δ: ppm 4.89 (p, 1H); 3.56 (m, 2H), 2.62-2.45 (br. m, 12H); 2.30 (t, 2H); 1.88-1.11 (br. m, 78H); 0.92-0.88 (m, 12H).

DA. Compound 20-10: Dinonyl 8,8'-((2-(dodecyl(2-hydroxyethyl)amino)ethyl)azanediyl)dioctanoate

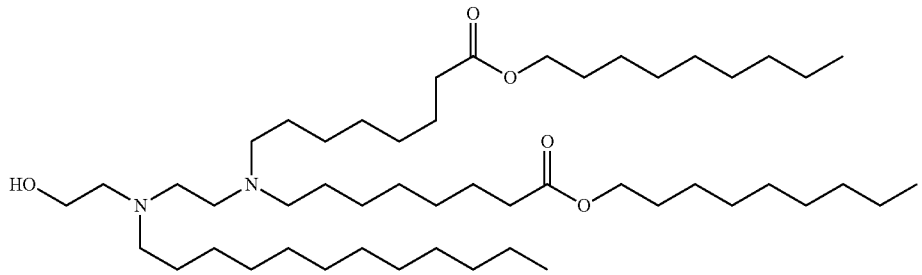

(Compound 20-10)

Chemical Formula: C$_{50}$H$_{100}$N$_2$O$_5$
Molecular Weight: 809.36

In the same manner as pentyl 6-(dodecyl(2-(dodecyl(2-hydroxyethyl)amino)ethyl)amino)hexanoate, dinonyl 8,8'-((2-(dodecyl(2-hydroxyethyl)amino)ethyl)azane diyl)dioctanoate was synthesized from 2-(dodecylamino)ethan-1-ol (100 mg, 0.44 mmol), dinonyl 8,8'-((2-chloroethyl) azanediyl)dioctanoate (269 mg, 0.44 mmol), $K_2CO_3$ (121 mg, 0.87 mmol), and KI (72 mg, 0.044 mmol) in MeCN (2.5 mL) and THF (2.5 mL). Yield (172 mg, 49%).

UPLC/ELSD: RT=4.09 min. MS (ES): m/z (MH$^+$) 810.31 for $C_{50}H_{100}N_2O_5$ $^1$H NMR (300 MHz, CDCl$_3$) δ: ppm 4.07 (t, 4H); 3.55 (m, 2H), 2.64-2.47 (br. m, 12H); 2.31 (t, 4H); 1.66-1.59 (br. m, 8H); 1.46-1.28 (br. m, 60H); 0.92-0.88 (m, 9H).

DB: Compound 20-11: 3-((2-(Ditetradecylamino)ethyl)(dodecyl)amino)propan-1-ol

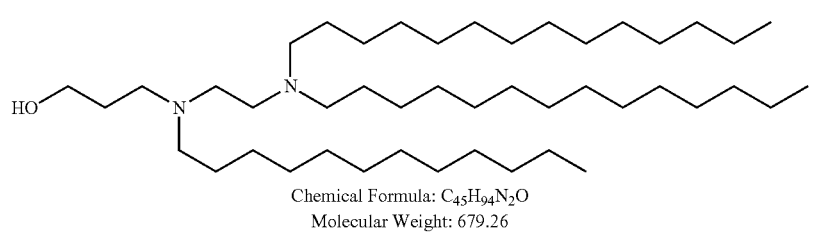

(Compound 20-11)

Chemical Formula: $C_{45}H_{94}N_2O$
Molecular Weight: 679.26

In the same manner as pentyl 6-(dodecyl(2-(dodecyl(2-hydroxyethyl)amino)ethyl)amino)hexanoate, 3-((2-(ditetradecylamino)ethyl)(dodecyl)amino)propan-1-ol was synthesized from 3-(dodecylamino)propan-1-oloctanoate (50 mg, 0.21 mmol), N-(2-chloroethyl)-N-tetradecyltetradecan-1-amine (109 mg, 0.23 mmol), $K_2CO_3$ (57 mg, 0.41 mmol), and KI (3.4 mg, 0.021 mmol) in MeCN (1 mL) and THF (1 mL). Yield (65 mg, 46%).

UPLC/ELSD: RT=3.65 min. MS (ES): m/z (MH$^+$) 679.81 for $C_{45}H_{94}N_2O$ $^1$H NMR (300 MHz, CDCl$_3$) δ: ppm 3.76 (t, 2H); 2.63-2.42 (br. m, 12H), 1.66-1.26 (br. m, 70H); 0.90-0.86 (m, 9H).

DC: Compound 20-12: 2-((2-(Ditetradecylamino)ethyl)(tetradecyl)amino)ethan-1-ol

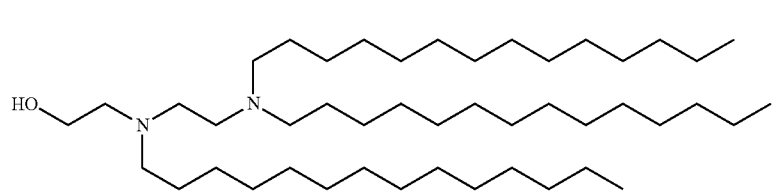

(Compound 20-12)

Chemical Formula: $C_{46}H_{96}N_2O$
Molecular Weight: 693.29

In the same manner as pentyl 6-(dodecyl(2-(dodecyl(2-hydroxyethyl)amino)ethyl)amino)hexanoate, 2-((2-(ditetradecylamino)ethyl)(tetradecyl)amino)ethan-1-ol was synthesized from 2-(tetradecylamino)ethan-1-ol (100 mg, 0.39 mmol), N-(2-chloroethyl)-N-tetradecyltetradecan-1-amine (184 mg, 0.39 mmol), $K_2CO_3$ (107 mg, 0.78 mmol), and KI (6.5 mg, 0.039 mmol) in MeCN (2 mL) and THF (2 mL). Yield (87 mg, 32%).

UPLC/ELSD: RT=3.81 min. MS (ES): m/z (MH$^+$) 694.02 for $C_{46}H_{96}N_2O$ $^1$H NMR (300 MHz, CDCl$_3$) δ: ppm 3.56 (m, 2H); 2.61-2.45 (br. m, 12H), 1.47-1.29 (br. m, 72H); 0.91 (m, 9H).

DD: Compound 20-13: 2-((2-(Di((9Z,12Z)-octa-deca-9,12-dien-1-yl)amino)ethyl)(dodecyl)amino)ethan-1-ol Step 1: (6Z,9Z)-18-(Methylsulfonyl)octadeca-6,9-diene

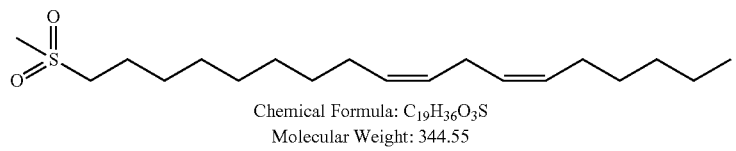 [SMILES: CCCCC/C=C\C/C=C\CCCCCCCCS(C)(=O)=O]

Chemical Formula: $C_{19}H_{36}O_3S$
Molecular Weight: 344.55

To a 0° C. solution of linoleyl alcohol (10 mL, 31.2 mmol) and triethylamine (5.68 mL, 40.5 mmol)) in DCM (50 mL) was added dropwise a solution of methanesulfonyl chloride (2.66 mL, 34.3 mmol) in DCM (20 mL). The reaction was allowed to return to room temperature and let stir for 4 hours. The mixture was quenched by the addition of water and extracted with DCM. The organic layer was washed with saturated $NaHCO_3$, brine, dried over anhydrous $Na_2SO4$, filtered, and concentrated in vacuo. Purification by ISCO silica flash chromatography (0-40% EtOAc/hexanes) provided (6Z,9Z)-18-(methylsulfonyl)octadeca-6,9-diene (10.0 g, 93%).

$^1$H-NMR (300 MHz, $CDCl_3$) δ: ppm 5.35 (m, 4H); 4.22 (t, 2H); 2.99 (s, 3H); 2.77 (t, 2H); 2.04 (q, 4H); 1.74 (m, 2H); 1.30 (br. m, 16H); 0.89 (t, 3H).

Step 2: (6Z,9Z)-18-Bromooctadeca-6,9-diene

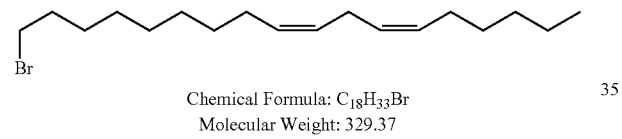

Chemical Formula: $C_{18}H_{33}Br$
Molecular Weight: 329.37

To a solution of (6Z,9Z)-18-(methylsulfonyl)octadeca-6,9-diene (10.0 g, 29.0 mmol) in diethyl ether (372 mL) was added magnesium bromide ethyl etherate (22.5 g, 87.1 mmol). The reaction was let stir at room temperature for 16 hours. The mixture was quenched by the addition of water and extracted with diethyl ether. The combined organic layers were washed with 1% $K_2CO_3$, brine, dried over anhydrous $Na_2SO_4$, filtered, and concentrated in vacuo. Purification by ISCO silica flash chromatography provided (6Z,9Z)-18-bromooctadeca-6,9-diene (8.9 g, 93%).

$^1$H-NMR (300 MHz, $CDCl_3$) δ: ppm 5.36 (m, 4H); 3.41 (t, 2H); 2.77 (t, 2H); 2.05 (q, 4H); 1.86 (m, 2H); 1.48-1.22 (br. m, 16H); 0.89 (t, 3H).

Step 3: 2-((2-(Di((9Z,12Z)-octadeca-9,12-dien-1-yl)amino)ethyl)(dodecyl)amino)ethan-1-ol

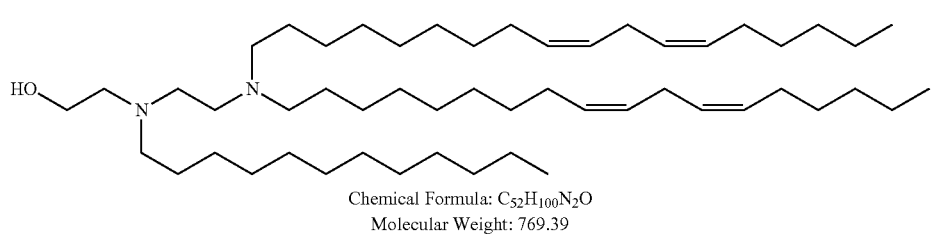

(Compound 20-13)

Chemical Formula: $C_{52}H_{100}N_2O$
Molecular Weight: 769.39

In the same manner as pentyl 6-(dodecyl(2-(dodecyl(2-hydroxyethyl)amino)ethyl)amino)hexanoate, 2-((2-(di((9Z,12Z)-octadeca-9,12-dien-1-yl)amino)ethyl)(dodecyl)amino)ethan-1-ol was synthesized from 2-(dodecylamino)ethan-1-ol (50 mg, 0.22 mmol), (9Z,12Z)—N-(2-chloroethyl)-N-((9Z,12Z)-octadeca-9,12-dien-1-yl)octadeca-9,12-dien-1-amine (126 mg, 0.22 mmol), K$_2$CO$_3$ (60 mg, 0.44 mmol), and KI (3.6 mg, 0.022 mmol) in MeCN (2 mL). Yield (33 mg, 20%).

UPLC/ELSD: RT=3.74 min. MS (ES): m/z (MH$^+$) 770.20 for C$_{52}$H$_{100}$N$_2$O $^1$H NMR (300 MHz, CDCl$_3$) δ: ppm 5.39 (m, 8H); 3.55 (m, 2H), 2.80 (m, 4H); 2.61-2.44 (br. m, 12H); 2.07 (m, 8H); 1.46-1.29 (br. m, 56H); 0.92 (m, 9H).

DE: Compound 20-14: 2-((2-(Di((9Z,12Z)-octadeca-9,12-dien-1-yl)amino)ethyl)((9Z,12Z)-octadeca-9,12-dien-1-yl)amino)ethan-1-ol Step 1: 2-(((9Z,12Z)-octadeca-9,12-dien-1-yl)amino)ethan-1-ol

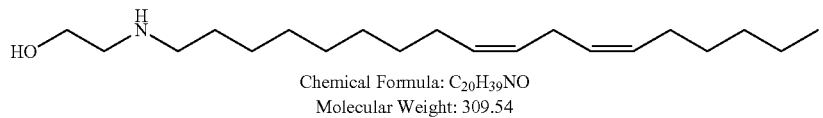 [SMILES: CCCCC/C=C\C/C=C\CCCCCCCCNCCO]

Chemical Formula: C$_{20}$H$_{39}$NO
Molecular Weight: 309.54

In the same manner as 2-(dodecylamino)ethan-1-ol, 2-(((9Z,12Z)-octadeca-9,12-dien-1-yl)amino)ethan-1-ol was synthesized from ethanolamine (0.37 mL, 6.1 mmol), (6Z,9Z)-18-bromooctadeca-6,9-diene (2.0 g, 6.1 mmol), K$_2$CO$_3$ (1.67 g, 12.1 mmol), and KI (101 mg, 0.607 mmol) in MeCN (28 mL). Yield (453 mg, 24%).

UPLC/ELSD: RT=5.457 min. MS (ES): m/z (MH$^+$) 311.38 for C$_{20}$H$_{39}$NO $^1$H-NMR (300 MHz, CDCl$_3$) δ: ppm 5.36 (m, 4H); 3.62 (t, 2H); 2.78 (m, 4H); 2.61 (t, 2H); 2.05 (m, 4H); 1.49 (m, 2H); 1.30 (br. m, 16H); 0.89 (t, 3H).

Step 2: 2-(Di((9Z,12Z)-octadeca-9,12-dien-1-yl)amino)ethan-1-ol

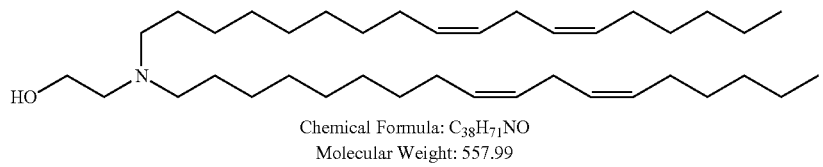 [SMILES: CCCCC/C=C\C/C=C\CCCCCCCCN(CCO)CCCCCCCC/C=C\C/C=C\CCCCC]

Chemical Formula: C$_{38}$H$_{71}$NO
Molecular Weight: 557.99

In the same manner as 2-(didodecylamino)ethan-1-ol, 2-(di((9Z,12Z)-octadeca-9,12-dien-1-yl)amino)ethan-1-ol was synthesized from (6Z,9Z)-18-bromooctadeca-6,9-diene (4 g, 12.1 mmol), ethanolamine, (0.334 mL, 5.52 mmol), K$_2$CO$_3$ (3.36 g, 24.3 mmol), and KI (92 mg, 0.552 mmol) in MeCN (26 mL). Yield (1.9 g, 62%).

UPLC/ELSD: RT=6.80 min. MS (ES): m/z (MH$^+$) 557.94 for C$_{38}$H$_{71}$NO $^1$H-NMR (300 MHz, CDCl$_3$) δ: ppm 5.35 (m, 8H); 3.52 (t, 2H); 2.77 (t, 4H); 2.57 (t, 2H); 2.43 (t, 4H); 2.04 (q, 8H); 1.48-1.18 (br. m, 36H); 0.89 (t, 6H).

Step 3: (9Z,12Z)—N-(2-chloroethyl)-N-((9Z,12Z)-octadeca-9,12-dien-1-yl)octadeca-9,12-dien-1-amine

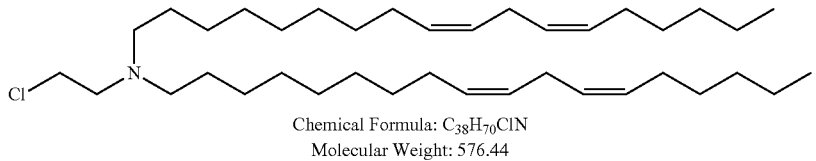 [SMILES: CCCCC/C=C\C/C=C\CCCCCCCCN(CCCl)CCCCCCCC/C=C\C/C=C\CCCCC]

Chemical Formula: $C_{38}H_{70}ClN$
Molecular Weight: 576.44

In a same manner as compound N-(2-chloroethyl)-N-dodecyldodecan-1-amine, (9Z,12Z)—N-(2-chloroethyl)-N-((9Z,12Z)-octadeca-9,12-dien-1-yl)octadeca-9,12-dien-1-amine was synthesized from 2-(di((9Z,12Z)-octadeca-9,12-dien-1-yl)amino)ethan-1-ol (250 mg, 0.45 mmol), triethylamine (81 µL, 0.58 mmol), and methanesulfonyl chloride (38 µL, 0.49 mmol) in DCM (2 mL). Yield (134 mg, 52%).

$^1$H-NMR (300 MHz, CDCl$_3$) δ: ppm 5.36 (m, 8H); 3.49 (t, 2H); 2.78 (m, 6H); 2.45 (t, 4H); 2.05 (q, 8H); 1.48-1.18 (br. m, 36H); 0.89 (t, 6H).

Step 4: 2-((2-(Di((9Z,12Z)-octadeca-9,12-dien-1-yl)amino)ethyl)((9Z,12Z)-octadeca-9,12-dien-1-yl)amino)ethan-1-ol In the same manner as pentyl 6-(dodecyl(2-(dodecyl(2-hydroxyethyl)amino)ethyl)amino)hexanoate, 2-((2-(didodecylamino)ethyl)(hexyl)amino)ethan-1-ol was synthesized from 2-(hexylamino)ethan-1-ol (50 mg, 0.34 mmol), N-(2-chloroethyl)-N-dodecyldodecan-1-amine (143 mg, 0.34 mmol), K$_2$CO$_3$ (95 mg, 0.69 mmol), and KI (5.7 mg, 0.034 mmol) in MeCN (2 mL). Yield (145 mg, 80%).

UPLC/ELSD: RT=2.73 min. MS (ES): m/z (MH$^+$) 525.66 for $C_{34}H_{72}N_2O$ $^1$H NMR (300 MHz, CDCl$_3$) δ: ppm 3.54 (m, 2H); 2.61-2.44 (br. m, 12H), 1.46-1.28 (br. m, 48H); 0.90 (m, 9H).

(Compound 20-14)

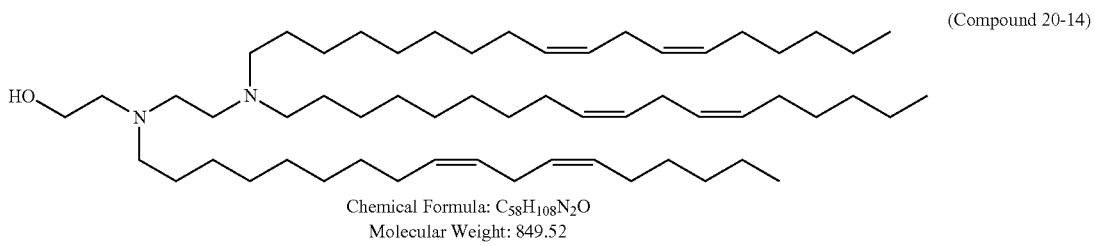 [SMILES: CCCCC/C=C\C/C=C\CCCCCCCCN(CCO)CCN(CCCCCCCC/C=C\C/C=C\CCCCC)CCCCCCCC/C=C\C/C=C\CCCCC]

Chemical Formula: $C_{58}H_{108}N_2O$
Molecular Weight: 849.52

In the same manner as pentyl 6-(dodecyl(2-(dodecyl(2-hydroxyethyl)amino)ethyl)amino)hexanoate, 2-((2-(di((9Z,12Z)-octadeca-9,12-dien-1-yl)amino)ethyl)((9Z,12Z)-octadeca-9,12-dien-1-yl)amino)ethan-1-ol was synthesized from 2-(((9Z,12Z)-octadeca-9,12-dien-1-yl)amino)ethan-1-ol (75 mg, 0.24 mmol), (9Z,12Z)—N-(2-chloroethyl)-N-((9Z,12Z)-octadeca-9,12-dien-1-yl)octadeca-9,12-dien-1-amine (154 mg, 0.27 mmol), K$_2$CO$_3$ (67 mg, 0.49 mmol), and KI (4 mg, 0.024 mmol) in MeCN (2 mL). Yield (35 mg, 17%).

UPLC/ELSD: RT=3.94 min. MS (ES): m/z (MH$^+$) 850.03 for $C_{58}H_{108}N_2O$ $^1$H-NMR (300 MHz, CDCl$_3$) δ: ppm 5.35 (br. m, 12H); 2.77 (t, 6H) 2.70-2.38 (br. m, 14H); 2.05 (m, 12H); 1.50-1.00 (br. m, 54H); 0.88 (t, 9H).

DF: Compound 20-15: 2-((2-(Didodecylamino)ethyl)(hexyl)amino)ethan-1-ol (Compound 20-15)

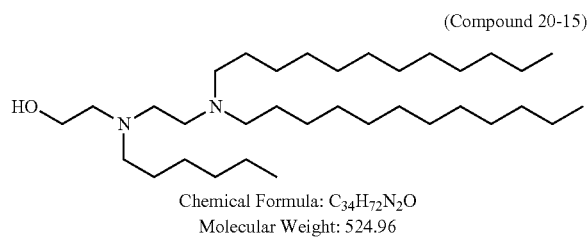 [SMILES: CCCCCCCCCCCCN(CCCCCCCCCCCC)CCN(CCO)CCCCCC]

Chemical Formula: $C_{34}H_{72}N_2O$
Molecular Weight: 524.96

DG: Compound 20-16: 2-((2-(Dinonylamino)ethyl)(nonyl)amino)ethan-1-ol (Compound 20-16)

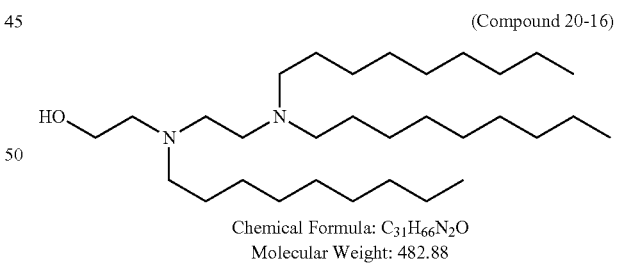

Chemical Formula: $C_{31}H_{66}N_2O$
Molecular Weight: 482.88

To a solution of 2-((2-aminoethyl)amino)ethan-1-ol (2.0 g, 18.6 mmol) and DCE (50 mL) at 0° C. was added nonanal (12.8 mL, 74.6 mmol), followed by AcOH (3.2 mL, 55.9 mmol). The reaction was allowed to stir at 0° C. for 20 min. Na(OAc)$_3$BH (15.8 g, 74.6 mmol) was added and the reaction was allowed to warm to room temperature and stir for 18 hours at room temperature. The mixture was quenched by the slow addition of aqueous saturated NaHCO$_3$ and extracted with DCM three times. The combined organic layers were dried over anhydrous Na$_2$SO$_4$, filtered, and concentrated in vacuo. Purification by ISCO silica flash chromatography provided 2-((2-(dinonylamino)ethyl)(nonyl)amino)ethan-1-ol. Yield (75 mg, 0.8%).

UPLC/ELSD: RT=2.28 min. MS (ES): m/z (MH$^+$) 483.47 for $C_{21}H_{66}N_2O$ $^1$H NMR (300 MHz, CDCl$_3$) δ: ppm 3.53 (m, 2H); 2.61-2.41 (br. m, 12H), 1.43-1.25 (br. m, 42H); 0.86 (m, 9H).

DH: Compound 20-17: 2-((2-(Didodecylamino)ethyl)(nonyl)amino)ethan-1-ol

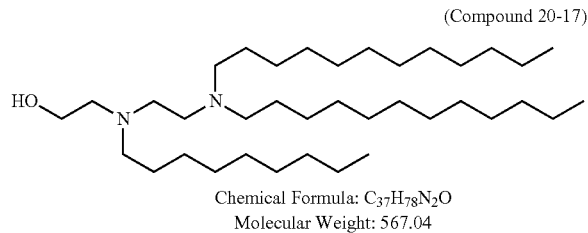 [SMILES: CCCCCCCCCCCCN(CCCCCCCCCCCC)CCN(CCO)CCCCCCCCC]

(Compound 20-17)

Chemical Formula: $C_{37}H_{78}N_2O$
Molecular Weight: 567.04

In the same manner as pentyl 6-(dodecyl(2-(dodecyl(2-hydroxyethyl)amino)ethyl)amino)hexanoate, 2-((2-(didodecylamino)ethyl)(nonyl)amino)ethan-1-ol was synthesized from 2-(nonylamino)ethan-1-ol (50 mg, 0.27 mmol), N-(2-chloroethyl)-N-dodecyldodecan-1-amine (111 mg, 0.27 mmol), K$_2$CO$_3$ (74 mg, 0.53 mmol), and KI (4.4 mg, 0.027 mmol) in 1,4-dioxane (1.5 mL). Yield (29 mg, 19%).

UPLC/ELSD: RT=3.05 min. MS (ES): m/z (MH$^+$) 567.91 for $C_{37}H_{78}N_2O$ $^1$H NMR (300 MHz, CDCl$_3$) δ: ppm 3.71 (m, 2H); 3.14-2.97 (br. m, 8H), 2.80 (m, 2H); 2.66 (m, 2H); 1.70 (m, 4H); 1.53 (m, 2H); 1.34-1.28 (br. m, 48H); 0.90 (m, 9H).

DI: Compound 20-18: 2-((2-(Dinonylamino)ethyl)(dodecyl)amino)ethan-1-ol

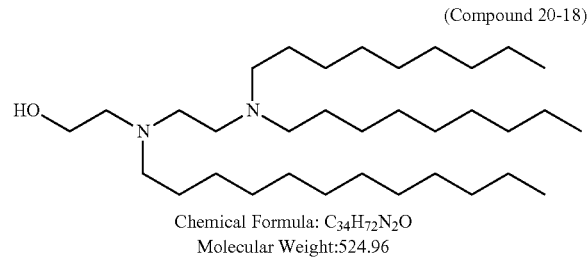 [SMILES: CCCCCCCCCCCCN(CCO)CCN(CCCCCCCCC)CCCCCCCCC]

(Compound 20-18)

Chemical Formula: $C_{34}H_{72}N_2O$
Molecular Weight: 524.96

In the same manner as pentyl 6-(dodecyl(2-(dodecyl(2-hydroxyethyl)amino)ethyl)amino)hexanoate, 2-((2-(dinonylamino)ethyl)(dodecyl)amino)ethan-1-ol was synthesized from 2-(dodecylamino)ethan-1-ol (100 mg, 0.44 mmol), N-(2-chloroethyl)-N-nonylnonan-1-amine (145 mg, 0.44 mmol), K$_2$CO$_3$ (120 mg, 0.87 mmol), and KI (7.2 mg, 0.044 mmol) in MeCN (1 mL) and THF (1 mL). Yield (155 mg, 67%).

UPLC/ELSD: RT=2.78 min. MS (ES): m/z (MH$^+$) 525.99 for $C_{34}H_{72}N_2O$ $^1$H NMR (300 MHz, CDCl$_3$) δ: ppm 3.55 (m, 2H); 2.63-2.47 (br. m, 12H), 1.47-1.28 (br. m, 48H); 0.90 (m, 9H).

DJ: Compound 20-19: 2-((2-(Didodecylamino)ethyl)amino)ethan-1-ol

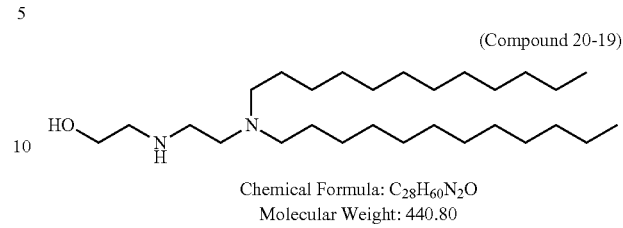

(Compound 20-19)

Chemical Formula: $C_{28}H_{60}N_2O$
Molecular Weight: 440.80

Ethanolamine (50 mg, 0.82 mmol), N-(2-chloroethyl)-N-dodecyldodecan-1-amine (0.75 g, 1.8 mmol), K$_2$CO$_3$ (0.25 g, 1.8 mmol) and KI (14 mg, 0.082) and 4 mL THF were combined in a round bottomed flask. The reaction was placed in a 65° C. heating mantle and was allowed to stir under N$_2$ for 12 h. After this time the reaction was allowed to cool to room temperature and was filtered. The filtrate was washed with H$_2$O and brine, dried over MgSO$_4$, filtered and concentrated. The crude material was purified by C$_{18}$ reverse phase chromatography (5-100% MeCN in H$_2$O with 0.1% TFA). The fractions were pooled and concentrated. The isolated material was taken up in CHCl$_3$, washed with 10% NaOH and brine, dried over MgSO$_4$, filtered and concentrated. The product was then re-purified via silica gel chromatography (0-20% MeOH in DCM with 1% NH$_4$OH) to afford 2-((2-(didodecylamino)ethyl)amino)ethan-1-ol (0.15 g, 41%).

UPLC/ELSD: RT=2.15 min. MS (ES): m/z (MH$^+$) 441.37 for $C_{28}H_{60}N_2O$ $^1$H-NMR (400 MHz, CDCl$_3$) δ: ppm 3.59 (t, 2H); 2.75 (t, 2H); 2.62 (t, 2H); 2.50 (t, 2H); 2.37 (t, 4H); 1.39 (m, 4H); 1.24 (m 38H); 0.86 (t, 6H).

DK: Compound 20-20: 2-((2-(Didodecylamino)ethyl)(dodecyl)amino)ethan-1-ol

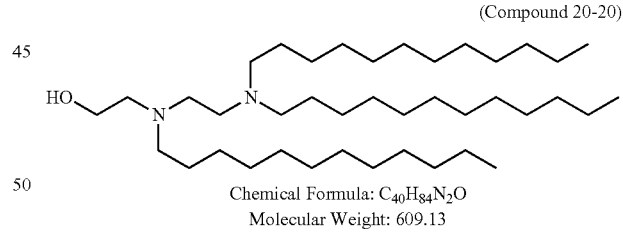

(Compound 20-20)

Chemical Formula: $C_{40}H_{84}N_2O$
Molecular Weight: 609.13

A solution of 2-((2-aminoethyl)amino)ethan-1-ol (2 g, 19.2 mmol) in 50 mL DCE was allowed to cool under N$_2$ in an ice bath. Dodecanal (26 mL, 76.8 mmol) was added followed by acetic acid (3.3 mL, 57.6 mmol). After 20 min., Na(OAc)$_3$BH (16.3 g, 76.8 mmol) was added. The reaction was allowed to slowly warm to room temperature and stir for 48 h. After this time the reaction was quenched via portion wise addition of saturated NaHCO$_3$. The mixture was extracted three times with DCM. The pooled organics were washed with brine, dried over MgSO$_4$, filtered and concentrated. The crude material was purified by silica gel chromatography (0-100% EtOAc in hexanes) twice to afford clean 2-((2-(didodecylamino) ethyl)(dodecyl)amino)ethan-1-ol (7.4 g, 63%).

UPLC/ELSD: RT=3.20 min. MS (ES): m/z (MH⁺) 609.97 for $C_{40}H_{84}N_2O$

¹H-NMR (400 MHz, CDCl₃) δ: ppm 3.51 (t, 2H); 2.57-2.40 (br. m, 12H); 1.41-1.23 (br. m., 60H); 0.86 (t, 9H).

DL: Compound 20-21: 3-((2-(Didodecylamino)ethyl)(dodecyl)amino)propan-1-ol (Compound 20-21)

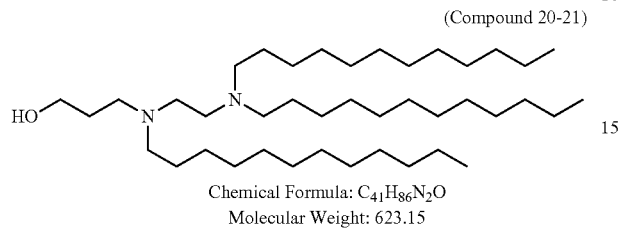

Chemical Formula: $C_{41}H_{86}N_2O$
Molecular Weight: 623.15

In the same manner as pentyl 6-(dodecyl(2-(dodecyl(2-hydroxyethyl)amino)ethyl)amino)hexanoate, 3-((2-(didodecylamino)ethyl)(dodecyl)amino)propan-1-ol was synthesized from 3-(dodecylamino)propan-1-ol (39 mg, 0.16 mmol), N-(2-chloroethyl)-N-dodecyldodecan-1-amine (75 mg, 0.18 mmol), K₂CO₃ (44 mg, 0.32 mmol), and KI (2.7 mg, 0.016 mmol) in THF (1 mL). Yield (170 mg, >98%).

UPLC/ELSD: RT=3.29 min. MS (ES): m/z (MH⁺) 623.71 for $C_{41}H_{86}N_2O$

¹H NMR (300 MHz, CDCl₃) δ: ppm 3.76 (m, 2H); 2.64-2.39 (br. m, 12H); 1.66 (m, 2H); 1.44-1.26 (br. m, 60H); 0.88 (m, 9H).

DM: Compound 20-22: 4-((2-(Didodecylamino)ethyl)(dodecyl)amino)butan-1-ol 4-(Dodecylamino)butan-1-ol

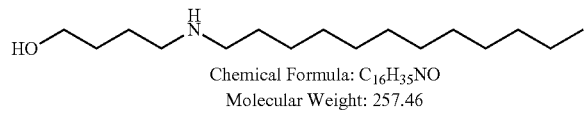 [SMILES: CCCCCCCCCCCCNCCCCO]

Chemical Formula: $C_{16}H_{35}NO$
Molecular Weight: 257.46

In the same manner as 2-(dodecylamino)ethan-1-ol, 4-(dodecylamino)butan-1-ol was synthesized from 4-aminobutan-1-ol (2.5 mL, 27 mmol), 1-bromododecane (6.75 g, 27 mmol), K₂CO₃ (7.5 g, 54 mmol), and KI (450 mg, 2.7 mmol) in MeCN (125 mL). Yield (303 mg, 4%).

UPLC/ELSD: RT=1.09 min. MS (ES): m/z (MH⁺) 258.22 for $C_{16}H_{35}NO$

¹H-NMR (300 MHz, CDCl₃) δ: ppm 3.60 (t, 2H); 2.76-2.62 (br. m, 4H); 1.72-1.58 (br. m, 6H); 1.29 (br. m, 18H); 0.89 (t, 3H).

(Compound 20-22)

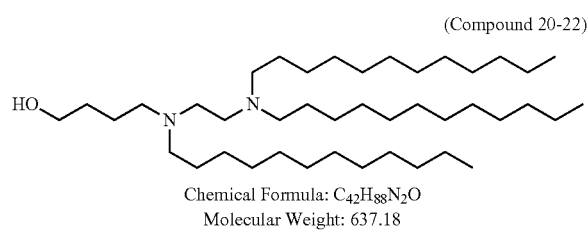 [SMILES: CCCCCCCCCCCCN(CCCCO)CCN(CCCCCCCCCCCC)CCCCCCCCCCCC]

Chemical Formula: $C_{42}H_{88}N_2O$
Molecular Weight: 637.18

In the same manner as pentyl 6-(dodecyl(2-(dodecyl(2-hydroxyethyl)amino)ethyl)amino)hexanoate, 4-((2-(didodecylamino)ethyl)(dodecyl)amino)butan-1-ol was synthesized from 4-(dodecylamino)butan-1-ol (75 mg, 0.29 mmol), N-(2-chloroethyl)-N-dodecyldodecan-1-amine (133 mg, 0.32 mmol), K₂CO₃ (80 mg, 0.58 mmol), and KI (5 mg, 0.029 mmol) in MeCN (2 mL). Yield (104 mg, 56%).

UPLC/ELSD: RT=3.27 min. MS (ES): m/z (MH⁺) 637.85 for $C_{42}H_{88}N_2O$

¹H-NMR (300 MHz, CDCl₃) δ: ppm 3.56 (br. m, 2H); 2.58 (br. m, 4H); 2.45 (br. m, 8H); 1.65 (br. m, 4H); 1.45 (br. m, 6H); 1.25 (br. m, 54H); 0.88 (t, 9H).

DN: Compound 20-23: (Z)-2-((2-(Didodecylamino)ethyl)(dodec-6-en-1-yl)amino)ethan-1-ol Step 1: (6-Hydroxyhexyl)triphenylphosphonium Bromide

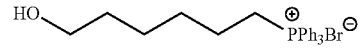

Chemical Formula: $C_{24}H_{28}BrOP$
Molecular Weight: 443.36

6-Bromo-1-hexanol (4.89 g, 27 mmol) and triphenylphosphine (7.87 g, 30 mmol) and 50 mL MeCN were combined in a round bottomed flask. The flask was fitted with a condenser and placed in a heating mantel and the reaction was allowed to stir at 82° C. for 48 h. After this time the reaction was allowed to cool to room temperature and the solution was cannulated into 200 mL Et₂O, producing a white precipitate. The solids were allowed to settle and the solvent was decanted off. 20 mL DCM was added to dissolve the solids and then 100 mL Et₂O was slowly added to afford a white precipitate. The solvent was then removed in vacuo to afford clean (6-hydroxyhexyl)triphenylphosphonium bromide (9.4 g, 21.2 mmol, for 78% yield).

¹H-NMR (300 MHz, CDCl₃) δ: ppm 7.80 (m, 15H); 3.80 (m, 2H); 3.65 (m, 2H); 2.23 (m, 2H); 1.68 (m, 4H); 1.52 (m, 4H).

Step 2: (Z)-Dodec-6-en-1-ol

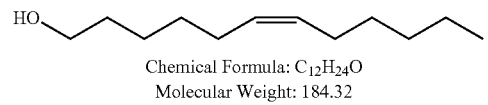

Chemical Formula: $C_{12}H_{24}O$
Molecular Weight: 184.32

A solution of (6-hydroxyhexyl)triphenylphosphonium bromide (3.0 g, 6.77 mmol) in 25 mL THF was allowed to cool in a −78° C. dry ice/acetone bath. Once cool n-BuLi (2.5 M in hexanes) (5.7 mL, 14.2 mmol) was added dropwise. After 1 h, an additional 10 mL THF and n-BuLi (1.35 mL) were added and stirring was continued at the same temperature for 1 h. After this time 1-hexanal (1.6 mL, 13.5 mmol) was added and the reaction was allowed to warm to rt and stir for 3 h. After this time the reaction was quenched by addition of excess sat'd NH₄Cl. The solution was extracted three times with EtOAc. The pooled organics were washed with brine, dried over MgSO₄, filtered and concentrated in vacuo. The crude material was purified by silica gel chromatography (0-50% EtOAc in hexanes) to afford the desired product as a clear oil (0.76 g, 4.1 mmol, 61%).

¹H-NMR (300 MHz, CDCl₃) δ: ppm 5.34 (m, 2H); 3.62 (t, 2H); 2.01 (m, 4H); 1.56 (m, 2H); 1.35-1.27 (m, 11H); 0.87 (t, 3H).

Step 3: (Z)-Dodec-6-en-1-yl Methanesulfonate

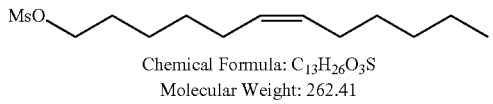

Chemical Formula: $C_{13}H_{26}O_3S$
Molecular Weight: 262.41

To a 0° C. solution of (Z)-dodec-6-en-1-ol (1.81 g, 9.3 mmol) in 20 mL DCM, was added $Et_3N$ (1.7 mL, 12.1 mmol) and methanesulfonyl chloride (0.80 mL, 10.2 mmol). The reaction was allowed to slowly warm to room temperature and stir overnight. The reaction was quenched by the addition of water and the mixture was extracted two times with DCM. The organics were pooled, washed with brine, dried over $MgSO_4$, filtered and concentrated. The crude material was purified by silica gel chromatography (0-30% EtOAc in hexanes) to afford clean desired product (2.2 g, 8.4 mmol, 90%).

$^1$H-NMR (300 MHz, $CDCl_3$) δ: ppm 5.34 (m, 2H); 4.20 (t, 2H); 2.98 (s, 3H); 2.01 (m, 4H); 1.74 (m, 2H); 1.38-1.27 (m, 10H); 0.87 (t, 3H).

Step 4: (Z)-1-Bromododec-6-ene

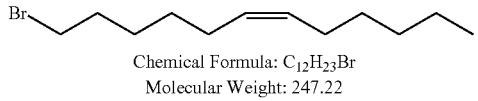

Chemical Formula: $C_{12}H_{23}Br$
Molecular Weight: 247.22

In a round bottomed flask, under $N_2$, (Z)-dodec-6-en-1-yl methanesulfonate (2.2 g, 8.3 mmol) was dissolved in 40 mL $Et_2O$. $MgBr_2.Et_2O$ (6.5 g, 25 mmol) was added and the reaction was allowed to stir for 48 h. After this time the reaction was quenched by the addition of ice. The mixture was then extracted with $Et_2O$ three times. The pooled organics were washed with brine, dried over $MgSO_4$, filtered and concentrated. The crude material was purified by silica gel chromatography (0-30% EtOAc in hexanes) to afford the desired product (1.8 g, 7.28 mmol, 88%).

$^1$H-NMR (300 MHz, $CDCl_3$) δ: ppm 5.34 (m, 2H); 3.39 (t, 2H); 2.01-1.84 (m, 6H); 1.28 (m, 10H); 0.87 (t, 3H).

Step 5: (Z)-2-((2-(Didodecylamino)ethyl)(dodec-6-en-1-yl)amino)ethan-1-ol (Compound 20-23)

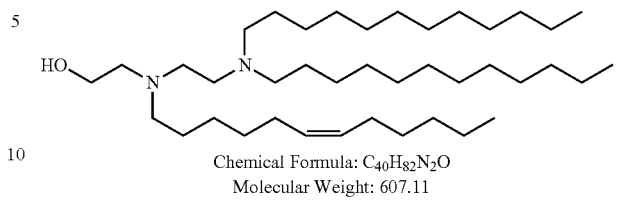

Chemical Formula: $C_{40}H_{82}N_2O$
Molecular Weight: 607.11

In the same manner as pentyl 6-(dodecyl(2-(dodecyl(2-hydroxyethyl)amino)ethyl)amino)hexanoate, (Z)-2-((2-(didodecylamino)ethyl)(dodec-6-en-1-yl)amino)ethan-1-ol was synthesized from (Z)-2-(dodec-6-en-1-ylamino)ethan-1-ol (100 mg, 0.44 mmol), N-(2-chloroethyl)-N-dodecyldodecan-1-amine (183 mg, 0.44 mmol), $K_2CO_3$ (122 mg, 0.88 mmol), and KI (7.3 mg, 0.044 mmol) in MeCN (1 mL) and THF (1 mL). Yield (90 mg, 34%).

UPLC/ELSD: RT=3.24 min. MS (ES): m/z ($MH^+$) 608.08 for $C_{40}H_{82}N_2O$ $^1$H NMR (300 MHz, $CDCl_3$) δ: ppm 5.42-5.35 (m, 2H); 3.55 (m, 2H), 2.62-2.45 (br. m, 12H); 2.06-2.00 (m, 4H); 1.48-1.28 (br. m, 52H); 0.91 (m, 9H).

DO: Compound 20-24: 2-((2-(Didodecylamino)ethyl)(tetradecyl)amino)ethan-1-ol (Compound 20-24)

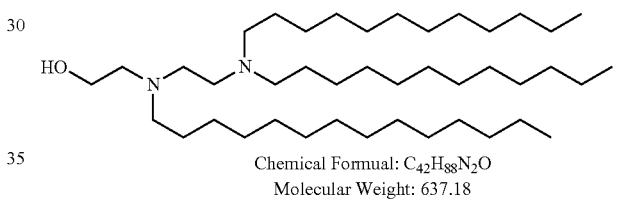

Chemical Formual: $C_{42}H_{88}N_2O$
Molecular Weight: 637.18

In the same manner as pentyl 6-(dodecyl(2-(dodecyl(2-hydroxyethyl)amino)ethyl)amino)hexanoate, 2-((2-(didodecylamino)ethyl)(tetradecyl)amino)ethan-1-ol was synthesized from 2-(tetradecylamino)ethan-1-ol (100 mg, 0.39 mmol), N-(2-chloroethyl)-N-dodecyldodecan-1-amine (162 mg, 0.39 mmol), $K_2CO_3$ (107 mg, 0.78 mmol), and KI (6.5 mg, 0.039 mmol) in MeCN (3 mL). Yield (128 mg, 52%).

UPLC/ELSD: RT=3.47 min. MS (ES): m/z ($MH^+$) 637.92 for $C_{42}H_{88}N_2O$ $^1$H NMR (300 MHz, $CDCl_3$) δ: ppm 3.54 (m, 2H); 2.61-2.44 (br. m, 12H); 1.46-1.28 (br. m, 64H); 0.91 (m, 9H).

DP: Compound 20-25: 2-((2-(Didodecylamino)ethyl)((9Z,12Z)-octadeca-9,12-dien-1-yl)amino)ethan-1-ol (Compound 20-25)

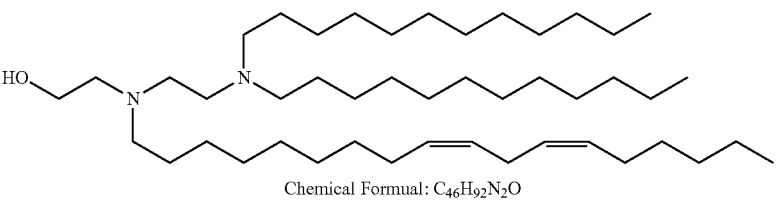

Chemical Formual: $C_{46}H_{92}N_2O$
Molecular Weight: 689.26

In the same manner as pentyl 6-(dodecyl(2-(dodecyl(2-hydroxyethyl)amino)ethyl) amino)hexanoate, 2-((2-(didodecylamino)ethyl)((9Z,12Z)-octadeca-9,12-dien-1-yl) amino)ethan-1-ol was synthesized from 2-(((9Z,12Z)-octadeca-9,12-dien-1-yl)amino)ethan-1-ol (50 mg, 0.16 mmol), N-(2-chloroethyl)-N-dodecyldodecan-1-amine (67 mg, 0.16 mmol), K$_2$CO$_3$ (45 mg, 0.32 mmol), and KI (3 mg, 0.016 mmol) in MeCN (2 mL). Yield (45 mg, 41%).

UPLC/ELSD: RT=3.64 min. MS (ES): m/z (MH$^+$) 689.95 for C$_{46}$H$_{92}$N$_2$O $^1$H NMR (300 MHz, CDCl$_3$) δ: ppm 5.39-5.32 (m, 4H); 3.56 (m, 2H), 2.80 (m, 2H); 2.62-2.52 (br. m, 12H); 2.08 (m, 4H); 1.48-1.28 (br. m, 58H); 0.91 (m, 9H).

DQ. Compound 21-1: 1-(2,2-Di((9Z,12Z)-octadeca-9,12-dien-1-yl)cyclopropyl)-N,N-dimethylmethanamine

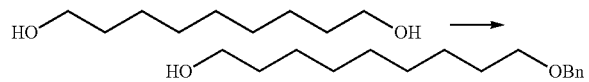

At 0° C., a solution of nonane-1,9-diol (96.16 g, 0.60 mol) in 100 mL DMF was slowly added into a suspension of NaH (24.0 g, 0.60 mol) in 800 mL DMF. After stirring for 1 h, a solution of benzyl bromide (71.4 mL, 0.60 mole) in 200 mL DMF was slowly added. After addition, the reaction mixture was warmed up to room temperature and stirred overnight. TLC showed starting material was almost consumed. The reaction mixture was poured onto ice, and then extracted with EtOAc (3×). The combined organic layers were washed with water and brine, and then dried over sodium sulfate. After filtration and concentration, the crude was purified by flash column chromatography (SiO$_2$: 0 to 100% EtOAc/hexanes then 0 to 5% MeOH/dichloromethane) to provide the product as a colorless oil (74.4 g, 50%).

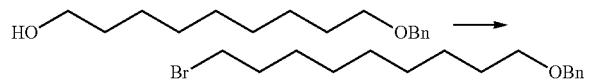

At 0° C., to a solution of 9-(benzyloxy)nonan-1-ol (14.88 g, 61.5 mmol) in 150 mL dichloromethane, CBr$_4$ (30.6 mmol, 92.2 mmol) was added. And then triphenylphosphine (27.4 g, 0.104 mole) was added portionwise. After stirring at room temperature overnight, TLC showed completed reaction. The reaction mixture was poured onto ice, and then extracted with dichloromethane (2×). The combined organic layers were washed with water and brine, and then dried over magnesium sulfate. After filtration and concentration, the residue was purified by ISCO (SiO$_2$: 0 to 10% EtOAc/hexanes) to provide the product as colorless oil (21.0 g, quant.).

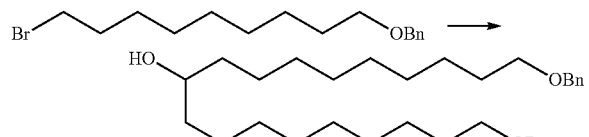

To a suspension of magnesium (3.23 g, 0.134 mole) in 80 mL THF, catalytic amount of iodine was added, and then stirred until the color disappeared. A solution of (((9-bromononyl)oxy)methyl)benzene (21.0 g, 67.2 mmol) in 40 mL THF was slowly added in 15 min at room temperature, and then the mixture was heated to reflux for 1 h. After cooling to room temperature, a solution of methyl formate (4.2 mL, 67.2 mmol) in 10 mL THF was added dropwise, and the mixture was stirred overnight. The reaction was quenched by addition of 5 N HCl and water, and the mixture was extracted with EtOAc (2×). The combined organic layers were washed with brine and dried over sodium sulfate. After filtration and concentration, the residue was dissolved in EtOH, and then KOH and water were added. After stirring overnight, the reaction mixture was concentrated to dryness. Water was added, and then adjusted pH ~7 with 1 N HCl. The mixture was extracted with EtOAc (2×), and the combined organic layer was dried over magnesium sulfate. After filtration and concentration, the crude was purified by ISCO (SiO$_2$: 0 to 10% EtOAc/hexanes) to provide the product as colorless oil (6.64 g, 40%).

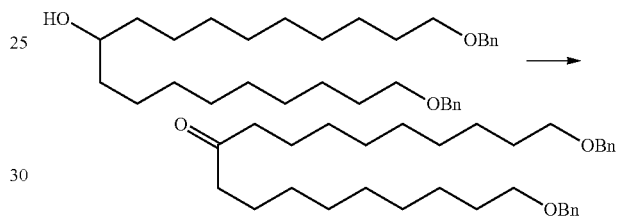

At 0° C., a solution of 1,19-bis(benzyloxy)nonadecan-10-ol (6.64 g, 13.4 mmol) in 30 mL dichloromethane was slowly added into a solution of Dess-Martin periodinane (7.94 g, 18.7 mmol) in 70 mL dichloromethane, and then the reaction mixture was stirred at this temperature for 3 h. TLC showed starting material was consumed. The reaction mixture was diluted with dichloromethane, and then 10% Na$_2$S$_2$O$_3$ solution and saturated sodium bicarbonate solution were added. After extraction with dichloromethane (2×), the combined organic layers were washed with brine and concentrated. The residue was dissolved in ether and washed with saturated sodium bicarbonate and brine. After drying over sodium sulfate, the solution was filtered and concentrated. The crude was purified by ISCO (SiO$_2$: 0 to 20% EtOAc/hexanes) to provide the product as colorless oil (6.23 g, 94%).

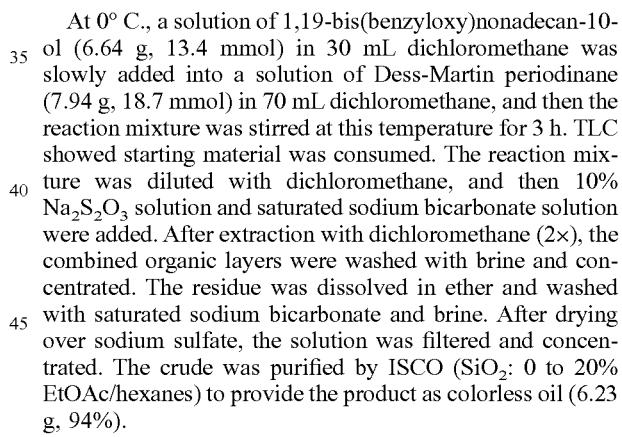

At 0° C., potassium tert-butoxide (1.70 g, 15.1 mmol) was added into a solution of methylphosphonium bromide (5.40 g, 15.1 mmol) in 80 mL THF which was purged with nitrogen 3 times. After 1 h, a solution of 1,19-bis(benzyloxy) nonadecan-10-one (6.23 g, 12.6 mmol) in 20 mL THF (purged with nitrogen 3 times) was transferred via cannula into the reaction mixture, and then the reaction was allowed to warm up to room temperature overnight. TLC showed completed reaction, and the reaction mixture was filtered through Celite. After concentration, the crude was purified by ISCO (SiO$_2$: 0 to 10% EtOAc/hexanes) to provide the product as colorless oil (6.0 g, 96%).

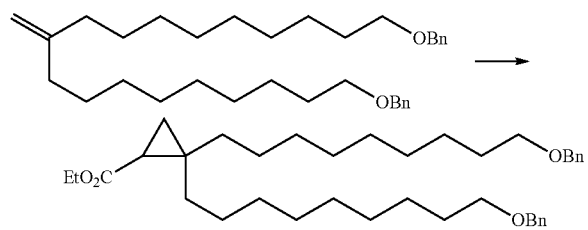

To a refluxing solution of (((10-methylenenonadecane-1, 19-diyl)bis(oxy))bis(methylene))dibenzene (2.99 g, 6.08 mmol) in 160 mL dichloromethane, a solution of Cu(acac)$_2$ (180 mg, 0.69 mmol) in 40 mL dichloromethane was added. And then ethyl diazoacetate (contains 13% dichloromethane, 9×1.1 mL) was added every 30 min. MS showed the formation of product. The reaction was quenched with MeOH and stirred for 1 h at room temperature. After concentration, the crude was purified by flash column chromatography (SiO$_2$: 0 to 10% EtOAc/hexanes) to provide the product as colorless oil (3.65 g, contains 1 equivalent of acetate by-product).

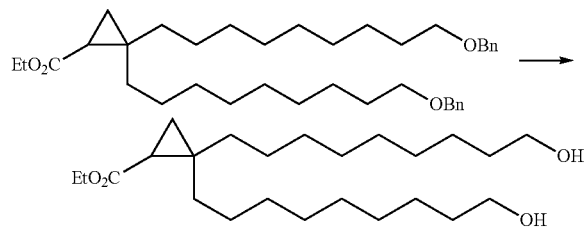

A mixture of ethyl 2,2-bis(9-(benzyloxy)nonyl)cyclopropane-1-carboxylate (2.8 g, 4.8 mmol) and Palladium on carbon (10 wt %, 500 mg) in 500 mL EtOAc was stirred at room temperature under hydrogen balloon for 4.5 h. MS and TLC showed completed reaction. The reaction mixture was filtered through Celite and washed with EtOAc. The filtrate was concentrated to provide the product mixed with by-product, diethyl succinate (2.53 g, contains 0.94 equivalent of by-product, 94%).

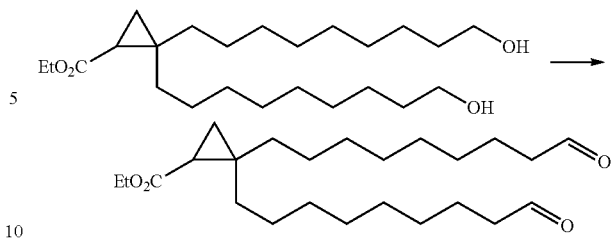

At 0° C., a solution of ethyl 2,2-bis(9-hydroxynonyl)cyclopropane-1-carboxylate (2.4 g, 6 mmol) in 100 mL dichloromethane was slowly added into a suspension of Dess-Martin periodinane (7.67 g, 18 mmol) in 100 mL dichloromethane, and then the reaction mixture was stirred at room temperature for 4 h. After quenching with 10% aqueous Na$_2$S$_2$O$_3$ and saturated sodium bicarbonate, the mixture was extracted with dichloromethane (2×). The combined organic layers were dried over sodium sulfate and concentrated to give the product as colorless oil (2.3 g, contains about 0.7 g by-product).

Preparation of
(Z)-non-3-en-1-yltriphenylphosphonium Iodide

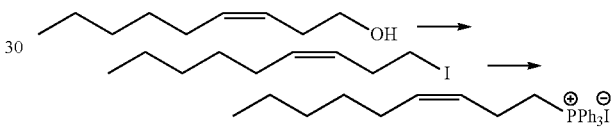

At 0° C., a solution of triphenylphosphine (110 g, 0.419 mole) in 200 mL dichloromethane was slowly added into a solution of (Z)-non-3-en-1-ol (49.6 g, 0.349 mole), imidazole (50.0 g, 0.732 mole) and iodine (124 g, 0.488 mole) in 800 mL dichloromethane, and then the reaction mixture was allowed to room temperature overnight. TLC showed small amount of (Z)-non-3-en-1-ol left. The reaction mixture was concentrated, and the residue was triturated with hexanes. The solution was filtered through a plug of silica gel and eluted with hexanes to provide the iodide as a colorless liquid (81 g, 92%).

A solution of (Z)-1-iodonon-3-ene (81 g, 0.321 mole) and triphenylphosphine (169 g, 0.643 mole) in acetonitrile (1.1 L) was refluxed overnight. After concentrated to dryness, the residue was triturated with hexanes. The white gum was dissolved in dichloromethane and purified by flash column chromatography (SiO$_2$: 0 to 5% MeOH/CH$_2$Cl$_2$) to provide the product as colorless oil which then turned into white solid (114 g, 69%).

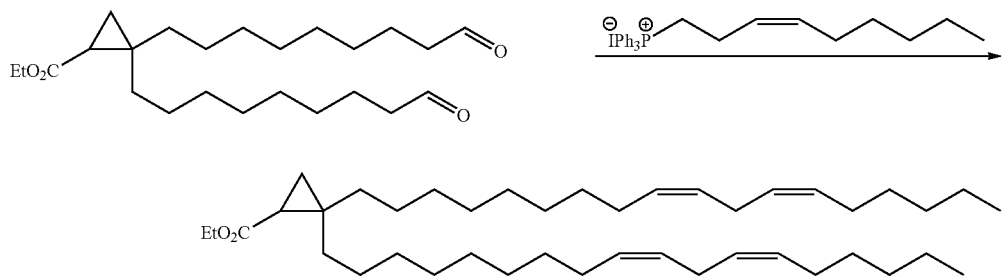

At 0° C., potassium tert-butoxide (1.98 g, 17.7 mmol) was added into a solution of (Z)-non-3-en-1-yltriphenylphosphonium iodide (9.2 g, 17.9 mmol) in 300 mL THF which was purged with nitrogen 3 times. After 1 h, a solution of ethyl 2,2-bis(9-oxononyl)cyclopropane-1-carboxylate (2.05 g, 5.2 mmol) in 100 mL THF (purged with nitrogen 3 times) was transferred via cannula into the reaction mixture, and then the reaction was allowed to warm up to room temperature overnight. TLC showed completed reaction. The reaction was quenched with saturated ammonium chloride, and then extracted with hexanes (2×). The combined organic layers were washed with brine and dried over sodium sulfate. After filtration and concentration, the residue was purified by ISCO (SiO₂: 0 to 5% EtOAc/hexanes) to provide the product as a colorless oil (1.54 g, 48%).

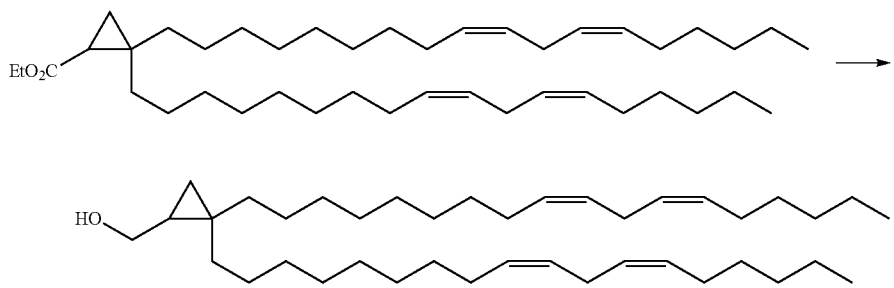

A solution of lithium aluminum hydride (2.0 M in THF, 1.9 mL, 3.8 mmol) was slowly added into a solution of ethyl 2,2-di((9Z,12Z)-octadeca-9,12-dien-1-yl)cyclopropane-1-carboxylate (1.54 g, 2.52 mmol) in 150 mL THF, and then the reaction mixture was stirred at room temperature for 30 min. TLC showed completed reaction. The reaction was quenched by slow addition of Na₂SO₄.10H₂O, then the mixture was filtered and washed with THF. The filtrate was concentrated and purified by flash column chromatography (SiO₂: 0 to 15% EtOAc/Hexanes) to give the product as a colorless oil (1.2 g, 84%).

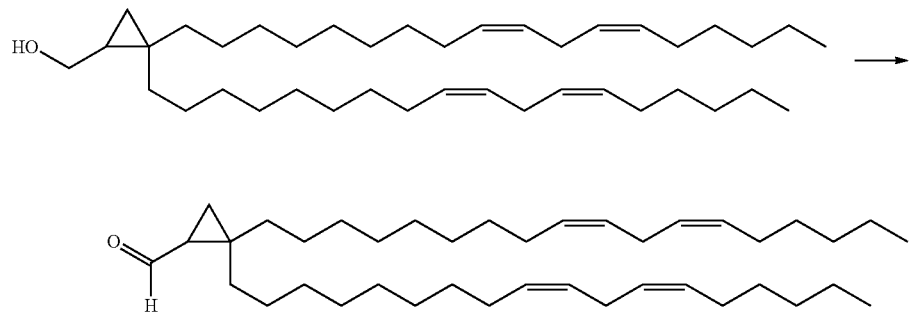

At 0° C., a solution of (2,2-di((9Z,12Z)-octadeca-9,12-dien-1-yl)cyclopropyl)methanol (1.04 g, 1.83 mmol) in 100 mL dichloromethane was slowly added into a suspension of Dess-Martin periodinane (1.18 g, 2.77 mmol) in 200 mL dichloromethane, and then the reaction mixture was stirred at room temperature for 3 h. After quenched with saturated sodium bicarbonate, the mixture was extracted with dichloromethane (2×). The combined organic layer was dried over sodium sulfate and concentrated to give the product as a colorless oil (0.95 g, 91%).

(Compound 21-1)

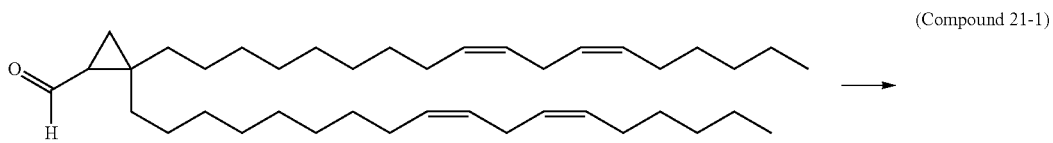

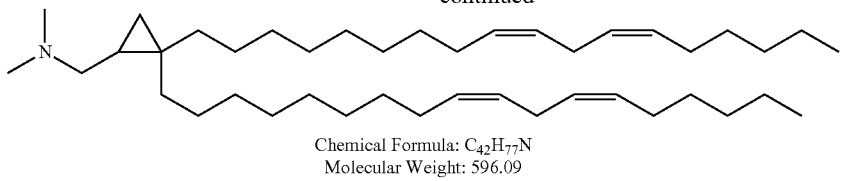

Chemical Formula: $C_{42}H_{77}N$
Molecular Weight: 596.09

To a solution of 2,2-di((9Z,12Z)-octadeca-9,12-dien-1-yl) cyclopropane-1-carbaldehyde (0.95 g, 1.68 mmol) in 300 mL THF, dimethylamine (2.0 M in THF, 2 mL, 4 mmol), sodium triacetoxyborohydride (840 mg, 4 mmol) and acetic acid (0.23 mL, 4 mmol) were added sequentially, and the reaction mixture was stirred at room temperature overnight. MS showed completed reaction, and saturated sodium bicarbonate was added to quench the reaction. The mixture was extracted with EtOAc (2×), and the combined organic layers were washed with brine and dried over sodium sulfate. After filtration and concentration, the residue was purified by flash column chromatography ($SiO_2$: 0 to 10% MeOH/dichloromethane) to give the product 1-(2,2-Di((9Z,12Z)-octadeca-9,12-dien-1-yl)cyclopropyl)-N,N-dimethylmethanamine as a colorless oil (0.56 g, 56%).

$^1$H NMR (300 MHz, $CDCl_3$) δ 5.27-5.42 (m, 8H), 2.76 (t, 4H, J=6.2 Hz), 2.38 (bs, 8H), 2.04 (q, 8H, J=6.6 Hz), 1.18-1.41 (m, 38H), 0.96-1.17 (m, 2H), 0.88 (t, 6H, J=6.6 Hz), 0.66-0.76 (m, 1H), 0.48-0.56 (m, 1H), 0.05-0.13 (m, 1H).

APCI: m/z=596.6 [M+H]$^+$.

DR. Compound 21-2: 3,3-Di((9Z,12Z)-octadeca-9,12-dien-1-yl)cyclobutyl 4-(dimethylamino)butanoate

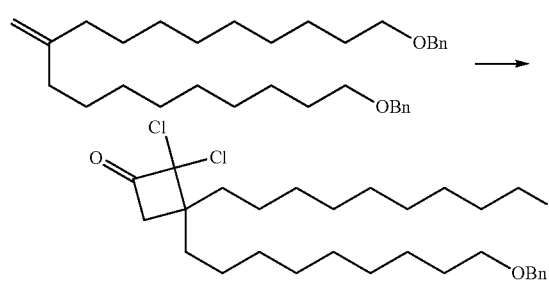

Preparation of Zn—Cu couple: A suspension of zinc dust (10 g) in 10 mL 4 M HCl was stirred for 10 min, and then the aqueous phase was decanted. After the solid was washed with water (2×20 mL), 20 mL water and copper sulfate (0.75 g) were added subsequently. After stirring overnight, water was decanted, and then the residue was washed with THF (2×10 mL). The black solid was dried under vacuum and store under nitrogen.

To a suspension of Zn—Cu couple (1.295 g, 19.8 mmol) in 30 mL ether purged with nitrogen 3 times, a solution of (((10-methylenenonadecane-1,19-diyl)bis(oxy))bis(methylene))dibenzene (2.96 g, 6.0 mmol) in 10 mL ether purged with nitrogen was added, and then a solution of $POCl_3$ (1.85 mL, 19.8 mmol) and 2,2,2-trichloroacetyl chloride (2.23 mL, 19.8 mmol) in 15 mL ether purged with nitrogen was added dropwise. After the addition, the mixture was heated to reflux for 22 h. TLC showed trace amounts of starting material. The reaction mixture was cooled in ice bath, and then 8.0 g potassium carbonate was added. 30 mL MeOH was added dropwise and stirred until no gas evolution. EtOAc was added and the mixture was filtered through Celite. The filtrate was concentrated and the residue was purified by ISCO ($SiO_2$: 0 to 10% EtOAc/hexanes) to provide the product as a colorless oil (3.02 g, 83%).

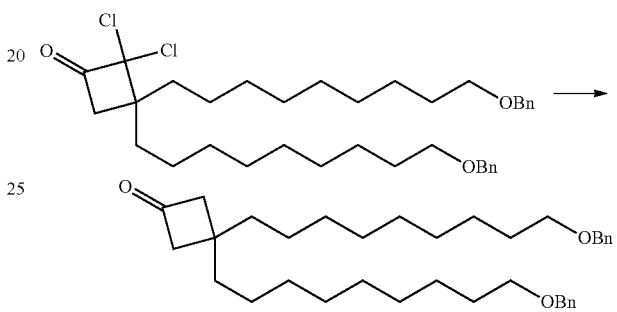

To a solution of 3,3-bis(9-(benzyloxy)nonyl)-2,2-dichlorocyclobutan-1-one (3.02 g, 5.0 mmol) in 80 mL MeOH, Zn dust (1.96 g, 30 mmol) was added. After stirring for 15 min, ammonium chloride (1.6 g, 30 mmol) was added, and the reaction mixture was stirred at room temperature for 3 h. TLC showed completed reaction, and the mixture was concentrated to dryness. 100 mL water and 100 mL EtOAc were added, and the mixture was filtered through Celite. The filtrate was washed with brine and dried over magnesium sulfate. After filtration and concentration, the product was obtained (2.58 g, 97%), which was used for the next step without purification.

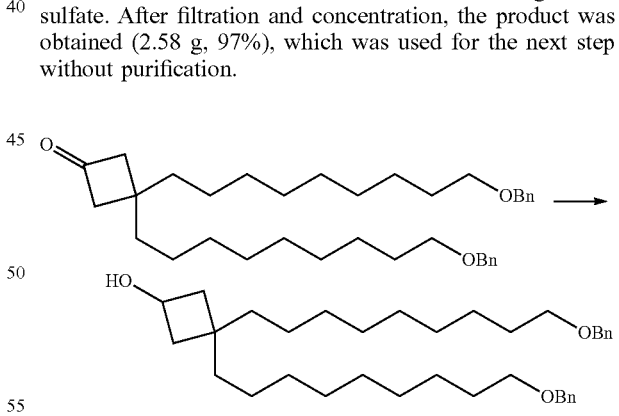

At 0° C., sodium borohydride (0.51 g, 13.51 mmol) was added into a solution of 3,3-bis(9-(benzyloxy)nonyl)cyclobutan-1-one (2.58 g, 4.82 mmol) in 48 mL MeOH/THF (5:1), and then the reaction was stirred at this temperature for 1 h. TLC showed completed reaction. The reaction was quenched with saturated sodium bicarbonate, and then extracted with EtOAc (2×). The combined organic layers were washed with brine and dried over sodium sulfate. After filtration and concentration, the product was obtained as a colorless oil (2.68 g, quant.), which was used for the next step without purification.

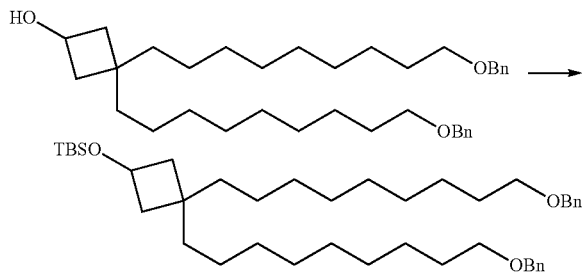

To a solution of 3,3-bis(9-(benzyloxy)nonyl)cyclobutan-1-ol (3.31 g, 6.17 mmol) and imidazole (0.92 g, 13.57 mmol) in 50 mL dichloromethane, tert-butyldimethylsilyl chloride (1.15 g, 7.28 mmol) was added and the reaction mixture was stirred at room temperature for 4 h. TLC showed completed reaction. Water was added to quench the reaction, and the mixture was extracted with dichloromethane (2×). The combined organic layers were washed with brine and dried over sodium sulfate. After filtration and concentration, the residue was purified by ISCO (SiO$_2$: 0 to 20% EtOAc/hexanes) to provide the product as a colorless oil (3.53 g, 90%).

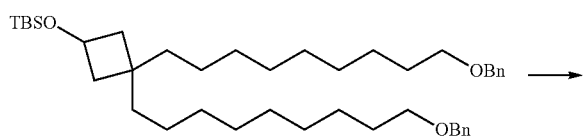

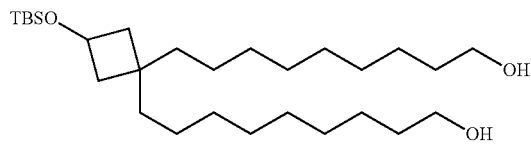

A mixture of (3,3-bis(9-(benzyloxy)nonyl)cyclobutoxy)(tert-butyl)dimethylsilane (3.53 g, 5.42 mmol) and palladium on carbon (10 wt %, 0.71 g) in 350 mL EtOAc was purged with nitrogen and hydrogen, respectively. After stirring under hydrogen balloon overnight, TLC showed completed reaction, and then the reaction mixture was filtered through Celite. After concentration, the residue was purified by ISCO (SiO2: 0 to 70% EtOAc/hexanes) to provide the product as a colorless oil (2.35 g, 92%).

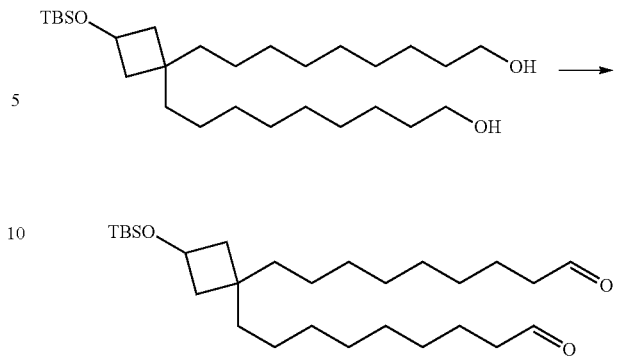

At 0° C., a solution of 9,9'-(3-((tert-butyldimethylsilyl)oxy)cyclobutane-1,1-diyl)bis(nonan-1-ol) (1.49 g, 3.16 mmol) in 20 mL dichloromethane was slowly added into a solution of Dess-Martin periodinane (2.68 g, 6.33 mmol) in 70 mL dichloromethane, and then the reaction mixture was stirred at this temperature for 3 h. After stirring at room temperature for 1 h, the reaction mixture was diluted with dichloromethane, and then 10% Na$_2$S$_2$O$_3$ solution and saturated sodium bicarbonate solution were added. After extraction with dichloromethane (2×), the combined organic layers were washed with saturated sodium bicarbonate and brine. The organic layer was dried over sodium sulfate and concentrated. The crude was purified by ISCO (SiO$_2$: 0 to 10% EtOAc/hexanes) to provide the product as a colorless oil (0.88 g, 60%).

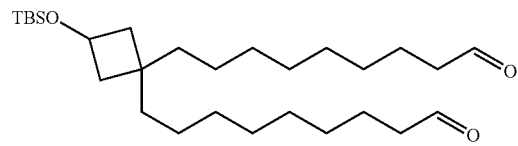
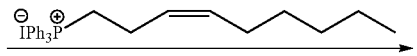

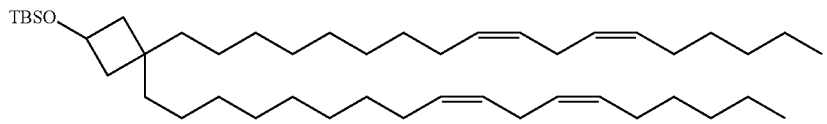

At 0° C., potassium tert-butoxide (0.51 g, 4.53 mmol) was added into a solution of (Z)-non-3-en-1-yltriphenylphosphonium iodide (2.33 g, 4.53 mmol) in 30 mL THF which was purged with nitrogen 3 times. After 1 h, a solution of 9,9'-(3-((tert-butyldimethylsilyl)oxy)cyclobutane-1,1-diyl)dinonanal (0.88 g, 1.89 mmol) in 25 mL THF (purged with nitrogen 3 times) was transferred via cannula into the reaction mixture, and then the reaction was allowed to warm up to room temperature overnight. TLC showed complete reaction. The reaction was quenched with saturated ammonium chloride, and then extracted with EtOAc (2×). The combined organic layers were washed with brine and dried over sodium sulfate. After filtration and concentration, the residue was purified by ISCO (SiO$_2$: 0 to 20% EtOAc/hexanes) to provide the product as a colorless oil (543 mg, 42%).

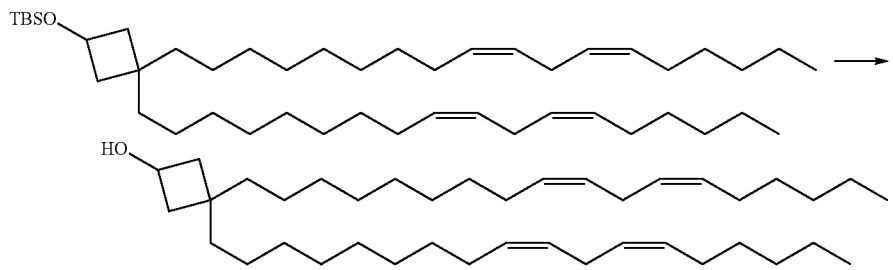

To a solution of tert-butyl(3,3-di((9Z,12Z)-octadeca-9,12-dien-1-yl)cyclobutoxy)dimethylsilane (0.67 g, 0.98 mmol) in 60 mL THF, a solution of TBAF (1.0 M in THF, 9.8 mL, 9.8 mmol) was added and the reaction mixture was stirred at room temperature for 3 h. TLC showed completed reaction. The solvent was removed under vacuum and the residue was purified by ISCO (SiO$_2$: 0 to 20% EtOAc/hexanes) to provide the product as a colorless oil (0.64 g, Quant.).

(Compound 21-2)

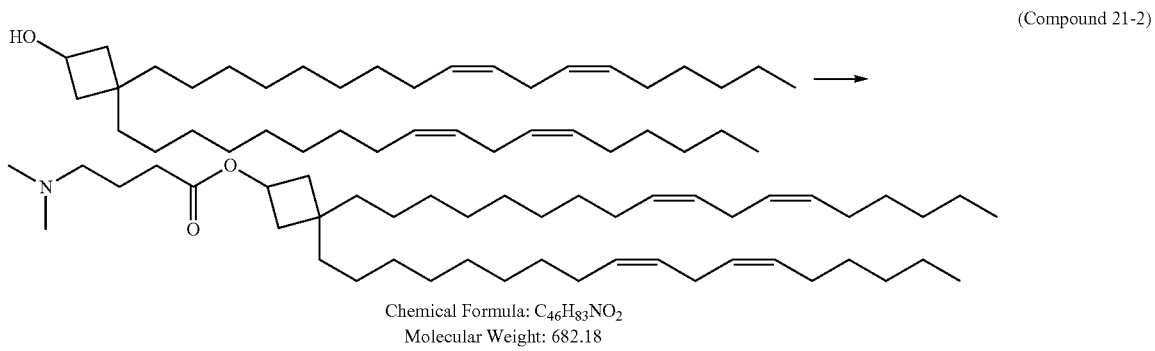

Chemical Formula: C$_{46}$H$_{83}$NO$_2$
Molecular Weight: 682.18

At 0° C., pyridine (2.4 mL) and propylphosphonic anhydride solution (50 wt % in DMF, 2.4 mL, 4.16 mmol) were added into a solution of 4-(dimethylamino)butanoic acid hydrochloride (564 mg, 3.37 mmol) in 6 mL DMF. After stirring for 10 min, a solution of 3,3-di((9Z,12Z)-octadeca-9,12-dien-1-yl)cyclobutan-1-ol (0.64 g, 1.12 mmol) in 4 mL DMF was added and the reaction mixture was stirred at room temperature overnight. MS and TLC showed the formation of product. Saturated sodium bicarbonate solution was added to quench the reaction, and then extracted with EtOAc (2×). The combined organic layers were washed with water and brine. After dried over sodium sulfate and concentration, the residue was purified by ISCO (SiO$_2$: 0 to 100% EtOAc/hexanes) to provide the product 3,3-Di((9Z,12Z)-octadeca-9,12-dien-1-yl)cyclobutyl 4-(dimethylamino)butanoate as a slight yellow oil (479 mg, 63%).

$^1$H NMR (300 MHz, CDCl$_3$) δ 5.28-5.42 (m, 8H), 4.89-4.99 (m, 1H), 2.76 (t, 4H, J=6.1 Hz), 2.30 (t, 4H, J=7.4 Hz), 2.23 (s, 6H), 2.15-2.21 (m, 2H), 2.04 (q, 8H, J=6.6 Hz), 1.68-1.84 (m, 4H), 1.08-1.40 (m, 40H), 0.88 (t, 6H, J=6.6 Hz).

APCI: m/z=682.6 [M+H]$^+$.

DS. Compound 21-3: 3,3-Di((9Z,12Z)-octadeca-9,12-dien-1-yl)cyclopentyl 3-(dimethylamino)propanoate

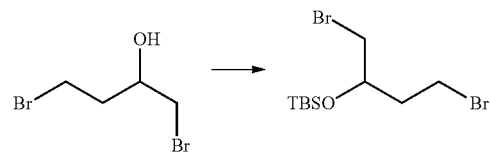 [SMILES: OC(CBr)CCBr ; CC(C)(C)[Si](C)(C)OC(CBr)CCBr]

At 0° C., to a solution of 1,4-dibromobutan-2-ol (75.0 g, 0.328 mole) and imidazole (49.0 g, 0.72 mole) in 500 mL dichloromethane, a solution of tert-butyldimethylsilyl chloride (57.0 g, 0.36 mole) in 300 mL dichloromethane was added dropwise. After the addition, the reaction mixture was warmed up to room temperature and kept stirring overnight. TLC showed clean conversion. The reaction mixture was filtered and washed with dichloromethane. After concentration, the residue was taken up with dichloromethane and washed with water and brine. The organic layer was dried over Na$_2$SO$_4$. After filtration and concentration, the crude was purified by flash column chromatography (SiO$_2$: 0 to 10% ether/hexanes) to provide pure product as a colorless liquid (83.05 g, 71%).

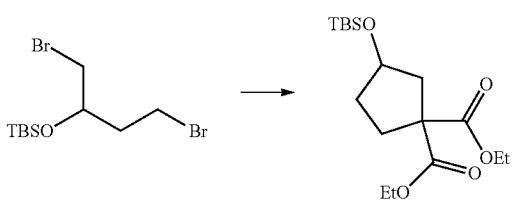 [SMILES: CC(C)(C)[Si](C)(C)OC(CBr)CCBr ; CCOC(=O)C1(C(=O)OCC)CCC(O[Si](C)(C)C(C)(C)C)C1]

A solution of tert-butyl((1,4-dibromobutan-2-yl)oxy)dimethylsilane (53.7 g, 0.152 mole), diethyl malonate (10.0 g, 0.138 mole), potassium carbonate (47.6 g, 0.345 mole) and tetrabutylammonium bromide (4.45 g, 13.8 mmol) in 700 mL DMF was stirred at room temperature for 3 days. TLC showed almost no starting material. The reaction mixture was diluted with water and extracted by EtOAc (3×), and the combined organic layers were washed with saturated ammonium chloride and brine. After drying over sodium sulfate, the solution was filtered and concentrated. The residue was purified by flash column chromatography (SiO$_2$: 0 to 10% EtOAc/hexanes) to give the desired product as a colorless oil (36.92 g, 77%).

At 0° C., a solution of lithium aluminium hydride (2.0 M in THF, 43.2 mL, 86.4 mmol) was added into a solution of diethyl 3-((tert-butyldimethylsilyl)oxy)cyclopentane-1,1-dicarboxylate (14.89 g, 43.2 mmol) in 60 mL THF, and then the reaction mixture was stirred at room temperature overnight. TLC showed clean conversion. The reaction was quenched by slowly adding of water (6 mL) and 1 N NaOH (20 mL), and then stirred for 30 min. The suspension was filtered through Celite and washed with EtOAc. After concentration, the residue was purified by flash column chromatography (SiO$_2$: 0 to 90% EtOAc/hexanes) to provide the product as a colorless oil (9.86 g, 88%).

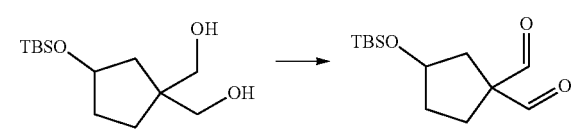

At −78° C., a solution of DMSO (2.15 mL, 30.3 mmol) in 10 mL dichloromethane was added dropwise into a solution of oxalyl chloride (1.35 mL, 15.2 mmol) in 15 mL dichloromethane, and then a solution of (3-((tert-butyldimethylsilyl)oxy)cyclopentane-1,1-diyl)dimethanol (1.88 g, 7.2 mmol) in 15 mL dichloromethane was added immediately. After stirring 30 min, triethylamine (7.25 mL, 52.0 mmol) was added and the reaction mixture was warmed up to room temperature. TLC showed clean conversion. The reaction was quenched with water and extracted with ether (2×). The combined organic layers were washed with saturated ammonium chloride and brine. After drying over sodium sulfate, the solution was filtered and concentrated to give the product as a yellow oil (2.00 g, quant.), which was used for the next step without further purification.

Preparation of
(8-(benzyloxy)octyl)triphenylphosphonium Iodide

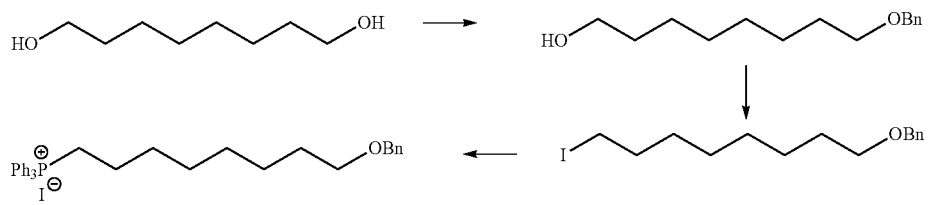

At 0° C., a solution of octane-1,8-diol (100 g, 0.684 mol) in 100 mL DMF was slowly added into a suspension of NaH (27.35 g, 0.684 mol) in 700 mL DMF. After stirring for 30 min, a solution of benzyl chloride (78.7 mL, 0.684 moles) in 200 mL DMF was slowly added. After addition, the reaction mixture was warmed up to room temperature and stirred overnight. TLC showed starting material was almost consumed. The reaction mixture was poured onto ice, and then extracted by EtOAc (2×). The combined organic layers were washed with water and brine, and then dried over sodium sulfate. After filtration and concentration, the crude was purified by flash column chromatography (SiO$_2$: 0 to 60% EtOAc/hexanes) to provide the product as a colorless oil (85.83 g, 53%).

At 0° C., a solution of triphenylphosphine (114.4 g, 0.436 mole) in 300 mL dichloromethane was slowly added into a solution of 8-(benzyloxy)octan-1-ol (85.83 g, 0.363 mole), imidazole (52 g, 0.76 mole) and iodine (129.1 g, 0.51 mole) in 1200 mL dichloromethane, and then the reaction mixture was allowed to equilibrate to room temperature over 3 days. After filtration, the filtrate was concentrated and the residue was triturated with hexanes. The solution was filtered through a plug of silica gel and eluted with 10% ether in hexanes to provide the product as a cloudy liquid (81.09 g). The gummy solid was dissolved in dichloromethane and passed through silica gel and eluted with 10% ether in hexanes to provide a cloudy liquid (20.0 g). Total yield: 101.1 g (80%).

A solution of (((8-iodooctyl)oxy)methyl)benzene (101.1 g, 0.293 mole) and triphenylphosphine (154.1 g, 0.586 mole) in acetonitrile (1 L) was refluxed overnight. After concentrated to dryness, the residue was dissolved in dichloromethane and purified by flash column chromatography (SiO$_2$: 0 to 10% MeOH/CH$_2$Cl$_2$) to provide the product as a yellow oil (144.1 g, 81%).

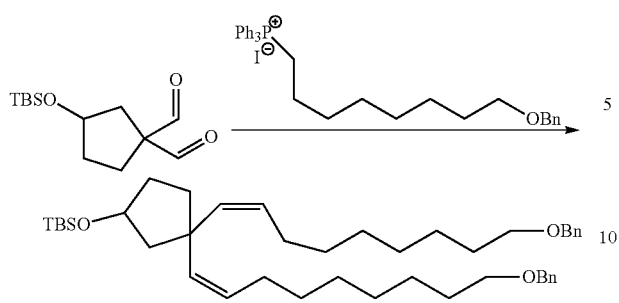

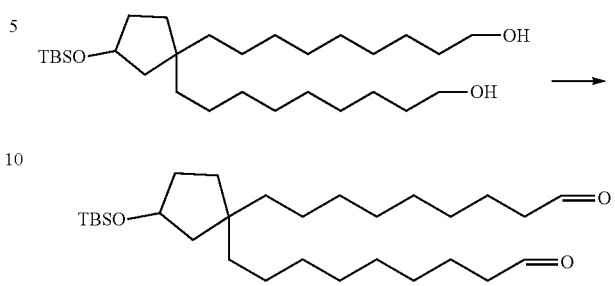

At 0° C., potassium tert-butoxide (2.42 g, 21.6 mmol) was added into a solution of (8-(benzyloxy)octyl)triphenylphosphonium iodide (14.2 g, 23.3 mmol) in 80 mL THF which was purged with nitrogen 3 times. After 1 h, a solution of 3-((tert-butyldimethylsilyl)oxy)cyclopentane-1,1-dicarbaldehyde (2.00 g, 7.2 mmol) in 20 mL THF (purged with nitrogen 3 times) was transferred via cannula into the reaction mixture, and then the reaction was allowed to warm up to room temperature overnight. TLC showed completed reaction. The reaction was quenched with saturated ammonium chloride, and then extracted with ether (2×). The combined organic layer was washed with brine and dried over sodium sulfate. After filtration and concentration, the residue was purified by flash column chromatography (SiO$_2$: 0 to 6% ether/hexanes) to provide the product as a colorless oil (3.77 g, 79%).

Celite and washed by EtOAc. The filtrate was concentrated to give the product as a colorless oil (2.32 g, Quant.).

At 0° C., a solution of 9,9'-(3-((tert-butyldimethylsilyl)oxy)cyclopentane-1,1-diyl)bis(nonan-1-ol) (2.32 g, 4.6 mmol) in 30 mL dichloromethane was slowly added into a solution of Dess-Martin periodinate (5.46 g, 12.88 mmol) in 70 mL dichloromethane, and then the reaction mixture was stirred at this temperature for 4 h. TLC showed starting material was consumed. The reaction mixture was diluted with dichloromethane, and then 10% Na$_2$S$_2$O$_3$ solution and saturated sodium bicarbonate solution were added. After extraction with dichloromethane (2×), the combined organic layers were washed with brine and concentrated. The residue was dissolved in ether and washed with saturated sodium bicarbonate and brine. After drying over sodium sulfate, the solution was filtered and concentrated. The crude was purified by ISCO (SiO$_2$: 0 to 50% EtOAc/hexanes) to provide the product as a colorless oil (0.73 g, 16%).

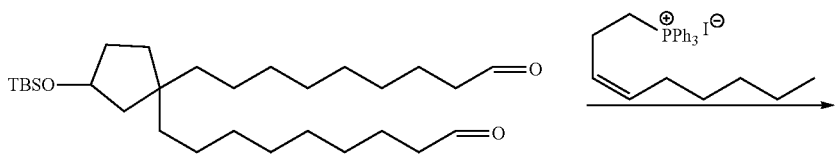

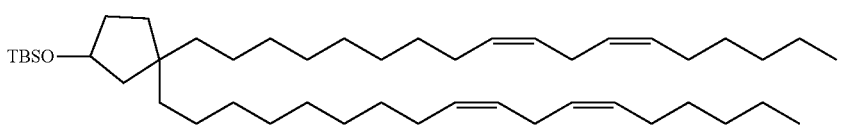

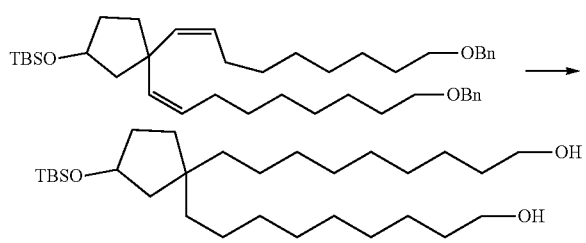

A mixture of ((3,3-bis((Z)-9-(benzyloxy)non-1-en-1-yl)cyclopentyl)oxy)(tert-butyl)dimethylsilane (3.04 g, 4.6 mmol) and palladium on carbon (10%, 600 mg) in 200 mL EtOAc was purged with nitrogen then hydrogen, and then stirred under hydrogen overnight. TLC and MS showed complete reaction. The reaction mixture was filtered through At 0° C., potassium tert-butoxide (363 mg, 3.23 mmol) was added into a solution of (Z)-non-3-en-1-yltriphenylphosphonium iodide (1.66 g, 3.23 mmol) in 30 mL THF which was purged with nitrogen 3 times. After 1 h, a solution of 9,9'-(3-((tert-butyldimethylsilyl)oxy)cyclopentane-1,1-diyl)dinonanal (0.52 g, 1.08 mmol) in 10 mL THF (purged with nitrogen 3 times) was transferred via cannula into the reaction mixture, and then the reaction was allowed to warm up to room temperature overnight. TLC showed complete reaction. The reaction was quenched with saturated ammonium chloride, and then extracted with ether (2×). The combined organic layers were washed with brine and dried over sodium sulfate. After filtration and concentration, the residue was purified by ISCO (SiO$_2$: 0 to 5% EtOAc/hexanes) to provide the product as a colorless oil (170 mg, 22%).

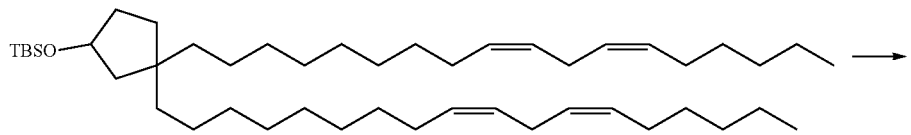

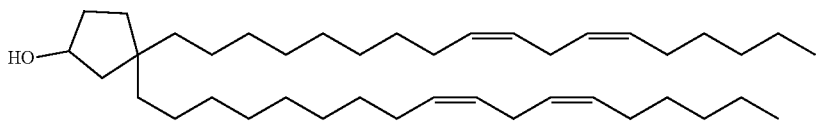

To a solution of tert-butyl((3,3-di((9Z,12Z)-octadeca-9,12-dien-1-yl)cyclopentyl)oxy)dimethylsilane (170 mg, 0.24 mmol) in 20 mL THF, a solution of TBAF (1.0 M in THF, 2.4 mL, 2.4 mmol) was added and the reaction mixture was stirred at room temperature for 2 h. TLC showed complete reaction. The solvent was removed under vacuum and the residue was purified by ISCO (SiO$_2$: 0 to 20% EtOAc/hexanes) to provide the product as a colorless oil (80 mg, 57%).

(Compound 21-3)

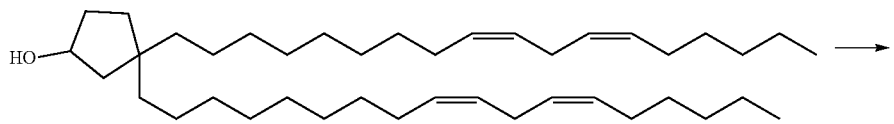

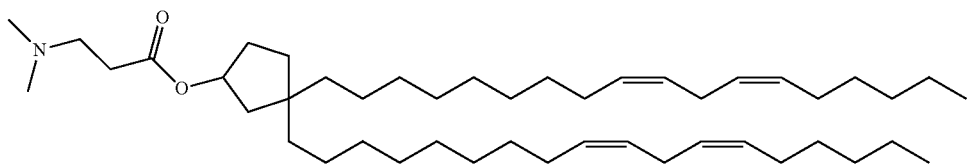

Chemical Formula: C$_{46}$H$_{83}$NO$_2$
Molecular Weight: 682.18

At 0° C., pyridine (0.1 mL) and propylphosphonic anhydride solution (50 wt % in EtOAc, 0.51 mmol) were added into a solution of 3-(dimethylamino)propanoic acid hydrochloride (63 mg, 0.41 mmol) in 3 mL DMF. After stirring for 10 min, a solution of 3,3-di((9Z,12Z)-octadeca-9,12-dien-1-yl)cyclopentan-1-ol (80 mg, 0.14 mmol) in 2 mL DMF was added and the reaction mixture was stirred at room temperature overnight. MS and TLC showed the formation of product. Saturated sodium bicarbonate solution was added to quench the reaction, and then extracted by EtOAc (2×). The combined organic layer was washed with water and brine. After drying over sodium sulfate and concentration, the residue was purified by ISCO (SiO$_2$: 0 to 100% EtOAc/hexanes) to provide the product 3,3-Di((9Z,12Z)-octadeca-9,12-dien-1-yl)cyclopentyl 3-(dimethylamino)propanoate as a colorless oil (59 mg, 62%).

$^1$H NMR (300 MHz, CDCl$_3$) δ 5.28-5.42 (m, 8H), 5.12-5.17 (m, 1H), 2.76 (t, 4H, J=6.0 Hz), 2.59 (t, 2H, J=6.9 Hz), 2.42 (t, 2H, J=6.9 Hz), 2.23 (s, 6H), 2.04 (q, 8H, J=6.9 Hz), 1.75-2.00 (m, 2H), 1.38-1.72 (m, 5H), 1.14-1.39 (m, 39H), 0.88 (t, 6H, J=6.9 Hz).
APCI: m/z=682.6 [M+H]$^+$

DT. Compound 21-4: 3,3-Di((9Z,12Z)-octadeca-9,12-dien-1-yl)cyclopentyl 4-(dimethylamino)butanoate (Compound 21-4)

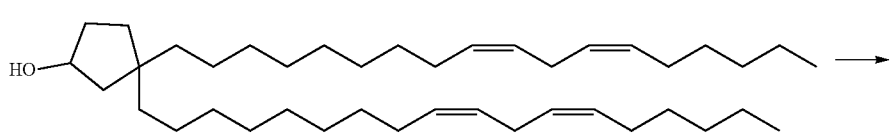

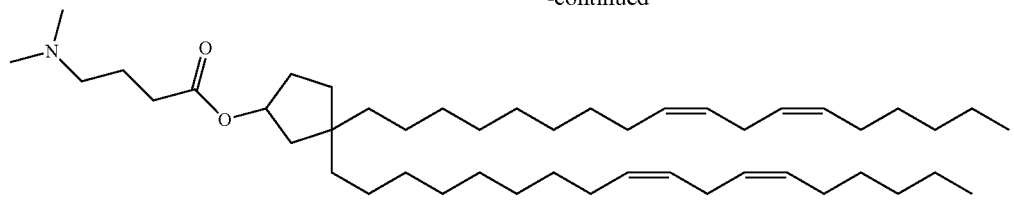

Chemical Formula: C$_{47}$H$_{85}$NO$_2$
Molecular Weight: 696.20

At 0° C., pyridine (0.6 mL) and propylphosphonic anhydride solution (50 wt % in DMF, 2.4 mL, 4.16 mmol) were added into a solution of 4-(dimethylamino)butanoic acid hydrochloride (565 mg, 3.37 mmol) in 3 mL DMF. After stirring for 10 min, a solution of 3,3-di((9Z,12Z)-octadeca-9,12-dien-1-yl)cyclopentan-1-ol (0.65 g, 1.115 mmol) in 1 mL DMF was added and the reaction mixture was stirred at room temperature overnight. MS and TLC showed the formation of product. Saturated sodium bicarbonate solution was added to quench the reaction, and then extracted with EtOAc (2×). The combined organic layer was washed with water and brine. After dried over sodium sulfate and concentration, the residue was purified by ISCO (SiO$_2$: 0 to 100% EtOAc/hexanes) to provide the product 3,3-Di((9Z,12Z)-octadeca-9,12-dien-1-yl)cyclopentyl 4-(dimethylamino)butanoate as colorless oil (556 mg, 72%).

$^1$H NMR (300 MHz, CDCl$_3$) δ 5.28-5.42 (m, 8H), 5.06-5.15 (m, 1H), 2.76 (t, 4H, J=6.0 Hz), 2.29 (t, 4H, J=7.4 Hz), 2.23 (s, 6H), 2.04 (q, 8H, J=6.6 Hz), 1.14-1.99 (m, 48H), 0.88 (t, 6H, J=6.9 Hz).

APCI: m/z=696.6 [M+H]$^+$.

DU. Compound 21-5: 3,3-Di((10Z,13Z)-nonadeca-10,13-dien-1-yl)cyclopentyl 3-(dimethylamino)propanoate

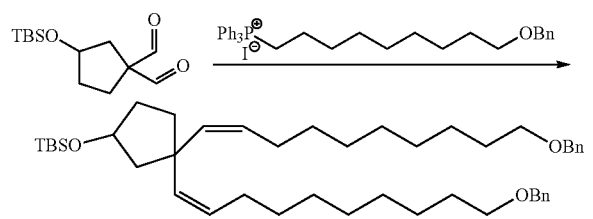

At 0° C., potassium tert-butoxide (10.03 g, 89.4 mmol) was added into a solution of (9-(benzyloxy)nonyl)triphenylphosphonium iodide (43.0 g, 69.0 mmol) in 160 mL THF which was purged with nitrogen 3 times. After 1 h, a solution of 3-((tert-butyldimethylsilyl)oxy)cyclopentane-1,1-dicarbaldehyde (7.70 g, 29.8 mmol) in 60 mL THF (purged with nitrogen 3 times) was transferred via cannula into the reaction mixture, and then the reaction was allowed to warm up to room temperature overnight. TLC showed complete reaction. The reaction was quenched with saturated ammonium chloride, and then extracted with ether (2×). The combined organic layer was washed with brine and dried over sodium sulfate. After filtration and concentration, the residue was purified by flash column chromatography (SiO$_2$: 0 to 6% ether/hexanes) to provide the product as a colorless oil (6.52 g, 32%).

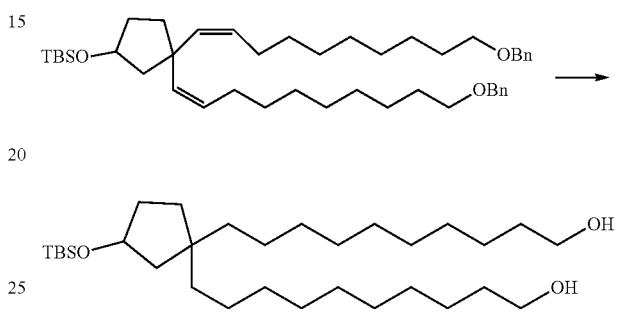

A mixture of ((3,3-bis((Z)-10-(benzyloxy)dec-1-en-1-yl)cyclopentyl)oxy)(tert-butyl)dimethylsilane (6.52 g, 9.86 mmol) and palladium on carbon (10%, 1.30 g) in 400 mL EtOAc was purged with nitrogen then hydrogen, and then stirred under hydrogen overnight. TLC and MS showed complete reaction. The reaction mixture was filtered through Celite and washed with EtOAc. The filtrate was concentrated, and the residue was purified by flash column chromatography (SiO$_2$: 0 to 80% EtOAc/hexanes) to give the product as a semi-solid (4.60 g, 96%).

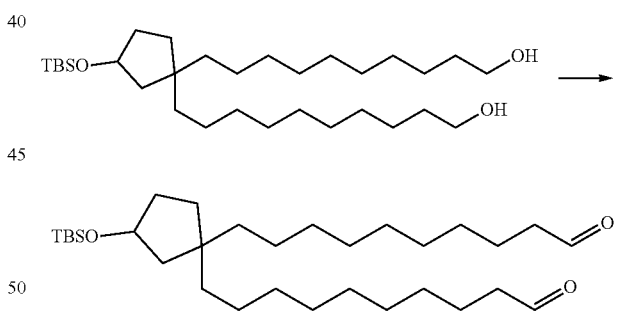

At 0° C., a solution of 10,10'-(3-((tert-butyldimethylsilyl)oxy)cyclopentane-1,1-diyl)bis(decan-1-ol) (4.60 g, 9.49 mmol) in 100 mL dichloromethane was slowly added into a solution of Dess-Martin periodinane (11.276 g, 26.6 mmol) in 50 mL dichloromethane, and then the reaction mixture was stirred at this temperature for 2 h. The reaction mixture was diluted with dichloromethane, and then 10% Na$_2$S2O3 solution and saturated sodium bicarbonate solution were added. After extracted with dichloromethane (2×), the combined organic layer was washed with saturated sodium bicarbonate and brine. The organic layer was dried over sodium sulfate and concentrated. The crude was purified by ISCO (SiO$_2$: 0 to 80% EtOAc/hexanes) to provide the product as a colorless oil (1.20 g, 26%).

Preparation of
(9-(benzyloxy)nonyl)triphenylphosphonium Iodide

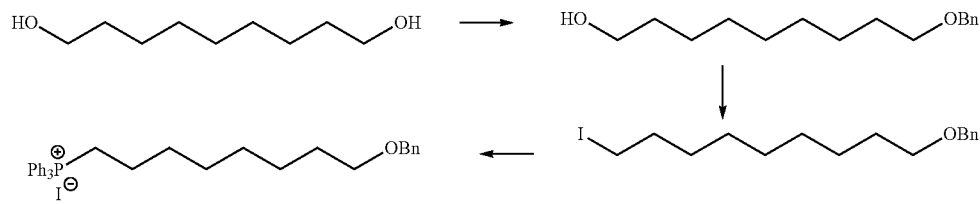

At 0° C., a solution of nonane-1,9-diol (96.16 g, 0.60 mol) in 100 mL DMF was slowly added into a suspension of NaH (24.0 g, 0.60 mol) in 800 mL DMF. After stirring for 1 h, a solution of benzyl bromide (71.4 mL, 0.60 mole) in 200 mL DMF was slowly added. After addition, the reaction mixture was warmed up to room temperature and stirred overnight. TLC showed was almost consumed. The reaction mixture was poured onto ice, and then extracted with EtOAc (3×). The combined organic layer was washed with water and brine, and then dried over sodium sulfate. After filtration and concentration, the crude was purified by flash column chromatography (SiO$_2$: 0 to 100% EtOAc/hexanes then 0 to 5% MeOH/dichloromethane) to provide the product as a colorless oil (74.4 g, 50%).

At 0° C., a solution of triphenylphosphine (30.65 g, 0.117 mole) in 100 mL dichloromethane was slowly added into a solution of 9-(benzyloxy)nonan-1-ol (23.0 g, 0.097 mole), imidazole (13.93 g, 0.204 mole) and iodine (34.60 g, 0.136 mole) in 200 mL dichloromethane, and then the reaction mixture was allowed to room temperature overnight. After filtration, the filtrate was concentrated and the residue was triturated with hexanes. The solution was filtered through a plug of silica gel and eluted with 10% ether in hexanes to provide the product as a cloudy liquid (32.2 g, 95%).

A solution of (((9-iodononyl)oxy)methyl)benzene (32.2 g, 0.093 mole) and triphenylphosphine (48.93 g, 0.186 mole) in acetonitrile (500 mL) was refluxed overnight. After concentrated to dryness, the residue was dissolved in dichloromethane and purified by flash column chromatography (SiO$_2$: 0 to 10% MeOH/CH$_2$Cl$_2$) to provide the product as a yellow oil (44.4 g, 78%).

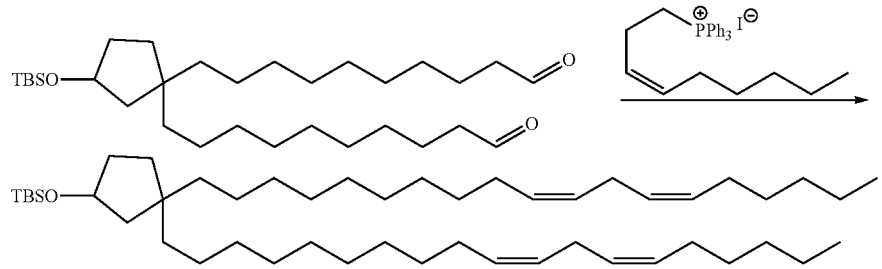

At 0° C., potassium tert-butoxide (587 mg, 5.23 mmol) was added into a solution of (Z)-non-3-en-1-yltriphenylphosphonium iodide (3.69 g, 7.17 mmol) in 70 mL THF which was purged with nitrogen 3 times. After 1 h, a solution of 10,10'-(3-(((tert-butyldimethylsilyl)oxy)cyclopentane-1,1-diyl)bis(decanal) 9' (838 mg, 1.65 mmol) in 30 mL THF (purged with nitrogen 3 times) was transferred via cannula into the reaction mixture, and then the reaction was allowed to warm up to room temperature overnight. TLC showed complete reaction. The reaction was quenched with saturated ammonium chloride, and then extracted with ether (2×). The combined organic layer was washed with brine and dried over sodium sulfate. After filtration and concentration, the residue was purified by ISCO (SiO$_2$: 0 to 5% EtOAc/hexanes) to provide the product as a colorless oil (926 mg, 77%).

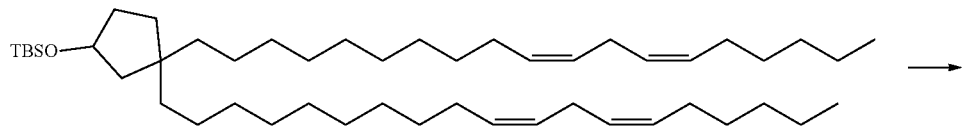

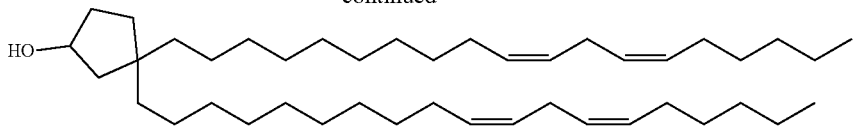

To a solution of tert-butyl((3,3-di((10Z,13Z)-nonadeca-10,13-dien-1-yl)cyclopentyl)oxy)dimethylsilane (926 mg, 1.27 mmol) in 100 mL THF, a solution of TBAF (1.0 M in THF, 13.3 mL, 13.3 mmol) was added and the reaction mixture was stirred at room temperature for 2 h. TLC showed complete reaction. The solvent was removed under vacuum and the residue was purified by ISCO ($SiO_2$: 0 to 20% EtOAc/hexanes) to provide the product as a colorless oil (830 mg, Quant.).

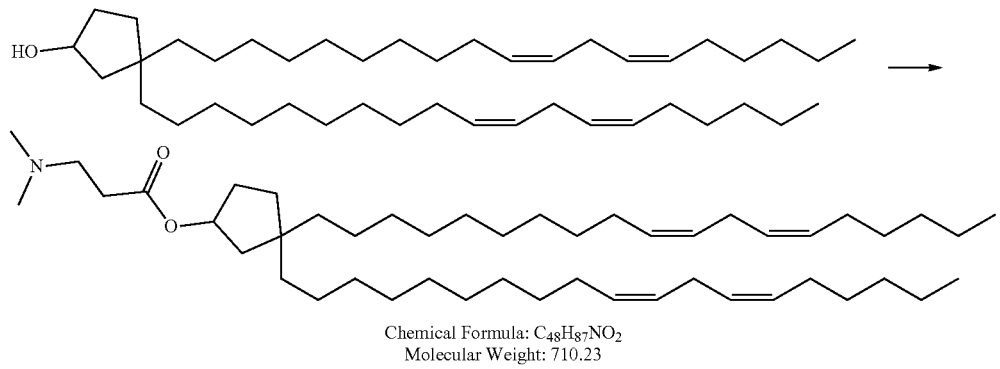

Chemical Formula: $C_{48}H_{87}NO_2$
Molecular Weight: 710.23

At 0° C., pyridine (0.35 mL) and propylphosphonic anhydride solution (50 wt % in EtOAc, 0.7 mL, 1.21 mmol) were added into a solution of 3-(dimethylamino)propanoic acid hydrochloride (151 mg, 0.98 mmol) in 6 mL DMF. After stirring for 10 min, a solution of 3,3-di((10Z,13Z)-nonadeca-10,13-dien-1-yl)cyclopentan-1-ol (200 mg, 0.33 mmol) in 4 mL DMF was added and the reaction mixture was stirred at room temperature overnight. MS and TLC showed the formation of product. Saturated sodium bicarbonate solution was added to quench the reaction, and then extracted with EtOAc (2×). The combined organic layers were washed with water and brine. After drying over sodium sulfate and concentration, the residue was purified by ISCO ($SiO_2$: 0 to 100% EtOAc/hexanes) to provide the product 3,3-Di((10Z,13Z)-nonadeca-10,13-dien-1-yl)cyclopentyl 3-(dimethylamino)propanoate as a colorless oil (135 mg, 58%).

$^1$H NMR (300 MHz, $CDCl_3$) δ 5.28-5.42 (m, 8H), 5.10-5.17 (m, 1H), 2.76 (t, 4H, J=6.1 Hz), 2.59 (t, 2H, J=6.9 Hz), 2.42 (t, 2H, J=6.9 Hz), 2.23 (s, 6H), 2.04 (q, 8H, J=6.9 Hz), 1.75-2.00 (m, 2H), 1.38-1.72 (m, 5H), 1.14-1.39 (m, 43H), 0.88 (t, 6H, J=6.9 Hz).

APCI: m/z=710.7 $[M+H]^+$.

DV. Compound 21-6: 1-(2,3-Di((8Z,11Z)-heptadeca-8,11-dien-1-yl)cyclopropyl)-N,N-dimethylmethanamine

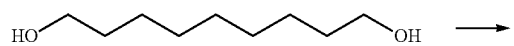

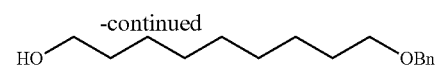

At 0° C., a solution of nonane-1,9-diol (96.16 g, 0.60 mol) in 100 mL DMF was slowly added into a suspension of NaH (24.0 g, 0.60 mol) in 800 mL DMF. After stirring for 1 h, a solution of benzyl bromide (71.4 mL, 0.60 mole) in 200 mL DMF was slowly added. After addition, the reaction mixture (Compound 21-5)

was warmed up to room temperature and stirred overnight. TLC showed starting material was almost consumed. The reaction mixture was poured onto ice, and then extracted with EtOAc (3×). The combined organic layers were washed with water and brine, and then dried over sodium sulfate. After filtration and concentration, the crude was purified with flash column chromatography ($SiO_2$: 0 to 100% EtOAc/hexanes then 0 to 5% MeOH/dichloromethane) to provide the product as a colorless oil (74.4 g, 50%).

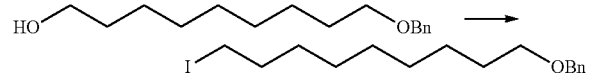

At 0° C., a solution of triphenylphosphine (6.29 g, 24 mmol) in 100 mL dichloromethane was slowly added into a solution of 9-(benzyloxy)nonan-1-ol (5.0 g, 20 mmol), imidazole (2.9 g, 42 mmol) and iodine (8.5 g, 33.6 mmol) in 100 mL dichloromethane, and then the reaction mixture was allowed to room temperature overnight. After concentration, the residue was triturated with hexanes to provide the product as a cloudy liquid (5.38 g, 75%).

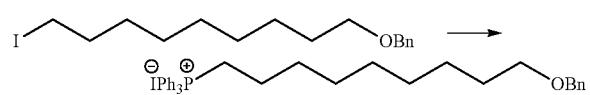

A solution of (((9-iodononyl)oxy)methyl)benzene (5.38 g, 14.9 mmol) and triphenylphosphine (7.8 g, 29.8 mmol) in acetonitrile (100 mL) was refluxed overnight. After concentrated to dryness, the residue was dissolved in dichloromethane and purified with flash column chromatography (SiO₂: 0 to 10% MeOH/CH₂Cl₂) to provide the product as a yellow oil (8.5 g, 92%).

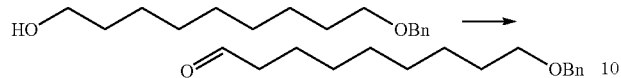

At 0° C., a solution of 9-(benzyloxy)nonan-1-ol (5.0 g, 20 mmol) in 50 mL dichloromethane was slowly added into a suspension of Dess-Martin periodinane (12.5 g, 29.5 mmol) in 100 mL dichloromethane, and then the reaction mixture was stirred at room temperature overnight. After quenching with saturated sodium bicarbonate, the mixture was extracted with dichloromethane (2×). The combined organic layer was dried over sodium sulfate and concentrated to give the product as a colorless oil (4.0 g, 80%).

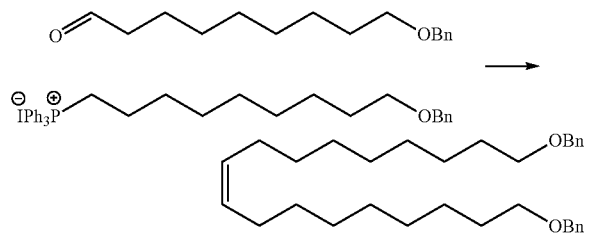

At 0° C., potassium tert-butoxide (1.54 g, 13.7 mmol) was added into a suspension of (9-(benzyloxy)nonyl)triphenylphosphonium iodide (8.5 g, 13.6 mmol) in 150 mL THF. After 1 h, a solution of 9-(benzyloxy)nonanal (3.0 g, 12 mmol) in 50 mL THF was added dropwise into the reaction mixture, and then the reaction was allowed to warm up to room temperature for 4 h. TLC showed completed reaction. The reaction was quenched with saturated ammonium chloride, and then extracted with hexanes (2×). The combined organic layers were dried over sodium sulfate. After filtration and concentration, the residue was purified with flash column chromatography (SiO₂: 0 to 100% dichloromethane/hexanes) to provide the product as colorless oil (3.5 g, 63%).

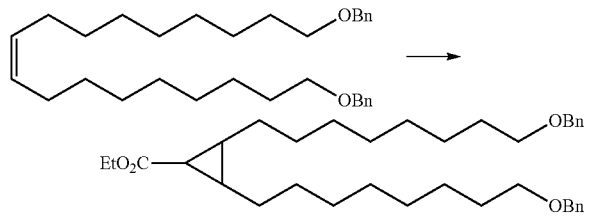

To a refluxing solution of (Z)-1,18-bis(benzyloxy)octadec-9-ene (3.5 g, 7.5 mmol) in 200 mL dichloromethane, a solution of Cu(acac)₂ (200 mg, 0.76 mmol) in 40 mL dichloromethane was added. And then ethyl diazoacetate (contains 13% dichloromethane, 9×1.3 mL) was added every 30 min. MS showed the formation of product. The reaction was quenched with MeOH and stirred for 1 h at room temperature. After concentration, the crude was purified by flash column chromatography (SiO2: 0 to 10% EtOAc/hexanes) to provide the product as colorless oil (2.23 g, 82% pure mixed with acetate by-product).

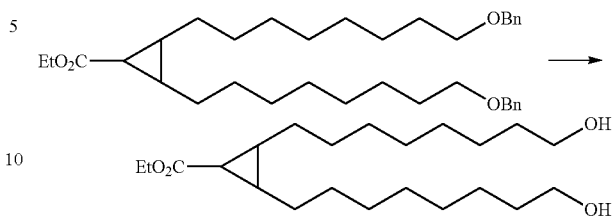

A mixture of ethyl 2,3-bis(8-(benzyloxy)octyl)cyclopropane-1-carboxylate (2.23 g, 4.05 mmol) and Palladium on carbon (10 wt %, 200 mg) in 200 mL EtOAc was stirred at room temperature under hydrogen balloon for 4.5 h. MS and TLC showed completed reaction. The reaction mixture was filtered through Celite and washed with EtOAc. The filtrate was concentrated to provide the product mixed with by-product, diethyl succinate (1.62 g, contains 0.55 equivalent of by-product, 84%).

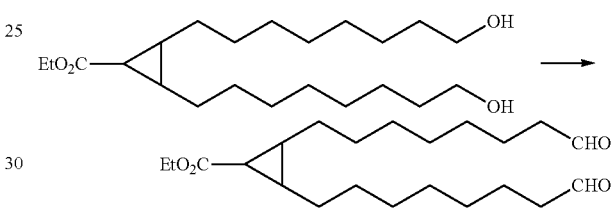

At 0° C., a solution of ethyl 2,3-bis(8-hydroxyoctyl)cyclopropane-1-carboxylate (1.43 g, 4.03 mmol) in 100 mL dichloromethane was slowly added into a suspension of Dess-Martin periodinane (3.63 g, 8.5 mmol) in 150 mL dichloromethane, and then the reaction mixture was stirred at room temperature for 2 h. After quenching with saturated sodium bicarbonate, the mixture was extracted with dichloromethane (2×). The combined organic layer was dried over sodium sulfate and concentrated to give the product as colorless oil (1.2 g, 81%).

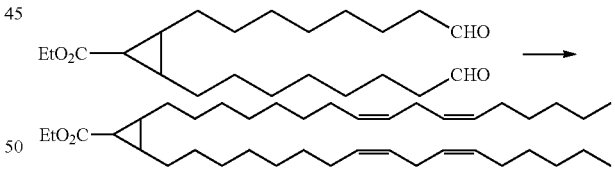

At 0° C., potassium tert-butoxide (1.7 g, 15.1 mmol) was added into a solution of (Z)-non-3-en-1-yltriphenylphosphonium iodide (5.8 g, 15.1 mmol) in 150 mL THF which was purged with nitrogen 3 times. After 1 h, a solution of ethyl 2,3-bis(8-oxooctyl)cyclopropane-1-carboxylate (1.2 g, 3.28 mmol) in 50 mL THF (purged with nitrogen 3 times) was transferred via cannula into the reaction mixture, and then the reaction was allowed to warm up to room temperature overnight. TLC showed completed reaction. The reaction was quenched with saturated ammonium chloride, and then extracted with hexanes (2×). The combined organic layers were washed with brine and dried over sodium sulfate. After filtration and concentration, the residue was purified by ISCO (SiO₂: 0 to 3% EtOAc/hexanes) to provide the product as colorless oil (1.3 g, 68%).

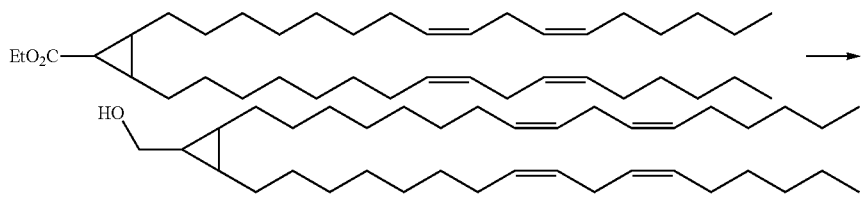

A solution of lithium aluminum hydride (2.0 M in THF, 1.7 mL, 3.35 mmol) was slowly added into a solution of ethyl 2,3-di((8Z,11Z)-heptadeca-8,11-dien-1-yl)cyclopropane-1-carboxylate (1.3 g, 2.23 mmol) in 150 mL THF, and then the reaction mixture was stirred at room temperature for 30 min. TLC showed completed reaction. The reaction was quenched by slow addition of $Na_2SO_4 \cdot 10H_2O$, then the mixture was filtered and washed with THF. The filtrate was concentrated and purified by flash column chromatography ($SiO_2$: 0 to 10% EtOAc/Hexanes) to give the product as colorless oil (1.1 g, 91%).

quently, and the reaction mixture was stirred at room temperature overnight. MS showed completed reaction, and saturated sodium bicarbonate was added to quench the reaction. The mixture was extracted with EtOAc (2×), and the combined organic layers were washed with brine and dried over sodium sulfate. After filtration and concentration, the residue was purified by flash column chromatography ($SiO_2$: 0 to 10% MeOH/dichloromethane) to give the product 1-(2,3-di((8Z,11Z)-heptadeca-8,11-dien-1-yl)cyclopropyl)-N,N-dimethylmethanamine as a colorless oil (620 mg, 65%).

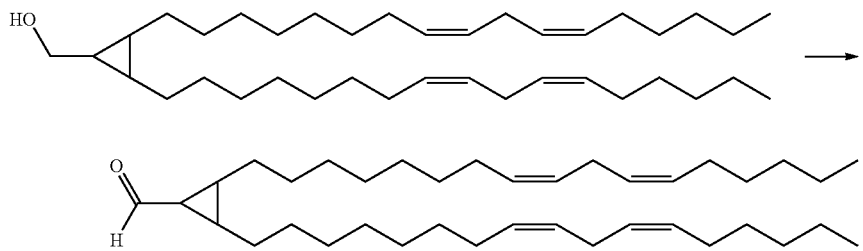

At 0° C., a solution of (2,3-di((8Z,11Z)-heptadeca-8,11-dien-1-yl)cyclopropyl)methanol (1.1 g, 2.03 mmol) in 50 mL dichloromethane was slowly added into a suspension of Dess-Martin periodinane (1.30 g, 3.05 mmol) in 150 mL dichloromethane, and then the reaction mixture was stirred at room temperature for 2 h. After quenching with saturated sodium bicarbonate, the mixture was extracted with dichloromethane (2×). The combined organic layers were dried over sodium sulfate and concentrated to give the product as a colorless oil (0.87 g, 79%).

$^1$H NMR (300 MHz, $CDCl_3$) δ 5.27-5.42 (m, 8H), 2.76 (t, 4H, J=6.0 Hz), 2.38 (bs, 8H), 2.04 (q, 8H, J=6.6 Hz), 1.18-1.59 (m, 36H), 0.88 (t, 6H, J=6.6 Hz), 0.52-0.58 (m, 2H), 0.28-0.38 (m, 1H).

APCI: m/z=568.6 [M+H]$^+$.

Example 2: Production of Nanoparticle Compositions

Production of Nanoparticle Compositions

In order to investigate safe and efficacious nanoparticle compositions for use in the delivery of therapeutic and/or prophylactic agents to cells, a range of formulations are prepared and tested. Specifically, the particular elements and ratios thereof in the lipid component of nanoparticle compositions are optimized.

(Compound 21-6)

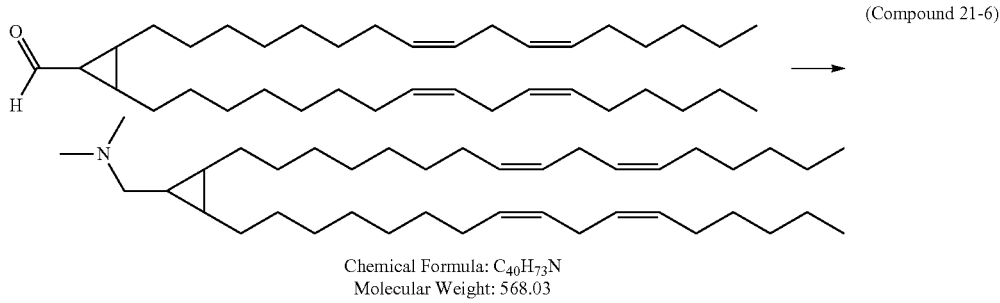

Chemical Formula: $C_{40}H_{73}N$
Molecular Weight: 568.03

To a solution of 2,3-di((8Z,11Z)-heptadeca-8,11-dien-1-yl)cyclopropane-1-carbaldehyde (0.87 g, 1.61 mmol) in 200 mL THF, dimethylamine (2.0 M in THF, 1.61 mL, 3.22 mmol), sodium triacetoxyborohydride (682 mg, 3.22 mmol) and acetic acid (0.19 mL, 3.22 mmol) were added subse- Nanoparticles can be made with mixing processes such as microfluidics and T-junction mixing of two fluid streams, one of which contains the therapeutic and/or prophylactic agent and the other has the lipid components.

Lipid compositions are prepared by combining a lipid according to one of formulae (I), (Ia1)-(Ia6), (Ib), (II), (IIa), (III), (IIIa), (IV), (17-I), (19-I), (19-II), (20-I) and (21-I), a phospholipid (such as DOPE or DSPC, obtainable from Avanti Polar Lipids, Alabaster, Ala.), a PEG lipid (such as 1,2-dimyristoyl-sn-glycerol methoxypolyethylene glycol, also known as PEG-DMG, obtainable from Avanti Polar Lipids, Alabaster, Ala.), and a structural lipid (such as cholesterol, obtainable from Sigma-Aldrich, Taufkirchen, Germany) at concentrations of about 50 mM in ethanol. Solutions should be refrigeration for storage at, for example, −20° C. Lipids are combined to yield desired molar ratios (see, for example, Table 1) and diluted with water and ethanol to a final lipid concentration of between about 5.5 mM and about 25 mM.

Nanoparticle compositions including a therapeutic and/or prophylactic agent and a lipid component are prepared by combining the lipid solution with a solution including the therapeutic and/or prophylactic agent at lipid component to therapeutic and/or prophylactic agent wt:wt ratios between about 5:1 and about 50:1. The lipid solution is rapidly injected using a NanoAssemblr microfluidic based system at flow rates between about 10 ml/min and about 18 ml/min into the therapeutic and/or prophylactic agent solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, Ill.) with a molecular weight cutoff of 10 kD. The first dialysis is carried out at room temperature for 3 hours. The formulations are then dialyzed overnight at 4° C. The resulting nanoparticle suspension is filtered through 0.2 m sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, may be used to achieve the same nano-precipitation.

Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a therapeutic and/or prophylactic agent (e.g., RNA) in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of therapeutic and/or prophylactic agent in the nanoparticle composition can be calculated based on the extinction coefficient of the therapeutic and/or prophylactic agent used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, Calif.) can be used to evaluate the encapsulation of an RNA by the nanoparticle composition. The samples are diluted to a concentration of approximately 5 µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2% Triton X-100 solution is added to the wells. The plate is incubated at a temperature of 37° C. for 15 minutes. The RIBOGREEN® reagent is diluted 1:100 in TE buffer, and 100 µL of this solution is added to each well. The fluorescence intensity can be measured using a fluorescence plate reader (Wallac Victor 1420 Multilablel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

In Vivo Formulation Studies

In order to monitor how effectively various nanoparticle compositions deliver therapeutic and/or prophylactic agents to targeted cells, different nanoparticle compositions including a particular therapeutic and/or prophylactic agent (for example, a modified or naturally occurring RNA such as an mRNA) are prepared and administered to rodent populations. Mice are intravenously, intramuscularly, intraarterially, or intratumorally administered a single dose including a nanoparticle composition with a formulation such as those provided in Table 1. In some instances, mice may be made to inhale doses. Dose sizes may range from 0.001 mg/kg to 10 mg/kg, where 10 mg/kg describes a dose including 10 mg of a therapeutic and/or prophylactic agent in a nanoparticle composition for each 1 kg of body mass of the mouse. A control composition including PBS may also be employed.

Upon administration of nanoparticle compositions to mice, dose delivery profiles, dose responses, and toxicity of particular formulations and doses thereof can be measured by enzyme-linked immunosorbent assays (ELISA), bioluminescent imaging, or other methods. For nanoparticle compositions including mRNA, time courses of protein expression can also be evaluated. Samples collected from the rodents for evaluation may include blood, sera, and tissue (for example, muscle tissue from the site of an intramuscular injection and internal tissue); sample collection may involve sacrifice of the animals.

Nanoparticle compositions including mRNA are useful in the evaluation of the efficacy and usefulness of various formulations for the delivery of therapeutic and/or prophylactic agents. Higher levels of protein expression induced by administration of a composition including an mRNA will be indicative of higher mRNA translation and/or nanoparticle composition mRNA delivery efficiencies. As the non-RNA components are not thought to affect translational machineries themselves, a higher level of protein expression is likely indicative of a higher efficiency of delivery of the therapeutic and/or prophylactic agent by a given nanoparticle composition relative to other nanoparticle compositions or the absence thereof.

Example 3: Sample Formulations

Nanoparticle compositions including a therapeutic and/or prophylactic agent can be optimized according to the selection of a compound according to one of formulae (I), (Ia1)-(Ia6), (Ib), (II), (IIa), (III), (IIIa), (IV), (17-I), (19-I), (19-II), (20-I) and (21-I), the selection of additional lipids, the amount of each lipid in the lipid component, and the wt:wt ratio of the lipid component to the therapeutic and/or prophylactic agent, as described herein.

Initial studies were performed to compare the delivery efficiency of nanoparticle compositions including various compounds according to one of formulae (I), (Ia1)-(Ia6), (Ib), (II), (IIa), (III), (IIIa), (IV), (17-I), (19-I), (19-II), (20-I) and (21-I). The cationic lipid MC3 is a current standard in the art. Accordingly, the standard MC3 formulation including about 50 mol % MC3, about 10 mol % DSPC, about 38.5 mol % cholesterol, and about 1.5 mol % PEG-DMG was used as a basis for this study. Nanoparticle compositions including DOPE or DSPC as a phospholipid, cholesterol as a structural lipid, PEG-DMG as a PEG lipid, an RNA, and a compound according to one of formulae disclosed herein, e.g., selected from compounds of formulae (I), (Ia1)-(Ia6), (Ib), (II), (IIa), (III), (IIIa), (IV), (17-I), (19-I), (19-II), (20-I) and (21-I), were prepared according to Examples 1 and 2. The ratios of the lipids were 40:20:38.5:1.5 mol % for the lipid described herein:DOPE:cholesterol:PEG-DMG or 50:10:38.5:1.5 mol % for the lipid described herein:DSPC:cholesterol:PEG-DMG. The RNA used was an mRNA encoding G5 luciferase (Luc) or G5 hEPO. Tables 1, 1b, 17-1, 19-1, 20-1 and 21-1 summarize the content and characteristics of the formulations.

As shown in Tables 1 and 1a, nanoparticle compositions including Compound 1 produced the largest particles amongst those of Tables 1 and 1a, while those including Compounds 34 and 50 produced the smallest particles amongst those of Tables 1 and 1da. Encapsulation efficiencies amongst those of Tables 1 and 1a were highest for compositions including Compounds 36, 37, 40, and 41 and lowest for those including Compounds 1 and 24.

TABLE 1

Characteristics of nanoparticle compositions including compounds of one of formulae (I), (Ia1)-(Ia6), (Ib), (II), (IIa), (III) and (IIIa).

| Compound No. | Size (nm) | PDI | EE (%) | pKa |
| --- | --- | --- | --- | --- |
| 1 | 203.2 | | 46.2 | 5.95 |
| 2* | 94.7 | 0.108 | 96 | 6.39 |
| 3 | 73.5 | 0.044 | 92.5 | n.d. |
| 4 | 89.7 | 0.120 | 96.78 | 7.12 |
| 5 | 85.1 | 0.140 | 98.1 | 7.01 |
| 6 | 81.4 | 0.160 | 98.9 | 6.62 |
| 7 | 85.1 | 0.130 | 99.1 | 6.94 |
| 8 | 83.3 | 0.110 | 98.5 | 6.87 |
| 9 | 78.0 | 0.170 | 99.5 | 6.76 |
| 10 | 81.3 | 0.130 | 99.2 | 6.58 |
| 11 | 87.4 | 0.099 | 99.5 | 6.54 |
| 12 | 87.8 | 0.096 | 96.9 | 5.44 |
| 13 | 97.7 | 0.080 | 64.2 | 6.30 |
| 14 | 88.7 | 0.008 | 96.6 | 6.31 |
| 15[#] | 100.3 | 0.120 | 90.2 | 6.32 |
| 16[#] | 77.4 | 0.140 | 98.2 | 6.28 |
| 17 | 82.3 | 0.180 | 96.6 | 6.67 |
| 18 | 76.7 | 0.120 | 98.4 | 6.17 |
| 19 | 76.1 | 0.100 | 97.2 | 6.29 |
| 20 | 106.4 | 0.150 | 84.2 | 6.12 |
| 21 | 98.3 | 0.239 | 98.6 | 6.29 |
| 22[#] | 75.4 | 0.130 | 98.3 | 6.15 |
| 23 | 85.4 | 0.058 | 82.9 | 6.07 |
| 24* | 110.4 | 0.131 | 36.4 | 6.01 |

TABLE 1-continued

Characteristics of nanoparticle compositions including compounds of one of formulae (I), (Ia1)-(Ia6), (Ib), (II), (IIa), (III) and (IIIa).

| Compound No. | Size (nm) | PDI | EE (%) | pKa |
| --- | --- | --- | --- | --- |
| 25 | 90.0 | 0.186 | 97.0 | 6.20 |
| 26* | 74.2 | 0.112 | 84.9 | 6.19 |
| 27 | 86.4 | 0.211 | 97.9 | 6.14 |
| 28 | 87.4 | 0.099 | 80.2 | 6.04 |
| 29 | 105.3 | 0.060 | 48.8 | 5.97 |
| 30 | 95.0 | 0.110 | 74.3 | 6.09 |
| 31 | 87.9 | 0.130 | 77.5 | 6.31 |
| 32 | 79.3 | 0.160 | 83.6 | 6.28 |
| 33 | 79.7 | 0.138 | 98.1 | 6.06 |
| 34* | 66.0 | 0.077 | 98.1 | 5.74 |
| 36* | 100.8 | 0.110 | 100.2 | 7.81 |
| 37* | 86.6 | 0.107 | 99.9 | 6.45 |
| 40* | 78.9 | 0.210 | 100.0 | 6.78 |
| 41* | 69.0 | 0.239 | 99.9 | 7.02 |
| 42 | 116.4 | 0.190 | 97.1 | 6.77 |
| 43 | 99.0 | 0.220 | 99.1 | 6.72 |
| 44 | 94.9 | 0.190 | 89.5 | 6.82 |
| 45 | 100.2 | 0.200 | 94.9 | 6.77 |
| 46 | 81.8 | 0.160 | 97.5 | 6.77 |
| 47 | 89.8 | 0.180 | 53.1 | 6.82 |
| 48 | 111.4 | 0.099 | 79.3 | 6.99 |
| 49 | 95.8 | 0.200 | 98.8 | 6.4 |
| 50 | 65.6 | 0.190 | 98.7 | 5.55 |
| 51 | 76.6 | 0.190 | 98.4 | 6.44 |
| 52 | 94.4 | 0.100 | 97.5 | 6.77 |
| Formula IV | 94.2 | | 97.6 | 6.25 |
| MC3 | 86.2 | 0.117 | 97.70 | n.d. | n.d. = not determined
*= Formulated with lipid:DSPC:Chol:PEG-DMG 50:10:38.5:1.5
[#]= Formulated with hEPO mRNA

TABLE 1b

Characteristics of nanoparticle compositions including compounds of one of formulae (I), (Ia1)-(Ia6), (Ib), (II), (IIa), (III) and (IIIa).

| Compound No. | Size (nm) | PDI | EE (%) |
| --- | --- | --- | --- |
| 53 | 103.0 | 0.23 | 82.8 |
| 54 | 93.0 | 0.23 | 96.9 |
| 55 | 119.5 | 0.23 | 95.2 |
| 56 | 117.4 | 0.24 | 99.0 |
| 57 | 101.9 | 0.23 | 98.8 |
| 58 | 112.8 | 0.23 | 98.9 |
| 59 | 104.7 | 0.23 | 98.6 |
| 60 | 105.7 | 0.23 | 98.8 |
| 61 | 86.8 | 0.23 | 99.1 |
| 62 | 61.7 | 0.18 | 97.73 |
| 69 | 74.4 | 0.24 | 99.31 |
| 70 | 79.8 | 0.24 | 99.14 |
| 71 | 99.9 | 0.18 | 91.0 |
| 72 | 102.5 | 0.22 | 92.7 |
| 73 | 84.3 | 0.25 | 98.85 |
| 80 | 65.8 | 0.2 | 98.93 |
| 81 | 65.3 | 0.17 | 99.27 |
| 82 | 76.1 | 0.24 | 99.23 |
| 83 | 73.2 | 0.22 | 99.12 |
| 84 | 68.6 | 0.19 | 98.48 |
| 85 | 69.9 | 0.24 | 99.18 |
| 86 | 53.6 | 0.14 | 97.42 |
| 87 | 80.9 | 0.21 | 98.67 |
| MC3 | 74.7 | 0.17 | 97.3 |

As shown in Table 17-1, Compounds 17-7 and 17-12 produced the smallest particles amongst those of Table 17-1, while Compounds 17-2 and 17-10 produced the largest particles amongst those of Table 17-1. The encapsulation efficiencies for Compounds 17-6 and 17-8 were comparable to that for MC3. Compounds 17-2 and 17-10 did not encapsulate RNA with high efficiency.

TABLE 17-1

Characteristics of nanoparticle compositions including compounds according to formula (17-I).

| Compound No. | Size (nm) | PDI | EE (%) | pKa |
|---|---|---|---|---|
| 17-2 | 136.9 | 0.104 | 57.2 | 6.92 |
| 17-3 | 117.9 | 0.095 | 82.1 | 6.69 |
| 17-4 | 95.6 | 0.154 | 94.5 | 6.34 |
| 17-5 | 88.4 | 0.137 | 94.2 | 6.92 |
| 17-6 | 80.2 | 0.117 | 97.3 | 6.73 |
| 17-7 | 68.5 | 0.110 | 95.6 | 5.68 |
| 17-8 | 86.4 | 0.20 | 96.9 | 6.16 |
| 17-9 | 87.1 | 0.138 | 95.0 | 4.93 |
| 17-10 | 165.0 | 0.239 | 30.3 | 2.85 |
| 17-11 | 87.3 | 0.24 | 88.7 | 6.76 |
| 17-12 | 76.1 | 0.148 | 95.04 | 6.83 |
| 17-13 | 90.4 | 0.176 | 89.22 | 6.89 |
| MC3 | 83.8 | 0.138 | 98.0 | n.d. | n.d. = not determined

As shown in Table 19-1, compositions including Compound 19-6 produced the largest particles amongst those of Table 19-1 with the lowest encapsulation efficiency, while those including Compound 19-3 produced the smallest particles amongst those of Table 19-1 with the highest encapsulation efficiency.

TABLE 19-1

Characteristics of nanoparticle compositions including compounds according to formula (19-I) or (19-II).

| Compound No. | Size (nm) | PDI | EE (%) | pKa |
|---|---|---|---|---|
| 19-1 | 98.0 | 0.071 | 83.4 | 6.76 |
| 19-2 | 72.0 | 0.239 | 98.8 | 7.32 |
| 19-3 | 47.9 | 0.076 | 99.7 | 7.24 |
| 19-4 | 111.4 | 0.071 | 95.2 | 7.09 |
| 19-5 | 106.9 | 0.204 | 93.6 | 6.32 |
| 19-6 | 137.7 | 0.088 | 16.9 | 5.89 |
| MC3 | 83.3 | 0.122 | 97.6 | n.d. | n.d. = not determined

As shown in Table 20-1, compositions including Compound 20-12 produced the largest particles amongst those of Table 20-1, while compositions including Compounds 20-8, 20-9, and 20-15 produced the smallest particles amongst those of Table 20-1. Encapsulation efficiencies for the compounds of Table 20-1 were highest for compositions including Compound 20-19.

TABLE 20-1

Characteristics of nanoparticle compositions including compounds according to formula (20-I).

| Compound No. | Size (nm) | PDI | EE (%) | pKa |
|---|---|---|---|---|
| 20-1* | 87.8 | 0.078 | 90.7 | 4.48 |
| 20-2 | 71.8 | 0.130 | 91.6 | 6.60 |
| 20-3 | 76.4 | 0.110 | 95.8 | 6.82 |
| 20-4 | 82.1 | 0.160 | 91.3 | 6.86 |
| 20-5 | 119.3 | 0.210 | 78.1 | 6.79 |
| 20-6 | 82.5 | 0.220 | 94.7 | 6.73 |
| 20-7 | 73.6 | 0.170 | 92.4 | 6.66 |
| 20-8 | 67.9 | 0.141 | 96.6 | 6.43 |
| 20-9 | 64.5 | 0.130 | 95.9 | 6.22 |
| 20-10 | 85.7 | 0.130 | 91.4 | 6.42 |
| 20-11 | 96.1 | 0.118 | 97.5 | 5.38 |
| 20-12 | 147.1 | 0.217 | 82.3 | 6.58 |
| 20-13 | 74.3 | 0.057 | 97.7 | 5.83 |
| 20-14 | 124.0 | 0.215 | 94.5 | 5.89 |
| 20-15 | 67.4 | 0.118 | 97.4 | 6.48 |
| 20-16 | 73.5 | 0.225 | 97.2 | 6.62 |
| 20-17 | 71.2 | 0.092 | 98.2 | 6.25 |
| 20-18 | 70.1 | 0.150 | 91.1 | 6.31 |
| 20-19 | 74.9 | 0.145 | 99.5 | 4.73 |
| 20-20 | 86.8 | 0.159 | 95.2 | 6.41 |
| 20-21 | 78.6 | 0.238 | 84.7 | 5.78 |
| 20-22 | 73.8 | 0.146 | 95.3 | 5.90 |
| 20-23 | 88.1 | 0.080 | 95.3 | 6.56 |
| 20-24 | 90.6 | 0.038 | 96.9 | 6.06 |
| 20-25 | 71.7 | 0.171 | 98.4 | 6.23 |
| MC3 | 84.0 | 0.117 | 97.4 | n.d. | n.d. = not determined
*= Formulated with DOPE

As shown in Table 21-1, compositions including Compound 21-1 produced the largest particles, amongst those of Table 21-1 while those including Compound 21-2 produced the smallest particles amongst those of Table 21-1. The encapsulation efficiency for all compositions of Table 21-1 was greater than 98%.

TABLE 21-1

Characteristics of nanoparticle compositions including compounds according to formula (21-I).

| Compound No. | Size (nm) | PDI | EE (%) | pKa |
|---|---|---|---|---|
| 21-1 | 119.9 | 0.237 | 98.4 | 6.07 |
| 21-2 | 83.0 | 0.200 | 99.4 | 6.98 |
| 21-4 | 94.9 | 0.193 | 98.8 | 7.01 |
| 21-6 | 86.8 | 0.110 | 98.9 | 6.99 |
| MC3 | 91.4 | 0.1191 | 98.1 | n.d. | n.d. = not determined

Example 4: Expression of Luc Induced by Sample Formulations

The efficacy of the nanoparticle compositions presented in Tables 1, 1a, 17-1, 19-1, 20-1 and 21-1 was evaluated with a bioluminescence study. Formulations were administered intravenously to mice (n=6) at a dosage of 0.5 mg/kg (mpk) and bioluminescence measured at 3, 6, and 24 hour time points. The standard MC3 formulation and a PBS control were evaluated for comparison.

As is evident in Table 2, the total flux for the compositions presented therein was generally comparable at 3 and 6 hours. The total flux after 24 hours was generally lower than that at earlier time points. Amongst the compositions of Table 2, compositions including Compounds 18, 23, and 30 displayed the highest flux after 3 hours. Of the compositions of Table 2, compositions including Compounds 36 and 37 displayed the lowest flux after 24 hours. In general, these results suggest that the compounds described herein may be useful in transfection applications.

TABLE 2

Expression of luciferase induced by administration of nanoparticle compositions including compounds according to one of formulae (I), (Ia1)-(Ia6), (Ib), (II), (IIa), (III) and (IIIa).

| Compound | Total Flux | | |
|---|---|---|---|
| No. | 3 hours | 6 hours | 24 hours |
| 2 | 6.01E+09 | 3.23E+09 | 3.23E+09 |
| 3 | 3.75E+08 | 1.12E+09 | n.d. |

TABLE 2-continued

Expression of luciferase induced by administration of nanoparticle compositions including compounds according to one of formulae (I), (Ia1)-(Ia6), (Ib), (II), (IIa), (III) and (IIIa).

| Compound No. | Total Flux 3 hours | 6 hours | 24 hours |
|---|---|---|---|
| 11 | 1.23E+10 | 3.81E+09 | 8.20E+08 |
| 12 | 1.06E+10 | 1.38E+10 | 6.03E+08 |
| 13 | 3.59E+09 | 3.80E+09 | 3.11E+08 |
| 14 | 9.86E+08 | 1.56E+09 | 1.02E+08 |
| 17 | 7.55E+09 | 2.49E+09 | 7.61E+08 |
| 18 | 2.13E+10 | 1.76E+10 | 7.00E+08 |
| 19 | 1.06E+10 | 6.52E+09 | 2.65E+09 |
| 20 | 1.00E+11 | 1.11E+11 | 4.60E+09 |
| 21 | 1.13E+10 | 1.08E+11 | 1.18E+08 |
| 23 | 2.33E+10 | 3.40E+10 | 1.06E+09 |
| 25 | 1.06E+10 | 1.08E+10 | 2.72E+08 |
| 26 | 1.65E+07 | 1.04E+07 | 2.75E+06 |
| 27 | 4.56E+09 | 4.70E+09 | 1.36E+08 |
| 28 | 6.18E+09 | 7.28E+09 | 4.02E+08 |
| 29 | 1.22E+08 | 2.51E+08 | 2.69E+07 |
| 30 | 2.87E+10 | 1.59E+10 | 1.95E+09 |
| 31 | 1.43E+10 | 1.42E+10 | 3.07E+08 |
| 32 | 6.85E+08 | 5.88E+08 | 4.37E+07 |
| 33 | 1.64E+09 | 4.71E+09 | 1.54E+08 |
| 34 | 7.77E+06 | 1.88E+07 | 2.19E+06 |
| 36 | 6.90E+05 | 3.93E+05 | 1.68E+05 |
| 37 | 1.19E+07 | 6.66E+06 | 9.38E+05 |
| 40 | 1.24E+08 | 1.07E+07 | 5.62E+06 |
| 41 | 4.06E+07 | 2.04E+07 | 6.05E+07 |
| 42 | n.d | 4.99E+10 | n.d |
| 43 | n.d | 4.54E+09 | n.d |
| 44 | n.d | 1.07E+10 | n.d |
| 45 | n.d | 7.86E+10 | n.d |
| 46 | n.d | 5.26E+09 | n.d |
| 47 | n.d | 2.64E+09 | n.d |
| 48 | n.d | 1.05E+08 | n.d |
| 49 | n.d | 5.67E+10 | n.d |
| 50 | n.d | 1.48E+08 | n.d |
| 51 | n.d | 6.70E+10 | n.d |
| 52 | n.d | 9.85E+10 | n.d |
| MC3 | 1.63E+10 | 1.73E+10 | 1.16E+09 | n.d. = not determined

As is evident in Table 17-2, nanoparticle compositions including MC3 displayed the highest total flux of Table 17-2, while those including Compounds 17-4 and 17-8 displayed substantially higher flux than compositions including Compounds 17-2, 17-3, and 17-7. The total flux at 6 hours was higher than that at 3 hours for some compositions of Table 17-2. Generally, for the compositions of Table 17-2, the total flux at 24 hours was lower than the total flux measured at 3 or 6 hours.

TABLE 17-2

Expression of luciferase induced by administration of nanoparticle compositions including compounds according to formula (17-I).

| Compound No. | Total Flux 3 hours | 6 hours | 24 hours |
|---|---|---|---|
| 17-2 | 2.83E+05 | 3.76E+05 | 2.64E+05 |
| 17-3 | 5.58E+05 | 1.38E+06 | 9.90E+05 |
| 17-4 | 1.22E+09 | 3.60E+08 | 6.05E+07 |
| 17-5 | 6.64E+08 | 8.54E+08 | 5.97E+07 |
| 17-6 | 6.27E+07 | 1.19E+07 | 1.27E+07 |
| 17-7 | 4.68E+05 | 6.82E+05 | 5.46E+05 |
| 17-8 | 1.02E+09 | 5.94E+08 | 3.79E+07 |
| 17-9 | 6.87E+06 | 9.97E+06 | 3.43E+05 |
| 17-10 | 6.61E+05 | 1.16E+06 | 4.06E+05 |
| 17-11 | 1.86E+06 | 2.82E+06 | 2.70E+05 |

TABLE 17-2-continued

Expression of luciferase induced by administration of nanoparticle compositions including compounds according to formula (17-I).

| Compound No. | Total Flux 3 hours | 6 hours | 24 hours |
|---|---|---|---|
| 17-12 | 2.94E+06 | 2.54E+06 | 4.66E+05 |
| 17-13 | 1.10E+06 | 1.80E+06 | 7.95E+05 |
| MC3 | 1.63E+10 | 2.13E+10 | 1.01E+09 |

As is evident in Table 19-2, compositions including MC3 induced the highest expression of the compositions of Table 19-2 at each time point. Compositions including Compounds 19-5 and 19-6 produced the next highest flux of Table 19-2 at each time point, while those including Compound 19-2 produced the lowest total flux of Table 19-2 at each time point.

TABLE 19-2

Expression of luciferase induced by administration of nanoparticle compositions including compounds according to formula (19-I) or (19-II).

| Compound No. | Total Flux 3 hours | 6 hours | 24 hours |
|---|---|---|---|
| 19-1 | 6.77E+05 | 1.85E+06 | 2.75E+05 |
| 19-2 | 1.96E+05 | 3.51E+05 | 2.29E+05 |
| 19-3 | 1.69E+06 | 1.21E+06 | 3.39E+05 |
| 19-4 | 6.61E+05 | 4.75E+05 | 3.44E+05 |
| 19-5 | 2.37E+07 | 1.44E+07 | 2.76E+06 |
| 19-6 | 1.07E+07 | 1.27E+07 | 1.29E+06 |
| MC3 | 1.53E+10 | 1.73E+10 | 1.13E+09 |

As is evident in Table 20-2, flux for the compositions of Table 20-2 was generally highest 3 hours after administration. Total flux for the compositions of Table 20-2 was highest after 3 hours for compositions including MC3, Compound 20-6, or Compound 20-7. Amongst the compositions of Table 20-2, expression 24 hours after administration was lowest for compositions including Compounds 20-1, 20-6, and 20-16.

TABLE 20-2

Expression of luciferase induced by administration of nanoparticle compositions including compounds according to formula (20-I).

| Compound No. | Total Flux 3 hours | 6 hours | 24 hours |
|---|---|---|---|
| 20-1 | 1.44E+06 | 8.30E+05 | 4.53E+05 |
| 20-2 | 1.35E+09 | 2.18E+09 | 6.49E+07 |
| 20-3 | 5.35E+09 | 3.00E+09 | 6.49E+07 |
| 20-4 | 3.01E+06 | 1.75E+06 | 6.82E+08 |
| 20-5 | 6.07E+07 | 1.99E+07 | 2.07E+06 |
| 20-6 | 3.39E+10 | 5.44E+06 | 5.48E+05 |
| 20-7 | 1.22E+10 | 8.94E+09 | 2.65E+08 |
| 20-8 | 2.76E+09 | 4.37E+09 | 1.30E+08 |
| 20-9 | 3.65E+08 | 6.91E+08 | 4.81E+07 |
| 20-10 | 5.05E+09 | 2.16E+09 | 2.54E+08 |
| 20-11 | 1.44E+09 | 8.83E+08 | 2.40E+07 |
| 20-12 | 1.57E+09 | 1.84E+09 | 1.24E+08 |
| 20-13 | 7.01E+08 | 1.82E+09 | 7.39E+07 |
| 20-14 | 1.76E+09 | 4.07E+08 | 8.10E+07 |
| 20-15 | 3.36E+08 | 2.25E+08 | 2.08E+07 |
| 20-16 | 7.88E+05 | 6.25E+05 | 2.16E+05 |
| 20-17 | 1.97E+07 | 1.44E+07 | 1.54E+06 |
| 20-18 | 5.80E+09 | 6.48E+09 | 1.54E+09 |

TABLE 20-2-continued

Expression of luciferase induced by administration of nanoparticle compositions including compounds according to formula (20-I).

| Compound No. | Total Flux | | |
|---|---|---|---|
| | 3 hours | 6 hours | 24 hours |
| 20-19 | 5.37E+05 | 7.60E+05 | 6.08E+05 |
| 20-20 | 4.56E+09 | 3.27E+09 | 3.56E+08 |
| 20-21 | 1.43E+09 | 1.02E+09 | 1.13E+08 |
| 20-22 | 4.00E+09 | 3.01E+09 | 2.20E+08 |
| 20-23 | 1.91E+09 | 1.42E+09 | 1.13E+08 |
| 20-24 | 7.47E+08 | 1.64E+08 | 9.72E+06 |
| 20-25 | 1.16E+09 | 1.78E+09 | 3.82E+07 |
| MC3 | 1.73E+10 | 1.94E+10 | 8.48E+08 |

As is evident in Table 21-2, compositions including MC3 produced the highest luciferase expression of Table 21-2 at each time point, while, amongst the compositions of Table 21-2, those including Compound 21-2 showed the least expression at 3 and 6 hours. Each composition of Table 21-2 showed substantial expression. Flux generally decreased over time. These results suggest that the compounds described herein may be useful in transfection applications.

TABLE 21-2

Expression of luciferase induced by administration of nanoparticle compositions including compounds according to formula (21-I).

| Compound No. | Total Flux | | |
|---|---|---|---|
| | 3 hours | 6 hours | 24 hours |
| 21-1 | 3.66E+09 | 4.19E+09 | 4.19E+09 |
| 21-2 | 5.99E+08 | 8.09E+08 | 8.09E+08 |
| 21-4 | 1.15E+09 | 1.26E+09 | 1.26E+09 |
| 21-6 | 2.92E+09 | 4.54E+09 | 1.40E+08 |
| MC3 | 1.69E+10 | 2.87E+10 | 2.23E+10 |

Example 5: Expression of Luc Induced by Sample Formulations in Different Organs

The efficacy of the nanoparticle compositions presented in Tables 1, 1a, 17-1, 19-1, 20-1 and 21-1 was further evaluated by measuring the expression of modified luciferase in the liver, lung, spleen, and femur upon administration of a given composition. Formulations were administered intravenously to mice (n=3) at a dosage of 0.5 mpk and bioluminescence measured after 6 hours. The standard MC3 formulation and a PBS control were also tested.

As is evident in Table 3, expression was highest in the liver for all formulations of Table 3. Of the compostions of Table 3, the highest total flux was measured for compositions including Compound 20. Lung and spleen expression were generally comparable for compounds of Table 3, while expression in the femur, where measured, was somewhat lower.

TABLE 3

Expression of luciferase in various organs 6 hours after administration of nanoparticle compositions including compounds according to one of formulae (I), (Ia1)-(Ia6), (Ib), (II), (IIa), (III) and (IIIa).

| Compound No. | Total Flux | | | |
|---|---|---|---|---|
| | Liver | Lung | Spleen | Femur |
| 2 | 3.33E+08 | 4.76E+05 | 1.14E+07 | n.d. |
| 3 | 1.36E+08 | 8.47E+05 | 9.51E+05 | n.d. |
| 11 | 1.67E+09 | 2.21E+06 | 7.21E+06 | 1.47E+06 |
| 12 | 1.05E+09 | 6.76E+06 | 1.11E+07 | n.d. |
| 13 | 6.10E+08 | 2.89E+06 | 3.63E+07 | 1.99E+06 |
| 14 | 2.62E+08 | 3.56E+06 | 1.46E+07 | n.d. |
| 17 | 4.26E+08 | 7.26E+05 | 3.20E+06 | 6.71E+05 |
| 18 | 3.91E+09 | 1.87E+07 | 1.60E+07 | 3.31E+06 |
| 19 | 1.89E+09 | 2.27E+06 | 8.28E+06 | 2.75E+06 |
| 20 | 1.42E+10 | 1.46E+08 | 6.11E+07 | 8.91E+06 |
| 21 | 1.24E+09 | 2.51E+06 | 1.17E+07 | n.d. |
| 23 | 4.94E+09 | 1.51E+07 | 2.95E+07 | 3.17E+06 |
| 25 | 2.68E+09 | 5.88E+06 | 6.00E+06 | n.d. |
| 26 | 2.35E+06 | 3.49E+04 | 2.30E+05 | n.d. |
| 27 | 7.84E+08 | 3.56E+06 | 3.34E+06 | n.d. |
| 28 | 8.10E+08 | 5.73E+06 | 5.67E+06 | 1.16E+06 |
| 29 | 2.27E+07 | 4.70E+06 | 2.97E+06 | n.d. |
| 30 | 2.42E+09 | 1.61E+07 | 7.18E+06 | 2.22E+06 |
| 31 | 1.54E+09 | 9.81E+06 | 1.28E+07 | 9.89E+05 |
| 32 | 8.36E+07 | 6.75E+05 | 9.38E+05 | 1.02E+05 |
| 33 | 6.15E+08 | 2.84E+06 | 4.82E+06 | 1.18E+06 |
| 34 | 2.79E+06 | 5.63E+04 | 1.22E+06 | n.d. |
| 36 | 5.85E+04 | 2.74E+04 | 1.24E+05 | n.d. |
| 37 | 1.92E+06 | 6.90E+05 | 9.75E+05 | n.d. |
| 40 | 1.33E+06 | 1.42E+05 | 5.68E+05 | n.d. |
| 41 | 3.00E+06 | 1.34E+05 | 2.13E+06 | n.d. |
| 42 | 5.53E+09 | n.d | 2.29E+08 | n.d |
| 43 | 2.60E+08 | n.d | 4.52E+07 | n.d |
| 44 | 1.11E+09 | n.d | 1.19E+08 | n.d |
| 45 | 7.87E+09 | n.d | 1.70E+08 | n.d |
| 46 | 3.84E+08 | n.d | 4.35E+07 | n.d |
| 47 | 4.95E+08 | n.d | 1.42E+08 | n.d |
| 48 | 1.04E+07 | n.d | 1.50E+07 | n.d |
| 49 | 1.21E+10 | n.d | 6.65E+07 | n.d |
| 50 | 2.14E+07 | n.d | 1.94E+05 | n.d |
| 51 | 3.55E+09 | n.d | 2.24E+07 | n.d |
| 52 | 1.18E+10 | n.d | 8.74E+08 | n.d |
| IV | 9.15E+08 | n.d | 6.15E+08 | n.d |
| MC3 | 2.31E+09 | 8.61E+06 | 1.95E+07 | 3.08E+06 | n.d. = not determined

As is evident in Table 17-3, the total flux for compositions of Table 17-3 was generally higher in the liver than in other organs. The total flux in the liver for nanoparticle compositions of Table 17-3 including Compounds 17-5 and 17-8 was somewhat comparable to those including MC3, which displayed the highest total flux of Table 17-3 in each organ. For compositions of Table 17-3, the total flux in the spleen was generally higher than that in the lung and was highest for compositions including Compounds 17-4, 17-5, and 17-8.

TABLE 17-3

Expression of luciferase in various organs 6 hours after administration of nanoparticle compositions including compounds according to formula (17-I).

| Compound No. | Total Flux | | | |
|---|---|---|---|---|
| | Liver | Lung | Spleen | Femur |
| 17-2 | 6.42E+04 | 1.96E+04 | 4.16E+04 | n.d. |
| 17-3 | 2.51E+05 | 1.56E+04 | 1.02E+05 | n.d. |
| 17-4 | 8.00E+07 | 1.95E+05 | 2.30E+06 | n.d. |
| 17-5 | 1.17E+08 | 8.13E+05 | 2.13E+06 | n.d. |
| 17-6 | 2.16E+07 | 1.54E+05 | 9.06E+05 | n.d. |
| 17-7 | 7.44E+04 | 1.35E+04 | 3.46E+04 | n.d. |

TABLE 17-3-continued

Expression of luciferase in various organs 6 hours after administration of nanoparticle compositions including compounds according to formula (17-I).

| Compound No. | Total Flux | | | |
|---|---|---|---|---|
| | Liver | Lung | Spleen | Femur |
| 17-8 | 2.27E+08 | 6.11E+05 | 4.25E+06 | n.d. |
| 17-9 | 1.39E+06 | 1.40E+04 | 3.72E+05 | 2.29E+04 |
| 17-10 | 2.00E+05 | 2.52E+04 | 1.74E+04 | n.d. |
| 17-11 | 5.06E+05 | 1.20E+04 | 3.37E+05 | n.d. |
| 17-12 | 4.94E+05 | 4.89E+04 | 7.81E+04 | n.d. |
| 17-13 | 3.56E+05 | 4.66E+04 | 1.90E+05 | n.d. |
| MC3 | 2.75E+09 | 7.25E+06 | 2.62E+07 | 6.03E+06 | n.d. = not determined

As is evident in Table 19-3, total flux for the compositions of Table 19-3 was highest for compositions including MC3. For compositions of Table 19-3, expression in the liver was higher than expression in the lung and spleen for all compounds of Table 19-3 tested. Of the compositions of Table 19-3, compositions including Compound 19-2 yielded the lowest total flux in the liver.

TABLE 19-3

Expression of luciferase in various organs 6 hours after administration of nanoparticle compositions including compounds according to formula (19-I) or (19-II).

| Compound No. | Total Flux | | |
|---|---|---|---|
| | Liver | Lung | Spleen |
| 19-1 | 8.53E+05 | 1.06E+04 | 1.58E+04 |
| 19-2 | 5.73E+04 | 2.33E+04 | 3.56E+04 |
| 19-3 | 2.65E+05 | 3.00E+04 | 2.55E+05 |
| 19-4 | 1.46E+05 | 4.49E+04 | 3.69E+04 |
| 19-5 | 5.99E+06 | 3.46E+04 | 2.10E+05 |
| 19-6 | 3.27E+06 | 1.81E+05 | 3.47E+06 |
| MC3 | 2.39E+09 | 5.83E+06 | 2.45E+07 |

As is evident in Table 20-3, expression for the compounds therein was generally highest in the liver and lowest in the lung and femur. Total flux for the compounds of Table 20-3 in the liver was highest for compositions including MC3 or Compound 20-7 and lowest for those including Compound 20-16.

TABLE 20-3

Expression of luciferase in various organs 6 hours after administration of nanoparticle compositions including compounds according to formula (20-I).

| Compound No. | Total Flux | | | |
|---|---|---|---|---|
| | Liver | Lung | Spleen | Femur |
| 20-1 | 3.19E+05 | 3.79E+04 | 1.70E+05 | n.d. |
| 20-2 | 6.01E+08 | 4.52E+06 | 3.12E+07 | 1.07E+06 |
| 20-3 | 4.33E+08 | 6.08E+05 | 6.35E+06 | 1.73E+06 |
| 20-4 | 2.93E+05 | 1.11E+04 | 4.51E+04 | 2.09E+04 |
| 20-5 | 2.67E+06 | 5.80E+04 | 3.40E+06 | 9.53E+04 |
| 20-6 | 7.75E+05 | 2.32E+04 | 2.35E+05 | n.d. |
| 20-7 | 1.00E+09 | 1.38E+07 | 4.58E+07 | n.d. |
| 20-8 | 8.09E+08 | 3.45E+06 | 2.70E+07 | 1.62E+06 |
| 20-9 | 1.57E+08 | 1.30E+06 | 5.11E+06 | 2.89E+05 |
| 20-10 | 4.40E+08 | 5.01E+06 | 9.67E+07 | 3.09E+06 |
| 20-11 | 3.60E+08 | 5.86E+05 | 9.24E+06 | n.d. |
| 20-12 | 3.08E+08 | 3.58E+06 | 6.15E+07 | 1.37E+06 |
| 20-13 | 1.65E+08 | 9.09E+05 | 1.04E+07 | 3.11E+05 |
| 20-14 | 5.22E+07 | 1.08E+05 | 7.03E+05 | n.d. |

TABLE 20-3-continued

Expression of luciferase in various organs 6 hours after administration of nanoparticle compositions including compounds according to formula (20-I).

| Compound No. | Total Flux | | | |
|---|---|---|---|---|
| | Liver | Lung | Spleen | Femur |
| 20-15 | 6.74E+07 | 5.56E+05 | 1.86E+06 | n.d. |
| 20-16 | 9.55E+04 | 1.44E+04 | 6.57E+04 | n.d. |
| 20-17 | 2.99E+06 | 2.79E+04 | 9.56E+04 | n.d. |
| 20-18 | 4.83E+08 | 1.84E+06 | 2.36E+06 | 3.78E+05 |
| 20-19 | 3.80E+05 | 1.96E+04 | 2.74E+04 | n.d. |
| 20-20 | 8.92E+08 | 1.12E+06 | 1.39E+07 | n.d. |
| 20-21 | 1.27E+08 | 1.98E+05 | 2.20E+06 | n.d. |
| 20-22 | 2.88E+08 | 5.04E+05 | 1.65E+06 | n.d. |
| 20-23 | 3.06E+08 | 1.28E+06 | 4.19E+06 | 5.10E+05 |
| 20-24 | 4.05E+07 | 1.08E+05 | 1.11E+06 | n.d. |
| 20-25 | 1.88E+08 | 7.85E+05 | 4.16E+06 | 3.13E+05 |
| MC3 | 2.48E+09 | 1.28E+07 | 2.85E+07 | 2.60E+06 | n.d. = not determined

As is evident in Table 21-3, expression was highest in the liver and lowest in the lung for all compositions of Table 21-3. Of the compositions of Table 21-3, compositions including MC3 produced the highest expression in each organ, while compositions including Compounds 21-2 and 21-4 produced the lowest expression in each organ.

TABLE 21-3

Expression of luciferase in various organs 6 hours after administration of nanoparticle compositions including compounds according to formula (21-I).

| Compound No. | Total Flux | | |
|---|---|---|---|
| | Liver | Lung | Spleen |
| 21-1 | 3.62E+08 | 5.44E+05 | 3.27E+07 |
| 21-2 | 5.50E+07 | 2.53E+05 | 1.56E+07 |
| 21-4 | 9.89E+07 | 2.13E+05 | 1.27E+07 |
| 21-6 | 4.79E+08 | 2.09E+06 | 1.94E+07 |
| MC3 | 3.05E+09 | 6.60E+06 | 4.73E+07 |

Example 6: Cytokine Production Induced by Sample Formulations

The introduction of foreign material into a mammalian body induces an innate immune response that promotes cytokine production. Such immune responses to, for example, nanoparticle compositions including therapeutic and/or prophylactic agents, are undesirable. The induction of certain cytokines is thus measured to evaluate the efficacy of nanoparticle compositions. The concentrations of various cytokines in mice upon intravenous administration of nanoparticle compositions presented in Tables 1, 1a, 17-1, 19-1, 20-1 and 21-1 at a dosage of 0.5 mpk was measured at 6 hours. The standard MC3 formulation and a PBS control were also tested.

As is evident in Table 4, IP-10 expression was lower than IL-6 expression for compositions of Table 4. Of the compositions of Table 4, compositions including Compound 13 induced the highest expression of both IL-6 and IP-10, while compositions including Compound 3 induced the lowest IL-6 expression and those including Compound 36 induced the lowest IP-10 expression.

TABLE 4

Cytokine induction 6 hours after administration of nanoparticle compositions including compounds according to one of formulae (I), (Ia1)-(Ia6), (Ib), (II), (IIa), (III) and (IIIa).

| Compound No. | IL-6 | IP-10 |
|---|---|---|
| 2 | n.d. | 3365 |
| 3 | 7 | 341 |
| 11 | 250 | 3305 |
| 12 | 31 | 2382 |
| 13 | 301 | 7266 |
| 14 | 17 | 209 |
| 17 | 164 | 545 |
| 18 | 263 | 655 |
| 19 | 70 | 2326 |
| 20 | 127 | 2080 |
| 21 | 48 | 652 |
| 23 | 259 | 3702 |
| 25 | 131 | 1823 |
| 26 | 17 | 175 |
| 27 | 42 | 2564 |
| 28 | 73 | 5364 |
| 29 | 108 | 3454 |
| 30 | 300 | 4235 |
| 31 | 188 | 2513 |
| 32 | 174 | 727 |
| 33 | 37 | 1577 |
| 34 | 28 | 159 |
| 36 | 41 | 118 |
| 37 | n.d. | 198 |
| 40 | 134 | 919 |
| 41 | 116 | 350 |
| MC3 | 92 | 438 | n.d. = not determined

As is evident in Table 17-4, nanoparticle compositions of Table 17-4 induced higher IP-10 levels than IL-6 levels. Of the nanoparticle compositions of Table 17-4, compositions including MC3 and Compound 17-4 induced the highest IL-6 and IP-10 levels while those including Compounds 17-2, 17-3, and 17-10 induced the lowest IL-6 levels and compositions including Compounds 17-2 and 17-3 induced the lowest IP-10 levels.

TABLE 17-4

Cytokine induction 6 hours after administration of nanoparticle compositions including compounds according to formula (17-I).

| Compound No. | IL-6 | IP-10 |
|---|---|---|
| 17-2 | 9.88 | 72.8 |
| 17-3 | 6.97 | 66.8 |
| 17-4 | 80.7 | 560 |
| 17-5 | 49.2 | 300 |
| 17-6 | 25.0 | 134 |
| 17-7 | 49.9 | 100 |
| 17-8 | n.d. | 135 |
| 17-9 | 35.2 | 112 |
| 17-10 | 7.33 | 243 |
| 17-11 | n.d. | n.d. |
| 17-12 | 83.1 | 148 |
| 17-13 | 84.3 | 222 |
| MC3 | 107 | 500 |

As is evident in Table 19-4, of the nanoparticle compositions of Table 19-4, compositions including Compound 19-6 induced the highest IL-6 expression, while those including Compound 19-3 induced the lowest IL-6 expression. Of the nanoparticle compositions of Table 19-4, compositions including Compounds 19-4 and 19-6 yielded the highest IP-10 expression, while those including Compound 19-1 induced the lowest IP-10 expression.

TABLE 19-4

Cytokine induction 6 hours after administration of nanoparticle compositions including compounds according to formula (19-I) or (19-II).

| Compound No. | IL-6 | IP-10 |
|---|---|---|
| 19-1 | 144.4 | 51.1 |
| 19-2 | n.d. | n.d. |
| 19-3 | 5.4 | 177.5 |
| 19-4 | 129.2 | 430.9 |
| 19-5 | n.d. | n.d. |
| 19-6 | 7571 | 433 |
| MC3 | 65.7 | 323.9 | n.d. = not determined

As is evident in Table 20-4, for nanoparticle compositions of Table 20-4, IP-10 induction was generally higher than IL-6 induction. For nanoparticle compositions of Table 20-4, IP-10 induction was highest for compositions including Compound 20-14 and lowest for compositions including Compound 20-6. IL-6 induction was highest for compositions including Compound 20-10 and lowest for compositions including Compound 20-6 for the nanoparticle compositions of Table 20-4.

TABLE 20-4

Cytokine induction 6 hours after administration of nanoparticle compositions including compounds according to formula (20-I).

| Compound No. | IL-6 | IP-10 |
|---|---|---|
| 20-1 | 62.4 | 2065.8 |
| 20-2 | 118.5 | 522.9 |
| 20-3 | 105.8 | 671.5 |
| 20-4 | 169.3 | 270.5 |
| 20-5 | 140.8 | 2012.3 |
| 20-6 | 0 | 25.3 |
| 20-7 | 24.5 | 696.3 |
| 20-8 | 18.4 | 134.0 |
| 20-9 | 152.1 | 271.1 |
| 20-10 | 739.0 | 2356.8 |
| 20-11 | 46.9 | 1700.5 |
| 20-12 | 445.7 | 3864.5 |
| 20-13 | 87.8 | 70.0 |
| 20-14 | 311.1 | 8436.6 |
| 20-15 | 49.4 | 136.3 |
| 20-16 | n.d. | 395.7 |
| 20-17 | 6.3 | 1207.0 |
| 20-18 | 102 | 572.7 |
| 20-19 | n.d. | 127.2 |
| 20-21 | 68.4 | 900.4 |
| 20-22 | 118.6 | 810.6 |
| 20-23 | 236.4 | 457.8 |
| 20-24 | 67.1 | 1678.6 |
| 20-25 | 20.6 | 188.0 |
| MC3 | 119.5 | 499.1 |

As is evident in Table 21-4, IP-10 induction by compositions therein was substantially higher than IL-6 induction.

TABLE 20-4

Cytokine induction 6 hours after administration of nanoparticle compositions including compounds according to formula (21-I).

| Compound No. | IL-6 | IP-10 |
|---|---|---|
| 21-1 | n.d. | 1265.1 |
| 21-2 | n.d. | 477.9 |
| 21-4 | n.d. | 577.2 |
| 21-6 | 10.2 | 641.3 |
| MC3 | 31.1 | 304.5 |

Example 7: Expression of hEPO Induced by Sample Formulations

Formulations were prepared according to Table 5 and included mRNA encoding hEPO.

TABLE 5

Characteristics of nanoparticle compositions including compounds according to one of formulae (I), (Ia1)-(Ia6), (Ib), (II), (IIa), (III) and (IIIa).

| Compound No. | Composition (mol %) | Components | Size (nm) | PDI | EE (%) | pKa | Conc. (ug/ml) |
|---|---|---|---|---|---|---|---|
| 12 | 40:20:38.5:1.5 | Lipid:DOPE:Chol:PEG-DMG | 87.5 | 0.13 | 93.79 | 5.444 | 320.14 |
| 14 | 40:20:38.5:1.5 | Lipid:DOPE:Chol:PEG-DMG | 76.8 | 0.14 | 98.91 | 6.308 | 603.76 |
| 15 | 40:20:38.5:1.5 | Lipid:DOPE:Chol:PEG-DMG | 100.3 | 0.12 | 90.15 | 6.323 | 713.00 |
| 16 | 40:20:38.5:1.5 | Lipid:DOPE:Chol:PEG-DMG | 77.4 | 0.14 | 98.22 | 6.282 | 665.11 |
| 20 | 40:20:38.5:1.5 | Lipid:DOPE:Chol:PEG-DMG | 114.5 | 0.14 | 94.39 | n.d. | 1264.28 |
| 22 | 40:20:38.5:1.5 | Lipid:DOPE:Chol:PEG-DMG | 75.4 | 0.13 | 98.29 | 6.153 | 564.97 |
| 23 | 40:20:38.5:1.5 | Lipid:DOPE:Chol:PEG-DMG | 98.5 | 0.16 | 77.19 | 6.070 | 438.20 |
| 23 | 50:10:38.5:1.5 | Lipid:DSPC:Chol:PEG-DMG | 95.2 | 0.11 | 51.46 | 6.164 | 454.58 |
| MC3 | 50:10:38.5:1.5 | Lipid:DSPC:Chol:PEG-DMG | 76.5 | 0.11 | 97.37 | n.d. | 470.45 | n.d. = not determined

Formulations were administered intravenously to rats (n=3 or 6) at a dosage of 0.2 mg/kg or 0.5 mg/kg (mpk) and hEPO levels measured at 3, 6, and 24 hour time points. After the 48 hour time point, livers and spleens were harvested and frozen. As is evident in Table 6, compositions including MC3 yielded the highest hEPO expression at each time point, while compositions including Compound 16 yielded the lowest hEPO expression at each time point.

TABLE 6

Expression of hEPO induced by administration of nanoparticle compositions including compounds according to one of formulae (I), (Ia1)-(Ia6), (Ib), (II), (IIa), (III) and (IIIa).

| Compound No. | hEPO (pg/mL) | | |
|---|---|---|---|
| | 3 hours | 6 hours | 24 hours |
| 12 | 592260 | 424740 | 165404 |
| 14 | 280973 | 158520 | 58805 |
| 15 | 103773 | 125320 | 67965 |
| 16 | 35387 | 41720 | 17184 |
| 20 | n.d. | 227420 | n.d. |
| 22 | 181627 | 267680 | 75571 |
| 23 (DOPE) | 249213 | 275440 | 120104 |
| 23 (DSPC) | 86627 | 71360 | 29008 |
| MC3 | 1407947 | 1036013 | 436243 | n.d. = not determined

As shown in Table 7a, hEPO expression in mice was substantially higher for compositions including Compound 12 than those including MC3. In contrast, hEPO expression in rats induced by administration of a nanoparticle composition including a compound according to one of formulae (I), (Ia1)-(Ia6), (Ib), (II), (IIa), (III), and (IIIa) was substantially lower than that measured for MC3. Luc expression in mice was several fold higher for Compound 23 than for MC3 but significantly lower for Compounds 12 and 14. Table 7b shows the Luc expressions in CD-1 mice vs. LDLr-/- mice. Table 7c and 7d show additional protein expressions and clearance data from compositions with various compounds disclosed herein as compared to with MC3. Table 7e shows hEPO expression data in CD-1 mice at a dose of 0.5 mpk. Similar results were achieved with different strains of mice, e.g. chimeric mice with humanized livers (PXB) or immunodefficient mice (SCID).

TABLE 7a

Comparison of expression induced by administration of nanoparticle compositions including MC3 or compounds according to one of formulae (I), (Ia1)-(Ia6), (Ib), (II), (IIa), (III), and (IIIa).

| Compound No. | Lipid/ MC3 Luc CD-1 (mice) | Lipid/ MC3 hEPO CD-1 (mice) | Lipid/ MC3 hEPO S.D. (rats) | % Dose remaining 6 h CD-1 mice | % Dose remaining 24 h CD-1 mice |
|---|---|---|---|---|---|
| 11 | 1.03 | n.d. | n.d. | | |
| 12 | 0.21 | 2.3 | 0.32 | | |
| 14 | 0.070 | n.d. | 0.12 | | |
| 15 | n.d. | n.d. | 0.095 | | |
| 16 | n.d. | n.d. | 0.031 | | |
| 20 | 5.0 | n.d. | n.d. | | |
| 22 | n.d. | n.d. | 0.20 | | |
| 23 (DOPE) | 5.2 | 2.4 | 0.21 | | |
| 42 | 3.99 | n.d. | n.d. | 58 | 53 |
| 43 | 0.34 | | | 69 | 64 |
| 44 | 0.82 | n.d. | n.d. | <1 | <1 |
| 45 | 6.50 | n.d. | n.d. | 33 | 24 |
| 46 | 0.46 | | | 1 | <1 |
| 47 | 0.22 | | | 1 | <1 |
| 48 | 0.01 | | | <1 | <1 |
| 49 | 5.23 | n.d. | n.d. | 49 | 40 |
| 50 | 0.01 | | | 56 | 47 |
| 51 | 5.22 | n.d. | n.d. | 54 | 41 |
| 52 | 7.46 | n.d. | n.d. | 46 | 40 |
| MC3 | 1 | 1 | 1 | 88 | 55 | n.d. = not determined

TABLE 7b

Comparison of Luc expression induced by administration of nanoparticle compositions including MC3 or compounds according to one of formulae (I), (Ia1)-(Ia6), (Ib), (II), (IIa), (III), and (IIIa) in CD-1 mice and LDLr-/- mice.

| Compound No. | Lipid/MC3 AUC CD-1 mice 0.5 mpk | Lipid/KL22 AUC LDLr-/- mice 0.5 mpk, LDLr | LDL levels lipid/untreated LDLr-/- mice 0.5 mpk, LDLr |
|---|---|---|---|
| 4 | 3.70 | 2.03 | 0.54 |
| 5 | 2.62 | 1.86 | 0.47 |
| 6 | 1.72 | 0.37 | 0.91 |
| 7 | 1.51 | 2.46 | 0.63 |
| 8 | 2.33 | 3.74 | 0.66 |
| 9 | 0.73 | 0.58 | 0.87 |
| 10 | 1.14 | 0.71 | 0.98 |
| MC3 | 1 | 0.15 | 0.55 |
| KL22 | | 1 | 0.51 |

TABLE 7c

Comparison of expression induced by administration of nanoparticle compositions including MC3 or compounds according to one of formulae (I), (Ia1)-(Ia6), (Ib), (II), (IIa), (III), and (IIIa).

| Compound No. | AUC (p/s*h) | Lipid/MC3 AUC | Liver/ Spleen Ratio | % Dose Remaining 6 hr | % Dose Remaining 24 hr |
|---|---|---|---|---|---|
| 53 | 9.22E+09 | 0.07 | 17 | 1.35 | 0.77 |
| 54 | 1.89E+10 | 0.13 | 32 | 5.18 | 4.77 |
| 55 | 2.00E+10 | 0.14 | 9 | 2.58 | 1.60 |
| 56 | 1.77E+11 | 1.25 | 29 | 1.21 | 0.16 |
| 57 | 1.21E+11 | 0.85 | 15 | 0.88 | 0.24 |
| 58 | 1.38E+11 | 0.97 | 11 | 1.37 | 0.61 |
| 59 | 1.19E+11 | 0.84 | 5 | 6.99 | 5.03 |
| 60 | 2.84E+11 | 2.00 | 15 | 21.18 | 15.98 |
| 61 | 4.65E+11 | 3.27 | 30 | 1.31 | 0.13 |
| 71 | 1.77E+11 | 1.25 | 25 | 12.39 | 9.25 |
| 72 | 6.53E+10 | 0.46 | 6 | 7.06 | 6.40 |
| MC3 | 1.42E+11 | — | 55 | 55.70 | 55.43 |

TABLE 7d

Comparison of hEPO expression in S.D. rats induced by administration of nanoparticle compositions including MC3 or compounds according to one of formulae (I), (Ia1)-(Ia6), (Ib), (II), (IIa), (III), and (IIIa).

| Compound No | AUC (0.1 mpk) | AUC/MC3 0.1 mpk | AUC (1 mpk) | AUC/MC3 1 mpk | % dose remainng Rat liver (48 h) | % dose remaining Mouse liver (24 h) |
|---|---|---|---|---|---|---|
| 4 | 2.12E+06 | 1.3 | 6.79E+07 | 0.58 | 37.82 | N.A. |
| 45 | 1.45E+06 | 0.90 | 2.00E+08 | 1.7 | 8.57 | 23.7 |
| 49 | 5.98E+06 | 3.7 | 1.44E+08 | 1.2 | 38.45 | 40.3 |
| MC3 | 1.62E+06 | — | 1.17E+08 | — | 43.11 | 55 |

TABLE 7e

Comparison of hEPO expression in CD-1 mice induced by administration of nanoparticle compositions including MC3 or compounds according to one of formulae (I), (Ia1)-(Ia6), (Ib), (II), (IIa), (III), and (IIIa) at a dose of 0.5 mpk.

| Compound No. | AUC (p/s*h) CD-1 mice 0.5 mpk | Lipid/MC3 AUC |
|---|---|---|
| 62 | 3.46E+7 | 0.97 |
| 69 | 2.33E+8 | 6.52 |
| 70 | 6.34E+7 | 1.77 |
| 73 | 1.41E+8 | 3.93 |
| 80 | 6.24E+7 | 1.74 |
| 81 | 1.08E+8 | 3.01 |
| 82 | 1.29E+8 | 3.62 |
| 83 | 5.21E+7 | 1.46 |
| 84 | 5.10E+7 | 1.43 |
| 85 | 1.27E+8 | 3.54 |
| 86 | 1.75E+7 | 0.49 |
| 87 | 2.86E+7 | 0.80 |

The amount of lipid in the liver and spleen 48 hours after administration of a nanoparticle composition was also measured. As shown in Table 8, less than 6% of doses including Compounds 14, 15, and 16 remained in the liver after 48 hours. In contrast, approximately 60% of doses including MC3 or Compound 22 remained in the liver after 48 hours. Less than 3% of the dose remained in the spleen for each composition tested.

TABLE 8

Lipids levels in the liver and spleen following administration of nanoparticle compositions including MC3 or compounds according to one of formulae (I), (Ia1)-(Ia6), (Ib), (II), (IIa), (III), and (IIIa).

| Compound No. | Lipid in liver (ng/g) | % remaining dose in liver | Lipid in spleen (ng/g) | % remaining dose in spleen |
|---|---|---|---|---|
| 4 | 21950 | 38 | 5345 | 0.61 |
| 12 | 16850 | 23.8 | 2325 | 0.22 |
| 14 | 3990 | 5.54 | 1620 | 0.15 |
| 15 | 3070 | 4.22 | 971 | 0.089 |
| 16 | 597 | 0.79 | 293 | 0.026 |
| 22 | 36800 | 58.7 | 3887 | 0.41 |
| 23 (DOPE) | 32900 | 51.4 | 26100 | 2.72 |
| MC3 | 21750 | 51 | 2785 | 0.44 |

Example 8: Optimization of Lipid:Therapeutic Agent Ratios

The relative amounts of lipid component and therapeutic and/or prophylactic agent in a nanoparticle composition can be optimized according to considerations of efficacy and tolerability. For compositions including an RNA as a therapeutic and/or prophylactic agent, the N:P ratio can serves as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition. Thus, the wt/wt ratio of total lipid to RNA is varied between 10:1, 15:1, 20:1, 32:1, 40:1, 50:1, and 60:1 for a lipid formulation including about 50 mol % of a compound according to one of formulae (I), (Ia1)-(Ia6), (Ib), (II), (IIa), (III), (IIIa), (IV), (17-I), (19-I), (19-II), (20-I) and (21-I), about 10 mol % phospholipid (e.g., DOPE or DSPC), about 38.5 mol % structural lipid (e.g., cholesterol), and about 1.5 mol % PEG lipid (e.g., PEG-DMG). N:P ratios are calculated for each nanoparticle composition assuming a single protonated nitrogen atom. The encapsulation efficiency (EE), size, and polydispersity index of each composition are also measured.

Generally, compositions with higher total lipid:RNA ratios yield smaller particles with higher encapsulation efficiencies, both of which are desirable. However, the N:P ratio for such formulations generally exceeds 4. Current standards in the art such as the MC3 formulation described above have N:P ratios of 5.67. Thus, a balance between the N:P ratio, size, and encapsulation efficiency should be struck.

In order to explore the efficacy of nanoparticle compositions with different N:P ratios, the expression of luciferase (Luc) or human erythropoietin (hEPO) in mice after low (0.05 mg/kg) or high (0.5 mg/kg) doses of intravenously administered nanoparticle compositions is examined. The concentration of Luc or hEPO expressed is measured 3, 6, and/or 24 hours after administration.

Example 9: Optimization of Content of a Composition Comprising a Compound According to One of Formulae (I), (Ia1)-(Ia6), (Ib), (II), (IIa), (III), (IIIa), (IV), (17-I), (19-I), (19-II), (20-I) and (21-I)

As smaller particles with higher encapsulation efficiencies are generally desirable, the relative amounts of various elements in lipid components of nanoparticle compositions are optimized according to these parameters.

A compound according to one of formulae (I), (Ia1)-(Ia6), (Ib), (II), (IIa), (III), (IIIa), (IV), (17-1), (19-1), (19-II), (20-I) and (21-I) is selected for optimization. The relative amount of the compound according to one of formulae (I), (Ia1)-(Ia6), (Ib), (II), (IIa), (III), (IIIa), (IV), (17-I), (19-I), (19-II), (20-I) and (21-I) is varied between 30 mol % and 60 mol % in compositions including DOPE or DSPC as phospholipids to determine the optimal amount of the compound according to one of formulae (I), (Ia1)-(Ia6), (Ib), (II), (IIa), (III), (IIIa), (IV), (17-I), (19-I), (19-II), (20-I) and (21-I) in the formulations. Formulations are prepared using a standardized process with a water to ethanol ratio in the lipid-mRNA solution of 3:1 and a rate of injection of the lipid solution into the mRNA solution of 12 mL/min on a Nano-Assemblr microfluidic based system. This method induces nano-precipitation and particle formation. Alternative processes including, but not limited to, T-junction or direct injection, may also be used to achieve the same nano-precipitation.

Formulations producing the smallest particles with the highest encapsulation efficiencies are generally preferred, however larger or smaller particle sizes may be desirable based on a given application (e.g., based on the fenestration size of a target organ). Compositions are also evaluated for their Luc or hEPO expression levels and cytokine profiles.

Example 10: Optimization of Phospholipid

The relative amount of phospholipid in a lipid component of a nanoparticle composition is varied to further optimize the formulation. A compound according to one of formulae (I), (Ia1)-(Ia6), (Ib), (II), (IIa), (III), (IIIa), (IV), (17-I), (19-I), (19-II), (20-I) and (21-I) is selected for use in the nanoparticle composition and DOPE and DSPC are selected as phospholipids. Additional phospholipids can also be evaluated. Nanoparticle compositions are prepared with the relative phospholipid content varying between 0 mol % and 30 mol %. Compositions are evaluated for their size, encapsulation efficiency, Luc or hEPO expression levels, and cytokine profiles.

Example 11: Optimization of Structural Lipid

The relative amount of structural lipid in a lipid component of a nanoparticle composition is varied to further optimize the formulation. A compound according to one of formulae (I), (Ia1)-(Ia6), (Ib), (II), (IIa), (III), (IIIa), (IV), (17-I), (19-I), (19-II), (20-I) and (21-I) is selected for use in the nanoparticle composition and cholesterol is selected as a structural lipid. Additional structural lipids can also be evaluated. Nanoparticle compositions are prepared with the relative structural lipid content varying between 18.5 mol % and 48.5 mol %. Compositions are evaluated for their size, encapsulation efficiency, Luc or hEPO expression levels, and cytokine profiles.

Example 12: Optimization of PEG Lipid

The relative amount of PEG lipid in a lipid component of a nanoparticle composition is varied to further optimize the formulation. A compound according to one of formulae (I), (Ia1)-(Ia6), (Ib), (II), (IIa), (III), (IIIa), (IV), (17-I), (19-I), (19-II), (20-I) and (21-I) is selected for use in the nanoparticle composition and PEG-DMG is selected as a PEG lipid. Additional PEG lipids can also be evaluated. Nanoparticle compositions are prepared with the relative PEG lipid content varying between 0 mol % and 10 mol %. Compositions are evaluated for their size, encapsulation efficiency, Luc or hEPO expression levels, and cytokine profiles.

Exemplary formulations useful in the optimization of nanoparticle composition formulations are presented in Table 9.

TABLE 9

Exemplary formulations including compounds according to one of formulae (I), (Ia1)-(Ia6), (Ib), (II), (IIa), (III), (IIIa), (IV), (17-I), (19-I), (19-II), (20-I) and (21-I).

| Composition (mol %) | Components |
| --- | --- |
| 40:20:38.5:1.5 | Compound:Phospholipid:Chol:PEG-DMG |
| 45:15:38.5:1.5 | Compound:Phospholipid:Chol:PEG-DMG |
| 50:10:38.5:1.5 | Compound:Phospholipid:Chol:PEG-DMG |

TABLE 9-continued

Exemplary formulations including compounds according to one of formulae (I), (Ia1)-(Ia6), (Ib), (II), (IIa), (III), (IIIa), (IV), (17-I), (19-I), (19-II), (20-I) and (21-I).

| Composition (mol %) | Components |
|---|---|
| 55:5:38.5:1.5 | Compound:Phospholipid:Chol:PEG-DMG |
| 60:5:33.5:1.5 | Compound:Phospholipid:Chol:PEG-DMG |
| 45:20:33.5:1.5 | Compound:Phospholipid:Chol:PEG-DMG |
| 50:20:28.5:1.5 | Compound:Phospholipid:Chol:PEG-DMG |
| 55:20:23.5:1.5 | Compound:Phospholipid:Chol:PEG-DMG |
| 60:20:18.5:1.5 | Compound:Phospholipid:Chol:PEG-DMG |
| 40:15:43.5:1.5 | Compound:Phospholipid:Chol:PEG-DMG |
| 50:15:33.5:1.5 | Compound:Phospholipid:Chol:PEG-DMG |
| 55:15:28.5:1.5 | Compound:Phospholipid:Chol:PEG-DMG |
| 60:15:23.5:1.5 | Compound:Phospholipid:Chol:PEG-DMG |
| 40:10:48.5:1.5 | Compound:Phospholipid:Chol:PEG-DMG |
| 45:10:43.5:1.5 | Compound:Phospholipid:Chol:PEG-DMG |
| 55:10:33.5:1.5 | Compound:Phospholipid:Chol:PEG-DMG |
| 60:10:28.5:1.5 | Compound:Phospholipid:Chol:PEG-DMG |
| 40:5:53.5:1.5 | Compound:Phospholipid:Chol:PEG-DMG |
| 45:5:48.5:1.5 | Compound:Phospholipid:Chol:PEG-DMG |
| 50:5:43.5:1.5 | Compound:Phospholipid:Chol:PEG-DMG |
| 40:20:40:0 | Compound:Phospholipid:Chol:PEG-DMG |
| 45:20:35:0 | Compound:Phospholipid:Chol:PEG-DMG |
| 50:20:30:0 | Compound:Phospholipid:Chol:PEG-DMG |
| 55:20:25:0 | Compound:Phospholipid:Chol:PEG-DMG |
| 60:20:20:0 | Compound:Phospholipid:Chol:PEG-DMG |
| 40:15:45:0 | Compound:Phospholipid:Chol:PEG-DMG |
| 45:15:40:0 | Compound:Phospholipid:Chol:PEG-DMG |
| 50:15:35:0 | Compound:Phospholipid:Chol:PEG-DMG |
| 55:15:30:0 | Compound:Phospholipid:Chol:PEG-DMG |
| 60:15:25:0 | Compound:Phospholipid:Chol:PEG-DMG |
| 40:10:50:0 | Compound:Phospholipid:Chol:PEG-DMG |
| 45:10:45:0 | Compound:Phospholipid:Chol:PEG-DMG |
| 50:0:48.5:1.5 | Compound:Phospholipid:Chol:PEG-DMG |
| 50:10:40:0 | Compound:Phospholipid:Chol:PEG-DMG |
| 55:10:35:0 | Compound:Phospholipid:Chol:PEG-DMG |
| 60:10:30:0 | Compound:Phospholipid:Chol:PEG-DMG |

Example 13: Optimization of Particle Sizes

The fenestration sizes for different bodily organs often vary; for example, the kidney is known to have a smaller fenestration size than the liver. Thus, targeting delivery of a therapeutic and/or prophylactic agent (e.g., specifically delivering) to a particular organ or group of organs may require the administration of nanoparticle compositions with different particle sizes. In order to investigate this effect, nanoparticle compositions with formulations such as those included in Table 9 are prepared with a variety of particle sizes using a Nanoassemblr instrument. Nanoparticle compositions include an RNA encoding Luc. Each differently sized nanoparticle composition is subsequently administered to mice to evaluate the effect of particle size on delivery selectivity. Luc expression in two or more organs or groups of organs can be measured using bioluminescence to evaluate the relative expression in each organ.

Example 14: Administration Following Pretreatment

Administration of nanoparticle compositions to subjects can result in inflammation, infusion related reactions, and other undesirable effects indicative of low tolerability. These effects can be attributed to undesirable immunoactivity.

In order to combat negative effects, nanoparticle compositions are co-administered with one or more substances (e.g., co-medications or additional therapeutic and/or prophylactic agents) to subjects. Potentially useful additional therapeutic and/or prophylactic agents include steroids (e.g., corticosteroids), anti-histamines, H1 receptor blockers, H2 receptor blockers, anti-inflammatory compounds, statins, BTK inhibitors, S1P1 agonists, glucocorticoid receptor modulators (GRMs), and estradiols. Non-human primates are pretreated with one or more additional therapeutic agents selected from dexamethasone and acetaminophen. The additional therapeutic agent is administered either 24 hours, 1 hour, or both 24 hours and 1 hour before administration of a nanoparticle composition. Sample protocol are summarized in Table 10. Cytokine profiles, inflammation, and other parameters are measured and compared to evaluate the effectiveness of pretreatment.

TABLE 10

Sample protocol for pretreatment study.

| Group | Pretreatment Time | Additional Therapeutic Agent(s) Administered |
|---|---|---|
| 1 | None | None |
| 2 | 24 hours | Dexamethasone |
| 3 | 24 hours | Acetaminophen |
| 4 | 24 hours | Dexamethasone and Acetaminophen |
| 5 | 1 hour | Dexamethasone |
| 6 | 1 hour | Acetaminophen |
| 7 | 1 hour | Dexamethasone and Acetaminophen |
| 8 | 24 hours and 1 hour | Dexamethasone |
| 9 | 24 hours and 1 hour | Acetaminophen |
| 10 | 24 hours and 1 hour | Dexamethasone and Acetaminophen |

For example, a useful therapeutic treatment course may involve administering an additional therapeutic and/or prophylactic agent both the day before and the day of (one hour prior) to administration of a nanoparticle composition at a dose level of 1.3 mpk. Additional therapeutic and/or prophylactic agents can be formulated for delivery by a variety of different routes. For example, dexamethasone may be delivered orally. In general, additional therapeutic and/or prophylactic agents are administered at clinically approved or typical dosage levels.

Example 15: Administration to Non-Human Primates

The tolerability and efficacy of nanoparticle compositions to non-human primates is evaluated in Cynomolgus monkeys. Monkeys are administered an optimized nanoparticle composition including an mRNA encoding hEPO once weekly for four weeks. The levels of hEPO protein, mRNA, and cytokine profiles are measured using ELISA-based techniques before and 2, 6, 12, 24, 48, 72, and 120 hours after each administration.

The effects of pretreatment to non-human primates are evaluated using a standard MC3 formulation including an mRNA encoding hEPO. The study design is summarized in Table 11. Male monkeys are administered the nanoparticle composition once weekly for four weeks at a dose rate of 5 ml/kg/h and are pretreated with either methotrexate or dexamethasone.

TABLE 11

Protocol for pretreatment study in Cynomolgus monkeys.

| Group | Test Material | Dose level (mg/kg) | Additional Therapeutic Agent Administered | Dose concentration (mg/ml) | Number of monkeys |
|---|---|---|---|---|---|
| 1 | MC3 | 0 | None | 0 | 3 |
| 2 | hEPO mRNA in MC3 | 0.3 | None | 0.06 | 3 |

TABLE 11-continued

Protocol for pretreatment study in Cynomolgus monkeys.

| Group | Test Material | Dose level (mg/kg) | Additional Therapeutic Agent Administered | Dose concentration (mg/ml) | Number of monkeys |
|---|---|---|---|---|---|
| 3 | hEPO mRNA in MC3 | 0.3 | Methotrexate | 0.06 | 3 |
| 4 | hEPO mRNA in MC3 | 0.3 | Dexamethasone | 0.06 | 3 |

Example 16: Methods of Treating Diseases and Disorders

A nanoparticle composition formulation having high tolerability (e.g., provoking a low immune response) and efficacy (e.g., facilitating efficient and effective encapsulation of a therapeutic and/or prophylactic agent and delivery of the agent to a desired target) is selected for use. A therapeutic and/or prophylactic agent for formulation with the nanoparticle composition is selected for use based on the condition of a subject. For example, an mRNA encoding a vascular endothelial growth factor A (VEGF-A) may be selected to promote angiogenesis to treat atherosclerotic renovascular disease, while an siRNA capable of knocking down apolipoprotein B (apoB) may be selected to treat a metabolic disease or disorder such as dyslipidemia.

A subject in need of treatment is pretreated with a small dose of dexamethasone one or more hours prior to treatment with the nanoparticle composition. The nanoparticle composition is preferably administered to the subject intravenously, however intramuscular, intradermal, subcutaneous, intranasal, or inhalation administration routes are also acceptable. Treatment is provided in a dose of about 0.001 mg/kg to about 10 mg/kg of therapeutic and/or prophylactic agent and is repeated daily, weekly, biweekly, or monthly according to needs of the subject.

Example 17: Expression Induced by Sample Formulations Upon Intramuscular Administration Sample formulations including both modified luciferase (Luc) mRNA and H10 mRNA were prepared and administered intramuscularly at day 1 and day 21 and the resulting expression and immunogenicity were evaluated simultaneously. Formulations including compounds according to formula (20-I) were prepared and administered at doses of 0.001 and 0.01 mpk (e.g., doses of 0.0005 mpk of a formulation including Luc mRNA and a formulation including H10 mRNA or doses of 0.005 mpk of a formulation including Luc mRNA and a formulation including H10 mRNA). As shown in Table 20-4, the total flux was higher upon administration of the second dose for each composition and at each dose level. Total flux was higher for the higher dose level.

TABLE 12

Total flux (p/s) measured 6 hours after intramuscular administration of nanoparticle compositions including compounds according to formula (20-I).

| Compound | 0.001 mpk Dose 1 | 0.001 mpk Dose 2 | 0.01 mpk Dose 1 | 0.01 mpk Dose 2 |
|---|---|---|---|---|
| 20-1 | 3.50E+05 | 1.99E+06 | 3.16E+06 | 1.04E+07 |
| 20-4 | 1.04E+06 | n.d. | 9.46E+06 | n.d. |
| 20-6 | 8.57E+05 | 9.79E+05 | 3.41E+06 | 6.04E+06 |
| MC3 | 1.23E+06 | 1.09E+06 | 1.79E+07 | 3.13E+07 |

It is to be understood that while the compounds and methods of the present disclosure have been described in conjunction with the detailed description thereof, the foregoing description is intended to illustrate and not limit the scope of the present disclosure, which is defined by the scope of the appended claims. Other aspects, advantages, and alterations are within the scope of the following claims.

What is claimed is:
1. A compound being

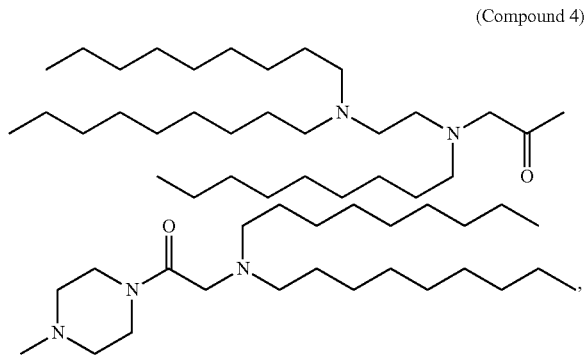

(Compound 4)

or a salt or isomer thereof.

2. The compound of claim 1, wherein the salt is a pharmaceutically acceptable salt.

3. A nanoparticle composition comprising a lipid component comprising the compound of claim 1.

4. The nanoparticle composition of claim 3, wherein the lipid component further comprises a phospholipid.

5. The nanoparticle composition of claim 4, wherein the phospholipid is selected from the group consisting of
1,2-dilinoleoyl-sn-glycero-3-phosphocholine (DLPC),
1,2-dimyristoyl-sn-glycero-phosphocholine (DMPC),
1,2-dioleoyl-sn-glycero-3-phosphocholine (DOPC),
1,2-dipalmitoyl-sn-glycero-3-phosphocholine (DPPC),
1,2-distearoyl-sn-glycero-3-phosphocholine (DSPC),
1,2-diundecanoyl-sn-glycero-phosphocholine (DUPC),
1-palmitoyl-2-oleoyl-sn-glycero-3-phosphocholine (POPC),
1,2-di-O-octadecenyl-sn-glycero-3-phosphocholine (18:0 Diether PC),
1-oleoyl-2-cholesterylhemisuccinoyl-sn-glycero-3-phosphocholine (OChemsPC),
1-hexadecyl-sn-glycero-3-phosphocholine (C16 Lyso PC),
1,2-dilinolenoyl-sn-glycero-3-phosphocholine,
1,2-diarachidonoyl-sn-glycero-3-phosphocholine,
1,2-didocosahexaenoyl-sn-glycero-3-phosphocholine,
1,2-dioleoyl-sn-glycero-3-phosphoethanolamine (DOPE),
1,2-diphytanoyl-sn-glycero-3-phosphoethanolamine (ME 16.0 PE),
1,2-distearoyl-sn-glycero-3-phosphoethanolamine,
1,2-dilinoleoyl-sn-glycero-3-phosphoethanolamine,
1,2-dilinolenoyl-sn-glycero-3-phosphoethanolamine,
1,2-diarachidonoyl-sn-glycero-3-phosphoethanolamine,
1,2-didocosahexaenoyl-sn-glycero-3-phosphoethanolamine,
1,2-dioleoyl-sn-glycero-3-phospho-rac-(1-glycerol) sodium salt (DOPG),
sphingomyelin, and
mixtures thereof.

6. The nanoparticle composition of claim 5, wherein the phospholipid is DSPC or DOPE.

7. The nanoparticle composition of claim 4, wherein the lipid component further comprises a structural lipid.

8. The nanoparticle composition of claim 7, wherein the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof.

9. The nanoparticle composition of claim 8, wherein the structural lipid is cholesterol.

10. The nanoparticle composition of claim 7, wherein the lipid component further comprises a PEG lipid.

11. The nanoparticle composition of claim 10, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

12. The nanoparticle composition of claim 10, wherein the lipid component comprises about 30 mol % to about 60 mol % said compound, about 0 mol % to about 30 mol % phospholipid, about 18.5 mol % to about 48.5 mol % structural lipid, and about 0 mol % to about 10 mol % PEG lipid.

13. The nanoparticle composition of claim 10, wherein the lipid component comprises about 35 mol % to about 55 mol % said compound, about 5 mol % to about 25 mol % phospholipid, about 30 mol % to about 40 mol % structural lipid, and about 0 mol % to about 10 mol % PEG lipid.

14. The nanoparticle composition of claim 10, wherein the lipid component comprises about 50 mol % said compound, about 10 mol % phospholipid, about 38.5 mol % structural lipid, and about 1.5 mol % PEG lipid.

15. The nanoparticle composition of claim 10, further comprising a therapeutic and/or prophylactic agent.

16. The nanoparticle composition of claim 12, further comprising a therapeutic and/or prophylactic agent.

17. The nanoparticle composition of claim 13, further comprising a therapeutic and/or prophylactic agent.

18. The nanoparticle composition of claim 15, wherein the therapeutic and/or prophylactic agent is a nucleic acid.

19. The nanoparticle composition of claim 15, wherein the therapeutic and/or prophylactic agent is a ribonucleic acid (RNA).

20. The nanoparticle composition of claim 19, wherein the RNA is selected from the group consisting of a small interfering RNA (siRNA), an asymmetrical interfering RNA (aiRNA), a microRNA (miRNA), a Dicer-substrate RNA (dsRNA), a small hairpin RNA (shRNA), a messenger RNA (mRNA), and mixtures thereof.

21. The nanoparticle composition of claim 19, wherein the RNA is mRNA.

22. The nanoparticle composition of claim 21, wherein the mRNA includes one or more of a stem loop, a chain terminating nucleoside, a polyA sequence, a polyadenylation signal, and/or a 5' cap structure.

23. The nanoparticle composition of claim 21, wherein the encapsulation efficiency of the therapeutic and/or prophylactic agent is at least 80% or at least 90%.

24. The nanoparticle composition of claim 21, wherein the wt/wt ratio of the lipid component to the mRNA is from about 10:1 to about 60:1.

25. The nanoparticle composition of claim 21, wherein the wt/wt ratio of the lipid component to the mRNA is about 20:1.

26. The nanoparticle composition of claim 21, wherein the N:P ratio is from about 5:1 to about 8:1.

27. A pharmaceutical composition comprising the nanoparticle composition of claim 21 and a pharmaceutically acceptable carrier.

28. A method of delivering a therapeutic and/or prophylactic agent to a mammalian cell, the method comprising administering to a subject the nanoparticle composition of claim 15, said administering comprising contacting the cell with the nanoparticle composition, whereby the therapeutic and/or prophylactic agent is delivered to the cell.

29. A method of producing a polypeptide of interest in a mammalian cell, the method comprising contacting the cell with the nanoparticle composition of claim 21, wherein the mRNA encodes the polypeptide of interest, whereby the mRNA is capable of being translated in the cell to produce the polypeptide of interest.

30. A method of treating a disease or disorder in a mammal in need thereof, the method comprising administering to the mammal a therapeutically effective amount of the nanoparticle composition of any claim 15.

\* \* \* \* \*